(12) United States Patent
Jones et al.

(10) Patent No.: US 11,878,020 B2
(45) Date of Patent: *Jan. 23, 2024

(54) MODULATORS OF RHO-ASSOCIATED PROTEIN KINASE

(71) Applicant: Redx Pharma PLC, Alderley Edge (GB)

(72) Inventors: Clifford D. Jones, Macclesfield (GB); Peter Bunyard, Macclesfield (GB); Gary Pitt, Macclesfield (GB); Liam Byrne, Macclesfield (GB); Thomas Pesnot, Macclesfield (GB); Nicolas E. S. Guisot, Macclesfield (GB)

(73) Assignee: Redx Pharma PLC, Macclesfield (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/896,626

(22) Filed: Aug. 26, 2022

(65) Prior Publication Data

US 2023/0021916 A1 Jan. 26, 2023

Related U.S. Application Data

(63) Continuation of application No. 16/964,904, filed as application No. PCT/GB2019/050215 on Jan. 25, 2019, now Pat. No. 11,497,751.

(30) Foreign Application Priority Data

Jan. 25, 2018 (GB) ..................................... 1801226

(51) Int. Cl.
| | | |
|---|---|---|
| A61K 31/538 | (2006.01) | |
| A61K 31/4196 | (2006.01) | |
| A61K 31/5377 | (2006.01) | |
| C07D 403/12 | (2006.01) | |
| C07D 403/14 | (2006.01) | |
| C07D 405/14 | (2006.01) | |
| C07D 413/14 | (2006.01) | |

(52) U.S. Cl.
CPC ........ *A61K 31/538* (2013.01); *A61K 31/4196* (2013.01); *A61K 31/5377* (2013.01); *C07D 403/12* (2013.01); *C07D 403/14* (2013.01); *C07D 405/14* (2013.01); *C07D 413/14* (2013.01)

(58) Field of Classification Search
CPC .. C07D 403/12; C07D 403/14; C07D 405/14; C07D 413/14; A61K 31/538; A61K 31/4196; A61K 31/5377
See application file for complete search history.

(56) References Cited

U.S. PATENT DOCUMENTS

| | | | |
|---|---|---|---|
| 7,951,820 B2 | 5/2011 | Bebbington et al. | |
| 11,497,751 B2 | 11/2022 | Jones et al. | |
| 2003/0055044 A1 | 3/2003 | Davies et al. | |
| 2004/0214817 A1 | 10/2004 | Pierce et al. | |
| 2005/0288347 A1 | 12/2005 | Hodge et al. | |
| 2011/0082136 A1 | 4/2011 | Machacek et al. | |
| 2011/0190355 A1 | 8/2011 | Klein et al. | |
| 2013/0123284 A1 | 5/2013 | Arnold et al. | |
| 2019/0002442 A1 | 1/2019 | Zhao et al. | |
| 2021/0038606 A1 | 2/2021 | Jones et al. | |
| 2023/0021916 A1 | 1/2023 | Jones et al. | |

FOREIGN PATENT DOCUMENTS

| | | |
|---|---|---|
| WO | WO-93/20066 A1 | 10/1993 |
| WO | WO-2004/052280 A2 | 6/2004 |
| WO | WO-2006/135383 A2 | 12/2006 |
| WO | WO-2007/139967 A2 | 12/2007 |
| WO | WO-2012/045883 A1 | 4/2012 |
| WO | WO-2012/084704 A1 | 6/2012 |
| WO | WO-2016/138335 A1 | 9/2016 |
| WO | WO-2019/145729 A1 | 8/2019 |

OTHER PUBLICATIONS

CA Office Action translation for CN 201980010083.3 dated Nov. 10, 2022.
Chinese Office Action for CN Application No. 201980010083.3 dated Nov. 10, 2022.
Masakatsu Nozaki et al., Pharmaceutical Chemistry, first edition, Kagaku-Dojin Publishing Company, Inc, 1995, pp. 98-99.
Aurelio et al., "From Sphingosine Kinase to Dihydroceramide Desaturase: A Structure-Activity Relationship (SAR) Study of the Enzyme Inhibitory and Anticancer Activity of 4-((4-(4-Chlorophenyl)thiazol-2-yl)amino)phenol (SKI-II)," J Med Chem, 59: 965-984 (2016).
Defert et al., "Rho kinase inhibitors: a patent review (2014-2016)," Expert Opin Ther Pat, 27(4): 507-515 (2017).
Dhar et al., "A Survey of Cyclic Replacements for the Central Diamide Moiety of Inhibitors of Inosine Monophosphate Dehydrogenase," Bioorg Med Chem, 12: 3125-3128 (2002).
El-Sherief et al., "Novel 1,2,4-triazole derivatives as potential anticancer agents: Design, synthesis, molecular docking and mechanistic studies," Biorg Chem, 76: 314-325 (2018).
Great Britain Search Report for Application No. GB1801226.0 dated Oct. 11, 2018.
International Search Report and Written Opinion for International Application No. PCT/GB2019/050215 dated Mar. 6, 2019.
Loirand, "Rho Kinases in Health and Disease: From Basic Science to translational Research," Pharmacol Rev, 67: 1074-1095 (2015).
Okawa et al., "Design, Synthesis, and Evaluation of the Highly Selective and Potent G-Protein-Coupled Receptor Kinase 2 (GRK2) Inhibitor for the Potential Treatment of Heart Failure," J Med Chem, 60: 6942-6990 (2017).

*Primary Examiner* — Daniel R Carcanague
(74) *Attorney, Agent, or Firm* — Foley Hoag LLP; Dana M. Gordon

(57) ABSTRACT

This invention relates to novel compounds and pharmaceutical compositions comprising. Compounds of the invention useful as modulators of Rho-associated protein kinase (ROCK), for example ROCK1 and/or ROCK2 inhibitors. Methods of treatment employing the compounds are also contemplated by the present invention. The compounds of the invention are useful in treating ROCK mediated diseases.

20 Claims, No Drawings

MODULATORS OF RHO-ASSOCIATED PROTEIN KINASE

RELATED APPLICATIONS

This application is a continuation of U.S. patent application Ser. No. 16/964,904, filed Jul. 24, 2020; which is a 371 U.S. National Stage Application of International Application No. PCT/GB2019/050215, filed Jan. 25, 2019, which claims the benefit of priority to Great Britain Application No. 1801226.0, filed Jan. 25, 2018.

This invention relates to novel compounds and pharmaceutical compositions comprising the novel compounds. More specifically, the invention relates to compounds useful as modulators of Rho-associated protein kinase (ROCK), for example ROCK1 and/or ROCK2 inhibitors. This invention also relates to processes for preparing the compounds, uses of the compounds and methods of treatment employing the compounds. The compounds of the invention may therefore be used in treating ROCK mediated diseases.

BACKGROUND

Rho-Kinase (ROCK) is a coiled-coil forming serine-threonine protein kinase family and exists in two isoforms, ROCK1 and ROCK2 (Ishizaki, T. et al, EMBO J. 15: 1885-1893 (1996)). ROCK has been identified as an effector molecule of RhoA, a small GTP-binding protein (G protein). Both molecules are ubiquitously expressed across tissues and play key-roles in multiple cellular signalling pathways. Upon receptor activation RhoA activates ROCK that in turn controls several cellular functions including cell migration, cell adhesion, actin reorganisation, cytokinesis and smooth muscle contraction (Riento, K. et al, Nat. Rev. Mol. Cell Biol, 4:446-456 (2003)); (Somyo, A. P., Nature, 389:908-911 (1997)). An aim of certain embodiments of the invention is to provide a modulator of ROCK, including both ROCK1 and ROCK2, for example an inhibitor of ROCK (ROCK1 and/or ROCK2).

Despite having similar kinase domains at 92% homology, ROCK1 and ROCK2 may have different downstream targets and therefore different modes of action in cellular physiology. ROCK2 for example specifically phosphorylate STAT3 in lymphocytes leading to Th17 cell differentiation and Treg suppression (Zanin-Zhorov A. et al, PNAS 111(47): 16814-16819 (2014)) whereas Myosin light chain (MLC) is specifically phosphorylated by ROCK1 in smooth muscle cells (Sebbagh M. et al. Nat Cell Biol 3: 346-352 (2001); showing a greater role for ROCK1 in vascular contraction leading to increases in blood pressure. SIRNA experiments have demonstrated distinct roles for ROCK1 and ROCK2 in many cell types for example in rat embryonic fibroblast cells where ROCK1 was found to be important for stress fiber formation and stabilization of focal adhesion sites, while ROCK2 activity was involved in phagocytosis of matrix-coated beads (Yoneda, A., et. al, J. Cell Biol. (2005). Therefore, an aim of certain embodiments of the invention is to provide a selective ROCK inhibitor, e.g. selective to ROCK1 inhibition or ROCK2 inhibition. Preferably, an aim of certain embodiments of the present invention is to provide a selective ROCK2 inhibitor.

ROCK deficient mice and small molecule inhibitors have helped the understanding of the roles that the ROCK isoforms play in disease and provided evidence that ROCK inhibitors will be useful for the treatment of several indications where unmet need is high including diabetes, inflammation, Alzheimer's hypertension and fibrosis. After feeding wild type and ROCK2(+/−) mice with a high fat diet for 17 weeks, it was shown that insulin resistance did not develop in the ROCK2(+/−) mice with normal insulin and GLUT4 expression observed. The myocardial performance index was also increased (Soliman et al., Am J Physiol Heart Circ Physiol. 309(1):H70-81 (2015)).

ROCK2 also plays a significant role in cardiac hypertrophy. Cardiomyocyte-specific deletion of ROCK2 display normal cardiac anatomy, function and hemodynamic parameters under basal conditions but following induction of cardiac hypertrophy induced by angiotensin II infusion the mice exhibited substantially less cardiac hypertrophy, intraventricular fibrosis, cardiac apoptosis, and oxidative stress compared to control mice. (Okamoto et al., FASEB J 4:1439-49 (2013)). The role of ROCK1 was further studied in a model of ischemia/reperfusion cardiomyopathy (I/RC) by occlusions of the left anterior descending artery. ROCK1 KO mice were protected from the development of I/RC-mediated myocardial dysfunction and had reduced cardiac fibrosis. Fibroblast formation from human peripheral blood mononuclear cells was impaired in cells with lower ROCK1 expression (Haudek et al., Cardiovasc Res. 83(3):511-8 (2009)). ROCK activity has also been shown to be increased in patients with myocardial function (Dong et al., Int J Cardiol 167(6):2813-9 (2013)). A combination of increased Rho kinase activity and N-terminal pro-B-type natriuretic peptide predicts worse cardiovascular outcome in patients with acute coronary syndrome.

ROCK2 also plays an important role in fibrosis: two reports have shown that bleomycin induced lung fibrosis is ameliorated in both ROCK1(+/−) and ROCK2(+/−) animals and mice with a targeted deletion of ROCK2 in cardiac fibroblasts showed reduced cardiac hypertrophy and fibrosis when infused with angiotensin II. (Shimizu T JACC Apr. 5, 2016 Volume 67, Issue 13; ATS 2014 A60. LUNG FIBROSIS: ANIMAL MODELS I). Furthermore, ROCK2 expression and function has been shown to be increased in bronchial epithelial tissue and fibrotic foci in idiopathic pulmonary fibrosis patients (Shimizu Y Int J Immunopathol Pharmacol. 27(1):37-44 (2014)).

A number of ATP competitive inhibitors of ROCK kinase activity have been developed with the non-isoform-selective Y-27632 and Fasudil being the most widely known and used. These inhibitors show a relatively high degree of specificity for ROCKs, however, when used at higher concentrations they can also inhibit other kinases such as protein kinase A and C family members and citron kinase (Ishizaki et al., 2000; Ikenoya et al., 2002). Fasudil was approved in Japan and China in 1995 for prevention and treatment of cerebral vasospasm following subarachnoid haemorrhage. In clinical studies, fasudil shows beneficial effects in patients with Pulmonary arterial hypertension, systemic hypertension, vasospastic angina, stroke, and chronic heart failure (Masumoto et al., 2001, 2002; Fukumoto et al., 2005; Kishi et al., 2005; Shibuya et al., 2005). Additional investigations suggest that a ROCK inhibitor would be useful in treating cardiovascular diseases. In a rat stroke model, Fasudil was shown to reduce both the infarct size and neurologic deficit and the ROCK inhibitor Y-27632 was shown to improve ventricular hypertrophy, fibrosis and function in a model of congestive heart failure in Dahl salt-sensitive rats ((Toshima, Y., Stroke, 31:2245-2250 (2000); Kobayashi, N. et al., Cardiovasc. Res., 55:757-767 (2002)). Other studies show a link between ROCK and atherosclerosis. In a porcine model of IL-1 beta-induced coronary stenosis, long term treatment with the Fasudil was shown to progressively reduce coronary stenosis, as well as promote a regression of coronary constrictive remodeling (Shimokawa, H. et al., Cardiovasc. Res., 51:169-177 (2001)). In a similar model, ROCK inhibitor Y-27632 also inhibited neointimal formation in rats (Sawada, N. et al., Circulation, 101:2030-2033 (2000)).

Furthermore, both Y27632 and Fasudil have demonstrated efficacy in the Neomycin induced lung fibrosis (Shimizu Y et al., Am J Respir Crit Care Med. 163(1):210-7 (2001)); Jiang C et al., Int J Mol Sd. 13(7):8293-307 (2012)) and Fasudil has been shown to be efficacious in a rat unilateral ureteral obstruction kidney fibrosis model (Shinichi S., Eur. J. Pharm. 29:169-174 (2002)) and against hepatic fibrosis in rats with type2 diabetes induced by a high fat diet combined with streptozotocin (Thou H et al., Chin Med J, 127(2):225-31 (2014)). In addition, Fasudil treated mice were significantly protected mice from lung and skin fibrosis after repeated subcutaneous injections of hypochlorous acid (HOCl) (Bel Y et al., Exp Lung Res, 42(1):44-45 (2016)). These results provide further evidence that ROCK signalling is instrumental to fibrotic processes across a number of tissues and fibrotic diseases and underlines the value in targeting ROCK as an anti-fibrotic in cardiovascular and metabolic diseases.

A selective ROCK2 inhibitor (KD025) has been described that has also shown efficacious effects in inflammatory disease models and cells isolated from diseased patients via suppression of Th17 and T follicular helper (TFH) cells. KD025 effectively ameliorated chronic graft-versus-host disease (cGVHD) in two models: a full major histocompatibility complex (MHC) mismatch model of multiorgan system cGVHD with bronchiolitis obliterans syndrome and a minor MHC mismatch model of sclerodermatous GVHD. Treatment with KD025 resulted in normalization of pathogenic pulmonary function via suppression of antibody and collagen deposition in the lungs (Flynn R et al., Blood 127(17):2144-54 (2016)). KD025 suppression of ROCK2 signalling in normal human T cells or peripheral blood mononuclear cells from patients with active systemic lupus erythematosus (SLE) was also shown to decrease the number and function of TFH cells induced by activation ex vivo (Weiss J M et al., Sci Signal, 9(437):ra73 (2016)). Further ex-vivo stimulation of T cell from healthy human subjects demonstrated that oral administration of KD025 was able to reduce the ability of T cells to secrete IL-21 and IL-17 by 90% and 60%, respectively (Zanin-Zhorov A et al., Proc Natl Acad Sci, 111(47):16814-9 (2014)). Given the demonstrated effect of ROCK on smooth muscle, ROCK inhibitors may also be useful in other diseases involving smooth muscle hyper-reactivity, including asthma and glaucoma (Shimokawa, H. et al., Arterioscler. Thromb. Vase. Biol., 25:1767-1775 (2005)). Selective suppression of ROCK2 therefore presents a novel opportunity to treat a number of auto-immune and inflammatory-fibrotic conditions.

ROCK also plays a significant role in pathologies of the central nervous system (CNS). For example, ROCK-signalling has been demonstrated to be elevated in the serum, spleen, brain and spinal cord of Multiple Sclerosis (MS) patients compared to healthy individuals. In vitro neuron injury with scratch and TNF-α stimulation also induces the up-regulation of ROCK activity. Wien serum of MS patients was co-cultured with mouse cortical neurons in vitro, MS serum caused neurite shortening and reduction of cell viability. Co-culture with Fasudil partially restored the synaptic morphology of the neurons strongly suggesting a neuroprotective effect of ROCK inhibition (Chen C et al., Neuromolecular Med. 17(4):465-65 (2015)). Intravitreal administration of Fasudil was able to improve the retinal function in the R6/2 mouse model of Huntington disease suggesting ROCK inhibition may be able to slow or reverse neuronal dysregulation (Li M et al., PBS One. 8(2):e56026 (2013)). Oral administration of Y-27632 was also able to improve coordination and balance in a rotarod performance test in the R6/2 model; the treatment also reduced the level of soluble huntingtin (Htt) protein (U M et al., Neurobiol Dis. 36(3): 413-20 (2009)). ROCKII interference (RI) with small hairpin RNA (ShRNA) also significantly improved movement disorder and attenuated dopaminergic (DA) neuron loss induced by 1-methyl-4-phenyl-1,2,3,6-tetrahydropyridine (MPTP) in a mouse model of Parkinson's disease. In addition, ROCK2 ShRNA inhibited the activation of M1 microglia in the substantia nigra (SN), exhibiting reduced activity of the TLR2/NF-κB signaling pathway and decreased expression levels of INOS and inflammatory factors, including interleukin (IL)-1β and IL-6. (Zhang Q et al., Mol Med Rep. 14(6):4947-4956 (2016)). In another study Fasudil was also shown to have protective effects on the DN in the MPTP model. (Zhao Y et al., J Neurol Sci 353(1-2):28-37 (2015)). Further experiments with RNAI knockdown demonstrated that reduced expression of both ROCK1 and ROCK2 suppressed endogenous Aβ40 production in neurons and Aβ40 levels were reduced in brains of ROCK1 heterozygous knock-out mice compared to wild-type littermate controls suggesting ROCK may also be a valid target for the treatment of Alzheimer's disease (Henderson B et al., J Neurochem, 138(4):525-31 (2016)).

Several studies also demonstrate that ROCK inhibition will have utility in cancer therapy. Y 27632 and Fasudil have been shown to down regulate surviving expression in the pancreatic cell line PANC-1 and sensitised the cells to gemcitabine induced cell death. (Takeda H., Anticancer Res 36(12):6311-6318 (2016)). Oral administration of Fasudil has also been shown to reduce the tumour size in mouse transgenic model of human gastric cancer (Hinsenkamp I et al., Neoplasia 18(8):500-11 (2016)). Fasudil has also been shown to suppress proliferation and migration and induce apoptosis in urothelial cancer cells (Abe H et al., BMC Cancer 7; 14:412 (2014)).

Furthermore, it is an aim of certain embodiments of this invention to provide new treatments, for example treatments for diabetes, inflammation, Alzheimer's, hypertension, fibrosis, cancer, pathologies of the central nervous system and other conditions associated with ROCK1 and/or ROCK2. In particular, it is an aim of certain embodiments of this invention to provide compounds which have comparable activity to existing ROCK therapies.

It is an aim of certain embodiments of this invention to provide compounds which exhibit reduced cytotoxicity or increased solubility relative to prior art compounds and existing therapies.

Another aim of certain embodiments of this invention is to provide compounds having a convenient pharmacokinetic profile and a suitable duration of action following dosing. A further aim of certain embodiments of this invention is to provide compounds in which the metabolised fragment or fragments of the drug after absorption are GRAS (Generally Regarded As Safe).

Certain embodiments of the present invention satisfy some or all of the above alms.

BRIEF SUMMARY OF THE DISCLOSURE

In embodiments, the present invention provides a compound of formula (I) and pharmaceutically acceptable salts thereof:

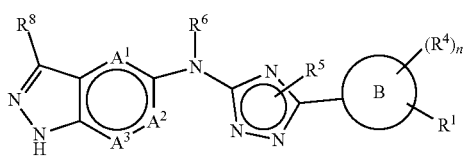

(I)

wherein
A¹, A² or A³ are each independently selected from CH, CR⁷ or N;
B represents a 5 to 10 membered carbocyclic ring system or a 5 to 10 membered heterocyclic ring system;
$R^1$ is L-$R^2$, wherein
  L is a bond or -$L^1$-$L^2$-,
    wherein $L^1$ is selected from: a bond, —$(CR^A R^B)_{1-3}$—, —O$(CR^A R^B)_{1-3}$—, —$(CR^A R^B)_{0-3}$O—, and —$NR^C(CR^A R^B)_{1-3}$—, and
    $L^2$ is selected from: a bond, —$(CR^A R^B)_{1-3}$—, —O—, —$NR^D$—, —C(O)$NR^D$—, —$NR^D$C(O)—, —C(O)O—, —OC(O)—, —C(O)—, —S(O)$_2NR^D$—, —$NR^D$S(O)$_2$—, —S(O)$_2$—, —S(O)($NR^D$)—, —$NR^D$C(O)$NR^E$—, —OC(O)$NR^D$—, and —C(O)$NR^D$S(O)$_2$—, and
    $R^2$ is selected from: H, CN, $C_{1-6}$ alkyl, $C_{1-6}$ haloalkyl, $C_{1-6}$ alkyl substituted with —$OR^F$, $C_{1-6}$ alkyl substituted with —$NR^F R^G$, $C_{1-4}$ haloalkyl substituted with —$OR^F$, $C_{3-8}$ cycloalkyl substituted with OH, $C_{1-4}$ alkyl substituted with 3 to 8 membered heterocycloalkyl, $C_{1-4}$ alkyl substituted with 6 membered heteroaryl, —$(CR^H R^I)_{1-3}OR^F$, —$(CR^H R^I)_{1-3}NR^F R^G$, —$(CR^N R^O)_{1-3}C(O)OR^F$, —$(CR^N R^O)_{1-3}C(O)NR^F R^G$, $C_{3-10}$ carbocyclic ring system, and 3 to 10 membered heterocyclic ring system, wherein the carbocyclic ring or heterocyclic ring system is unsubstituted or substituted with: =O, —$NR^F R^G$, —C(O)$R^F$, halo, —CN, $C_{1-4}$ alkyl, $C_{1-4}$ haloalkyl, or $C_{1-4}$ alkyl substituted with —$OR^F$;
$R^4$ is independently selected at each occurrence from: halo, $C_{1-4}$ alkyl, $C_{1-6}$ haloalkyl, —CN, —$OR^J$, =O, $C_{1-4}$ alkyl substituted with —$OR^J$, —$NR^J R^K$, $C_{1-4}$ alkyl substituted with —$NR^J R^K$, $C_{3-8}$ cycloalkyl, $C_{1-4}$ alkyl substituted with $C_{3-8}$ cycloalkyl, 3 to 8 membered heterocycloalkyl and $C_{1-4}$ alkyl substituted with 3 to 8 membered heterocycloalkyl;
$R^5$ is selected from: H, $C_{1-4}$ alkyl, $C_{1-4}$ alkyl substituted with —$OR^L$, $C_{1-4}$ alkyl substituted with —$NR^L R^L$, $C_{3-8}$ cycloalkyl, substituted or unsubstituted phenyl, 3 to 8 membered heterocycloalkyl, $C_{1-4}$ alkyl substituted with $C_{3-8}$ cycloalkyl, $C_{1-4}$ alkyl substituted with 3 to 8 membered heterocycloalkyl and substituted or unsubstituted 5 or 6 membered heteroaryl, wherein the phenyl or heteroaryl group may be substituted by 1 or 2 $R^9$;
$R^6$ is selected from: H and $C_{1-4}$ alkyl;
$R^7$ is selected from: H, halo, —$OR^M$, $C_{1-4}$ alkyl, $C_{1-6}$ haloalkyl, $C_{1-4}$ alkenyl, —CN, and $C_{3-8}$ cycloalkyl;
$R^8$ is selected from: H, halo, $C_{1-4}$ alkyl, $C_{1-6}$ haloalkyl, —CN, and $C_{3-8}$ cycloalkyl;
$R^9$ is selected from halo or $C_{1-4}$ alkyl;
n is 0, 1, or 2;
$R^A$ and $R^B$ are selected from H, $C_{1-4}$ alkyl, or $C_{1-4}$ haloalkyl or $R^A$ and $R^B$ together with the atom to which they are attached form a 3 to 8 membered cycloalkyl ring or a 3 to 8 membered heterocycloalkyl ring;
$R^C$, $R^D$, $R^E$, $R^F$ and $R^G$ are each independently selected from H, $C_{1-4}$ alkyl and $C_{1-4}$ haloalkyl;

$R^H$ and $R^I$ are each H except one pair of $R^H$ and $R^I$ on the same carbon atom, together with that carbon atom, form a 3 to 8 membered cycloalkyl ring or a 3 to 8 membered heterocycloalkyl ring; and
$R^J$, $R^K$, $R^L$, $R^M$, $R^N$ and $R^O$ are each independently at each occurrence selected from H or $C_{1-4}$ alkyl.
In embodiments, the present invention provides a compound of formula (I) and pharmaceutically acceptable salts thereof:

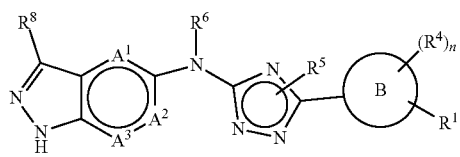

(I)

wherein
A¹, A² or A³ are each independently selected from CH, CR⁷ or N;
B represents a 5 to 10 membered carbocyclic ring system or a 5 to 10 membered heterocyclic ring system;
$R^1$ is L-$R^2$, wherein
  L is -$L^1$-$L^2$-,
    wherein $L^1$ is selected from: a bond, —$(CR^A R^B)_{1-3}$—, —O$(CR^A R^B)_{1-3}$—, —$(CR^A R^B)_{0-3}$O—, and —$NR^C(CR^A R^B)_{1-3}$—, and
    $L^2$ is selected from: a bond, —$(CR^A R^B)_{1-3}$—, —O—, —$NR^D$—, —C(O)$NR^D$—, —$NR^D$C(O)—, —C(O)O—, —OC(O)—, —C(O)—, —S(O)$_2NR^D$—, —$NR^D$S(O)$_2$—, —S(O)$_2$—, —S(O)($NR^D$)—, —$NR^D$C(O)$NR^E$—, —OC(O)$NR^D$—, and —C(O)$NR^D$S(O)$_2$—, and
    $R^2$ is selected from: H, CN, $C_{1-6}$ alkyl, $C_{1-6}$ haloalkyl, $C_{1-6}$ alkyl substituted with —$OR^F$, $C_{1-6}$ alkyl substituted with —$NR^F R^G$, $C_{3-8}$ cycloalkyl substituted with OH, $C_{1-4}$ alkyl substituted with 3 to 8 membered heterocycloalkyl, $C_{1-4}$ alkyl substituted with 8 membered heteroaryl, —$(CR^H R^I)_{1-3}OR^F$, —$(CR^H R^I)_{1-3}NR^F R^G$, $C_{3-10}$ carbocyclic ring system, and 3 to 10 membered heterocyclic ring system, wherein the carbocyclic ring or heterocyclic ring system is unsubstituted or substituted with: =O, —$NR^F R^G$, halo, $C_{1-4}$ alkyl, or $C_{1-4}$ alkyl substituted with —$OR^F$;
$R^4$ is selected from: halo, $C_{1-4}$ alkyl, $C_{1-6}$ haloalkyl, —CN, —$OR^J$, =O, $C_{1-4}$ alkyl substituted with —$OR^J$, —$NR^J R^K$, $C_{1-4}$ alkyl substituted with —$NR^J R^K$, $C_{3-8}$ cycloalkyl, $C_{1-4}$ alkyl substituted with $C_{3-8}$ cycloalkyl, 3 to 8 membered heterocycloalkyl and $C_{1-4}$ alkyl substituted with 3 to 8 membered heterocycloalkyl;
$R^5$ is selected from: H, $C_{1-4}$ alkyl, $C_{1-4}$ alkyl substituted with —$OR^L$—, $C_{3-8}$ cycloalkyl, substituted or unsubstituted phenyl, 3 to 8 membered heterocycloalkyl, $C_{1-4}$ alkyl substituted with $C_{3-8}$ cycloalkyl, $C_{1-4}$ alkyl substituted with 3 to 8 membered heterocycloalkyl and substituted or unsubstituted 5 or 8 membered heteroaryl, wherein the phenyl or heteroaryl group may be substituted by 1 or 2 $R^9$;
$R^6$ is selected from: H and $C_{1-4}$ alkyl;
$R^7$ is selected from: H, halo, —$OR^M$, $C_{1-4}$ alkyl, $C_{1-6}$ haloalkyl, —CN, and $C_{3-8}$ cycloalkyl;
$R^8$ is selected from: H, halo, $C_{1-4}$ alkyl, $C_{1-6}$ haloalkyl, —CN, and $C_{3-8}$ cycloalkyl;
$R^9$ is selected from halo or $C_{1-4}$ alkyl;

n is 0, 1, or 2;

$R^A$ and $R^B$ are selected from H, $C_{1-4}$ alkyl, or $C_{1-4}$ haloalkyl or $R^A$ and $R^B$ together with the atom to which they are attached form a 3 to 8 membered cycloalkyl ring or a 3 to 8 membered heterocycloalkyl ring;

$R^C$, $R^D$, $R^E$, $R^F$ and $R^G$ are each independently selected from H and $C_{1-4}$ alkyl;

$R^H$ and $R^I$ are each H except one pair of $R^H$ and $R^I$ on the same carbon atom, together with that carbon atom, form a 3 to 8 membered cycloalkyl ring or a 3 to 8 membered heterocycloalkyl ring; and $R^J$, $R^K$, $R^L$ and $R^M$ are each independently at each occurrence selected from H or $C_{1-4}$ alkyl.

In embodiments, $A^1$, $A^2$ and $A^3$ are each independently selected from: C—H, C—F, C—Cl, C-Me, C-Et, C-i-Pr, C-cyclopropyl, C—CN, C—$CF_3$ or N. Optionally, at least two of $A^1$, $A^2$ and $A^3$ are C—H.

In embodiments, $A^1$, $A^2$ and $A^3$ are each independently selected from: C—H, C—F, C—Cl, C-Me, C-Et, C-i-Pr, C-cyclopropyl, C-ethenyl, C-propenyl, C—CN, C—$CF_3$ or N. Optionally, at least two of $A^1$, $A^2$ and $A^3$ are C—H.

In embodiments $A^1$ is C—H, C—Cl, C—F, C-ethenyl, C-propenyl, or C-Me. In embodiments $A^2$ is C—H or C—F. In embodiments $A^3$ is C—H. In embodiments $A^1$ is C—H, C—Cl, C—F, C-ethenyl, C-propenyl, or C-Me; $A^2$ is C—H or C—F; and $A^3$ is C—H.

In embodiments, $A^1$, $A^2$ and $A^3$ are each C—H. In embodiments $A^1$ is C—Cl, $A^2$ is C—H and $A^3$ is C—H. In embodiments $A^1$ is C—F, $A^2$ is C—H and $A^3$ is C—H. In embodiments $A^1$ is C-Me, $A^2$ is C—H and $A^3$ is C—H. In embodiments $A^1$ is C—H, $A^2$ is C—F and $A^3$ is C—H. In embodiments $A^1$ is C-ethenyl, $A^2$ is C—H and $A^3$ is C—H. In embodiments $A^1$ is C-propenyl, $A^2$ is C—H and $A^3$ is C—H.

Accordingly, $R^7$ may be H, Cl, F, CN, methyl, ethyl, iso-propyl, ethenyl, propenyl, trifluoromethyl or cyclopropyl. In embodiments $R^7$ is H, Cl, F, CN, methyl, ethyl or cyclopropyl.

$R^8$ may be H, Cl, F, CN or Me. In embodiments, $R^8$ is H or methyl.

In embodiments $R^6$ is selected from H or methyl. Preferably, $R^6$ is H.

As the skilled person will be aware, and for the avoidance of doubt, the structure shown below:

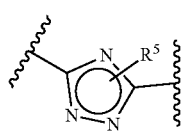

represents an aromatic 5 membered ring, where one of the nitrogen atoms within the ring is substituted by $R^5$.

As the skilled person will be aware, and for the avoidance of doubt, the structure shown below:

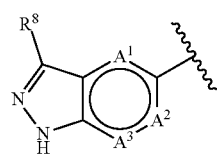

represents a bicyclic group with a 5-membered and a 6-membered ring, wherein the 6-membered ring is an aromatic ring.

In embodiments

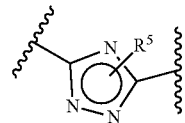

represents:

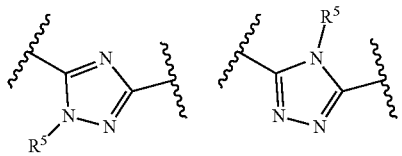

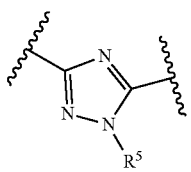

In embodiments $R^5$ is selected from: H, $C_{1-4}$ alkyl, $C_{1-4}$ alkyl substituted with —$OR^L$, $C_{1-4}$ alkyl substituted with —$NR^LR^L$, $C_{3-8}$ cycloalkyl, substituted or unsubstituted phenyl, $C_{1-4}$ alkyl substituted with a 3 to 8 membered heterocycloalkyl, and substituted or unsubstituted 5 or 6 membered heteroaryl, wherein the phenyl or heteroaryl group may be substituted by 1 or 2 $R^9$.

In embodiments $R^5$ is selected from: H, $C_{1-4}$ alkyl, $C_{1-4}$ alkyl substituted with —$OR^L$, $C_{1-4}$ alkyl substituted with —$NR^LR^L$, $C_{3-8}$ cycloalkyl, substituted or unsubstituted phenyl, $C_{1-4}$ alkyl substituted with a 3 to 8 membered heterocycloalkyl, and substituted or unsubstituted 5 or 6 membered heteroaryl, wherein the phenyl or heteroaryl group may be substituted by 1 or 2 $R^9$. Optionally, $R^5$ is selected from: H or $C_{1-4}$ alkyl. Optionally, $R^L$ is independently selected at each occurrence from: H or methyl.

In embodiments $R^5$ is selected from: H, methyl, ethyl, isobutyl, isopropyl, isopropanol, cyclopropyl, —$CH_2CH_2OH$, —$CH_2CH_2OCH_3$, —$CH_2CH_2NHCH_3$, phenyl, fluorophenyl, pyridyl, piperidyl, ethyl substituted with morpholine, and ethyl substituted with piperidine. Optionally, $R^5$ may be selected from: H or methyl.

In embodiments

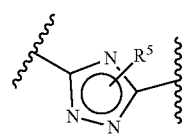

represents:

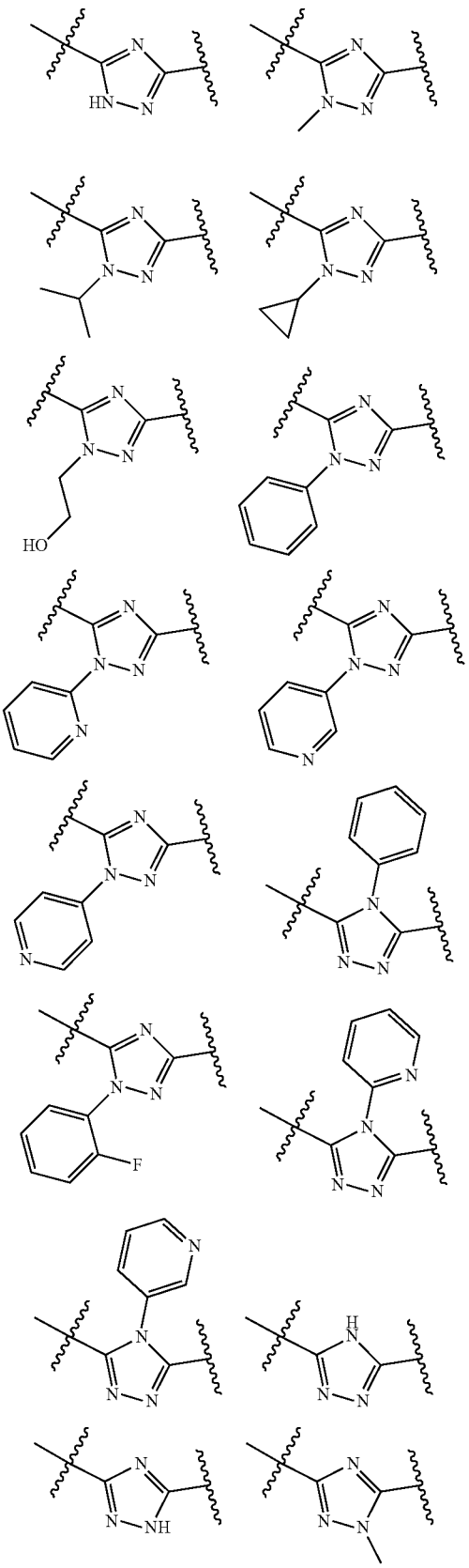
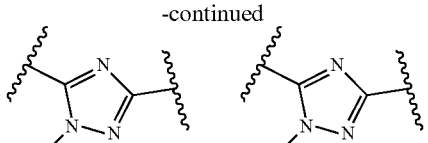
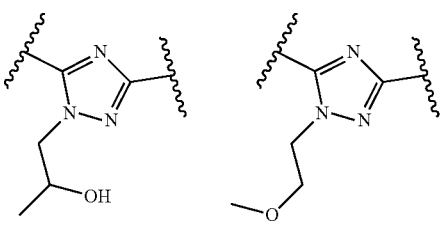
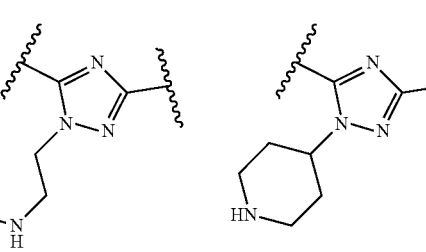
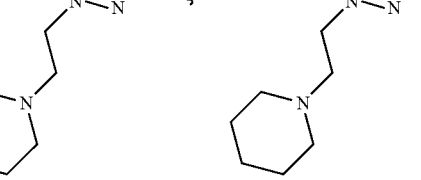

In embodiments $R^5$ is selected from: H, $C_{1-4}$ alkyl, $C_{1-4}$ alkyl substituted with —$OR^L$—, $C_{3-8}$ cycloalkyl, substituted or unsubstituted phenyl, and substituted or unsubstituted 5 or 6 membered heteroaryl, wherein the phenyl or heteroaryl group may be substituted by 1 or 2 $R^9$.

In embodiments $R^5$ is selected from: H, $C_{1-4}$ alkyl, $C_{1-4}$ alkyl substituted with —$OR^L$—, $C_{3-8}$ cycloalkyl, substituted or unsubstituted phenyl, and substituted or unsubstituted 5 or 6 membered heteroaryl, wherein the phenyl or heteroaryl group may be substituted by 1 or 2 $R^9$. Optionally, $R^5$ is selected from: H or $C_{1-4}$ alkyl.

In embodiments $R^5$ is selected from: H, methyl, isopropyl, cyclopropyl, —$CH_2CH_2OH$, phenyl, fluorophenyl, and pyridyl. Optionally $R^5$ may be selected from: H or methyl.

In preferred embodiments

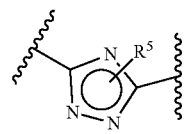

represents:
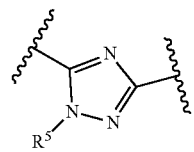
optionally wherein $R^5$ is methyl.
In the embodiments
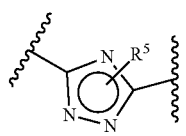
represents:
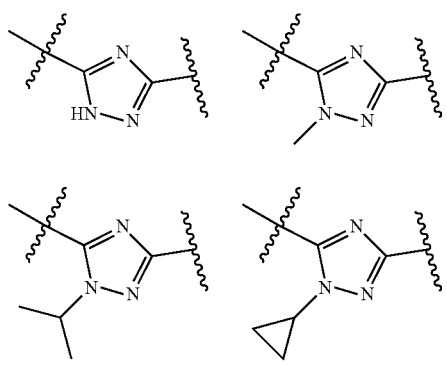
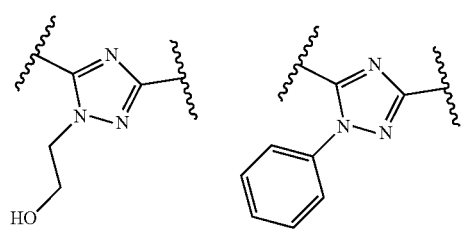
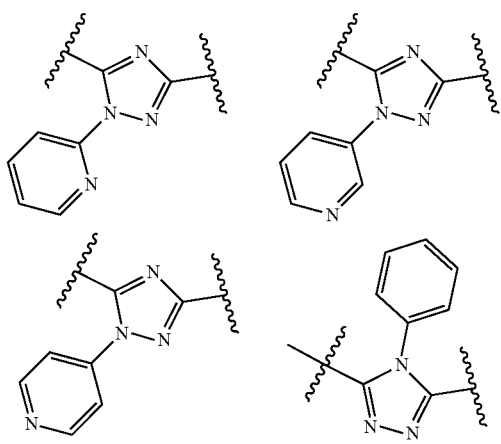
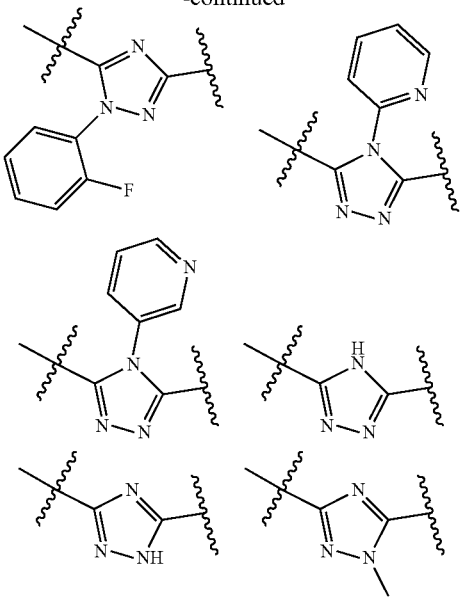
In embodiments the compound of formula (I) is a compound according to formula (Ia):
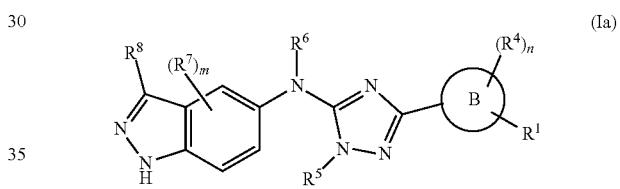
(Ia)
wherein m is 1 or 2.
Preferably, m is 1.
In embodiments
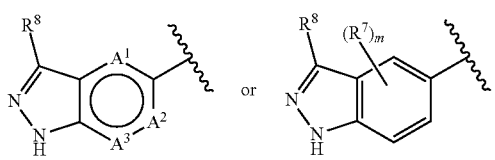
may be:
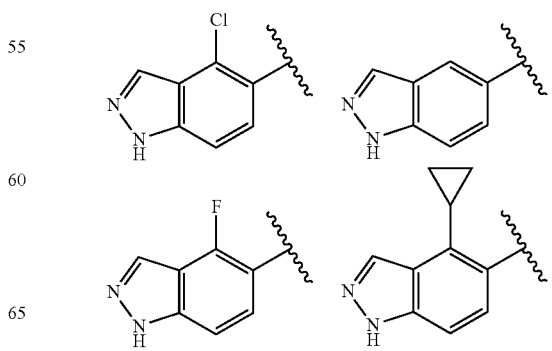

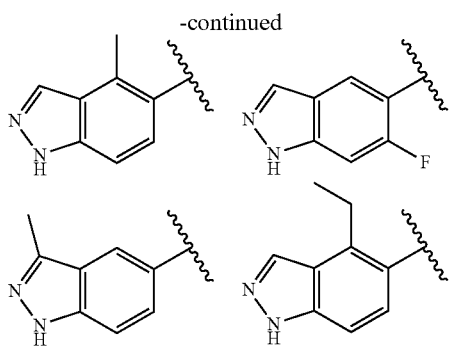

Preferably,

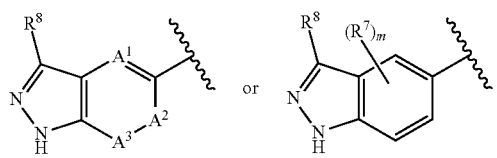

may be:

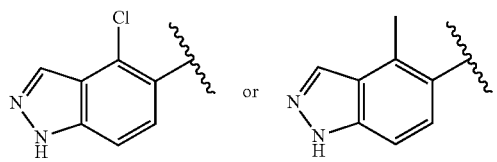 [SMILES: *c1ccc2[nH]ncc2c1Cl ; *c1ccc2[nH]ncc2c1C]

Any discussion of formula (I) in this application may relate equally to the compound of formula (Ia).

B may be selected from: a 5 or 6 membered carbocyclic ring which is aromatic or unsaturated, a 5 or 6 membered heterocyclic ring which is aromatic or unsaturated, a 9 or 10 membered carbocyclic bicyclic ring system, or a 9 or 10 membered heterocyclic bicyclic ring system, wherein the bicyclic ring system is ether aromatic or one of the rings within the bicyclic ring system is aromatic or unsaturated and the other ring is saturated.

B may be selected from: a 5 or 6 membered carbocyclic ring which is aromatic or unsaturated. B may be selected from: a 5 or 6 membered heterocyclic ring which is aromatic or unsaturated. B may be selected from: a 9 or 10 membered carbocyclic bicyclic ring system wherein the bicyclic ring system is either aromatic or one of the rings within the bicyclic ring system is aromatic or unsaturated and the other ring is saturated. B may be selected from: a 9 or 10 membered heterocyclic bicyclic ring system, wherein the bicyclic ring system is either aromatic or one of the rings within the bicyclic ring system is aromatic or unsaturated and the other ring is saturated.

In a preferred embodiment B is selected from a 6 membered carbocyclic ring (optionally wherein the ring is aromatic or unsaturated) or a 10 membered heterocyclic fused bicyclic ring system (optionally wherein one of the rings is aromatic).

In embodiments B is selected from: phenyl, pyrazole, pyridyl, piperidyl, azaindole, isoindoline, tetrahydroisoquionoline, tetrahydroisoquinolone, furan, indazole, benzpyrazole, pyrimidine, pyridone, tetrahydropyridine, dihydropyran, cyclopentene, cyclohexenyl, chromane, chromanone, benzodioxan, tetrahydronapthalene, dihydrobenzoxazine, benzomorpholine, tetrahydroquinoline, napthyridine, quinoline, isoquinoline, and dihydroisobenzofuran or B is

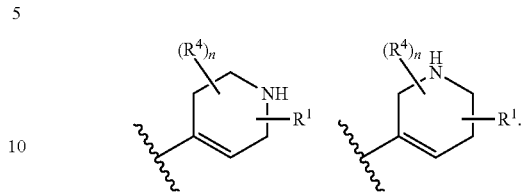

In embodiments B is selected from: phenyl, pyrazole, pyridyl, azaindole, isoindoline, tetrahydroisoquionoline, tetrahydroquinolone, furan, indazole, benzpyrazole, pyrimidine, pyridone, tetrahydropyridine, dihydropyran, cyclopentene, cyclohexenyl, chromane, chromanone, benzodioxan, tetrahydronapthalene, dihydrobenzoxazine, benzomorpholine and tetrahydroquinoline or B is

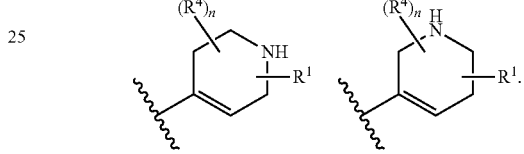

In embodiments B is selected from: phenyl, pyridyl, tetrahydroisoquionoline, tetrahydroquinolone, and tetrahydroquinoline.

In embodiments

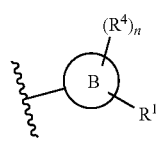

may be:

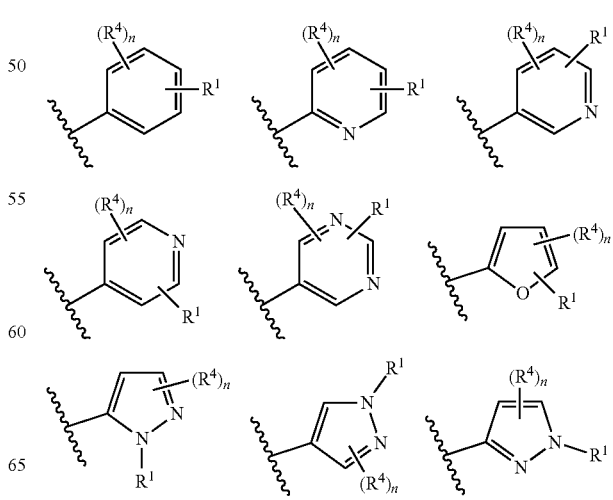

-continued
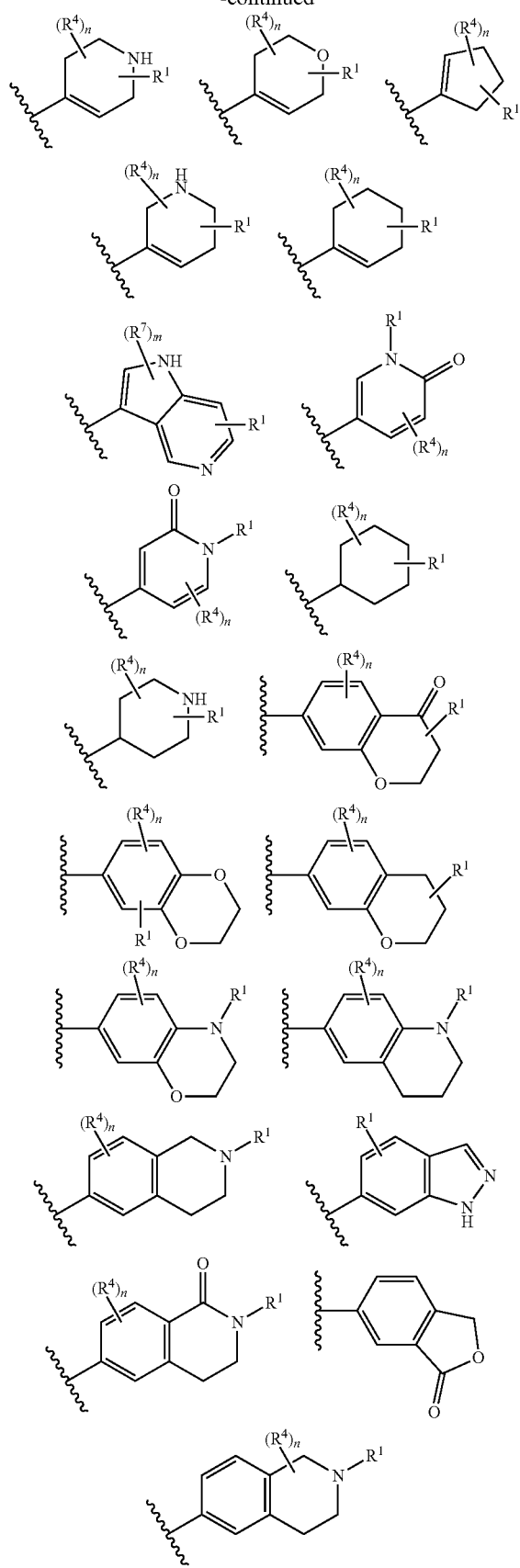
In embodiments
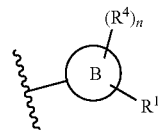
may be:
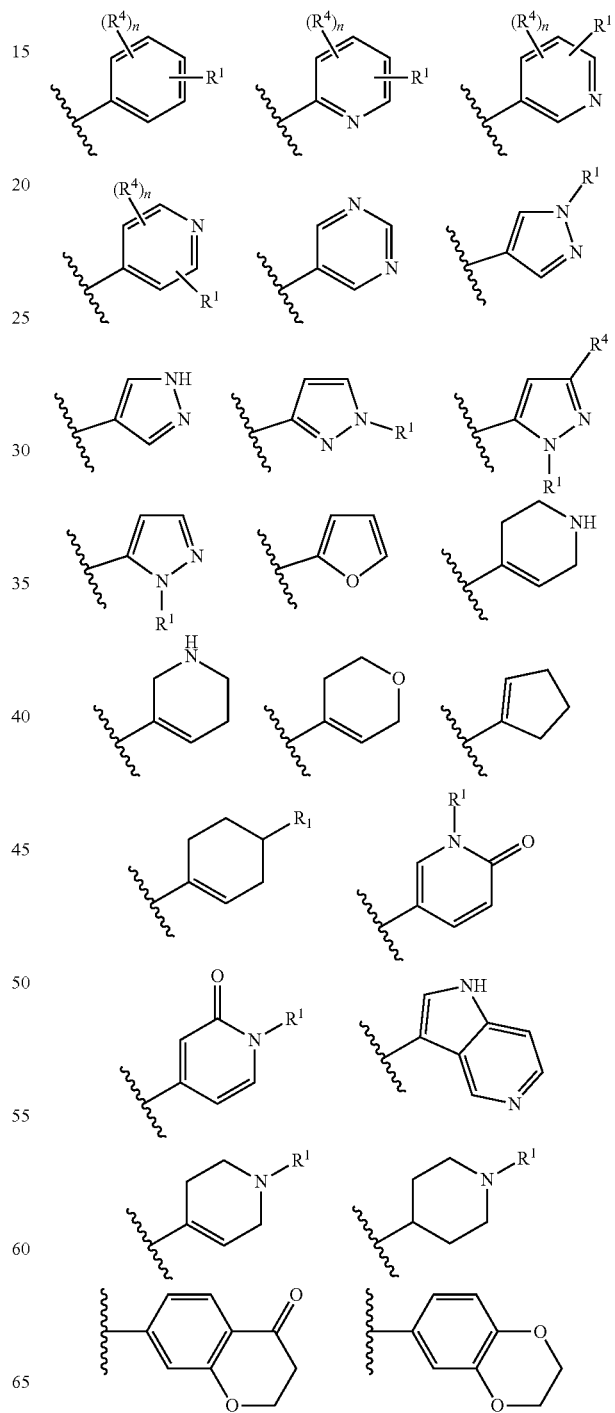

-continued
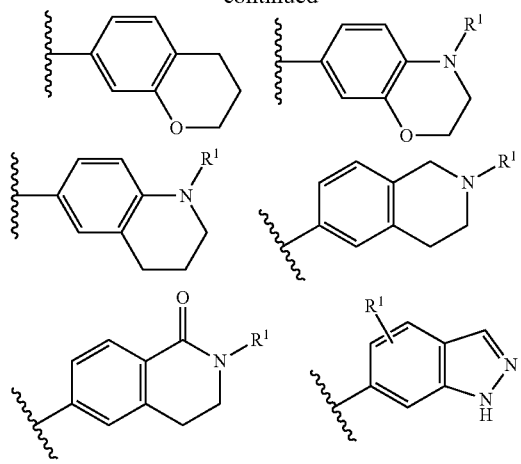
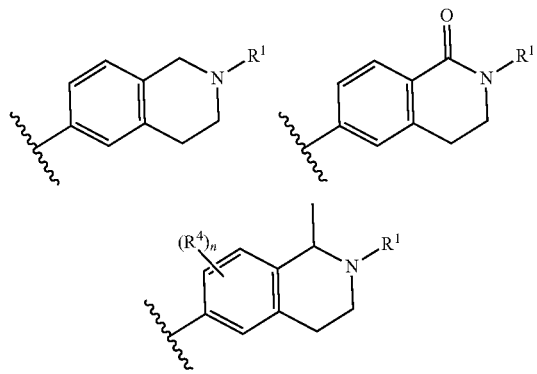
In embodiments
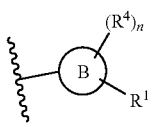
may be:
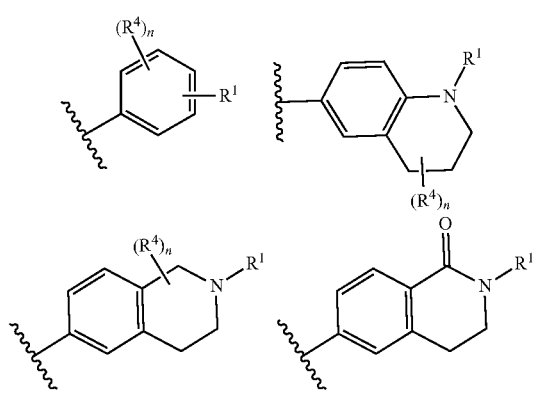
In embodiments the compound of formula (I) is a compound according to formulae (IIa), (IIb), or (IIc):
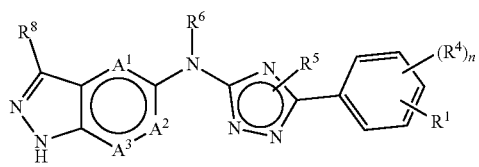
(IIa)
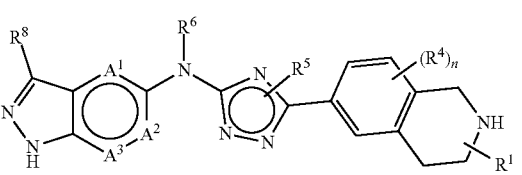
(IIb)
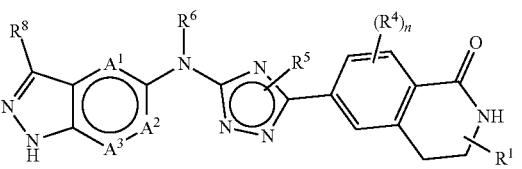
(IIc)
In embodiments
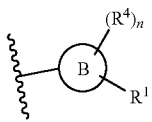
may be:
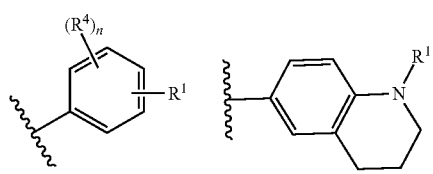
In embodiments the compound of formula (I) is a compound according to formulae (IIIa), (IIIb), or (IIIc):
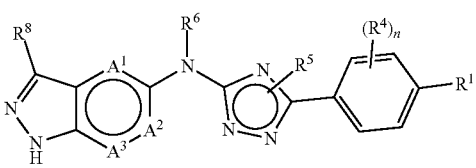
(IIIa)
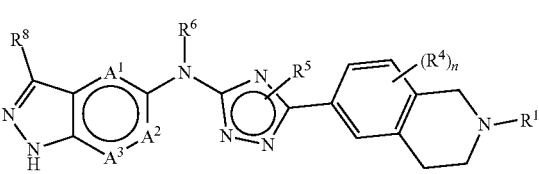
(IIIb)

-continued (IIIc)

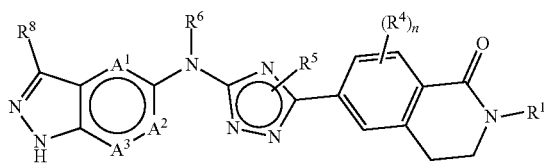

$L^1$ may be selected from: a bond, —(CR$^A$R$^B$)$_{1-3}$—, and —O(CR$^A$R$^B$)$_{1-3}$—. Preferably, $L^1$ is a bond or —O(CR$^A$R$^B$)$_{1-3}$—.

$L^2$ may be selected from: a bond, —NR$^D$—, —C(O) NR$^D$—, —NR$^D$C(O)—, —C(O)O—, —C(O)—, —NR$^D$C(O)NR$^E$, and —OC(O)NR$^D$—.

For the avoidance of doubt, when $L^1$ is a bond and $L^2$ is a bond then L in its entirety is a bond. This may be considered to result in L being absent.

In embodiments L is selected from: bond, —(CR$^A$R$^B$)$_{0-3}$O—, —(CR$^A$R$^B$)$_{0-3}$NR$^C$—, —(CR$^A$R$^B$)$_{0-3}$C(O) NR$^C$—, —(CR$^A$R$^B$)$_{0-3}$NR$^C$C(O)—, —(CR$^A$R$^B$)$_{0-3}$C(O) O—, —(CR$^A$R$^B$))$_{0-3}$OC(O)—, —C(O)—, —(CR$^A$R$^B$)$_{0-3}$S (O)$_2$NR$^C$—, —(CR$^A$R$^B$)$_{0-3}$NR$^C$S(O)$_2$—, —S(O)$_2$—, —NR$^C$C(O)NR$^D$—, —(CR$^A$R$^B$)$_{0-3}$OC(O)NR$^C$—, —O(CR$^A$R$^B$)$_{1-3}$O—, —O(CR$^A$R$^B$)$_{1-3}$NR$^C$—, —O(CR$^A$R$^B$)$_{0-3}$C(O)NR$^C$—, —O(CR$^A$R$^B$)$_{1-3}$S(O)$_2$NR$^C$—, —O(CR$^A$R$^B$)$_{1-3}$C(O)NR$^C$S(O)$_2$—, and —NR$^D$(CR$^A$R$^B$)$_{1-3}$C(O)NR$^C$—.

$R^A$ and $R^B$ may be independently selected from H, $C_{1-4}$ alkyl, and $C_{1-4}$ haloalkyl. Optionally, $R^A$ and $R^B$ may be independently selected from H, methyl, trifluoromethyl and difluoromethyl. Optionally, $R^A$ and $R^B$ may be H or methyl. Preferably, $R^A$ and $R^B$ are H.

$R^C$ and $R^D$ may be independently selected from H and methyl. Preferably, $R^C$ and $R^D$ are both H.

In embodiments L is selected from: a bond, —CH$_2$—, —CH$_2$CH$_2$—, —O—, —OC(O)—, —C(O)O—, —OCH$_2$—, —O(CH$_2$)$_2$—, —OCH$_2$CH$_2$NH—, —OCH$_2$C (O)NH—, —OC(Me)HC(O)NH—, —OC(Me)$_2$C(O)NH—, —OCH$_2$C(O)O—, —OCH$_2$S(O)$_2$NH—, —OCH$_2$CH$_2$NHC (O)—, —O(CH$_2$)$_3$NHC(O)—, —OCH$_2$CH$_2$NHS(O)$_2$—, —OCH$_2$CH$_2$NHC(O)NH—, —CH$_2$NHC(O)—, —CH$_2$NHS(O)$_2$—, —CH$_2$NHC(O)NH—, —CH$_2$C(O)—, —(CH$_2$)$_2$C(O)—, —CH$_2$C(O)NH—, —(CH$_2$)$_2$C(O)NH—, —CH$_2$C(O)O—, —CH$_2$OC(O)NH—, —C(O)—, —C(O) CH$_2$NH—, —C(O)NH—, —C(O)NHCH$_2$—, —NHCH$_2$C (O)—, —NHCH$_2$C(O)NH—, —N(Me)CH$_2$C(O)NH—, —NHC(O)—, —NHC(O)NH—, —S(O)$_2$—, —CH(CHF$_2$) NH— or —CH(CF$_3$)NH—.

Optionally, L is selected from: a bond, —O—, —OCH$_2$—, —OCH$_2$CH$_2$NH—, —OCH$_2$C(O)NH—, —OC (Me)HC(O)NH—, —OC(Me)$_2$C(O)NH—, —OCH$_2$CH$_2$ NHC(O)—, —O(CH$_2$)$_3$NHC(O)—, —OCH$_2$CH$_2$NHC(O) NH—, —CH$_2$NHC(O)—, —CH$_2$NHC(O)NH—, —CH$_2$C (O)NH—, —(CH$_2$)$_2$C(O)NH—, —CH$_2$OC(O)NH—, —C(O)—, —C(O)CH$_2$NH—, —C(O)NH—, —C(O) NHCH$_2$—, —NHCH$_2$C(O)NH—, —N(Me)CH$_2$C(O) NH—, —NHC(O)—, —NHC(O)NH—, —CH(CHF$_2$) NH— or —CH(CF$_3$)NH—.

Preferably, L is selected from: a bond, —O—, —OCH$_2$C (O)NH—, —CH$_2$C(O)NH—, —C(O)—, —C(O) CH$_2$NH—, —C(O)NH—, or —C(O)NHCH$_2$—.

In embodiments of formulae (IIa) or (IIIa) $L^1$ is preferably a bond, or —O(CR$^A$R$^B$)$_{1-3}$—. In embodiments of formulae (IIa) or (IIIa) $L^2$ is preferably —C(O)NR$^D$—. In embodiments of formulae (IIa) or (IIIa) L is preferably a bond, —OCH$_2$C(O)NH—, or —C(O)NH—.

In embodiments of formulae (IIb) or (IIIb) $L^1$ is preferably a bond. In embodiments of formulae (IIb) or (IIIb) $L^2$ is preferably —C(O)—. In embodiments of formulae (IIb) or (IIIb) L is preferably a bond, or —C(O)NH—.

In embodiments of formulae (IIc) or (IIIc) $L^1$ is preferably a bond. In embodiments of formulae (IIc) or (IIIc) $L^2$ is preferably a bond or —C(O)—. In embodiments of formulae (IIc) or (IIIc) L is preferably a bond.

In embodiments $R^2$ is selected from H, $C_{1-4}$ alkyl, $C_{1-4}$ haloalkyl, $C_{1-4}$ alkyl substituted with —OR$^F$, $C_{3-8}$ cycloalkyl (optionally $C_{3-5}$ cycloalkyl), $C_{4-6}$ cycloalkyl substituted with —OH, phenyl, 3 to 6 membered heterocyclic ring system, wherein the phenyl and heterocyclic ring system are unsubstituted or substituted with: halo, $C_{1-4}$ alkyl or —C(O) R$^F$.

In embodiments $R^2$ is selected from H, $C_{1-4}$ alkyl, $C_{1-4}$ haloalkyl, $C_{1-4}$ alkyl substituted with —OR$^F$, $C_{3-8}$ cycloalkyl (optionally $C_{3-5}$ cycloalkyl), $C_{4-6}$ cycloalkyl substituted with —OH, 3 to 6 membered heterocyclic ring system, wherein the heterocyclic ring system is unsubstituted or substituted with: $C_{1-4}$ alkyl or —C(O)R$^F$.

In embodiments $R^2$ is selected from: H, CN, methyl, ethyl, n-propyl, i-propyl, n-butyl, i-butyl, ten-butyl, sec-butyl, tert-pentyl, allyl, propargyl, difluoroethyl, difluoropropyl, trifluoroethyl, trifluoropropyl, trifluoroisopropyl, isopropanol, n-butanol, sec-butanol, propanol, tert-butanol, cyclopropyl, cyclobutyl, cyclopentyl, cyclohexyl, cycloheptyl, cyclopropanol, cyclobutanol, cyclopentanol, cyclohexanol, cycloheptanol, aziridinyl, N-acetylaziridinyl, N-alkylaziridinyl, azetidinyl, N-acetylazetidinyl, N-alkylazetidinyl, 2-methylpropan-2-amine, phenyl, chlorophenyl, pyrrolidinyl, difluoropyrrolidinyl, trifluoroethylpyrrolidinyl, N-methylpyrrolidinyl, tetrahydrofuranyl, sulfolanyl, dihydropyran, tetrahydropyranyl, tetrahydropyranoimidazoyl, morpholinyl, imidazoyl, ethyltetrahydroimidazopyridine, methylimidazoyl, piperazinyl, N-methylpiperazinyl, trifluoromethylpiperazinyl, oxadiazoyl, dimethyldihydrooxazoyl, pyrazolyl, N-methylpyrazolyl, ethylpyrazoyl, 4-pyridone, 2-pyridone, pyridyl, methyl substituted with tetrahydrofuran, ethyl substituted with pyridine, ethyl substituted with —NMe$_2$, ethyl substituted with OMe, ethyl substituted with OH; or selected from:

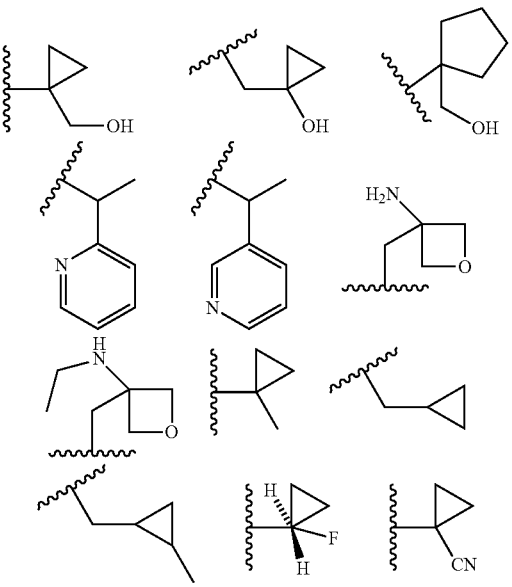

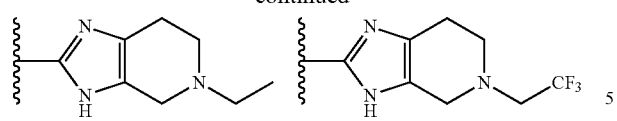

In embodiments R² is selected from: H, CN, methyl, ethyl, isopropyl, tert-butyl, sec-butyl, trifluoroethyl, trifluoropropyl, trifluoroisopropyl, isopropanol, sec-butanol, propanol, tert-butanol, cyclopropyl, cyclopentyl, cyclobutanol, cyclohexanol, azetidinyl, N-acetylazetidinyl, tetrahydrofuranyl, phenyl, chlorophenyl, pyrrolidinyl, difluoropyrrolidinyl, trifluoroethylpyrrolidinyl, N-methylpyrrolidinyl, sulfolanyl, tetrahydropyranyl, morpholinyl, pyridyl, imidazoyl, methyl substituted with tetrahydrofuran, ethyl substituted with pyridine, ethyl substituted with —NMe₂, ethyl substituted with OMe, ethyl substituted with OH; or selected from:

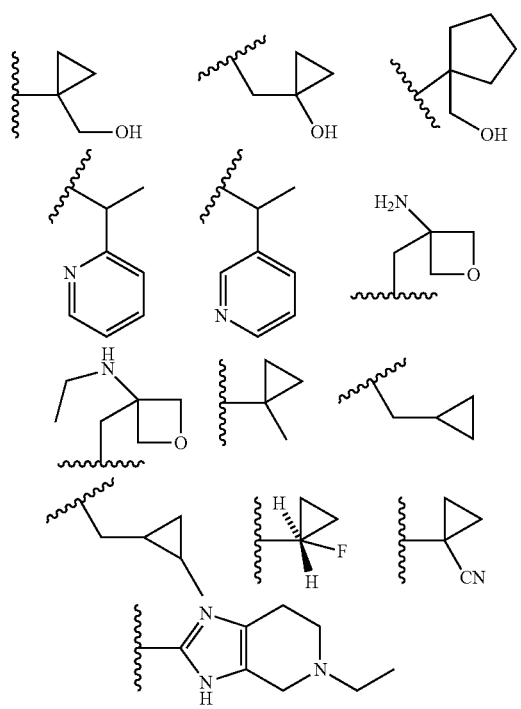

In embodiments R² is selected from: H, CN, methyl, ethyl, n-propyl, i-propyl, n-butyl, tert-butyl, sec-butyl, ally, propargyl, trifluoroethyl, trifluoroisopropyl, isopropanol, sec-butanol, propanol, tert-butanol, cyclopropyl, cyclobutyl, cyclopentyl, cyclohexyl, cycloheptyl, cyclopropanol, cyclobutanol, cyclopentanol, cyclohexanol, cycloheptanol, aziridinyl, N-acetylaziridinyl, N-alkylaziridinyl, azetidinyl, N-acetylazetidinyl, N-alkylazetidinyl, pyrrolidinyl, N-methylpyrrolidinyl, tetrahydrofuranyl, sulfolanyl, dihydropyran, tetrahydropyranyl, morpholinyl, piperazinyl, N-methylpiperazinyl, oxadiazolyl, 4-pyridone, 2-pyridone, pyridyl, methyl substituted with tetrahydrofuran, ethyl substituted with pyridine, ethyl substituted with —NMe₂, ethyl substituted with OMe, ethyl substituted with OH; or selected from:

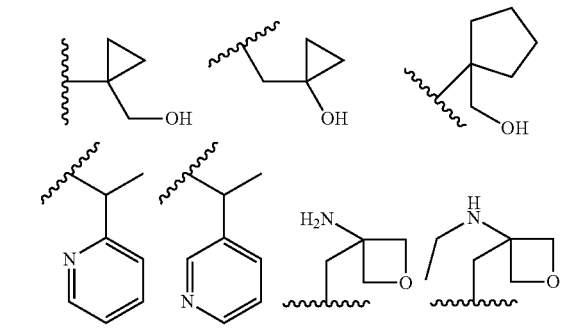

In embodiments R² is selected from: H, CN, methyl, ethyl, isopropyl, tert-butyl, sec-butyl, trifluoroethyl, trifluoroisopropyl, isopropanol, sec-butanol, propanol, tert-butanol, cyclopropyl, cyclopentyl, cyclobutanol, cyclohexanol, azetidinyl, N-acetylazetidinyl, tetrahydrofuranyl pyrrolidinyl, N-methylpyrrolidinyl, sulfolanyl, tetrahydropyranyl, morpholinyl, pyridyl, methyl substituted with tetrahydrofuran, ethyl substituted with pyridine, ethyl substituted with —NMe₂, ethyl substituted with OMe, ethyl substituted with OH; or selected from:

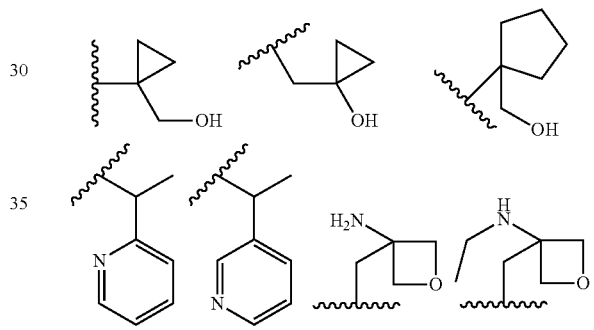

In embodiments R² is selected from: H, methyl, ethyl, isopropyl, tert-butyl, sec-butyl, trifluoroethyl, trifluoroisopropyl, isopropanol, sec-butanol, propanol, tert-butanol, cyclopropyl, cyclopentyl, cyclobutanol, cyclohexanol, azetidinyl, N-acetylazetidinyl, tetrahydrofuranyl, pyrrolidinyl, N-methylpyrrolidinyl, tetrahydropyranyl, morpholinyl, and pyridyl.

In embodiments R² is not selected from H when B is a 6-membered monocyclic ring, e.g. phenyl, pyridyl, pyrimidinyl. In embodiments R² is not selected from H when B is a phenyl ring. Accordingly, the skilled person will appreciate that this results in the situation where B cannot be an unsubstituted 6-membered ring or phenyl ring, as appropriate.

In embodiments R⁴ is selected from: halo, $C_{1-4}$ alkyl, $C_{1-4}$ haloalkyl, —CN, $C_{1-4}$ alkyl substituted with —OR^J, $C_{1-4}$ alkyl substituted with —NR^JR^K, and 3 to 8 membered heterocycloalkyl.

R^J and R^K are each independently at each occurrence selected from H or methyl.

In embodiments R⁴ is F, Cl, methyl, CF₃, Et, Pr, CN, OH, OMe, Oi-Pr, =O, CH₂OH, CH₂OMe, NH₂, NMe₂, CH₂NH₂, CH₂NMe₂, or morpholinyl.

In embodiments n is 0. In an alternative embodiment n is 1.

In embodiments n is 1 or 2. In an alternative embodiment n is 2.

In embodiments the compound of formula (I) is a compound according to formula (IV):

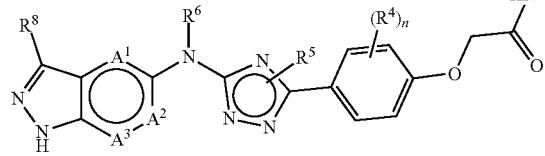

(IV)

In embodiments n is preferably 1. In embodiments $R^4$ is preferably —OMe. In embodiments of formula (IV) n is preferably 1 and $R^4$ is preferably —OMe.

In embodiments the compound of formula (I) is a compound according to formula (IVa):

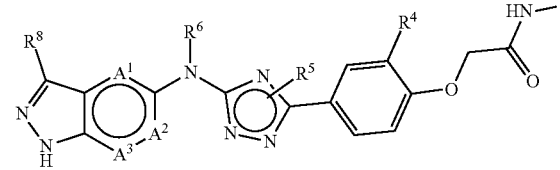

(IVa)

In embodiments the compound of formula (I) is a compound according to formula (V):

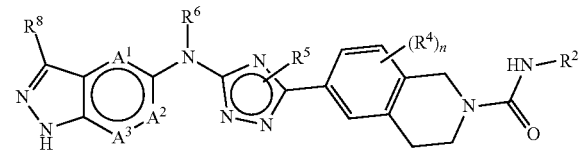

(V)

In embodiments of formula (V) n is preferably 0.

In embodiments the compound of formula (I) is a compound according to formulae (VIa), (VIb) or (VIc):

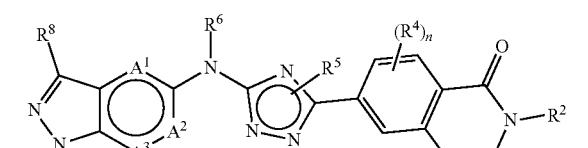

(VIa)

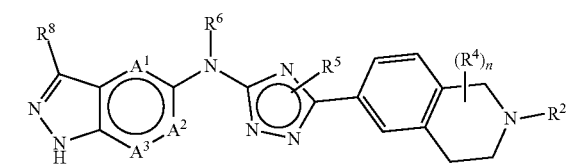

(VIb)

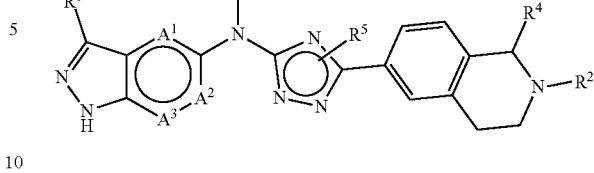

(VIc)

In embodiments of formulae (VIa) or (VIb) n is preferably 0. In embodiments of formulae (VIa) or (VIb) n may be 1 or 2.

In embodiments the compound of formula (I) is a compound according to formulae (VIIa), (VIIb) or (VIIc):

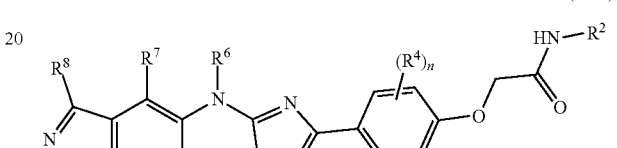

(VIIa)

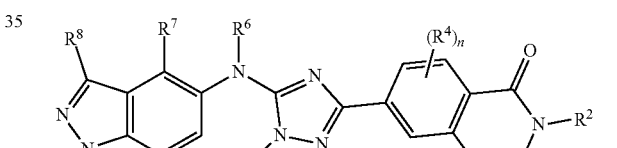

(VIIb)

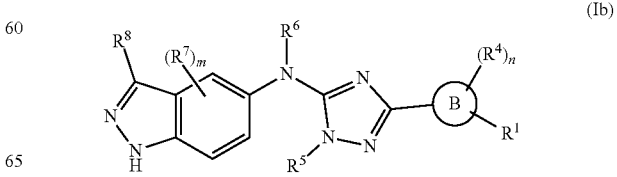

(VIIc)

In embodiments of formulae (VIIa), (VIIb) or (VIIc) $R^8$ may be H. In embodiments of formulae (VIIa), (VIIb) or (VIIc) $R^7$ may be H, Cl, ethyl, or cyclopropyl. In embodiments of formulae (VIIa), (VIIb) or (VIIc) $R^5$ may be H or Me. In embodiments of formulae (VIIa), (VIIb) or (VIIc) $R^4$ may be OMe and n is 0 or 1. Any of the embodiments of this paragraph may be combined in any way to provide an embodiment of the invention.

In embodiments of formulae (VIIa), (VIIb) or (VIIc) $R^8$ is H; $R^7$ is H, Cl, ethyl, or cyclopropyl; $R^5$ is H or Me; $R^4$ is OMe; and n is ° or 1.

In embodiments, the present invention provides the compound of formula (Ib) and pharmaceutically acceptable salts thereof:

(Ib)

wherein
B represents a 5 to 10 membered carbocyclic ring system or a 5 to 10 membered heterocyclic ring system, wherein the ring systems are either monocyclic or fused bicyclic systems;

$R^1$ is L-$R^{2A}$, $R^{2B}$ or absent;

L is -$L^1$-$L^2$-, wherein $L^1$ is selected from: a bond, —$(CR^AR^B)_{1-3}$—, —$O(CR^AR^B)_{1-3}$—, —$(CR^AR^B)_{0-3}O$—, and —$NR^C(CR^AR^B)_{1-3}$—, and $L^2$ is selected from: —O—, —$NR^D$—, —$C(O)NR^D$—, —$NR^DC(O)$—, —$C(O)O$—, —$OC(O)$—, —$C(O)$—, —$S(O)_2NR^D$—, —$NR^DS(O)_2$—, —$S(O)_2$—, —$NR^DC(O)NR^E$—, —$OC(O)NR^D$—, and —$C(O)NR^DS(O)_2$—;

$R^{2A}$ is selected from: H, CN, $C_{1-6}$ alkyl, $C_{1-6}$ haloalkyl, $C_{1-6}$ alkyl substituted with —$OR^D$, $C_{1-6}$ alkyl substituted with —$NR^FR^G$, $C_{3-8}$ cycloalkyl, $C_{3-8}$ cycloalkyl substituted with OH, substituted or unsubstituted 3 to 8 membered heterocycloalkyl, 6 membered heteroaryl, $C_{1-4}$ alkyl substituted with 3 to 8 membered heterocycloalkyl, $C_{1-4}$ alkyl substituted with 6 membered heteroaryl, —$(CR^HR^I)_{1-3}OR^F$, —$(CR^HR^I)_{1-3}NR^FR^G$;

$R^{2B}$ is a phenyl, $C_{1-4}$ alkyl substituted with phenyl, 5 to 10 membered heterocyclic ring system, $C_{1-4}$ alkyl substituted with a 5 to 10 membered heterocyclic ring system, —O—$C_{1-4}$ alkyl substituted with a 5 to 10 membered heterocyclic ring system, wherein the heterocyclic ring system is unsubstituted or substituted with: halo, $C_{1-4}$ alkyl or =O;

$R^4$ is selected from: halo, $C_{1-4}$ alkyl, $C_{1-6}$ haloalkyl, —CN, —$OR^J$, =O, $C_{1-4}$ alkyl substituted with —$OR^J$, —$NR^JR^K$, $C_{1-4}$ alkyl substituted with —$NR^JR^K$, $C_{3-8}$ cycloalkyl, and 3 to 8 membered heterocycloalkyl;

$R^5$ is selected from: H, $C_{1-4}$ alkyl, $C_{3-8}$ cycloalkyl, substituted or unsubstituted phenyl and substituted or unsubstituted 5 or 6 membered heteroaryl, wherein the phenyl or heteroaryl group may be substituted by 1 or 2 $R^9$;

$R^6$ is selected from: H and $C_{1-4}$ alkyl;

$R^7$ is selected from: H, halo, $C_{1-4}$ alkyl, $C_{1-6}$ haloalkyl, —CN, and $C_{3-8}$ cycloalkyl;

$R^8$ is selected from: H, halo, $C_{1-4}$ alkyl, $C_{1-6}$ haloalkyl, —CN, and $C_{3-8}$ cycloalkyl;

$R^9$ is selected from halo or $C_{1-4}$ alkyl;

n is 0, 1, or 2 m is 0, 1, or 2

$R^A$ and $R^B$ are selected from H, $C_{1-4}$ alkyl, or $C_{1-4}$ haloalkyl or $R^A$ and $R^B$ together with the atom to which they are attached form a 3 to 8 membered cycloalkyl ring or a 3 to 8 membered heterocycloalkyl ring;

$R^C$, $R^D$, $R^E$, $R^F$ and $R^G$ are each independently selected from H and $C_{1-4}$ alkyl;

$R^H$ and $R^I$ are each H except one pair of $R^H$ and $R^I$ on the same carbon atom, together with that carbon atom, form a 3 to 8 membered cycloalkyl ring or a 3 to 8 membered heterocycloalkyl ring; and $R^J$ and $R^K$ are selected from H or $C_{1-4}$ alkyl.

In embodiments the compound of formula (I) is a compound according to formula (VIII):

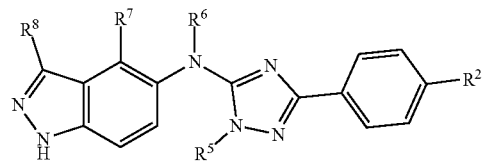

(VIII)

In embodiments of formula (VIII) $R^8$ may be H. In embodiments of formula (VIII) $R^7$ may be $C_{3-8}$ cycloalkyl. In embodiments of formula (VIII) $R^6$ may be H. In embodiments of formula (VIII) $R^5$ may be $C_{1-4}$ alkyl. In embodiments of formula (VIII) $R^2$ may be a substituted or unsubstituted 3 to 10 membered heterocylic ring. Any of the embodiments of this paragraph may be combined in any way to provide an embodiment of the invention.

In embodiments of formula (VIII) $R^8$ is H; $R^7$ is cyclopropyl; $R^8$ is H; $R^5$ is methyl; and $R^2$ is a substituted or unsubstituted 3 to 10 membered heterocyclic ring comprising two or three nitrogen atoms.

In embodiments of formula (VIII) $R^2$ is a substituted or unsubstituted 5 membered ring comprising two nitrogen atoms. In embodiments of formula (VIII) $R^2$ is a substituted or unsubstituted 9 membered ring comprising two nitrogen atoms. In embodiments of formula (VIII) $R^2$ is a substituted or unsubstituted 9 membered ring comprising three nitrogen atoms.

In embodiments of formula (VIII) $R^2$ is a substituted or unsubstituted 9 membered heterocyclic ring comprising a 5 membered heterocyclic ring containing 1 or 2 nitrogen atoms fused to a 6 membered heterocyclic ring comprising 1 or 2 nitrogen atoms. In embodiments of formula (VIII) $R^2$ is unsubstituted or substituted with: hydrogen, methyl, ethyl, n-propyl, i-propyl, halo, trifluoromethyl or trifluoroethyl.

In embodiments of formula (VIII) $R^2$ is selected from: methylpyrazole, ethylpyrazole, methylimidazole, and tetrahydropyranoimidazole.

In embodiments of formula (VIII), $R^2$ may be:

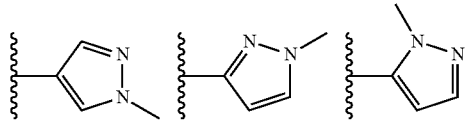

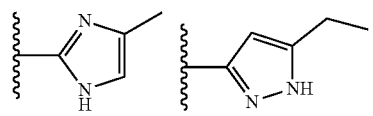

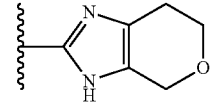

In embodiments, the compound of formula (I) is a compound according to formulae (IXa) or (IXb):

(IXa)
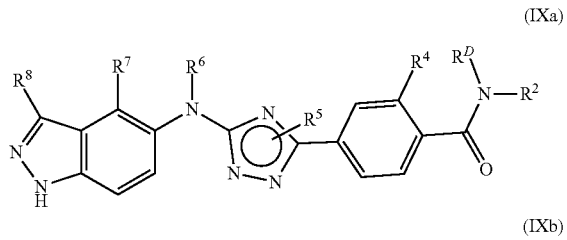

(IXb)
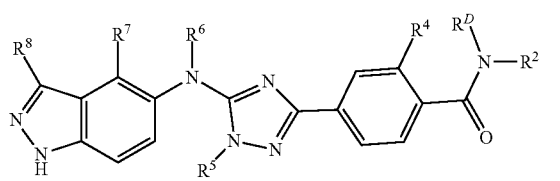

In embodiments of formulae (IXa) or (IXb) $R^8$ may be H. In certain embodiments $R^7$ may be H, halo, $C_{1-4}$ alkyl or $C_{3-8}$ cycloalkyl. In certain embodiments $R^6$ may be H. In certain embodiments $R^5$ may be $C_{1-4}$ alkyl. In certain embodiments $R^4$ may be H or —$OR^J$, wherein $R^J$ is selected from H or $C_{1-4}$ alkyl. In certain embodiments $R^D$ may be H. In embodiments $R^2$ may be $C_{1-6}$ alkyl, $C_{1-6}$ haloalkyl or $C_{3-8}$ cycloalkyl.

In embodiments of formulae (IXa) or (IXb) $R^8$ is H; $R^7$ is $C_{1-4}$ alkyl or $C_{3-8}$ cycloalkyl; $R^8$ is H; $R^5$ is methyl, $R^4$ is H or —OMe, $R^D$ is H and $R^2$ is $C_{1-6}$ alkyl, $C_{1-6}$ haloalkyl or $C_{3-8}$ cycloalkyl.

In embodiments of formulae (IXa) or (IXb) $R^7$ is selected from methyl, ethyl, isopropyl, tert-butyl, cyclopropyl, cyclobutyl, cyclopentyl and cyclohexyl.

In embodiments of formulae (IXa) or (IXb) $R^2$ is selected from: methyl, ethyl, n-propyl, I-propyl, n-butyl, I-butyl, tert-butyl, sec-butyl, tert-pentyl, difluoroethyl, difluoropropyl, trifluoroethyl, trifluoropropyl, trifluoroisopropyl, cyclopropyl, cyclobutyl, cyclopentyl, cyclohexyl, and cycloheptyl.

In embodiments, the compound of formula (I) is a compound according to formula (Xa) or (Xb):

(Xa)
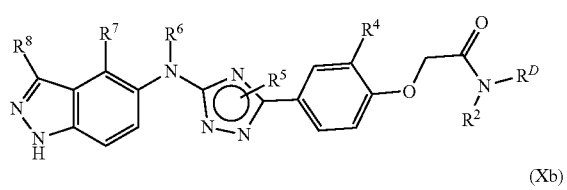

(Xb)
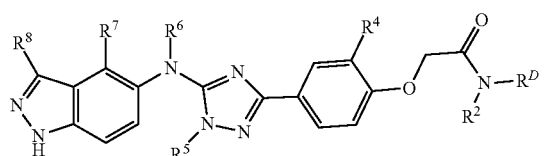

In embodiments of formulae (Xa) or (Xb) $R^8$ may be H. In certain embodiments $R^7$ may be $C_{1-4}$ alkyl or $C_{3-8}$ cycloalkyl. In certain embodiments $R^6$ may be H. In certain embodiments $R^5$ may be $C_{1-4}$ alkyl. In certain embodiments $R^4$ may be H or —$OR^J$, wherein $R^J$ is selected from H or $C_{1-4}$ alkyl. In certain embodiments $R^D$ may be H. In embodiments $R^2$ may be $C_{1-6}$ alkyl, $C_{1-6}$ haloalkyl or $C_{3-8}$ cycloalkyl.

In embodiments of formulae (Xa) or (Xb) $R^8$ is H; $R^7$ is $C_{1-4}$ alkyl or $C_{3-8}$ cycloalkyl; $R^6$ is H; $R^5$ is methyl, $R^4$ is H or —OMe, $R^D$ is H and $R^2$ is $C_{1-6}$ alkyl, $C_{1-6}$ haloalkyl or $C_{3-8}$ cycloalkyl.

In embodiments of formulae (Xa) or (Xb) $R^7$ is selected from methyl, ethyl, isopropyl, tert-butyl, cyclopropyl, cyclobutyl, cyclopentyl and cyclohexyl.

In embodiments of formulae (Xa) or (Xb) $R^2$ is selected from: methyl, ethyl, n-propyl, I-propyl, n-butyl, i-butyl, test-butyl, sec-butyl, tert-pentyl, difluoroethyl, difluoropropyl, trifluoroethyl, trifluoropropyl, trifluoroisopropyl, cyclopropyl, cyclobutyl, cyclopentyl, cyclohexyl, and cycloheptyl.

In embodiments the compound of formula (I) is a compound according to formula (XI):

(XI)
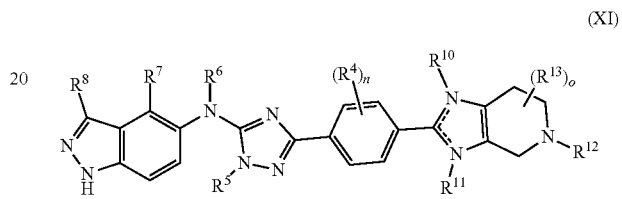

wherein:
$R^{10}$ is absent, H, $C_{1-4}$ alkyl or $C_{1-4}$ haloalkyl;
$R^{11}$ is absent, H, $C_{1-4}$ alkyl or $C_{1-4}$ haloalkyl;
$R^{12}$ is H, $C_{1-4}$ alkyl or $C_{1-4}$ haloalkyl;
$R^{13}$ is independently selected at each occurrence from H, =O, —$NR^FR^G$, halo, —CN, $C_{1-4}$ alkyl, $C_{1-4}$ haloalkyl, or $C_{1-4}$ alkyl substituted with —$OR^E$; and
o is 1, 2 or 3.

In embodiments the compound of formula (I) is a compound according to formulae (XIa), (XIb), (XIc) or (XId):

(XIa)
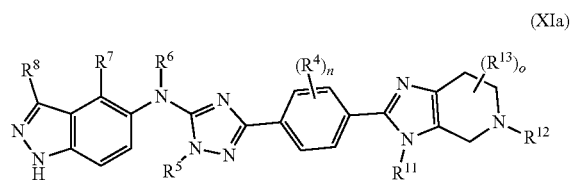

(XIb)
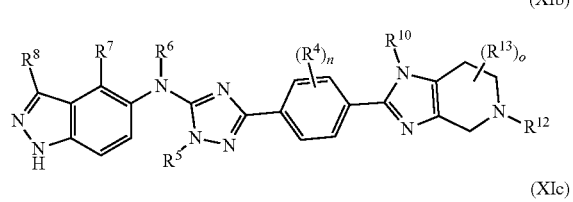

(XIc)
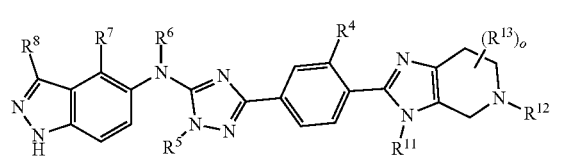

(XId)
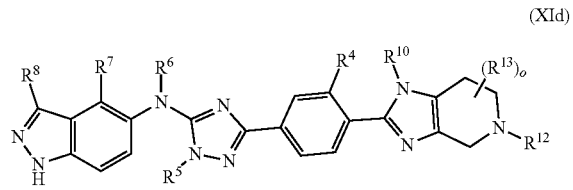

In embodiments of formulae (XI), (XIa), (XIb), (XIc) or (XId) $R^8$ may be H. In certain embodiments $R^7$ may be H, halo, $C_{1-4}$ alkyl or $C_{3-8}$ cycloalkyl. In certain embodiments $R^6$ may be H. In certain embodiments $R^5$ may be $C_{1-4}$ alkyl. In certain embodiments $R^4$ may be H or —$OR^J$, wherein $R^J$ is selected from H or $C_{1-4}$ alkyl. In certain embodiments $R^{10}$ may be absent, H, $C_{1-4}$ alkyl, $C_{1-4}$ alkyl substituted with —$OR^L$—, $C_{1-4}$ alkyl substituted with —$NR^L$—$R^L$, $C_{3-8}$ cycloalkyl, 3 to 8 membered heterocycloalkyl, $C_{1-4}$ alkyl substituted with $C_{3-8}$ cycloalkyl, or $C_{1-4}$ alkyl substituted with 3 to 8 membered heterocycloalkyl. In certain embodiments $R^{11}$ may be absent, H, $C_{1-4}$ alkyl, $C_{1-4}$ alkyl substituted with —$OR^L$, $C_{1-4}$ alkyl substituted with —$NR^LR^L$, $C_{3-8}$ cycloalkyl, 3 to 8 membered heterocycloalkyl, $C_{1-4}$ alkyl substituted with $C_{3-8}$ cycloalkyl, or $C_{1-4}$ alkyl substituted with 3 to 8 membered heterocycloalkyl. In certain embodiments, $R^{12}$ may be H, $C_{1-4}$ alkyl, $C_{1-4}$ haloalkyl, $C_{1-4}$ alkyl substituted with —$OR^L$, $C_{1-4}$ alkyl substituted with —$NR^LR^L$, $C_{3-8}$ cycloalkyl, 3 to 8 membered heterocycloalkyl, $C_{1-4}$ alkyl substituted with $C_{3-8}$ cycloalkyl, or $C_{1-4}$ alkyl substituted with 3 to 8 membered heterocycloalkyl. In certain embodiments, $R^{13}$ is independently selected at each occurrence from H, =O, —$NR^FR^G$, halo, —CN, $C_{1-4}$ alkyl, $C_{1-4}$ haloalkyl, or $C_{1-4}$ alkyl substituted with —$OR^F$.

In embodiments of formulae (XI), (XIa), (XIb), (XIc) or (XId) $R^{10}$ is absent, H, $C_{1-4}$ alkyl, $C_{1-4}$ alkyl substituted with —$OR^L$, $C_{1-4}$ alkyl substituted with —$NR^LR^L$—, $C_{3-8}$ cycloalkyl, 3 to 8 membered heterocycloalkyl, $C_{1-4}$ alkyl substituted with $C_{3-8}$ cycloalkyl, or $C_{1-4}$ alkyl substituted with 3 to 8 membered heterocycloalkyl. Optionally, $R^{10}$ is absent, H or $C_{1-4}$ alkyl.

In embodiments of formulae (XI), (XIa), (XIb), (XIc) or (XId) $R^{11}$ is absent, H, $C_{1-4}$ alkyl, $C_{1-4}$ alkyl substituted with —$OR^L$, $C_{1-4}$ alkyl substituted with —$NR^LR^L$—, $C_{3-8}$ cycloalkyl, 3 to 8 membered heterocycloalkyl, $C_{1-4}$ alkyl substituted with $C_{3-8}$ cycloalkyl, or $C_{1-4}$ alkyl substituted with 3 to 8 membered heterocycloalkyl. Optionally, $R^{11}$ is absent, H or $C_{1-4}$ alkyl.

In embodiments of formulae (XI), (XIa), (XIb), (XIc) or (XId) $R^{12}$ is H, $C_{1-4}$ alkyl, $C_{1-4}$ haloalkyl, $C_{1-4}$ alkyl substituted with —$OR^L$, $C_{1-4}$ alkyl substituted with —$NR^LR^L$, $C_{3-8}$ cycloalkyl, 3 to 8 membered heterocycloalkyl, $C_{1-4}$ alkyl substituted with $C_{3-8}$ cycloalkyl, or $C_{1-4}$ alkyl substituted with 3 to 8 membered heterocycloalkyl. Optionally $R^{12}$ is H, $C_{1-4}$ alkyl or $C_{1-4}$ haloalkyl.

In embodiments of formulae (XI), (XIa), (XIb), (XIc) or (XId) $R^{10}$ and $R^{11}$ are independently selected from: hydrogen, methyl, ethyl, n-propyl, i-propyl, n-butyl, i-butyl, test-butyl, cyclopropyl, —CH$_2$CH$_2$OH, —CH$_2$CH$_2$OCH$_3$, —CH$_2$CH$_2$NHCH$_3$, piperidyl, ethyl substituted with morpholine, and ethyl substituted with piperidine. Optionally, $R^{10}$ and $R^{11}$ are independently selected from: hydrogen, methyl, ethyl, n-propyl, i-propyl or tert-butyl.

In embodiments of formulae (XI), (XIa), (XIb), (XIc) or (XId) $R^{12}$ is selected from: hydrogen, methyl, ethyl, n-propyl, i-propyl, n-butyl, i-butyl, tert-butyl, trifluoromethyl, trifluoroethyl, cyclopropyl, —CH$_2$CH$_2$OH, —CH$_2$CH$_2$OCH$_3$, —CH$_2$CH$_2$NHCH$_3$, piperidyl, ethyl substituted with morpholine, and ethyl substituted with piperidine. Optionally, $R^{12}$ is selected from hydrogen, methyl, ethyl, n-propyl, i-propyl, test-butyl, trifluoromethyl or trifluoroethyl.

The present invention provides compounds of formula (I) selected from:

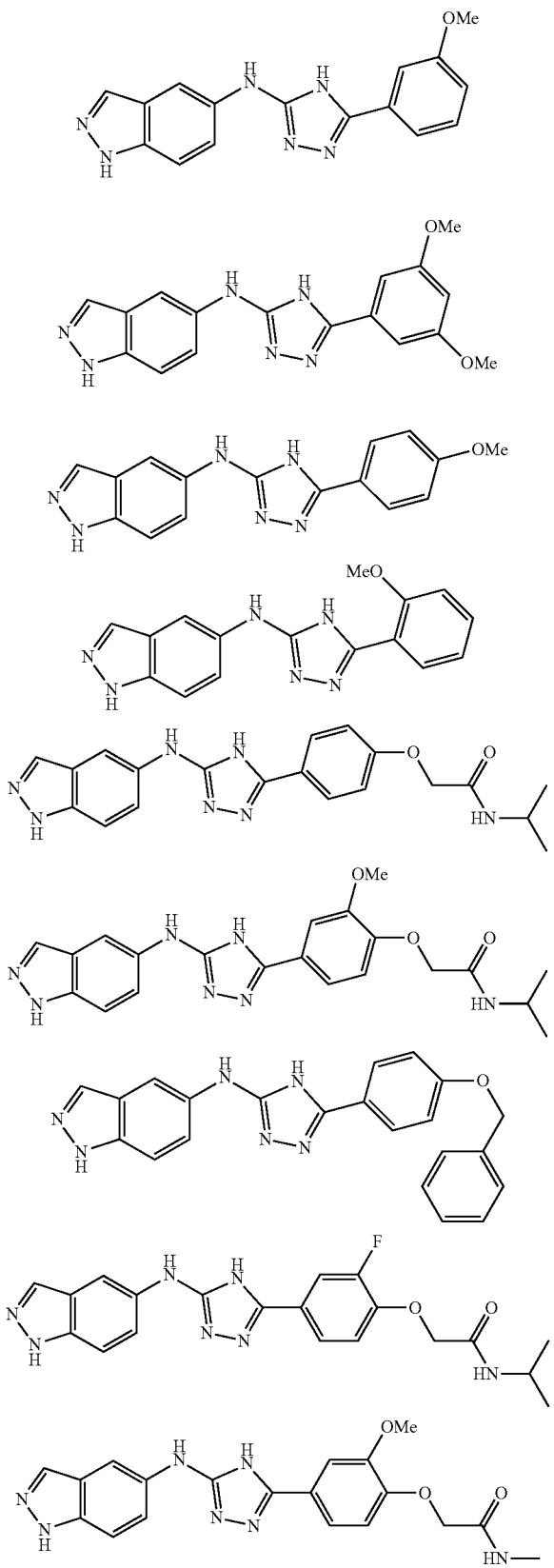

-continued
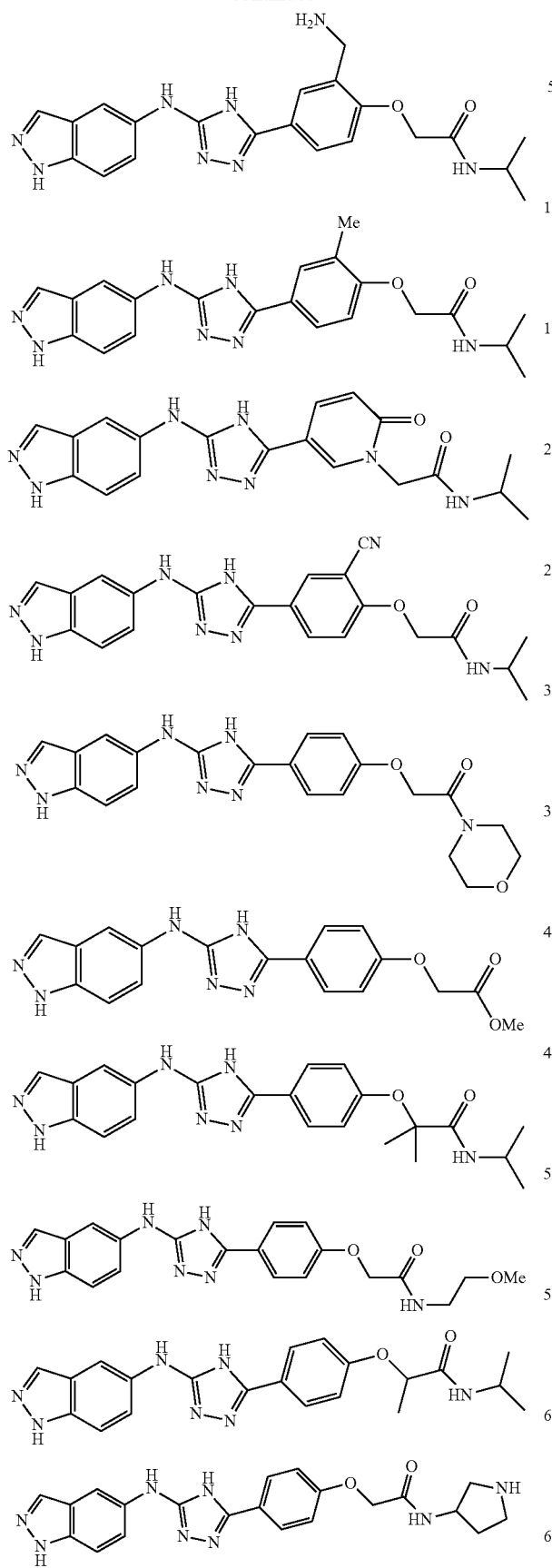
-continued
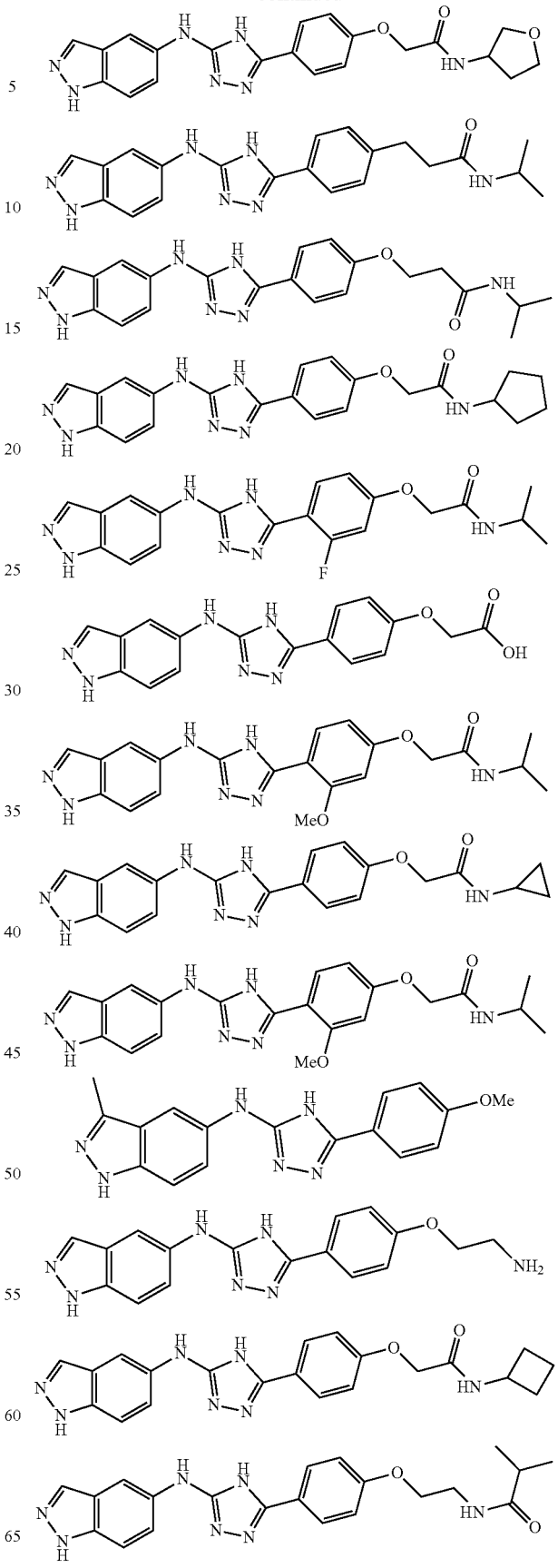

-continued
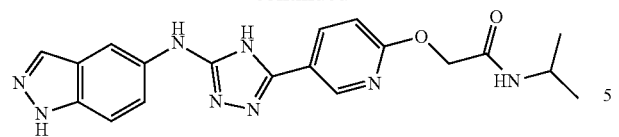
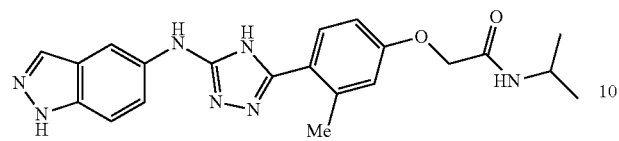
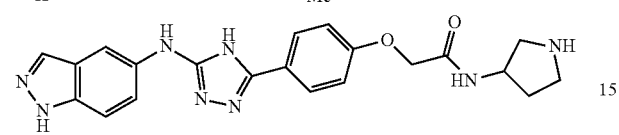
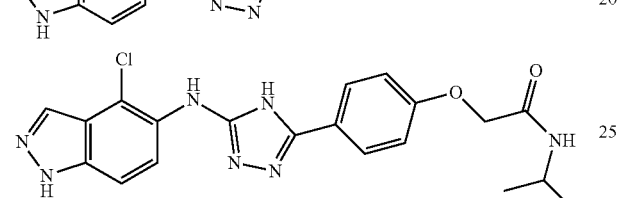
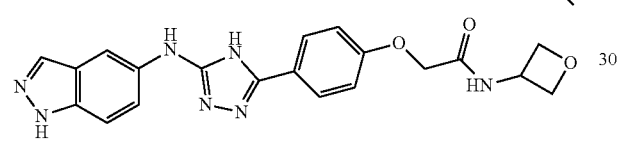
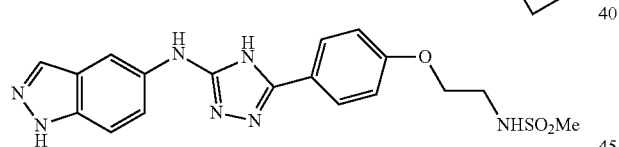
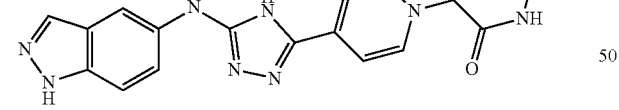
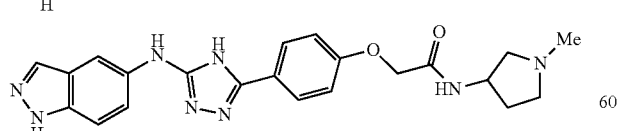
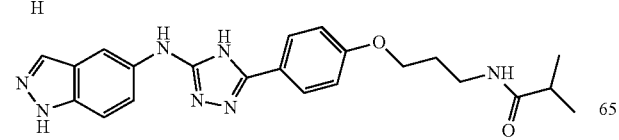
-continued
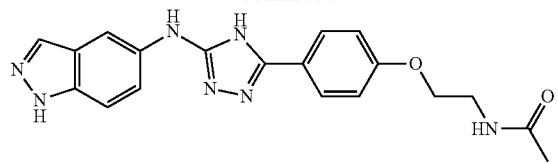
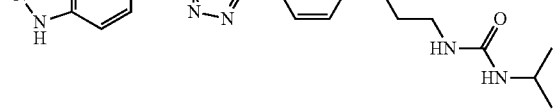
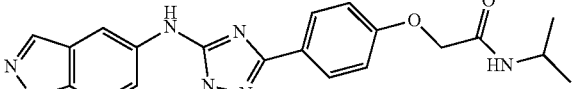
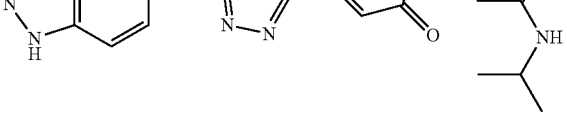
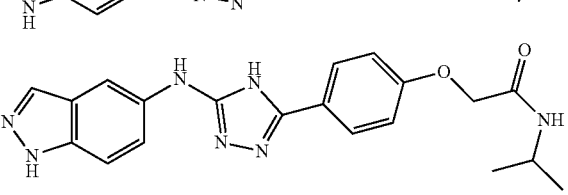
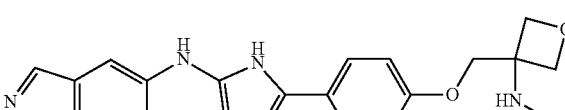
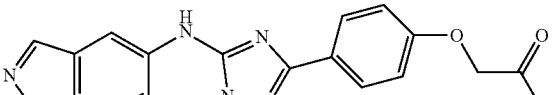

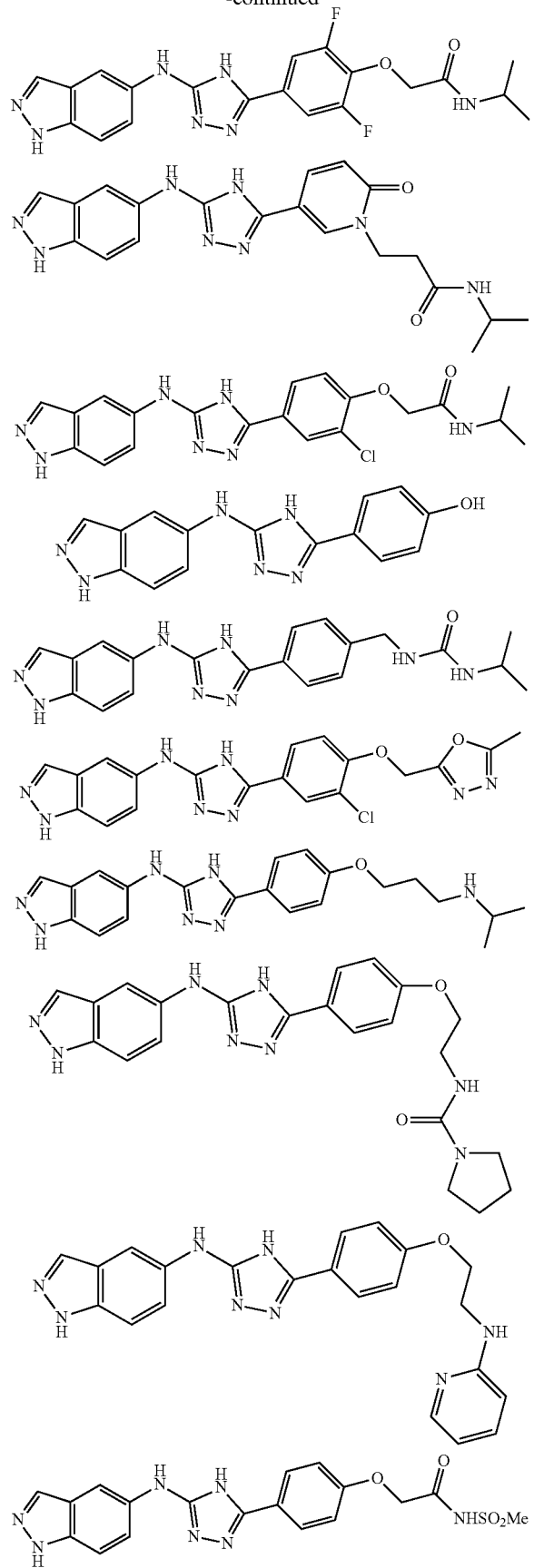
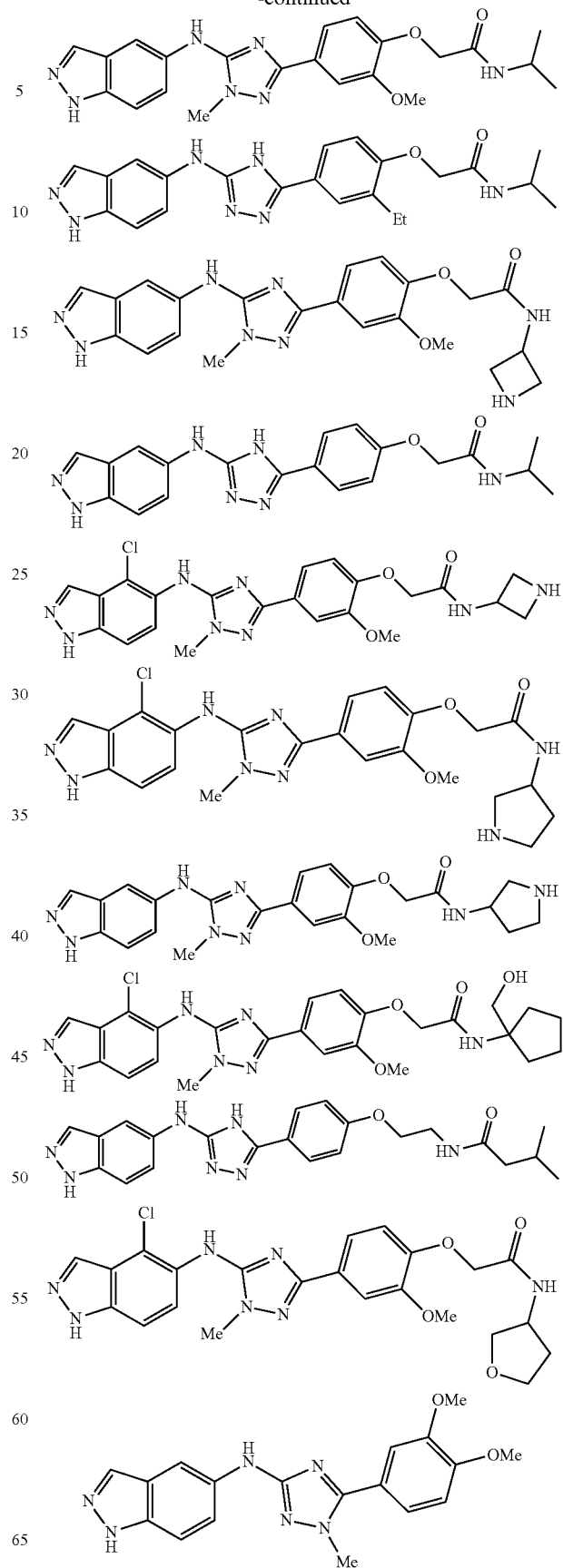

-continued
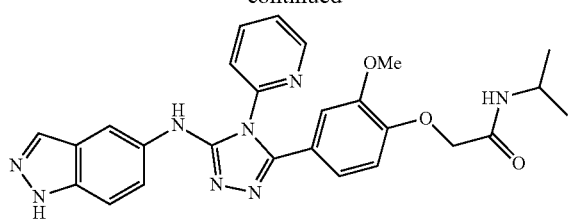
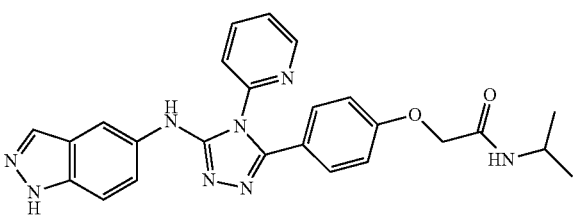
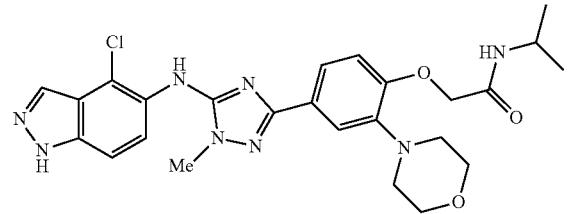
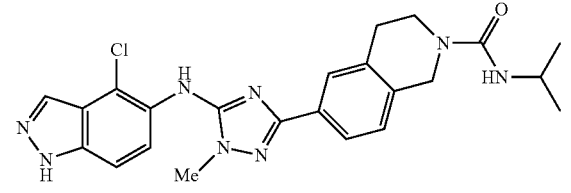
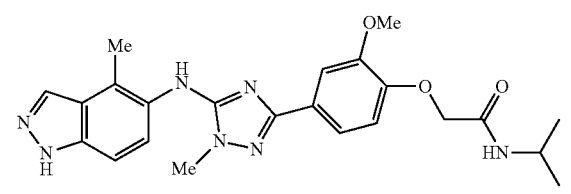
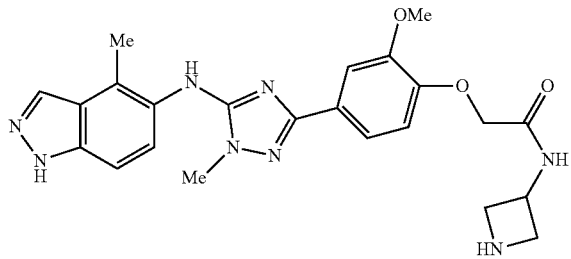
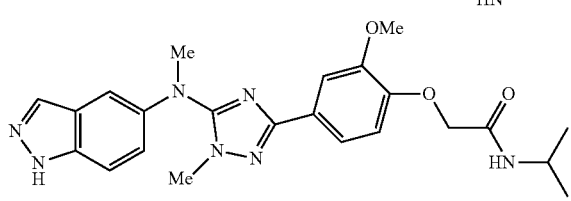
-continued
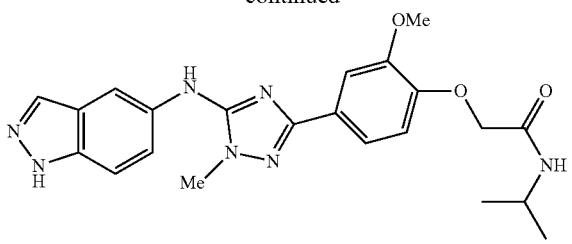
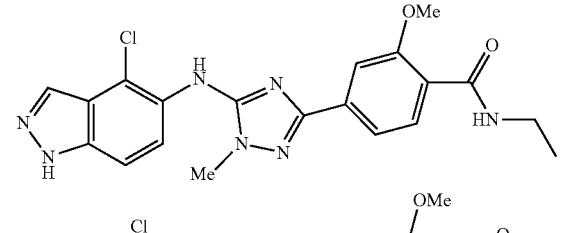
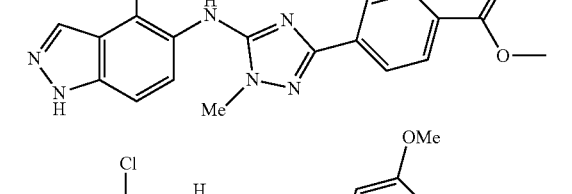
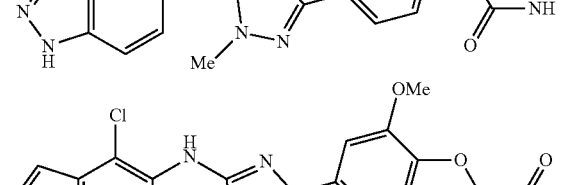
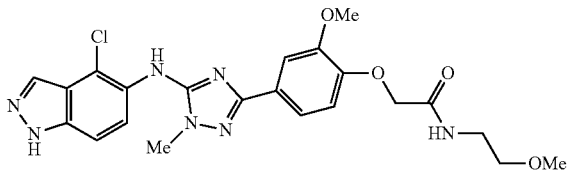
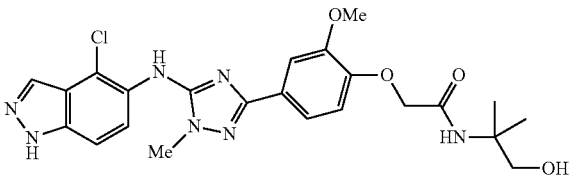
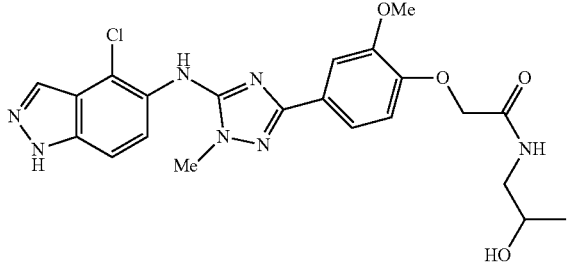

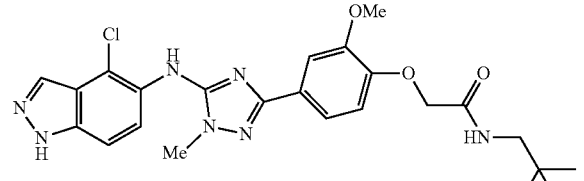
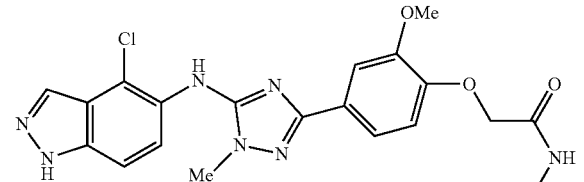
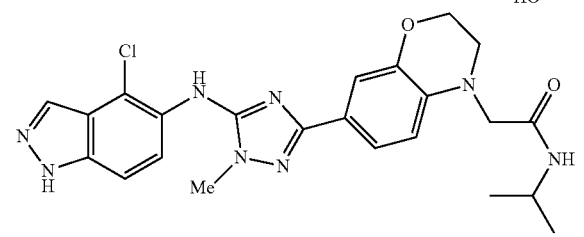

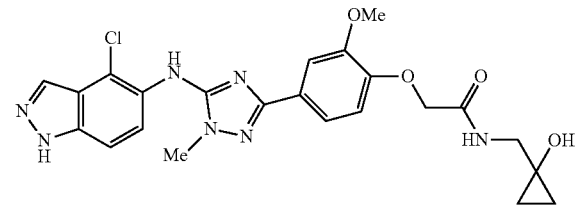
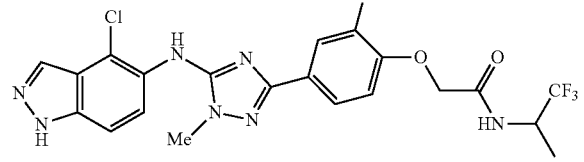
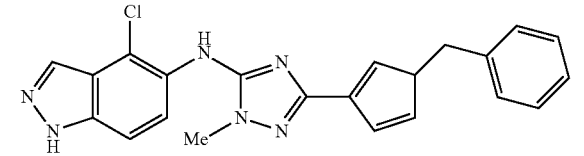
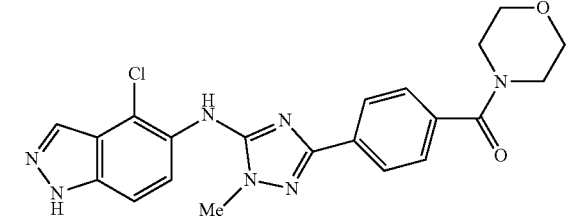
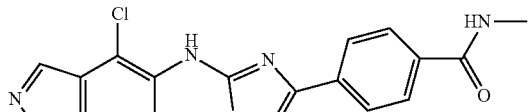
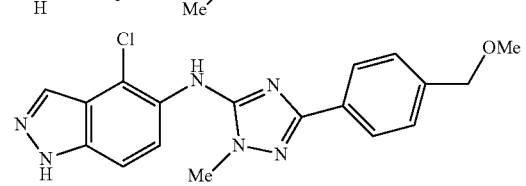
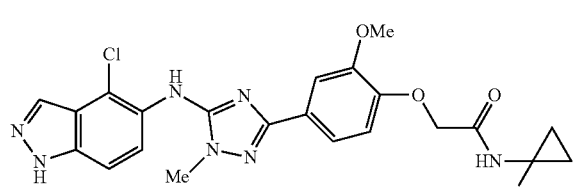
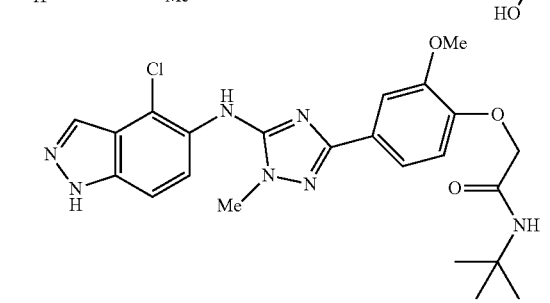
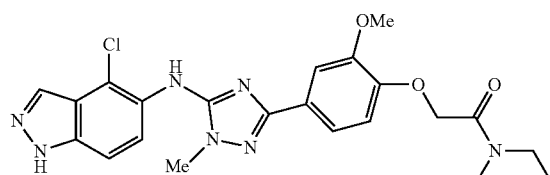
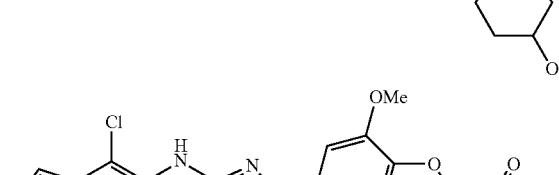
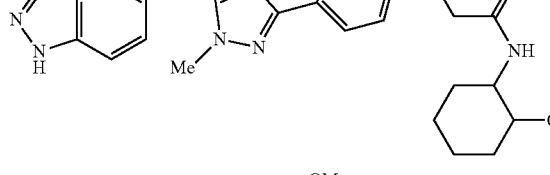
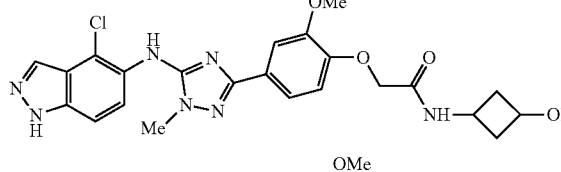
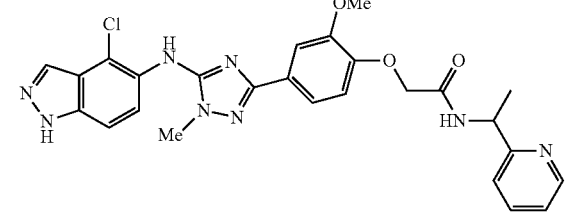

-continued
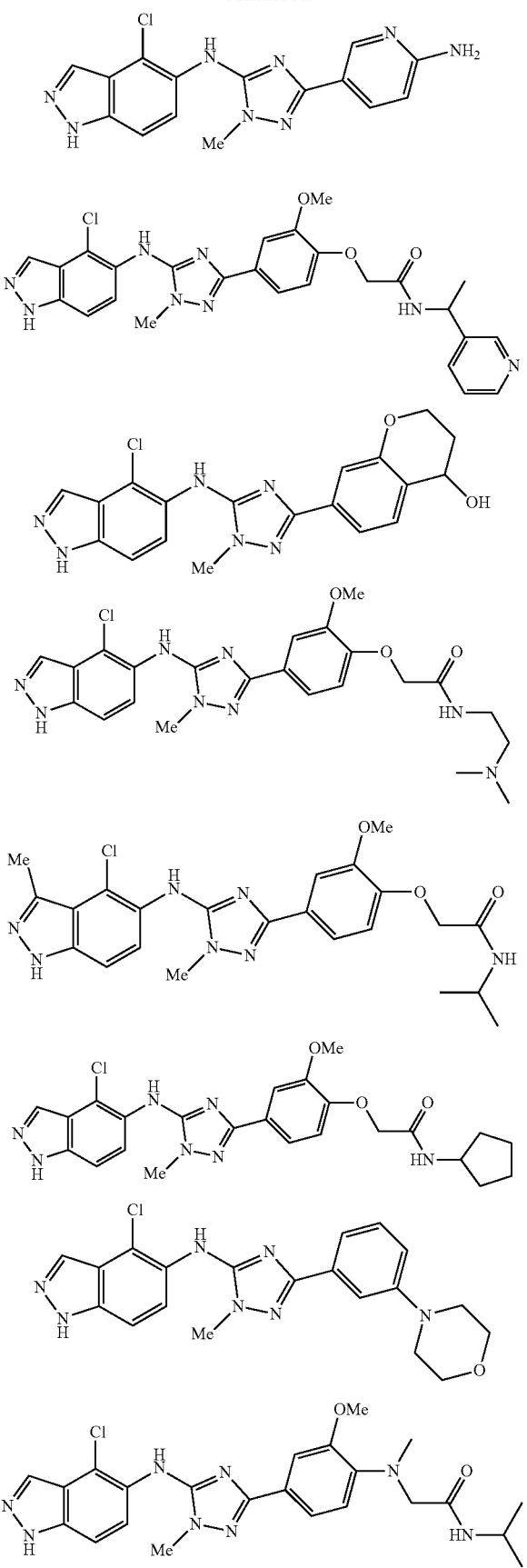
-continued
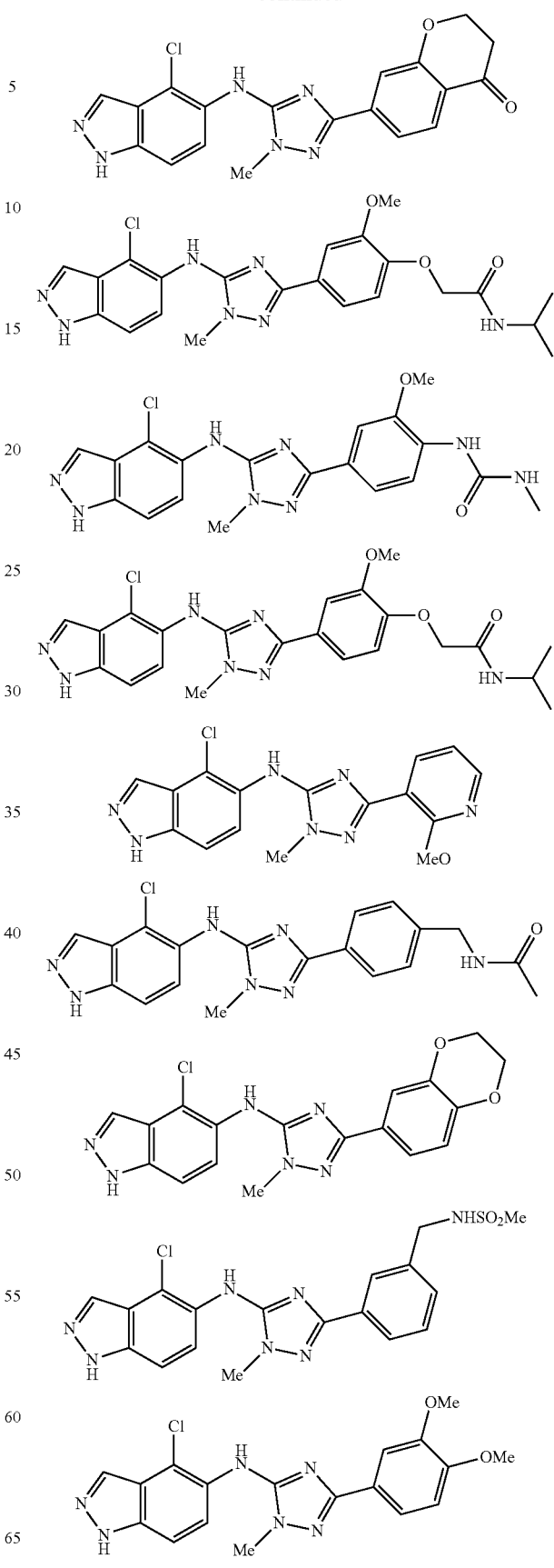

-continued

-continued
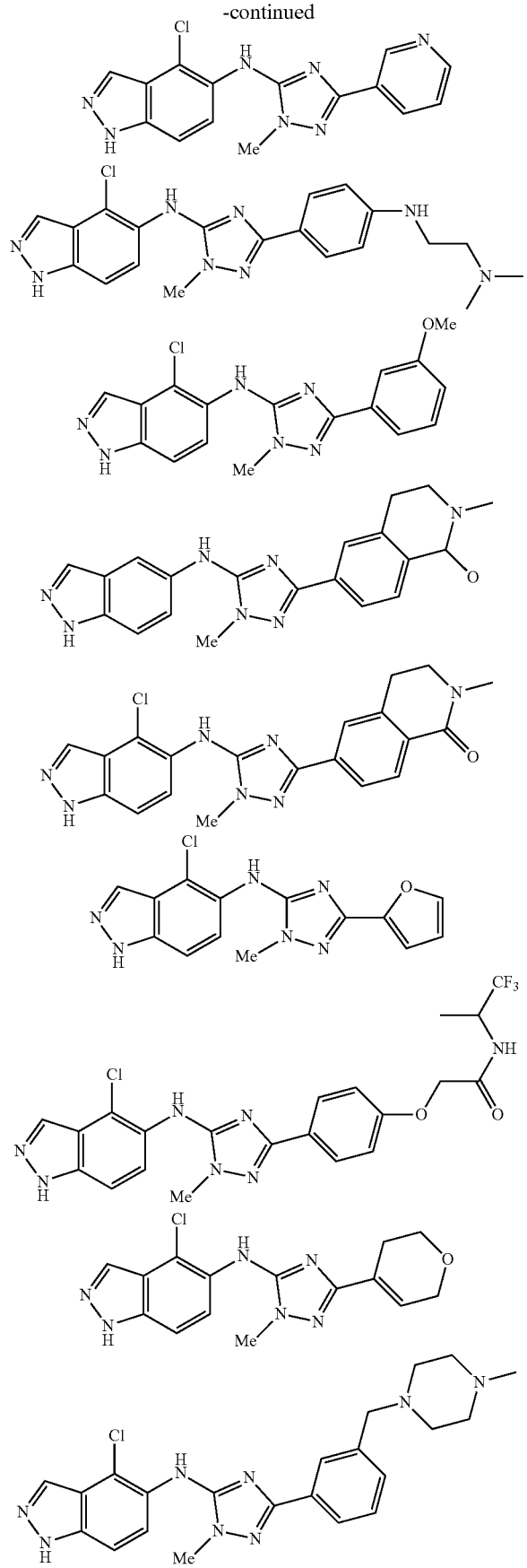
-continued
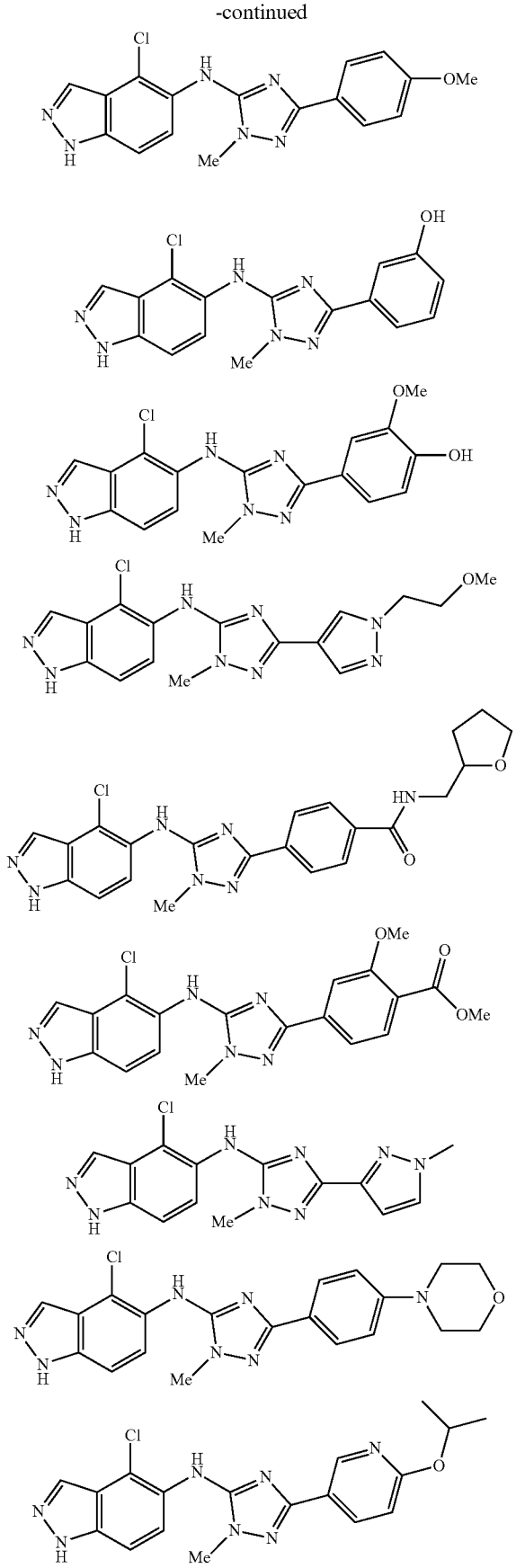

47
-continued
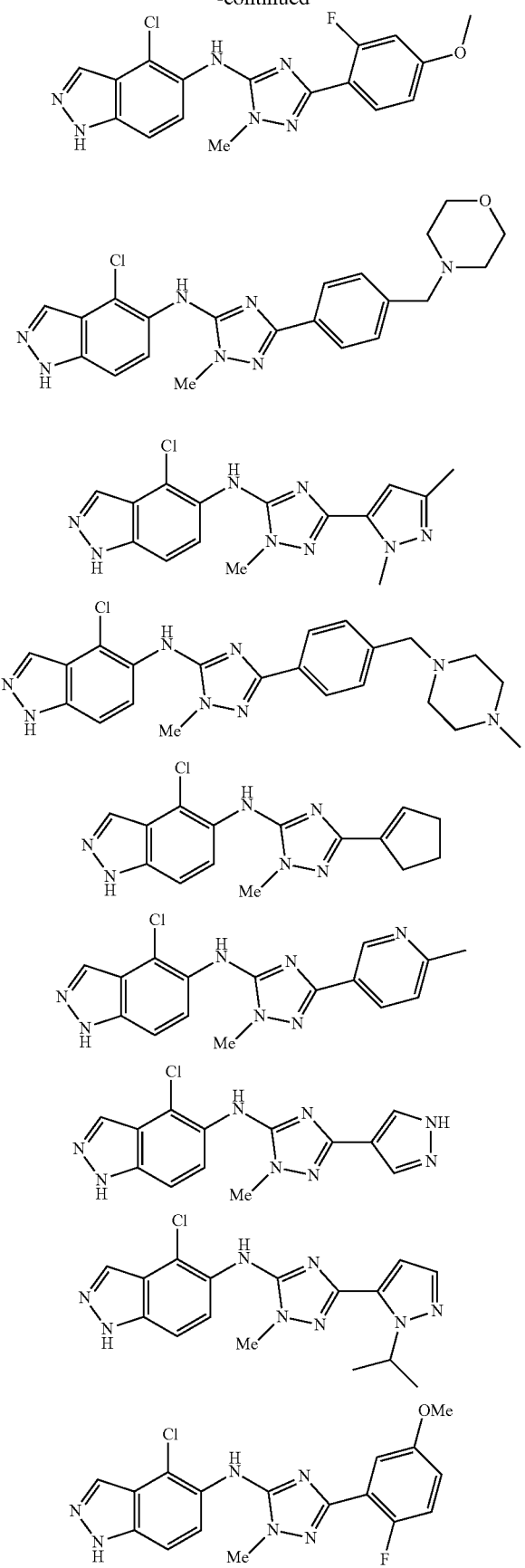
48
-continued
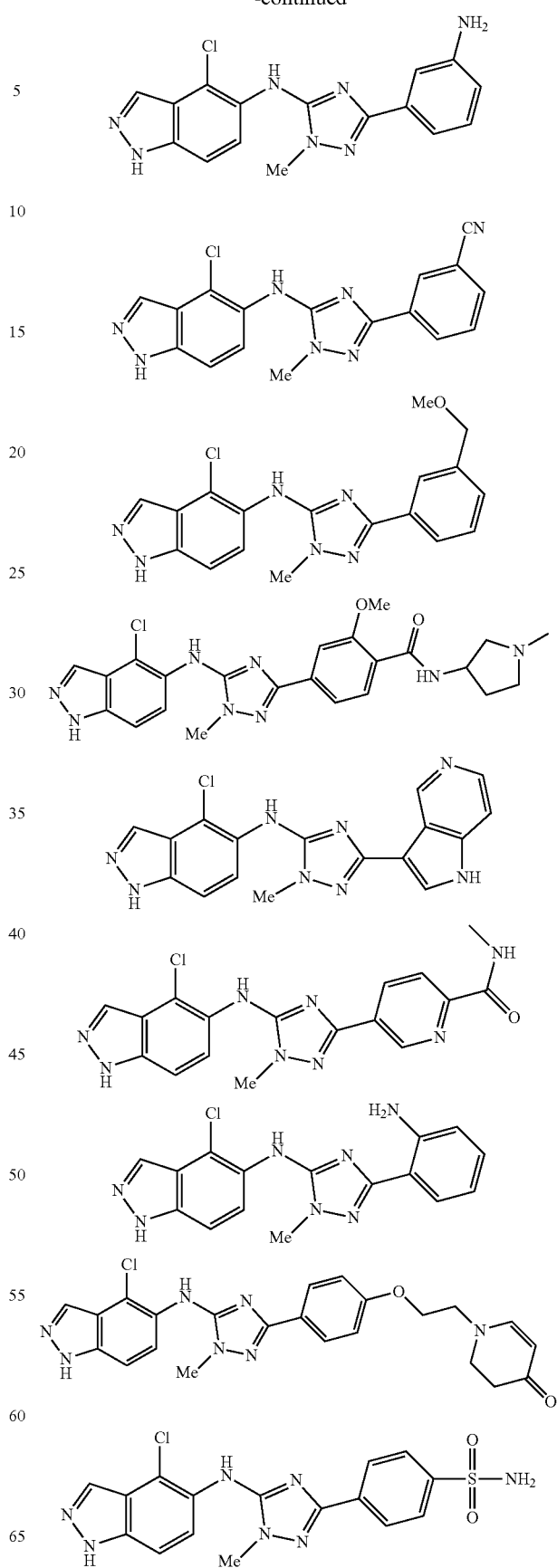

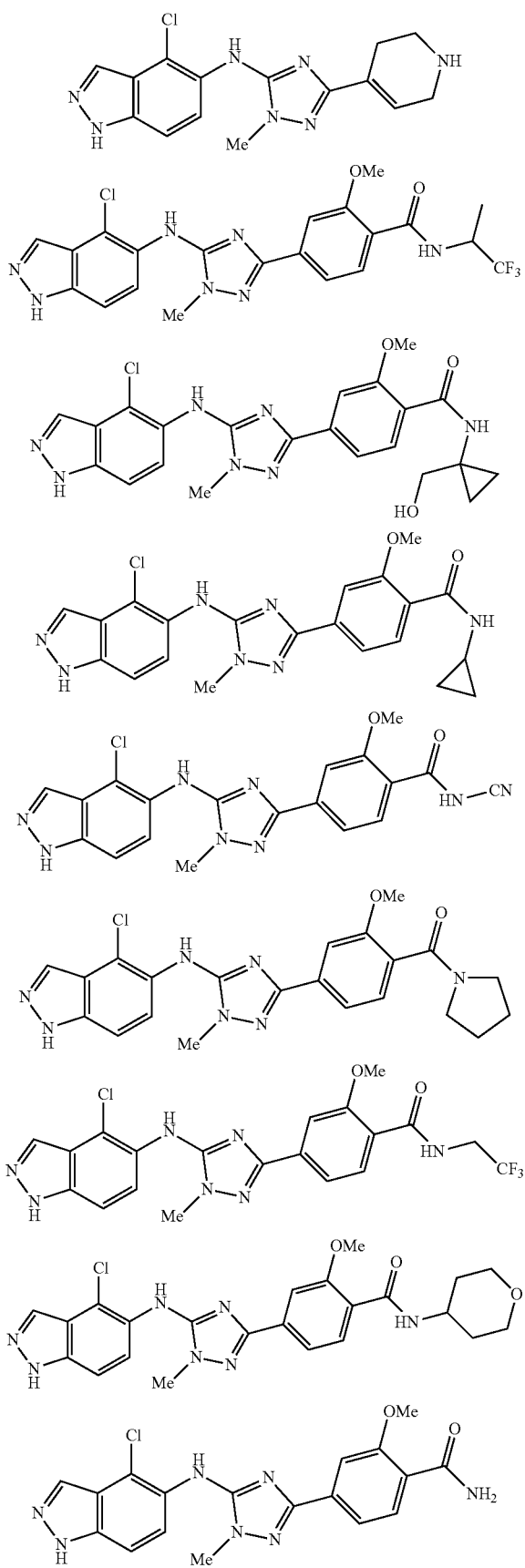
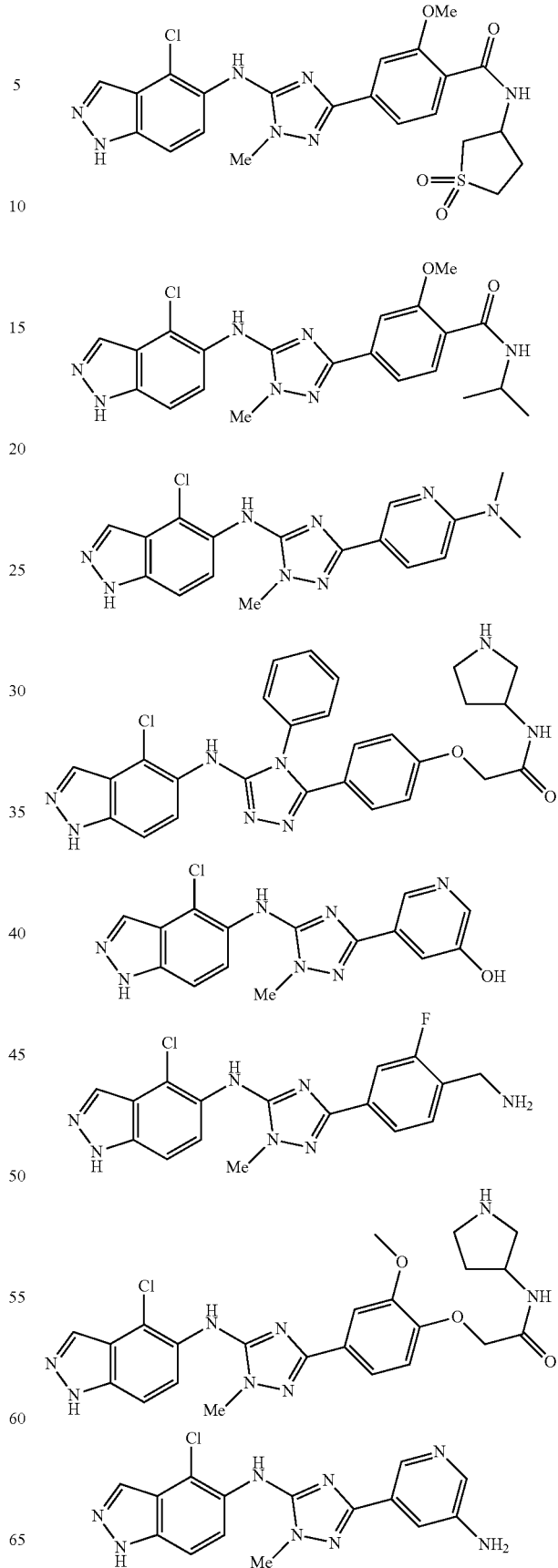

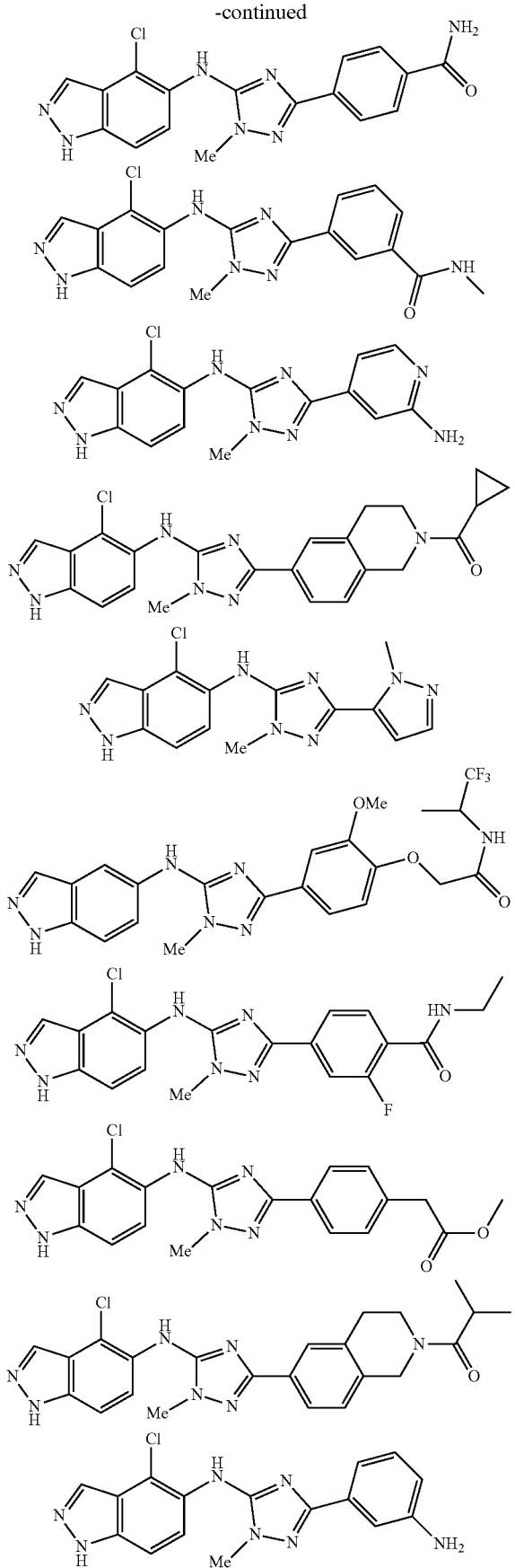
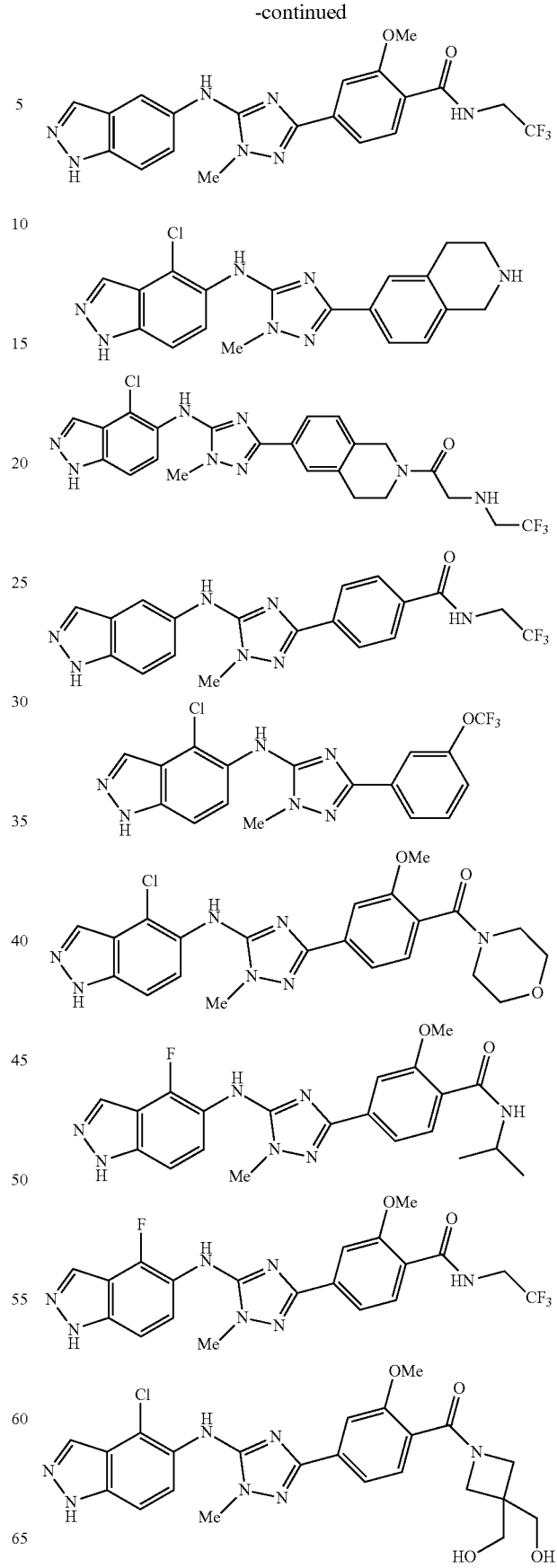

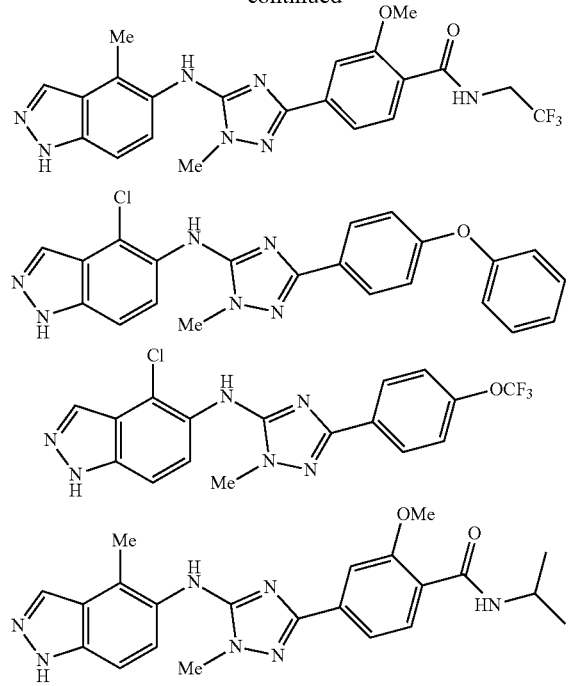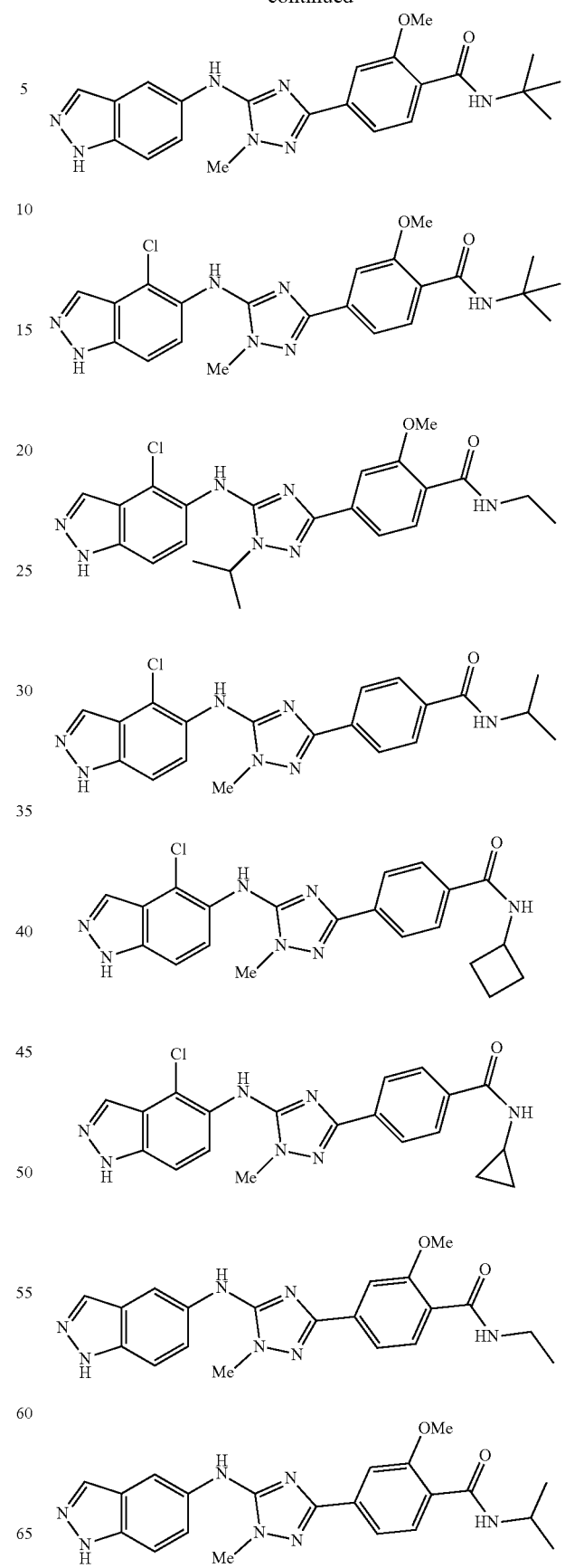

-continued
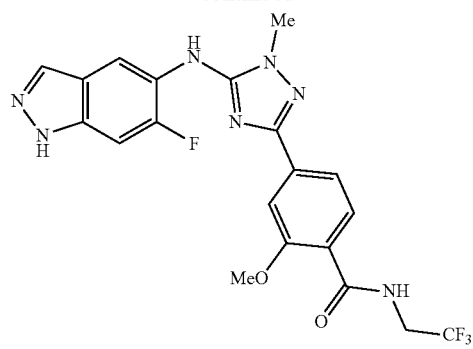
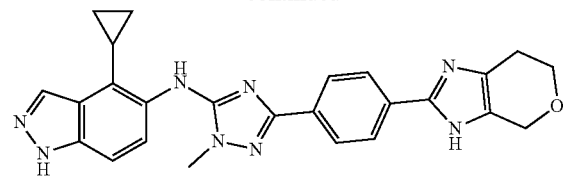
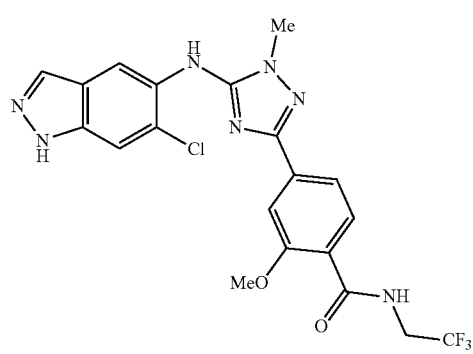
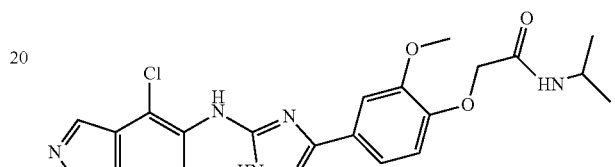
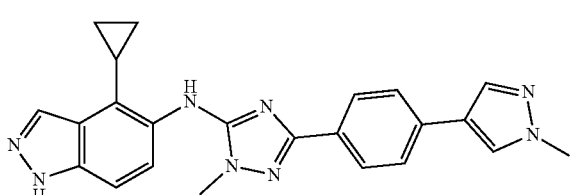
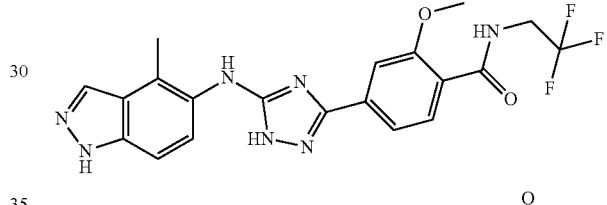
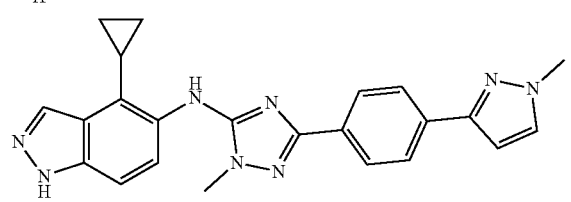
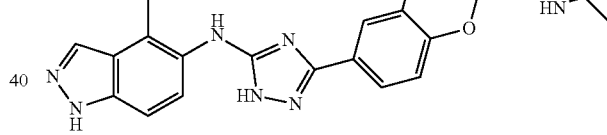
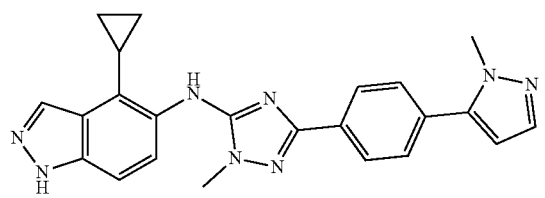
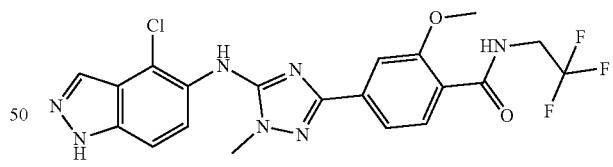
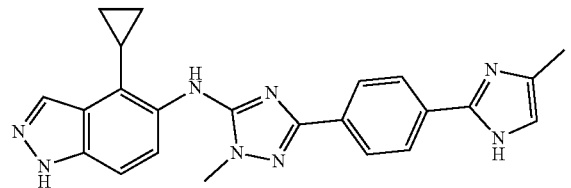
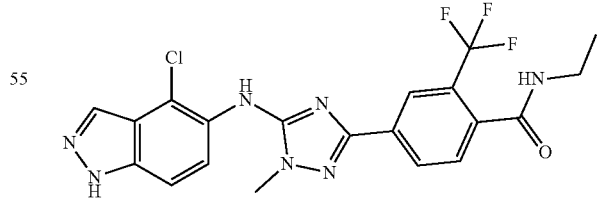
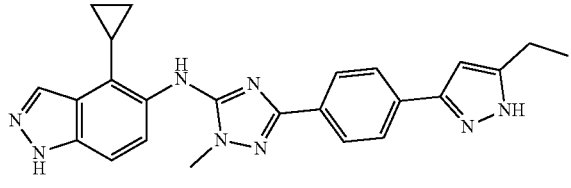
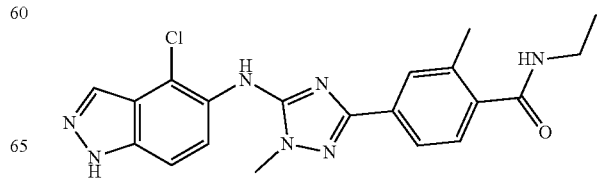

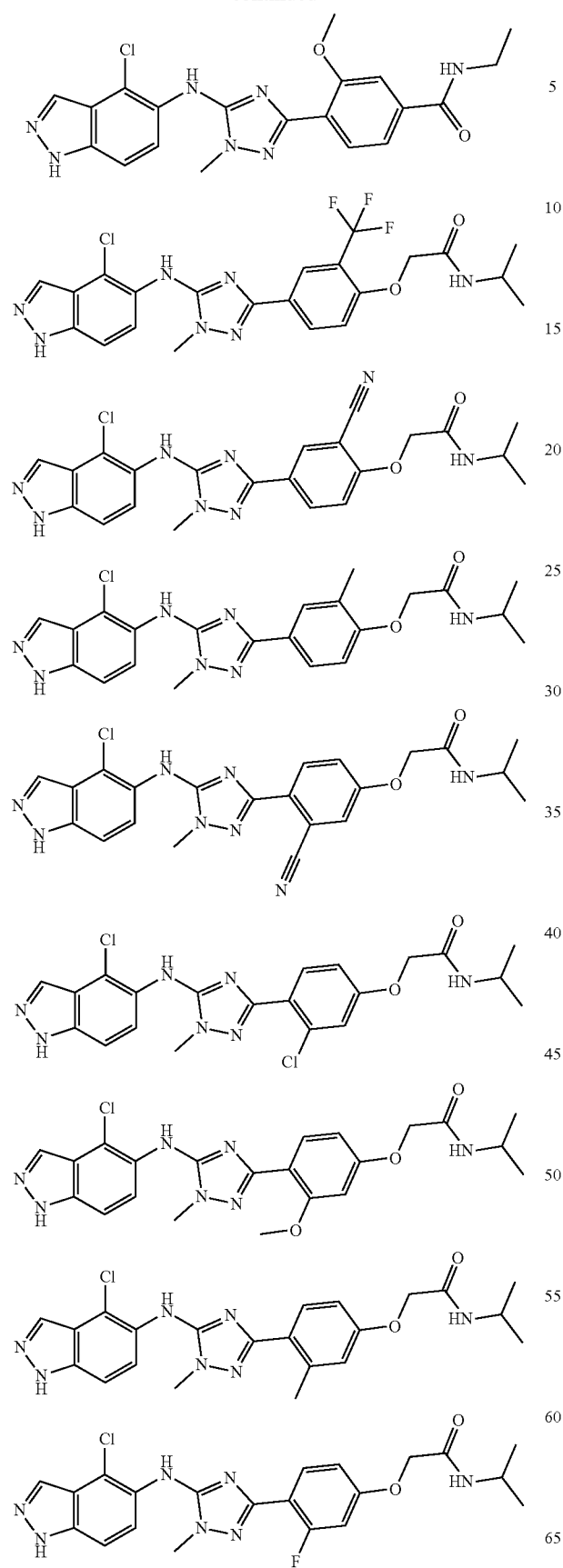
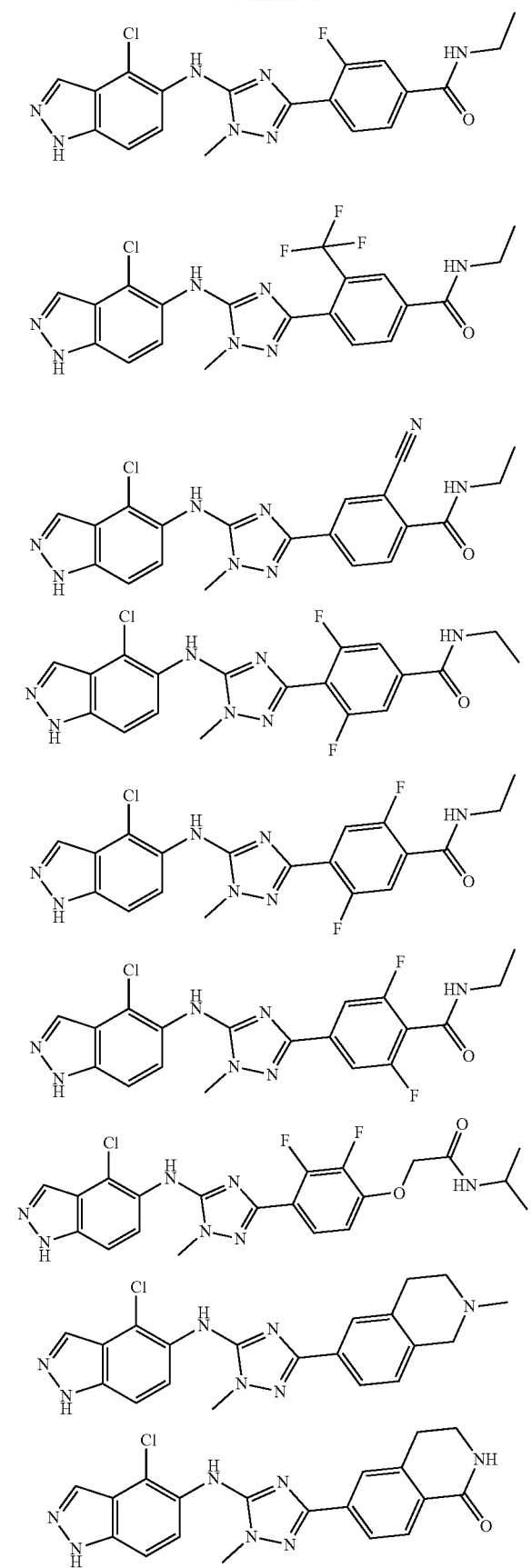

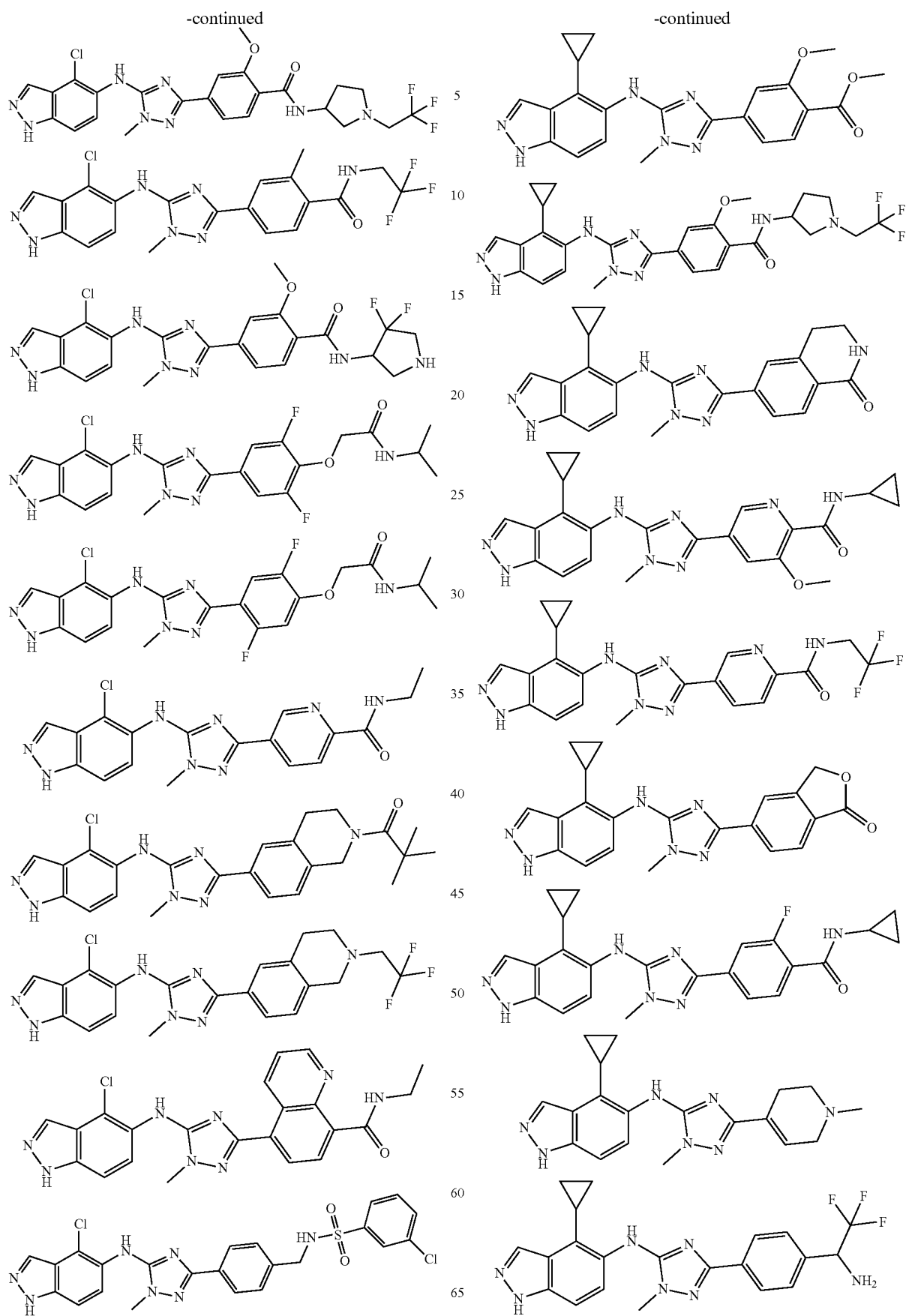

-continued
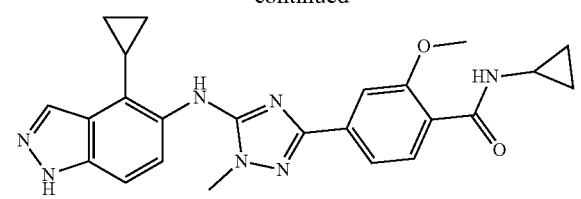
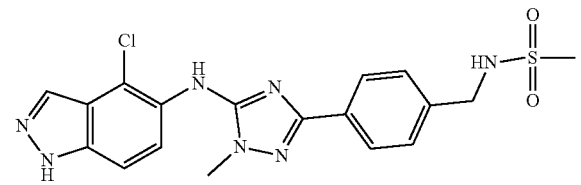
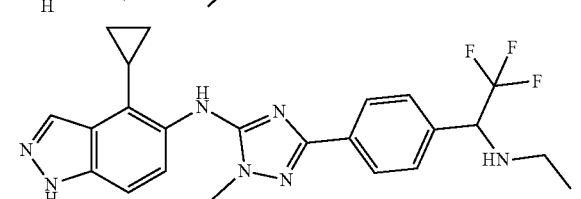
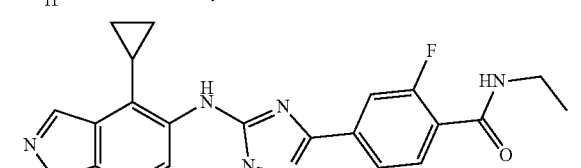
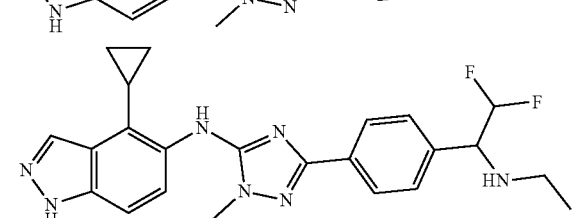
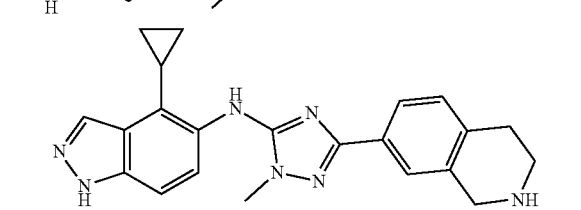
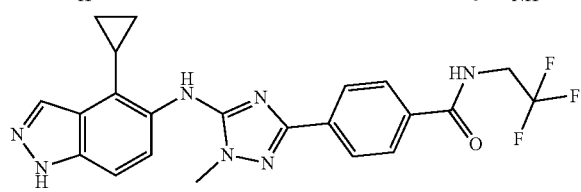
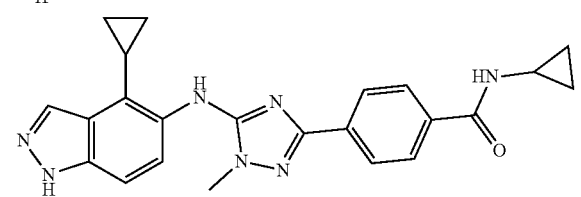
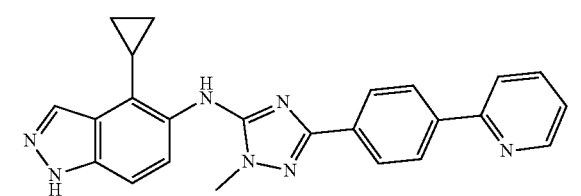
-continued
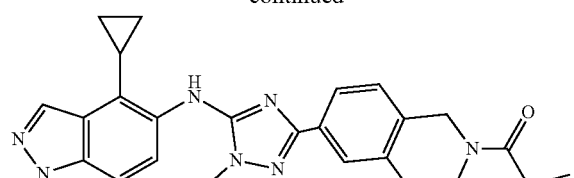
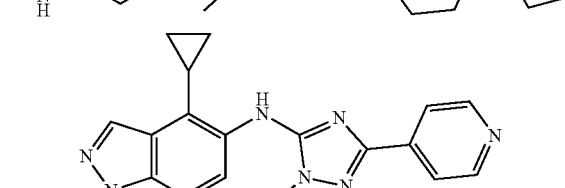
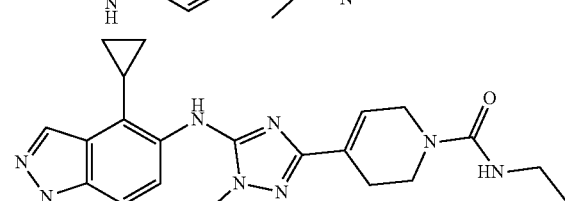
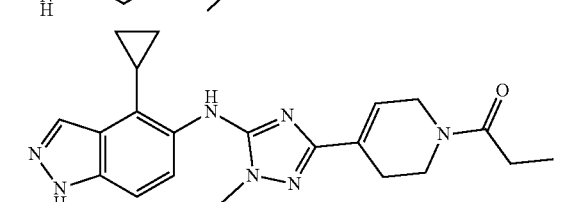
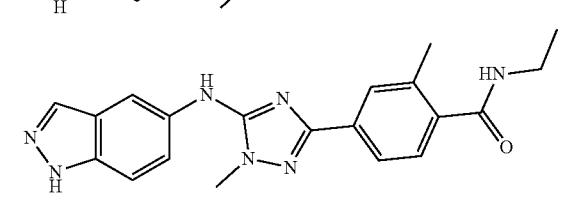
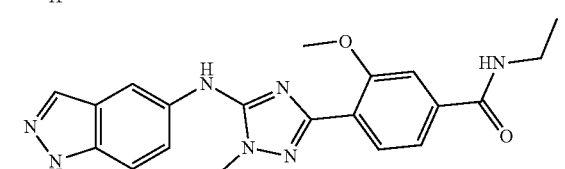
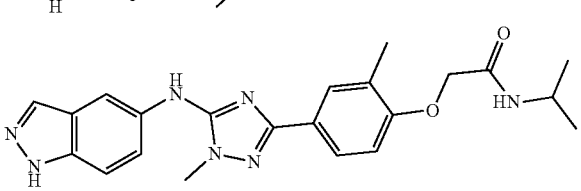
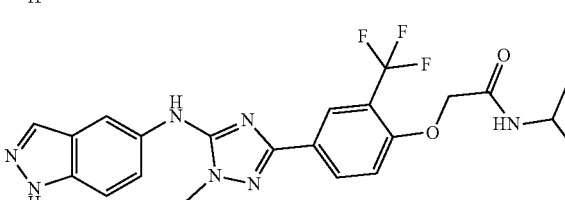
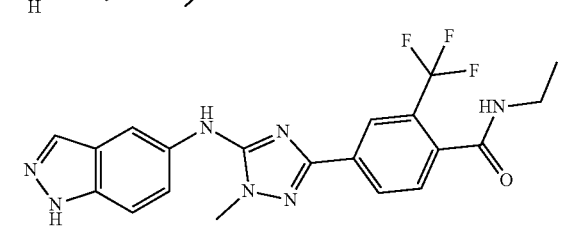

-continued
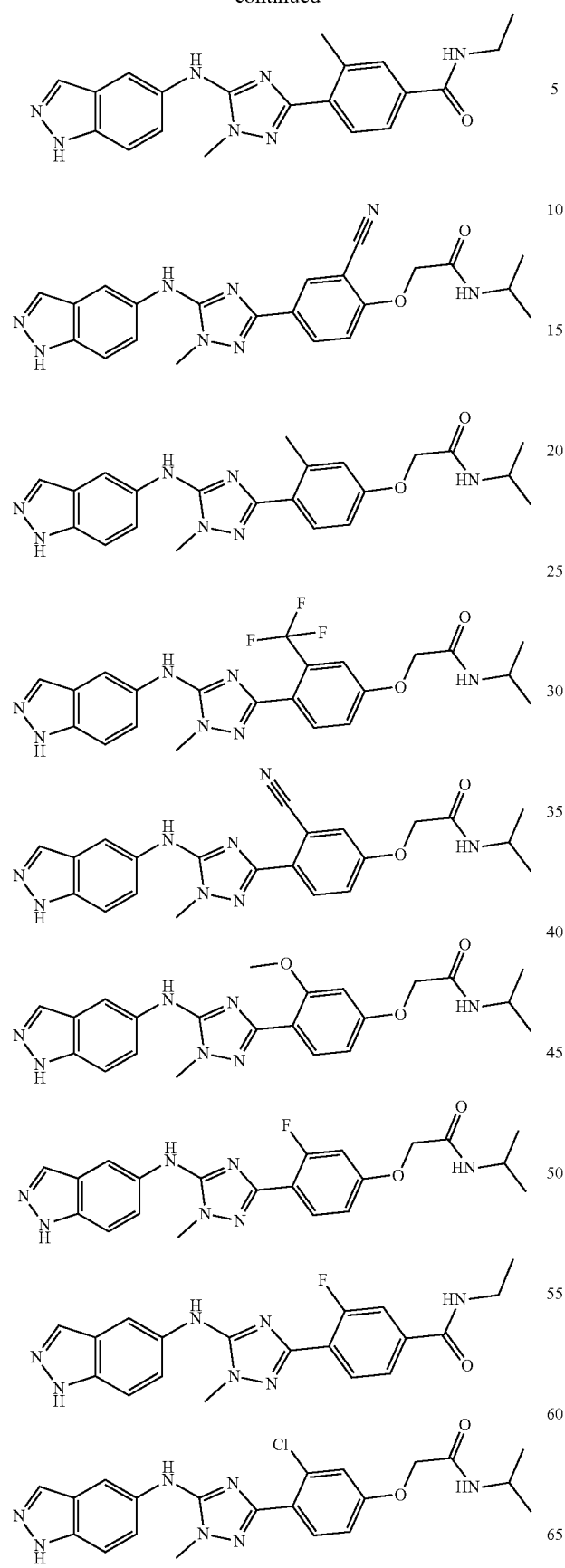
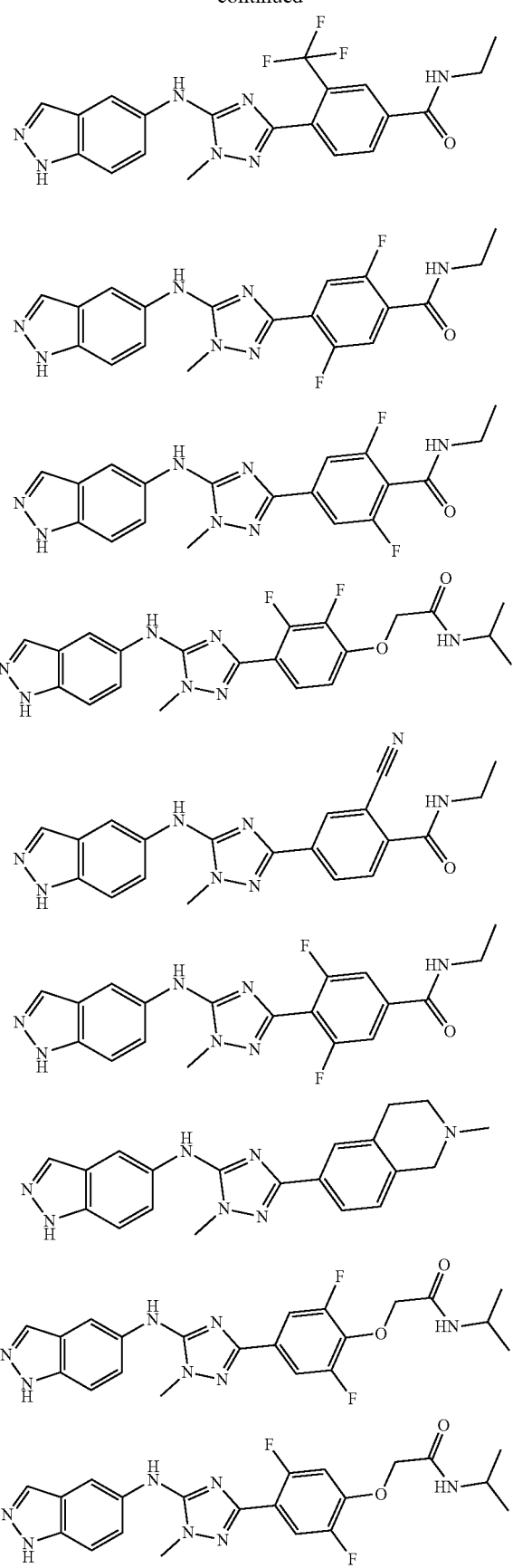

65
-continued
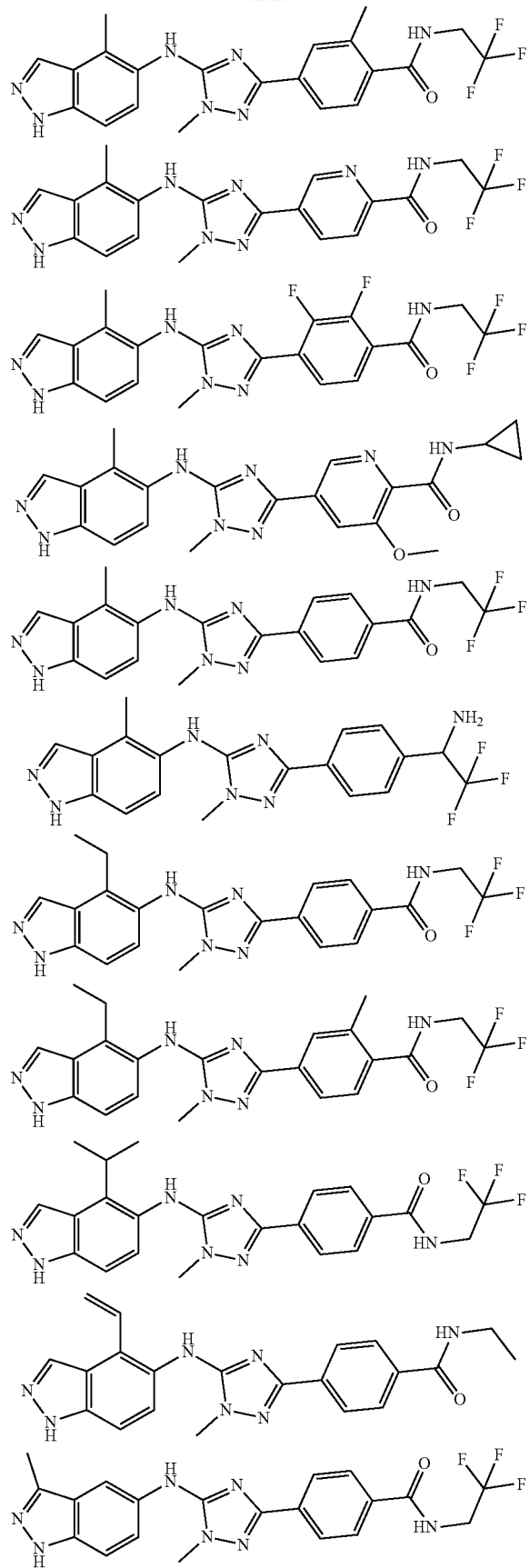
66
-continued
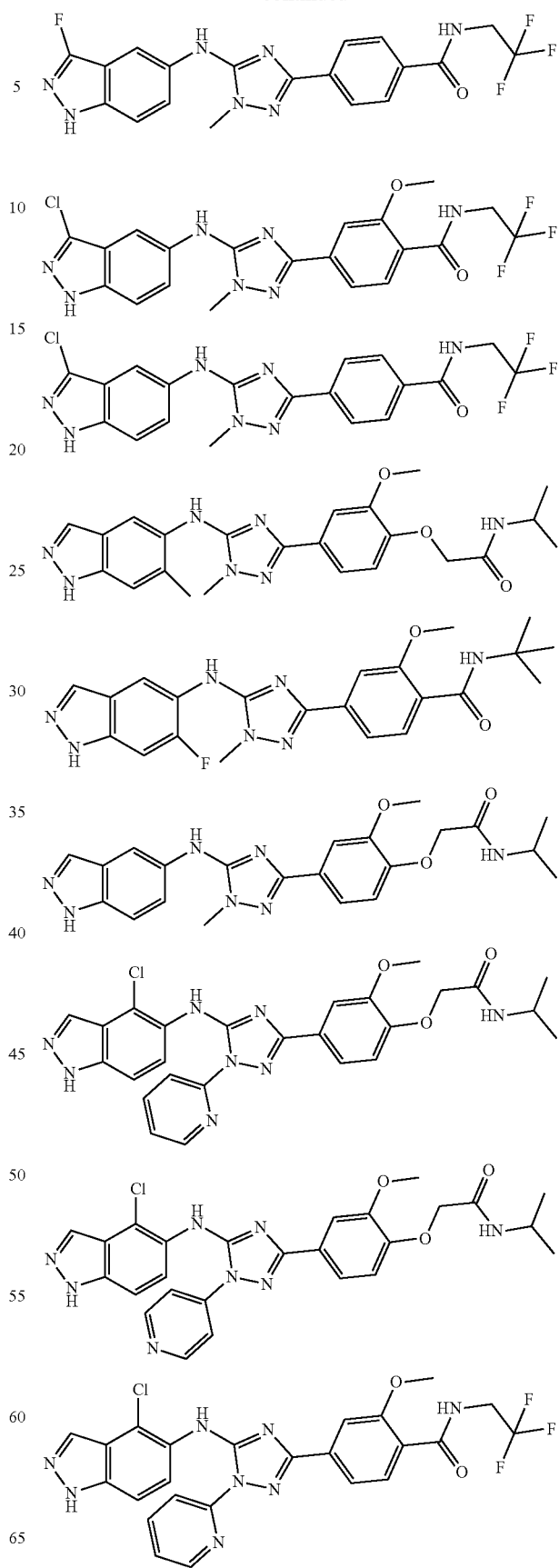

67
-continued
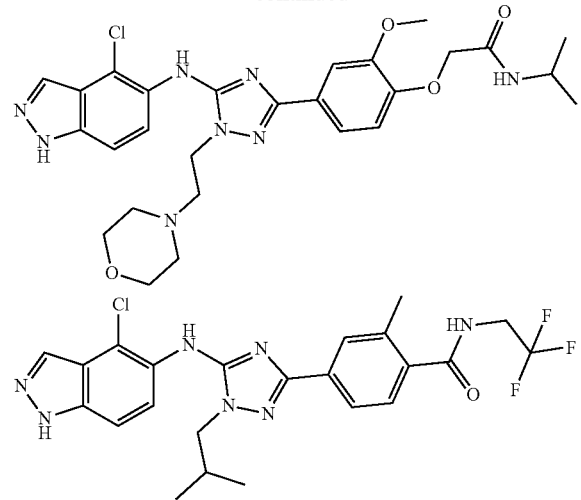
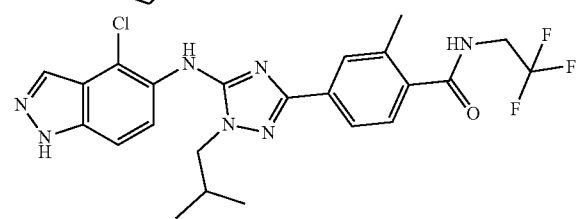
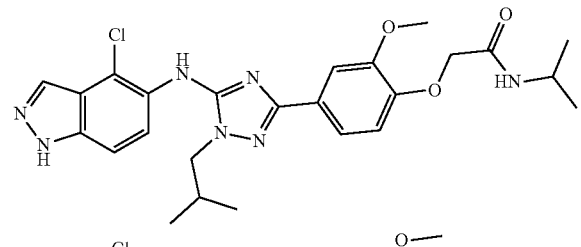
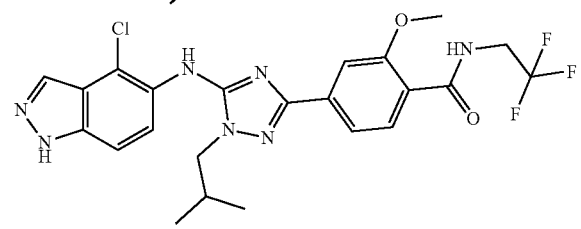
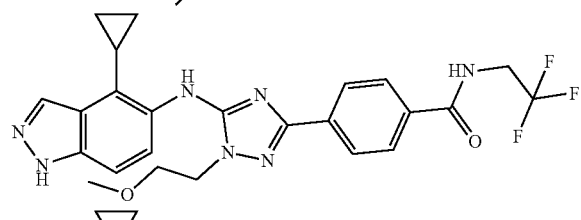
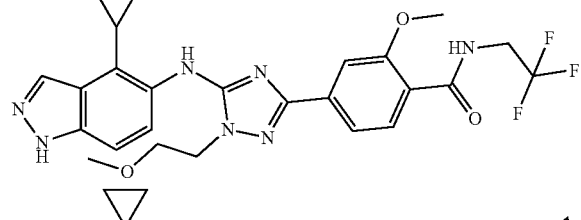
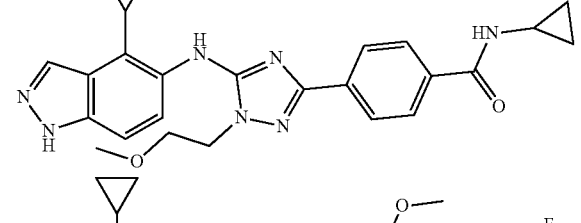
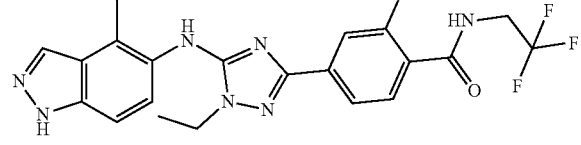
68
-continued
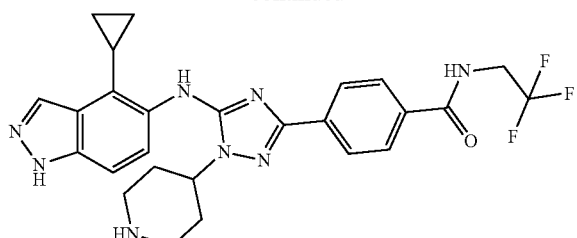
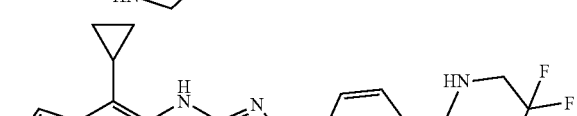
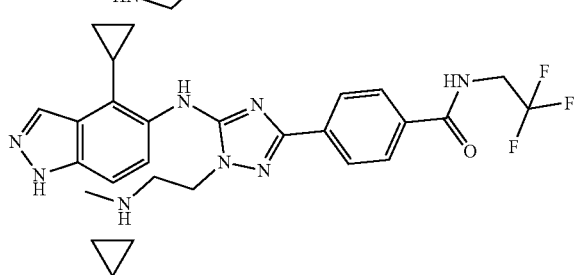
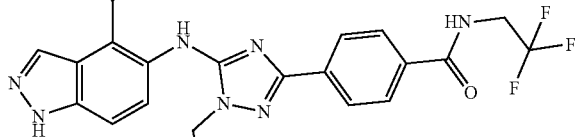
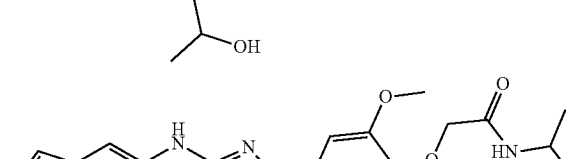
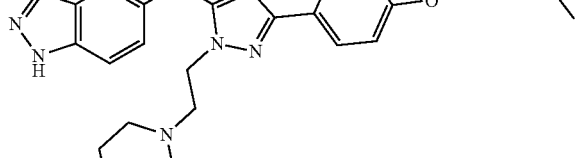
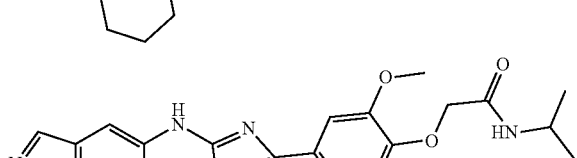
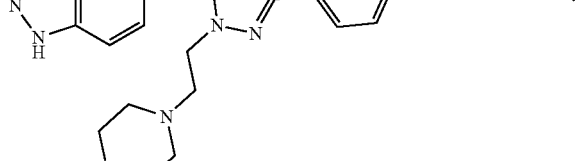

-continued

-continued
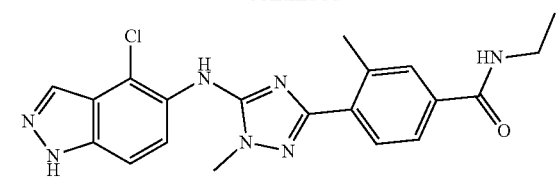
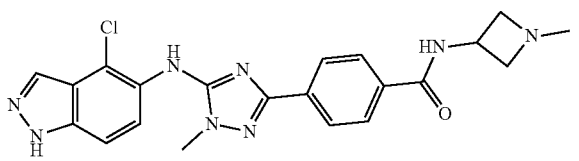
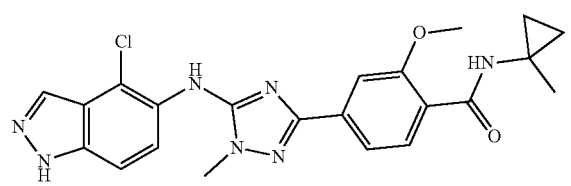
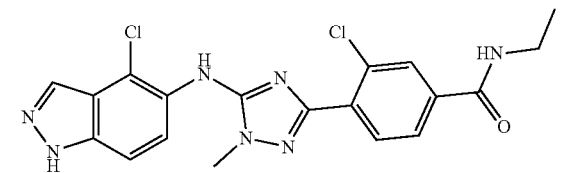
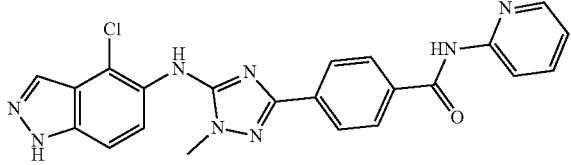
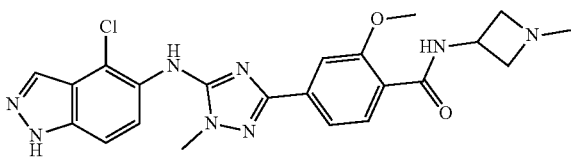
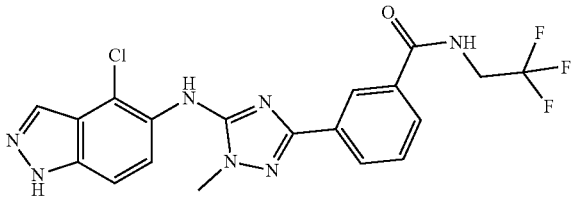
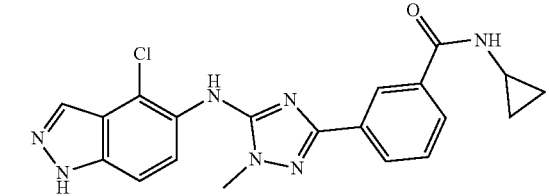
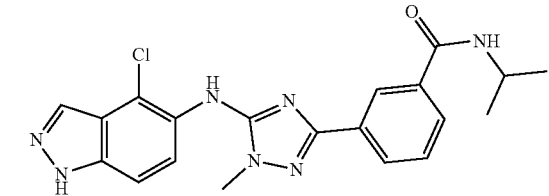
-continued
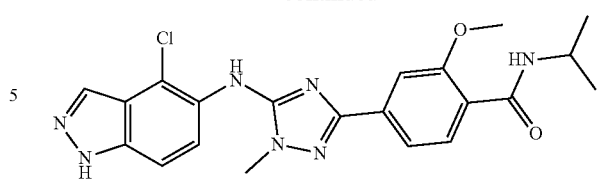
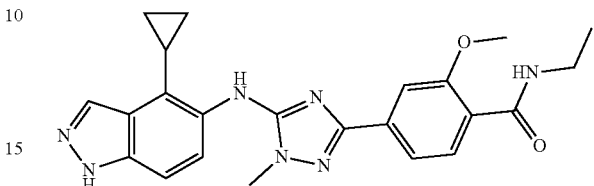
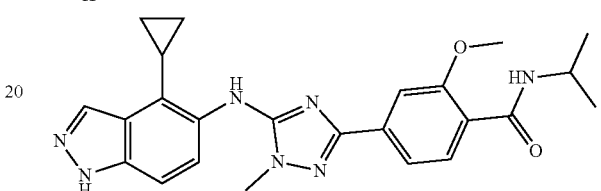
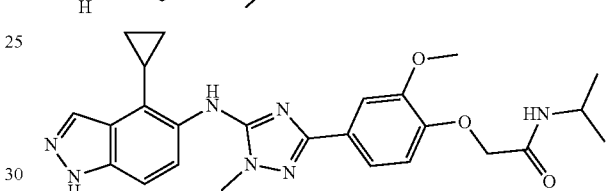
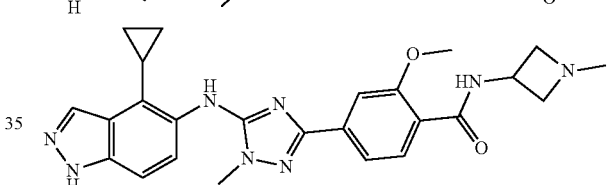
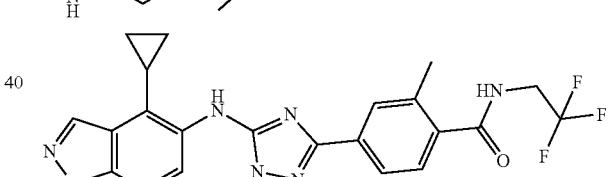
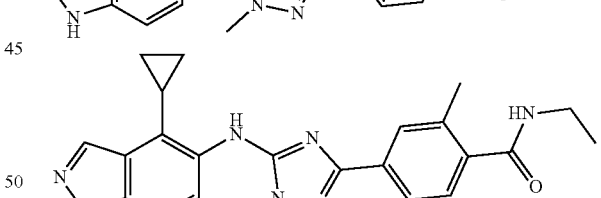
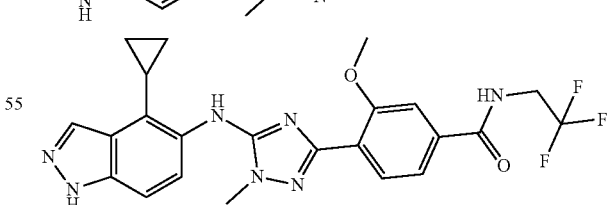
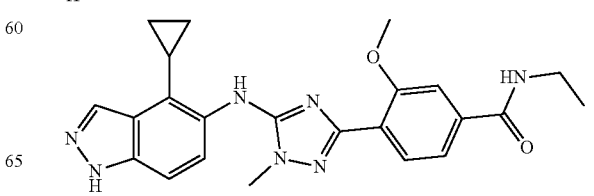

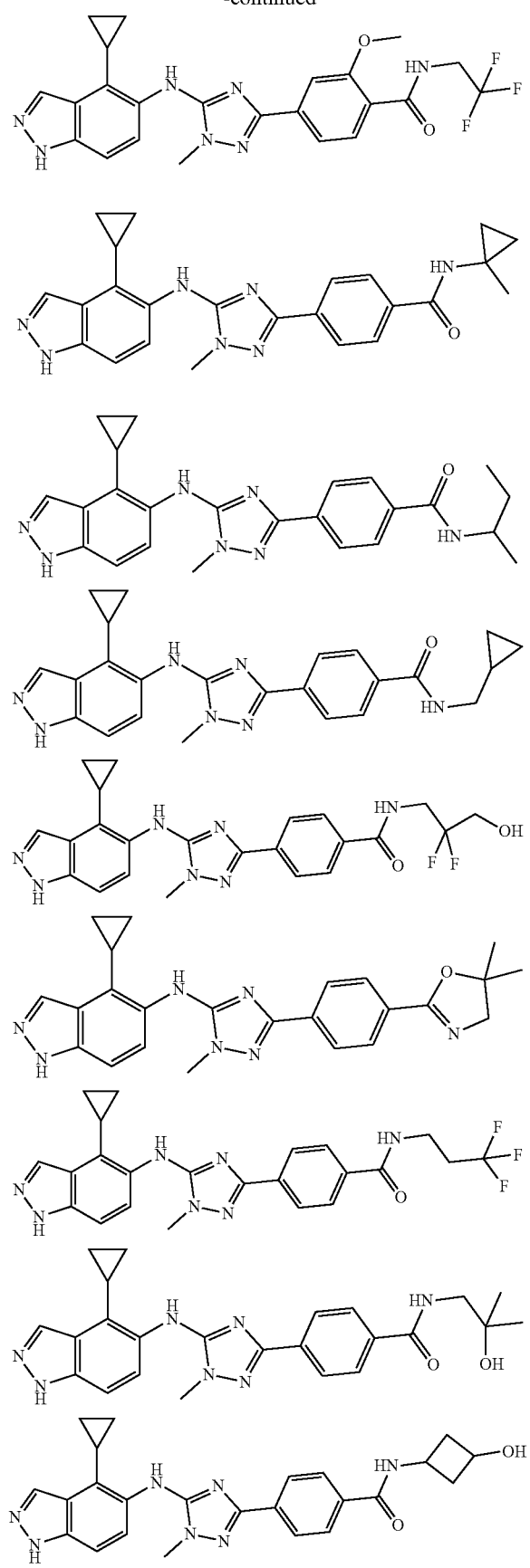
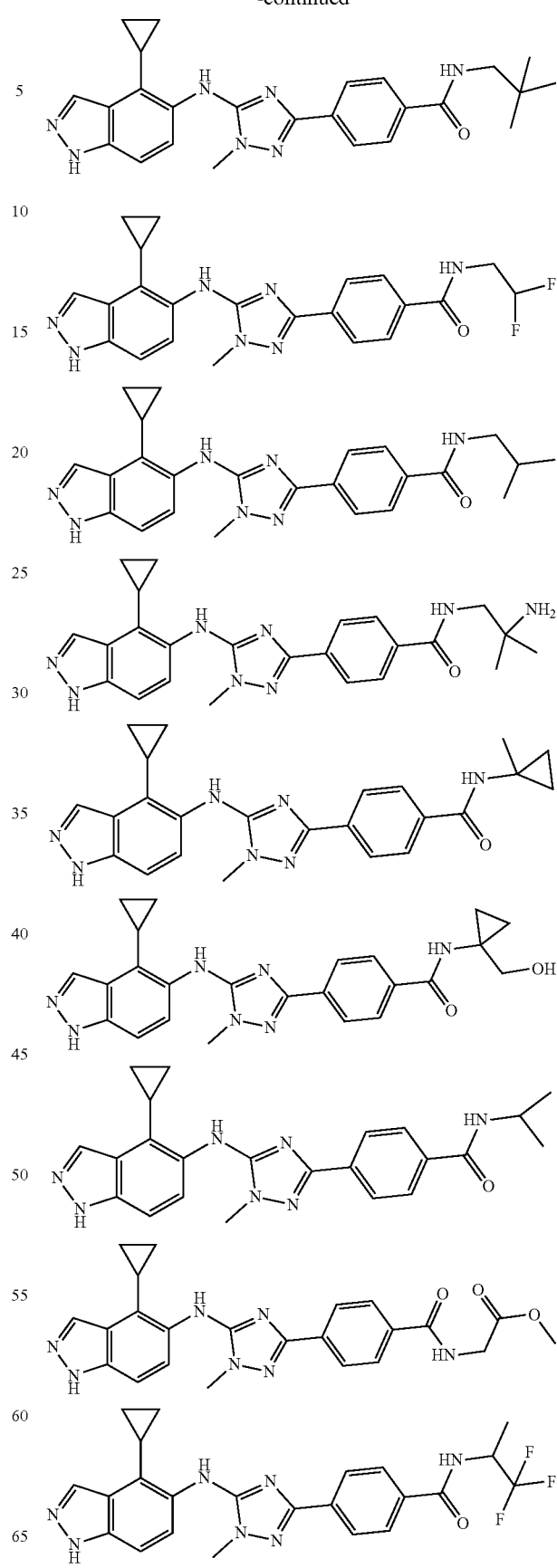

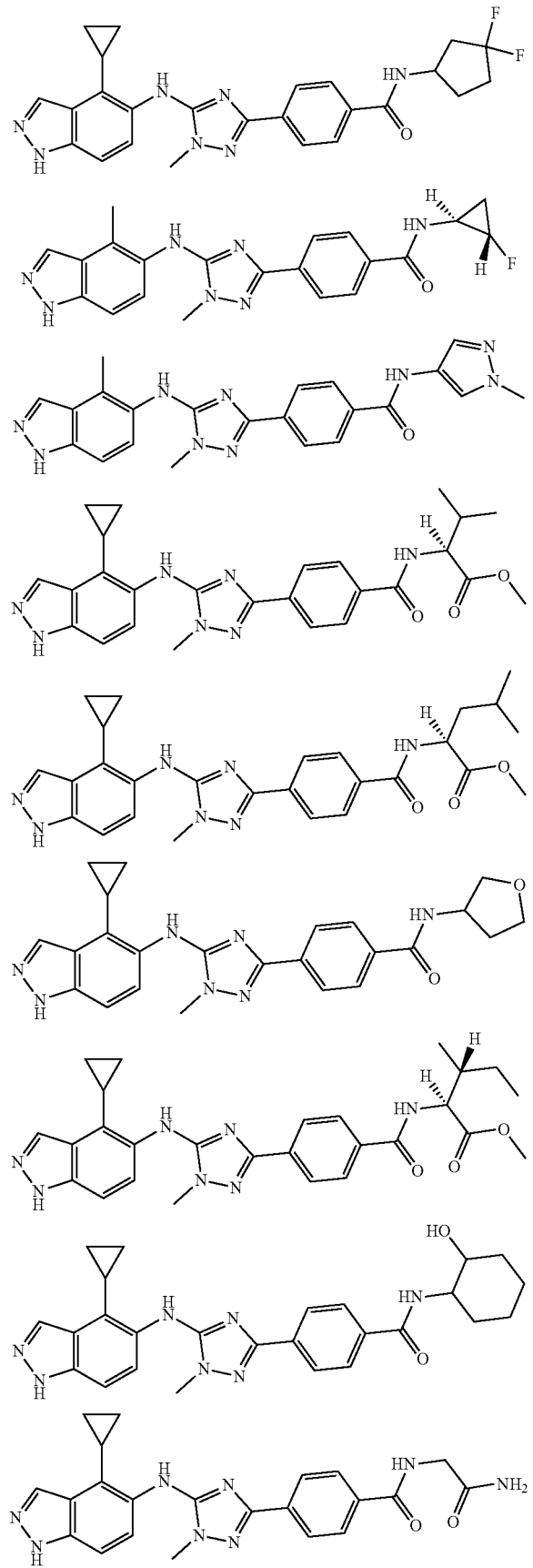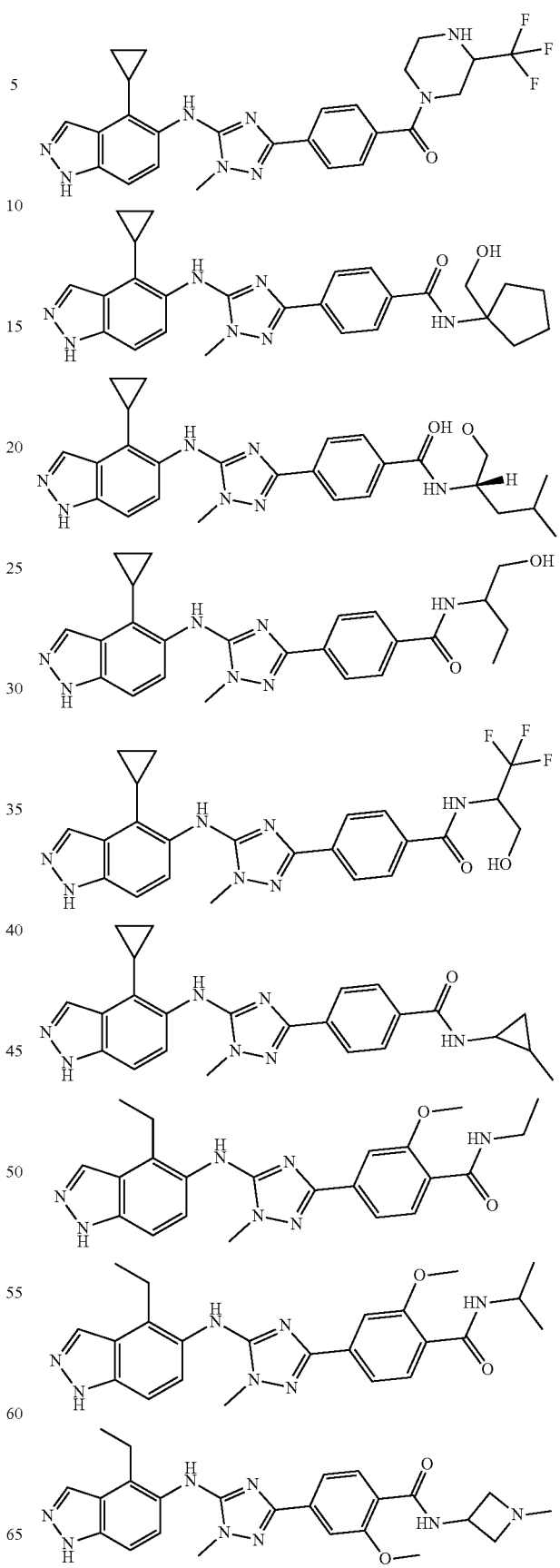

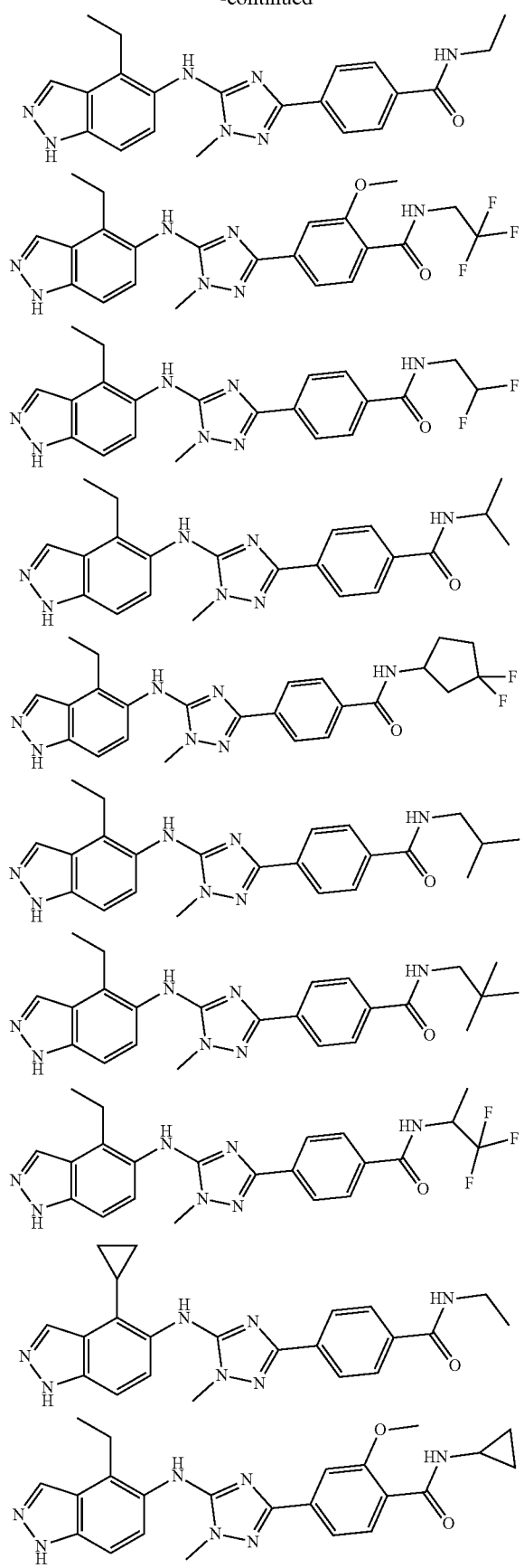
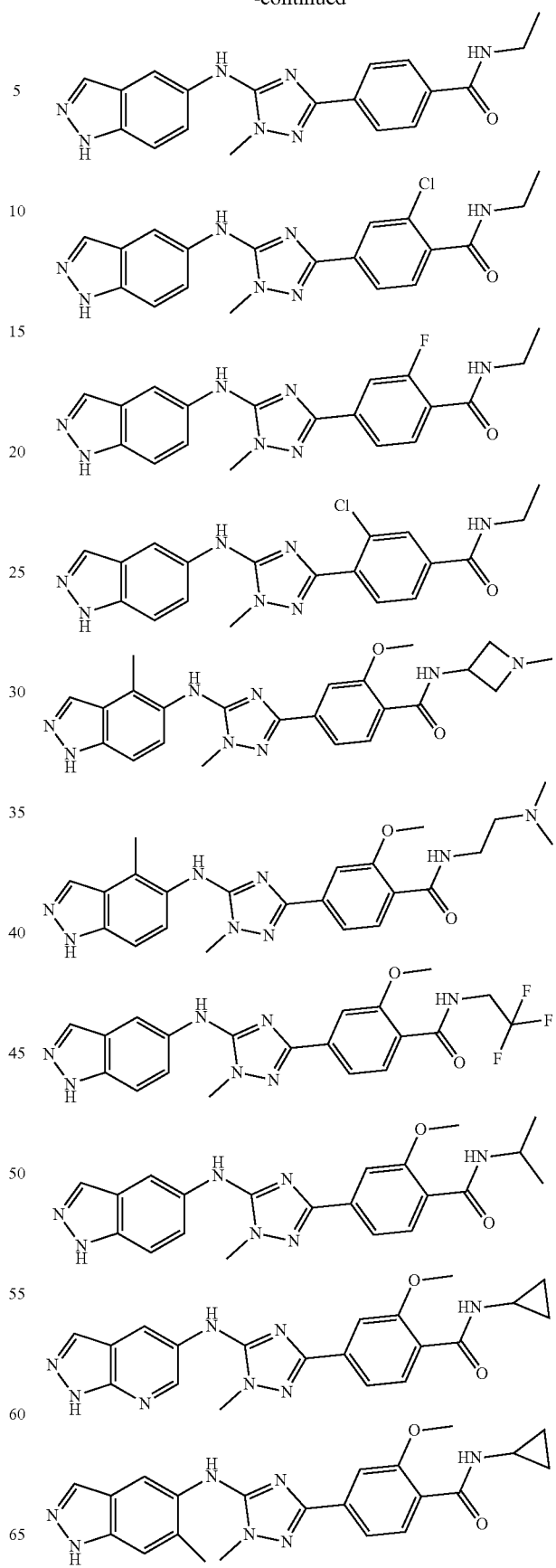

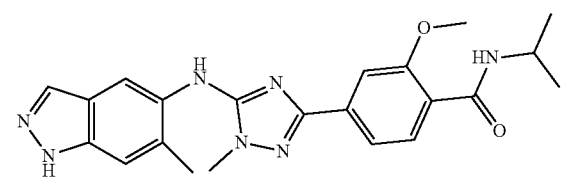
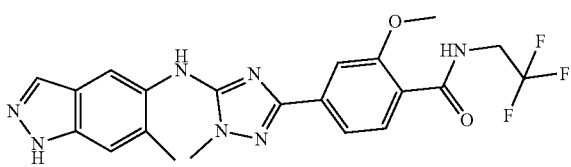
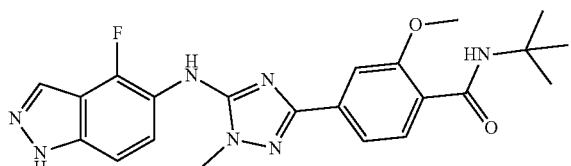
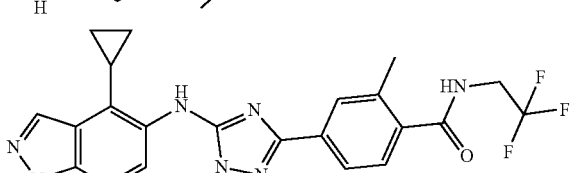
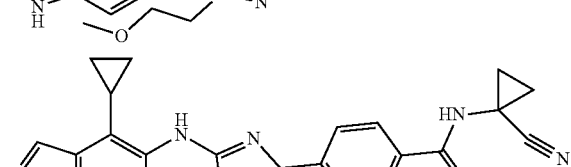

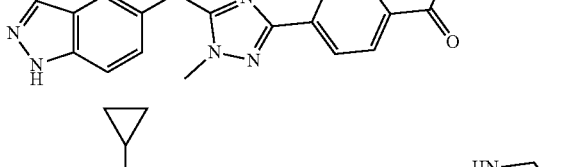
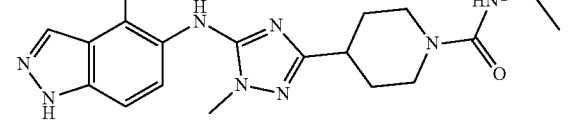
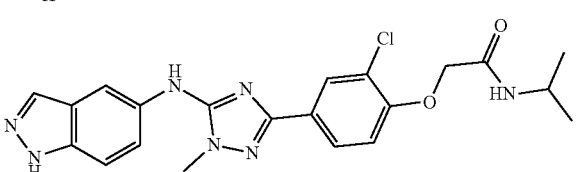
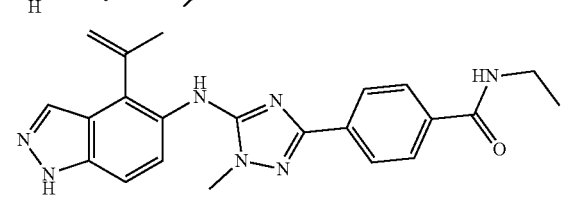
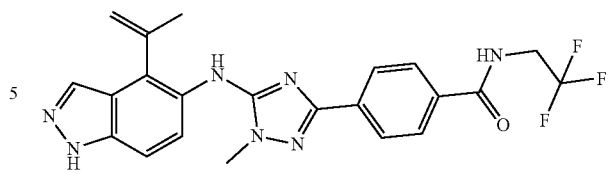

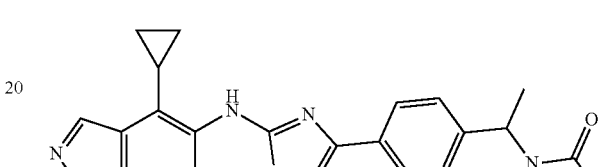
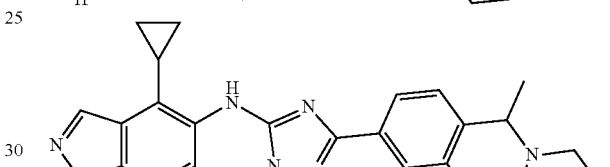
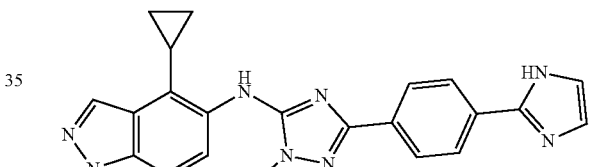
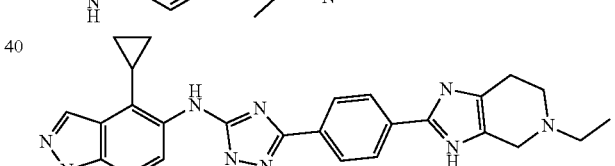
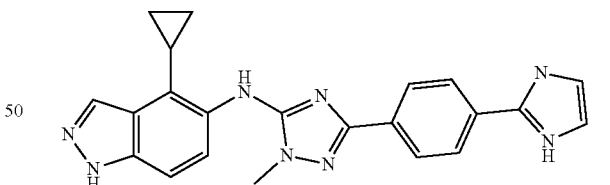
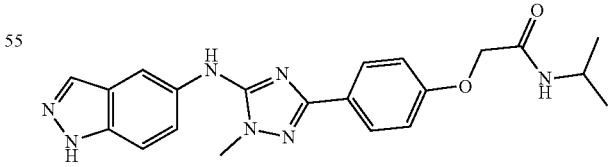
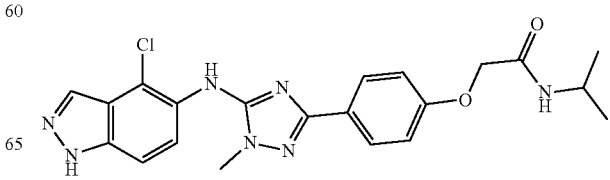

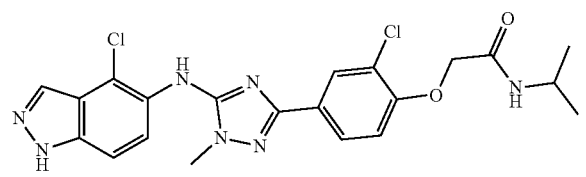
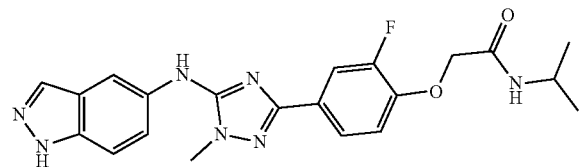
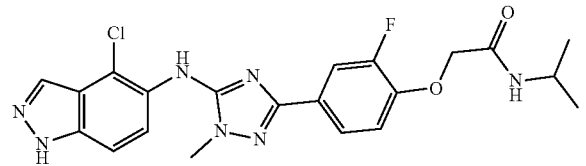
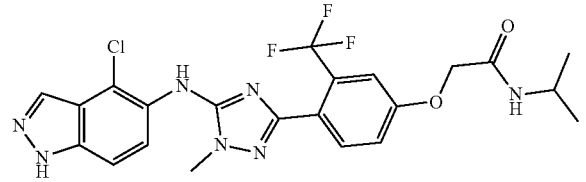
The present invention also provides compounds of formula (I) selected from:
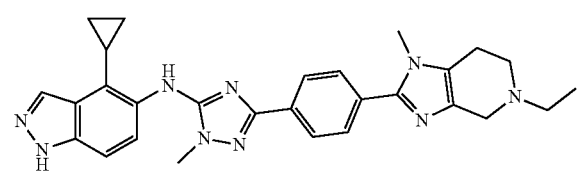
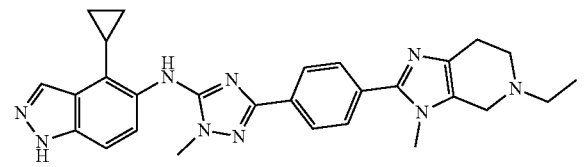
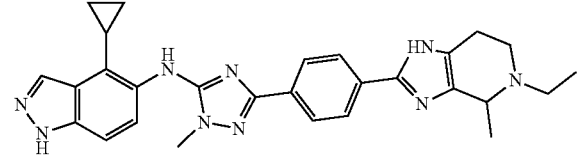
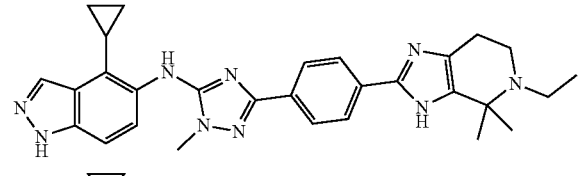
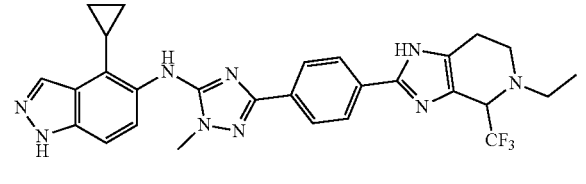
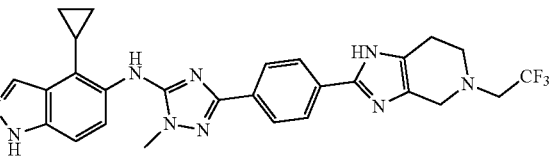
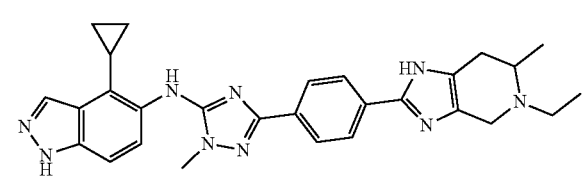
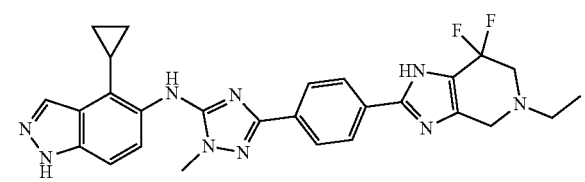
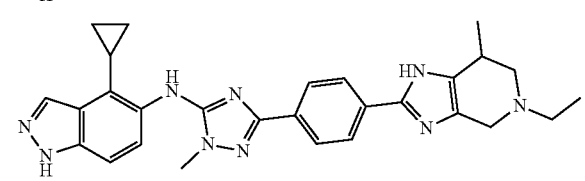
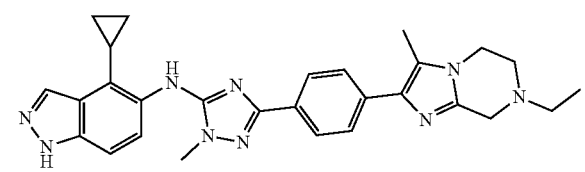
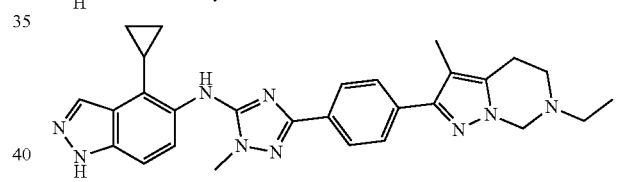
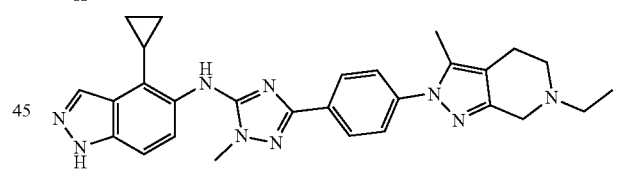
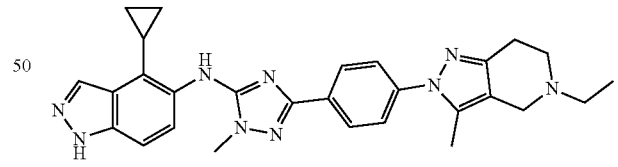
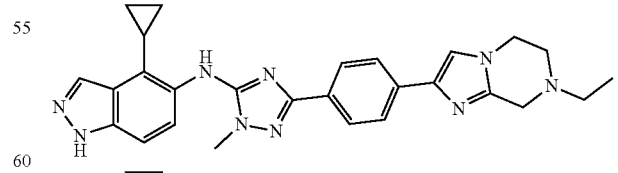
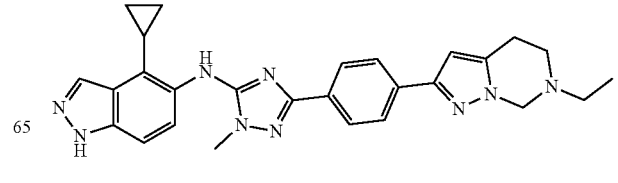

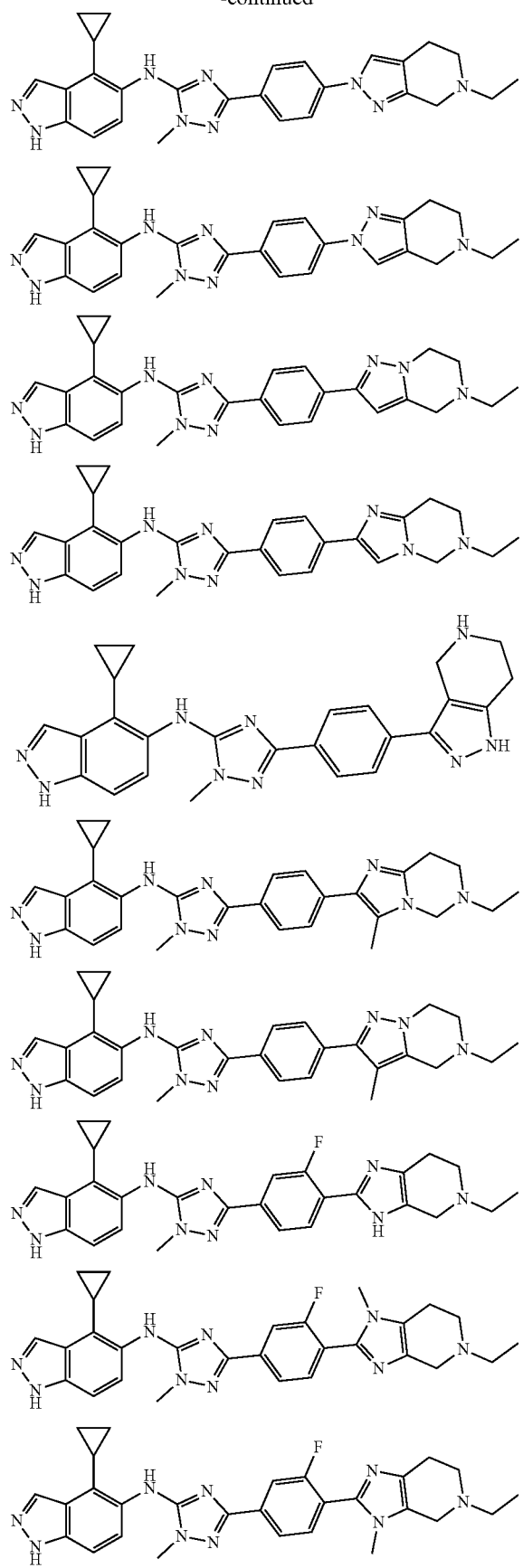
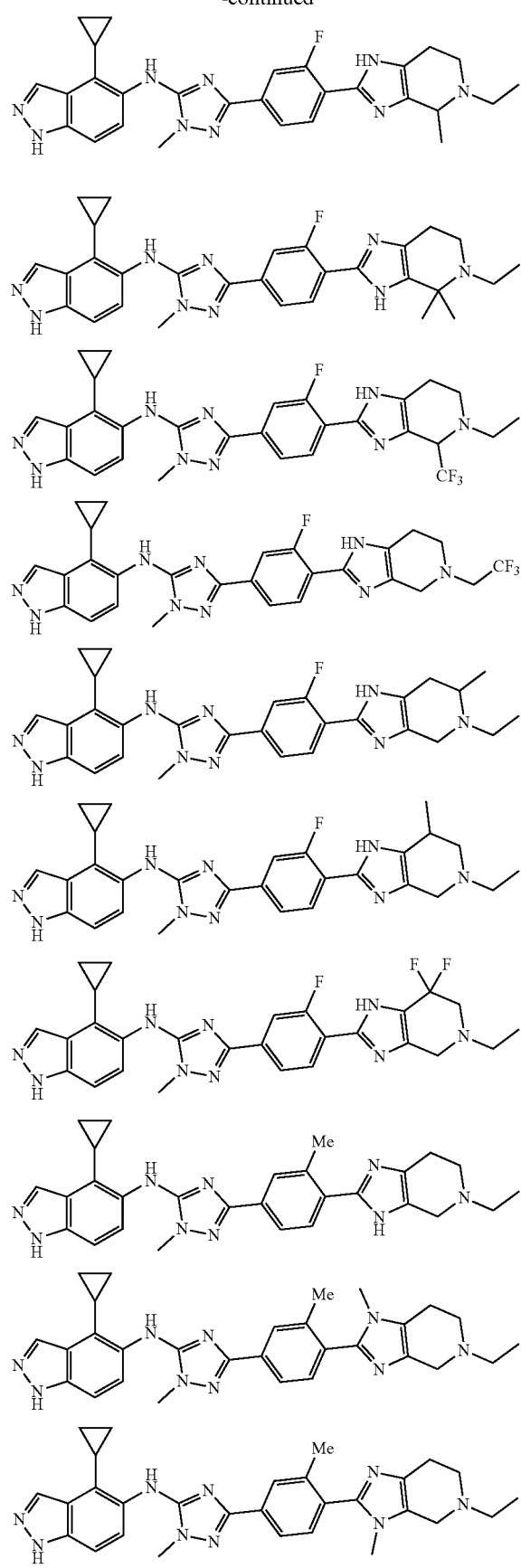

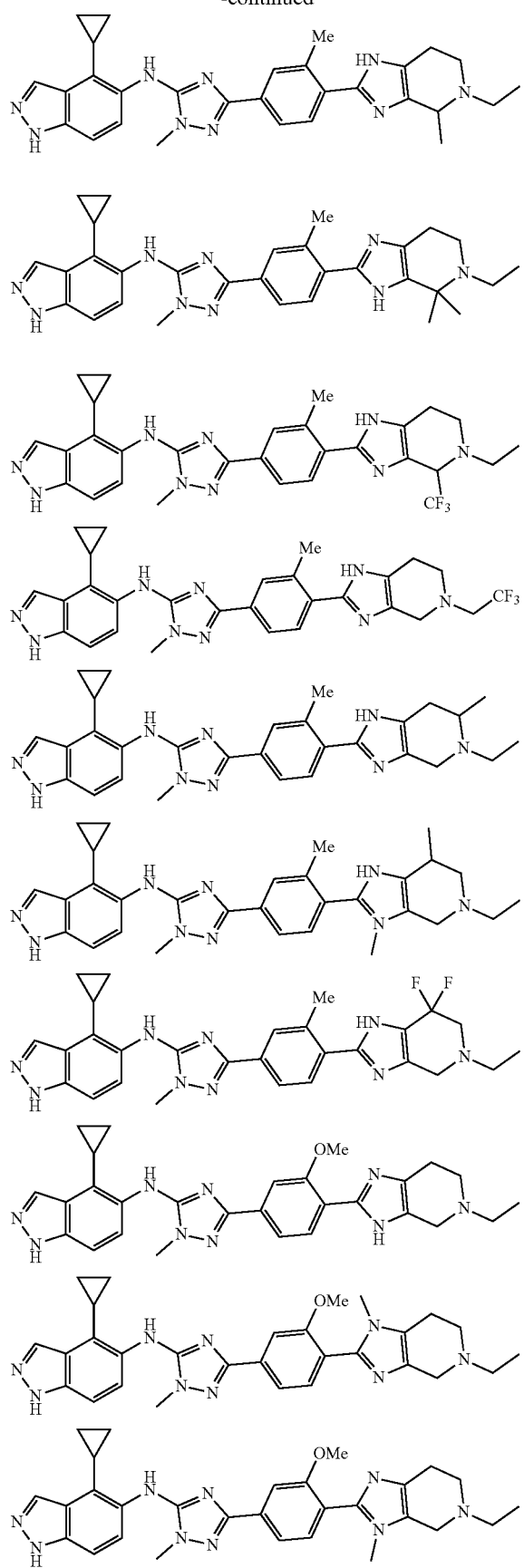
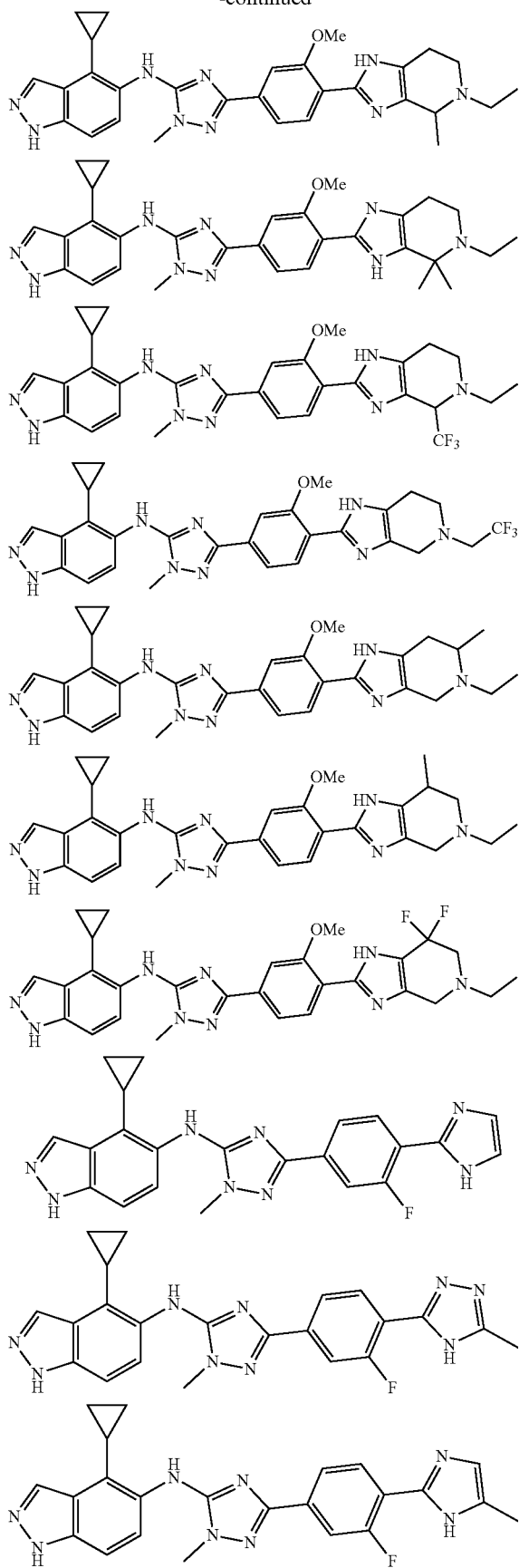

-continued

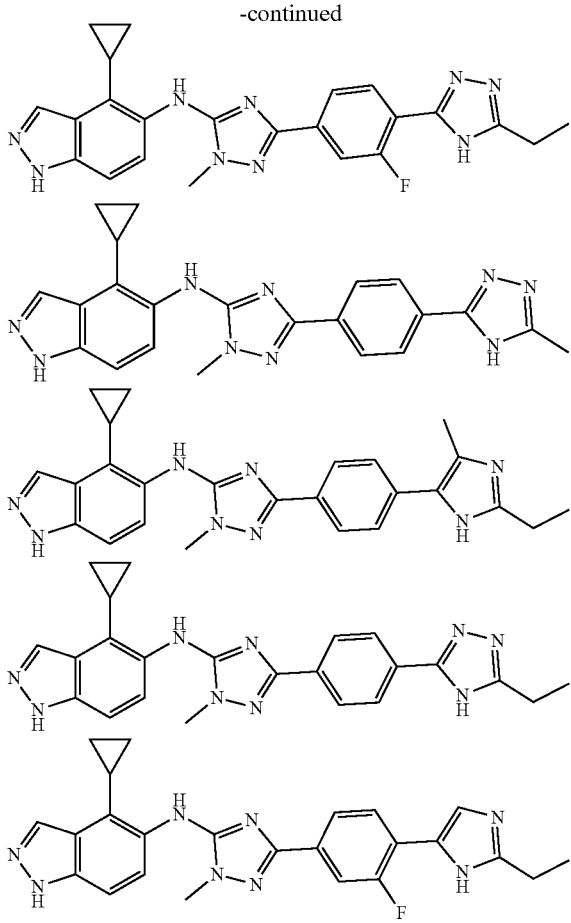

In an embodiment there is provided compounds of the present invention having a ROCK2 binding affinity within category +++ or ++++ as defined elsewhere herein. In an embodiment there is provided compounds of the present invention having a ROCK2 binding of inky IC50 value of <3 µM.

In an embodiment there is provided compounds of the present invention having a ROCK2 binding affinity IC50 value of <0.3 µM. Optionally, the binding activity is determined using the assay for ROCK2 inhibition defined in the examples.

In an aspect of the invention there is provided the compounds of the present invention for use as a medicament.

In accordance with another aspect, the present invention provides a pharmaceutical formulation comprising a compound of the present invention and a pharmaceutically acceptable excipient.

In an embodiment, the pharmaceutical composition may be a combination product comprising an additional pharmaceutically active agent. The additional pharmaceutically active agent may be, for example anti-inflammatory agents, anti-fibrotic agents, chemotherapeutics, anti-cancer agents, immunosuppressants, anti-tumour vaccines, cytokine therapy, or tyrosine kinase inhibitors.

In accordance with another aspect, there is provided a compound of the present invention for use in the treatment of a condition which is modulated by ROCK1 and/or ROCK2. Usually conditions that are modulated by ROCKs (please note that ROCKs refer to ether or both of ROCK1 and ROCK2) are conditions that would be treated by the inhibition of ROCKs using a compound of the present invention. A compound of any formula disclosed herein may be for use in the treatment of a condition treatable by the inhibition of ROCKs.

As discussed above, ROCK signalling is instrumental in a number of conditions. Therefore, the condition treatable by the inhibition of ROCK1 and/or ROCK2 is selected from: fibrotic diseases, auto-immune, inflammatory-fibrotic conditions, inflammatory conditions, central nervous system disorders, or cancer.

The condition treatable by the inhibition of ROCK1 and/or ROCK2 is selected from: Sarcoidosis, sclerosis, primary Mary sclerosis, sclerosing cholangitis, dermatitis, atopic dermatitis, Still's disease, chronic obstructive pulmonary disease, Guillain-Barre disease, Graves' disease, Addison's disease, Raynaud's phenomenon, or autoimmune hepatitis. Arthritis, rheumatoid arthritis, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, and fibromyalgia. Additional types of arthritis include Achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate dihydrate deposition disease (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-Induced osteoporosis, costosternal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-Induced lupus, Duchenne's muscular dystrophy, Dupuytren's contracture, Ehlers-Danlos syndrome, enteropathic arthritis, epicondylitis, erosive inflammatory osteoarthritis, exercise-Induced compartment syndrome, Fabry's disease, familial Mediterranean fever, Farber's lipogranulomatosis, Felty's syndrome, Fifth's disease, flat feet, foreign body synovitis, Freiberg's disease, fungal arthritis, Gaucher's disease, giant cell arteritis, gonococcal arthritis, Goodpasture's syndrome, granulomatous arteritis, hem arthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, linear scleroderma, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopoysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis Paget's disease of bone, palindromic rheumatism, patellofemoral pain syndrome, Pellegrini-Stieda syndrome, pigmented vilonodular synovitis, piriformis syndrome, plantar fascitis, poyarteritis nodos, Polymyalgia rheumatic, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, retrocalcaneal bursitis, rheumatic fever, rheumatoid vasculitis, rotator cuff tendinitis, sacroiliitis, salmonella osteomyelitis, sarcoidosis, saturnine gout, Scheuermann's osteochondritis, scleroderma, septic arthritis, seronegative arthritis, shigella arthritis, shoulder-hand syndrome, sickle cell arthropathy, Sjogren's syndrome, slipped capital femoral epiphysis, spinal stenosis, spondylolysis, staphylococcus arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tsetse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, yersinial arthritis and conditions involving vascularization and/or inflammation, include atherosclerosis, rheumatoid arthritis (RA), hemangiomas, angiofibromas, and psoriasis. Other non-limiting examples of angiogenic disease are retinopathy of prematurity (retrolental fibroplastic), corneal graft rejection, corneal neovascularization related to complications of refractive surgery, corneal neovascularization related to contact lens complications, corneal neovascularization related to pterygium and recurrent pterygium, corneal ulcer disease, and non specific ocular surface disease, insulin-dependent diabetes mellitus, multiple sclerosis, myasthenia gravis, Chrorfs disease, autoimmune nephritis, primary biliary cirrhosis, acute pancreatitis, allograph rejection, allergic inflammation, contact dermatitis and delayed hypersensitivity reactions, inflammatory bowel disease, septic shock, osteoporosis, osteoarthritis, cognition defects induced by neuronal inflammation, Osier-Weber syndrome, restinosis, and fungal, parasitic and viral infections, including cytomegalo viral infections.

Any of the conditions disclosed above as being treatable by ROCK1 and/or ROCK2 inhibition may be treated by a compound of the invention, or may be treated in a method comprising administering a compound of the invention, or may be treated by a medicament manufactured through the use of a compound of the present invention.

In an aspect of the invention, a compound of the invention may be for use in the treatment of: fibrotic diseases, auto-immune, inflammatory-fibrotic conditions, inflammatory conditions, central nervous system disorders, or cancer.

In embodiments, a compound of the invention may be for use in the treatment of and condition selected from: Idiopathic Pulmonary Fibrosis (IPF); systemic sclerosis (SSC); interstitial lung disease (ILD); type 1 and type 2 diabetes; diabetic nephropathy; Nonalcoholic Steatohepatitis (NASH); Nonalcoholic fatty liver disease (NAFLD); hypertension, atherosclerosis, restenosis, stroke, heart failure, coronary vasospasm, cerebral vasospasm, peripheral circulatory disorder, peripheral artery occlusive disease, ischemia/reperfusion injury, pulmonary hypertension and angina, erectile dysfunction, fibroid lung, fibroid liver and fibroid kidney. glaucoma, ocular hypertension, retinopathy, rheumatoid arthritis, psoriasis, psoriatic arthritis, Sjogren's syndrome, asthma, adult respiratory distress syndrome, chronic obstructive pulmonary disease (COPD), SLE, cGVHD, inflammatory bowel disease, stenosis of the bowel, disorders involving neuronal degeneration or physical injury to neural tissue, Huntington's disease, Parkinson's Disease, Alzheimers, Amyotrophic lateral sclerosis (ALS), multiple sclerosis, liver cancer, bladder cancer, hepatoma, squamous carcinoma of the lung, non-small cell lung cancer, adenocarcinoma of the lung, small-cell lung cancer, various types of head and neck cancer, breast cancer, colon cancer, colorectal cancer, cancer of the peritoneum, hepatocellular cancer, gastrointestinal cancer, esophageal cancer, endometrial or uterine carcinoma, salivary gland carcinoma, squamous cell cancer, pituitary cancer, astrocytoma, soft tissue sarcoma, pancreatic cancer, glioblastoma, cervical cancer, ovarian cancer, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer and melanoma.

In an aspect of the invention there is provided a method of treating a condition which is modulated by ROCK1 and/or ROCK2 wherein the method comprises administering a therapeutic amount of a compound of the invention, to a patient in need thereof.

The method of treatment may be a method of treating a condition treatable by the inhibition of ROCK1 and/or ROCK2.

The invention also provides a method of treating a condition selected from: fibrotic diseases, auto-immune, inflammatory-fibrotic conditions, inflammatory conditions, central nervous system disorders, or cancer, wherein the method comprises administering a therapeutic amount of a compound of any formula disclosed herein, to a patient in need thereof.

In embodiments, the method may be for use in the treatment of a condition selected from: Idiopathic Pulmonary Fibrosis (IPF); systemic sclerosis (SSC); interstitial lung disease (ILD); type 1 and type 2 diabetes; diabetic nephropathy; Nonalcoholic Steatohepatitis (NASH); Nonalcoholic fatty liver disease (NAFLD); hypertension, atherosclerosis, restenosis, stroke, heart failure, coronary vasospasm, cerebral vasospasm, peripheral circulatory disorder, peripheral artery occlusive disease, ischemia/reperfusion injury, pulmonary hypertension and angina, erectile dysfunction, fibroid lung, fibroid liver and fibroid kidney. glaucoma, ocular hypertension, retinopathy, rheumatoid arthritis, psoriasis, psoriatic arthritis, Sjogren's syndrome, asthma, adult respiratory distress syndrome, chronic obstructive pulmonary disease (COPD), SLE, cGVHD, inflammatory bowel disease, stenosis of the bowel, disorders involving neuronal degeneration or physical injury to neural tissue, Huntington's disease, Parkinson's Disease, Alzheimers, Amyotrophic lateral sclerosis (ALS), multiple sclerosis, liver cancer, bladder cancer, hepatoma, squamous carcinoma of the lung, non-small cell lung cancer, adenocarcinoma of the lung, small-cell lung cancer, various types of head and neck cancer, breast cancer, colon cancer, colorectal cancer, cancer of the peritoneum, hepatocellular cancer, gastrointestinal cancer, esophageal cancer, endometrial or uterine carcinoma, salivary gland carcinoma, squamous cell cancer, pituitary cancer, astrocytoma, soft tissue sarcoma, pancreatic cancer, glioblastoma, cervical cancer, ovarian cancer, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer and melanoma, wherein the method comprises administering a therapeutic amount of a compound of any formula disclosed herein, to a patient in need thereof.

In certain embodiments, compounds of the invention are for use in the treatment of or are used in a method of treatment of: Idiopathic Pulmonary Fibrosis (IPF); systemic sclerosis (SSC); interstitial lung disease (ILD); type 1 and type 2 diabetes; diabetic nephropathy; Nonalcoholic Steatohepatitis (NASH); Nonalcoholic fatty liver disease (NAFLD); hypertension, atherosclerosis, restenosis, stroke, heart failure, coronary vasospasm, cerebral vasospasm, peripheral circulatory disorder, peripheral artery occlusive disease, ischemia/reperfusion injury, pulmonary hypertension and angina, and erectile dysfunction, fibroid lung, fibroid liver and fibroid kidney.

In certain embodiments compounds of the invention are for use in the treatment of or are used in a method of treatment of: glaucoma, ocular hypertension, retinopathy, rheumatoid arthritis, psoriasis, psoriatic arthritis, Sjogren's syndrome, asthma, adult respiratory distress syndrome, chronic obstructive pulmonary disease (COPD), SLE and cGVHD, inflammatory bowel disease and stenosis of the bowel.

In certain embodiments, compounds of the invention are for use in the treatment of or are used in a method of treatment of central nervous system disorders. Such disorders may involve neuronal degeneration or physical injury to neural tissue, including without limitation, Huntington's disease, Parkinson's Disease, Alzheimer's, Amyotrophic lateral sclerosis (ALS), or multiple sclerosis.

In certain embodiments compounds of the invention are for use in the treatment of or are used in a method of treatment of cancer. Examples include but are not limited to: liver cancer, bladder cancer, hepatoma, squamous carcinoma of the lung, non-small cell lung cancer, adenocarcinoma of the lung, small-cell lung cancer, various types of head and neck cancer, breast cancer, colon cancer, colorectal cancer, cancer of the peritoneum, hepatocellular cancer, gastrointestinal cancer, esophageal cancer, endometrial or uterine carcinoma, salivary gland carcinoma, squamous cell cancer, pituitary cancer, astrocytoma, soft tissue sarcoma, pancreatic cancer, glioblastoma, cervical cancer, ovarian cancer, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer and melanoma.

In another aspect of the invention there is provided a pharmaceutical composition, wherein the composition comprises a compound of the invention and pharmaceutically acceptable excipients.

In an embodiment the pharmaceutical composition may be a combination product comprising an additional pharmaceutically active agent. The additional pharmaceutically active agent may be one disclosed elsewhere herein.

In an aspect of the present invention there is provided the use of a compound of the invention in the manufacture of a medicament for use in the treatment of any condition disclosed herein.

In an embodiment the compounds of the present invention are at least five times more potent inhibitors of ROCK2 compared to ROCK1. Accordingly, the compounds of the invention may be at least five times more selective towards ROCK2 than ROCK1.

DETAILED DESCRIPTION

Given below are definitions of terms used in this application. Any term not defined herein takes the normal meaning as the skilled person would understand the term.

The term "halo" refers to one of the halogens, group 17 of the periodic table. In particular, the term refers to fluorine, chlorine, bromine and iodine. Preferably, the term refers to bromine or iodine.

The term "alkyl" refers to a linear or branched hydrocarbon chain. For example, the term "$C_{1-6}$ alkyl" refers to a linear or branched hydrocarbon chain containing 1, 2, 3, 4, 5 or 6 carbon atoms, for example methyl, ethyl, n-propyl, iso-propyl, n-butyl, sec-butyl, ten-butyl, n-pentyl and n-hexyl. Alkylene groups may likewise be linear or branched and may have two places of attachment to the remainder of the molecule. Furthermore, an alkylene group may, for example, correspond to one of those alkyl groups listed in this paragraph. The alkyl and alkylene groups may be unsubstituted or substituted by one or more substituents. Possible substituents are described below. Substituents for the alkyl group may be halogen, e.g. fluorine, chlorine, bromine and iodine, OH, $C_{1-6}$ alkoxy.

The term "alkylether" refers to a linear or branched hydrocarbon chain interrupted by a single oxygen atom. For example, the term "$C_{2-6}$ alkylether" refers to a linear or branched hydrocarbon chain containing 1, 2, 3, 4, 5 or 6 carbon atoms where the chain of carbon atoms is interrupted by a single oxygen atom, for example —$CH_2OCH_3$, —$(CH_2)_2OCH_3$, —$(CH_2)_3OCH_3$, —$CH_2OCH_2CH_3$, —$CH_2O(CH_2)_2CH_3$, or —$(CH_2)_2OCH_2CH_3$.

The term "alkoxy" refers to an alkyl group which is attached to a molecule via oxygen. For example, the term "$C_{1-6}$ alkoxy" refers to a group where the alkyl part may be linear or branched and may contain 1, 2, 3, 4, 5 or 6 carbon atoms, for example methyl, ethyl, n-propyl, iso-propyl, n-butyl, sec-butyl, ten-butyl, n-pentyl and n-hexyl. Therefore, the alkoxy group may be methoxy, ethoxy, n-propoxy, iso-propoxy, n-butoxy, sec-butoxy, tert-butoxy, n-pentoxy and n-hexoxy. The alkyl part of the alkoxy group may be unsubstituted or substituted by one or more substituents. Possible substituents are described below. Substituents for the alkyl group may be halogen, e.g. fluorine, chlorine, bromine and iodine, OH, $C_{1-6}$ alkoxy.

The term "haloalkyl" refers to a hydrocarbon chain substituted with at least one halogen atom independently chosen at each occurrence, for example fluorine, chlorine, bromine and iodine. For example, the term "$C_{1-6}$ haloalkyl" refers to a linear or branched hydrocarbon chain containing 1, 2, 3, 4, 5 or 6 carbon atoms substituted with at least one halogen. The halogen atom may be present at any position on the hydrocarbon chain. For example, $C_{1-6}$ haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "alkenyl" refers to a branched or linear hydrocarbon chain containing at least one double bond. For example, the term "$C_{2-6}$ alkenyl" refers to a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl.

The term "alkynyl" refers to a branched or linear hydrocarbon chain containing at least one triple bond. For example, the term "$C_{2-6}$ alkynyl" refers to a branched or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl.

The term "heteroalkyl" refers to a branched or linear hydrocarbon chain containing at least one heteroatom selected from N, O and S positioned between any carbon in the chain or at an end of the chain. For example, the term "$C_{1-6}$ heteroalkyl" refers to a branched or linear hydrocarbon chain containing 1, 2, 3, 4, 5, or 8 carbon atoms and at least one heteroatom selected from N, O and S positioned between any carbon in the chain or at an end of the chain. For example, the hydrocarbon chain may contain one or two heteroatoms. The $C_{1-6}$ heteroalkyl may be bonded to the rest of the molecule through a carbon or a heteroatom. For example, the "$C_{1-6}$ heteroalkyl" may be $C_{1-6}$ N-alkyl, $C_{1-6}$ N,N-alkyl, or $C_{1-6}$ O-alkyl.

The term "carbocyclic" refers to a saturated, unsaturated or aromatic carbon containing ring system. A "carbocyclic" system may be monocyclic or a fused polycyclic ring system, for example, bicyclic or tricyclic. A "carbocyclic" moiety may contain from 3 to 14 carbon atoms, for example, 3 to 8 carbon atoms in a monocyclic system and 7 to 14 carbon atoms in a polycyclic system. "Carbocyclic" encompasses cycloalkyl moieties, cycloalkenyl moieties, aryl ring systems and fused ring systems including an aromatic portion.

The term "heterocyclic" refers to a saturated, unsaturated or aromatic ring system containing at least one heteroatom selected from N, O or S. A "heterocyclic" system may contain 1, 2, 3 or 4 heteroatoms, for example 1 or 2. A "heterocyclic" system may be monocyclic or a fused polycyclic ring system, for example, bicyclic or tricyclic. A "heterocyclic" moiety may contain from 3 to 14 carbon atoms, for example, 3 to 8 carbon atoms in a monocyclic system and 7 to 14 carbon atoms in a polycyclic system. "Heterocyclic" encompasses heterocycloalkyl moieties, heterocycloalkenyl moieties and heteroaromatic moieties. For example, the heterocyclic group may be: oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The term "$C_{3-8}$ cycloalkyl" refers to a saturated hydrocarbon ring system containing 3, 4, 5, 6, 7 or 8 carbon atoms. For example, the "$C_{3-8}$ cycloalkyl" may be cyclopropyl, cyclobutyl, cyclopentyl, cyclohexyl, cycloheptyl and cyclooctyl.

The term "$C_{3-8}$ cycloalkenyl" refers to an unsaturated hydrocarbon ring system containing 3, 4, 5, 6, 7 or 8 carbon atoms that is not aromatic. The ring may contain more than one double bond provided that the ring system is not aromatic. For example, the "$C_{3-8}$ cycloalkyl" may be cyclopropenyl, cyclobutenyl, cyclopentenyl, cyclopentadienyl, cyclohexenyl, cyclohexadienly, cycloheptenyl, cycloheptadiene, cyclooctenyl and cycloatadienyl.

The term "heterocycloalkyl" refers to a saturated hydrocarbon ring system containing carbon atoms and at least one heteroatom within the ring selected from N, O and S. For example, there may be 1, 2 or 3 heteroatoms, optionally 1 or 2. The "heterocycloalkyl" may be bonded to the rest of the molecule through any carbon atom or heteroatom. The "heterocycloalkyl" may have one or more, e.g. one or two, bonds to the rest of the molecule: these bonds may be through any of the atoms in the ring. For example, the "heterocycloalkyl" may be a "$C_{3-8}$ heterocycloalkyl". The term "$C_{3-8}$ heterocycloalkyl" refers to a saturated hydrocarbon ring system containing 3, 4, 5, 6, 7 or 8 atoms at least one of the atoms being a heteroatom within the ring selected from N, O and S. The "heterocycloalkyl" may be oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The term "heterocycloalkenyl" refers to an unsaturated hydrocarbon ring system that is not aromatic, containing carbon atoms and at least one heteroatom within the ring selected from N, O and S. For example there may be 1, 2 or 3 heteroatoms, optionally 1 or 2. The "heterocycloalkenyl" may be bonded to the rest of the molecule through any carbon atom or heteroatom. The "heterocycloalkenyl" may have one or more, e.g. one or two, bonds to the rest of the molecule: these bonds may be through any of the atoms in the ring. For example, the "heterocycloalkenyl" may be a "$C_{3-8}$ heterocycloalkenyl". The term "$C_{3-8}$ heterocycloalkenyl" refers to a saturated hydrocarbon ring system containing 3, 4, 5, 6, 7 or 8 atoms at least one of the atoms being a heteroatom within the ring selected from N, O and S. The "heterocycloalkenyl" may be tetrahydropyridine, dihydropyran, dihydrofuran, pyrroline.

The term "aromatic" when applied to a substituent as a whole means a single ring or polycyclic ring system with 4n+2 electrons in a conjugated π system within the ring or ring system where all atoms contributing to the conjugated π system are in the same plane.

The term "aryl" refers to an aromatic hydrocarbon ring system. The ring system has 4n+2 electrons in a conjugated π system within a ring where all atoms contributing to the conjugated π system are in the same plane. For example, the "aryl" may be phenyl and naphthyl. The aryl system itself may be substituted with other groups.

The term "heteroaryl" refers to an aromatic hydrocarbon ring system with at least one heteroatom within a single ring or within a fused ring system, selected from O, N and S. The ring or ring system has 4n+2 electrons in a conjugated π system where all atoms contributing to the conjugated π system are in the same plane. For example, the "heteroaryl" may be imidazole, thiene, furane, thianthrene, pyrrol, benzimidazole, pyrazole, pyrazine, pyridine, pyrimidine and indole.

The term "alkaryl" refers to an aryl group, as defined above, bonded to a $C_{1-4}$ alkyl, where the $C_{1-4}$ alkyl group provides attachment to the remainder of the molecule. Benzyl refers to —$CH_2$phenyl and benzoyl refers to —C(O)phenyl.

The term "alkheteroaryl" refers to a heteroaryl group, as defined above, bonded to a $C_{1-4}$ alkyl, where the alkyl group provides attachment to the remainder of the molecule.

The term "halogen" herein includes reference to F, Cl, Br and I. Halogen may be Br. Halogen may be I.

A bond terminating in a "  " represents that the bond is connected to another atom that is not shown in the structure. A bond terminating inside a cyclic structure and not terminating at an atom of the ring structure represents that the bond may be connected to any of the atoms in the ring structure where allowed by valency.

A bond drawn as a solid line and a dotted line represents a bond which can be either a single bond or a double bond, where chemically possible. For example, the bond drawn below could be a single bond or a double bond.

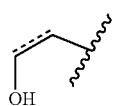

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different. The substituent(s) may be selected from: OH, NHR, amidino, guanidino, hydroxyguanidino, formamidino, isothioureido, ureido, mercapto, C(O)H, acyl, acyloxy, carboxy, sulfo, sulfamoyl, carbamoyl, cyano, azo, nitro, halo, $C_{1-6}$ alkyl, $C_{1-6}$ alkoxy, $C_{1-6}$ haloalkyl, $C_{3-8}$ cycloalkyl, $C_{2-6}$ alkenyl, $C_{2-6}$ alkynyl, aryl, heteroaryl or alkaryl. Where the group to be substituted is an alkyl group the substituent may be =O. R may be selected from H, $C_{1-6}$ alkyl, $C_{3-8}$ cycloalkyl, phenyl, benzyl or phenethyl group, e.g. R is H or $C_{1-3}$ alkyl. Where the moiety is substituted with two or more substituents and two of the substituents are adjacent the adjacent substituents may form a $C_{4-8}$ ring along with the atoms of the moiety on which the substituents are substituted, wherein the $C_{4-8}$ ring is a saturated or unsaturated hydrocarbon ring with 4, 5, 6, 7, or 8 carbon atoms or a saturated or unsaturated hydrocarbon ring with 4, 5, 6, 7, or 8 carbon atoms and 1, 2 or 3 heteroatoms.

Substituents are only present at positions where they are chemically possible, the person skilled in the art being able to decide (either experimentally or theoretically) without inappropriate effort which substitutions are chemically possible and which are not.

Ortho, meta and pare substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in " ".

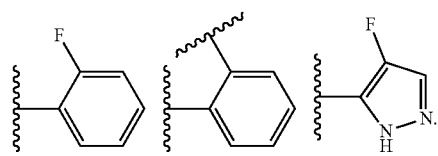

"Meta" substitution is a substitution pattern where two substituents are on carbons one carbon removed from each other, i.e with a single carbon atom between the substituted carbons. In other wombs there is a substituent on the second atom away from the atom with another substituent. For example the groups below are meta substituted.

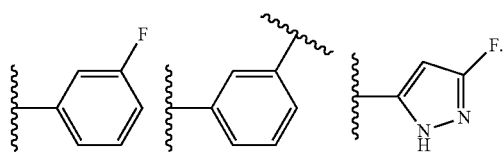

"Para" substitution is a substitution pattern where two substituents are on carbons two carbons removed from each other, i.e with two carbon atoms between the substituted carbons. In other wombs there is a substituent on the thins atom away from the atom with another substituent. For example the groups below are pare substituted.

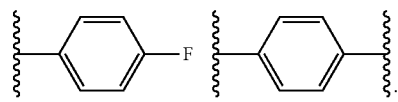

By "acyl" is meant an organic radical derived from, for example, an organic acid by the removal of the hydroxyl group, e.g. a radical having the formula R—C(O)—, where R may be selected from H, $C_{1-6}$ alkyl, $C_{3-8}$ cycloalkyl, phenyl, benzyl or phenethyl group, eg R is H or $C_{1-3}$ alkyl. In one embodiment acyl is alkyl-carbonyl. Examples of acyl groups include, but are not limited to, formyl, acetyl, propionyl and butyryl. A particular acyl group is acetyl.

Throughout the description the disclosure of a compound also encompasses pharmaceutically acceptable salts, solvates and stereoisomers thereof. Where a compound has a stereocentre, both (R) and (S) stereoisomers are contemplated by the invention, equally mixtures of stereoisomers or a racemic mixture are completed by the present application. Where a compound of the invention has two or more stereocentres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diastereomeric mixtures. Where the mixture is a mixture of enantiomers the enantomeric excess may be any of those disclosed above. Where the compound is a single stereoisomer the compounds may still contain other diastereoisomers or enantiomers as impurities. Hence a single stereoisomer does not necessarily have an enantiomeric excess (e.e.) or diastereomeric excess (d.e.) of 100% but could have an e.e. or d.e. of about at least 85%, at least 60% or less. For example, the e.e. or d.e. may be 90% or more, 90% or more, 80% or more, 70% or more, 60% or more, 50% or more, 40% or more, 30% or more, 20% or more, or 10% or more.

The invention contemplates pharmaceutically acceptable salts of the compounds of the invention. These may include the acid addition and base salts of the compounds. These may be acid addition and base salts of the compounds. In addition the invention contemplates solvates of the compounds. These may be hydrates or other solvated forms of the compound.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of the invention with the desired acid or base;
(ii) by removing an acid- or base-labile protecting group from a suitable precursor of the compound of the invention or by ring-opening a suitable cyclic precursor, for example, a lactone or lectern, using the desired acid or base; or
(iii) by converting one salt of the compound of the invention to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of any formula include references to salts, solvates and complexes thereof and to solvates and complexes of salts thereof.

The compounds of the invention include compounds of a number of formula as herein defined, including all polymorphs and crystal habits thereof, prodrugs and isomers thereof (including optical, geometric and tautomeric isomers) as hereinafter defined and isotopically-labelled compounds of the invention.

The present invention also includes all pharmaceutically acceptable isotopically-labelled compounds of the invention wherein one or more atoms are replaced by atoms having the same atomic number, but an atomic mass or mass number different from the atomic mass or mass number most commonly found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{35}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo haft-life or reduced dosage requirements, and hence may be preferred in some circumstances.

Before purification, the compounds of the present invention may exist as a mixture of enantiomers depending on the synthetic procedure used. The enantiomers can be separated by conventional techniques known in the art. Thus the invention covers individual enantiomers as well as mixtures thereof.

For some of the steps of the process of preparation of the compounds of the invention, it may be necessary to protect potential reactive functions that are not wished to react, and to cleave said protecting groups in consequence. In such a case, any compatible protecting radical can be used. In particular methods of protection and deprotection such as those described by T. W. GREENE (Protective Groups in Organic Synthesis, A. Wiley-Interscience Publication, 1981) or by P. J. Kocienski (Protecting groups, Georg Thieme Verlag, 1994), can be used. AN of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of the present invention as well as intermediates for the preparation thereof can be purified according to various well-known methods, such as for example crystallization or chromatography.

One or more compounds of the invention may be combined with one or more pharmaceutical agents, for example anti-Inflammatory agents, anti-fibrotic agents, chemotherapeutics, anti cancer agents, immunosuppressants, anti-tumour vaccines, cytokine therapy, or tyrosine kinase inhibitors, for the treatment of conditions modulated by the inhibition of ROCK, for example fibrotic diseases, auto-immune, inflammatory-fibrotic conditions, inflammatory conditions, central nervous system disorders, or cancer.

The method of treatment or the compound for use in the treatment of fibrotic diseases, auto-immune, inflammatory-fibrotic conditions, Inflammatory conditions, central nervous system disorders, or cancer as defined hereinbefore may be applied as a sole therapy or be a combination therapy with an additional active agent.

The method of treatment or the compound for use in the treatment of fibrotic diseases, auto-immune, inflammatory-fibrotic conditions, Inflammatory conditions, central nervous system disorders diseases may involve, in addition to the compound of the invention, additional active agents. The additional active agents may be one or more active agents used to treat the condition being treated by the compound of the invention and additional active agent. The additional active agents may include one or more of the following active agents:—
(i) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixcocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(ii) TNF inhibitors for example etanercept; monoclonal antibodies (e.g. infliximab (Remicade), adalimumab (Humira), certolizumab pegol (Cimzia), golimumab (Simponi); fusion proteins (e.g. etanercept (Enbrel)); and 5-$HT_{2A}$ agonists (e.g. 2,5-dimethoxy-4-iodoamphetamine, TCB-2, lysergic acid diethylamide (LSD), lysergic acid dimethylazetidide);

(iii) anti-Inflammatory drugs, for example non-steroidal anti-Inflammatory drugs;

(iv) dihydrofolate reductase inhibitors/antifolates, for example methotrexate, trimethoprim, brodimoprim, tetroxoprim, iclaprim, pemetrexed, ralitrexed and pralatrexate; and (v) immunosuppressants for example cyclosporins, tacrolimus, sirolimus pimecrolimus, angiotensin II inhibitors (e.g. Valsartan, Telmisartan, Losartan, Irbesatan, Azilsartan, Olmesartan, Candesartan, Eprosartan) and ACE inhibitors e.g. sulfhydryl-containing agents (e.g. Captopril, Zofenopril), dicarboxylate-containing agents (e.g. Enalapril, Ramipril, Quinapril, Perindopril, Lisinopril, Benazepril, Imidapril, Zofenopril, Trandolapril), phosphate-containing agents (e.g. Fosinopril), casokinins, lactokinins and lactotripeptides.

(vi) Anti-fibrotic agents for example: Pirfenidone, Nintedanib, Anti-IL-13 monoclonal antibodies (e.g. Tralokinumab, QAX576, Lebrikizumab), simtuzumab, FG-3019, lysophosphatidic acid receptor antagonists (e.g. BMS-986020, AM966), LOXL2 inhibitors, BET bromodomain inhibitors (e.g. JQ1), HDAC inhibitors (e.g. Vorinostat), thrombin inhibitors (e.g. Dabigatran), FactorXa inhibitors (e.g. Apixban, Rivaroxaban) 15PGDH inhibitors, anti-αvβ6 monoclonal antibodies (e.g. BG00011), Anti-CTGF monoclonal antibodies (e.g. FG-3019), PAR1 inhibitors, Nox4 inhibitors and PAI-1 inhibitors.

(vii) CNS therapies, for example: Levodopa, Dopamine agonists, Apomorphine, Glutamate antagonist, Anticholinergics, COMT inhibitors, MAO-B inhibitors, riluzole (Rilutek), Tetrabenazine (Xenazine), haloperidol (Haldol), chlorpromazine, risperidone (Risperdal), quetiapine (Seroquel), amantadine, levetiracetam (Keppra), clonazepam (Klonopin), Donepezil (Aricept), Galantamine (Razadyne), Rivastigmine (Exelon)), Memantine (Ebixa, Axura), Aducanumab, Ocrelizumab, interferon beta-1a (Avonex, Rebif), peginterferon beta-1a (Plegridy), teriflunomide (Aubagio), fingolimod (Gilenya), mitoxantrone (Novantrone), dimethyl fumarate (Tecfidera), natalizumab (Tysabri)

The method of treatment or the compound for use in the treatment of cancer, sarcoma, melanoma, skin cancer, haematological tumors, lymphoma, carcinoma, leukemia, and central nervous system disorders may involve, in addition to the compound of the invention, conventional surgery or radiotherapy or chemotherapy. Such chemotherapy may include one or more of the following categories of anti-tumor agents:

(i) antiproliferative/antineoplastic drugs and combinations thereof, such as alkylating agents (for example cis-platin, oxaliplatin, carboplatin, cyclophosphamide, nitrogen mustard, uracil mustard, bendamustin, melphalan, chlorambucil, chlormethine, busulphan, temozolamide, nitrosoureas, ifosamide, melphalan, pipobroman, triethylene-melamine, triethylenethiophoporamine, carmustine, lomustine, stroptozocin and dacarbazine); antimetabolites (for example gemcitabine and antifolates such as fluoropyrimidines like 5-fluorouracil and tegafur, raftitrexed, methotrexate, pemetrexed, cytosine arabinoside, floxur dine, cytarabine, 6-mercaptopurine, 6-thioguanine, fludarabine phosphate, pentostatine, and gemcitabine and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example ulna alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, mitoxantrone and camptothecin); bleomcin, dactinomycin, daunorubicin, doxorubicin, epirubicin, idarubicin, ara-C, paclitaxel (Taxol™), nabpaclitaxel, docetaxel, mithramycin, deoxyco-formycin, mitomycin-C, L-asparaginase, interferons (especially IFN-α), etoposide, and teniposide;

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride; and navelbene, CPT-II, anastrazole, letrazole, capecitabine, reloxafme, cyclophosphamide, ifosamide, and droloxafine;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib, 6-acrylamido-N-(3-chloro-4-fluorophenyl)-7-(3-morpholinopropoxy)-quinazolin-4-amine (CI 1033), erbB2 tyrosine kinase inhibitors such as lapatinib) and antibodies to costimulatory molecules such as CTLA-4, 4-IBB and PD-I, or antibodies to cytokines (IL-I0, TGF-beta); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); Inhibitors of serine/threonine kinases (for example Ras/Raf signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, PI3 kinase inhibitors, PIt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors; and CCR2, CCR4 or CCR6 modulator, (v) antiangiogenic agents such as those which inhibit the effects of vascular endothelial growth factor, for example the anti-vascular endothelial cell growth factor antibody bevacizumab (Avastin™); thalidomide; lenalidomide; and for example, a VEGF receptor tyrosine kinase inhibitor such as vandetanib, vatalanib, sunitinib, axitinib and pazopanib;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); gp100; dendritic cell-based vaccines (such as Ad.p53 DC); and toll-like receptor modulators for example TLR-7 or TLR-9 agonists; and (viii) cytotoxic agents for example fludarabine (fludara), cladribine, pentostatin (Nipent™);

(ix) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixcocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(x) targeted therapies, for example PI3Kd Inhibitors, for example idelalisib and perifosine; PD-1, PD-L1, PD-L2 and CTL4-A modulators, antibodies and vaccines; other IDO inhibitors (such as indoximod); anti-PD-1 monoclonal antibodies (such as MK-3475 and nivolumab); anti-PD-L1 monoclonal antibodies (such as MEDI-4736 and RG-7446); anti-PD-L2 monoclonal antibodies; and anti-CTLA-4 antibodies (such as ipilimumab);

(xii) chimeric antigen receptors, anticancer vaccines and arginase inhibitors.

Such combination treatment may be achieved by way of the simultaneous, sequential or separate dosing of the individual components of the treatment. Such combination products employ the compounds of this invention within a therapeutically effective dosage range described hereinbefore and the other pharmaceutically-active agent within its approved dosage range.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

For the above-mentioned compounds of the invention the dosage administered will, of course, vary with the compound employed, the mode of administration, the treatment desired and the disorder indicated. For example, if the compound of the invention is administered orally, then the daily dosage of the compound of the invention may be in the range from 0.01 micrograms per kilogram body weight (μg/kg) to 100 milligrams per kilogram body weight (mg/kg).

A compound of the invention, or pharmaceutically acceptable salt thereof, may be used on their own but will generally be administered in the form of a pharmaceutical composition in which the compounds of the invention, or pharmaceutically acceptable salt thereof, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration of the compounds of the invention, the pharmaceutical composition which is used to administer the compounds of the invention will preferably comprise from 0.05 to 99% w (percent by weight) compounds of the invention, more preferably from 0.05 to 80% w compounds of the invention, still more preferably from 0.10 to 70% w compounds of the invention, and even more preferably from 0.10 to 50% w compounds of the invention, all percentages by weight being based on total composition.

The pharmaceutical compositions may be administered topically (e.g. to the skin) in the form, e.g., of creams, gels, lotions, solutions, suspensions, or systemically, e.g. by oral administration in the form of tablets, capsules, syrups, powders or granules; or by parenteral administration in the form of a sterile solution, suspension or emulsion for injection (Including Intravenous, subcutaneous, intramuscular, Intravascular or infusion); by rectal administration in the form of suppositories; or by inhalation in the form of an aerosol.

For oral administration the compounds of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using either the above-mentioned excipients for tablets. Also liquid or semi-solid formulations of the compound of the invention may be filed into hard gelatine capsules. Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

For Intravenous (parenteral) administration the compounds of the invention may be administered as a sterile aqueous or oily solution.

The size of the dose for therapeutic purposes of compounds of the invention will naturally vary according to the nature and severity of the conditions, the age and sex of the animal or patient and the route of administration, according to well-known principles of medicine.

Dosage levels, dose frequency, and treatment durations of compounds of the invention are expected to differ depending on the formulation and clinical indication, age, and co-morbid medical conditions of the patient.

EXAMPLES AND SYNTHESIS

As used herein the following terms have the meanings given: "Boc" refers to test-butoxycarbonyl; "dba" refers to dibenzylideneacetone; "DCE" refers to 1,2-dichloroethane; "DCM" refers to dichloromethane; "DIPEA" refers to N,N-Diisopropylethylamine; "DMAP" refers to 4-(dimethylamino)pyridine; "DMF" refers to N,N-dimethylformamide; "DMSO" refers to dimethylsulfoxide; "dppf" refers to 1,1'-bis(diphenylphosphino)ferrocene; "EDC" refers to N-(3-dimethylaminopropyl)-N-ethylcarbodiimide; "EtOAc" refers to ethyl acetate; "HATU" refers to 1-[bis(dimethylamino)methylene]-1H-1,2,3-triazolo[4,5-b]pyridinium 3-oxide hexafluorophosphate; "HOBt" refers to 1-hydroxybenzotriazole hydrate; "HPLC" refers to high performance liquid chromatography; "IPA" refers to 2-propanol; "LCMS" or "LC-MS" refers to liquid chromatography/mass spectrometry; LiHMDS' refers to lithium bis(trimethylsilyl)amide; "MIM" refers to monoisotopic mass; "min" refers to min; "Pet. Ether" refers to Pet. Ether, "PG" refers to protecting group; "PTSA" refers to p-toluenesulfonic acid monohydrate; "TLC" refers to thin layer chromatography; "Rf" refers to Retention factor, "RT" refers to retention time; "r.t." refers to room temperature; "SCX" refers to strong cation exchange; "SEM" refers to 2-(trimethylsilyl)ethoxymethyl; TBME" refers to tert-butyl methyl ether, "TEA" refers to triethylamine; "TFA" refers to trifluoroacetic acid; "THF" refers to tetrahydrofuran; and "THP" refers to tetrahydropyran.

Solvents, reagents and starting materials were purchased from commercial vendors and used as received unless otherwise described. AN reactions were performed at RT unless otherwise stated. Compound identity and purity confirmations were performed by LCMS UV using a Waters Acquity SQ Detector 2 (ACQ-SQD2 #CA081). The diode array detector wavelength was 254 nM and the MS was in positive and negative electrospray mode (m/z: 150-800). A 2 µL aliquot was injected onto a guard column (0.2 µm×2 mm fillers) and UPLC column (C18, 50×2.1 mm, <2 µm) in sequence maintained at 40° C. The samples were eluted at a flow rate of 0.6 mL/min with a mobile phase system composed of A (0.1% (v/v) Formic Add in Water) and B (0.1% (v/v) Formic Add in Acetonitrile) according to the gradients outlined in Table 1 below. Retention times RT are reported in min.

| Time (min) | % A | % B |
|---|---|---|
| Method A: Short Acidic | | |
| 0 | 95 | 5 |
| 0.3 | 95 | 5 |
| 2 | 5 | 95 |
| 2.6 | 95 | 5 |
| 3 | 95 | 5 |
| Method B: Long Acidic | | |
| 0 | 95 | 5 |
| 1.1 | 95 | 5 |
| 6.1 | 5 | 95 |
| 7 | 5 | 95 |
| 7.5 | 95 | 5 |
| 8 | 95 | 5 |

Compound identity confirmations were also performed by LCMS UV using a Waters Alliance 2695 micromass ZQ (K98SM4 512M-LAA434). The diode array detector wavelength was 254 nM and the MS was in positive and negative electrospray mode (m/z: 150-650). A 10 µL aliquot was injected onto an HPLC column (C18, 75×4.6 mm, 2.5 µm) at RT which was controlled at 19° C. The samples were eluted at a flow rate of 0.9 mL/min with a mobile phase system composed of A (0.1% (v/v) Formic Acid in 95:5 (v/v) Water. Acetonitrile) and B (0.1% (v/v) Formic Acid in 95:5 (v/v) Acetonitrile:Water) according to the gradients outlined in Table 2 below. Retention times RT are reported in min.

| Time (min) | % A | % B | % C | % D |
|---|---|---|---|---|
| Method C (5 minute acidic) | | | | |
| 0 | 90 | 5 | 5 | 0 |
| 4.0 | 0 | 95 | 5 | 0 |
| 4.49 | 0 | 95 | 5 | 0 |
| 4.5 | 95 | 5 | 0 | 0 |

-continued

| Time (min) | % A | % B | % C | % D |
|---|---|---|---|---|
| Method D (7 minute acidic) | | | | |
| 0 | 90 | 5 | 5 | 0 |
| 0.5 | 90 | 5 | 5 | 0 |
| 5.0 | 0 | 95 | 5 | 0 |
| 5.49 | 0 | 95 | 5 | 0 |
| 6.0 | 90 | 10 | 0 | 0 |
| 7.0 | 90 | 10 | 0 | 0 |
| Method E (15 minute acidic) | | | | |
| 0 | 95 | 0 | 5 | 0 |
| 2.0 | 95 | 0 | 5 | 0 |
| 12.0 | 0 | 95 | 5 | 0 |
| 14.0 | 0 | 95 | 5 | 0 |
| 14.1 | 95 | 0 | 5 | 0 |

Compound identity confirmations were also performed by LCMS UV using the following:
1. LC: Agilent Technologies 1290 series, Binary Pump, Diode Array Detector. Agilent Poroshell 120 EC-C18, 2.7 µm, 4.6×50 mm column. Mobile phase: A: 0.05% Formic acid in water (v/v), B: 0.05% Formic acid in MeCN (v/v). Flow Rate: 1 mL/min at 25° C. Detector. 214 nm, 254 nm. Gradient stop time, 5 min.
2. MS: G6120A, Quadrupole LC/MS, ion Source: API-ES, TIC: 701000 m/z, Fragmentor. 70, Drying gas flow: 12 L/min, Nebulizer pressure: 36 psi, Drying gas temperature: 350° C., Vcap: 3000V.
3. Sample preparation: samples were dissolved in methanol at 1~10 µg/mL, then filtered through a 0.22 µm filter membrane. Injection volume: 1~10 µL.

| Method F | | |
|---|---|---|
| Time (min) | % A | % B |
| 0.00 | 90 | 10 |
| 0.50 | 90 | 10 |
| 4.00 | 10 | 90 |
| 4.50 | 0 | 100 |
| 4.51 | 90 | 10 |
| 5.00 | 90 | 10 |

NMR was also used to characterise final compounds. $^1$H NMR spectra were obtained at r.t., unless otherwise stated, on a Bruker AVI 500 with either a 5 mm Dual or 5 mm QNP probe with Z gradients, a Bruker DRX500 with a 5 mm QNP probe with Z gradients or a Bruker AVIII 400 Nanobay with 5 mm BBFO probe. Chemical shifts are reported in ppm and referenced to either TMS (0.00 ppm), DMSO-d$_6$ (2.50 ppm), CDCl$_3$ (7.26 ppm) or MeOD-d$_4$ (3.31 ppm). NH or OH signals that exchange with deuterated solvent are not reported.

Optionally, compound Rf values on silica thin layer chromatography (TLC) plates were measured. Compound purification was performed by flash column chromatography on silica or by preparative LCMS. LCMS purification was performed using a Waters 3100 Mass detector in positive and negative electrospray mode (m/z: 150-800) with a Waters 2489 UV/Vis detector. Samples were eluted at a flow rate of 20 mL/min on a XBridge™ prep C18 5 µM OBD 19×100 mm column with a mobile phase system composed of A (0.1% (v/v) Formic Acid in Water) and B (0.1% (v/v) Formic Acid in Acetonitrile) according to the gradient outlined in Table 3 below.

| Time (min) | % A | % B |
|---|---|---|
| 0 | 90 | 10 |
| 1.5 | 90 | 10 |
| 11.7 | 5 | 95 |
| 13.7 | 5 | 95 |
| 14 | 90 | 90 |
| 15 | 90 | 90 |

Intermediate 1:
3,5-Dibromo-1-tetrahydropyran-2-yl-1,2,4-triazole

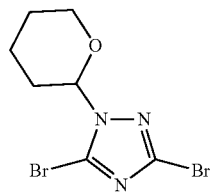 [SMILES: Brc1nc(Br)n(C2CCCCO2)n1]

To a stirred solution of 3,5-dibromo-4H-1,2,4-triazole (567 mg, 2.50 mmol) and PTSA (24 mg, 0.13 mmol) in THF (10 mL) at r.t. under N$_2$ was added 3,4-dihydro-2H-pyran (025 mL, 2.75 mmol) and the reaction was stirred at r.t. for 18 h. The solvents were removed under reduced pressure and the residual solid taken up with EtOAc (25 mL) and washed with sat. aq. NaHCO$_3$ solution (2×20 mL). The aqueous layer was extracted with EtOAc (2×20 mL). The combined organic extracts were dried (phase separator) and concentrated. The crude material was purified by flash column chromatography (SiO$_2$) eluting with 20-55% EtOAc in Pet. Ether to give 3,5-dibromo-1-tetrahydropyran-2-yl-1,2,4-triazole (753 mg, 2.42 mmol, 97% yield) as a white solid. LC-MS (ES$^+$, Method C): 2.73 min, m/z 311.8 [M+H]$^+$. $^1$H NMR (500 MHz, DMSO-d$_6$): δ 5.47 (dd, J=9.0, 3.0 Hz, 1H), 4.02-4.09 (m, 1H), 3.66-3.71 (m, 1H), 2.28-2.39 (m, 1H), 2.10-2.19 (m, 1H), 1.92-1.96 (m, 1H), 1.62-1.77 (m, 3H).

Intermediate 2: 2-[(3,5-Dibromo-1,2,4-triazol-1-yl)methoxy]ethyltrimethylsilane

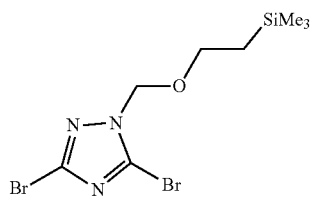 [SMILES: C[Si](C)(C)CCOCn1nc(Br)nc1Br]

To a stirred suspension of sodium hydride (60% dispersion in mineral oil; 88 mg, 2.20 mmol) in THF (4.5 mL) at 0° C. under N$_2$ was added a solution of 3,5-dibromo-4H-1,2,4-triazole (454 mg, 2.00 mmol) in THF (4.5 mL) and the mixture stirred at 0° C. for 30 min. 2-(Trimethylsilyl)ethoxymethyl chloride (0.42 mL, 2.40 mmol) was added dropwise, the cooling bath removed and the reaction stirred at r.t. overnight. The reaction was quenched by the addition of water (10 mL) and extracted with EtOAc (3×15 mL). The combined organics were dried (phase separator) and concentrated giving 2-[(3,5-dibromo-1,2,4-triazol-1-yl)

methoxy]ethyl-trimethyl-silane (663 mg, 1.86 mmol, 93% yield) as a colourless oil. LC-MS (ES⁺, Method C): 3.66 min, m/z 357.9 [M+H]⁺. ¹H NMR (500 MHz, CDCl₃): δ 5.45 (s, 2H), 3.70-3.65 (m, 2H), 0.96-0.91 (m, 2H), 0.00 (s, 9H).

General Method for the Synthesis of Intermediates 3 and 4

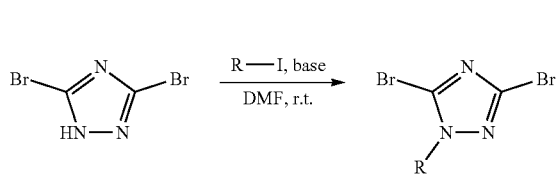

Intermediate 3: 3,5-dibromo-1-methyl-1,2,4-triazole

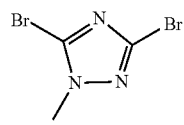

To a solution of 3,5-dibromo-1H-1,2,4-triazole (10.0 g, 44.1 mmol) in DMF (75 mL) and potassium carbonate (12.2 g, 88.2 mmol) was added iodomethane (3.02 mL, 48.5 mmol) in one portion. This gave rise to a strong exotherm from 17° C. to 38° C. after one minute. The reaction mixture was stirred overnight, diluted with 150 mL of EtOAc and then filtered to remove most of the inorganics. The solvent was removed under reduced pressure and the resultant yellow oily solid was partitioned between EtOAc (250 mL) and water (100 mL) and the aqueous washed with EtOAc (150 mL). The combined organics were washed with washed with brine (50 mL), dried over magnesium sulfate, filtered and the solvent removed in vacuo to give 3,5-dibromo-1-methyl-1,2,4-triazole (6.2 g, 25.8 mmol, 58% yield) as a yellow solid. UPLC-MS (ES⁺, Method A): 1.79 min, m/z 241.7 [M+H]⁺. ¹H NMR (400 MHz, DMSO-d₆) δ 3.83 (3H).

Intermediate 4:
3,5-dibromo-1-isopropyl-1,2,4-triazole

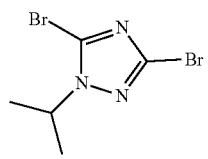

To a solution of 3,5-dibromo-1H-1,2,4-triazole (750 mg, 3.31 mmol) In DMF (12 mL) was added sodium hydride (172 mg, 4.30 mmol). This was stirred at 40° C. for 30 min. Upon formation of the sodium salt, 2-iodopropane (0.40 mL, 3.97 mmol) was added. The reaction mixture was diluted with water (120 mL) and extracted with diethyl ether. The aqueous was extracted with twice further diethyl ether and the combined organic layers dried over MgSO₄. The solvents were then removed in vacuo to yield 3,5-dibromo-1-isopropyl-1,2,4-triazole (631 mg, 2.23 mmol, 67% yield). ¹H NMR (400 MHz, DMSO-d₆) δ 4.68 (hept, J=6.6 Hz, 1H), 1.39 (d, J=6.6 Hz, 6H).

Intermediate 5: 3,5-dibromo-1-phenyl-1,2,4-triazole

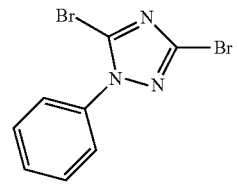 [SMILES: Brc1nc(Br)n(-c2ccccc2)n1]

3,5-Dibromo-1H-1,2,4-triazole (419 mg, 1.85 mmol) was added to a solution of phenylboronic acid (300 mg, 2.46 mmol), pyridine (0.2 mL, 2.46 mmol), copper(II) acetate (335 mg, 1.85 mmol) and 3 Å molecular sieves in dry DCM (8 mL) and stirred at 25° C. overnight. Upon completion monitored by LC/MS, sat. NH₄Cl (20 mL) was added to the reaction mixture which was then washed with water, the organic layers were then combined and concentrated. The crude product was purified by flash column chromatography eluting with 15-50% EtOAc in Pet. Ether to give 3,5-dibromo-1-phenyl-1,2,4-triazole (454 mg, 1.50 mmol, 60% yield). LC-MS (ES⁺, Method A): 1.74 min, m/z 304.0 [M+H]⁺

Intermediate 6:
3,5-dibromo-1-(2-fluorophenyl)-1,2,4-triazole

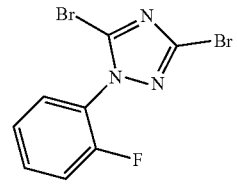 [SMILES: Fc1ccccc1-n1nc(Br)nc1Br]

A suspension of 3,5-dibromo-4H-1,2,4-triazole (453.7 mg, 2 mmol) 2-fluorophenylboronic acid (420 mg, 3 mmol) copper(II) acetate (363 mg, 2 mmol) sodium carbonate (318 mg, 3 mmol) and pyridine (0.24 mL, 3 mmol) in toluene (2 mL) was heated at 70° C. overnight. The reaction mixture was cooled to r.t. and filtered through celite (eluting with EtOAc). The filtrate was washed with sat. aq. NH₄Cl solution (15 mL) and water (10 mL), dried and concentrated. The chide product was purified by flash column chromatography (SiO₂) eluting with 20-50% EtOAc in Pet. Ether to give 3,5-dibromo-4-(2-fluorophenyl)-1,2,4-triazole (98 mg, 0.31 mmol, 15% yield) as a colourless oil, which crystallised on standing. Regioisomer confirmed by DEPT-quat expt. LC-MS (ES⁺, Method D): 5.61 min, m/z 321.7 [M+H]⁺. ¹H NMR (400 MHz, CDCl₃): δ 7.57 (m, 1H), 7.46 (m, 1H), 7.36-7.32 (m, 1H), 7.32-7.28 (m, 1H).

Intermediate 7: 2-(3,5-dibromo-1,2,4-triazol-4-yl)pyridine

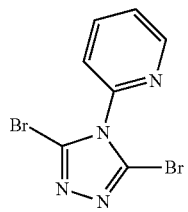

To a stirred solution of N,N-diisopropylethylamine (1.15 mL, 6.61 mmol), bromotripyrrolidinophosphonium hexafluorophosphate (1028 mg, 2.2 mmol) and pyridine oxide (157 mg, 1.65 mmol) in DCM (10 mL) at r.t under nitrogen was added 3,5-dibromo-4H-1,2,4-triazole (0.08 mL, 2.20 mmol) in a single portion and the reaction stirred at 25° C. overnight. The reaction mixture cooled to r.t. and solvents were removed under reduced pressure. The residue was dissolved in EtOAc (15 mL) and washed with H₂O (15 mL). The aqueous layer was extracted with EtOAc (2×15 mL) and the combined organics were washed with brine, dried (phase sep.) and concentrated. The crude material was purified by column chromatography (SiO₂) eluting with 30-60% EtOAc in pet ether to give 2-(3,5-dibromo-1,2,4-triazol-4-yl)pyridine (285 mg, 0.94 mmol, 43% yield). UPLC-MS (ES⁺, Method A): 1.53 min, m/z 304.9 [M+H]⁺

Intermediate 8: 2-(3,5-dibromo-1,2,4-triazol-1-yl)pyridine and Intermediate 9: 4-(3,5-dibromo-1,2,4-triazol-1-yl)pyridine

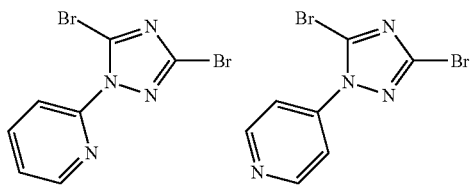 [SMILES: Brc1nc(Br)n(-c2ccccn2)n1 ; Brc1nc(Br)n(-c2ccncc2)n1]

To a stirred solution of N,N-diisopropylethylamine (5.7 mL, 33.0 mmol), bromotripyrrolidinophosphonium hexafluorophosphate (5.14 g, 11.02 mmol) and pyridine oxide (1.05 g, 11.0 mmol) in DCM (25 mL) at r.t under nitrogen was added 3,5-dibromo-1H-1,2,4-triazole (0.08 mL, 11.02 mmol) in a single portion and the reaction stirred at 25° C. overnight. The solvents were removed in-vacuo and the residue partitioned between 50 mL of DCM and 35 mL of water, passed through a phase separation cartridge and concentrated in-vacuo. The crude material was purified by column chromatography (SiO₂) eluting with 10-60% EtOAc in Pet. Ether to give 2-(3,5-dibromo-1,2,4-triazol-1-yl)pyridine (1.95 g, 6.4 mmol, 58% yield) as a white crystalline solid. Intermediate 8: UPLC-MS (ES⁺, Method A): 1.53 min, m/z 304.9 [M+H]⁺. ¹H NMR (400 MHz, DMSO-d₆) δ 8.66 (ddd, J=4.7, 1.9, 0.8 Hz, 1H), 8.15 (td, J=7.8, 1.9 Hz, 1H), 7.82 (dt, J=8.1, 1.0 Hz, 1H), 7.66 (ddd, J=7.5, 4.9, 1.0 Hz, 1H). Structure confirmed by DEPT NMR. A second compound was isolated to give 4-(3,5-dibromo-1,2,4-triazol-1-yl)pyridine (120 mg, 0.40 mmol, 3.6% yield). Intermediate 9: UPLC-MS (ES⁺, Method A): 1.33 min, m/z 304.9 [M+H]⁺. ¹H NMR (400 MHz, DMSO-d₆) δ 8.93-8.80 (m, 2H), 7.82-7.74 (m, 2H). Structure confirmed by DEPT NMR

Intermediate 10: 5-Bromo-1-tetrahydropyran-2-yl-indazole

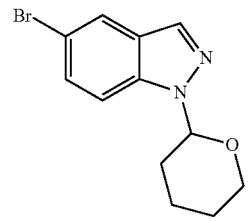 [SMILES: Brc1ccc2c(cnn2C2CCCCO2)c1]

To a stirred solution of 5-bromoindazole (394 mg, 2.0 mmol) in anhydrous DCM (4.0 mL) was added 3,4-dihydro-2H-pyran (0.36 mL, 4.0 mmol) and PTSA (190 mg, 1.0 mmol) and the reaction stirred at r.t for 3 h. The reaction was quenched with sat. aq. NaHCO₃ (10 mL) and diluted with DCM (20 mL). The layers were separated and the aqueous portion extracted with DCM (15 mL). The combined organics were dried (phase separator) and concentrated and the crude product purified by flash column chromatography (SiO₂, eluting with 5-15% EtOAc in Pet. Ether) giving 5-bromo-1-tetrahydropyran-2-yl-indazole (427 mg, 1.43 mmol, 71% yield) as an orange oil. LC-MS (ES⁺, Method C): 3.37 min, m/z 282.0 [M+H]⁺

Intermediate 11: 5-isothiocyanato-1-tetrahydropyran-2-yl-indazole

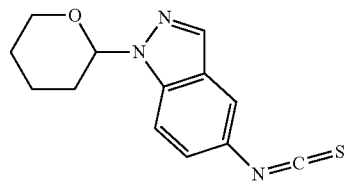 [SMILES: S=C=Nc1ccc2c(cnn2C2CCCCO2)c1]

N,N'-Thiocarbonyldiimidazole (164 mg, 0.92 mmol) was added to a stirred solution of 1-(tetrahydro-2H-pyran-2-yl)-1H-indazol-5-amine (200 mg, 0.92 mmol) in DCM (5 mL) and the reaction stirred at r.t. overnight. The reaction mixture was diluted with water (10 mL), the layers were separated and the aqueous portion extracted with DCM (2×10 mL). The combined organics were washed with brine (10 mL), dried (phase separator) and concentrated under reduced pressure. The crude product was purified by flash column chromatography (SiO₂) eluting with 45-75% EtOAc in Pet. Ether to give 5-isothiocyanato-1-tetrahydropyran-2-yl-indazole (143 mg, 0.55 mmol, 60% yield) as an orange oil. LC-MS (ES⁺, Method C): 3.62 min, m/z 260.0 [M+H]⁺. ¹H NMR (500 MHz, DMSO-d₆): δ 8.18 (s, 1H), 7.93 (d, J=2.0 Hz, 1H), 7.86-7.82 (m, 1H), 7.50 (d, J=9.0, 2.0 Hz, 1H), 5.90 (dd, J=9.5, 2.5 Hz, 1H), 3.89 (m, 1H), 3.82-3.69 (m, 1H), 2.43-2.34 (m, 1H), 2.01 (m, 2H), 1.83-1.71 (m, 1H), 1.60 (m, 2H).

Method for the Synthesis of Intermediate 12

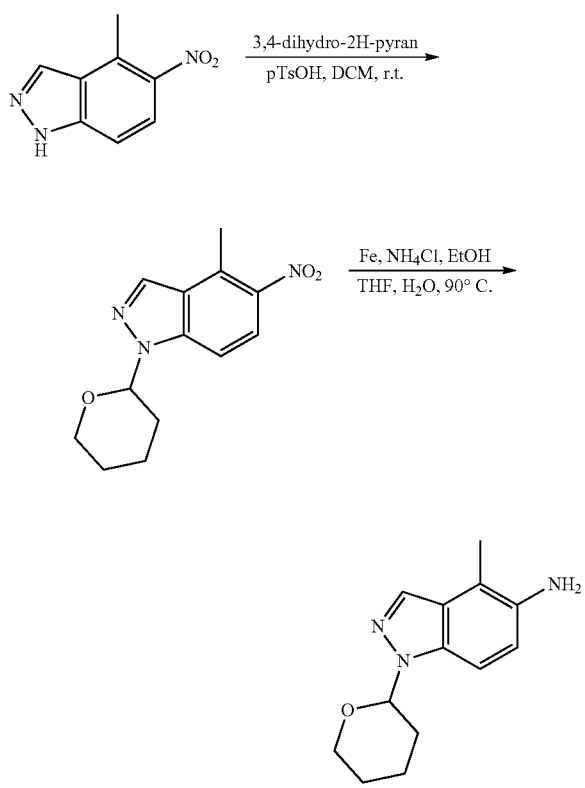

Step 1:
4-methyl-5-nitro-1-tetrahydropyran-2-yl-indazole

A suspension of 4-methyl-5-nitro-1H-indazole (1.00 g, 5.64 mmol) in DCM (10 mL) was treated with 3,4-dihydro-2H-pyran (1.55 mL, 16.93 mmol) and PTSA (107 mg, 0.56 mmol). After 16 h LCMS showed full conversion. The reaction mixture was diluted with sat. aq. NaHCO₃ and extracted three times with DCM. The combined organic layers were passed through a phase separator and concentrated in vacuo. Purification by flash column chromatography (80 g SiO₂, EtOAc/heptane—10% to 30%) gave 4-methyl-5-nitro-1-tetrahydropyran-2-yl-indazole (1.42 g, 5.45 mmol, 97% yield) as an orange amorphous solid. UPLC-MS (ES⁺, Method A): 1.80 min, m/z 262.1 [M+H]⁺

Intermediate 12:
4-methyl-1-tetrahydropyran-2-yl-indazol-5-amine

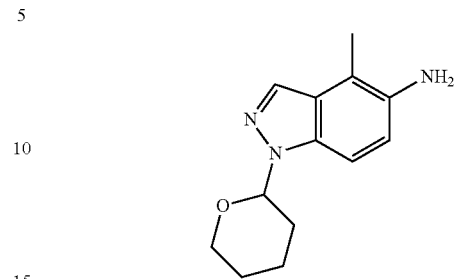

A solution of 4-methyl-5-nitro-1-tetrahydropyran-2-yl-indazole (1.42 g, 5.45 mmol), EtOH (20 mL), THF (20 mL) and water (5 mL) was treated with iron (3.65 g, 65.44 mmol) and ammonium chloride (3.50 g, 65.44 mmol). The reaction mixture was warmed to 60° C. After 1 h, LCMS showed slow conversion and the reaction mixture was warmed to 90° C. After 4 h, LCMS showed no starting material remained. The reaction mixture was diluted with sat. aq. NaHCO₃ and extracted five times with DCM. The combined organic layers were passed through a phase separator and concentrated in vacuo to provide 4-methyl-1-tetrahydropyran-2-yl-indazol-5-amine (1.25 g, 5.45 mmol, 100% yield) as an amorphous solid. UPLC-MS (ES⁺, Method A): 1.06 min, m/z 232.2 [M+H]⁺

Intermediate 13:
1-tetrahydropyran-2-ylindazol-5-amine

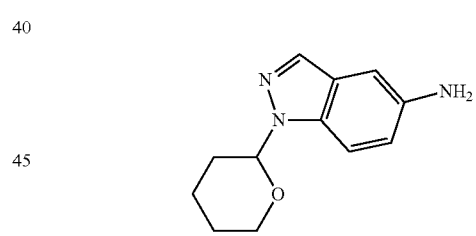

A solution of 5-nitro-1-tetrahydropyran-2-yl-indazole (72 g, 291.2 mmol) in EtOAc (750 mL) was evacuated and flushed with nitrogen several times, palladium, 10 wt. % on carbon powder, 50% wet (3.83 g, 18 mmol) was added and the evacuation/flushing repeated, after which the mixture was exposed to hydrogen with maximum agitation from a stirrer bar. An exothermic reaction occurred over a prolonged period (~2 h) After 3 h, the mixture was filtered to remove Pd/C and washed through thoroughly with ethyl acetate. The solution was reduced in vacuo to give a white solid that was triturated with 1:1 Pet Ether/diethyl ether and filtered, finally washing with Pet. Ether and pulled dry to give 1-tetrahydropyran-2-ylindazol-5-amine (58.9 g, 271.1 mmol, 93% yield) as a white solid. LC-MS (ES⁺, Method C): 1.14 min, m/z 218.1 [M+H]⁺

Step 1: 5-nitro-1-tetrahydropyran-2-yl-indazole

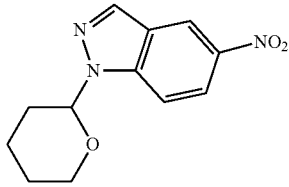 [SMILES: O=[N+]([O-])c1ccc2c(cnn2C2CCCCO2)c1]

To a suspension of 5-nitroindazole (100 g, 613.0 mmol) in DCM (1200 mL) was added p-toluenesulfonic acid monohydrate (11.7 g, 61.3 mmol) and the solution stirred at 25° C. 3,4-Dihydro-2H-pyran (168 mL, 1839 mmol) was then added slowly with the reactor jacket at 20° C. and the reaction slowly formed a dark brown solution. After addition, the reaction was stirred at 25° C. for 1 h. The mixture was transferred to the separator, washed with water (1.5 L), dried over MgSO4, filtered and then reduced in-vacuo to give a dark brown oil. The residue was taken up with DCM (100 mL) purified through a 1.2 kg sinter silica pad (Eluent: 100% DCM to DCM/EtOAc; 95:5) and then triturated with diethyl ether to yield 5-nitro-1-tetrahydropyran-2-yl-indazole (144 g, 582.4 mmol, 95% yield) as a crystalline off-white solid. $^1$H NMR (400 MHz, DMSO-$d_6$) δ 8.81 (d, J=2.1 Hz, 1H), 8.41 (d, J=0.8 Hz, 1H), 8.24 (dd, J=9.3, 2.2 Hz, 1H), 7.93-7.91 (m, 1H), 5.96-5.93 (m, 1H), 3.91-3.86 (m, 1H), 3.80-3.74 (m, 1H), 2.45-2.30 (m, 1H), 1.99-2.02 (m, 2H), 1.82-1.67 (m, 1H), 1.61-1.56 (m, 2H).

Intermediate 14: 4-chloro-1-tetrahydropyran-2-yl-indazol-5-amine

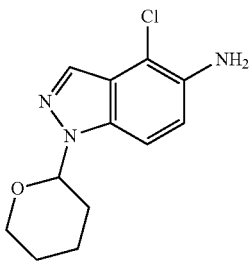 [SMILES: Nc1ccc2c(cnn2C2CCCCO2)c1Cl]

N-Chlorosuccinimide (29.5 g, 220.9 mmol) was added portion wise to a stirred solution of 1-(tetrahydro-2H-pyran-2-yl)-1H-indazol-5-amine (30.00 g, 138.08 mmol) in MeCN (1250 mL) in a completely foil coated round bottomed flask to remove all light from the reaction at 0° C. The reaction was stirred in the dark and checked regularly for reaction progress by LCMS. After 2 h, 3.50 g of NCS was added and the reaction stirred for a further 30 min by which time the reaction was complete. The reaction was allowed to warm to r.t. (final temp was 15° C.). 10% Sodium metabisulfite (500 mL) was added to the reaction and stirring continued for 20 min. The reaction was extracted with diethyl ether, the organic layer washed with water and brine, dried over MgSO$_4$, filtered and concentrated in vacuo. The crude mixture was purified by flash chromatography eluting in EtOAc/Pet. Ether (0-40%) to give 4-chloro-1-tetrahydropyran-2-yl-indazol-5-amine (22.20 g, 88.20 mmol, 64% yield) as a yellow powder after trituration in diethyl ether. UPLC-MS (ES$^+$, Method A): 1.53 min, m/z 252.1 [M+H]$^+$

General Method for the Synthesis of 4-alkyl-5-amino indazoles 15 and 16

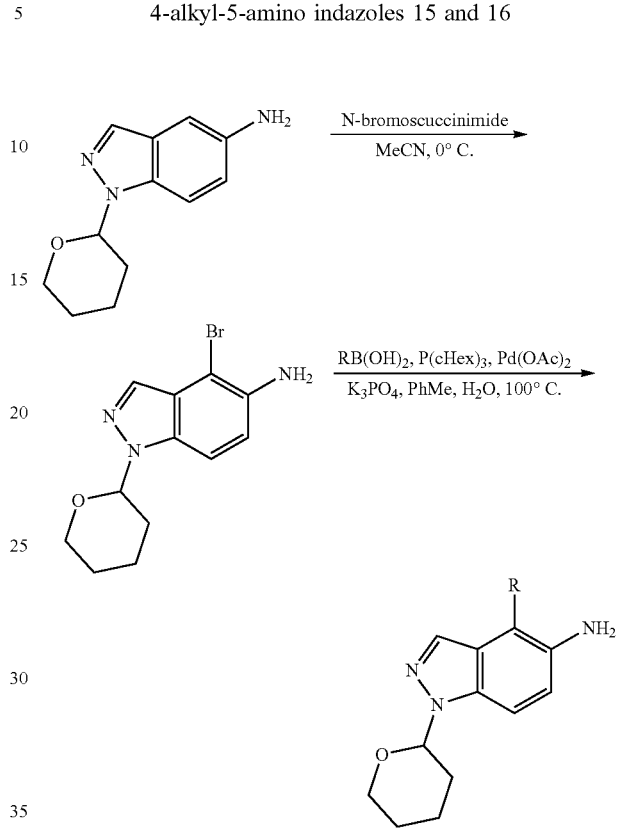

Step 1: 4-bromo-1-tetrahydropyran-2-yl-indazol-5-amine

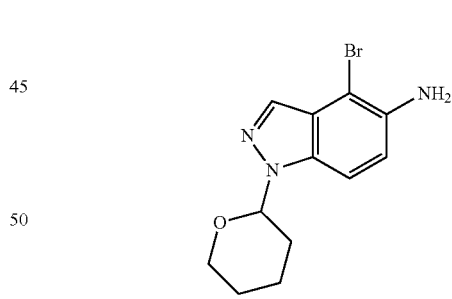

N-Bromosuccinimide (4.71 g, 26.46 mmol) was added portionwise to a stirred solution of 1-(tetrahydro-2H-pyran-2-yl)-1H-indazol-5-amine (5.00 g, 23.01 mmol) in MeCN (150 mL) in a completely foil coated round bottomed flask to remove all light from the reaction. The reaction was stirred in the dark and followed by UPLC-MS until completion. The reaction was quenched with 150 mL of water and 100 mL of EtOAc and the layers separated. The aqueous layer was further extracted with 100 mL of EtOAc and the combined organics washed with sodium thiosulfate solution and brine before drying over magnesium sulfate, filtering and concentrating in-vacuo to give a dark orange sticky solid. This was triturated with diethyl ether and Pet. Ether to give a dark pink solid. This material was purified by column chromatography eluting with 5-30% EtOAc in Pet. Ether to give a solid which was triturated with Pet. Ether and filtered to give a 4-bromo-1-tetrahydropyran-2-yl-indazol-5-amine (3.50 g, 11.82 mmol, 51% yield) as a yellow solid. UPLC-MS (ES+, Method A): 1.59 min, m/z 298.0 [M+H]+

Intermediate 15: 4-cyclopropyl-1-tetrahydropyran-2-yl-indazol-5-amine

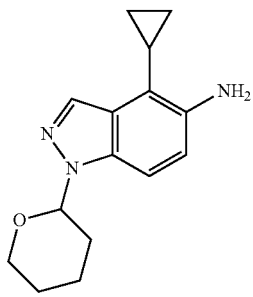 [SMILES: Nc1ccc2c(cnn2C2CCCCO2)c1C1CC1]

4-Bromo-1-tetrahydropyran-2-yl-indazol-5-amine (1.00 g, 321 mmol), potassium phosphate tribasic (2.04 g, 9.62 mmol) and cyclopropylboronic acid (826 mg, 9.62 mmol) were suspended in toluene (15 mL) and water (3 mL) and fully degassed with bubbling nitrogen. Palladium (II) acetate (72 mg, 0.32 mmol) and tricyclohexylphosphine (90 mg, 0.32 mmol) were added followed by further degassing and the reaction was capped and heated to 100° C. for 18 h. The reaction was cooled and partitioned. The organics were dry loaded onto silica and purified on a 40 g silica column eluting with 0-50% EtOAc in Pet. Ether to give 4-cyclopropyl-1-tetrahydropyran-2-yl-indazol-5-amine (580 mg, 2.23 mmol, 70% yield) as a pale brown oil which crystallised upon standing. UPLC-MS (ES+, Method A): 1.19 min, m/z 258.4 [M+H]+

Intermediate 16: 4-ethyl-1-tetrahydropyran-2-yl-indazol-5-amine

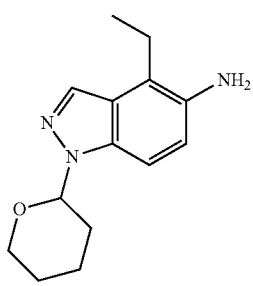 [SMILES: CCc1c(N)ccc2c1cnn2C1CCCCO1]

Following the method used for intermediate 15, 4-bromo-1-tetrahydropyran-2-yl-indazol-5-amine (1.00 g, 3.21 mmol) and ethylboronic add (711 mg, 9.62 mmol) gave 4-ethyl-1-tetrahydropyran-2-yl-indazol-5-amine (500 mg, 2.02 mmol, 63% yield) as a brown oil. UPLC-MS (ES+, Method A): 1.13 min, m/z 246.5 [M+H]+

Method for the Synthesis of Intermediate 17

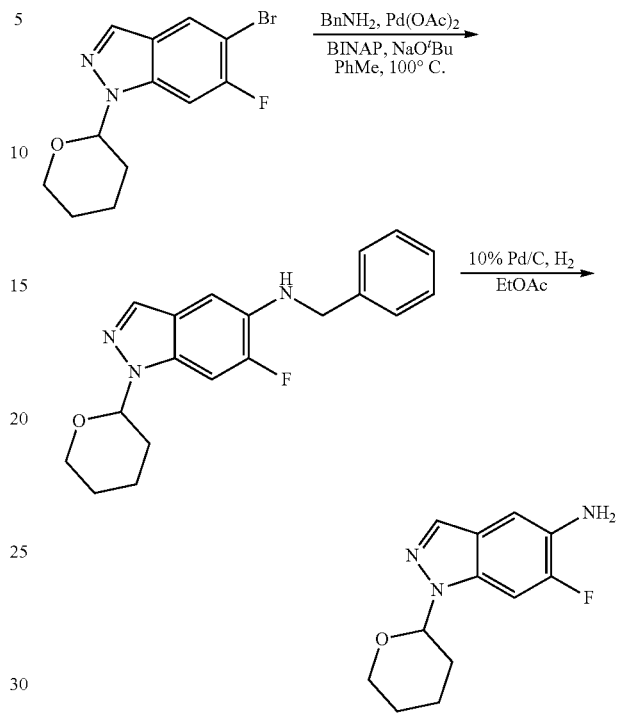

Step 1: N-benzyl-6-fluoro-1-tetrahydropyran-2-yl-indazol-5-amine

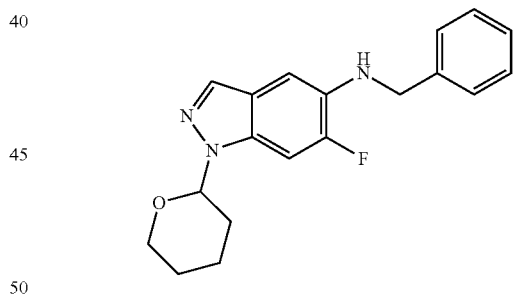

Sodium tert-butoxide (321 mg, 3.34 mmol) was added to a stirred mixture of 5-bromo-6-fluoro-1-tetrahydropyran-2-yl-indazole (500 mg, 1.67 mmol), benzylamine (0.55 mL, 5.01 mmol), palladium (II) acetate (37 mg, 0.17 mmol), (+/−)-BINAP (208 mg, 0.33 mmol) and toluene (5 mL) at r.t. The reaction was evacuated, flushed with nitrogen and stirred at 100° C. for 18 h. It was then cooled to r.t. and solvent removed in vacuo. The residue was loaded onto silica and purified by column chromatography eluting with 0-100% EtOAc in Pet. Ether to give N-benzyl-6-fluoro-1-tetrahydropyran-2-yl-indazol-5-amine (294 mg, 0.90 mmol, 54% yield) as a yellow oil. UPLC-MS (ES+, Method A), 1.92 min, m/z 326.3 [M+H]+

Intermediate 17: 6-fluoro-1-tetrahydropyran-2-yl-indazol-5-amine

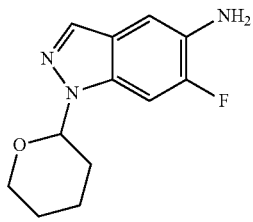 [SMILES: Nc1cc2cnn(C3CCCCO3)c2cc1F]

A solution of N-benzyl-6-fluoro-1-tetrahydropyran-2-yl-indazol-5-amine (367 mg, 1.12 mmol) and ethyl acetate (20 mL) was stirred at r.t. Palladium, 10 wt. % on carbon powder, (50 mg) was added to the reaction mixture and the flask was fitted with a hydrogen balloon. The reaction was degassed and flushed with hydrogen twice and then stirred under a hydrogen atmosphere for 18 h, after which time the reaction was complete by LCMS. The reaction was then degassed and flushed with nitrogen, filtered through Celite® and the filter cake washed with EtOAc (20 mL). The filtrate was purified by column chromatography eluting with 0-10% MeOH in DCM to give 6-fluoro-1-tetrahydropyran-2-yl-indazol-5-amine (240 mg, 1.02 mmol, 80% yield) as a brown oil. UPLC-MS (ES+, Method A), 1.29 min, m/z 236.2 [M+H]+. $^1$H NMR (400 MHz, CDCl$_3$) δ/ppm: 7.89 (1H, d, J=0.8 Hz), 7.32 (1H, d, J=10.4 Hz), 7.30 (1H, d, J=8.0 Hz), 5.62 (1H, dd, J=9.2 Hz, 2.4 Hz), 4.07-3.99 (1H, m), 3.80-3.72 (1H, m), 2.58-2.46 (1H, m), 2.20-2.05 (2H, m), 1.84-1.61 (3H, m), exchangeable NH$_2$ not seen.

Method for the Synthesis of Intermediate 18

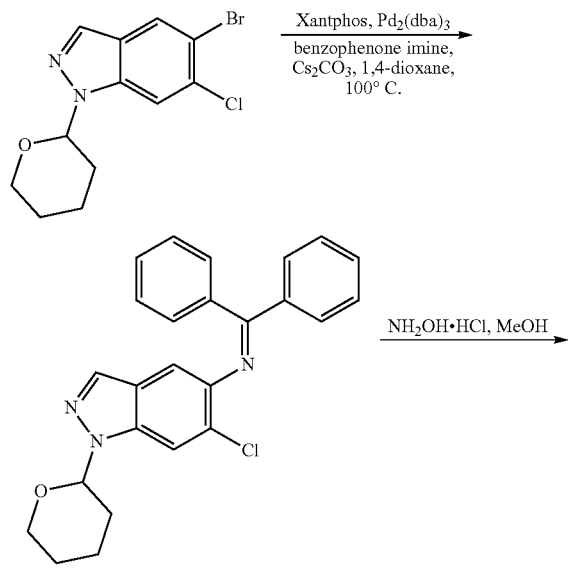

Step 1: N-(6-chloro-1-tetrahydropyran-2-yl-indazol-5-yl)-1,1-diphenyl-methanimine

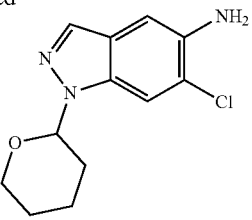

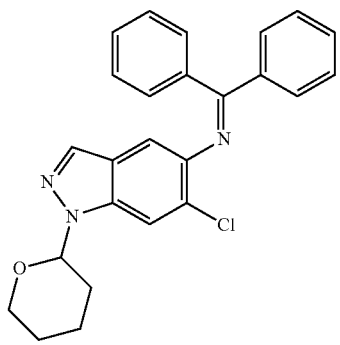 [SMILES: Clc1cc2c(cnn2C2CCCCO2)cc1N=C(c1ccccc1)c1ccccc1]

4,5-Bis(diphenylphosphino)-9,9-dimethylxanthene (183 mg, 0.32 mmol) and bis(dibenzylideneacetone)dipalladium (0) (145 mg, 0.16 mmol) were added to a stirred mixture of 5-bromo-6-chloro-1-tetrahydropyran-2-yl-indazole (1.00 g, 3.17 mmol), benzophenone amine (0.64 mL, 3.8 mmol), cesium carbonate (2.06 g, 6.34 mmol) and 1,4-dioxane (20 mL) at r.t. under a nitrogen atmosphere. The reaction was degassed, flushed with nitrogen and heated to 100° C. for 2 h after which time k was complete by LCMS. The reaction was cooled to r.t. and solvent removed in vacuo. The residue was suspended in EtOAc (10 mL) and filtered through Celite® and the cake washed with EtOAc (10 mL). The filtrate was concentrated in vacuo and then residue purified by column chromatography eluting with 0-50% EtOAc in Pet. Ether to give N-(6-chloro-1-tetrahydropyran-2-yl-indazol-5-yl)-1,1-diphenyl-methanimine (944 mg, 2.27 mmol, 71% yield) as a yellow solid. UPLC-MS (ES+, Method A) 2.20 min, m/z 416.3, 418.3 [M+H]+. $^1$H NMR (400 MHz, CDCl$_3$) δ/ppm: 7.85-7.79 (3H, m), 7.62 (1H, m), 7.55-7.50 (1H, m), 7.48-7.43 (2H, m), 7.27-7.24 (3H, m), 7.21-7.17 (2H, m), 6.83 (1H, s), 5.59 (1H, dd, J=9.6 Hz, 2.4 Hz), 4.09-4.03 (1H, m), 3.79-3.74 (1H, m), 2.55-2.45 (1H, m), 2.17-2.03 (2H, m), 1.83-1.65 (3H, m).

Intermediate 18: 6-chloro-1-tetrahydropyran-2-yl-indazol-5-amine

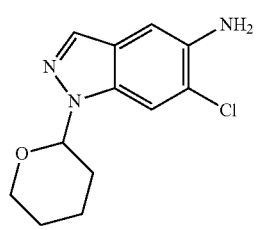

Sodium acetate (2.38 mg, 29.05 mmol) was added to a stirred solution of N-(6-chloro-1-tetrahydropyran-2-yl-indazol-5-yl)-1,1-diphenyl-methanimine (944 mg, 2.27 mmol), hydroxylamine hydrochloride (221 mg, 3.18 mmol) and methanol (10 mL) at r.t. The reaction was stirred for 2 h then heated to 50° C. for 1 h where LCMS showed complete consumption of the starting material. The reaction was cooled to r.t. and solvent removed in vacuo. The residue was partitioned between sat. aq. NH$_4$Cl (100 mL) and EtOAc (100 mL). The organic layer was separated and the aqueous extracted with EtOAc (100 mL). The combined organic layers were dried over sodium sulfate and solvent removed in vacuo. The residue was purified by column chromatography eluting with 0-10% MeOH in DCM to give 6-chloro-1-tetrahydropyran-2-yl-indazol-5-amine (400 mg, 1.59 mmol, 70% yield) as a brown solid. UPLC-MS (ES$^+$, Method A), 1.49 min, m/z 252.1 [M+H]$^+$. $^1$H NMR (400 MHz, CDCl$_3$) δ/ppm: 7.94 (1H, s), 7.72 (1H, s), 6.54-6.28 (1H, m), 5.66 (1H, dd, J=9.2 Hz, 2.4 Hz), 4.05-3.99 (1H, m), 3.81-3.73 (1H, m), 2.56-2.46 (1H, m), 2.12-2.05 (2H, m), 1.83-1.66 (3H, m), 1.95-1.35 (2H, br s).

General Method for the Synthesis of Intermediates 19-23

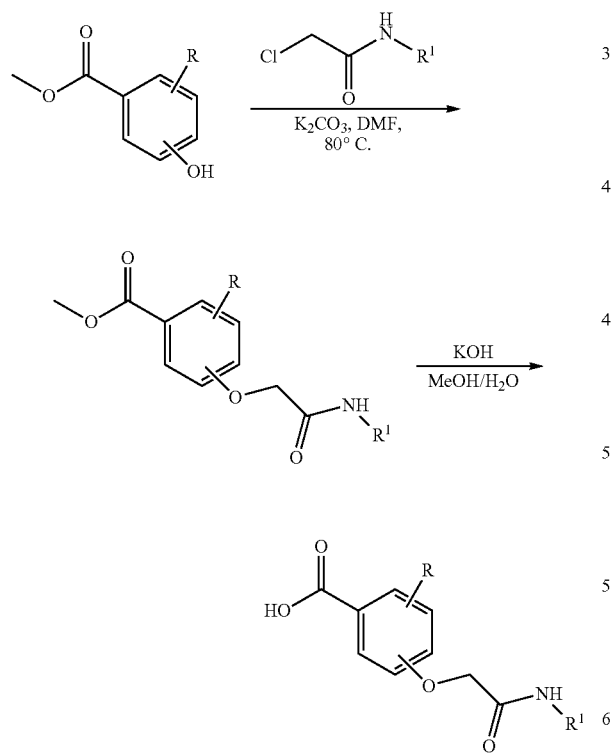

A method for preparing intermediate 19 is given below. Further intermediates that were prepared in a similar manner from commercially available methyl hydroxybenzoates are given in Table 4.

Intermediate 19: 4-[2-(isopropylamino)-2-oxoethoxy]-3-methoxybenzoic acid

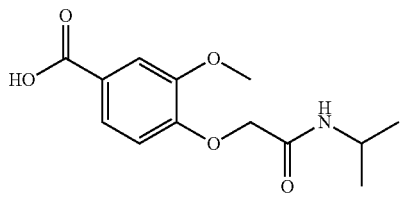 [SMILES: COc1cc(C(=O)O)ccc1OCC(=O)NC(C)C]

To a stirred solution of methyl 4-[2-(isopropylamino)-2-oxoethoxy]-3-methoxybenzoate (273 mg, 0.97 mmol) in MeOH (4 mL) and H$_2$O (1 mL) at r.t. N$_2$ was added potassium hydroxide (109 mg, 1.9 mmol) and the reaction stirred at r.t. for 18 h. The methanol was removed under reduced pressure and EtOAc (20 mL) and 1 M aq. HCl (15 mL) added. The layers were separated and the aqueous layer extracted with EtOAc (2×20 mL). The combined organics were dried (phase separator) and concentrated under reduced pressure. The crude product was purified by flash column chromatography (SiO$_2$) eluting with 1-15% MeOH in DCM to give 4-[2-(isopropylamino)-2-oxoethoxy]-3-methoxybenzoic acid (229 mg, 0.86 mmol, 88% yield) as a white solid. LC-MS (ES$^+$, Method C): 1.70 min, m/z 268.1 [M+H]$^+$. $^1$H NMR (500 MHz, CD$_3$OD): δ 7.81 (br s, 1H), 7.67-7.62 (m, 2H), 7.04 (d, J=8.0 Hz, 1H), 4.57 (s, 2H), 4.13-4.04 (m, 1H), 3.93 (s, 3H), 1.20 (s, 3H), 1.18 (s, 3H).

Step 1: Methyl 4-[2-(isopropylamino)-2-oxoethoxy]-3-methoxybenzoate

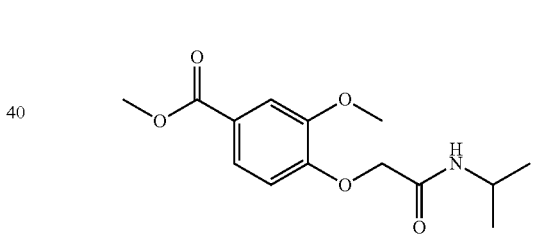

To a stirred solution of methyl vanillate (228 mg, 1.50 mmol) and potassium carbonate (829 mg, 6.00 mmol) in DMF (10 mL) at r.t. under N$_2$ was added 2-chloro-N-isopropylacetamide (274 mg, 2.00 mmol) in a single portion and the reaction heated at 80° C. for 18 h. The solvents were removed under reduced pressure and the residue partitioned between EtOAc (20 mL) and H$_2$O (20 mL). The layers were separated and the aqueous layer extracted with further EtOAc (2×15 mL). The combined organics were washed with H$_2$O (20 mL) and brine (20 mL), dried (phase separator) and concentrated. The crude product was purified by flash column chromatography (SiO$_2$, eluting with 30-80% EtOAc in Pet. Ether) giving methyl 4-[2-(isopropylamino)-2-oxoethoxy]-3-methoxybenzoate (278 mg, 0.99 mmol, 66% yield) as an off-white solid. LC-MS (ES$^+$, Method C): 2.22 min, m/z 282.1 [M+H]$^+$. $^1$H NMR (500 MHz, CDCl$_3$): δ 7.66 (dd, J=8.5, 2.0 Hz, 1H), 7.60 (d, J=2.0 Hz, 1H), 6.89 (d, J=8.5 Hz, 1H), 6.68 (s, 1H), 4.54 (s, 2H), 4.15 (dp, J=8.0, 6.5 Hz, 1H), 3.95 (s, 3H), 3.91 (s, 3H), 1.19 (s, 3H), 1.18 (s, 3H)

Compounds prepared in a similar manner to that set out above are given below in Table 4.

TABLE 4

| Intermediate No. | Structure | LC/MS |
|---|---|---|
| 20 | 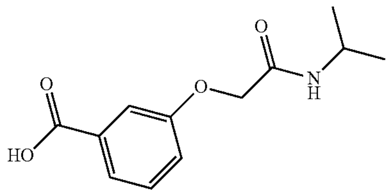 [SMILES: CC(C)NC(=O)COc1cccc(C(=O)O)c1] | LC-MS (ES+, Method C): 1.79 min, m/z 238.1 [M + H]+ |
| 21 | 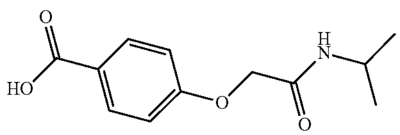 [SMILES: CC(C)NC(=O)COc1ccc(C(=O)O)cc1] | LC-MS (ES+, Method C): 1.73 min, m/z 238.0 [M + H]+ |
| 22 | 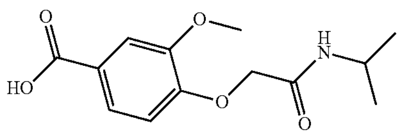 | LC-MS (ES+, Method C): 1.28 min, m/z 262.2 [M + Na]+ |
| 23 | 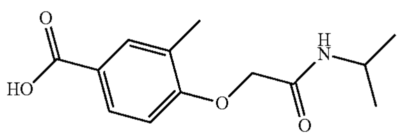 [SMILES: Cc1cc(C(=O)O)ccc1OCC(=O)NC(C)C] | LC-MS (ES+, Method C): 1.99 min, m/z 252.3 [M + H]+ |

General Method for the Synthesis of Intermediates 24-45

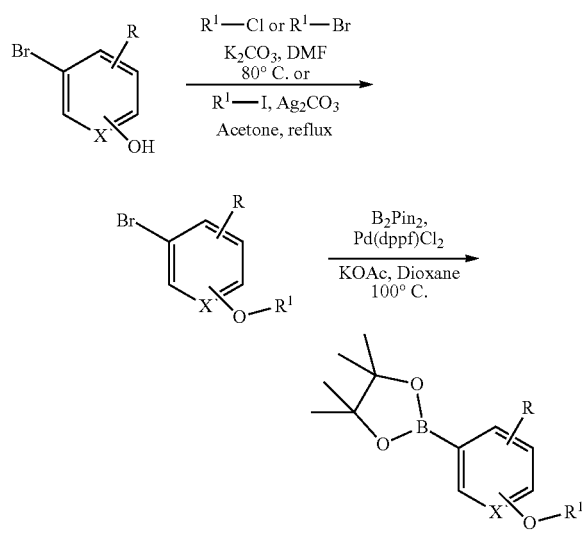

A method for preparing intermediate 24 is given below. Further intermediates that were prepared in a similar manner from commercially available bromophenols are given in Table 5.

Intermediate 24—2-[2-Fluoro-4-(4,4,5,5-tetramethyl-1,3,2-dioxaborolan-2-yl)phenoxy]-N-isopropyl-acetamide

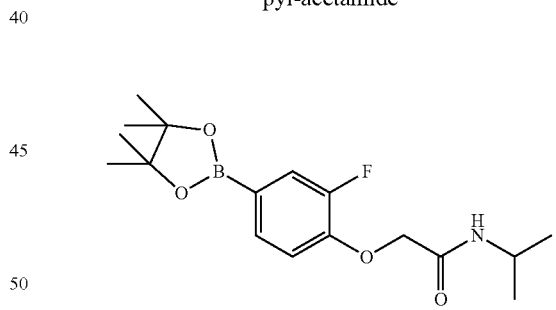

A vial was charged with 2-(4-bromo-2-fluoro-phenoxy)-N-isopropyl-acetamide (306 mg, 1.05 mmol), bis(pinacolato)diboron (348 mg, 1.37 mmol) and potassium acetate (311 mg, 3.16 mmol). 1,4-dioxane (8.5 mL) was added and the solution degassed with $N_2$ for 10 min. Pd(dppf)Cl$_2$·DCM complex (86 mg, 0.11 mmol) was added, and the sealed reaction heated at 100° C. for 18 h. The mixture was filtered through Celite (eluting with EtOAc) and washed with H$_2$O (20 mL). The aqueous layer was back-extracted with EtOAc (2×20 mL) and the combined organics dried (phase separator) and concentrated. The crude product was purified by flash column chromatography (SiO$_2$, eluting with 30-80% EtOAc in Pet. Ether) giving 2-[2-fluoro-4-(4,4,5,5-tetramethyl-1,3,2-dioxaborolan-2-yl)phenoxy]-N-isopropyl-acetamide (288 mg, 0.85 mmol, 81% yield) as a yellow oil, which solidified upon standing. LC-MS (ES+, Method C): 3.20 min, m/z 338.2 [M+H]+. 1H NMR (500 MHz, CDCl3): δ 7.57-7.49 (m, 2H), 6.93 (t, J=8.0 Hz, 1H), 6.48 (s, 1H), 4.52 (s, 2H), 4.18 (dp, J=8.0, 6.5 Hz, 1H), 1.33 (s, 12H), 1.21 (d, J=6.5 Hz, 6H).

Step 1:
2-(4-Bromo-2-fluoro-phenoxy)-N-isopropyl-acetamide

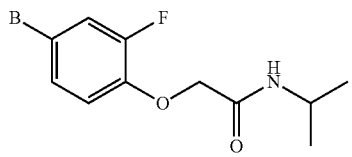

To a stirred solution of 4-bromo-2-fluorophenol (110 μL, 1.0 mmol) and potassium carbonate (553 mg, 4.0 mmol) in 1,4-dioxane (5.0 mL) at r.t. under N2 was added 2-chloro-N-isopropylacetamide (176 mg, 1.30 mmol) and the reaction heated at 80° C. for 18 h. The solvents were removed under reduced pressure and the residue partitioned between EtOAc (20 mL) and H2O (20 mL). The layers were separated and the aqueous portion extracted with EtOAc (2×15 mL). The combined organics were dried (phase separator) and concentrated. The crude product was purified by flash column chromatography (SiO2, eluting with 30-60% EtOAc in Pet. Ether) giving 2-(4-bromo-2-fluoro-phenoxy)-N-isopropyl-acetamide (307 mg, 0.95 mmol, 95% yield) as a brown oil. LC-MS (ES+, Method C): 2.80 min, m/z 292.0 [M+H]+.

Compounds prepared in a similar manner to that set out above are given below in Table 5.

TABLE 5

| Intermediate No. | Structure | LC/MS |
|---|---|---|
| 25 | 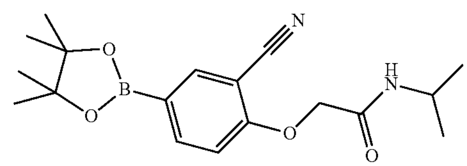 [SMILES: CC(C)NC(=O)COc1ccc(B2OC(C)(C)C(C)(C)O2)cc1C#N] | LC-MS (ES+, Method C): 3.17 min, m/z 367.3 [M + Na]+ |
| 26 | 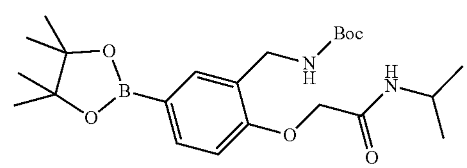 [SMILES: CC(C)NC(=O)COc1ccc(B2OC(C)(C)C(C)(C)O2)cc1CNC(=O)OC(C)(C)C] | LC-MS (ES+, Method C): 3.51 min, m/z 449.4 [M + H]+ |
| 27 | 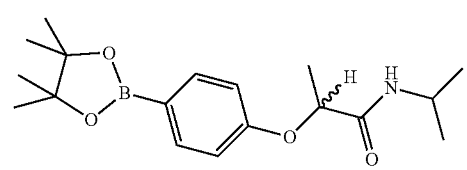 [SMILES: CC(C)NC(=O)C(C)Oc1ccc(B2OC(C)(C)C(C)(C)O2)cc1] | LC-MS (ES+, Method C): 3.17 min, m/z 334.2 [M + H]+ |
| 28 | 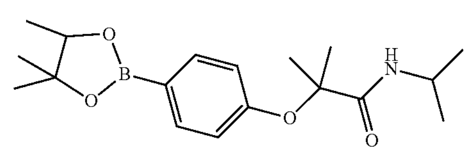 | LC-MS (ES−, Method C): 3.48 min, m/z 346.2 [M − H]− |
| 29 | 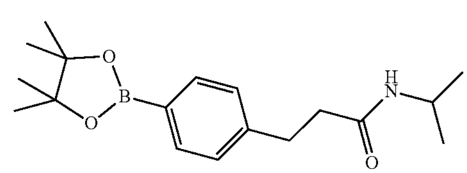 [SMILES: CC(C)NC(=O)CCc1ccc(B2OC(C)(C)C(C)(C)O2)cc1] | LC-MS (ES+, Method C): 2.95 min, m/z 318.2 [M + H]+ |
| 30 | 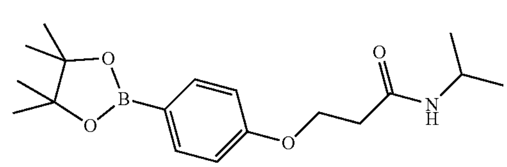 [SMILES: CC(C)NC(=O)CCOc1ccc(B2OC(C)(C)C(C)(C)O2)cc1] | LC-MS (ES+, Method C): 2.96 min, m/z 334.2 [M + H]+ |

TABLE 5-continued

| Intermediate No. | Structure | LC/MS |
|---|---|---|
| 31 | 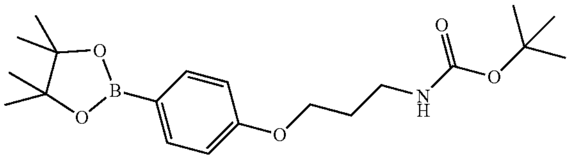 [SMILES: CC(C)(C)OC(=O)NCCCOc1ccc(B2OC(C)(C)C(C)(C)O2)cc1] | LC-MS (ES+, Method C): 3.84 min, m/z 378.1 [M + H]+ |
| 32 | 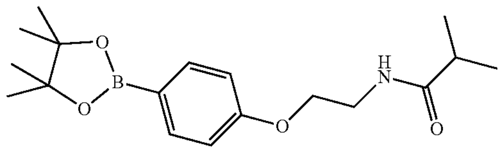 [SMILES: CC(C)C(=O)NCCOc1ccc(B2OC(C)(C)C(C)(C)O2)cc1] | LC-MS (ES+, Method C): 3.02 min, m/z 334.1 [M + H]+ |
| 33 | 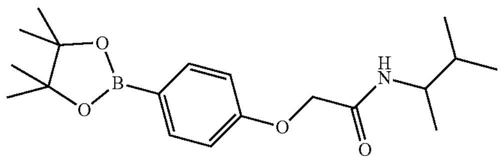 | LC-MS (ES+, Method C): 1.76 min, m/z 320.0 [M + H]+ |
| 34 | 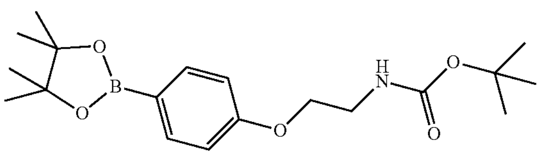 [SMILES: CC(C)(C)OC(=O)NCCOc1ccc(B2OC(C)(C)C(C)(C)O2)cc1] | LC-MS (ES+, Method D): 3.68 min, m/z 364.1 [M + H]+ |
| 35 | 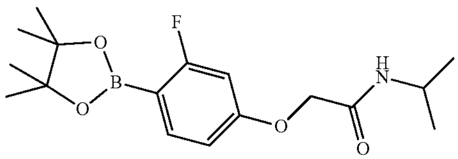 | LC-MS (ES+, Method C): 3.08 min, m/z 337.2 [M + H]+ |
| 36 | 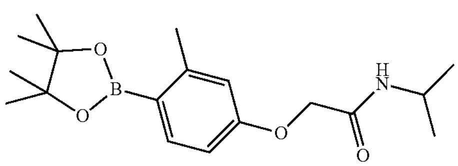 [SMILES: Cc1cc(OCC(=O)NC(C)C)ccc1B1OC(C)(C)C(C)(C)O1] | LC-MS (ES+, Method C): 3.38 min, m/z 334.2 [M + H]+ |
| 37 | 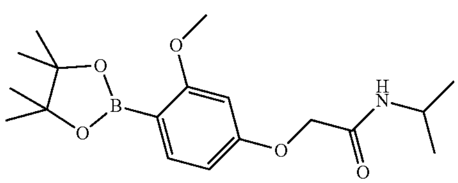 [SMILES: COc1cc(OCC(=O)NC(C)C)ccc1B1OC(C)(C)C(C)(C)O1] | LC-MS (ES+, Method C): 2.78 min, m/z 349.1 [M + H]+ |
| 38 | 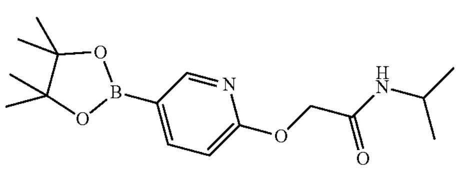 [SMILES: CC(C)NC(=O)COc1ccc(B2OC(C)(C)C(C)(C)O2)cn1] | LC-MS (ES+, Method A): 1.73 min, m/z 321.0 [M + H]+ |
| 39 | 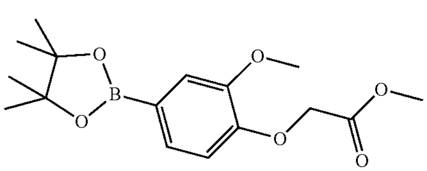 | UPLC-MS (ES+, Method A): 1.81 min, m/z 323.3 [M + H]+ |

TABLE 5-continued

| Intermediate No. | Structure | LC/MS |
|---|---|---|
| 40 | 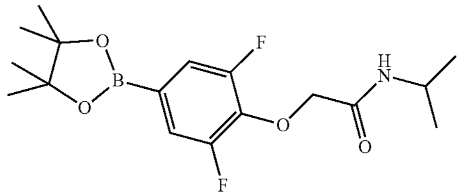 | LC-MS (ES+, Method D): 3.94 min, m/z 273.9 [M − pinacol + H]+ |
| 41 | 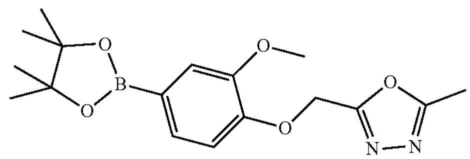 | LC-MS (ES+, Method C): 2.83 min, m/z 347.1 [M + H]+ |
| 42 | 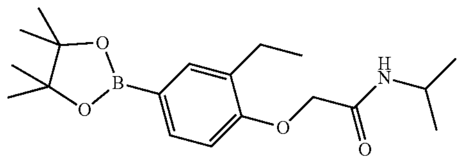 [SMILES: CCc1cc(B2OC(C)(C)C(C)(C)O2)ccc1OCC(=O)NC(C)C] | UPLC-MS (ES+, Method A): 2.02 min, m/z 348.0 [M + H]+ |
| 43 | 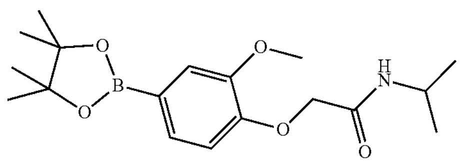 [SMILES: COc1cc(B2OC(C)(C)C(C)(C)O2)ccc1OCC(=O)NC(C)C] | LC-MS (ES+, Method C): 3.03 min, m/z 350.1 [M + H]+ |
| 44 | 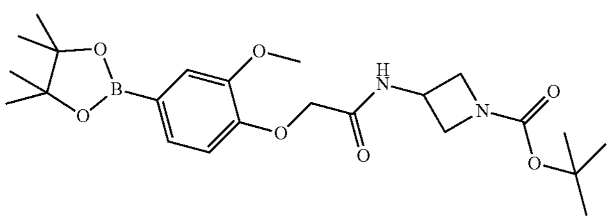 [SMILES: COc1cc(B2OC(C)(C)C(C)(C)O2)ccc1OCC(=O)NC1CN(C(=O)OC(C)(C)C)C1] | LC-MS (ES+, Method C): 3.18 min, m/z 463.1 [M + H]+ |

Intermediate 45: N-isopropyl-2-[2-oxo-4-(4,4,5,5-tetramethyl-1,3,2-dioxaborolan-2-yl)-1-pyridyl]acetamide

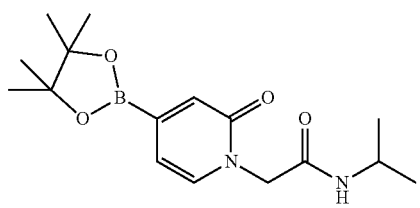 [SMILES: CC(C)NC(=O)Cn1ccc(B2OC(C)(C)C(C)(C)O2)cc1=O]

Following the procedure used for intermediate 24, bis(pinacolato)diboron (66 mg, 0.26 mmol) and 2-(4-bromo-2-oxo-1-pyridyl)-N-isopropyl-acetamide (55 mg, 0.2 mmol) gave N-isopropyl-2-[2-oxo-4-(4,4,5,5-tetramethyl-1,3,2-dioxaborolan-2-yl)-1-pyridyl]acetamide (64 mg, 100%). $^1$H NMR (500 MHz, CDCl$_3$) δ 7.37 (dd, 1H), 7.05 (s, 1H), 6.80 (dd, 1H), 4.48 (s, 2H), 3.95 (m, 1H), 1.30 (s, 12H), 1.10 (d, 6H).

Step 1: 2-(4-bromo-2-oxo-1-pyridyl)-N-isopropyl-acetamide

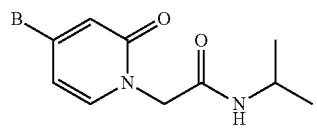

To a stirred solution of 4-bromopyridin-2-ol (210 mg, 1.21 mmol) and potassium carbonate (667 mg, 4.83 mmol) in dry DMF (7 mL) at r.t. under nitrogen was added 2-chloro-N-isopropylacetamide (213 mg, 1.57 mmol) and the reaction heated at 80° C. overnight. The mixture was cooled to r.t. and solvents removed under reduced pressure. The residue was dissolved in EtOAc (20 mL) and washed with H$_2$O (15 mL). The aqueous layer extracted with EtOAc (2×15 mL) and the combined organics washed with brine, dried (phase sep.) and concentrated. The crude material was purified by column chromatography (SiO$_2$, eluting with 1-10% MeOH in DCM) giving an inseparable 96:4 mixture of 2-(4-bromo-2-oxo-1-pyridyl)-N-isopropyl-acetamide (143 mg, 0.52 mmol, 43% yield) and 2-[(4-bromo-2- pyridyl)oxy]-N-isopropyl-acetamide (6 mg, 0.02 mmol, 2% yield). UPLC-MS (ES+, Method A): 1.14 min, m/z 274.8 [M+H]+. $^1$H NMR (500 MHz, CDCl$_3$) δ 7.24 (d, J=4.9 Hz, 1H), 6.82 (d, J=2.1 Hz, 1H), 6.48 (s, 1H), 6.38 (dd, J=7.3, 2.2 Hz, 1H), 4.42 (s, 2H), 4.03-3.87 (m, 1H), 1.10 (d, J=6.6 Hz, 6H).

Compounds prepared in a similar manner to that set out above are given below in Table 6a and 6b.

TABLE 6a

| Intermediate No. | Structure | LC/MS |
| --- | --- | --- |
| 46a | [structure] | LC-MS (ES+, Method C): 1.43 min, m/z 273 [M + H]+ |
| 47a | [structure] | LC-MS (ES+, Method A): 1.22 min, m/z 288.9 [M + H]+ |
| 48a | [structure] | UPLC-MS (ES+, Method A): 1.21 min, m/z 288.8 [M + H]+ |

TABLE 6b

| | | |
| --- | --- | --- |
| 46 | [structure] | LC-MS (ES+, Method C): 2.15 min, m/z 321 [M + H]+ |
| 47 | [structure] | LC-MS (ES+, Method A): 0.89 min, m/z 252.9 [M(− pinacol) + H]+ |
| 48 | [structure] | UPLC-MS (ES+, Method A): 0.90 min, m/z 253.0 [M − pinacol) + H]+ |

Synthesis of Carbamate and Urea Boronates 49 and 50

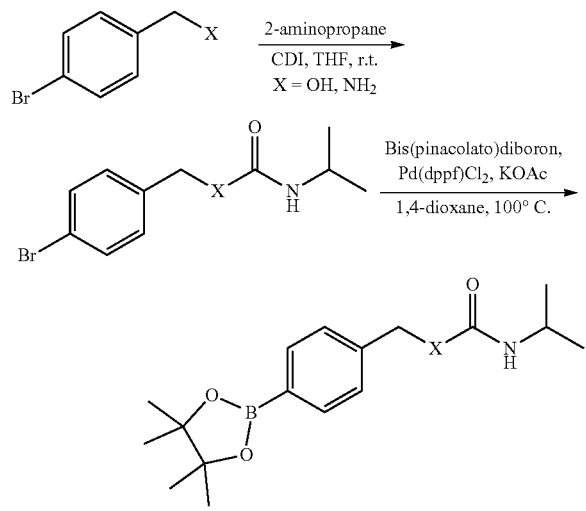

Intermediate 49: [4-(4,4,5,5-tetramethyl-1,3,2-dioxaborolan-2-yl)phenyl]methyl N-isopropylcarbamate

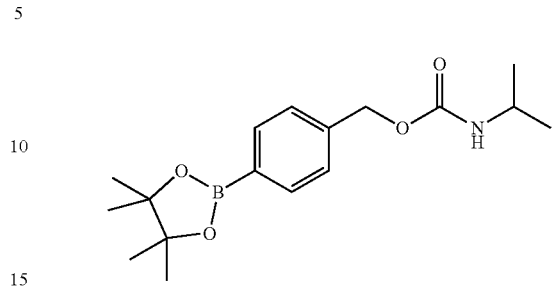

Following the intermediate 24 procedure, bis(pinacolato)diboron (145 mg, 0.57 mmol) and (4-bromophenyl)methyl N-isopropylcarbamate (120 mg, 0.44 mmol) gave [4-(4,4,5,5-tetramethyl-1,3,2-dioxaborolan-2-yl)phenyl]methyl N-isopropylcarbamate (130 mg, 0.44 mmol, 100% yield) as a brown gum. UPLC-MS (ES+, Method A): 3.50 min, m/z 320.1 [M+H]$^+$

Intermediate 51: 1-isopropyl-3-[[4-(4,4,5,5-tetramethyl-1,3,2-dioxaborolan-2-yl)phenyl]methyl]urea Step 1: 1-[(4-bromophenyl)methyl]-3-isopropyl-urea

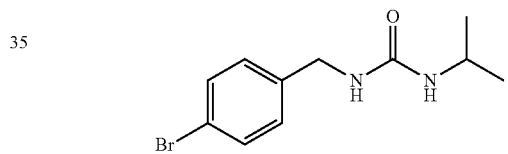

1,1'-Carbonyldiimidazole (0.25 mL, 1.8 mmol) was added to a stirred solution of 4-bromobenzylamine hydrochloride (200 mg, 0.90 mmol) in THF (8 mL) and the reaction mixture was stirred at 25° C. for 2 h. 2-Aminopropane (0.23 mL, 2.7 mmol) was added and the reaction mixture was stirred at 25° C. overnight. LCMS showed reaction complete therefore solvents were removed under vacuum. The residue was taken up in EtOAc (10 mL) and 1 M HCl (10 mL). The layers were separated and the aqueous layer extracted with EtOAc (2×10 mL). The combined organic were washed with brine (10 mL), dried (phase separator) and concentrated under vacuum. The crude product was purified by column chromatography (SiO$_2$, eluting with 0-60% EtOAc in Pet. Ether) giving 1-[(4-bromophenyl)methyl]-3-isopropyl-urea (245 mg, 0.90 mmol, 100% yield) as a white solid. UPLC-MS (ES$^+$, Method A): 2.48 min, m/z 274.0 [M+H]$^+$. $^1$H NMR (400 MHz, CDCl$_3$) δ 7.46-7.41 (m, 2H), 7.19-7.14 (m, 2H), 4.58 (s, 1H), 4.31 (d, J=5.9 Hz, 2H), 4.17 (d, J=7.9 Hz, 1H), 3.91-3.83 (m, 1H), 1.15-1.13 (m, 6H).

Intermediate 49: [4-(4,4,5,5-tetramethyl-1,3,2-dioxaborolan-2-yl)phenyl]methyl N-isopropylcarbamate Step 1: (4-bromophenyl)methyl N-isopropylcarbamate

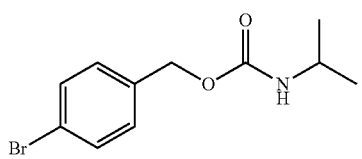

1,1'-Carbonyldiimidazole (0.45 mL, 3.21 mmol) was added to a stirred solution of 4-bromobenzyl alcohol (300 mg, 1.6 mmol) in THF (8 mL) and the reaction mixture was stirred at 25° C. for 2 h. 2-Aminopropane (0.41 mL, 4.81 mmol) was added and the reaction mixture was stirred at 25° C. for a further 4 h. Solvent was then removed under vacuum and the residue was taken up in EtOAc (10 mL) and water (10 mL). The layers were separated and the aqueous portion back extracted with EtOAc (2×10 mL). The combined organics were washed with brine (10 mL), dried (phase sep.) and concentrated under vacuum. The crude product was purified by column chromatography (SiO$_2$, eluting with 20-70% EtOAc in Pet. Ether) giving (4-bromophenyl)methyl N-isopropylcarbamate (334 mg, 1.23 mmol, 76% yield) as a white solid. UPLC-MS (ES$^+$, Method A): 3.12 min, m/z 272.20 [M+H]$^+$. $^1$H NMR (400 MHz, DMSO-d$_6$) δ 7.59-7.53 (m, 2H), 7.33-7.27 (m, 2H), 7.19 (d, J=7.7 Hz, 1H), 4.97 (s, 2H), 3.65-3.53 (m, 1H), 1.05 (d, J=6.6 Hz, 6H).

Intermediate 50: 1-isopropyl-3-[[4-(4,4,5,5-tetramethyl-1,3,2-dioxaborolan-2-yl)phenyl]methyl]urea

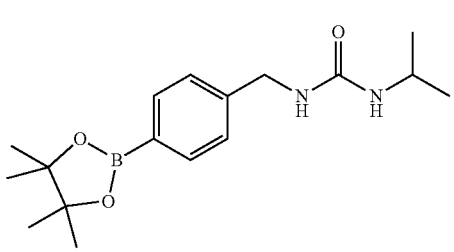 [SMILES: CC(C)NC(=O)NCc1ccc(B2OC(C)(C)C(C)(C)O2)cc1]

Following the intermediate 24 procedure, 1-[(4-bromophenyl)methyl]-3-isopropyl-urea (80 mg, 0.30 mmol) and bis(pinacolato)diboron (97 mg, 0.38 mmol) afforded 1-isopropyl-3-[[4-(4,4,5,5-tetramethyl-1,3,2-dioxaborolan-2-yl)phenyl]methyl]urea (95 mg, 0.30 mmol, 100% yield) as a brown gum. UPLC-MS (ES$^+$, Method A): 2.80 min, m/z 319.08 [M+H]+

Intermediate 51: N-isopropyl-2-[2-morpholino-4-(4,4,5,5-tetramethyl-1,3,2-dioxaborolan-2-yl)phenoxy]acetamide

Step 1: 4-(5-bromo-2-methoxy-phenyl)morpholine

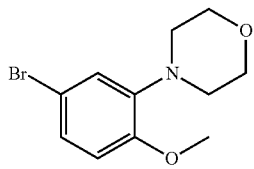

A vial was charged with 4-bromo-2-iodoanisole (500 mg, 1.6 mmol), 4,5-bis(diphenylphosphino)-9,9-dimethylxanthene (92 mg, 0.16 mmol), tris(dibenzylideneacetone)dipalladium (0) (73 mg, 0.08 mmol) and sodium tert-butoxide (0.2 mL, 1.92 mmol) in Toluene (7 mL). Morpholine (0.14 mL, 1.6 mmol) was added and the mixture sealed and stirred at 80° C. for 2 h. The reaction mixture was cooled to r.t., diluted with EtOAc (15 mL) and water (10 mL) and filtered through celite twice. Layers separated, aqueous layer extracted with EtOAc (2×10 mL) and combined organics dried (phase sep.) and concentrated. Purification by flash column chromatography (SiO$_2$, eluting with 25-35% EtOAc in pet ether) giving 4-(5-bromo-2-methoxy-phenyl)morpholine (113 mg, 0.41 mmol, 26% yield) as a yellow oil which crystallised upon standing. UPLC-MS (ES$^+$, Method A): 1.73 min, m/z 273.9 [M+H]$^+$. $^1$H NMR (400 MHz, CDCl$_3$) δ 7.10 (dd, J=8.6, 2.4 Hz, 1H), 6.99 (d, J=2.4 Hz, 1H), 6.73 (d, J=8.6 Hz, 1H), 3.90-3.85 (m, 4H), 3.84 (s, 3H), 3.08-3.02 (m, 4H).

Step 2: 4-bromo-2-morpholino-phenol

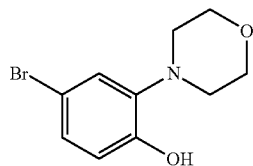 [SMILES: Oc1ccc(Br)cc1N1CCOCC1]

Boron tribromide solution (1 M in heptane) (0.7 mL, 4.1 mmol) was added to a solution of 4-(5-bromo-2-methoxyphenyl)morpholine (223 mg, 0.82 mmol) in dry DCM (3 mL) at −78° C., under nitrogen. The mixture was allowed to warm to r.t. and stirred overnight. Another 3 equivalents of boron tribromide solution (1 M in heptane) were added and the reaction stirred or 48 h. The mixture was then cooled to −78° C. and quenched with sat. aq. NaHCO$_3$ (15 mL) and then extracted with EtOAc (2×15 mL), the combined organics were washed with water, and brine (15 mL), dried (phase separator) and concentrated in vacuo. The residue was purified by flash chromatography eluting with 20-33% EtOAc in Pet ether to give 4-bromo-2-morpholino-phenol (100 mg, 0.39 mmol, 47% yield) as a brown oil. UPLC-MS (ES$^+$, Method A): 1.55 min, m/z 2806.0 [M+H]$^+$. $^1$H NMR (500 MHz, CDCl$_3$) δ 7.25 (d, J=2.4 Hz, 1H), 7.20 (dd, J=8.6, 2.4 Hz, 1H), 6.88-6.71 (m, 2H), 3.86 (t, J=4.4 Hz, 4H), 2.86 (t, J=4.5 Hz, 4H).

Step 3: 2-(4-bromo-2-morpholino-phenoxy)-N-isopropyl-acetamide

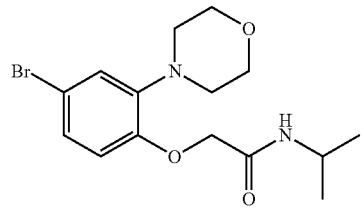 [SMILES: CC(C)NC(=O)COc1ccc(Br)cc1N1CCOCC1]

To a stirred solution of 4-bromo-2-morpholino-phenol (115 µL, 0.37 mmol) and potassium carbonate (205 mg, 1.49 mmol) in 1,4-dioxane (3 mL) at r.t. under nitrogen was added 2-chloro-N-isopropylacetamide (81 mg, 0.60 mmol) in a single portion and the reaction heated at 80° C. overnight. A further 0.2 equivalents of 2-chloro-N-isopropylacetamide (81 mg, 0.60 mmol) was added and the reaction left to stir overnight. Solvents were removed under reduced pressure and the residue partitioned between EtOAc (20 mL) and H$_2$O (20 mL) and layers separated. The aqueous layer was extracted with EtOAc (2×15 mL) and the combined organics were washed with brine, dried (phase sep.) and concentrated in vacuo. The residue was purified by flash chromatography (eluted with 60-100% EtOAc in Petroleum ether) to give 2-(4-bromo-2-morpholino-phenoxy)-N-isopropyl-acetamide (89 mg, 0.25 mmol, 67% yield) as a yellow oil which crystallised upon standing. UPLC-MS (ES$^+$, Method A): 1.63 min, m/z 359.1 [M+H]$^+$. $^1$H NMR (400 MHz, CDCl$_3$) δ 7.14 (dd, J=8.6, 2.4 Hz, 1H), 7.07 (d, J=2.3 Hz, 1H), 6.91 (d, J=8.2 Hz, 1H), 6.76 (d, J=8.6 Hz, 1H), 4.51 (s, 2H), 4.18 (dp, J=8.2, 6.6 Hz, 1H), 3.93-3.82 (m, 4H), 3.10-3.00 (m, 4H), 1.19 (d, J=6.6 Hz, 6H).

Intermediate 51: N-isopropyl-2-[2-morpholino-4-(4,4,5,5-tetramethyl-1,3,2-dioxaborolan-2-yl)phenoxy]acetamide

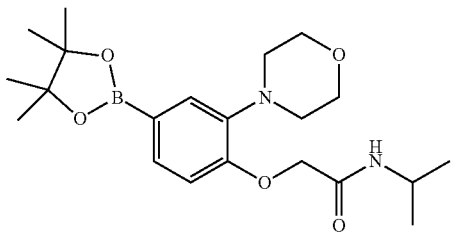 [SMILES: CC(C)NC(=O)COc1ccc(B2OC(C)(C)C(C)(C)O2)cc1N1CCOCC1]

Following the intermediate 24 procedure, bis(pinacolato)diboron (95 mg, 0.38 mmol) and 2-(4-bromo-2-morpholino-phenoxy)-N-isopropyl-acetamide (112 mg, 0.31 mmol) gave N-isopropyl-2-[2-morpholino-4-(4,4,5,5-tetramethyl-1,3,2-dioxaborolan-2-yl)phenoxy]acetamide (125 mg, 0.31 mmol, 100% yield). UPLC-MS (ES+, Method A): 1.71 min, m/z 405.3 [M+H]+

General Route to Intermediates 52-55

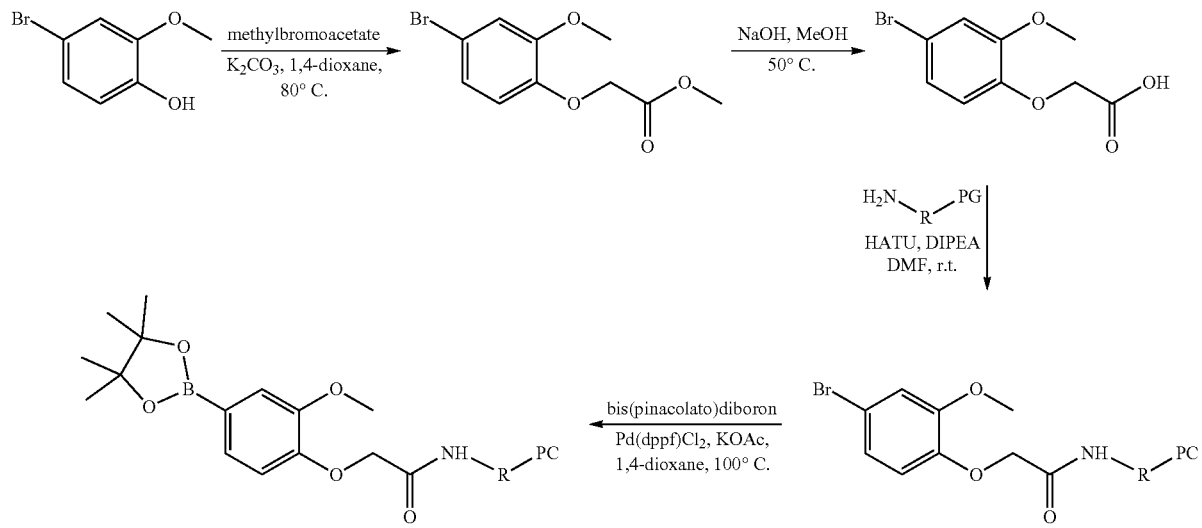

Intermediate 52: tert-butyl 3-[[2-[2-methoxy-4-(4,4,5,5-tetramethyl-1,3,2-dioxaborolan-2-yl)phenoxy]acetyl]amino]pyrrolidine-1-carboxylate

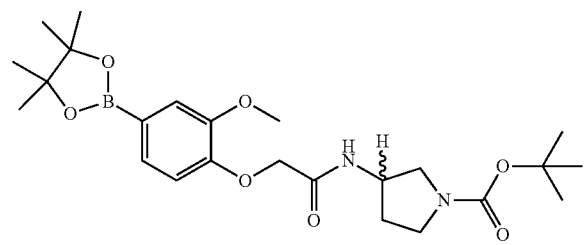 [SMILES: COc1cc(B2OC(C)(C)C(C)(C)O2)ccc1OCC(=O)NC1CCN(C(=O)OC(C)(C)C)C1]

A vial was charged with tert-butyl 3-[[2-(4-bromo-2-methoxy-phenoxy)acetyl]amino]pyrrolidine-1-carboxylate (109 mg, 0.25 mmol), potassium acetate (75 mg, 0.76 mmol) and bis(pinacolato)diboron (77 mg, 0.30 mmol). 1,4-dioxane (2.5 mL) was added and the solution degassed with nitrogen for 10 min. [1,1'-bis(diphenylphosphino)ferrocene]paladium(II) chloride dichloromethane complex (21 mg, 0.03 mmol) was added. The sealed vial was heated at 100° C. for 4 h. The mixture was cooled to r.t., filtered through a phase separator and concentrated under reduced pressure to give tert-butyl 3-[[2-[2-methoxy-4-(4,4,5,5-tetramethyl-1,3,2-dioxaborolan-2-yl)phenoxy]acetyl]amino]pyrrolidine-1-carboxylate (119 mg, 0.25 mmol, 100% yield). LC-MS (ES+, Method C): 3.24 min, m/z 477.1 [M+H]+ Compounds prepared in a similar manner to that set out above are given below in Table 7.

Step 1: methyl 2-(4-bromo-2-methoxy-phenoxy)acetate

A solution of 4-bromo-2-methoxyphenol (10 g, 49.25 mmol), methyl bromoacetate (5.59 mL, 59.11 mmol) and potassium carbonate (27.23 g, 197.02 mmol) in 1,4-dioxane (100 mL) was heated to 80° C. for 18 h. The mixture was concentrated under reduced pressure to a white solid, which was partitioned between water and dichloromethane. The organic layer was separated, the aqueous washed three times with dichloromethane and the organics combined, washed with water and brine, dried (MgSO₄) and concentrated under reduced pressure to yield methyl 2-(4-bromo-2-methoxy-phenoxy)acetate (13 g, 47.26 mmol, 96% yield) as a colourless oil which crystallized overnight. LC-MS (ES+, Method C): 2.89 min, m/z 276.85 [M+H]+. ¹H NMR (400 MHz, CDCl₃) δ 7.05-7.02 (m, 1H), 7.01 (d, J=2.3 Hz, 1H), 6.73 (d, J=8.3 Hz, 1H), 4.69 (s, 2H), 3.90 (s, 3H), 3.82 (s, 3H).

Step 2: 2-(4-bromo-2-methoxy-phenoxy)acetic acid

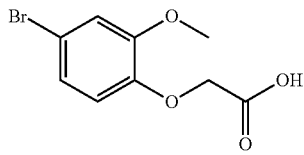

A solution of methyl 2-(4-bromo-2-methoxy-phenoxy)acetate (13.00 g, 47.3 mmol) and sodium hydroxide (9.45 g, 236 mmol) in methanol (150 mL) was heated to 50° C. for 18 h, after which the mixture was concentrated under reduced pressure to a white powder, dissolved in water and the product crashed out of solution by dropwise addition of 2N HCl. The white solid was filtered off and dried under vacuum to yield 2-(4-bromo-2-methoxy-phenoxy)acetic acid (12 g, 46.0 mmol, 97% yield) as a white powder. LC-MS (ES$^+$, Method C): 2.24 min, m/z 262.81 [M+H]$^+$. $^1$H NMR (400 MHz, DMSO-d$_6$) δ 7.14 (d, J=2.3 Hz, 1H), 7.04 (dd, J=8.6, 2.3 Hz, 1H), 6.82 (d, J=8.6 Hz, 1H), 4.67 (s, 2H), 3.80 (s, 3H), 3.36 (s, 1H).

Step 3: tert-butyl 3-[[2-(4-bromo-2-methoxy-phenoxy)acetyl]amino]pyrrolidine-1-carboxylate

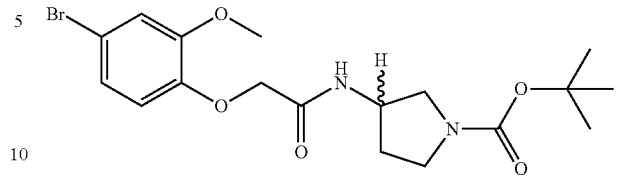

A solution of 2-(4-bromo-2-methoxy-phenoxy)acetic acid (3.2 g, 12.26 mmol) and N,N-diisopropylethylamine (10.68 mL, 61.29 mmol) in DMF (5 mL) was stirred for 5 min, 2-(7-aza-1H-benzotriazole-1-yl)-1,1,3,3-tetramethyluronium hexafluorophosphate (HATU) (5.59 g, 14.71 mmol) was added and the solution stirred for 1 h, after which was added 1-Boc-3-aminopyrrolidine (2.68 mL, 14.71 mmol) and the reaction stirred at r.t. for 24 h. The solvent was removed under reduced pressure, yielding an orange, oily solid which was dissolved in EtOAc and washed with water followed by brine and dried (MgSO$_4$). The organics were concentrated under reduced pressure to give an orange solid. Further purification by flash chromatography eluting which 30-50% EtOAc in Pet. Ether, afforded tert-butyl 3-[[2-(4-bromo-2-methoxy-phenoxy)acetyl]amino]pyrrolidine-1-carboxylate (3.74 g, 8.71 mmol, 71% yield) as a yellow oil which produced a foam under vacuum. LC-MS (ES$^+$, Method C): 3.02 min, m/z 430.9 [M+H]$^+$. $^1$H NMR (400 MHz, DMSO-d$_6$) δ 8.22 (s, 1H), 7.16 (d, J=2.3 Hz, 1H), 7.05 (dd, J=8.6, 2.3 Hz, 1H), 6.85 (d, J=8.6 Hz, 1H), 4.48 (s, 2H), 4.25 (t, J=6.2 Hz, 1H), 3.81 (s, 3H), 3.45 (td, J=13.1, 12.0, 6.2 Hz, 1H), 3.31-3.22 (m, 2H), 3.07 (dd, J=11.0, 5.0 Hz, 1H), 2.02 (dt, J=13.4, 6.7 Hz, 1H), 1.79 (s, 1H), 1.41 (s, 9H).

TABLE 7

| Intermediate No. | Structure | LC/MS |
| --- | --- | --- |
| 53 | 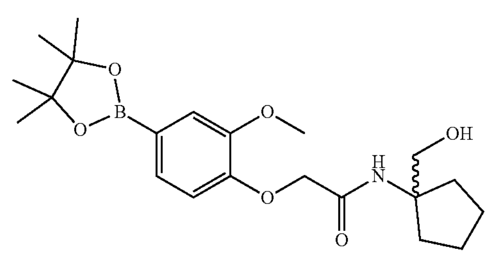 [SMILES: COc1cc(B2OC(C)(C)C(C)(C)O2)ccc1OCC(=O)NC1(CO)CCCC1] | Method C, 2.98 min, m/z 428.0 [M + Na]$^+$ |
| 54 | 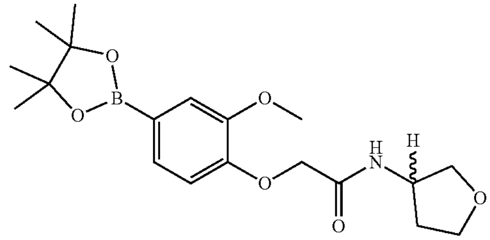 [SMILES: COc1cc(B2OC(C)(C)C(C)(C)O2)ccc1OCC(=O)NC1CCOC1] | Method C, 2.64 min, m/z 378.1 [M + H]$^+$ |

TABLE 7-continued

| Intermediate No. | Structure | LC/MS |
|---|---|---|
| 55 | 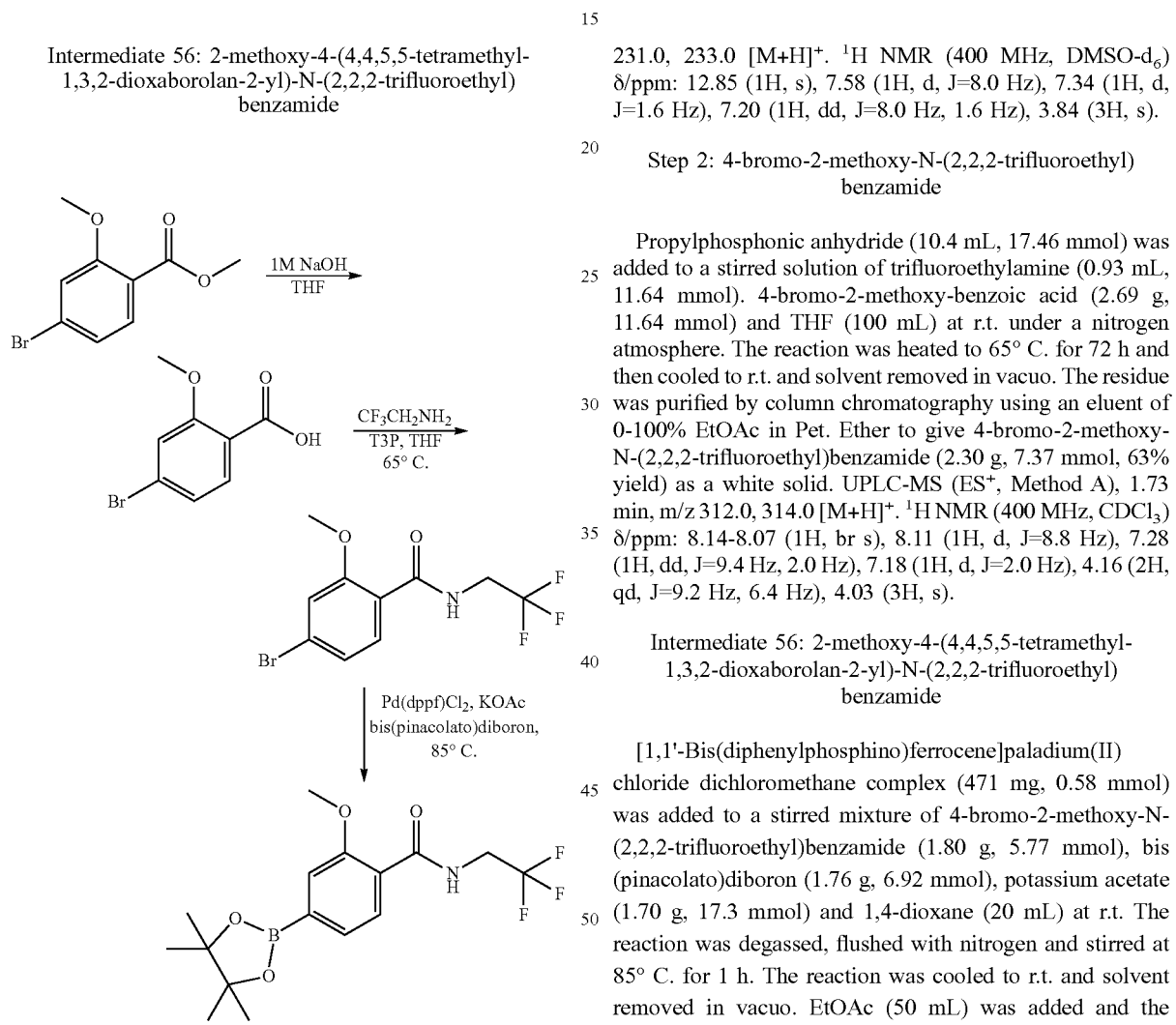 | Method A, 1.27 min, m/z 379.0 [M + H]+ |

Intermediate 56: 2-methoxy-4-(4,4,5,5-tetramethyl-1,3,2-dioxaborolan-2-yl)-N-(2,2,2-trifluoroethyl)benzamide Step 1: 4-bromo-2-methoxy-benzoic acid Methyl 4-bromo-2-methoxybenzoate (3.00 g, 12.24 mmol) was stirred in a mixture of sodium hydroxide (20 mL, 20 mmol) and THF (20 mL) at 40° C. for 18 h. It was then cooled to r.t. and organic solvent removed in vacuo. The resulting solution was stirred and concentrated HCl added dropwise until a pH ~5. This caused a white solid to crash out which was filtered and dried in vacuo to give 4-bromo-2-methoxy-benzoic acid (2.69 g, 11.64 mmol, 95% yield) as white solid. UPLC-MS (ES+, Method A), 1.43 min, m/z 231.0, 233.0 [M+H]+. $^1$H NMR (400 MHz, DMSO-$d_6$) δ/ppm: 12.85 (1H, s), 7.58 (1H, d, J=8.0 Hz), 7.34 (1H, d, J=1.6 Hz), 7.20 (1H, dd, J=8.0 Hz, 1.6 Hz), 3.84 (3H, s).

Step 2: 4-bromo-2-methoxy-N-(2,2,2-trifluoroethyl)benzamide

Propylphosphonic anhydride (10.4 mL, 17.46 mmol) was added to a stirred solution of trifluoroethylamine (0.93 mL, 11.64 mmol). 4-bromo-2-methoxy-benzoic acid (2.69 g, 11.64 mmol) and THF (100 mL) at r.t. under a nitrogen atmosphere. The reaction was heated to 65° C. for 72 h and then cooled to r.t. and solvent removed in vacuo. The residue was purified by column chromatography using an eluent of 0-100% EtOAc in Pet. Ether to give 4-bromo-2-methoxy-N-(2,2,2-trifluoroethyl)benzamide (2.30 g, 7.37 mmol, 63% yield) as a white solid. UPLC-MS (ES+, Method A), 1.73 min, m/z 312.0, 314.0 [M+H]+. $^1$H NMR (400 MHz, CDCl$_3$) δ/ppm: 8.14-8.07 (1H, br s), 8.11 (1H, d, J=8.8 Hz), 7.28 (1H, dd, J=9.4 Hz, 2.0 Hz), 7.18 (1H, d, J=2.0 Hz), 4.16 (2H, qd, J=9.2 Hz, 6.4 Hz), 4.03 (3H, s).

Intermediate 56: 2-methoxy-4-(4,4,5,5-tetramethyl-1,3,2-dioxaborolan-2-yl)-N-(2,2,2-trifluoroethyl)benzamide

[1,1'-Bis(diphenylphosphino)ferrocene]paladium(II) chloride dichloromethane complex (471 mg, 0.58 mmol) was added to a stirred mixture of 4-bromo-2-methoxy-N-(2,2,2-trifluoroethyl)benzamide (1.80 g, 5.77 mmol), bis(pinacolato)diboron (1.76 g, 6.92 mmol), potassium acetate (1.70 g, 17.3 mmol) and 1,4-dioxane (20 mL) at r.t. The reaction was degassed, flushed with nitrogen and stirred at 85° C. for 1 h. The reaction was cooled to r.t. and solvent removed in vacuo. EtOAc (50 mL) was added and the resulting suspension filtered through celite and the filter cake washed with EtOAc (50 mL). The filtrate was concentrated in vacuo and the residue purified by flash column chromatography eluting eluent of 0-100% EtOAc in Pet. Ether to give 2-methoxy-4-(4,4,5,5-tetramethyl-1,3,2-dioxaborolan-2-yl)-N-(2,2,2-trifluoroethyl)benzamide (1.90 g, 5.29 mmol, 92% yield) as a brown oil which solidified upon standing. UPLC-MS (ES+, Method A), 1.89 min, m/z 360.3 [M+H]+. $^1$HNMR (400 MHz, CDCl$_3$) δ/ppm: 8.37-8.31 (1H, m), 8.22 (1H, d, J=8.0 Hz), 7.54 (1H, d, J=8.0 Hz), 7.43 (1H, s), 4.23-4.14 (2H, m), 4.06 (3H, s), 1.38 (12H, s).

Intermediate 57: N-isopropyl-2-[2-methoxy-4-(4,4,5,5-tetramethyl-1,3,2-dioxaborolan-2-yl)anilino]acetamide

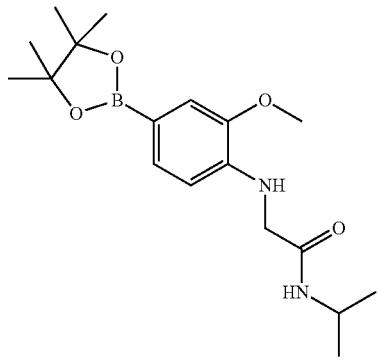 [SMILES: COc1cc(B2OC(C)(C)C(C)(C)O2)ccc1NCC(=O)NC(C)C]

2-(4-Bromo-2-methoxy-anilino)-N-isopropyl-acetamide (110 mg, 0.37 mmol), potassium acetate (79 mg, 0.81 mmol) and bis(pinacolato)diboron (104 mg, 0.40 mmol) were suspended in 1,4-dioxane (1.46 mL). The suspension was then degassed using nitrogen for 5 min before the addition of [1,1'-bis(diphenylphosphino)ferrocene]palladium(II) chloride dichloromethane complex (15 mg, 0.02 mmol). The mixture was further degassed for another 5 min before heating to 80° C. with stirring overnight. The reaction mixture was allowed to cool to r.t., filtered through a celite plug which was washed with EtOAc. The filtrate was concentrated under reduced pressure and the residue purified by flash column chromatography on silica gel eluting with 0-40% ethyl acetate in Pet. Ether to yield N-isopropyl-2-[2-methoxy-4-(4,4,5,5-tetramethyl-1,3,2-dioxaborolan-2-yl)anilino]acetamide (58 mg, 0.16 mmol, 45% yield) as a yellow oil that solidified on standing. UPLC-MS (ES$^+$, Method A): 1.75 min, m/z 3492 [M+H]$^+$. $^1$H NMR (400 MHz, CDCl$_3$) δ 7.37 (dd, J=7.8, 1.2 Hz, 1H), 7.20 (d, J=1.0 Hz, 1H), 6.49 (d, J=7.8 Hz, 1H), 4.18-4.08 (m, 1H), 3.92 (s, 3H), 3.79 (s, 2H), 1.33 (s, 12H), 1.09 (d, J=6.6 Hz, 6H) 2H exchangeable.

Step 1: 2-(4-bromo-2-methoxy-anilino)-N-isopropyl-acetamide

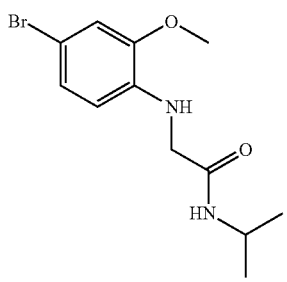 [SMILES: COc1cc(Br)ccc1NCC(=O)NC(C)C]

To a solution of 2-chloro-N-isopropylacetamide (201 mg, 1.48 mmol) in ethanol (1.73 mL) was added 4-bromo-o-anisidine (300 mg, 1.48 mmol) and potassium carbonate (615 mg, 4.45 mmol). The reaction mixture was then allowed to stir at 80° C. overnight. The reaction was cooled to r.t. and concentrated under reduced pressure. The residue was taken up in EtOAc, and washed with NaOH (4.0 M). The aqueous layer was extracted with EtOAc (×3), the organic layers combined, washed with saturated brine, dried over Na$_2$SO$_4$, filtered and concentrated under reduced pressure. The residue was purified by reverse phase chromatography eluting with 30-50% acetonitrile (0.1% formic acid additive) in water (0.1% formic acid additive) to yield 2-(4-bromo-2-methoxy-anilino)-N-isopropyl-acetamide (110 mg, 0.36 mmol, 25% yield) as a white solid. UPLC-MS (ES$^+$, Method A): 1.65 min, m/z 301.2 [M+H]$^+$. $^1$H NMR (400 MHz, CDCl$_3$) δ 6.98 (dd, J=8.3, 2.7 Hz, 1H), 6.90 (d, J=2.0 Hz, 1H), 6.47-6.41 (m, 1H), 6.34 (d, J=8.3 Hz, 1H), 4.18-4.08 (m, 1H), 3.87 (s, 3H), 3.73 (s, 2H), 1.11 (d, J=6.6 Hz, 6H).

Intermediate 58: 2-methyl-6-(4,4,5,5-tetramethyl-1,3,2-dioxaborolan-2-yl)-3,4-dihydroisoquinolin-1-one

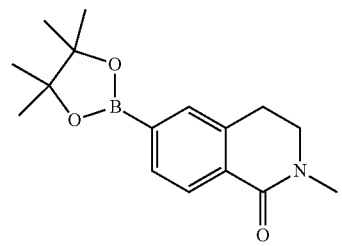

6-Bromo-2-methyl-3,4-dihydroisoquinolin-1-one (250 mg, 1.04 mmol), bis(pinacolato)diboron (397 mg, 1.56 mmol), potassium acetate (306 mg, 3.12 mmol) and 1,4-dioxane (10 mL) were degassed with bubbling nitrogen then [1,1'-bis(diphenylphosphino)ferrocene]palladium(II) chloride dichloromethane complex (85 mg, 0.10 mmol) was added and further 1,4-dioxane (10 mL). The resulting mixture was further degassed and then heated to 95° C. for 18 h. The reaction mixture was allowed to cool to r.t., filtered through a plug of celite. Solvents were evaporated to afford crude 2-methyl-6-(4,4,5,5-tetramethyl-1,3,2-dioxaborolan-2-yl)-3,4-dihydroisoquinolin-1-one as a brown gum. UPLC-MS (ES$^+$, Method A): 1.71 min, m/z 288.2 [M+H]$^+$ Intermediate 59: 7-(4,4,5,5-tetramethyl-1,3,2-dioxaborolan-2-yl)chroman-4-one

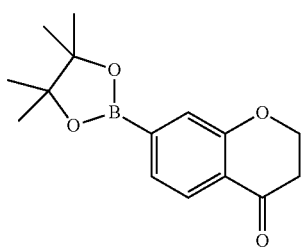 [SMILES: CC1(C)OB(c2ccc3c(c2)OCCC3=O)OC1(C)C]

Following Intermediate 58 procedure, 7-bromochroman-4-one (500 mg, 2.2 mmol) and bis(pinacolato)diboron (1678 mg, 6.61 mmol) afforded 7-(4,4,5,5-tetramethyl-1,3,2-dioxaborolan-2-yl)chroman-4-one (422 mg, 1.54 mmol, 70% yield) as a Gear gum. UPLC-MS (ES$^+$, Method A): 1.88 min, m/z 275.2 [M+H]$^+$

Intermediate 60: N-[2-methoxy-4-(4,4,5,5-tetramethyl-1,3,2-dioxaborolan-2-yl)phenyl]propenamide

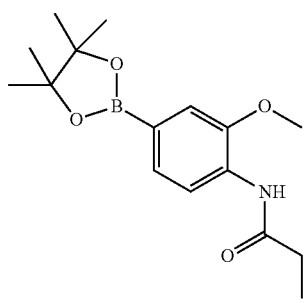 [SMILES: CCC(=O)Nc1ccc(B2OC(C)(C)C(C)(C)O2)cc1OC]

Following intermediate 58 procedure, N-(4-bromo-2-methoxy-phenyl)propanamide (255 mg, 0.99 mmol) and bis(pinacolato)diboron (281 mg, 1.09 mmol) gave crude N-[2-methoxy-4-(4,4,5,5-tetramethyl-1,3,2-dioxaborolan-2-yl)phenyl]propenamine (302 mg, assumed quantitative yield) as a yellow oil. UPLC-MS (ES$^+$, Method A): 1.81 min, m/z 306.3 [M+H]$^+$. $^1$H NMR (400 MHz, CDCl$_3$) δ 8.42 (d, J=7.9 Hz, 1H), 7.88 (s, 1H), 7.44 (dd, J=8.0, 1.0 Hz, 1H), 7.27 (d, J=1.1 Hz), 3.92 (s, 3H), 2.49-2.38 (m, 2H), 1.34 (s, 12H), 1.31-1.24 (m, 3H)

Step 1: N-(4-bromo-2-methoxy-phenyl)propanamide

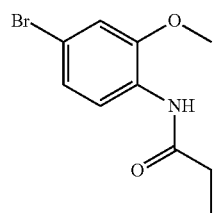

To a solution of 4-bromo-o-anisidine (300 mg, 1.48 mmol) and triethylamine (0.21 mL, 1.48 mmol) in DCM (1.86 mL) was added propionyl chloride (0.13 mL, 1.48 mmol) dropwise at r.t. The reaction mixture was allowed to stir for 1 h. The reaction mixture was diluted with DCM, washed with water and saturated brine. The organic layer was dried over Na$_2$SO$_4$, filtered and then the solvent was removed under reduced pressure. The residue was purified by flash column chromatography on silica gel eluting with 0-40% EtOAc in Pet. Ether to give N-(4-bromo-2-methoxy-phenyl)propanamide (309 mg, 1.19 mmol, 81% yield) as a yellow oil. UPLC-MS (ES$^+$, Method A): 1.64 min, m/z 258.1 [M+H]$^+$. $^1$H NMR (400 MHz, CDCl$_3$) δ 8.30 (d, J=8.7 Hz, 1H), 7.72-7.62 (m, 1H), 7.08 (dd, J=8.6, 2.4 Hz, 1H), 6.99 (d, J=2.1 Hz, 1H), 3.88 (s, 3H), 2.42 (q, J=7.6 Hz, 2H), 1.25 (t, J=7.5 Hz, 3H).

Intermediate 61: 1-[2-methoxy-4-(4,4,5,5-tetramethyl-1,3,2-dioxaborolan-2-yl)phenyl]-3-methyl-urea

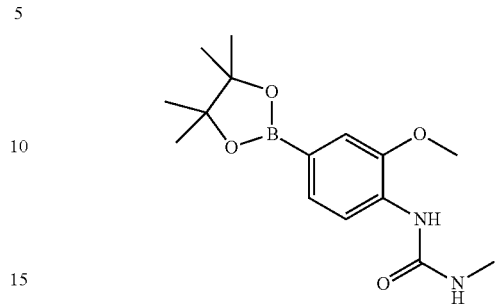

Following intermediate 58 procedure, 1-(4-bromo-2-methoxy-phenyl)-3-methyl-urea (127 mg, 0.49 mmol) and bis(pinacolato)diboron (137 mg, 0.54 mmol) afforded 1-[2-methoxy-4-(4,4,5,5-tetramethyl-1,3,2-dioxaborolan-2-yl)phenyl]-3-methyl-urea (151 mg, 0.59 mmol, 100% yield) as a yellow-orange oil. UPLC-MS (ES$^+$, Method A): 1.62 min, m/z 307.3 [M+H]$^+$. $^1$H NMR (400 MHz, CDCl$_3$) δ 8.08 (d, J=8.5 Hz, 1H), 7.43 (dd, J=8.0, 1.2 Hz, 1H), 7.25-7.24 (m, 1H), 6.91 (br s, 1H), 4.71-4.53 (br s, 1H), 3.89 (s, 3H), 2.87 (s, 3H), 1.34 (s, 12H)

Step 1: phenyl N-(4-bromo-2-methoxy-phenyl)carbamate

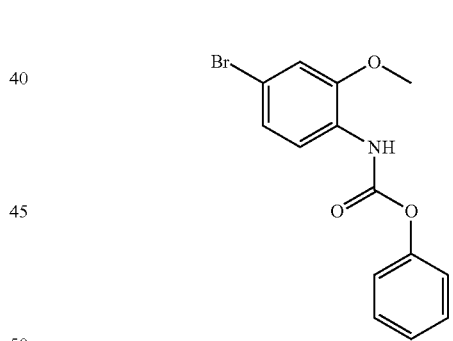

To a solution of 4-bromo-o-anisidine (300 mg, 1.48 mmol) and pyridine (0.01 mL, 0.11 mmol) in ethyl acetate (2.55 mL) was added phenyl chloroformate (0.2 mL, 1.56 mmol) with stirring at 0° C. The reaction mixture was stirred overnight at r.t. The reaction mixture was washed with water (×3) and dried over Na$_2$SO$_4$ before filtering. The filtrate was concentrated in vacuo and the residue purified by flash column chromatography eluting with 0-45% EtOAc in Pet. Ether to yield phenyl N-(4-bromo-2-methoxy-phenyl)carbamate (400 mg, 1.24 mmol, 84% yield) as an off white solid. UPLC-MS (ES$^+$, Method A): 1.99 min, m/z 322.2 [M+H]$^+$. $^1$H NMR (400 MHz, CDCl$_3$) δ 8.03 (d, J=8.2 Hz, 1H), 7.53 (br s, 1H), 7.45-7.39 (m, 2H), 7.28-7.24 (m, 1H), 7.24-7.19 (m, 2H), 7.13 (dd, J=8.7, 2.1 Hz, 1H), 7.05 (d, J=2.0 Hz, 1H), 3.94 (s, 3H)

Step 2: 1-(4-bromo-2-methoxy-phenyl)-3-methyl-urea

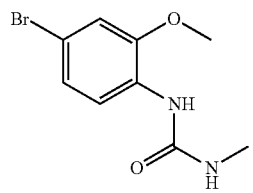

To a solution of phenyl N-(4-bromo-2-methoxy-phenyl) carbamate (400 mg, 1.24 mmol) in DCM (4.97 mL) was added methylamine solution (2.0M in THF) (0.62 mL, 1.24 mmol). The reaction mixture was stirred at 35° C. for 10 days. The reaction mixture was concentrated in vacuo and the residue was purified using flash column chromatography on silica gel eluting with 20-100% EtOAc in Pet. Ether followed by 0-10% MeOH in DCM to yield 1-(4-bromo-2-methoxy-phenyl)-3-methyl-urea (127 mg, 0.49 mmol, 39% yield). UPLC-MS (ES+, Method A): 1.46 min, m/z 259.1 [M+H]+. 1H NMR (400 MHz, CDCl3) δ 7.97 (d, J=8.6 Hz, 1H), 7.07 (dd, J=8.6, 2.0 Hz, 1H), 6.96 (d, J=2.1 Hz, 1H), 6.68-6.63 (m, 1H), 4.57-4.47 (m, 1H), 3.85 (s, 3H), 2.86 (d, J=4.8 Hz, 3H).

General Route to Intermediates 62 and 63

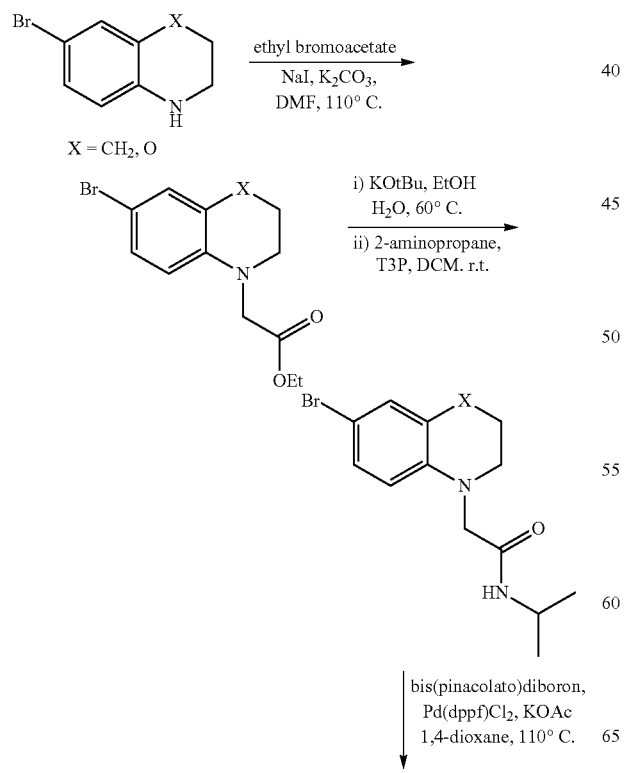

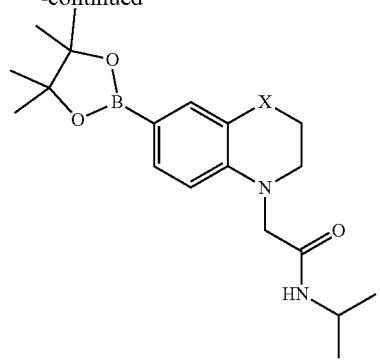

Step 1: ethyl 2-(6-bromo-3,4-dihydro-2H-quinolin-1-yl)acetate

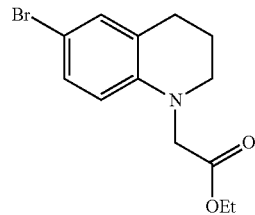 [SMILES: CCOC(=O)CN1CCCc2cc(Br)ccc21]

6-Bromo-1,2,3,4-tetrahydroquinoline (250 mg, 1.18 mmol), ethyl bromoacetate (0.18 mL, 1.65 mmol), sodium iodide (265 mg, 1.77 mmol) and potassium carbonate (326 mg, 2.36 mmol) in DMF (2 mL) were heated to 110° C. and the resulting yellow suspension left to stir at this temperature for 1 h. The reaction was quenched with water (50 mL) and extracted using EtOAc (3×25 mL). The organic layers were collected, dried over sodium sulfate, filtered and reduced in vacuo to afford ethyl 2-(6-bromo-3,4-dihydro-2H-quinolin-1-yl)acetate (383 mg, 0.87 mmol, 74% yield) as an orange oil. UPLC-MS (ES+, Method A), 2.04 min, m/z 298.0 [M+H]+

Step 2: 2-(6-bromo-3,4-dihydro-2H-quinolin-1-yl)-N-isopropyl-acetamide

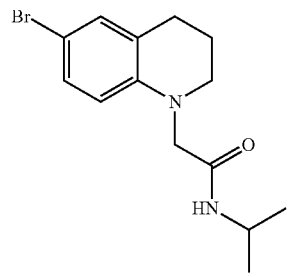 [SMILES: CC(C)NC(=O)CN1CCCc2cc(Br)ccc21]

2-(6-Bromo-3,4-dihydro-2H-quinolin-1-yl)acetate (360 mg, 1.21 mmol) was dissolved in ethanol (3.5 mL) and water (0.50 mL). Potassium 2-methylpropan-2-olate (203 mg, 1.81 mmol) was added and the mixture was left to stir at 60° C. for 30 min. The reaction was allowed to cool to r.t. and cooled further by adding ice. To that fully soluble mixture was added a 1M HCl solution until a precipitate appeared (~pH 2-3). The pale yellow orange precipitate was filtered, washing with ice cold water. The solid turned into an orange gum under filtration. This was washed off the filter with DCM. The organic layer was dried over $Na_2SO_4$, and filtered. To the filtrate was directly added 2-aminopropane (0.1 mL, 1.21 mmol) followed by propylphosphonic anhydride (0.36 mL, 1.21 mmol) and the mixture stirred for 20 min. The reaction mixture was then diluted with water and extracted with DCM. The organic layer was dried over $Na_2SO_4$, filtered and concentrated under reduced pressure to afford a yellow crude oil. Further purification by flash column chromatography eluting with 5-95% ethyl acetate in Pet. Ether to afford 2-(6-bromo-3,4-dihydro-2H-quinolin-1-yl)-N-isopropyl-acetamide (214 mg, 0.69 mmol, 57% yield) as a colourless powder. UPLC-MS (ES+, Method A), 1.83 min, m/z 311.1 [M+H]+.

Intermediate 62: N-isopropyl-2-[6-(4,4,5,5-tetramethyl-1,3,2-dioxaborolan-2-yl)-3,4-dihydro-2H-quinolin-1-yl]acetamide

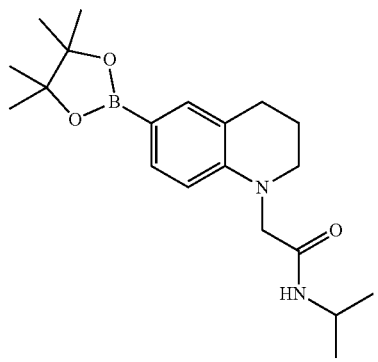 [SMILES: CC(C)NC(=O)CN1CCCc2cc(B3OC(C)(C)C(C)(C)O3)ccc21]

Following Intermediate 58 procedure, 2-(6-bromo-3,4-dihydro-2H-quinolin-1-yl)-N-isopropyl-acetamide (100 mg, 0.32 mmol) and bis(pinacolato)diboron (106 mg, 0.42 mmol) afforded N-isopropyl-2-[6-(4,4,5,5-tetramethyl-1,3,2-dioxaborolan-2-yl)-3,4-dihydro-2H-quinolin-1-yl]acetamide (139 mg, 0.31 mmol, 97% yield) as a clear gum. UPLC-MS (ES+, Method A), 1.91 min, m/z 359.4 [M+H]+

Compounds prepared in a similar manner to that set out above are given below in Table 8.

Intermediate 64: 2-[2-methoxy-4-(4,4,5,5-tetramethyl-1,3,2-dioxaborolan-2-yl)phenyl]-N-methylacetamide

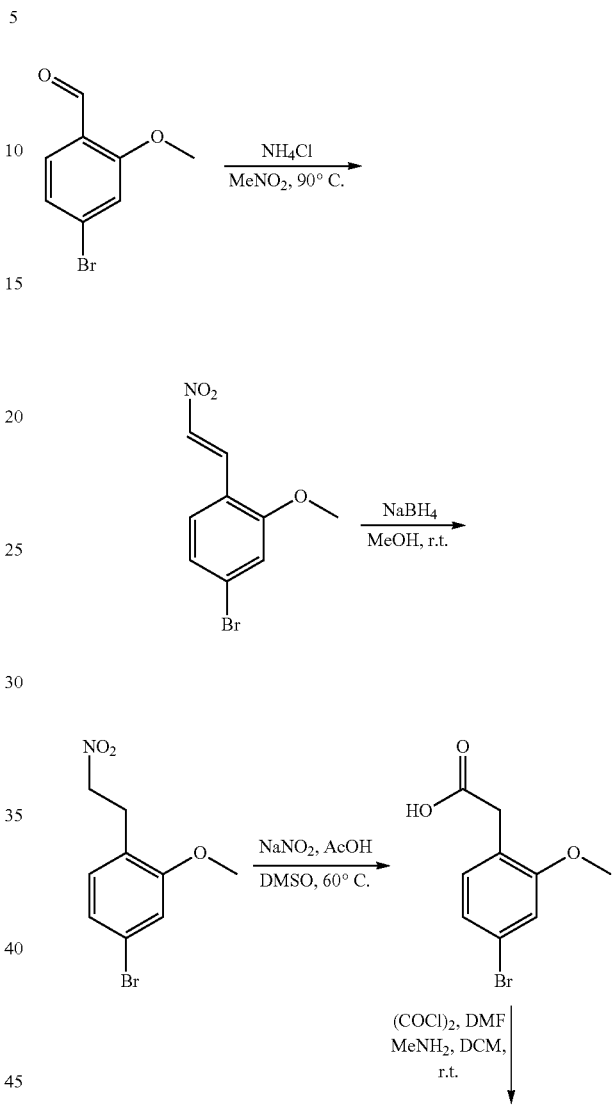

TABLE 8

| Intermediate No. | Structure | LC/MS |
|---|---|---|
| 63 | ![structure] | Method A, 1.76 min, m/z 361.4 [M + H]+ |

-continued

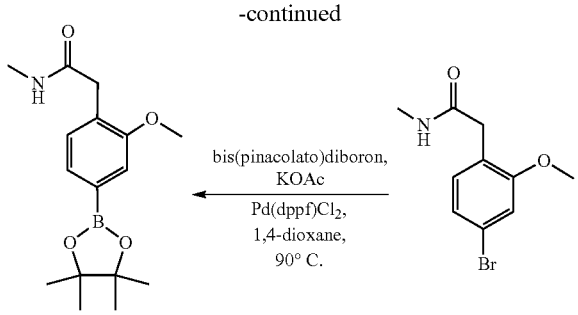

Step 1: 4-bromo-2-methoxy-1-[(E)-2-nitrovinyl]benzene

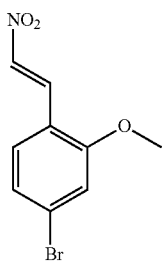

Nitromethane (4.19 mL) was added to a flask containing 4-bromo-2-methoxybenzaldehyde (300 mg, 1.4 mmol) and ammonium acetate (140 mg, 1.81 mmol). The reaction was then allowed to stir at 90° C. for 90 min. The reaction mixture was then allowed to cool down to r.t. and partitioned between saturated solution of sodium bicarbonate and DCM. The aqueous layer was extracted with DCM (×3). The combined organic extracts combined, filtered over a hydrophobic frit and solvent removed under reduced pressure to afford crude 4-bromo-2-methoxy-1-[(E)-2-nitrovinyl]benzene (332 mg, 1.29 mmol, 92% yield) as an orange oil which was used directly in the next step. UPLC-MS (ES+, Method A): 1.91 min, m/z 258 [M+H]+

Step 2: 4-bromo-2-methoxy-1-(2-nitroethyl)benzene

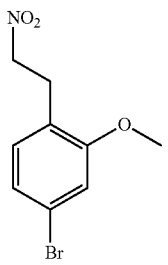

Sodium borohydride (53 mg, 1.42 mmol) was added to a solution of 4-bromo-2-methoxy-1-[(E)-2-nitrovinyl]benzene (332 mg, 1.29 mmol) in methanol (4.29 mL) and the reaction allowed to stir at r.t for 1 h. The reaction mixture was then carefully quenched with a saturated solution of ammonium chloride and the aqueous layer was extracted three times with DCM. The organic extracts were combined, filtered over a hydrophobic frit and all solvent removed under reduced pressure. Purification by flash column chromatography on silica gel eluting with 0-15% ethyl acetate in Pet. Ether afforded 4-bromo-2-methoxy-1-(2-nitroethyl)benzene (91 mg, 0.35 mmol, 27% yield) as a clear gum. UPLC-MS (ES+, Method A): 1.86 min, no mass ion is detectable.

Step 3: 2-(4-bromo-2-methoxy-phenyl)acetic acid

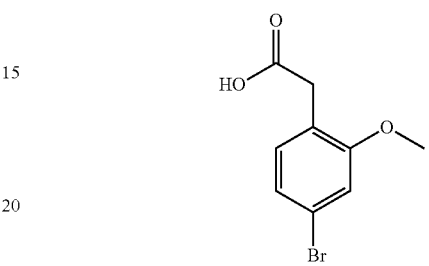

Sodium nitrite (90 mg, 1.27 mmol) was added to a solution of 4-bromo-2-methoxy-1-(2-nitroethyl)benzene (132 mg, 0.51 mmol) in DMSO (1.27 mL) and glacial acetic add (0.29 mL, 5.07 mmol) and the reaction stirred at 60° C. overnight. Then the reaction mixture was allowed to cool to r.t. and acidified to pH 1 with a 2M aqueous solution of HCl. This mixture was partitioned between ethyl acetate and water. The organic layer was washed twice with water, a saturated solution of brine, dried over sodium sulfate, filtered and solvent removed under reduced pressure. Purification by flash column chromatography on silica gel eluting with 0-25% ethyl acetate in Pet. Ether afforded 2-(4-bromo-2-methoxy-phenyl)acetic add (51 mg, 0.21 mmol, 41% yield) as a yellow oil. UPLC-MS (ES+, Method A): 1.53 min, m/z 245.0 [M+H]+

Step 4: 2-(4-bromo-2-methoxy-phenyl)-N-methyl-acetamide

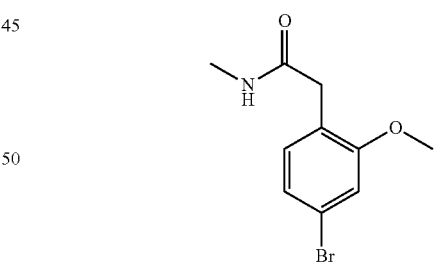

A drop of DMF was added to a solution of oxallyl chloride (0.02 mL, 0.25 mmol) and 2-(4-bromo-2-methoxy-phenyl)acetic acid (51 mg, 0.21 mmol) in DCM (1.04 mL) at r.t. Afterwards, allowed to stir at r.t. for 10 min. Then the reaction mixture was cooled down to 0° C., then 2 M methylamine solution (0.26 mL, 0.52 mmol) in THF was added carefully. The reaction mixture was allowed to stir at r.t. for 10 min, partitioned between water and DCM. The aqueous layer was extracted with DCM (×3). The combined extracts were filtered over a hydrophobic frit and all volatiles removed under reduced pressure. Purification by column chromatography eluting with 40-100% ethyl acetate in Pet. Ether afforded 2-(4-bromo-2-methoxy-phenyl)-N-methylacetamide (9 mg, 0.04 mmol, 18% yield) as a clear gum. UPLC-MS (ES+, Method A) 1.42 min, m/z 260.1 [M+H]+

Intermediate 65: 2-[2-methoxy-4-(4,4,5,5-tetramethyl-1,3,2-dioxaborolan-2-yl)phenyl]-N-methyl-acetamide

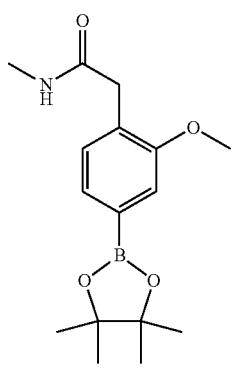

A suspension of 2-(4-bromo-2-methoxy-phenyl)-N-methyl-acetamide (21 mg, 0.08 mmol), bis(pinacolato)diboron (26 mg, 0.10 mmol) and potassium acetate (20 mg, 0.21 mmol) in 1,4-dioxane (1.59 mL) was degassed under nitrogen for 5 min then [1,1'-bis(diphenylphosphino)ferrocene]paladium(II) chloride dichloromethane complex (6 mg, 0.01 mmol) was added. The mixture was degassed for another 5 min and then was heated to 90° C. overnight. The reaction mixture was allowed to cool back down to r.t., filtered over a plug of celite and the plug was washed with DCM. The filtrate was collected and water was added. The aqueous layer was extracted with DCM (×3). The organic extracts were filtered over a hydrophobic irk and solvent removed under reduced pressure. Purification by flash column chromatography on silica gel eluting with 0-100% ethyl acetate in Pet. Ether afforded 2-[2-methoxy-4-(4,4,5,5-tetramethyl-1,3,2-dioxaborolan-2-yl)phenyl]-N-methyl-acetamide (16 mg, 0.05 mmol, 65% yield) as a clear gum. UPLC-MS (ES+, Method B): 1.59 min, m/z 306.3 [M+H]+

General Method A:

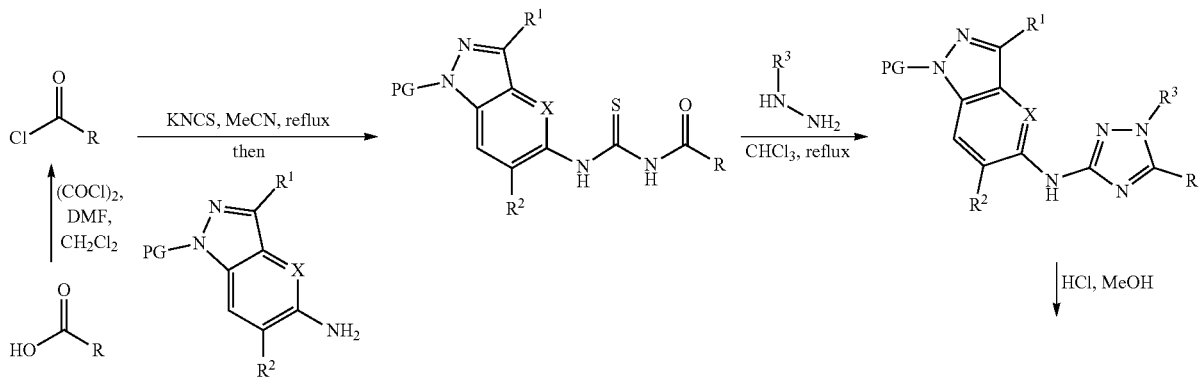

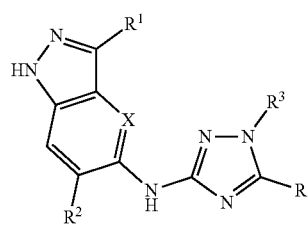

A method for preparing a compound of the invention is given below. Further compounds that can be prepared in a similar manner from commercially available acid chlorides or intermediates 11, 13, 19, 20-23 using general method A are given in Table 9.

Example 1: N-[5-(4-Methoxyphenyl)-4H-1,2,4-triazol-3-yl]-1H-indazol-5-amine dihydrochloride

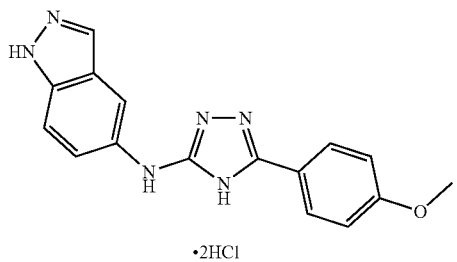 [SMILES: COc1ccc(-c2nnc(Nc3ccc4[nH]ncc4c3)[nH]2)cc1]

A solution of N-[5-(4-methoxyphenyl)-4H-1,2,4-triazol-3-yl]-1-tetrahydropyran-2-yl-indazol-5-amine (110 mg, 0.28 mmol) in hydrochloric acid (1.25 M in MeOH, 0.38 mL, 0.48 mmol) was stirred at r.t. under $N_2$ for 48 h. The solvents were removed under reduced pressure giving N-[5-(4-methoxyphenyl)-4H-1,2,4-triazol-3-yl]-1H-indazol-5-amine dihydrochloride (10 mg, 0.28 mmol, 99% yield) as a white solid. LC-MS (ES$^+$, Method E): 5.84 min, m/z 307.1 [M+H]$^+$. $^1$H NMR (500 MHz, DMSO-d$_6$): δ 9.69 (s, 1H), 8.04 (s, 1H), 8.01 (s, 1H), 7.96 (d, J=9.0 Hz, 2H), 7.51 (d, J=9.0 Hz, 1H), 7.42 (dd, J=9.0, 2.0 Hz, 1H), 7.11 (d, J=9.0 Hz, 2H), 3.83 (s, 3H).

Step 1: N-4 Methoxy-N-[(1-tetrahydropyran-2-ylindazol-5-yl)carbamothioyl]benzamide

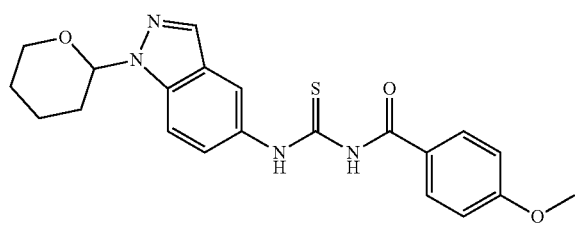 [SMILES: COc1ccc(C(=O)NC(=S)Nc2ccc3c(cnn3C3CCCCO3)c2)cc1]

To a stirred solution of potassium thiocyanate (64 mg, 0.66 mmol) in anhydrous MeCN (3.0 mL) at r.t. under $N_2$ was added 4-methoxybenzoyl chloride (90 μL, 0.66 mmol) and the mixture heated at 85° C. for 3.5 h. The mixture was allowed to cool to r.t. and then filtered under reduced pressure. 1-(Tetrahydro-2H-pyran-2-yl)-1H-indazol-5-amine (130 mg, 0.60 mmol) was added in a single portion and the reaction stirred at r.t. for an additional 2 h. The solvents were removed under reduced pressure and the crude product purified by flash column chromatography (SiO$_2$) eluting with 0-8% MeOH in DCM giving 4-methoxy-N-[(1-tetrahydropyran-2-ylindazol-5-yl)carbamothioyl]benzamide (251 mg, 0.60 mmol, 100% yield) as a foamy orange solid. LC-MS (ES$^+$, Method C): 3.39 min, m/z 411.1 [M+H]$^+$. $^1$H NMR (500 MHz, CDCl$_3$): δ 12.64 (s, 1H), 9.05 (s, 1H), 8.12 (d, J=2.0 Hz, 1H), 8.05 (s, 1H), 7.88 (d, J=9.0 Hz, 2H), 7.64 (d, J=9.0 Hz, 1H), 7.56 (dd, J=9.0, 2.0 Hz, 1H), 7.03 (d, J=9.0 Hz, 2H), 5.73 (dd, J=9.0, 3.0 Hz, 1H), 4.07-4.00 (m, 1H), 3.91 (s, 3H), 3.79-3.72 (m, 1H), 2.61-2.51 (m, 1H), 2.21-2.12 (m, 1H), 2.09 (dd, J=13.3, 3.6 Hz, 1H), 1.84-1.62 (m, 3H).

Step 2: N-[5-(4-Methoxyphenyl)-4H-1,2,4-triazol-3-yl]-1-tetrahydropyran-2-yl-indazol-5-amine

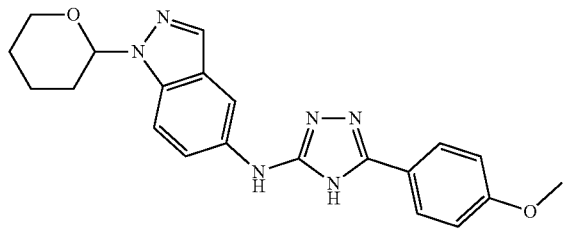 [SMILES: COc1ccc(-c2nnc(Nc3ccc4c(cnn4C4CCCCO4)c3)[nH]2)cc1]

To a stirred solution of 4-methoxy-N-[(1-tetrahydropyran-2-ylindazol-5-yl)carbamothioyl]benzamde (246 mg, 0.60 mmol) in chloroform (6.5 mL) at r.t. under $N_2$ was added hydrazine hydrate (146 μL, 3.00 mmol) and the reaction heated at 65° C. for 3.5 h. The mixture was allowed to cool to r.t. and the resulting precipitate collected by filtration under reduced pressure giving N-[5-(4 methoxyphenyl)-4H-1,2,4-triazol-3-yl]-1-tetrahydropyran-2-yl-indazol-5-amine (11 mg, 0.28 mmol, 47% yield) as an off-white solid. LC-MS (ES$^+$, Method C): 2.63 min, m/z 391.1 [M+H]$^+$.

Compounds prepared in a similar manner to that set out above are given below in Table 9.

TABLE 9

| Example | Structure | LC/MS | $^1$H NMR |
|---|---|---|---|
| 2 | 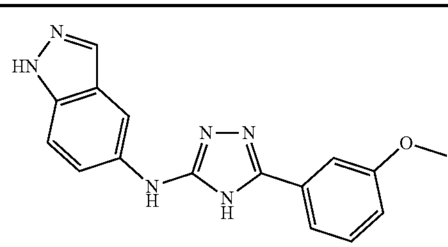 | Method E, 5.95 min, m/z 307.1 [M + H]$^+$ | $^1$H NMR (500 MHz, DMSO-d$_6$): δ 13.64 (s, 1H), 12.81 (s, 1H), 9.23 (s, 1H), 8.09 (s, 1H), 7.95 (s, 1H), 7.57 (d, J = 7.7 Hz, 1H), 7.53 (dd, J = 2.6, 1.5 Hz, 1H), 7.50-7.35 (m, 3H), 7.04 (s, 1H), 3.83 (s, 3H). |

TABLE 9-continued

| Example | Structure | LC/MS | $^1$H NMR |
|---|---|---|---|
| 3 | 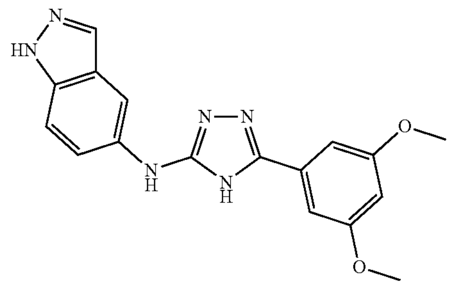 [SMILES: COc1cc(OC)cc(-c2nnc(Nc3ccc4[nH]ncc4c3)[nH]2)c1] | Method E, 6.15 min, m/z 337.1 [M + H]$^+$ | $^1$H NMR (500 MHz, DMSO6): δ 9.63 (br s, 2H), 8.04 (d, J = 1.0 Hz, 1H), 8.02 (d, J = 2.0 Hz, 1H), 7.50 (d, J = 9.0 Hz, 1H), 7.42 (dd, J = 9.0, 2.0 Hz, 1H), 7.20 (d, J = 2.0 Hz, 2H), 6.63 (dd, J = 2.0 Hz, 1H), 3.82 (s, 6H). |
| 4 | 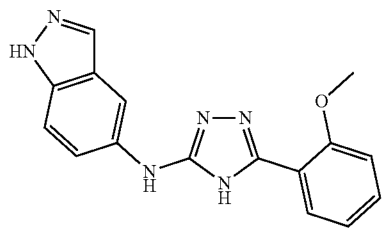 [SMILES: COc1ccccc1-c1nnc(Nc2ccc3[nH]ncc3c2)[nH]1] | Method E, 6.10 min, m/z 307.1 [M + H]$^+$ | $^1$H NMR (500 MHz, DMSO-d$_6$): δ 9.41 (s, 1H), 8.10 (s, 1H), 8.04 (d, J = 7.5 Hz, 1H), 7.99 (s, 1H), 7.55-7.49 (m, 1H), 7.47 (d, J = 9.0 Hz, 1H), 7.42 (dd, J = 9.0, 2.0 Hz, 1H), 7.23 (d, J = 8.5 Hz, 1H), 7.13 (dd, J = 7.5 Hz, 1H), 3.98 (s, 3H). |
| 5 | 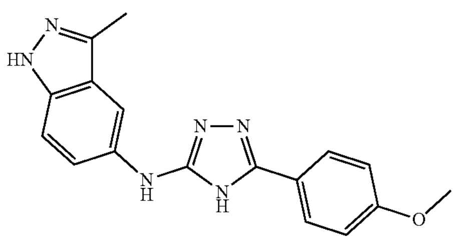 [SMILES: COc1ccc(-c2nnc(Nc3ccc4[nH]nc(C)c4c3)[nH]2)cc1] | Method E, 5.86 min, m/z 321.0 [M + H]$^+$ | $^1$H NMR (500 MHz, DMSO-d$_6$) δ 12.38 (s, 1H), 9.15 (s, 1H), 8.15-7.97 (m, 1H), 7.92 (d, J = 8.5 Hz, 2H), 7.39 (dd, J = 9.0, 2.0 Hz, 1H), 7.34 (d, J = 9.0 Hz, 1H), 7.09 (d, J = 8.5 Hz, 2H), 3.83 (s, 3H), 2.45 (s, 3H). |
| 6 | 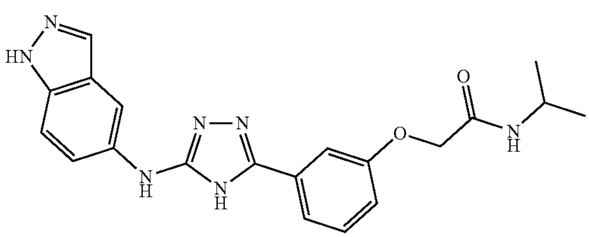 [SMILES: CC(C)NC(=O)COc1cccc(-c2nnc(Nc3ccc4[nH]ncc4c3)[nH]2)c1] | Method E, 5.83 min, m/z 392.1 [M + H]$^+$ | $^1$H NMR (500 MHz, DMSO-d$_6$): δ 13.61 (s, 1H), 12.82 (s, 1H), 9.21 (s, 1H), 8.09 (s, 1H), 8.01-7.90 (m, 2H), 7.63-7.55 (m, 2H), 7.51-7.35 (m, 3H), 7.04 (s, 1H), 4.51 (s, 2H), 4.02-3.92 (m, 1H), 1.10 (d, J = 6.5 Hz, 6H). |
| 7 | 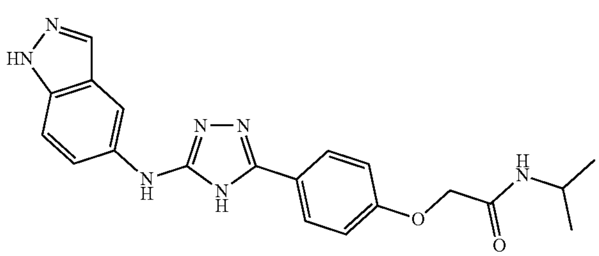 [SMILES: CC(C)NC(=O)COc1ccc(-c2nnc(Nc3ccc4[nH]ncc4c3)[nH]2)cc1] | Method E 5.72 min, m/z 392.1 [M + H]$^+$ | $^1$H NMR (500 MHz, DMSO-d$_6$): δ 13.38 (br s, 1H), 12.81 (s, 1H), 9.18 (5, 1H), 8.10 (s, 1H), 8.01-7.93 (m, 2H), 7.91 (d, J = 8.5 Hz, 2H), 7.42 (s, 2H), 7.09 (d, J = 8.5 Hz, 2H), 4.51 (s, 2H), 3.96 (m, 1H), 1.10 (d, J = 6.5 Hz, 6H). |
| 8 | ·2HCl | Method E, 5.68 min, m/z 422.1 [M + H]$^+$ | $^1$H NMR (500 MHz, D MSO-d$_6$): δ 9.50 (s, 1H), 8.03 (s, 1H), 8.01 (s, 1H), 7.82 (d, J = 7.8 Hz, 1H), 7.62 (d, J = 2.1 Hz, 1H), 7.54 (dd, J = 8.3, 2.1 Hz, 1H), 7.48 (d, J = 8.8 Hz, 1H), 7.41 (dd, J = 8.8, 2.2 Hz, 1H), 7.05 (d, J = 8.5 Hz, 1H), 4.52 (s, 2H), 3.97-3.85 (m, 4H), 1.10 (d, J = 6.5 Hz, 6H). |

TABLE 9-continued

| Example | Structure | LC/MS | ¹H NMR |
|---|---|---|---|
| 9 | 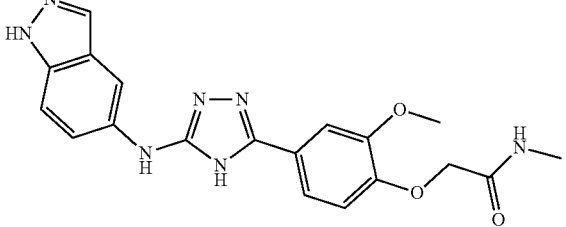 ·2HCl | Method E, 5.09 min, m/z 394.3 [M + H]⁺ | ¹H NMR (500 MHz, DMSO-d$_6$) δ 9.39 (s, 1H), 8.05 (s, 1H), 7.98 (s, 1H), 7.91 (q, J = 4.5 Hz, 1H), 7.60 (d, J = 2.0 Hz, 1H), 7.53 (dd, J = 8.5, 2.0 Hz, 1H), 7.46 (d, J = 9.0 Hz, 1H), 7.41 (dd, J = 9.0, 2.0 Hz, 1H), 7.04 (d, J = 8.5 Hz, 1H), 4.53 (s, 2H), 3.88 (s, 3H), 2.67 (d, J = 4.5 Hz, 3H). |
| 10 | 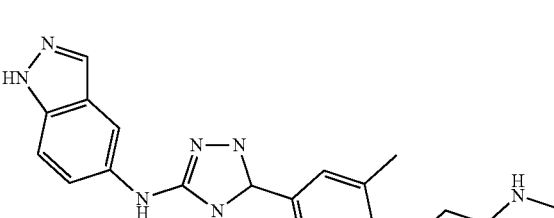 | Method E, 6.07 min, m/z 406.3 [M + H]⁺ | ¹H NMR (500 MHz, DMSO-d$_6$): δ 13.26 (s, 1H), 12.79 (s, 1H), 9.14 (s, 1H), 8.09 (s, 1H), 7.94 (s, 1H), 7.84-7.73 (m, 3H), 7.41 (s, 2H), 6.95 (d, J = 8.5 Hz, 1H), 4.53 (s, 2H), 3.94 (ddt, J = 14.5, 13.0, 6.5 Hz, 1H), 2.30 (s, 3H), 1.10 (d, J = 6.5 Hz, 6H). |
| 11 | 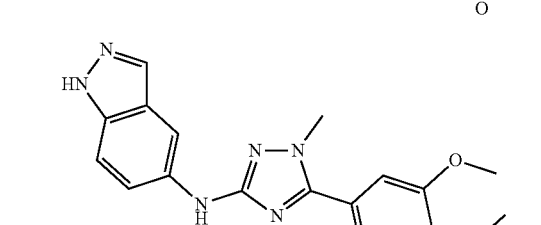 | Method E, 6.08 min, m/z 351.0 [M + H]⁺ | ¹H NMR (400 MHz, DMSO-d$_6$) δ 12.78 (s, 1H), 9.14 (s, 1H), 8.08 (t, J = 1.4 Hz, 1H), 7.94 (s, 1H), 7.40 (q, J = 1.9, 1.4 Hz, 2H), 7.32 (d, J = 7.6 Hz, 2H), 7.12 (dt, J = 8.8, 1.1 Hz, 1H), 3.90 (s, 3H), 3.85 (s, 3H), 3.84 (s, 3H) |

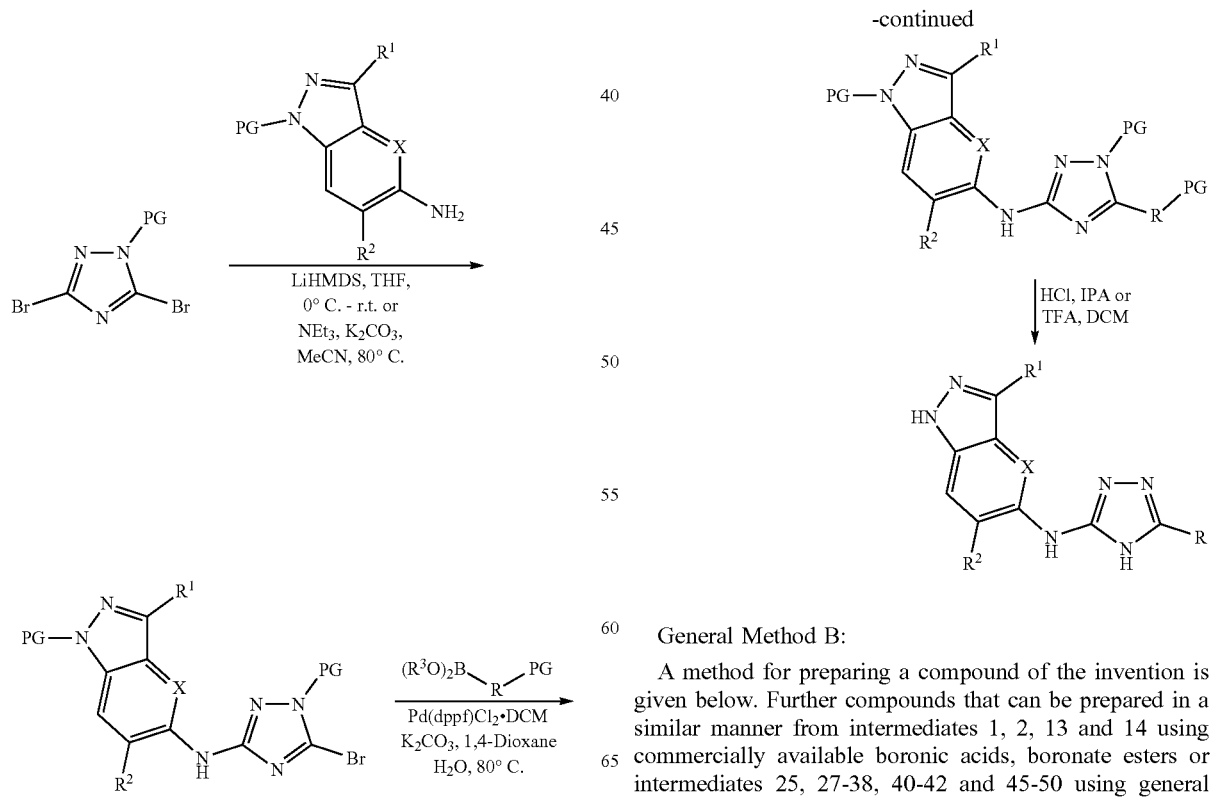

General Method B:

A method for preparing a compound of the invention is given below. Further compounds that can be prepared in a similar manner from intermediates 1, 2, 13 and 14 using commercially available boronic acids, boronate esters or intermediates 25, 27-38, 40-42 and 45-50 using general method B are given in Table 10.

Example 12: 2-[2-fluoro-4-[5-(1H-indazol-5-ylamino)-4H-1,2,4-triazol-3-yl]phenoxy]-N-isopropyl-acetamide

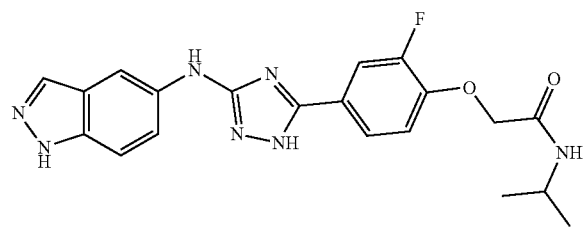 [SMILES: CC(C)NC(=O)COc1ccc(-c2nc(Nc3ccc4[nH]ncc4c3)n[nH]2)cc1F]

A solution of 2-[2-fluoro-4-[5-[(1-tetrahydropyran-2-ylindazol-5-yl)amino]-2-(2-trimethylsilylethoxymethyl)-1,2,4-triazol-3-yl]phenoxy]-N-isopropyl-acetamide (100 mg, 0.16 mmol) in hydrogen chloride-isopropanol solution, 5 N (3.00 mL, 9.00 mmol) was heated at 80° C. for 2 h. The reaction mixture was cooled to r.t. and passed through an ion-exchange cartridge (SCX, eluting with 1M $NH_3$ in MeOH). The crude product was purified by preparative HPLC (30-80% MeCN in $H_2O$) to give 2-[2-fluoro-4-[5-(1H-indazol-5-ylamino)-4H-1,2,4-triazol-3-yl]phenoxy]-N-isopropyl-acetamide (15 mg, 0.03 mmol, 21% yield) as an off-white solid. LC-MS ($ES^+$, Method E): 5.90 min, m/z 410 $[M+H]^+$. $^1$H NMR (500 MHz, DMSO-$d_6$): δ 12.51 (s, 1H), 8.66 (s, 1H), 7.97 (s, 1H), 7.92 (s, 1H), 7.49-7.41 (m, 3H), 7.22 (t, J=8.5 Hz, 1H), 4.58 (s, 2H), 3.99-3.94 (m, 1H), 1.15 (d, J=6.5 Hz, 6H).

Step 1: N-[5-Bromo-1-(2-trimethylsilylethoxymethyl)-1,2,4-triazol-3-yl]-1-tetrahydropyran-2-yl-indazol-5-amine

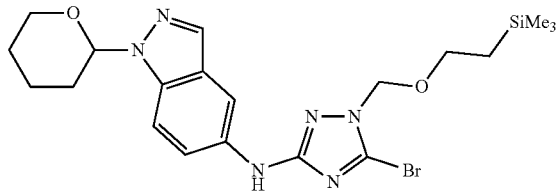 [SMILES: C[Si](C)(C)CCOCn1nc(Nc2ccc3c(cnn3C3CCCCO3)c2)nc1Br]

To a stirred solution of 1-(tetrahydro-2H-pyran-2-yl)-1H-indazol-5-amine (99 mg, 0.46 mmol) in THF (3 mL) at 0° C. was added LiHMDS (1 M in THF, 0.46 mL, 0.46 mmol) dropwise. The solution was stirred at 0° C. for 30 min before a solution of 2-[(3,5-dibromo-1,2,4-triazol-1-yl)methoxy]ethyl-trimethylsilane (125 mg, 0.35 mmol) in THF (1 mL) was added. The cooling bath was removed and the mixture stirred at r.t. for 1.5 h. The reaction was quenched by the careful addition of sat. aq. $NH_4Cl$ soln. (10 mL) and extracted with DCM (3×15 mL). The combined organics were dried (phase separator) and concentrated. The crude product purified by flash column chromatography ($SiO_2$, eluting with 30-80% EtOAc in Pet. Ether) giving N-[5-bromo-1-(2-trimethylsilylethoxymethyl)-1,2,4-triazol-3-yl]-1-tetrahydropyran-2-yl-indazol-5-amine (123 mg, 0.25 mmol, 71% yield) as an orange oil. LC-MS ($ES^+$, Method C): 3.83 min, m/z 495.0 $[M+H]^+$. $^1$H NMR (500 MHz, $CDCl_3$): δ 7.99 (d, J=1.0 Hz, 1H), 7.97 (d, J=2.0 Hz, 1H), 7.57 (d, J=9.0 Hz, 1H), 7.35 (dd, J=9.0, 2.0 Hz, 1H), 6.86 (s, 1H), 5.70 (dd, J=9.5, 3.0 Hz, 1H), 5.40 (s, 2H), 4.05-3.96 (m, 1H), 3.78-3.71 (m, 1H), 3.71-3.65 (m, 2H), 2.60-2.50 (m, 1H), 2.20-2.05 (m, 2H), 1.79-1.65 (m, 3H), 1.02-0.94 (m, 2H), 0.02 (s, 9H).

Step 2: 2-[2-fluoro-4-[5-[(1-tetrahydropyran-2-ylindazol-5-yl)amino]-2-(2-trimethylsilylethoxymethyl)-1,2,4-triazol-3-yl]phenoxy]-N-isopropyl-acetamide

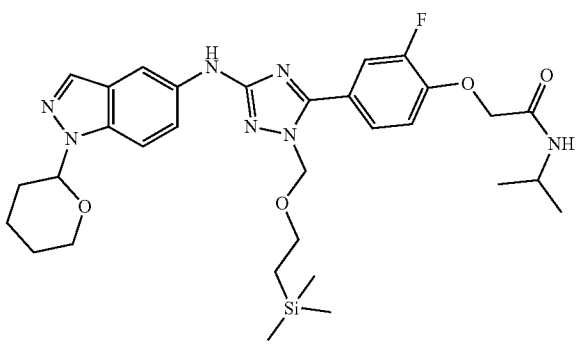 [SMILES: CC(C)NC(=O)COc1ccc(-c2nc(Nc3ccc4c(cnn4C4CCCCO4)c3)nn2COCC[Si](C)(C)C)cc1F]

A vial was charged with N-[5-bromo-1-(2-trimethylsilylethoxymethyl)-1,2,4-triazol-3-yl]-1-tetrahydropyran-2-yl-indazol-5-amine (74 mg, 0.15 mmol), 2-[2-fluoro-4-(4,4,5,5-tetramethyl-1,3,2-dioxaborolan-2-yl)phenoxy]-N-isopropyl-acetamide (Intermediate 24) (56 mg, 0.17 mmol) and potassium carbonate (62 mg, 0.45 mmol). 1,4-dioxane (1.25 mL) and water (0.25 mL) were added and the mixture degassed with nitrogen for 10 min. [1,1'-bis(diphenylphosphino)ferrocene]palladium(II) chloride dichloromethane complex (6 mg, 0.01 mmol) was added in a single portion, the vial sealed and the reaction heated at 80° C. overnight. The reaction mixture was diluted with EtOAc (15 mL) and water (10 mL) and the layers separated. The aqueous layer was extracted with EtOAc (2×10 mL) and the combined organics dried (phase sep.) and concentrated. The crude product was purified by flash column chromatography ($SiO_2$, eluting with 0-5% MeOH in DCM) to give 2-[2-fluoro-4-[5-[(1-tetrahydropyran-2-ylindazol-5-yl)amino]-2-(2-trimethylsilylethoxymethyl)-1,2,4-triazol-3-yl]phenoxy]-N-isopropyl-acetamide (101 mg, 0.14 mmol, 93% yield) as a brown oily solid. LC-MS ($ES^+$, Method C): 3.80 min, m/z 624.3 $[M+H]^+$ Compounds prepared in a similar manner to that set out above are given below in Table 10.

TABLE 10

| Example | Structure | LC/MS | ¹H NMR |
|---|---|---|---|
| 13 | 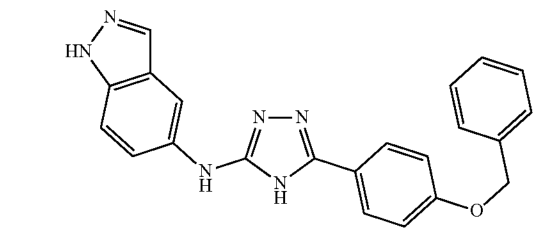 [SMILES: c1ccc(COc2ccc(-c3nnc(Nc4ccc5[nH]ncc5c4)[nH]3)cc2)cc1] | Method E, 7.28 min, m/z 383.1 [M + H]⁺ | ¹H NMR (500 MHz, DMSO-d₆): δ 13.36 (s, 1H), 12.80 (s, 1H), 9.18 (s, 1H), 8.10 (s, 1H), 7.94 (s, 1H), 7.91 (d, J = 8.5 Hz, 2H), 7.48 (d, J = 7.0 Hz, 2H), 7.44-7.39 (m, 4H), 7.37-7.33 (m, 1H), 7.16 (d, J = 8.5 Hz, 2H), 5.18 (s, 2H). |
| 14 | 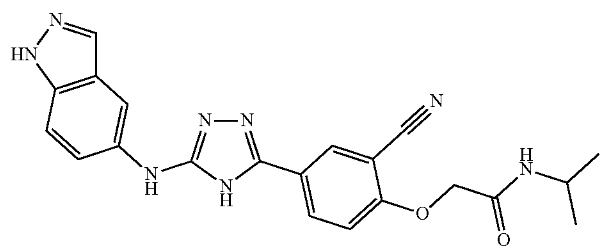 [SMILES: CC(C)NC(=O)COc1ccc(-c2nnc(Nc3ccc4[nH]ncc4c3)[nH]2)cc1C#N] | Method E, 6.00 min, m/z 417.1 [M + H]⁺ | ¹H NMR (500 MHz, DMSO-d₆ @343K): δ 13.46 (s, 1H), 12.66 (s, 1H), 9.11-8.72 (m, 1H), 8.21 (dd, J = 9.0, 2.0 Hz, 2H), 7.96 (s, 2H), 7.68 (s, 1H), 7.46 (s, 2H), 7.26 (s, 1H), 4.72 (s, 2H), 3.95 (dq, J = 13.0, 6.5 Hz, 1H), 1.13 (d, J = 6.5 Hz, 6H). |
| 15 | 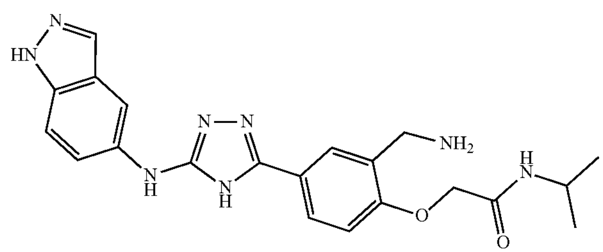 [SMILES: CC(C)NC(=O)COc1ccc(-c2nnc(Nc3ccc4[nH]ncc4c3)[nH]2)cc1CN] | Method E, 4.43 min, m/z 421.4 [M + H]⁺ | ¹H NMR (500 MHz, DMSO-d₆): δ 12.81 (s, 1H), 9.31 (s, 1H), 8.55 (d, J = 8.0 Hz, 1H), 8.11 (t, J = 1.5 Hz, 1H), 7.95 (s, 1H), 7.94 (d, J = 2.5 Hz, 1H), 7.82 (dd, J = 8.5, 2.5 Hz, 1H), 7.43 (d, J = 1.5 Hz, 2H), 7.06 (d, J = 8.5 Hz, 1H), 4.61 (s, 2H), 3.93 (dp, J = 8.0, 6.5 Hz, 1H), 3.81 (s, 2H), 1.07 (d, J = 6.5 Hz, 6H). |
| 16 | 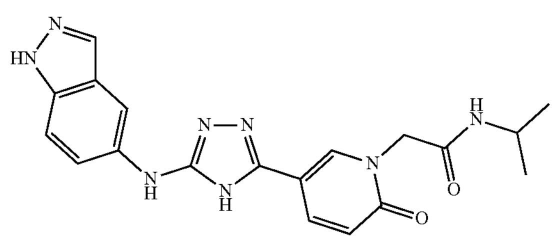 [SMILES: CC(C)NC(=O)Cn1cc(-c2nnc(Nc3ccc4[nH]ncc4c3)[nH]2)ccc1=O] | Method E, 4.65 min, m/z 393.2 [M + H]⁺ | ¹H NMR (500 MHz, DMSO-d₆): δ 13.33-12.62 (m, 2H), 9.16 (s, 1H), 8.21 (d, J = 2.5 Hz, 1H), 8.15 (d, J = 7.5 Hz, 1H), 8.07 (s, 1H), 7.97 (dd, J = 9.5, 2.5 Hz, 1H), 7.94 (s, 1H), 7.45-7.39 (m, 2H), 6.51 (d, J = 9.5 Hz, 1H), 4.62 (s, 2H), 3.85 (dq, J = 13.5, 6.5 Hz, 1H), 1.09 (d, J = 6.5 Hz, 6H). |

TABLE 10-continued

| Example | Structure | LC/MS | ¹H NMR |
|---|---|---|---|
| 17 | (structure) | Method E, 5.77 min, m/z 365.1 [M + H]⁺ | ¹H NMR (500 MHz, DMSO-d₆): δ 13.45 (s, 1H), 12.80 (s, 1H), 9.14 (s, 1H), 8.10 (s, 1H), 7.94 (s, 1H), 7.91 (d, J = 9.0 Hz, 2H), 7.41 (s, 2H), 7.08 (s, 2H), 4.88 (s, 2H), 3.72 (s, 3H). |
| 18 | (structure) | Method E, 5.78 min, m/z 406.2 [M + H]⁺ | ¹H NMR (500 MHz, DMSO-d₆): δ 8.05 (d, J = 2.0 Hz, 1H), 7.99 (d, J = 8.5 Hz, 2H), 7.92-7.88 (m, 2H), 7.47 (d, J = 9.0 Hz, 1H), 7.41 (dd, J = 9.0, 2.0 Hz, 1H), 7.06-7.01 (m, 2H), 4.74 (q, J = 6.5 Hz, 1H), 3.87 (dp, J = 8.0, 6.5 Hz, 1H), 1.44 (d, J = 6.5 Hz, 3H), 1.08 (d, J = 6.5 Hz, 3H), 1.02 (d, J = 6.5 Hz, 3H). |
| 19 | (structure) | Method E, 6.17 min, m/z 418.0 [M − H]⁻ | ¹H NMR (500 MHz, DMSO-d₆): δ 8.09 (d, J = 2.0 Hz, 1H), 7.99 (s, 1H), 7.92-7.87 (m, 3H), 7.47 (d, J = 9.0 Hz, 1H), 7.42 (dd, J = 9.0, 2.0 Hz, 1H), 7.02-6.97 (m, 2H), 3.97 (dp, J = 8.0, 6.5 Hz, 1H), 1.49 (s, 6H), 1.06 (d, J = 6.5 Hz, 6H). |
| 20 | (structure) | Method E, 5.54 min, m/z 390.2 [M + H]⁺ | ¹H NMR (500 MHz, DMSO-d₆): δ 13.55 (s, 1H), 12.78 (s, 1H), 9.15 (s, 1H), 8.12 (s, 1H), 8.05-7.84 (m, 3H), 7.70 (d, J = 7.5 Hz, 1H), 7.51-7.24 (m, 4H), 3.82 (dq, J = 13.5, 6.5 Hz, 1H), 2.85 (dt, J = 14.0, 7.5 Hz, 2H), 2.36 (dq, J = 4.5, 2.5, 2.0 Hz, 2H), 1.01 (dd, J = 6.5, 1.5 Hz, 6H). |

TABLE 10-continued

| Example | Structure | LC/MS | ¹H NMR |
|---|---|---|---|
| 21 | (structure) | Method E, 2.68 min, m/z 406.2 [M + H]⁺ | ¹H NMR (500 MHz, DMSO-d₆): δ 9.55 (s, 1H), 8.03 (d, J = 16.5 Hz, 2H), 7.96-7.86 (m, 3H), 7.48 (d, J = 9.0 Hz, 2H), 7.41 (dd, J = 9.0, 2.0 Hz, 1H), 7.11-7.04 (m, 2H), 4.24 (t, J = 6.0 Hz, 2H), 3.86 (dt, J = 7.5, 6.5 Hz, 1H), 2.52 (t, 2H), 1.06 (d, J = 6.5 Hz, 6H). |
| 22 | (structure) | Method E, 4.42 min, m/z 350.0 [M + H]⁺ | ¹H NMR (400 MHz, DMSO-d₆): δ 9.51 (s, 1H), 8.04 (d, J = 2.0 Hz, 3H), 8.01 (d, J = 1.0 Hz, 1H), 7.99-7.92 (m, 2H), 7.48 (d, J = 9.0 Hz, 1H), 7.42 (dd, J = 9.0, 2.0 Hz, 1H), 7.13-7.07 (m, 2H), 4.15 (t, J = 6.0 Hz, 2H), 2.97 (q, J = 6.5 Hz, 2H), 2.06 (p, J = 6.5 Hz, 2H). |
| 23 | (structure) | Method E, 5.59 min, m/z 406.1 [M + H]⁺ | ¹H NMR (500 MHz, DMSO-d₆): δ 9.40 (s, 1H), 8.05 (d, J = 2.0 Hz, 1H), 8.02 (s, 2H), 7.89-7.89 (m, 2H), 7.47 (d, J = 9.0 Hz, 1H), 7.41 (dd, J = 9.0, 2.0 Hz, 1H), 7.13-7.06 (m, 2H), 4.06 (t, J = 6.0 Hz, 2H), 3.43 (q, J = 5.5 Hz, 2H), 2.40 (q, J = 6.5 Hz, 1H), 1.00 (d, J = 6.5 Hz, 6H). |
| 24 | (structure) | Method E, 4.23 min, m/z 336.1 [M + H]⁺ | ¹H NMR (500 MHz, DMSO-d₆): δ 12.79 (s, 1H), 9.18 (s, 1H), 8.10 (s, 1H), 7.93 (d, J = 6.5 Hz, 1H), 7.92-7.87 (m, 2H), 7.44-7.38 (m, 2H), 7.10-7.03 (m, 2H), 3.98 (t, J = 6.0 Hz, 2H), 2.89 (t, J = 6.0 Hz, 2H). |

TABLE 10-continued

| Example | Structure | LC/MS | ¹H NMR |
|---|---|---|---|
| 25 | (indazole-NH-triazole-NH, phenyl with F, OCH₂C(O)NH-iPr) | Method E, 5.73 min, m/z 410.0 [M + H]⁺ | ¹H NMR (400 MHz, DMSO-d₆): δ 9.22 (s, 1H), 8.13 (d, J = 1.5 Hz, 1H), 7.99-7.85 (m, 3H), 7.43-7.34 (m, 2H), 6.96-6.87 (m, 2H), 4.51 (s, 2H), 4.00-3.89 (m, 1H), 1.09 (d, J = 6.5 Hz, 6H). |
| 26 | (indazole-NH-triazole-NH, phenyl with CH₃, OCH₂C(O)NH-iPr) | Method E, 2.83 min, m/z 406.1 [M + H]⁺ | ¹H NMR (400 MHz, DMSO-d₆): δ 12.52 (s, 2H), 8.59 (s, 1H), 8.01 (s, 1H), 7.91 (s, 1H), 7.70 (d, J = 8.5 Hz, 1H), 7.53-7.38 (m, 3H), 6.96-6.85 (m, 2H), 4.49 (s, 2H), 4.06-3.92 (m, 1H), 2.58 (s, 3H), 1.15 (d, J = 6.5 Hz, 6H). |
| 27 | (indazole-NH-triazole-NH, phenyl with OMe, OCH₂C(O)NH-iPr) | Method E, 2.84 min, m/z 422.2 [M + H]⁺ | ¹H NMR (400 MHz, DMSO-d₆): δ 12.79 (m 2H), 9.05 (s, 1H), 8.15 (s, 1H), 8.01-7.88 (m, 3H), 7.45-7.35 (m, 2H), 6.78 (d, J = 2.5 Hz, 1H), 6.69 (dd, J = 8.5, 2.5 Hz, 1H), 4.53 (s, 2H), 3.96 (m, 4H), 1.11 (d, J = 6.5 Hz, 6H). |
| 28 | (indazole-NH-triazole-pyridinone-N-CH₂C(O)NH-iPr) | Method B, 2.31 min, m/z 393.1 [M + H]⁺ | ¹H NMR (400 MHz, DMSO-d₆): δ 13.96 (s, 1H), 12.89 (s, 1H), 9.45 (s, 1H), 8.06 (m, 3H), 7.67 (s, 1H), 7.54-7.36 (m, 2H), 7.01-6.88 (m, 1H), 6.76 (d, J = 7.0 Hz, 1H), 4.53 (s, 2H), 3.90-3.79 (m, 1H), 1.09 (d, J = 6.5 Hz, 6H). |

TABLE 10-continued

| Example | Structure | LC/MS | ¹H NMR |
|---|---|---|---|
| 29 | 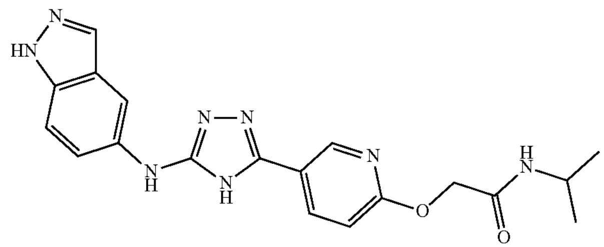 | Method B, 2.67 min, m/z 393.1 [M + H]⁺ | ¹H NMR (400 MHz, DMSO-d₆): δ 12.82 (s, 1H), 9.40 (s, 1H), 8.70 (d, J = 2.5, 1.0 Hz, 1H), 8.24 (dd, J = 8.5, 2.5 Hz, 1H), 8.09 (s, 1H), 7.95 (s, 1H), 7.87 (d, J = 8.0 Hz, 1H), 7.45-7.38 (m, 2H), 7.04 (d, J = 8.5, 1.0 Hz, 1H), 4.72 (s, 2H), 3.95-3.85 (m, 1H), 1.07 (d, J = 6.5 Hz, 6H). |
| 30 | 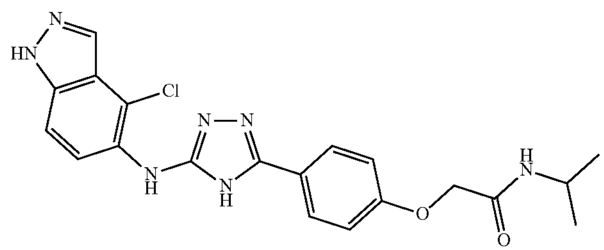 | Method E, 6.18 min, m/z 426.0 [M + H]⁺ | ¹H NMR (400 MHz, CD₃OD): δ 8.25 (d, J = 1.0 Hz, 1H), 7.89 (d, J = 9.0 Hz, 2H), 7.69 (dd, J = 9.0, 1.0 Hz, 1H), 7.59 (d, J = 9.0 Hz, 1H), 7.18 (d, J = 9.0 Hz, 2H), 4.60 (s, 2H), 4.11 (p, J = 6.5 Hz, 1H), 1.20 (d, J = 6.5 Hz, 6H). |
| 31 | 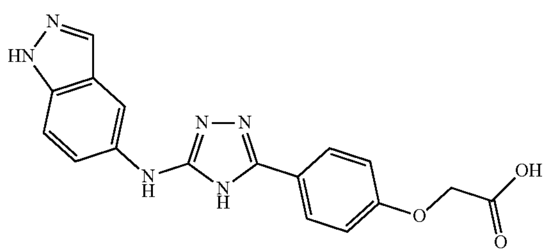 [SMILES: O=C(O)COc1ccc(-c2nnc(Nc3ccc4[nH]ncc4c3)[nH]2)cc1] | Method E, 4.92 min, m/z 351.0 [M + H]⁺ | ¹H NMR (500 MHz, DMSO-d₆): δ 12.82 (s, 1H), 9.43 (s, 1H), 8.13 (s, 1H), 7.94 (s, 1H), 7.88 (d, J = 8.5 Hz, 2H), 7.41 (s, 2H), 6.96 (d, J = 8.5 Hz, 2H), 4.37 (s, 2H). |
| 32 | 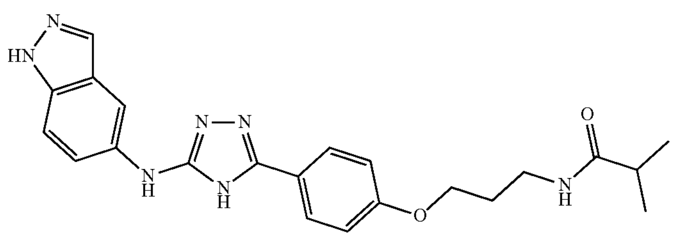 [SMILES: CC(C)C(=O)NCCCOc1ccc(-c2nnc(Nc3ccc4[nH]ncc4c3)[nH]2)cc1] | Method C, 1.98 min, m/z 420.1 [M + H]⁺ | ¹H NMR (500 MHz, DMSO-d₆): δ 13.27 (s, 1H), 12.80 (s, 1H), 9.21 (s, 1H), 8.10 (d, J = 1.5 Hz, 1H), 7.94 (s, 1H), 7.93-7.88 (m, 2H), 7.82 (t, J = 5.5 Hz, 1H), 7.41 (d, J = 1.5 Hz, 2H), 7.06 (d, J = 8.5 Hz, 2H), 4.05 (t, J = 6.5 Hz, 2H), 3.20 (q, J = 6.5 Hz, 2H), 2.36-2.31 (m, 1H), 1.87 (p, J = 6.5 Hz, 2H), 1.00 (d, J = 6.5 Hz, 6H). |

TABLE 10-continued

| Example | Structure | LC/MS | ¹H NMR |
|---|---|---|---|
| 33 | 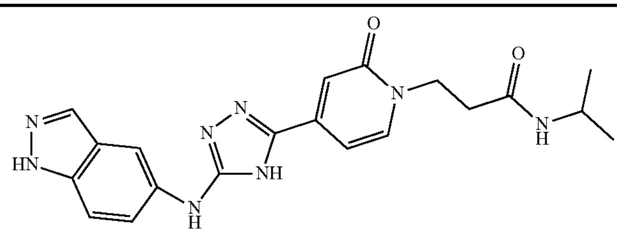 | Method B, 2.41, m/z 407.2 [M + H]⁺ | 1H NMR (400 MHz, DMSO-d₆): δ 12.88 (s, 1H), 9.41 (s, 1H), 8.11-7.94 (m, 2H), 7.83 (d, J = 7.6 Hz, 1H), 7.67 (d, J = 7.1 Hz, 1H), 7.52-7.36 (m, 2H), 6.94 (d, J = 1.8 Hz, 1H), 6.73 (dd, J = 7.0, 1.9 Hz, 1H), 4.09 (t, J = 6.7 Hz, 2H), 3.88-3.73 (m, J = 6.8 Hz, 1H), 2.60-2.40 (m, 2H, under DMSO peak), 0.99 (d, J = 6.6 Hz, 6H), 1 exchangeable NH not seen. |
| 34 | 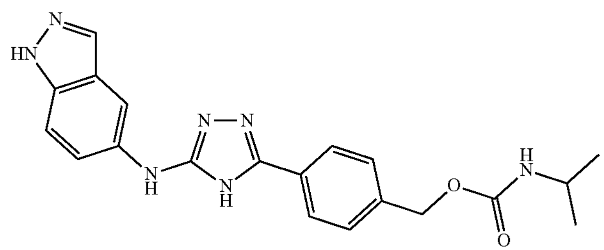 | Method E, 6.23 min, m/z 355.4 [M + H]⁺ | ¹H NMR (400 MHz, DMSO-d₆) δ 9.51 (s, 1H), 8.05 (d, J = 1.9 Hz, 1H), 8.03-7.96 (m, 3H), 7.52-7.47 (m, 3H), 7.42 (dd, J = 8.9, 2.0 Hz, 1H), 7.21 (d, J = 7.8 Hz, 1H), 5.06 (s, 2H), 3.67-3.57 (m, 1H), 1.06 (d, J = 6.6 Hz, 6H). 2 exchangeable NH's not seen. |
| 35 | 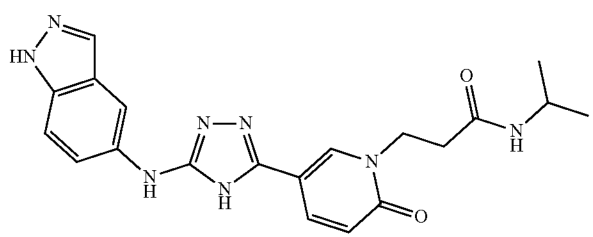 [SMILES: CC(C)NC(=O)CCn1cc(-c2nnc(Nc3ccc4[nH]ncc4c3)[nH]2)ccc1=O] | Method E, 4.87 min, m/z 407.0 [M + H]⁺ | ¹H NMR (400 MHz, DMSO-d₆) δ 12.53 (s, 2H), 8.65 (s, 1H), 8.19 (s, 1H), 7.97-7.88 (m, 3H), 7.44 (d, J = 1.5 Hz, 3H), 6.48 (d, J = 9.4 Hz, 1H), 4.18 (t, J = 6.6 Hz, 2H), 3.90-3.80 (m, 1H), 2.55 (t, J = 6.7 Hz, 2H), 1.02 (d, J = 6.6 Hz, 6H). |
| 36 | 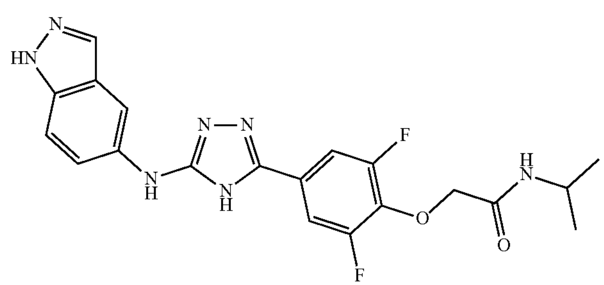 [SMILES: CC(C)NC(=O)COc1c(F)cc(-c2nnc(Nc3ccc4[nH]ncc4c3)[nH]2)cc1F] | Method E, 6.31 min, m/z 428.0 [M + H]⁺ | ¹H NMR (400 MHz, DMSO-d₆) δ 13.14 (s, 1H), 12.85 (s, 1H), 9.30 (s, 1H), 8.06 (d, J = 2.0 Hz, 1H), 7.98 (s, 1H), 7.92 (d, J = 8.0 Hz, 1H), 7.69-7.60 (m, 2H), 7.46 (d, J = 9.0 Hz, 1H), 7.41 (dd, J = 9.0, 2.0 Hz, 1H), 4.59 (s, 2H), 3.99-3.87 (m, 1H), 1.09 (d, J = 6.5 Hz, 6H). |

TABLE 10-continued

| Example | Structure | LC/MS | ¹H NMR |
|---|---|---|---|
| 37 | (structure) | Method E, 5.17 min, m/z 427.9 [M + H]⁺ | ¹H NMR (400 MHz, DMSO-$d_6$) δ 12.15 (s, 1H), 9.70 (s, 1H), 8.04 (d, J = 0.9 Hz, 1H), 8.02 (d, J = 1.9 Hz, 1H), 7.97-7.92 (m, 2H), 7.51 (d, J = 8.9 Hz, 1H), 7.42 (dd, J = 8.9, 2.0 Hz, 1H), 7.12-7.06 (m, 2H), 4.82 (s, 2H), 3.29 (s, 3H), 2 exchangeable NH's not seen: |
| 38 | (structure) | Method E, 6.35 min, m/z 426.0 [M + H]⁺ | ¹H NMR (400 MHz DMSO-$d_6$): δ 13.22 (s, 1H), 12.83 (s, 1H), 9.20 (s, 1H), 8.07 (s, 1H), 8.01 (d, J = 2.0 Hz, 1H), 7.96 (s, 1H), 7.88 (dd, J = 8.5, 2.0 Hz, 1H), 7.85 (d, J = 8.0 Hz, 1H), 7.46-7.38 (m, 2H), 7.15 (d, J = 8.5 Hz, 1H), 4.64 (s, 2H), 3.93 (m, 1H), 1.11 (d, J = 6.5 Hz, 6H). |
| 39 | (structure) | Method E, 4.99 min, m/z 293.0 [M + H]⁺ | ¹H NMR (400 MHz, CD₃OD): δ 8.37-8.32 (m, 1H), 8.03 (d, J = 1.9 Hz, 1H), 7.82-7.77 (m, 2H), 7.74 (d, J = 8.9 Hz, 1H), 7.58 (dd, J = 9.0, 2.0 Hz, 1H), 7.00-6.94 (m, 2H), 4 exchangeable protons (3 × NH and 1 × OH) not observed due to this being a hydrochloride salt |
| 40 | (structure) | Method E, 5.46 min, m/z 419.0 [M + H]⁺ | ¹H NMR (400 MHz, DMSO-$d_6$): δ 9.37 (s, 1H), 8.07- 8.04 (m, 1H), 7.99 (s, 1H), 7.61 (d, J = 2.0 Hz, 1H), 7.55 (dd, J = 8.4, 2.0 Hz, 1H), 7.46 (d, J = 8.9 Hz, 1H), 7.41 (dd, J = 8.9, 2.0 Hz, 1H), 7.26 (d, J = 8.4 Hz, 1H), 5.40 (s, 2H), 3.86 (s, 3H), 2.54 (s, 3H). 3 NH not visible. TFA salt |

TABLE 10-continued

| Example | Structure | LC/MS | $^1$H NMR |
|---|---|---|---|
| 41 | 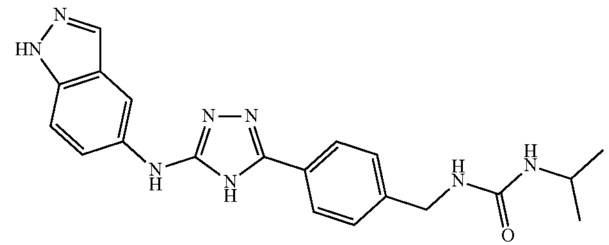 [SMILES: CC(C)NC(=O)NCc1ccc(-c2nnc(Nc3ccc4[nH]ncc4c3)[nH]2)cc1] | Method E, 5.44 min, m/z 391.1 [M + H]$^+$ | $^1$H NMR (400 MHz, DMSO-d$_6$): δ 13.49 (s, 1H), 12.81 (s, 1H), 9.28 (s, 1H), 8.10 (t, J = 1.4 Hz, 1H), 7.98-7.89 (m, 3H), 7.42 (d, J = 1.9 Hz, 2H), 7.37 (d, J = 7.9 Hz, 2H), 6.25 (t, J = 5.9 Hz, 1H), 5.82 (d, J = 7.8 Hz, 1H), 4.25 (d, J = 5.4 Hz, 2H), 3.70 (m, 1H), 1.05 (d, J = 6.5 Hz, 6H) |
| 42 | 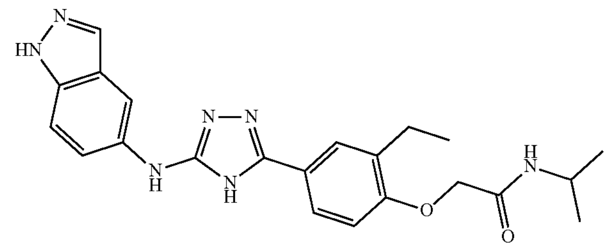 [SMILES: CCc1cc(-c2nnc(Nc3ccc4[nH]ncc4c3)[nH]2)ccc1OCC(=O)NC(C)C] | Method B, 3.18 min, m/z 420.3 [M + H]$^+$ | $^1$H NMR (400 MHz, DMSO-d$_6$) 613.40 (s, 1H), 12.77 (s, 1H), 9.11 (s, 1H), 8.10 (s, 1H), 7.93 (s, 1H), 7.83-7.69 (m, 3H), 7.41 (s, 2H), 6.97 (s, 1H), 4.54 (s, 2H), 4.00-3.88 (m, 1H), 2.75-2.69 (m, 2H), 1.23 (d, J = 7.2 Hz, 3H), 1.10 (d, J = 6.5 Hz, 6H) |
| 460 | 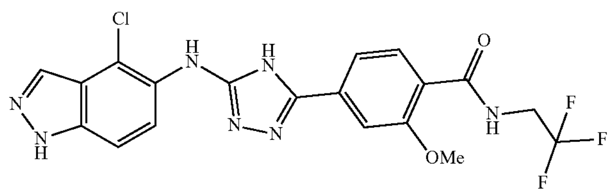 | Method B, 3.32 min, m/z 466.1 [M + H]$^+$ | 1H NMR (400 MHz, DMSO-d6) 613.35 (s, 1H), 12.73 (s, 1H), 8.72 (s, 1H), 8.70 (t, 1H), 8.08 (s, 1H), 7.91 (d, J = 8.9 Hz, 1H), 7.84 (d, J = 8.0 Hz, 1H), 7.68 (d, J = 1.4 Hz, 1H), 7.64 (dd, J = 8.1, 1.4 Hz, 1H), 7.56 (d, J = 8.9 Hz, 1H), 4.13 (m, 2H), 3.98 (s, 3H) |
| 461 | 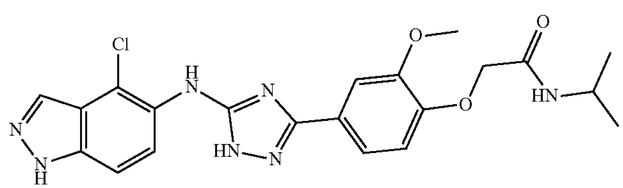 | Method B, 3.05 min, m/z 456.2 [M + H]$^+$ | 1H NMR (400 MHz, DMSO-d6 δ 13.29 (s, 1H), 12.30 (bs, 1H), 8.78 (bs, 1H), 8.05 (s, 1H), 7.98 (s, 1H), 7.79 (d, J = 7.9 Hz, 1H), 7.57-7.51 (m, 2H), 7.49 (dd, J = 8.3, 1.9 Hz, 1H), 7.02 (d, J = 8.3 Hz, 1H), 4.50 (s, 2H), 3.98-3.89 (m, 1H), 3.87 (s, 3H), 1.10 (d, J = 6.6 Hz, 6H) |

TABLE 10-continued

| Example | Structure | LC/MS | ¹H NMR |
|---|---|---|---|
| 462 | 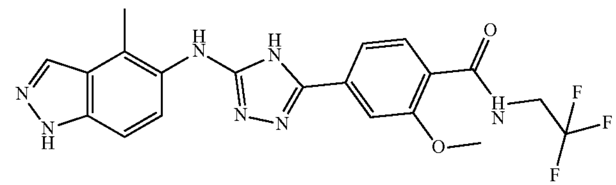 | Method B, 3.08 min, m/z 446.4 [M + H]⁺ | 1H NMR (400 MHz, DMSO-d6) δ 13.01 (s, 1H), 12.36 (s, 1H), 8.70 (s, 2H), 8.13 (s, 1H), 7.82 (d, J = 8.0 Hz, 1H), 7.64 (s, 1H), 7.60 (dd, J = 8.0, 1.4 Hz, 1H), 7.37 (s, 2H), 4.13 (m, 2H), 3.96 (s, 3H), 2.46 (s, 3H). |
| 463 | 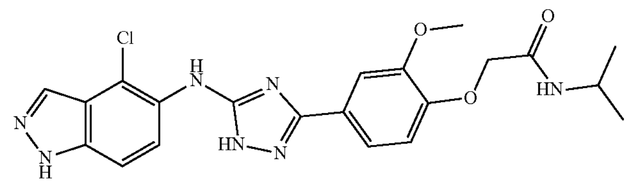 | Method B, 2.75 min, m/z 436.3 [M + H]⁺ | 1H NMR (400 MHz, DMSO-d6) δ 12.97 (s, 1H), 12.12 (s, 1H), 8.58 (s, 1H), 8.10 (s, 1H), 7.77 (d, J = 7.8 Hz, 1H), 7.52 (s, 1H), 7.44 (dd, J = 8.4, 1.9 Hz, 1H), 7.35 (s, 2H), 6.99 (s, 1H), 4.48 (s, 2H), 3.92 (m, 1H), 3.85 (s, 3H), 2.45 (s, 3H), 1.10 (d, J = 6.6 Hz, 6H). |

General Method C:

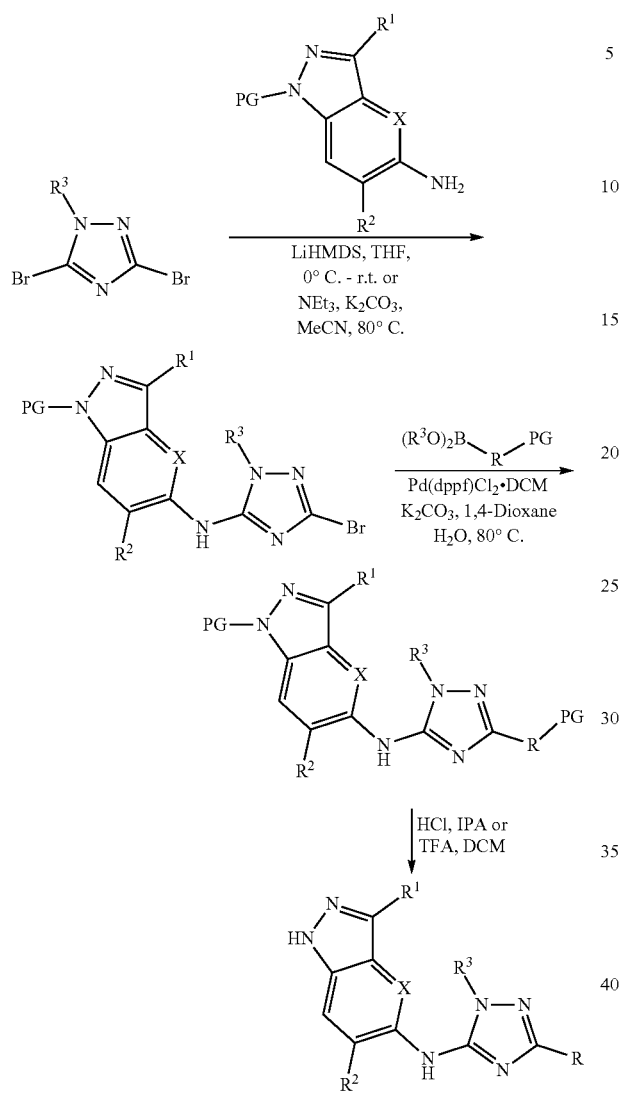

A method for preparing a compound of the invention is given below. Further compounds that can be prepared in a similar manner from intermediates 3-9, 12-14, 17 and 18 using commercially available boronic acids, boronate esters or intermediates 43, 44, 51-65 using general method C are given in Table 11.

Example 43: 4-[5-[(4-chloro-1H-indazol-5-yl) amino]-1-methyl-1,2,4-triazol-3-yl]-N-ethyl-2-fluoro-benzamide

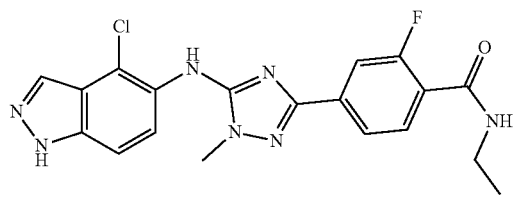 [SMILES: CCNC(=O)c1ccc(-c2nc(Nc3ccc4[nH]ncc4c3Cl)n(C)n2)cc1F]

4-[5-[(4-Chloro-1-tetrahydropyran-2-yl-indazol-5-yl) amino]-1-methyl-1,2,4-triazol-3-yl]-N-ethyl-2-fluoro-benzamide (100 mg, 0.20 mmol) was dissolved/suspended in methanol (3 mL) and HCl (4.0 M in dioxane) (6.01 mL, 24.02 mmol) was added. The reaction was stirred at 25° C. for 18 h, forming a white precipitate. The reaction was concentrated in vacuo and dissolved in water and the solution was purified directly by ion exchange chromatography (SCX, eluting with 1 M $NH_3$ in MeOH). The solvent was removed in vacuo and the gummy residue was dissolved in DCM and a white solid immediately precipitated. The solid was triturated with diethyl ether and filtered. The solid was then dried under vacuum for 3 days to give 4-[5-[(4-chloro-1H-indazol-5-yl)amino]-1-methyl-1,2,4-triazol-3-yl]-N-ethyl-2-fluoro-benzamide (50 mg, 0.12 mmol, 60% yield) as a white solid. UPLC-MS (ES$^+$, Method B): 3.19 min, m/z 414.3 [M+H]$^+$. $^1$H NMR (400 MHz, DMSO-$d_6$) δ 13.42 (s, 1H), 8.63 (s, 1H), 8.32 (dt, J=6.1, 3.0 Hz, 1H), 8.11 (s, 1H), 7.74-7.53 (m, 5H), 3.82 (s, 3H), 3.27 (qd, J=7.2, 5.5 Hz, 2H), 1.11 (t, J=7.2 Hz, 3H).

Step 1: N-(5-bromo-2-methyl-1,2,4-triazol-3-yl)-4-chloro-1-tetrahydropyran-2-yl-indazol-5-amine

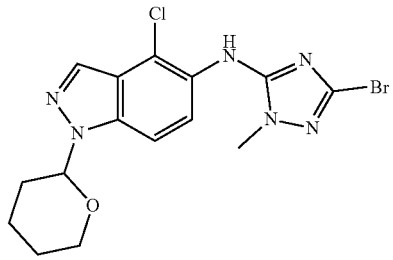 [SMILES: Cn1nc(Br)nc1Nc1ccc2c(cnn2C2CCCCO2)c1Cl]

To a stirred solution of 4-chloro-1-tetrahydropyran-2-yl-indazol-5-amine (14.47 g, 57.50 mmol) and 3,5-dibromo-1-methyl-1H-1,2,4-triazole (13.85 g, 57.50 mmol) in dry THF (150 mL) at −20° C. under $N_2$ was added sodium bis(trimethylsilyl)amide solution (1.0 M in THF) (57.50 mL, 57.50 mmol) and the mixture stirred at 0° C. for 20 min. Further sodium bis(trimethylsilyl)amide solution (1.0M in THF, 28.75 mL) was added and the reaction was stirred for 20 min. The mixture was quenched with sat. aq. $NH_4Cl$ (150 mL) and extracted with EtOAc (250 mL). The layers were separated, and the aqueous layer extracted with further EtOAc (2×100 mL). The combined organics were dried over $MgSO_4$. and concentrated in vacuo. The solid residue was triturated with diethyl ether and filtered, washed with further diethyl ether to give N-(5-bromo-2-methyl-1,2,4-triazol-3-yl)-4-chloro-1-tetrahydropyran-2-yl-indazol-5-amine (19.75 g, 47.97 mmol, 83% yield) as a white solid. UPLC-MS (ES$^+$, Method A): 2.79 min, m/z 413.0 [M+H]$^+$. $^1$H NMR (400 MHz, DMSO-$d_6$) δ 8.86 (s, 1H), 8.15 (d, J=0.8 Hz, 1H), 7.74 (dd, J=8.9, 0.9 Hz, 1H), 7.51 (d, J=8.9 Hz, 1H), 5.88 (dd, J=9.5, 2.4 Hz, 1H), 3.94-3.86 (m, 1H), 3.79-3.73 (m, 1H), 3.71 (s, 3H), 2.46-2.33 (m, 1H), 2.11-1.95 (m, 2H), 1.83-1.54 (m, 3H).

Step 2: 4-[5-[(4-chloro-1-tetrahydropyran-2-yl-indazol-5-yl)amino]-1-methyl-1,2,4-triazol-3-yl]-N-ethyl-2-fluoro-benzamide

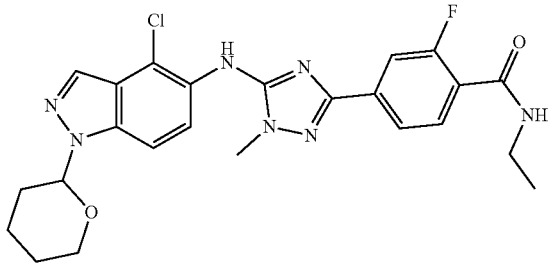 [SMILES: CCNC(=O)c1ccc(-c2nc(Nc3ccc4c(cnn4C4CCCCO4)c3Cl)n(C)n2)cc1F]

N-Ethyl-2-fluoro-4-(4,4,5,5-tetramethyl-1,3,2-dioxaborolan-2-yl)benzamide (83 mg, 0.28 mmol), N-(5-bromo-2-methyl-1,2,4-triazol-3-yl)-4-chloro-1-tetrahydropyran-2-yl-indazol-5-amine (117 mg, 0.28 mmol) and potassium carbonate (82 mg, 0.60 mmol) were dissolved/suspended in 1,4-dioxane (2 mL) and water (0.5 mL). The reaction mixture was fully degassed with bubbling nitrogen. [1,1'-bis(diphenylphosphino)ferrocene]paladium(II) chloride dichloromethane complex (23 mg, 0.03 mmol) was then added followed by further degassing and then the reaction was heated to 90° C. for 4 h. The reaction was reduced in vacuo onto silica and purified on a 4 g silica column eluting with 25-100% EtOAc in Pet. Ether to give 4-[5-[(4-chloro-1-tetrahydropyran-2-yl-indazol-5-yl)amino]-1-methyl-1,2,4 triazol-3-yl]-N-ethyl-2-fluoro-benzamide (100 mg, 0.19 mmol, 67% yield) as a pale yellow oil. UPLC-MS (ES$^+$, Method A): 1.73 min, m/z 498.5 [M+H]$^+$ $^1$H NMR (400 MHz, CDCl$_3$) δ 8.20 (d, J=8.9 Hz, 1H), 8.12 (t, J=8.1 Hz, 1H), 8.03 (d, J=0.8 Hz, 1H), 7.93 (dd, J=8.2, 1.5 Hz, 1H), 7.79 (dd, J=13.2, 1.5 Hz, 1H), 7.59 (dd, J=9.1, 0.9 Hz, 1H), 6.77 (dt, J=12.1, 5.4 Hz, 1H), 6.59 (s, 1H), 5.70 (dd, J=9.2, 2.7 Hz, 1H), 4.02 (dq, J=10.4, 2.5, 2.1 Hz, 1H), 3.82 (s, 3H), 3.75 (ddd, J=13.1, 8.5, 3.1 Hz, 1H), 3.52 (tt, J=7.4, 5.8 Hz, 2H), 2.60-2.46 (m, 1H), 2.23-2.05 (m, 3H), 1.84-1.64 (m, 2H), 1.32-1.17 (m, 3H).

Compounds prepared in a similar manner to that set out above are given below in Table 11.

TABLE 11

| Example | Structure | LC/MS | ¹H NMR |
|---|---|---|---|
| 44 | 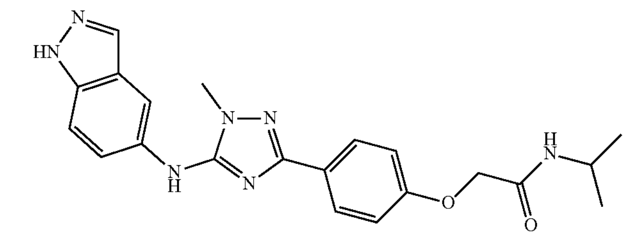 [SMILES: CC(C)NC(=O)COc1ccc(-c2nc(Nc3ccc4[nH]ncc4c3)n(C)n2)cc1] | Method B, 5.96 min, m/z 406.0 [M + H]⁺ | ¹H NMR (400 MHz, DMSO-d₆): δ 12.90 (s, 1H), 8.84 (s, 1H), 8.18 (dd, J = 2.0, 1.0 Hz, 1H), 8.02 (d, J = 1.0 Hz, 1H), 7.90 (d, J = 9.0 Hz, 3H), 7.56 (dd, J = 9.0, 2.0 Hz, 1H), 7.50 (d, J = 9.0 Hz, 1H), 7.02 (d, J = 9.0 Hz, 2H), 4.48 (s, 2H), 3.96 (dp, J = 8.0, 6.5 Hz, 1H), 3.78 (s, 3H), 1.10 (d, J = 6.5 Hz, 6H) |
| 45 | 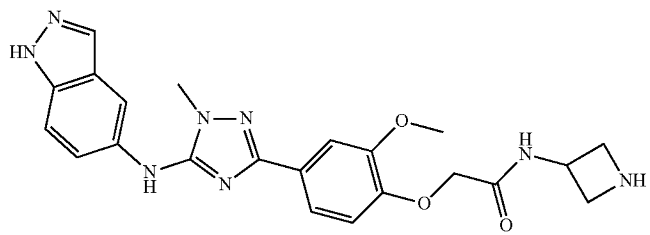 [SMILES: COc1cc(-c2nc(Nc3ccc4[nH]ncc4c3)n(C)n2)ccc1OCC(=O)NC1CNC1] | Method E, 4.82 min, m/z 449.1 [M + H]⁺ | ¹H NMR (400 MHz, DMSO-d₆) δ 12.91 (s, 1H), 8.85 (s, 1H), 8.46 (d, J = 7.5 Hz, 1H), 8.17 (d, J = 1.5 Hz, 1H), 8.01 (d, J = 1.0 Hz, 1H), 7.57-7.48 (m, 4H), 6.98 (d, J = 8.9 Hz, 1H), 4.59-4.5 (m, 1H), 4.46 (s, 2H), 3.87 (s, 3H), 3.79 (s, 3H), 3.53 (t, J = 7.5 Hz, 2H), 3.43 (t, J = 7.5 Hz, 2H). |
| 46 | 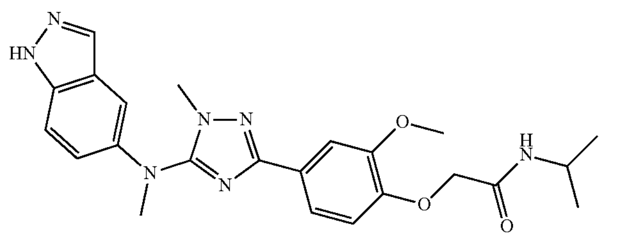 [SMILES: COc1cc(-c2nc(N(C)c3ccc4[nH]ncc4c3)n(C)n2)ccc1OCC(=O)NC(C)C] | Method B, 3.26 min, m/z 450.4 [M + H]⁺ | ¹H NMR (400 MHz, DMSO-d₆) δ 13.06 (s, 1H), 8.00 (s, 1H), 7.77 (d, J = 7.8 Hz, 1H), 7.54-7.49 (m, 3H), 7.32 (d, J = 1.8 Hz, 1H), 7.06 (dd, J = 8.9, 2.2 Hz, 1H), 6.99 (d, J = 8.3 Hz, 1H), 4.48 (s, 2H), 3.97-3.88 (m, 3H), 3.86 (s, 3H), 3.39 (s, 3H), 3.28 (s, 3H), 1.09 (d, J = 6.6 Hz, 6H). |
| 47 | 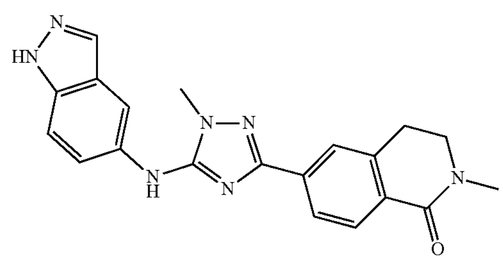 [SMILES: CN1CCc2cc(-c3nc(Nc4ccc5[nH]ncc5c4)n(C)n3)ccc2C1=O] | Method B, 2.83 min, m/z 374.4 [M + H]⁺ | ¹H NMR (400 MHz, DMSO-d₆) δ 12.92 (s, 1H), 8.92 (s, 1H), 8.18 (s, 1H), 8.02 (s, 1H), 7.92 (s, 2H), 7.87 (s, 1H), 7.57 (dd, J = 8.8, 1.8 Hz, 1H), 7.50 (d, J = 8.8, 1H), 3.81 (s, 3H), 3.58 (t, J = 6.8 Hz, 2H), 3.06 (t, J = 6.8 Hz, 2H), 3.04 (s, 3H). |

TABLE 11-continued

| Example | Structure | LC/MS | ¹H NMR |
|---|---|---|---|
| 48 | (structure) | Method E, 5.07 min, m/z 483.0 [M + H]⁺ | ¹H NMR (400 MHz, DMSO-d₆) δ 13.38 (br s, 1H), 8.47 (m, 2H), 8.08 (s, 1H), 7.57-7.50 (m, 2H), 7.41 (d, J = 2.0 Hz, 1H), 7.35 (dd, J = 8.5, 2.0 Hz, 1H), 6.91 (d, J = 8.5 Hz, 1H), 4.54 (m, 1H), 4.47 (s, 2H), 3.81 (s, 3H), 3.76 (s, 3H), 3.56 (t, J = 7.5 Hz, 2H), 3.47 (t, J = 7.5 Hz, 2H). One NH not observed |
| 49 | (structure) | Method E, 4.88 min, m/z 497.0 [M + H]⁺ | ¹H NMR (400 MHz, DMSO-d₆) δ 13.39 (s, 1H), 8.45 (s, 1H), 8.08 (d, J = 1.0 Hz, 1H), 7.94 (d, J = 7.5 Hz, 1H), 7.57-7.50 (m, 2H), 7.41 (d, J = 2.0 Hz, 1H), 7.35 (dd, J = 8.5, 2.0 Hz, 1H), 6.91 (d, J = 8.5 Hz, 1H), 4.45 (s, 2H), 4.13 (ddq, J = 12.0, 7.5, 4.5 Hz, 1H), 3.80 (s, 3H), 3.76 (s, 3H), 2.87 (dd, J = 11.0, 6.5 Hz, 1H), 2.81 (m, 1H), 2.69 (m, 1H), 1.90 (dtd, J = 13.0, 8.1, 6.2 Hz, 1H), 1.48 (m, 1H). One CH hidden under DMSO peak and one NH not observed |
| 50 | (structure) | Method E, 6.07 min, m/z 526.0 [M + H]⁺ | ¹H NMR (400 MHz, DMSO-d₆) δ 13.38 (s, 1H), 8.46 (s, 1H), 8.10 (s, 1H), 7.65 (d, J = 8.5 Hz, 1H), 7.48 (m, 2H), 7.40 (m, 3H), 6.96 (d, J = 7.0 Hz, 1H), 4.87 (s, 1H), 4.45 (s, 2H), 3.82 (s, 3H), 3.78 (s, 3H), 3.53-3.42 (m, 2H), 1.84 (s, 2H), 1.71-1.50 (m, 6H). |
| 51 | (structure) | Method E, 5.86 min, m/z 498.0 [M + H]⁺ | ¹H NMR (400 MHz, DMSO-d₆) δ 13.36 (s, 1H), 8.44 (s, 1H), 8.16 (d, J = 7.0 Hz, 1H), 8.10-8.05 (m, 1H), 7.57 (d, J = 9.0 Hz, 1H), 7.52 (d, J = 11.5 Hz, 1H), 7.41 (d, J = 2.0 Hz, 1H), 7.35 (dd, J = 8.5, 2.0 Hz, 1H), 6.90 (d, J = 8.5 Hz, 1H), 4.48 (s, 2H), 4.29 (dtd, J = 11.0, 7.5, 4.0 Hz, 1H), 3.80 (s, 3H), 3.76 (s, 3H), 3.73 (m, 2H), 3.67 (td, J = 8.0, 5.5 Hz, 1H), 3.47 (dd, J = 9.0, 4.0 Hz, 1H), 2.09 (dq, J = 12.5, 7.5 Hz, 1H), 1.81-1.69 (m, 1H). |

TABLE 11-continued

| Example | Structure | LC/MS | ¹H NMR |
|---|---|---|---|
| 52 | 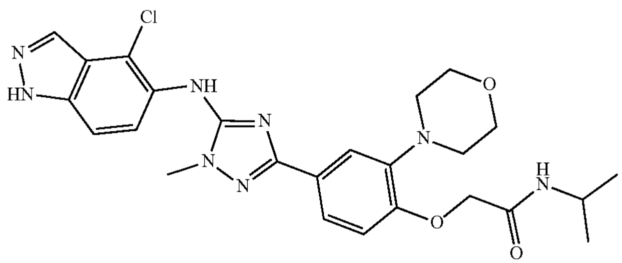 [SMILES: CC(C)NC(=O)COc1ccc(-c2nc(Nc3ccc4[nH]ncc4c3Cl)n(C)n2)cc1N1CCOCC1] | Method E, 3.12 min, m/z 525.4 [M + H]⁺ | ¹H NMR (400 MHz, DMSO-d₆) δ 13.37 (s, 1H), 8.43 (s, 1H), 8.22 (s, 1H), 8.09 (d, J = 9.3 Hz, 1H), 7.70 (d, J = 8.0 Hz, 1H), 7.54 (d, J = 3.6 Hz, 1H), 7.45-7.39 (m, 2H), 6.93 (d, J = 8.2 Hz, 1H), 4.50 (s, 2H), 3.92 (dq, J = 13.5, 6.7 Hz, 1H), 3.75 (m, 7H), 3.02 (t, J = 4.5 Hz, 4H), 1.08 (d, J = 6.6 Hz, 6H). |
| 53 | 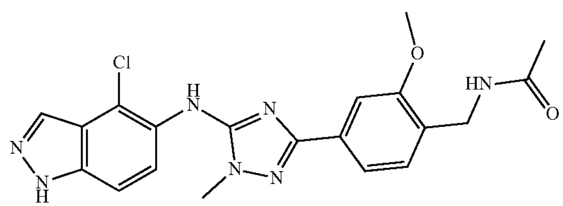 [SMILES: COc1cc(-c2nc(Nc3ccc4[nH]ncc4c3Cl)n(C)n2)ccc1CNC(C)=O] | Method E, 2.87 min, m/z 426.3 [M + H]⁺ | ¹H NMR (400 MHz, DMSO-d₆) δ 13.37 (s, 1H), 8.48 (s, 1H), 8.17 (t, J = 5.8 Hz, 1H), 8.09 (s, 1H), 7.61-7.51 (m, 2H), 7.43-7.37 (m, 2H), 7.16 (d, J = 8.2 Hz, 1H), 4.21 (d, J = 5.8 Hz, 2H), 3.83 (s, 3H), 3.79 (s, 3H), 1.88 (s, 3H). |
| 54 | 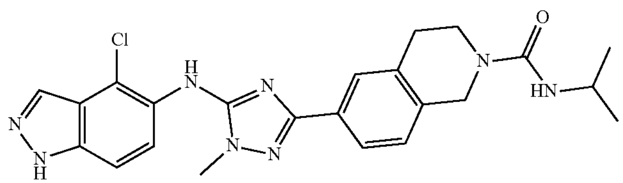 [SMILES: CC(C)NC(=O)N1CCc2cc(-c3nc(Nc4ccc5[nH]ncc5c4Cl)n(C)n3)ccc2C1] | Method B, 3.28 min, m/z 465.4 [M + H]⁺ | ¹H NMR (400 MHz, CDCl₃ + TMS): δ 10.32 (br.s 1H), 8.22 (d, J = 9.0 Hz, 1H), 8.10 (s, 1H), 7.92-7.86 (m, 2H), 7.47 (d, J = 9.0 Hz, 1H), 7.18 (d, J = 8.0 Hz, 1H), 6.49 (s, 1H), 4.56 (s, 2H), 4.24 (d, J = 7.4 Hz, 1H), 4.09-4.00 (m, 1H), 3.84 (s, 3H), 3.62 (t, J = 6.0 Hz, 2H), 2.93 (t, J = 5.7 Hz, 2H), 1.19 (d, J = 6.6 Hz, 6H). |
| 55 | 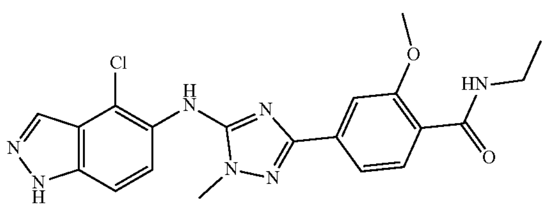 | Method B, 3.15 min, m/z 465.4 [M + H]⁺ | ¹H NMR (400 MHz, DMSO-d₆) δ 13.39 (s, 1H), 8.56 (s, 1H), 8.18 (t, J = 5.7 Hz, 1H), 8.11-8.09 (m, 1H), 7.76 (d, J = 8.0 Hz, 1H), 7.61-7.53 (m, 2H), 7.52-7.45 (m, 2H), 3.91 (s, 3H), 3.81 (s, 3H), 3.34-3.23 (m, 2H), 1.11 (t, J = 7.2 Hz, 3H). |

TABLE 11-continued

| Example | Structure | LC/MS | ¹H NMR |
|---|---|---|---|
| 56 | 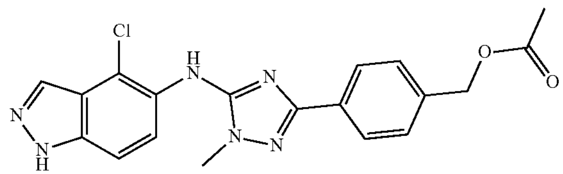 | Method B, 3.52 min, m/z 383.3 [M + H]⁺ | H NMR (400 MHz, DMSO-d₆) δ13.40 (s, 1H), 8.61 (s, 1H), 8.11 (s, 1H), 8.02, 7.92 (m, 4H), 7.60 (d, J = 8.8 Hz, 1H), 7.56 (d, J = 8.9 Hz, 1H), 3.86 (s, 3H), 3.83 (s, 3H) |
| 57 | 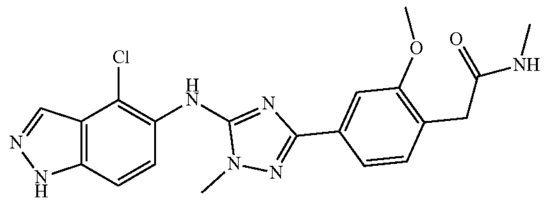 [SMILES: CNC(=O)Cc1ccc(-c2nc(Nc3ccc4[nH]ncc4c3Cl)n(C)n2)cc1OC] | Method B, 2.85 min, m/z 426.4 [M + H]⁺ | ¹H NMR (400 MHz, DMSO-d₆) δ 13.37 (s, 1H), 8.48 (s, 1H), 8.11-8.06 (m, 1H), 7.75-7.64 (m, 1H), 7.61-7.51 (m, 2H), 7.40-7.35 (m, 2H), 7.16 (d, J = 8.2 Hz, 1H), 3.79 (s, 3H), 3.78 (s, 3H), 3.38 (s, 2H), 2.57 (d, J = 4.6 Hz, 3H) |
| 58 | 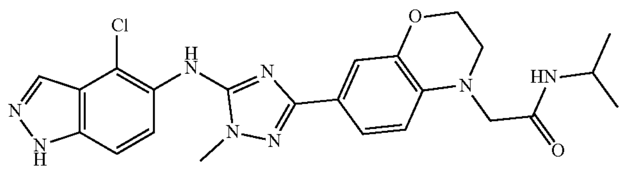 [SMILES: CC(C)NC(=O)CN1CCOc2cc(-c3nc(Nc4ccc5[nH]ncc5c4Cl)n(C)n3)ccc21] | Method B, 3.13 min, m/z 481.4 [M + H]⁺ | ¹H NMR (400 MHz, DMSO-d₆): δ 13.35 (s, 1H), 8.34 (s, 1H), 8.07 (s, 1H), 7.82 (d, J = 7.7 Hz, 1H), 7.61-7.51 (m, 2H), 7.20 (dd, J = 8.4, 2.1 Hz, 1H), 7.13 (d, J = 2.1 Hz, 1H), 6.47 (d, J = 8.2 Hz, 1H), 4.22-4.18 (m, 2H), 3.90-3.81 (m, 3H), 3.73 (s, 3H), 3.47-3.42 (m, 2H), 1.04 (d, J = 7.0 Hz, 6H) |
| 59 | 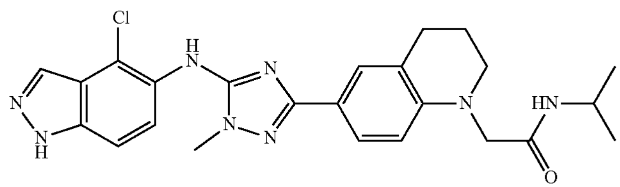 [SMILES: CC(C)NC(=O)CN1CCCc2cc(-c3nc(Nc4ccc5[nH]ncc5c4Cl)n(C)n3)ccc21] | Method B, 3.32 min, m/z 479.4 [M + H]⁺ | ¹H NMR (400 MHz, DMSO-d₆): δ 13.35 (s, 1H), 8.31 (s, 1H), 8.07 (s, 1H), 7.72 (d, J 7.2 Hz, 1H), 7.59-7.49 (m, 2H), 7.43-7.36 (m, 2H), 6.35 (d, J 8.6 Hz, 1H), 3.91-3.81 (m, 1H), 3.78 (s, 2H), 3.72 (s, 3H), 3.37-3.34 (m, 2H), 2.72-2.67 (m, 2H), 1.91-1.85 (m, 2H), 1.04 (d, 7.0 Hz, 6H). |
| 60 | 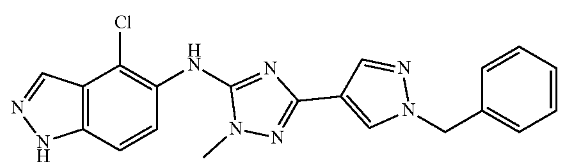 [SMILES: Cn1nc(-c2cnn(Cc3ccccc3)c2)nc1Nc1ccc2[nH]ncc2c1Cl] | Method B, 3.22 min, m/z 405.3 [M + H]⁺ | ¹H NMR (400 MHz, DMSO-d₆): δ 13.36 (s, 1H), 8.40 (s, 1H), 8.10 (s, 1H), 8.09-8.05 (m, 1H), 7.71-7.69 (m, 1H), 7.53-7.50 (m, 2H), 7.38-7.21 (m, 5H), 5.31 (s, 2H), 3.72 (s, 3H) |

TABLE 11-continued

| Example | Structure | LC/MS | ¹H NMR |
|---|---|---|---|
| 61 | 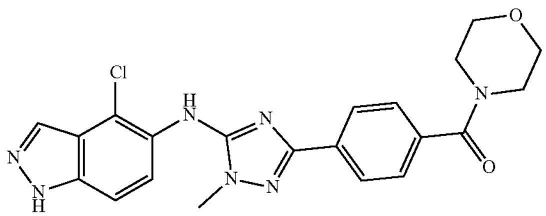 [SMILES: Cn1nc(-c2ccc(C(=O)N3CCOCC3)cc2)nc1Nc1ccc2[nH]ncc2c1Cl] | Method B, 2.92 min, m/z 438.3 [M + H]⁺ | ¹H NMR (400 MHz, DMSO-d₆): δ 13.38 (s, 1H), 8.56 (s, 1H), 8.10 (s, 1H), 7.92-7.86 (m, 2H), 7.61 (d, J = 8.9 Hz, 1H), 7.58-7.52 (m, 1H), 7.46-7.40 (m, 2H), 3.81 (s, 3H), 3.76-3.21 (m, 8H) |
| 62 | 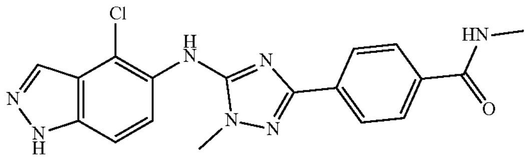 [SMILES: CNC(=O)c1ccc(-c2nc(Nc3ccc4[nH]ncc4c3Cl)n(C)n2)cc1] | Method B, 2.79 min, m/z 382.3 [M + H]⁺ | ¹H NMR (400 MHz, DMSO-d₆): δ 13.39 (s, 1H), 8.56 (s, 1H), 8.46 (q, J = 4.3 Hz, 1H), 8.10 (s, 1H), 7.92-7.87 (m, 2H), 7.87-7.82 (m, 2H), 7.60 (d, J = 8.8 Hz, 1H), 7.56 (d, J = 8.8 Hz, 1H), 3.81 (s, 3H), 2.78 (d, J = 4.5 Hz, 3H) |
| 63 | 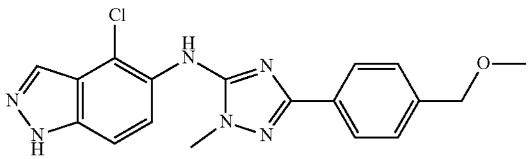 [SMILES: COCc1ccc(-c2nc(Nc3ccc4[nH]ncc4c3Cl)n(C)n2)cc1] | Method B, 3.31 min, m/z 369.3 [M + H]⁺ | ¹H NMR (400 MHz, DMSO-d₆): δ 13.38 (s, 1H), 8.49 (s, 1H), 8.09 (s, 1H), 7.85-7.78 (m, 2H), 7.60 (d, J = 8.8 Hz, 1H), 7.55 (d, J = 9.0 Hz, 1H), 7.35-7.29 (m, 2H), 4.42 (s, 2H), 3.79 (s, 3H), 3.29 (s, 3H) |
| 64 | 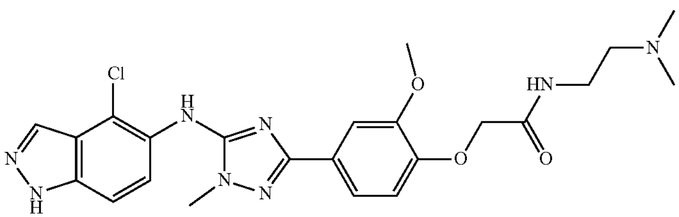 [SMILES: COc1cc(-c2nc(Nc3ccc4[nH]ncc4c3Cl)n(C)n2)ccc1OCC(=O)NCCN(C)C] | Method B, 2.47 min, m/z 499.5, 501.5 [M + H]⁺ | ¹H NMR (400 MHz, DMSO-d₆): δ 13.38 (S1H), 8.46 (S1H), 8.09 (s, 1H), 7.92-7.85 (m, 1H), 7.59- 7.51 (m, 2H), 6.94 (d, J 8.4 Hz, 1H), 4.49 (s, 2H), 3.82 (s, 3H), 3.77 (s, 3H), 3.39- 3.22 (m, 3H), 2.55- 2.42 (m, 2H), 2.28 (br s, 6H) |
| 65 | 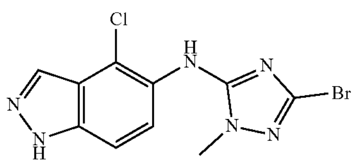 [SMILES: Cn1nc(Br)nc1Nc1ccc2[nH]ncc2c1Cl] | Method B, 2.78 min, m/z 327.1, 329.1, 331.1 [M + H]⁺ | ¹H NMR (400 MHz, DMSO-d₆): δ 13.41 (s 1H), 8.81 (s 1H), 8.10 (s, 1H), 7.54 (d, J 8.8 Hz 1H) 7.43 (d, J 8.8, 1H), 3.71 (s, 3H) |

TABLE 11-continued

| Example | Structure | LC/MS | ¹H NMR |
|---|---|---|---|
| 66 | 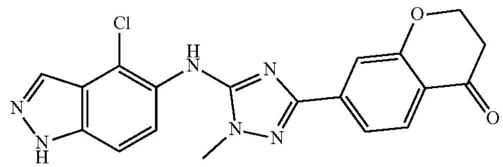 [SMILES: Cn1nc(-c2ccc3c(c2)OCCC3=O)nc1Nc1ccc2[nH]ncc2c1Cl] | Method B, 1.47 min, m/z 395.3, 397.3 [M + H]⁺ | ¹H NMR (400 MHz, DMSO-d₆): δ 13.39 (s, 1H), 8.61 (s, 1H), 8.10 (s, 1H), 7.78 (d, J 8.2 Hz, 1H), 7.62-7.48 (m, 3H), 7.38 (d, J 1.2 Hz, 1H), 4.54 (t, J 6.3 Hz, 2H), 3.81 (s, 3H), 2.79 (t, J 6.3 Hz, 2H). |
| 67 | 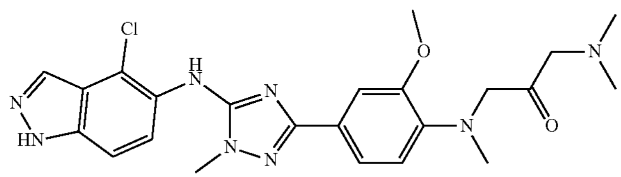 | Method B, 3.29 min, m/z 493.4 [M + H]⁺ | ¹H NMR (400 MHz, DMSO-d₆) δ 13.36 (s, 1H), 8.42 (s, 1H), 8.08 (s, 1H), 7.63-7.50 (m, 3H), 7.39-7.32 (m, 2H), 6.90 (d, J = 8.8 Hz, 1H), 3.97-3.87 (m, 1H), 3.80-3.74 (m, 6H), 3.53 (s, 2H), 2.75 (s, 3H), 1.08 (d, J = 6.6 Hz, 6H). |
| 68 | 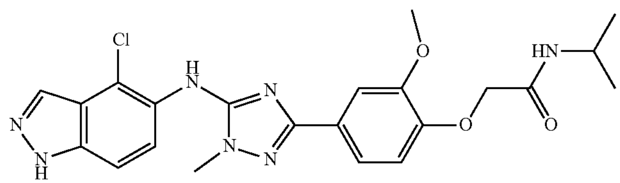 [SMILES: COc1cc(-c2nc(Nc3ccc4[nH]ncc4c3Cl)n(C)n2)ccc1OCC(=O)NC(C)C] | Method B, 3.22 min, m/z 470.4 [M + H]⁺ | ¹H NMR (400 MHz, DMSO-d₆) δ 13.38 (s, 1H), 8.46 (s, 1H), 8.08 (s, 1H), 7.76 (d, J = 8.0 Hz, 1H), 7.59-7.50 (m, 2H), 7.41 (d, J = 2.0 Hz, 1H), 7.34 (dd, J = 8.4, 1.9 Hz, 1H), 6.92 (d, J = 8.4 Hz, 1H), 4.43 (s, 2H), 3.89 (dq, J = 13.5, 6.5 Hz, 1H), 3.80 (s, 3H), 3.75 (s, 3H), 1.07 (d, J = 6.6 Hz, 6H). |
| 69 | 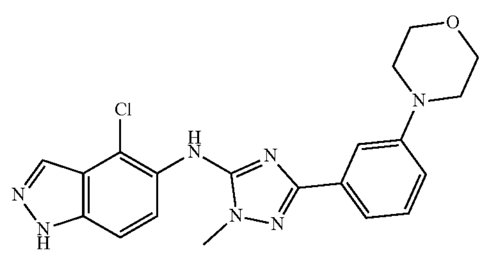 [SMILES: Cn1nc(-c2cccc(N3CCOCC3)c2)nc1Nc1ccc2[nH]ncc2c1Cl] | Method B, 3.20 min, m/z 410.4 [M + H]⁺ | ¹H NMR (400 MHz, DMSO-d₆) δ 13.37 (s, 1H), 8.47 (s, 1H), 8.08 (s, 1H), 7.60-7.51 (m, 2H), 7.38 (dd, J = 2.6, 1.4 Hz, 1H), 7.30 (dt, J = 7.6, 1.2 Hz, 1H), 7.24 (d, J = 7.9 Hz, 1H), 6.95 (ddd, J = 8.2, 2.6, 1.1 Hz, 1H), 3.77 (s, 3H), 3.75-3.70 (m, 4H), 3.12-3.07 (m, 4H). |
| 70 | 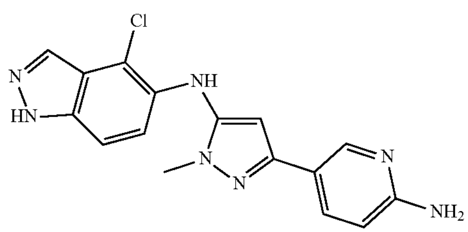 [SMILES: Cn1nc(-c2ccc(N)nc2)cc1Nc1ccc2[nH]ncc2c1Cl] | Method B, 2.24 min, m/z 341.3 [M + H]⁺ | ¹H NMR (400 MHz, DMSO-d₆) δ 13.38 (s, 1H), 8.46 (s, 1H), 8.34 (d, J = 2.2 Hz, 1H), 8.08 (s, 1H), 7.82 (dd, J = 8.7, 2.3 Hz, 1H), 7.55 (q, J = 8.9 Hz, 2H), 6.52 (d, J = 8.7 Hz, 1H), 6.45 (s, 2H), 3.74 (s, 3H). |

TABLE 11-continued

| Example | Structure | LC/MS | ¹H NMR |
|---|---|---|---|
| 71 | 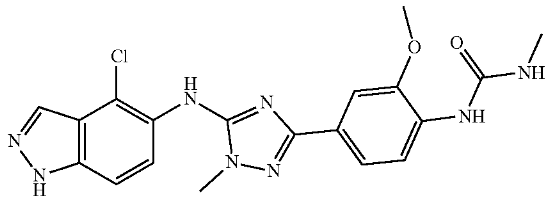 [SMILES: CNC(=O)Nc1ccc(-c2nc(Nc3ccc4[nH]ncc4c3Cl)n(C)n2)cc1OC] | Method B, 2.88 min, m/z 427.3 [M + H]⁺ | ¹H NMR (400 MHz, DMSO-d₆): δ 13.37 (s, 1H), 8.42 (s, 1H), 8.14-8.07 (m, 2H), 7.98 (s, 1H), 7.62-7.50 (m, 2H), 7.40-7.30 (m, 2H), 6.77 (dd, J = 9.3, 4.6 Hz, 1H), 3.86 (s, 3H), 3.76 (s, 3H), 2.63 (d, J = 4.6 Hz, 3H) |
| 72 | 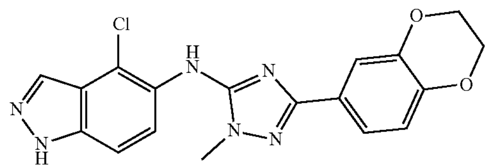 [SMILES: Cn1nc(-c2ccc3c(c2)OCCO3)nc1Nc1ccc2[nH]ncc2c1Cl] | Method B, 3.29 min, m/z 383.3 [M + H]⁺ | ¹H NMR (400 MHz, DMSO-d₆): δ 13.37 (s, 1H), 8.44 (s, 1H), 8.08 (s, 1H), 7.61 (d, J = 8.8 Hz, 1H), 7.56-7.51 (m, 1H), 7.31 (dd, J = 8.4, 2.0 Hz, 1H), 121 (d, J = 1.9 Hz, 1H), 6.85 (d, J = 8.4 Hz, 1H), 4.25 (s, 4H), 3.81 (s, 3H) |
| 73 | 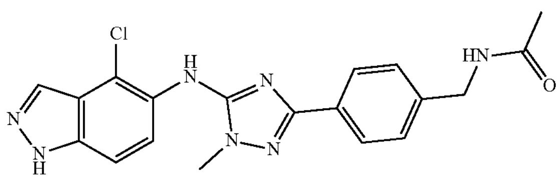 [SMILES: CC(=O)NCc1ccc(-c2nc(Nc3ccc4[nH]ncc4c3Cl)n(C)n2)cc1] | Method B, 2.77 min, m/z 396.3 [M + H]⁺ | ¹H NMR (400 MHz, DMSO-d₆): δ 13.38 (s, 1H), 8.48 (s, 1H), 8.35 (t, J = 5.9 Hz, 1H), 8.09 (dd, J = 1.6, 1.0 Hz, 1H), 7.81-7.76 (m, 2H), 7.60 (d, J = 8.8 Hz, 1H), 7.54 (dd, J = 8.8, 0.8 Hz, 1H), 7.26 (d, J = 5.7 Hz, 2H), 4.25 (d, J = 8.8 Hz, 2H), 3.78 (s, 3H), 1.87 (s, 3H) |
| 74 | 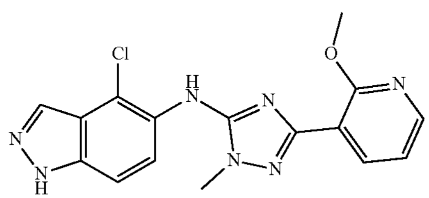 [SMILES: COc1ncccc1-c1nc(Nc2ccc3[nH]ncc3c2Cl)n(C)n1] | Method B, 3.13 min, m/z 356.3 [M + H]⁺ | ¹H NMR (400 MHz, DMSO-d₆): δ 13.40 (s, 1H), 8.64 (s, 1H), 8.18 (dd, J = 5.3, 0.7 Hz, 1H), 8.12-8.08 (m, 1H), 7.60 (d, J = 8.8 Hz, 1H), 7.58-7.53 (m, 1H), 7.36 (dd, J = 5.3, 1.3 Hz, 1H), 7.11-7.09 (m, 1H), 3.86 (s, 3H), 3.82 (s, 3H) |
| 75 | 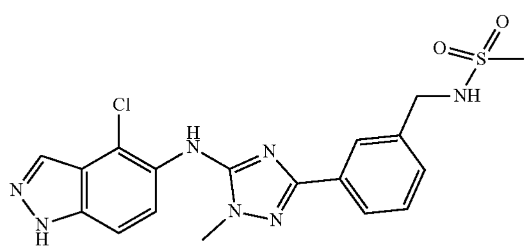 [SMILES: Cn1nc(-c2cccc(CNS(C)(=O)=O)c2)nc1Nc1ccc2[nH]ncc2c1Cl] | Method B, 3.01 min, m/z 432.3 [M + H]⁺ | ¹H NMR (400 MHz, DMSO-d₆): δ 13.38 (s, 1H), 8.51 (s, 1H), 8.11-8.08 (m, 1H), 7.86-7.82 (m, 1H), 7.78-7.72 (m, 1H), 7.62-7.52 (m, 3H), 7.40-7.34 (m, 1H), 7.34-7.29 (m, 1H), 4.17 (d, J = 6.4 Hz, 2H), 3.80 (s, 3H), 2.85 (s, 3H) |

TABLE 11-continued

| Example | Structure | LC/MS | ¹H NMR |
|---|---|---|---|
| 76 | 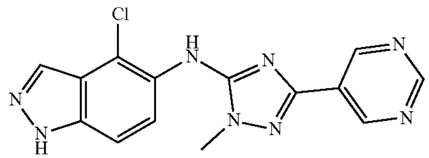 [SMILES: Cn1nc(-c2cncnc2)nc1Nc1ccc2[nH]ncc2c1Cl] | Method B, 2.65 min, m/z 327.3 [M + H]⁺ | ¹H NMR (400 MHz, DMSO-d₆): δ 13.41 (s, 1H), 9.18 (s, 1H), 9.13 (s, 2H), 8.72 (s, 1H), 8.10 (dd, J = 1.6, 1.0 Hz, 1H), 7.61 (d, J = 8.8 Hz, 1H), 7.56 (dd, J = 8.9, 0.8 Hz, 1H), 3.84 (s, 3H) |
| 77 | 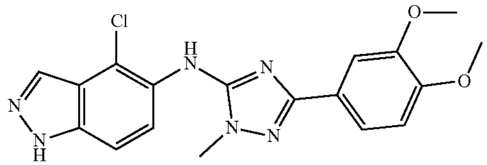 [SMILES: COc1ccc(-c2nc(Nc3ccc4[nH]ncc4c3Cl)n(C)n2)cc1OC] | Method B, 3.12 min, m/z 385.3 [M + H]⁺ | ¹H NMR (400 MHz, DMSO-d₆): δ 13.38 (s, 1H), 8.45 (s, 1H), 8.08 (s, 1H), 7.60-7.49 (m, 2H), 7.38 (d, J = 7.8 Hz, 2H), 6.95 (d, J = 8.2 Hz, 1H), 3.76 (s, 9H). |
| 78 | 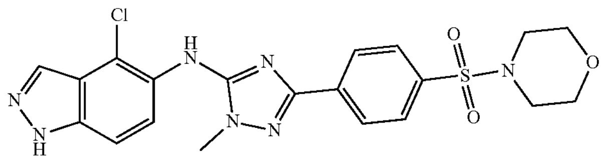 [SMILES: Cn1nc(-c2ccc(S(=O)(=O)N3CCOCC3)cc2)nc1Nc1ccc2[nH]ncc2c1Cl] | Method B, 3.39 min, m/z 474.4 [M + H]⁺ | ¹H NMR (400 MHz, DMSO-d₆): δ 13.40 (s, 1H), 8.66 (s, 1H), 8.10 (dd, J = 1.5, 0.7 Hz, 1H), 8.10-8.05 (m, 2H), 7.78-7.72 (m, 2H), 7.58 (d, J = 8.8 Hz, 1H), 7.57-7.53 (m, 1H), 3.84 (s, 3H), 3.66-3.58 (m, 4H), 2.90-2.82 (m, 4H) |
| 79 | 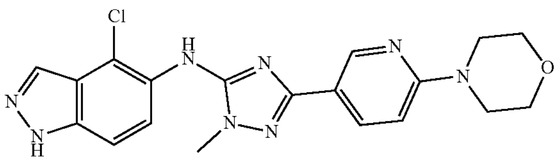 [SMILES: Cn1nc(-c2ccc(N3CCOCC3)nc2)nc1Nc1ccc2[nH]ncc2c1Cl] | Method B, 2.57 min, m/z 411.3 [M + H]⁺ | ¹H NMR (400 MHz, DMSO-d₆): δ 13.37 (s, 1H), 8.57 (d, J = 2.4 Hz, 1H), 8.46 (s, 1H), 8.08 (s, 1H), 7.91 (dd, J = 8.9, 2.4 Hz, 1H), 7.63-7.48 (m, 2H), 6.84 (d, J = 8.9 Hz, 1H), 3.75 (s, 3H), 3.68 (t, J = 4.9 Hz, 4H), 3.47 (t, J = 4.8 Hz, 4H). |
| 80 | 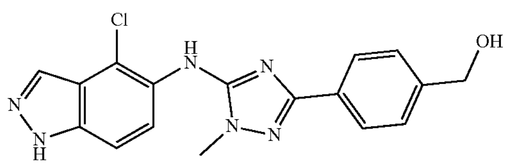 [SMILES: Cn1nc(-c2ccc(CO)cc2)nc1Nc1ccc2[nH]ncc2c1Cl] | Method B, 2.86 min, m/z 355.4 [M + H]⁺ | ¹H NMR (400 MHz, DMSO-d₆): δ 13.39 (s, 1H), 8.49 (s, 1H), 8.11-8.08 (m, 1H), 7.84-7.80 (m, 1H), 7.74-7.68 (m, 1H), 7.60 (d, J = 8.8 Hz, 1H), 7.57-7.53 (m, 1H), 7.36-7.30 (m, 1H), 7.30-7.24 (m, 1H), 5.22 (t, J = 5.8 Hz, 1H), 4.50 (d, J = 5.8 Hz, 2H), 3.79 (s, 3H) |
| 81 | 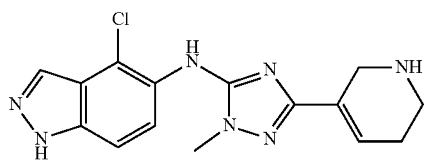 [SMILES: Cn1nc(C2=CCCNC2)nc1Nc1ccc2[nH]ncc2c1Cl] | Method B, 2.04 min, m/z 330.3 [M + H]⁺ | ¹H NMR (400 MHz, DMSO-d₆): δ 13.37 (s, 1H), 8.35 (s, 1H), 8.07 (s, 1H), 7.51 (s, 2H), 6.41 (s, 1H), 3.68 (s, 3H), 3.50 (s, 2H), 2.81 (d, J = 6.0 Hz, 2H), 2.09 (s, 2H), 1.23 (s, 1H). |

TABLE 11-continued

| Example | Structure | LC/MS | ¹H NMR |
|---|---|---|---|
| 82 | 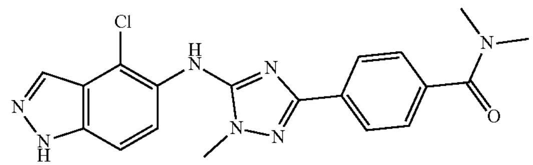 | Method B, 2.95 min, m/z 369.4 [M + H]⁺ | ¹H NMR (400 MHz, DMSO-d₆): δ 13.40 (s, 1H), 8.56 (s, 1H), 8.10 (s, 1H), 7.91-7.84 (m, 2H), 7.61 (d, J = 8.8 Hz, 1H), 7.58-7.53 (m, 1H), 7.45-7.38 (m, 2H), 3.81 (s, 3H), 2.98 (brs, 3H), 2.92 (brs, 3H) |
| 83 | 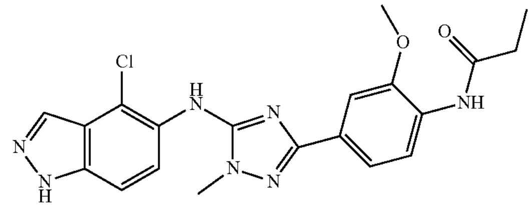 [SMILES: CCC(=O)Nc1ccc(-c2nc(Nc3ccc4[nH]ncc4c3Cl)n(C)n2)cc1OC] | Method B, 3.18 min, m/z 426.4 [M +H]⁺ | ¹H NMR (400 MHz, DMSO-d₆) δ 13.38 (s, 1H), 9.06 (s, 1H), 8.47 (s, 1H), 8.09 (s, 1H), 8.02 (d, J = 8.3 Hz, 1H), 7.61-7.52 (m, 2H), 7.45-7.36 (m, 2H), 3.86 (s, 3H), 3.78 (s, 2H), 2.45-2.35 (m, 3H), 1.06 (t, J = 7.5 Hz, 3H) |
| 84 | 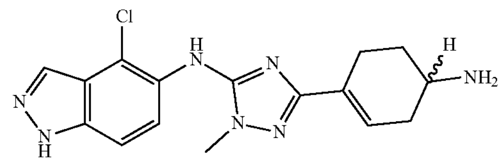 [SMILES: Cn1nc(C2=CCC(N)CC2)nc1Nc1ccc2[nH]ncc2c1Cl] | Method B, 2.15 min, m/z 344.3 [M + H]⁺ | ¹H NMR (400 MHz, DMSO-d₆) δ 13.64-13.10 (brs, 1H), 8.32 (s, 1H), 8.09-8.04 (m, 1H), 7.55-7.48 (m, 2H), 6.34-6.27 (m, 1H), 3.69 (s, 3H), 3.18 (s, 1H), 3.02-2.92 (m, 1H), 2.04-1.82 (m, 3H), 1.72-1.59 (m, 1H), 1.49-1.37 (m, 1H), 2 exchangeable NH's not seen. |
| 85 | 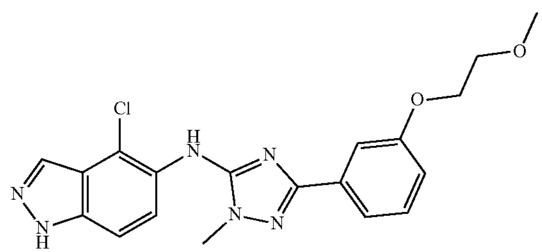 [SMILES: COCCOc1cccc(-c2nc(Nc3ccc4[nH]ncc4c3Cl)n(C)n2)c1] | Method B, 3.35 min, m/z 399.4 [M + H]⁺ | ¹H NMR (400 MHz, DMSO-d₆) δ 13.38 (s, 1H), 8.50 (s, 1H), 8.10 (s, 1H), 7.65-7.52 (m, 2H), 7.47-7.40 (m, 1H), 7.40-7.34 (m, 1H), 7.29 (t, J = 7.9 Hz, 1H), 6.98-6.89 (m, 1H), 4.16-4.03 (m, 2H), 3.79 (s, 3H), 3.70-3.63 (m, 2H), 3.30 (s, 3H) |
| 86 | 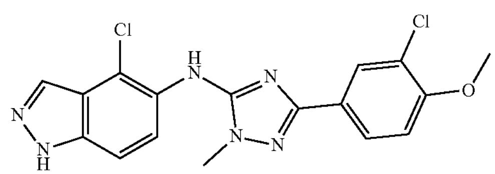 [SMILES: COc1ccc(-c2nc(Nc3ccc4[nH]ncc4c3Cl)n(C)n2)cc1Cl] | Method B, 3.69 min, m/z 389.3 [M + H]⁺ | ¹H NMR (400 MHz, DMSO-d₆) δ 13.39 (s, 1H), 8.51 (s, 1H), 8.10 (s, 1H), 7.82-7.73 (m, 2H), 7.64-7.53 (m, 2H), 7.17 (d, J = 8.5 Hz, 1H), 3.88 (s, 3H), 3.78 (s, 3H). |

TABLE 11-continued

| Example | Structure | LC/MS | ¹H NMR |
|---|---|---|---|
| 87 | 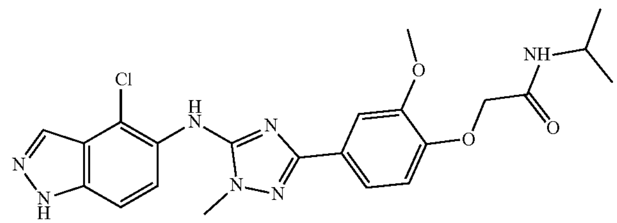 [SMILES: COc1cc(-c2nc(Nc3ccc4[nH]ncc4c3Cl)n(C)n2)ccc1OCC(=O)NC(C)C] | Method B, 3.09 min, m/z 469.5 [M + H]⁺ | ¹H NMR (400 MHz, DMSO-d₆) δ 13.36 (s, 1H), 8.36 (s, 1H), 8.08 (s, 1H), 7.80 (d, J = 7.8 Hz, 1H), 7.61-7.50 (m, 2H), 7.33-7.25 (m, 2H), 6.34 (d, J = 8.2 Hz, 1H), 5.41-5.31 (m, 1H), 3.94-3.85 (m, 1H), 3.83 (s, 3H), 3.74 (s, 3H), 3.64 (d, J = 4.8 Hz, 2H), 1.05 (d, J = 6.6 Hz, 6H) |
| 88 | 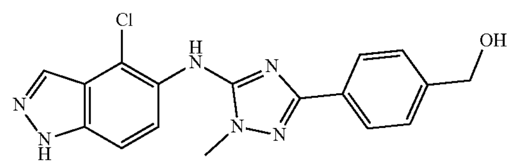 [SMILES: Cn1nc(-c2ccc(CO)cc2)nc1Nc1ccc2[nH]ncc2c1Cl] | Method B, 2.80 min, m/z 355.3 [M + H]⁺ | ¹H NMR (400 MHz, DMSO-d₆) δ 13.39 (s, 1H), 8.49 (s, 1H), 8.09 (s, 1H), 7.79 (d, J = 8.3 Hz, 2H), 7.64-7.52 (m, 2H), 7.32 (d, J = 8.4 Hz, 2H), 5.21 (t, J = 5.7 Hz, 1H), 4.50 (d, J = 5.6 Hz, 2H), 3.79 (s, 3H) |
| 89 | 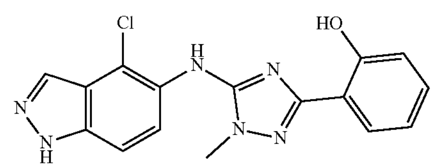 [SMILES: Cn1nc(-c2ccccc2O)nc1Nc1ccc2[nH]ncc2c1Cl] | Method B, 2.80 min, m/z 341.3 [M + H]⁺ | ¹H NMR (400 MHz, DMSO-d₆); δ 13.46 (s, 1H), 10.91 (s, 1H), 8.97 (s, 1H), 8.14 (dd, J = 1.4, 1.0 Hz, 1H), 7.78 (dd, J = 7.8, 1.7 Hz, 1H), 7.58 (dd, J = 8.8, 0.8 Hz, 1H), 7.51 (d, J = 8.8 Hz, 1H), 7.26-7.18 (m, 1H), 6.90-6.80 (m, 2H), 3.84 (s, 3H) |
| 90 | 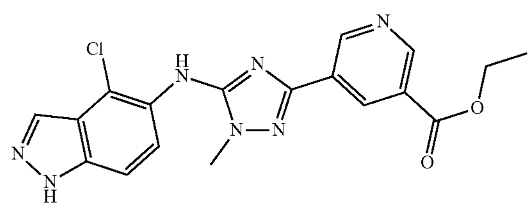 [SMILES: CCOC(=O)c1cncc(-c2nc(Nc3ccc4[nH]ncc4c3Cl)n(C)n2)c1] | Method B, 3.34 min, m/z 398.3 [M + H]⁺ | ¹H NMR (400 MHz, DMSO-d₆): δ 13.42 (s, 1H), 9.20 (d, J = 2.1 Hz, 1H), 9.05 (d, J = 2.1 Hz, 1H), 8.71 (s, 1H), 8.56 (t, J = 2.1 Hz, 1H), 8.11 (dd, J = 1.5, 0.6 Hz, 1H), 7.62-7.54 (m, 2H), 4.37 (q, J = 7.1 Hz, 2H), 3.84 (s, 3H), 1.33 (t, J = 7.1 Hz, 3H) |
| 91 | 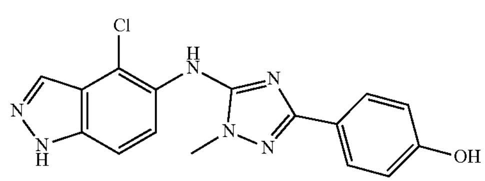 [SMILES: Cn1nc(-c2ccc(O)cc2)nc1Nc1ccc2[nH]ncc2c1Cl] | Method B, 2.79 min, m/z 341.3 [M + H]⁺ | ¹H NMR (400 MHz, DMSO-d₆) δ 13.36 (s, 1H), 9.59 (s, 1H), 8.39 (s, 1H), 8.07 (d, J = 1.5 Hz, 1H), 7.68-7.61 (m, 2H), 7.59 (d, J = 8.8 Hz, 1H), 7.53 (d, J = 8.9 Hz, 1H), 6.75 (d, J = 8.7 Hz, 2H), 3.74 (s, 3H) |

TABLE 11-continued

| Example | Structure | LC/MS | ¹H NMR |
|---|---|---|---|
| 92 | 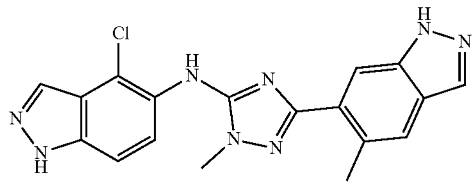 [SMILES: Cc1cc2cn[nH]c2cc1-c1nc(Nc2ccc3[nH]ncc3c2Cl)n(C)n1] | Method B, 3.16 min, m/z 379.3 [M + H]⁺ | ¹H NMR (400 MHz, DMSO-d₆) δ 13.37 (s, 1H), 12.91 (s, 1H), 8.51 (s, 1H), 8.10 (d, J = 1.5 Hz, 1H), 7.96 (s, 1H), 7.90 (s, 1H), 7.64-7.51 (m, 3H), 3.82 (s, 3H), 2.61 (s, 3H). |
| 93 | 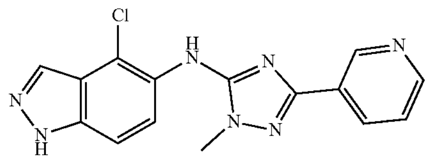 [SMILES: Cn1nc(-c2cccnc2)nc1Nc1ccc2[nH]ncc2c1Cl] | Method B, 2.36 min, m/z 326.2 [M + H]⁺ | ¹H NMR (400 MHz, DMSO-d₆) δ 13.39 (s, 1H), 9.00 (d, J = 2.1 Hz, 1H), 8.62 (s, 1H), 8.54 (dd, J = 4.8, 1.7 Hz, 1H), 8.15-8.08 (m, 2H), 7.41 (dd, J = 8.0, 4.8 Hz, 1H), 3.81 (s, 3H). |
| 94 | 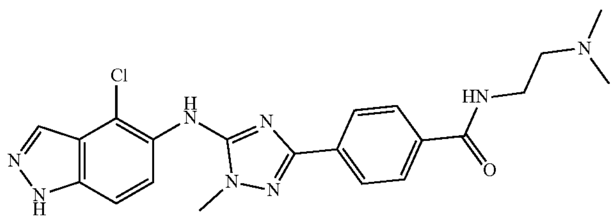 [SMILES: CN(C)CCNC(=O)c1ccc(-c2nc(Nc3ccc4[nH]ncc4c3Cl)n(C)n2)cc1] | Method B, 2.41 min, m/z 439.4 [M + H]⁺ | ¹H NMR (400 MHz, DMSO-d₆) δ 13.41 (s, 1H), 8.58 (s, 1H), 8.53-8.45 (m 1H), 8.10 (s, 1H), 7.87 (q, J = 8.6 Hz, 4H), 7.60-7.52 (m, 2H), 3.81 (s, 3H), 3.41 (q, J = 6.3 Hz, 2H), 2.36-2.29 (m, 6H), 2 exchangeable NH's not seen. |
| 95 | 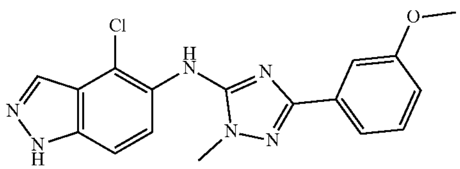 [SMILES: COc1cccc(-c2nc(Nc3ccc4[nH]ncc4c3Cl)n(C)n2)c1] | Method B, 3.41 min, m/z 355.3 [M + H]⁺ | ¹H NMR (400 MHz, DMSO-d₆) δ 13.38 (s, 1H), 8.50 (s, 1H), 8.09 (s, 1H), 7.64-7.52 (m, 2H), 7.46-7.41 (m, 1H), 7.39-7.35 (m, 1H), 7.30 (t, J = 7.9 Hz, 1H), 6.92 (ddd, J = 8.2, 2.7, 0.9 Hz, 1H), 3.79 (s, 3H), 3.77 (s, 3H) |
| 96 | 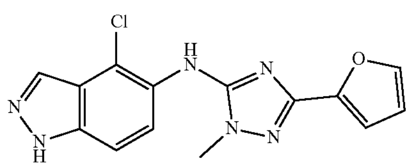 [SMILES: Cn1nc(-c2ccco2)nc1Nc1ccc2[nH]ncc2c1Cl] | Method B, 3.41 min, m/z 315.3 [M + H]⁺ | ¹H NMR (400 MHz, DMSO-d₆) δ 13.39 (s, 1H), 8.56 (S, 1H), 8.10 (s, 1H), 7.69 (s, 1H), 7.58-7.49 (m, 2H), 6.71 (d, J = 3.4 Hz, 1H), 6.56-6.51 (m, 1H), 3.77 (s, 3H) |

TABLE 11-continued

| Example | Structure | LC/MS | ¹H NMR |
|---|---|---|---|
| 97 | 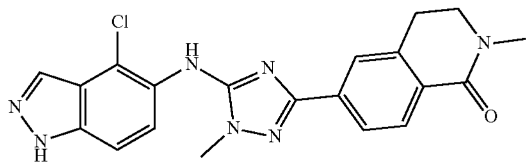 [SMILES: CN1CCc2cc(-c3nc(Nc4ccc5[nH]ncc5c4Cl)n(C)n3)ccc2C1=O] | Method B, 3.05 min, m/z 408.3 [M + H]⁺ | ¹H NMR (400 MHz, DMSO-d₆): δ 13.40 (s, 1H), 8.57 (s, 1H), 8.10 (s, 1H), 7.86 (d, J 7.9 Hz, 1H), 7.78 (d, J 7.8 Hz, 1H), 7.72 (s, 1H), 7.61-7.53 (m, 2H), 3.81 (s, 3H), 3.52 (t, J 6.8 Hz, 2H), 3.01 (s, 3H), 2.99 (t, J 6.8 Hz, 2H). |
| 98 | 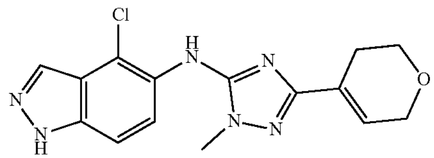 [SMILES: Cn1nc(C2=CCOCC2)nc1Nc1ccc2[nH]ncc2c1Cl] | Method B, 2.71 min, m/z 331.3 [M + H]⁺ | ¹H NMR (400 MHz, CDCl₃) δ 10.82 (s, 1H), 8.06 (d, J = 1.0 Hz, 1H), 8.02 (d, J = 9.0 Hz, 1H), 7.36 (dd, J = 9.0, 1.0 Hz, 1H), 6.70 (tt, J = 3.0, 1.6 Hz, 1H), 6.48 (s, 1H), 4.34 (q, J = 2.8 Hz, 2H), 3.91 (t, J = 5.4 Hz, 2H), 3.77 (s, 3H), 2.60 (ddd, J = 4.4, 2.5, 1.2 Hz, 2H). |
| 99 | 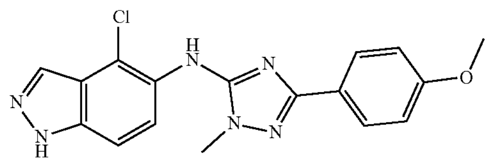 [SMILES: COc1ccc(-c2nc(Nc3ccc4[nH]ncc4c3Cl)n(C)n2)cc1] | Method B, 3.32 min, m/z 355.3 [M + H]⁺ | ¹H NMR (400 MHz, CDCl₃) δ 8.07 (s, 2H), 8.01 (d, J = 24.8 Hz, 2H), 7.72 (s, 1H), 7.54 (d, J = 4.7 Hz, 1H), 7.42 (d, J = 9.0 Hz, 1H), 6.99-6.91 (m, 2H), 3.85 (s, 3H), 3.80 (s, 3H). |
| 100 | 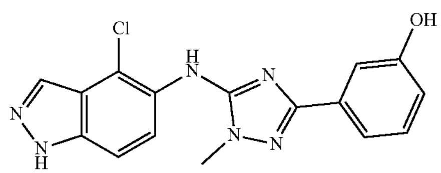 [SMILES: Cn1nc(-c2cccc(O)c2)nc1Nc1ccc2[nH]ncc2c1Cl] | Method B, 3.32 min, m/z 341.3 [M + H]⁺ | ¹H NMR (400 MHz, DMSO-d₆): δ 13.38 (s, 1H), 9.41 (s, 1H), 8.47 (s, 1H), 8.11-8.08 (m, 1H), 7.59 (d, J = 8.8 Hz, 1H), 7.57-7.52 (m, 1H), 7.30-7.25 (m, 2H), 7.17 (t, J = 8.0 Hz, 1H), 7.59 (ddd, J = 8.0, 2.5, 1.1 Hz, 1H), 3.78 (s, 3H). |
| 101 | 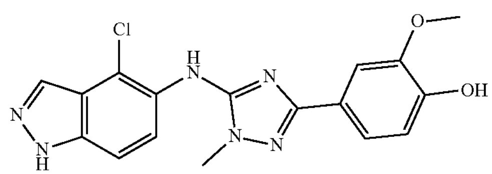 [SMILES: COc1cc(-c2nc(Nc3ccc4[nH]ncc4c3Cl)n(C)n2)ccc1O] | Method B, 2.86 min, m/z 371.3 [M + H]⁺ | ¹H NMR (400 MHz, DMSO-d₆): δ 13.36 (s, 1H), 9.19 (s, 1H), 8.40 (s, 1H), 8.08 (dd, J = 1.7, 0.9 Hz, 1H), 7.58 (d, J = 8.9 Hz, 1H), 7.55-7.51 (m, 1H), 7.35 (d, J = 1.9 Hz, 1H), 7.27 (dd, J = 8.2, 1.9 Hz, 1H), 6.76 (d, J = 8.2 Hz, 1H), 3.78 (s, 3H), 3.75 (s, 3H). |
| 102 | 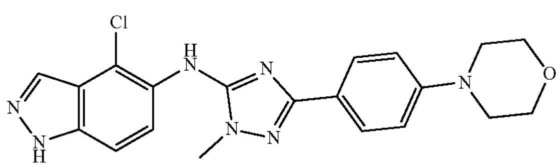 [SMILES: Cn1nc(-c2ccc(N3CCOCC3)cc2)nc1Nc1ccc2[nH]ncc2c1Cl] | Method A, 1.41 min, m/z 410.3 [M + H]⁺ | ¹H NMR (400 MHz, DMSO-d₆): δ 13.37 (s, 1H), 8.40 (s, 1H), 8.08 (s, 1H), 7.73-7.66 (m, 2H), 7.60 (d, J = 8.8 Hz, 1H), 7.57-7.51 (m, 1H), 6.98-6.89 (m, 2H), 3.75 (s, 3H), 3.75-3.70 (m, 4H), 3.17-3.10 (m, 4H) |

TABLE 11-continued

| Example | Structure | LC/MS | ¹H NMR |
|---|---|---|---|
| 103 | 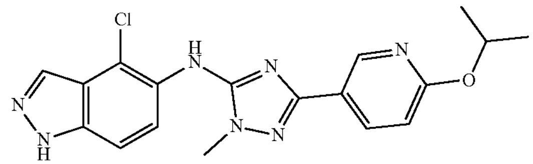 [SMILES: CC(C)Oc1ccc(-c2nc(Nc3ccc4[nH]ncc4c3Cl)n(C)n2)cn1] | Method B, 3.68 min, m/z 384.4 [M +H]⁺ | ¹H NMR (400 MHz, DMSO-d₆): δ 3.38 (s, 1H), 8.57 (dd, J = 2.3, 0.6 Hz, 1H), 8.53 (s, 1H), 8.09 (dd, J = 1.5, 1.0 Hz, 1H), 8.02 (dd, J = 8.5, 2.4 Hz, 1H), 7.61 (d, J = 8.8 Hz, 1H), 7.54 (dd, J = 8.8, 0.8 Hz, 1H), 6.78-6.73 (m, 1H), 5.31-5.21 (m, 1H), 3.78 (s, 3H), 1.29 (d, J = 6.2 Hz, 6H) |
| 104 | 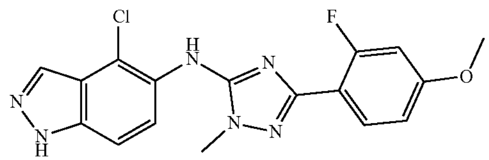 [SMILES: COc1ccc(-c2nc(Nc3ccc4[nH]ncc4c3Cl)n(C)n2)c(F)c1] | Method B, 3.33 min, m/z 373.3 [M +H]⁺ | ¹H NMR (400 MHz, DMSO-d₆): δ 13.37 (s, 1H), 8.49 (s, 1H), 8.09 (dd, J = 1.5, 1.0 Hz, 1H), 7.72 (t, J = 8.8 Hz, 1H), 7.59 (d, J = 8.8 Hz, 1H), 7.53 (dd, J = 8.8, 0.8 Hz, 1H), 6.87 (dd, J = 12.8, 2.4 Hz, 1H), 6.80 (dd, J = 8.7, 2.5 Hz, 1H), 3.79 (s, 3H), 3.78 (s, 3H) |
| 105 | 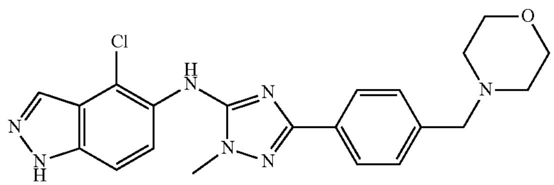 [SMILES: Cn1nc(-c2ccc(CN3CCOCC3)cc2)nc1Nc1ccc2[nH]ncc2c1Cl] | Method B, 2.41 min, m/z 424.4 [M +H]⁺ | ¹H NMR (400 MHz, DMSO-d₆): δ 13.38 (s, 1H), 8.49 (s, 1H), 8.09 (s, 1H), 7.82-7.76 (m, 2H), 7.59 (d, J = 8.8 Hz, 1H), 7.57-7.52 (m, 1H), 7.32 (d, J = 8.3 Hz, 2H), 3.79 (s, 3H), 3.60-3.53 (m, 4H), 3.46 (s, 2H), 2.38-2.30 (m, 4H) |
| 106 | 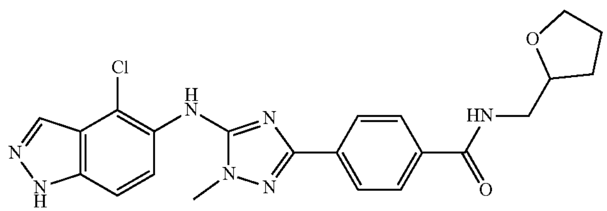 [SMILES: Cn1nc(-c2ccc(C(=O)NCC3CCCO3)cc2)nc1Nc1ccc2[nH]ncc2c1Cl] | Method B, 3.06 min, m/z 452.4 [M +H]⁺ | ¹H NMR (400 MHz, CDCl₃) δ 8.07 (d, J = 8.3Hz, 2H), 8.06-7.88 (m, 2H), 7.80 (d, J = 8.3Hz, 2H), 7.32 (d, J = 9.0Hz, 1H), 6.95-6.87 (m, 1H), 6.74 (s, 1H), 4.09 (qd, J = 7.2, 3.0Hz, 1H), 3.88 (dt, J = 8.3, 6.7Hz, 1H), 3.78 (d, J = 4.6Hz, 5H), 3.34 (ddd, J = 13.9, 7.6, 4.9Hz 1H), 2, 08-1.95 (m, 1H), 1.98-1.83 (m, 2H), 1.67-1.53 (m, 1H), 1 exchangeable NH not seen. |
| 107 | 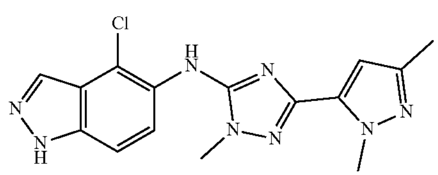 [SMILES: Cc1cc(-c2nc(Nc3ccc4[nH]ncc4c3Cl)n(C)n2)n(C)n1] | Method B, 2.94 min, m/z 343.3 [M +H]⁺ | ¹H NMR (400 MHz, CD₃OD) δ 8.10 (s, 1H), 7.60 (dd, J = 8.8, 1.1 Hz, 1H), 7.52 (d, J = 8.9 Hz, 1H), 6.45 (s, 1H), 4.06 (s, 3H), 3.85 (s, 3H), 2.21 (s, 3H), 2 exchangeable NH's not seen. |

TABLE 11-continued

| Example | Structure | LC/MS | ¹H NMR |
|---|---|---|---|
| 108 | 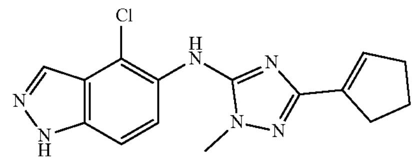 [SMILES: Cn1nc(C2=CCCC2)nc1Nc1ccc2[nH]ncc2c1Cl] | Method B, 2.94 min, m/z 315.3 [M + H]⁺ | ¹H NMR (400 MHz, CD₃OD) δ 8.09 (dd, J = 7.3, 0.8Hz, 1H), 7.51-7.48 (m, 2H), 6.41-6.37 (m, 1H), 3.77 (s, 3H), 2.74-2.66 (m, 2H), 2.49 (tp, J = 7.6, 2.8Hz, 2H), 1.99 (tt, J = 8.1, 6.9Hz, 2H), 2 exchangeable NH's not seen. |
| 109 | 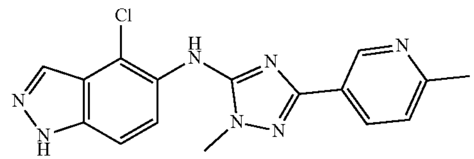 [SMILES: Cc1ccc(-c2nc(Nc3ccc4[nH]ncc4c3Cl)n(C)n2)cn1] | Method B, 2.32 min, m/z 340.3 [M + H]⁺ | ¹H NMR (400 MHz, CD₃OD) δ 8.94 (dd, J = 2.2, 0.8Hz, 1H), 8.20 (dd, J = 8.1, 2., 1H), 8.11 (d, J = 1.0Hz, 1H), 7.63 (d, J = 8.9 Hz, 1H), 7.54 (dd, J = 8.8, 1.0 Hz, 1H), 7.34 (d, J = 8.1 Hz, 1H), 3.86 (s, 3H), 2.56 (s, 3H), 2 exchangeable NH's not seen. |
| 110 | 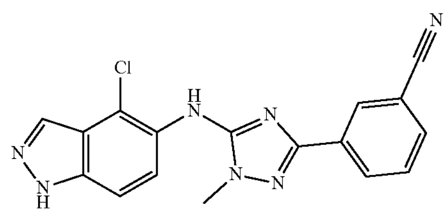 [SMILES: Cn1nc(-c2cccc(C#N)c2)nc1Nc1ccc2[nH]ncc2c1Cl] | Method B, 3.44 min, m/z 350.3 [M + H]⁺ | ¹H NMR (400 MHz, DMSO-d₆) δ 13.42 (s, 1H), 8.65 (s, 1H), 8.14-8.09 (m, 3H), 7.82 (dt, J = 7.7, 1.5 Hz, 1H), 7.64-7.53 (m, 3H), 3.82 (s, 3H). |
| 111 | 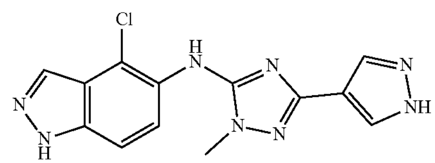 [SMILES: Cn1nc(-c2cn[nH]c2)nc1Nc1ccc2[nH]ncc2c1Cl] | Method B, 2.39 min, m/z 315.2 [M + H]⁺ | ¹H NMR (400 MHz, CD₃OD) δ 8.11 (s, 1H), 7.99 (s, 1H), 7.80 (s, 1H), 7.52 (d, J = 1.1 Hz, 2H), 3.82 (s, 3H), 2 exchangeable NH's not seen. |
| 112 | 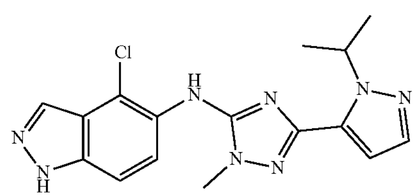 [SMILES: CC(C)n1nccc1-c1nc(Nc2ccc3[nH]ncc3c2Cl)n(C)n1] | Method B, 3.23 min, m/z 357.4 [M + H]⁺ | ¹H NMR (400 MHz, CD₃OD): δ 8.10 (d, J = 1.0 Hz, 1H), 7.61 (d, J = 8.9 Hz, 1H), 7.54-7.48 (m, 2H), 6.64 (d, J = 2.0 Hz, 1H), 5.57 (hept, J = 6.7 Hz, 1H), 3.86 (s, 3H), 1.46 (d, J = 6.6 Hz, 6H). (2 × H exchangeable) |

TABLE 11-continued

| Example | Structure | LC/MS | ¹H NMR |
|---|---|---|---|
| 113 | 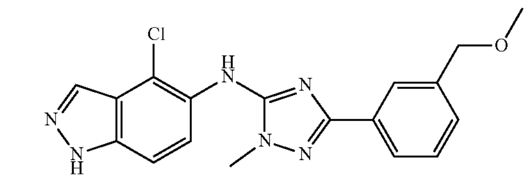 [SMILES: COCc1cccc(-c2nc(Nc3ccc4[nH]ncc4c3Cl)n(C)n2)c1] | Method B, 3.36 min, m/z 369.3 [M + H]⁺ | ¹H NMR (400 MHz, CD₃OD): δ 8.11 (s, 1H), 7.92 (q, J = 1.3, 0.9 Hz, 1H), 7.86 (dt, J = 7.3, 1.8 Hz, 1H), 7.62 (d, J = 8.9 Hz, 1H), 7.53 (d, J = 8.8 Hz, 1H), 7.42-7.35 (m, 2H), 4.49 (s, 2H), 3.85 (s, 3H), 3.39 (s, 3H). (2 × H exchangeable) |
| 114 | 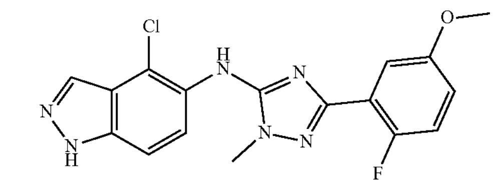 [SMILES: COc1ccc(F)c(-c2nc(Nc3ccc4[nH]ncc4c3Cl)n(C)n2)c1] | Method B, 3.36 min, m/z 373.3 [M + H]⁺ | ¹H NMR (400 MHz, CD₃OD): δ 8.10 (s, 1H), 7.61 (d, J = 8.9 Hz, 1H), 7.53 (d, J = 9.0Hz, 1H), 7.37 (dd, J = 5.9, 3.2 Hz, 1H), 7.11 (dd, J = 10.2, 9.0 Hz, 1H), 6.95 (dt, J = 9.0, 3.5 Hz, 1H), 3.86 (s, 3H), 3.78 (s, 3H). (2 × H exchangeable) |
| 115 | 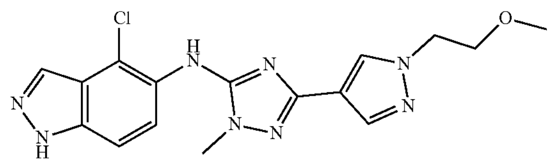 [SMILES: COCCn1cc(-c2nc(Nc3ccc4[nH]ncc4c3Cl)n(C)n2)cn1] | Method B, 2.63 min, m/z 373.3 [M + H]⁺ | ¹H NMR (400 MHz, CD₃OD): δ 8.11 (d, J = 0.6 Hz, 1H), 8.02 (d, J = 0.7 Hz, 1H), 7.87 (d, J = 0.7 Hz, 1H), 7.52 (s, J = 0.8 Hz, 1H), 4.30 (t, J = 5.2 Hz, 2H), 3.81 (s, 3H), 3.76-3.71 (m, 2H), 3.31 (s, 3H). (2 × H exchangeable) |
| 116 | 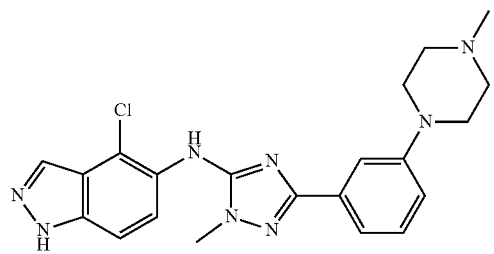 | Method B, 2.35 min, m/z 437.4 [M + H]⁺ | ¹H NMR (400 MHz, DMSO-d₆) δ 13.40 (s, 1H), 8.49 (s, 1H), 8.09 (s, 1H), 7.80-7.76 (m, 2H), 7.61-7.51 (m, 2H), 7.30 (ddd, J = 6.2, 4.4, 1.5 Hz, 2H), 3.78 (s, 3H), 3.55- 3.40 (m, 5H), 2.38 (s, 8H). |
| 117 | 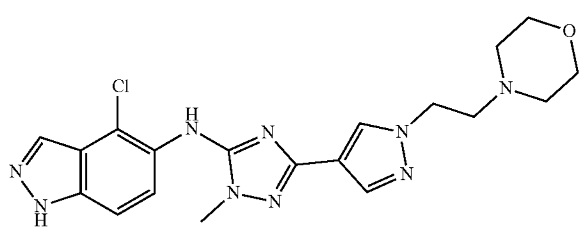 [SMILES: Cn1nc(-c2cnn(CCN3CCOCC3)c2)nc1Nc1ccc2[nH]ncc2c1Cl] | Method B, 2.20 min, m/z 428.4 [M + H]⁺ | ¹H NMR (400 MHz, DMSO-d₆): δ 13.39- 13.33 (m, 1H), 8.40 (s, 1H), 8.08 (d, J = 1.6 Hz, 1H), 8.01 (s, 1H), 7.66 (d, J = 0.7 Hz, 1H), 7.52 (s, 2H), 4.21 (t, J = 6.4 Hz, 2H), 3.72 (s, 3H), 3.51 (s, J = 4.8 Hz, 4H), 2.71 (s, 2H), 2.40 (s, 4H). |

TABLE 11-continued

| Example | Structure | LC/MS | ¹H NMR |
|---|---|---|---|
| 118 | 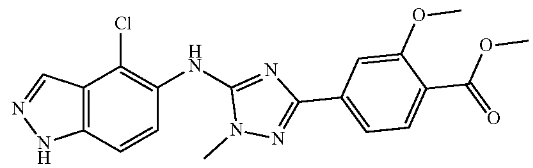 [SMILES: COC(=O)c1ccc(-c2nc(Nc3ccc4[nH]ncc4c3Cl)n(C)n2)cc1OC] | Method B, 3.36 min, m/z 413.3 [M + H]⁺ | ¹H NMR (400 MHz, DMSO-d₆): δ 13.40 (s, 1H), 8.60 (s, 1H), 8.10 (s, 1H), 7.68 (d, J = 8.0 Hz, 1H), 7.56 (d, J = 3.0 Hz, 2H), 7.52 (d, J = 1.4 Hz, 1H), 7.47 (dd, J = 8.0, 1.4 Hz, 1H), 3.84 (s, 3H), 3.81 (s, 3H), 3.77 (s, 3H). |
| 119 | 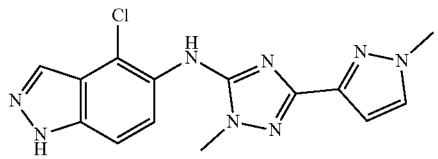 [SMILES: Cn1ccc(-c2nc(Nc3ccc4[nH]ncc4c3Cl)n(C)n2)n1] | Method B, 2.83 min, m/z 329.3 [M + H]⁺ | ¹H NMR (400 MHz, DMSO-d₆): δ 13.39 (s, 1H), 8.64 (s, 1H), 8.10 (s, 1H), 7.60-7.51 (m, 2H), 7.40 (d, J = 1.9 Hz, 1H), 6.52 (d, J = 1.9 Hz, 1H), 4.05 (s, 3H), 3.81 (s, 3H) |
| 120 | 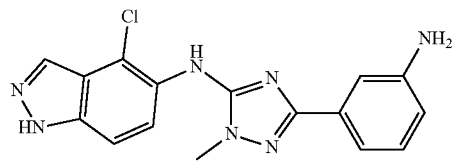 [SMILES: Cn1nc(-c2cccc(N)c2)nc1Nc1ccc2[nH]ncc2c1Cl] | Method B, 2.45 min, m/z 340.3 [M + H]⁺ | ¹H NMR (400 MHz, DMSO-d₆): δ 13.38 (s, 1H), 8.42 (s, 1H), 8.09 (s, 1H), 7.57 (d, J = 8.8 Hz, 1H), 7.56-7.51 (m, 1H), 7.12-7.08 (m, 1H), 7.03-6.96 (m, 2H), 6.54-6.48 (m, 1H), 5.10 (s, 2H), 3.76 (s, 3H) |
| 121 | 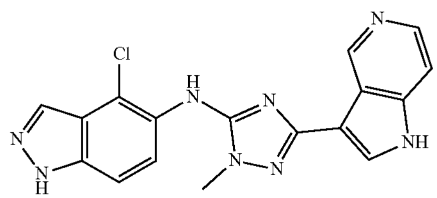 [SMILES: Cn1nc(-c2c[nH]c3ccncc23)nc1Nc1ccc2[nH]ncc2c1Cl] | Method B, 2.28 min, m/z 365.3 [M + H]⁺ | ¹H NMR (400 MHz, DMSO-d₆): δ 13.38 (s, 1H), 11.67 (s, 1H), 9.32 (s, 1H), 8.42 (s, 1H), 8.20 (d, J = 5.7 Hz, 1H), 8.10 (s, 1H), 7.75 (d, J = 2.3 Hz, 1H), 7.63 (d, J = 8.9 Hz, 1H), 7.58-7.52 (m, 1H), 7.38 (dd, J = 5.7, 1.0 Hz, 1H), 3.81 (s, 3H) |
| 122 | 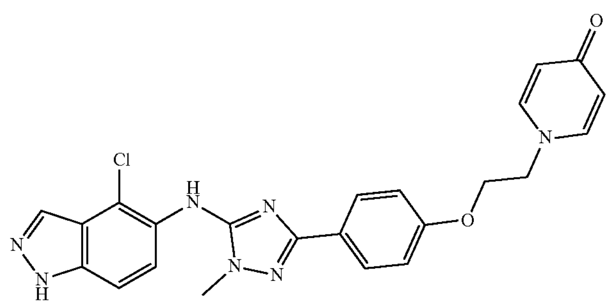 [SMILES: Cn1nc(-c2ccc(OCCn3ccc(=O)cc3)cc2)nc1Nc1ccc2[nH]ncc2c1Cl] | Method B, 2.68 min, m/z 462.4 [M + H]⁺ | ¹H NMR (400 MHz, CD₃OD): δ 8.10 (s, 1H), 7.93-7.89 (m, 2H), 7.87-7.81 (m, 2H), 7.62-7.49 (m, 2H), 6.97-6.92 (m, 2H), 6.49-6.44 (m, 2H), 4.38 (dd, J = 5.4, 4.0 Hz, 2H), 4.33 (dd, J = 5.5, 4.1 Hz, 2H), 3.82 (s, 3H). (2 × H exchangeable) |

TABLE 11-continued

| Example | Structure | LC/MS | ¹H NMR |
|---|---|---|---|
| 123 | 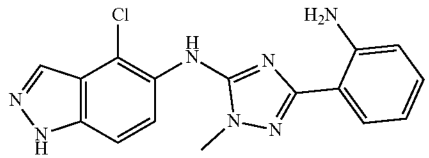 [SMILES: Cn1nc(-c2ccccc2N)nc1Nc1ccc2[nH]ncc2c1Cl] | Method B, 3.07 min, m/z 340.3 [M + H]⁺ | ¹H NMR (400 MHz, CD₃OD): δ 8.10 (s, 1H), 7.81 (dd, J = 7.9, 1.6 Hz, 1H), 7.65 (d, J = 8.9 Hz, 1H), 7.52 (dd, J = 8.9, 1.0 Hz, 1H), 7.10 (ddd, J = 8.6, 7.2, 1.6 Hz, 1H), 6.79 (dd, J = 8.2, 1.2 Hz, 1H), 6.66 (ddd, J = 8.2, 7.1, 1.2 Hz, 1H), 3.85 (s, 3H). (4 × H exchangeable) |
| 124 | 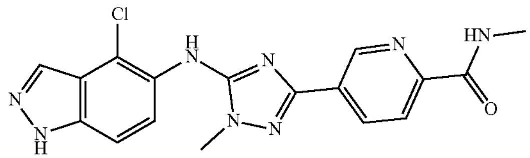 [SMILES: CNC(=O)c1ccc(-c2nc(Nc3ccc4[nH]ncc4c3Cl)n(C)n2)cn1] | Method B, 2.89 min, m/z 383.3 [M + H]⁺ | ¹H NMR (400 MHz, DMSO-d₆): δ 13.41 (s, 1H), 9.01 (dd, J = 2.1, 0.9 Hz, 1H), 8.80 (d, J = 5.1 Hz, 1H), 8.69 (s, 1H), 8.29 (dd, J = 8.2, 2.1 Hz, 1H), 8.11 (s, 1H), 8.04 (dd, J = 8.2, 0.8 Hz, 1H), 7.57 (d, J = 3.8 Hz, 2H), 3.83 (s, 3H), 2.81 (d, J = 4.8 Hz, 3H) |
| 125 | 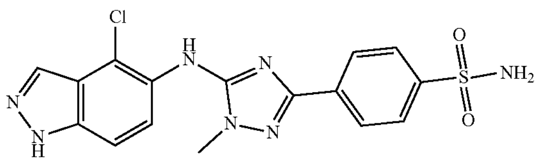 [SMILES: Cn1nc(-c2ccc(S(N)(=O)=O)cc2)nc1Nc1ccc2[nH]ncc2c1Cl] | Method B, 2.84 min, m/z 404.2 [M + H]⁺ | ¹H NMR (400 MHz, DMSO-d₆): δ 13.40 (s, 1H), 8.62 (s, 1H), 8.10 (s, 1H), 8.01-7.94 (m, 2H), 7.86-7.79 (m, 2H), 7.61-7.53 (m, 2H), 7.38 (s, 2H), 3.82 (s, 3H). |
| 126 | 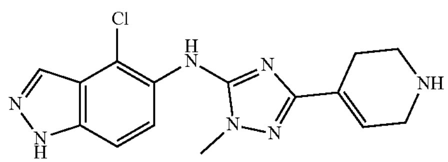 [SMILES: Cn1nc(C2=CCNCC2)nc1Nc1ccc2[nH]ncc2c1Cl] | Method B, 2.07 min, m/z 330.3 [M + H]⁺ | ¹H NMR (400 MHz, DMSO-d₆): δ 13.37 (brs, 1H), 8.33 (s, 1H), 8.07 (s, 1H), 7.56-7.49 (m, 2H), 6.39-6.34 (m, 1H), 3.69 (s, 3H), 3.31-3.27 (m, 2H), 2.83 (dd, J = 5.6, 5.6 Hz, 2H), 2.32-2.45 (m, 2H). 1 × H proton exchangeable. |
| 127 | 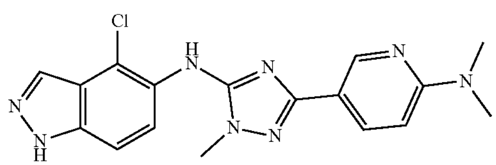 [SMILES: CN(C)c1ccc(-c2nc(Nc3ccc4[nH]ncc4c3Cl)n(C)n2)cn1] | Method B, 2.36 min, m/z 369.3 [M + H]⁺ | ¹H NMR (400 MHz, DMSO-d₆): δ 13.37 (s, 1H), 8.53 (d, J = 3.0 Hz, 1H), 8.43 (s, 1H), 8.08 (t, J = 1.3 Hz, 1H), 7.86 (dd, J = 8.9, 2.4 Hz, 1H), 7.62-7.49 (m, 2H), 6.63 (d, J = 8.9 Hz, 1H), 3.74 (s, 3H), 3.03 (s, 6H). |
| 128 | 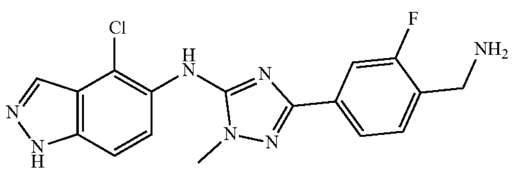 [SMILES: Cn1nc(-c2ccc(CN)c(F)c2)nc1Nc1ccc2[nH]ncc2c1Cl] | Method B, 2.38 min, m/z 372.3 [M + H]⁺ | ¹H NMR (400 MHz, DMSO-d₆): δ 8.58 (s, 1H), 8.30 (s, 1H), 8.10 (s, 1H), 7.65 (dd, J = 8.0, 1.6 Hz, 1H), 7.61-7.47 (m, 4H), 3.85 (s, 2H), 3.79 (s, 3H). NH2 protons exchangeable |

TABLE 11-continued

| Example | Structure | LC/MS | ¹H NMR |
|---|---|---|---|
| 129 | 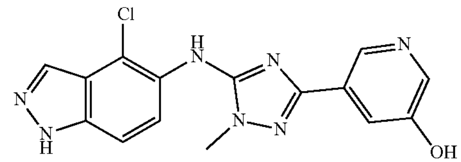 [SMILES: Cn1nc(-c2cncc(O)c2)nc1Nc1ccc2[nH]ncc2c1Cl] | Method B, 2.35 min, m/z 342.3 [M + H]⁺ | ¹H NMR (400 MHz, DMSO-d₆): δ 13.39 (s, 1H), 9.99 (s, 1H), 8.59 (s, 1H), 8.48 (d, J = 1.8 Hz, 1H), 8.12-8.05 (m, 2H), 7.18-7.05 (m, 3H), 3.79 (s, 3H). |
| 130 | 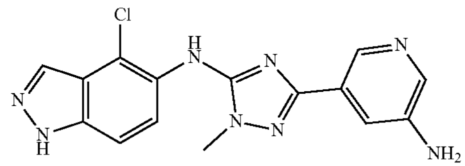 | Method B, 2.24 min, m/z 341.3 [M + H]⁺ | ¹H NMR (400 MHz, DMSO-d₆): δ 13.39 (s, 1H), 8.54 (s, 1H), 8.20 (d, J = 1.85 Hz, 1H), 8.12-8.09 (m, 1H), 7.87 (d, J = 2.851H), 7.58- 7.52 (m, 2H), 7.36-7.31 (m, 1H), 5.39 (brs, 2H), 3.79 (s, 3H) |
| 131 | 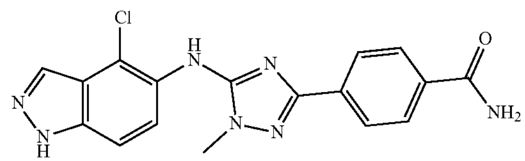 [SMILES: Cn1nc(-c2ccc(C(N)=O)cc2)nc1Nc1ccc2[nH]ncc2c1Cl] | Method B, 2.70 min, m/z 368.3 [M + H]⁺ | ¹H NMR (400 MHz, DMSO-d₆): δ 13.40 (s, 1H), 8.57 (s, 1H), 8.10 (s, 1H), 7.99 (s, 1H), 7.88 (m, 4H), 7.64-7.52 (m, 2H), 7.37 (s, 1H), 3.81 (s, 3H) |
| 132 | 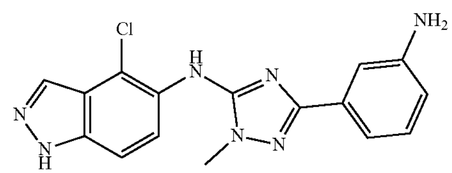 | Method B, 2.35 min, m/z 342.3 [M + H]⁺ | ¹H NMR (400 MHz, DMSO-d₆): δ 13.38 (s, 1H), 8.43 (s, 1H), 8.09 (s, 1H), 7.59-7.01 (m, 1H), 7.11-7.08 (m, 1H), 7.03-6.97 (m, 2H), 6.53-6.48 (m, 2H), 5.14 (bs, 2H), 3.76 (s, 3H) |
| 133 | 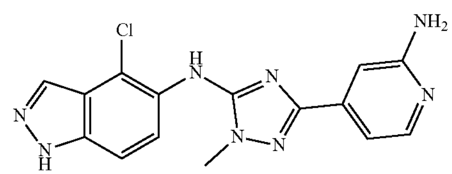 [SMILES: Cn1nc(-c2ccnc(N)c2)nc1Nc1ccc2[nH]ncc2c1Cl] | Method A, 1.09 min, m/z 342.3 [M + H]⁺ | ¹H NMR (400 MHz, DMSO-d₆): δ 13.40 (s, 1H), 8.62 (s, 1H), 8.12-8.09 (m, 1H), 7.88 (d, J = 5.41 Hz, 1H), 7.54 (m, 2H), 6.96-6.91 (m, 2H), 6.26 (br.s, 2H), 3.81 (s, 3H) |
| 134 | 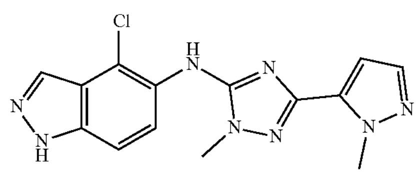 [SMILES: Cn1nccc1-c1nc(Nc2ccc3[nH]ncc3c2Cl)n(C)n1] | Method A, 1.29 min, m/z 329.3 [M + H]⁺ | ¹H NMR (400 MHz, DMSO-d₆): δ 13.40 (s, 1H), 8.65 (s, 1H), 8.11-8.07 (m, 1H), 7.58-7.51 (m, 2H), 7.40 (d, J = 2.0 Hz, 1H), 6.51 (d, J = 2.0 Hz, 1H), 4.05 (s, 3H), 3.80 (s, 3H) |

TABLE 11-continued

| Example | Structure | LC/MS | ¹H NMR |
|---|---|---|---|
| 135 | 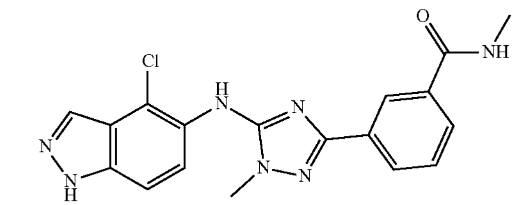 [SMILES: CNC(=O)c1cccc(-c2nc(Nc3ccc4[nH]ncc4c3Cl)n(C)n2)c1] | Method A, 1.28 min, m/z 382.3 [M + H]⁺ | ¹H NMR (400 MHz, DMSO-d₆): δ 13.41 (s, 1H), 8.56 (s, 1H), 8.55-8.49 (m, 1H), 8.31-8.27 (m, 1H), 8.11-8.07 (m, 1H), 7.99-7.92 (m, 1H), 7.82-7.52 (m, 1H), 7.60 (d, J = 8.8 Hz, 1H), 7.57-7.54 (m, 1H), 7.47 (t, J = 7.66 Hz, 1H) 3.81 (s, 3H) 3.17 (d, J = 5.1 Hz, 3H) |
| 136 | 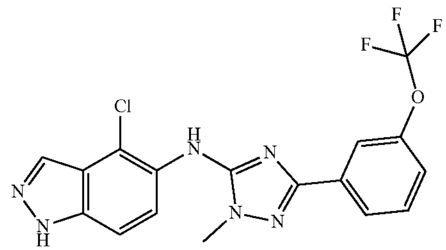 [SMILES: Cn1nc(-c2cccc(OC(F)(F)F)c2)nc1Nc1ccc2[nH]ncc2c1Cl] | Method B, 4.15 min, m/z 409.2 [M + H]⁺ | ¹H NMR (400 MHz, DMSO-d₆) δ 13.41 (s, 1H), 8.62 (s, 1H), 8.12-8.09 (m, 1H), 7.85 (dt, J = 7.8, 1.3 Hz, 1H), 7.71-7.68 (m, 1H), 7.66-7.50 (m, 3H), 7.39-7.34 (m, 1H), 3.81 (s, 3H). |
| 137 | 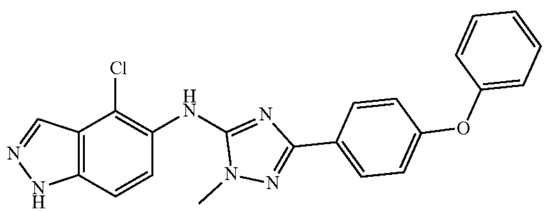 [SMILES: Cn1nc(-c2ccc(Oc3ccccc3)cc2)nc1Nc1ccc2[nH]ncc2c1Cl] | Method B, 4.21 min, m/z 417.3 [M + H]⁺ | ¹H NMR (400 MHz, DMSO-d₆) δ 13.40-13.35 (m, 1H), 8.50 (s, 1H), 8.09 (t, J = 1.2 Hz, 1H), 7.89-7.80 (m, 2H), 7.63-7.50 (m, 2H), 7.49-7.36 (m, 2H), 7.24-7.10 (m, 1H), 7.09-6.94 (m, 4H), 3.78 (s, 3H) |
| 138 | 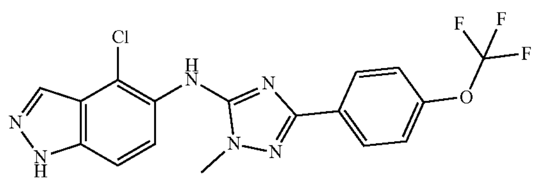 [SMILES: Cn1nc(-c2ccc(OC(F)(F)F)cc2)nc1Nc1ccc2[nH]ncc2c1Cl] | Method B, 4.13 min, m/z 409.2 [M + H]⁺ | ¹H NMR (400 MHz, DMSO-d₆) δ 13.40 (s, 1H), 8.59 (s, 1H), 8.10 (s, 1H), 7.98-7.89 (m, 2H), 7.57 (q, J = 8.9 Hz, 2H), 7.42-7.31 (m, 2H), 3.80 (s, 3H). |

TABLE 11-continued

| Example | Structure | LC/MS | ¹H NMR |
|---|---|---|---|
| 139 | 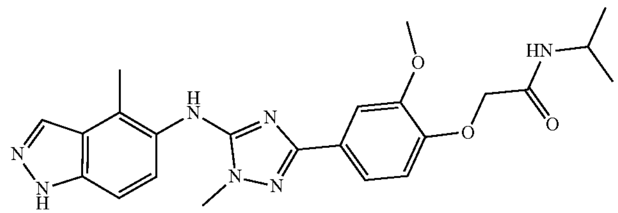 [SMILES: COc1cc(-c2nc(Nc3ccc4[nH]ncc4c3C)n(C)n2)ccc1OCC(=O)NC(C)C] | Method B, 2.96 min, m/z 450.4 [M + H]⁺ | ¹H NMR (400 MHz, DMSO-d₆): δ 13.02 (brs, 1H), 8.40 (brs, 2H), 8.24 (s, 1H), 8.11 (s, 1H), 7.75 (d, J = 7.8 Hz, 1H), 7.38-7.29 (m, 3H), 6.89 (d, J = 8.4 Hz, 1H), 4.42 (s, 2H), 3.97-3.85 (m, 1H), 3.79 (s, 3H), 3.72 (s, 3H), 2.44 (s, 3H), 1.07 (d, J = 6.6 Hz, 6H). |
| 140 | 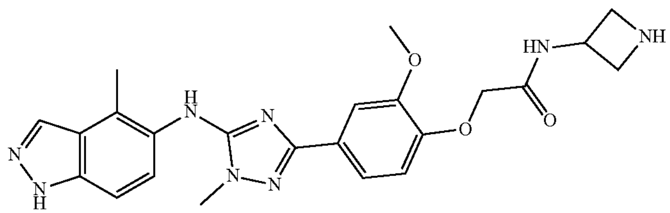 [SMILES: COc1cc(-c2nc(Nc3ccc4[nH]ncc4c3C)n(C)n2)ccc1OCC(=O)NC1CNC1] | Method B, 2.30 min, m/z 463.4 [M + H]⁺ | ¹H NMR (400 MHz, DMSO-d₆): δ 12.99 (br s, 1H), 8.72 (d, J = 7.3 Hz, 1H), 8.26 (br s, 1H), 8.23 (s, 1H), 8.12 (s, 1H), 7.39-7.29 (m, 4H), 6.90 (d, J = 8.4 Hz, 1H), 4.65 (sex tet, J = 7.4 Hz, 1H), 4.49 (s, 2H), 3.98 (t, J = 8.9 Hz, 2H), 3.88 (t, J = 8.7 Hz, 2H), 3.80 (s, 3H), 3.72 (s, 3H), 2.44 (s, 3H), 1H exchangeable |
| 141 | 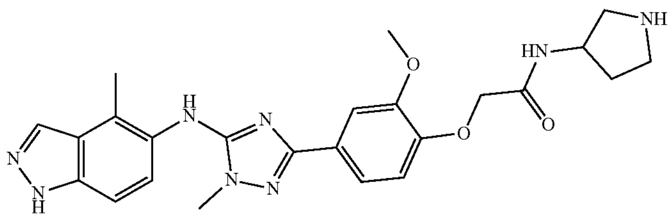 [SMILES: COc1cc(-c2nc(Nc3ccc4[nH]ncc4c3C)n(C)n2)ccc1OCC(=O)NC1CCNC1] | Method B, 2.34 min, m/z 477.4 [M + H]⁺ | ¹H NMR (400 MHz, DMSO-d₆): δ 3.01 (s, 1H), 8.23 (s, 1H), 8.12 (s, 1H), 7.95 (d, J = 7.5 Hz, 1H), 7.40-7.28 (m, 4H), 6.88 (d, J = 8.4 Hz, 1H), 4.44 (s, 2H), 4.18-4.09 (m, 1H), 3.79 (s, 3H), 3.72 (s, 3H), 2.85 (ddd, J = 24.7, 9.6, 6.3 Hz, 2H), 2.74-2.69 (m, 1H), 2.45 (s, 3H), 1.93-1.85 (m, 1H), 1.52-1.43 (m, 1H). 1 pyrrolidine proton under DMSO peak. 1H exchangeable. |
| 142 | 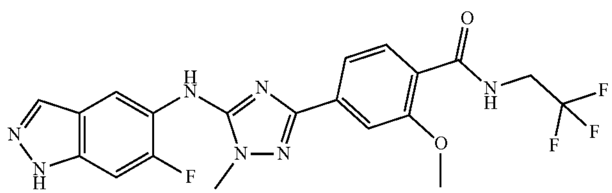 [SMILES: COc1cc(-c2nc(Nc3cc4cn[nH]c4cc3F)n(C)n2)ccc1C(=O)NCC(F)(F)F] | Method B, 3.43 min, m/z 464.3 [M + H]⁺ | ¹H NMR (400 MHz, DMSO-d₆) δ ppm: 13.08 (1H, s), 8.69 (1H, t, J = 6.4Hz), 8.62 (1H, s), 8.12-8.07 (2H, m), 7.80 (1H, d, J = 8.0Hz), 7.60-7.56 (2H, m), 7.46 (1H, d, J = 11.2Hz), 4.11 (2H, qd, J = 6.4Hz, 10.0Hz), 3.95 (3H, s), 3.83 (3H, s). |
| 143 | 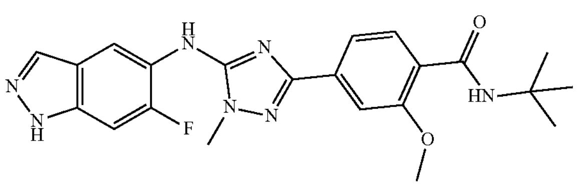 | Method B, 3.64 min, m/z 438.4 [M + H]⁺ | ¹H NMR (400 MHz, DMSO-d₆) δ ppm: 13.07 (1H, s), 8.61 (1H, s), 8.12-8.08 (2H, m), 7.86 (1H, s), 7.79 (1H, d, J = 8.8Hz), 7.58-7.49 (2H, m), 7.46 (1H, d, J = 10.8Hz), 3.95 (3H, S), 3.82 (3H, s), 1.38 (9H, s) |

TABLE 11-continued

| Example | Structure | LC/MS | ¹H NMR |
|---|---|---|---|
| 144 | 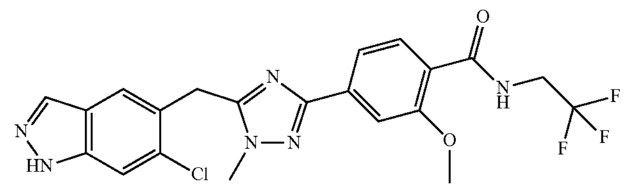 [SMILES: COc1cc(-c2nc(Cc3cc4cn[nH]c4cc3Cl)n(C)n2)ccc1C(=O)NCC(F)(F)F] | Method B, 3.57 min, m/z 480.2 [M + H]⁺ | ¹H NMR (400 MHz, DMSO-d₆) δ ppm: 13.15 (1H, s), 8.68 (1H, t, J = 6.4Hz), 8.47 (1H, s), 8.11 (1H, s), 8.02 (1H, s), 7.80-7.76 (2H, m), 7.56-7.52 (2H, m), 4.16-4.06 (2H, m), 3.93 (3H, s), 3.81 (3H, s). |
| 145 | 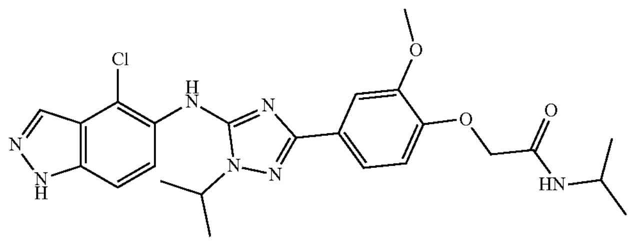 [SMILES: COc1cc(-c2nc(Nc3ccc4[nH]ncc4c3Cl)n(C(C)C)n2)ccc1OCC(=O)NC(C)C] | Method B, 3.66 min, m/z 498.5 [M + H]⁺ | ¹H NMR (400 MHz, DMSO-d₆) δ 13.37 (s, 1H), 8.38 (s, 1H), 8.08 (s, 1H), 7.75 (d, J = 7.9 Hz, 1H), 7.51 (q, J = 8.9 Hz, 2H), 7.43-7.33 (m, 2H), 6.93 (d, J = 8.4 Hz, 1H), 4.72 (p, J = 6.5 Hz, 1H), 4.44 (s, 2H), 3.91 (dq, J = 13.7, 6.8 Hz, 1H), 3.82 (s, 3H), 1.45 (d, J = 6.5 Hz, 6H), 1.08 (d, J = 6.6 Hz, 6H). |
| 146 | 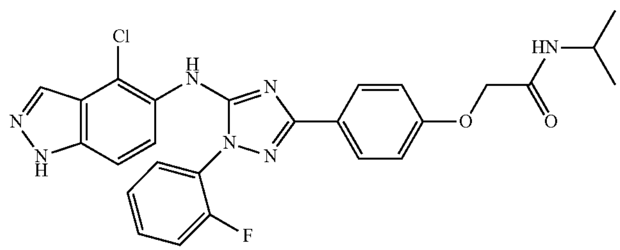 | Method E, 7.19 min, m/z 485.9 [M + H]⁺ | ¹H NMR (400 MHz, DMSO-d₆): δ 12.91 (s, 1H), 8.96 (s, 1H), 8.19 (d, J = 2.0 Hz, 1H), 8.02 (s, 1H), 7.96 (d, J = 9.0 Hz, 2H), 7.92 (d, J = 8.0 Hz, 1H), 7.71 (td, J = 8.0, 1.5 Hz, 1H), 7.66-7.58 (m, 1H), 7.58-7.38 (m, 4H), 7.06 (d, J = 9.0 Hz, 2H), 4.50 (s, 2H), 3.96 (dp, J = 8.0, 6.5 Hz, 1H), 1.10 (d, J = 6.5 Hz, 6H). |
| 147 | 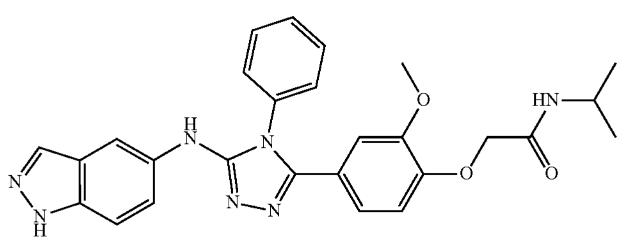 [SMILES: COc1cc(-c2nnc(Nc3ccc4[nH]ncc4c3)n2-c2ccccc2)ccc1OCC(=O)NC(C)C] | Method B, 4.08 min, m/z 499.4 [M + H]⁺ | ¹H NMR (400 MHz, DMSO-d₆) δ 13.02 (s, 1H), 11.09 (s, 1H), 8.64 (m, Hz, 1H), 8.44 (d, J = 1.3 Hz, 1H), 8.14-8.07 (m, 2H), 8.01 (dt, J = 8.4, 1.0 Hz, 1H), 7.82 (d, J = 7.8 Hz, 1H), 7.75-7.65 (m, 3H), 7.58 (d, J = 8.8 Hz, 1H), 7.42 (m, Hz, 1H), 7.06 (d, J = 8.9 Hz, 1H), 4.52 (s, 2H), 3.98-3.89 (m, 1H), 3.93 (3, 3H), 1.11 (d, J = 6.6 Hz, 6H). |

TABLE 11-continued

| Example | Structure | LC/MS | ¹H NMR |
|---|---|---|---|
| 148 | 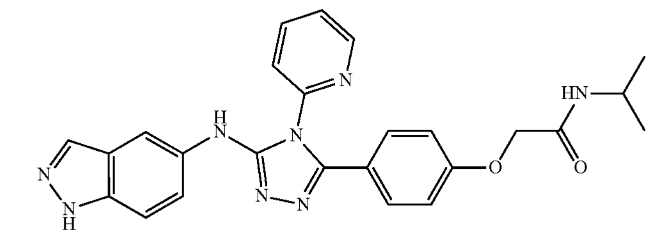 [SMILES: CC(C)NC(=O)COc1ccc(-c2nnc(Nc3ccc4[nH]ncc4c3)n2-c2ccccn2)cc1] | Method B, 4.13 min, m/z 469.3 [M + H]⁺ | ¹H NMR (400 MHz, DMSO-d₆) δ 13.02 (s, 1H), 11.10 (s, 1H), 8.64 (dd, J = 5.0, 1.0 Hz, 1H), 8.45 (d, J = 1.9 Hz, 1H), 8.15-8.06 (m, 4H), 8.01-7.92 (m, 2H), 7.69 (dd, J = 8.9, 2.0 Hz, 1H), 7.58 (d, J = 8.9 Hz, 1H), 7.41 (m, 1H), 7.15-7.08 (m, 2H), 4.53 (s, 2H), 3.97 (m, 1H), 1.11 (d, J = 6.6 Hz, 6H). |
| 149 | 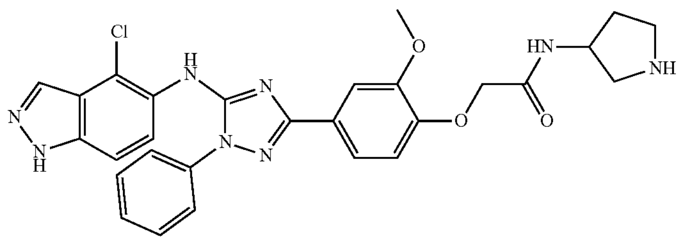 [SMILES: COc1cc(-c2nc(Nc3ccc4[nH]ncc4c3Cl)n(-c3ccccc3)n2)ccc1OCC(=O)NC1CCNC1] | Method B, 3.06 min, m/z 559.5 [M + H]⁺ | ¹H NMR (400 MHz, DMSO-d₆): δ 13.38 (s, 1H), 8.62 (s, 1H), 8.27 (d, J = 21.3 Hz, 2H), 8.07 (d, J = 0.9 Hz, 1H), 7.74-7.70 (m, 2H), 7.60-7.54 (m, 3H), 7.52-7.46 (m, 2H), 7.45-7.39 (m, 2H), 6.94 (d, J = 8.4 Hz, 1H), 4.50 (d, J = 2.0 Hz, 2H), 4.31 (s, 1H), 3.82 (s, 3H), 3.03 (s, 2H), 2.87 (d, J = 11.5 Hz, 1H), 2.07 (dt, J = 13.7, 6.9 Hz, 2H), 1.73 (m, 1H). |
| 150 | 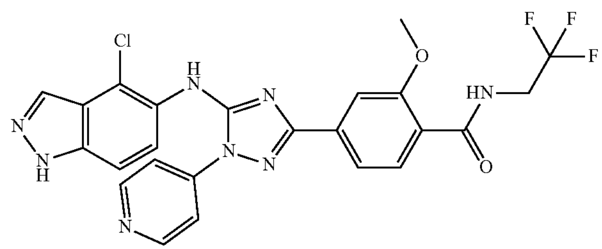 [SMILES: COc1cc(-c2nc(Nc3ccc4[nH]ncc4c3Cl)n(-c3ccncc3)n2)ccc1C(=O)NCC(F)(F)F] | Method B, 3.41 min, m/z 543.2 [M + H]⁺ | ¹H NMR (400 MHz, DMSO-d₆) δ 13.40 (s, 1H), 9.14 (s, 1H), 8.73 (d, J = 6.8 Hz, 3H), 8.11 (s, 1H), 7.90 (s, 2H), 7.81 (d, J = 8.0 Hz, 1H), 7.68-7.51 (m, 4H), 4.12 (qd, J = 9.7, 6.4 Hz, 2H), 3.95 (s, 3H). |
| 151 | 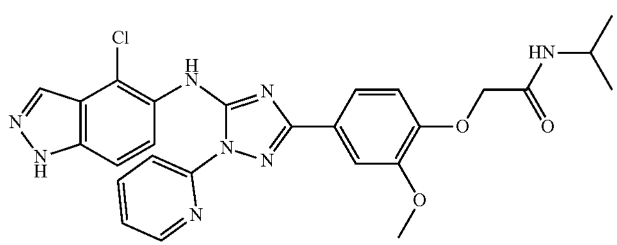 [SMILES: COc1cc(-c2nc(Nc3ccc4[nH]ncc4c3Cl)n(-c3ccccn3)n2)ccc1OCC(=O)NC(C)C] | Method B, 4.61 min, m/z 533.3 [M + H]⁺ | ¹H NMR (400 MHz, DMSO-d₆) δ 13.41 (s, 1H), 11.74 (s, 1H), 8.85 (d, J = 9.0 Hz, 1H), 8.67 (dd, J = 4.9, 1.6 Hz, 1H), 8.16-8.11 (m, 2H), 8.05 (d, J = 8.3 Hz, 1H), 7.82 (d, J = 7.8 Hz, 1H), 7.70 (dd, J = 7.8, 2.8 Hz, 3H), 7.45 (dd, J = 7.3, 5.0 Hz, 1H), 7.06 (d, J = 8.7 Hz, 1H), 4.53 (s, 2H), 4.01-3.88 (m, 1H), 3.94 (s, 3H), 1.12 (d, J = 6.5 Hz, 6H). |

TABLE 11-continued

| Example | Structure | LC/MS | ¹H NMR |
|---|---|---|---|
| 152 | 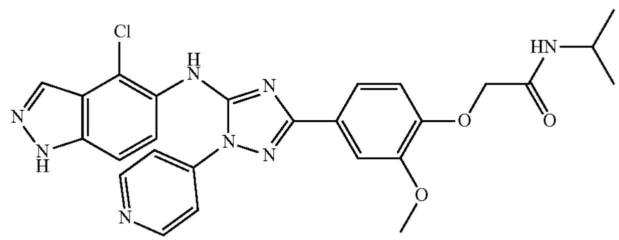 [SMILES: COc1cc(-c2nc(Nc3ccc4[nH]ncc4c3Cl)n(-c3ccncc3)n2)ccc1OCC(=O)NC(C)C] | Method B, 3.08 min, m/z 533.3 [M + H]⁺ | ¹H NMR (400 MHz, CDCl₃) δ 10.49 (s, 1H), 8.87-8.81 (m 2H), 8.47 (d, J = 9.0 Hz, 1H), 8.16-8.03 (m, 1H), 7.81-7.68 (m, 3H), 7.51 (dd, J = 9.0, 1.0 Hz, 1H), 7.21 (s, 1H), 6.98 (d, J = 8.4 Hz, 1H), 6.83 (d, J = 7.8 Hz, 1H), 4.57 (s, 2H), 4.25-4.07 (m, 1H), 4.00 (s, 3H), 1.20 (d, J = 6.6 Hz, 6H). |
| 153 | 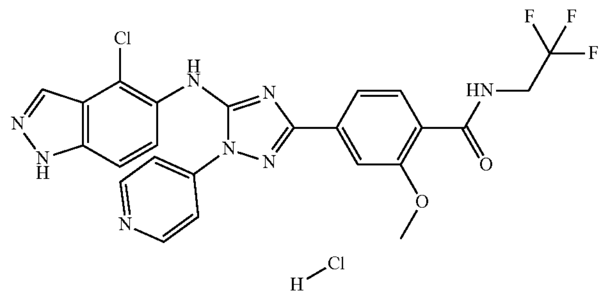 [SMILES: COc1cc(-c2nc(Nc3ccc4[nH]ncc4c3Cl)n(-c3ccncc3)n2)ccc1C(=O)NCC(F)(F)F ; Cl] | Method B, 4.86 min, m/z 543.2 [M + H]⁺ | ¹H NMR (400 MHz, DMSO-d₆) δ 13.44 (s, 1H), 11.76 (s, 1H), 8.86-8.73 (m, 2H), 8.70 (dd, J = 5.0, 1.8 Hz, 1H), 8.23-8.12 (m, 2H), 8.09 (d, J = 8.3 Hz, 1H), 7.94-7.81 (m, 3H), 7.71 (d, J = 9.0 Hz, 1H), 7.49 (ddd, J = 7.3, 5.0, 1.1 Hz, 1H), 4.15 (qd, J = 9.7, 6.4 Hz, 2H), 4.05 (s, 3H). |

General Method D:

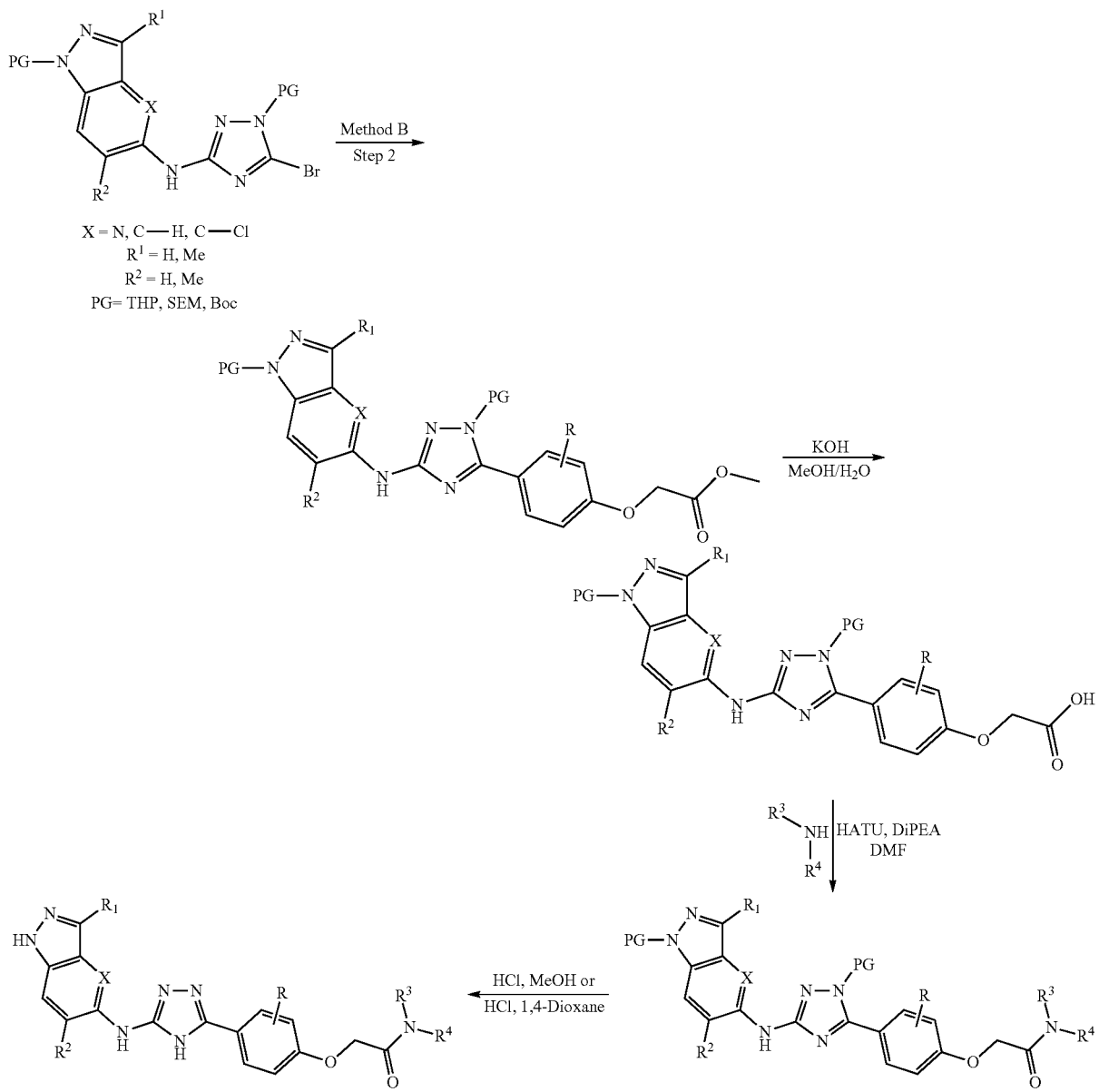

A method for preparing a compound of the invention is given below. Further compounds that can be prepared in a similar manner using intermediates 1, 2 and 39 and general method D are given in Table 12.

Example 154: 2-[4-(5-(1H-indazol-5-ylamino)-4H-1,2,4-triazol-3-yl]phenoxy]-1-morpholinoethanone

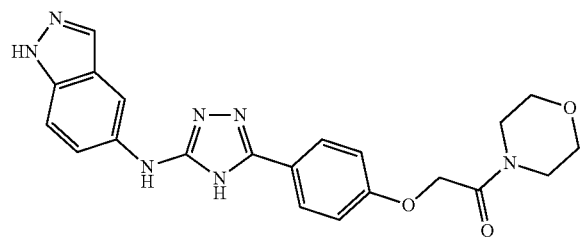 [SMILES: O=C(COc1ccc(-c2nnc(Nc3ccc4[nH]ncc4c3)[nH]2)cc1)N1CCOCC1]

A solution of 1-morpholino-2-[4-[2-tetrahydropyran-2-yl-5-[(1-tetrahydropyran-2-ylindazol-5-yl)amino]-1,2,4-triazol-3-yl]phenoxy]ethanone (44 mg, 0.07 mmol) in hydrochloric acid (1.25 M in MeOH, 3.0 mL, 3.75 mmol) was stirred at r.t. under $N_2$ overnight. The solvents were removed under reduced pressure and the residual solid purified by preparative HPLC giving 2-[4-[5-(1H-indazol-5-ylamino)-4H-1,2,4-triazol-3-yl]phenoxy]-1-morpholinoethanone (15 mg, 0.03 mmol, 45% yield) as a white solid. LC-MS (ES+, Method E): 5.22 min, m/z 420.1 [M+H]+. $^1$H NMR (500 MHz, DMSO-$d_6$): δ 13.36 (s, 1H), 12.80 (s, 1H), 9.17 (s, 1H), 8.10 (s, 1H), 7.94 (s, 1H), 7.89 (d, J=9.0 Hz, 2H), 7.41 (d, J=1.5 Hz, 2H), 7.06 (d, J=8.5 Hz, 2H), 4.92 (s, 2H), 3.63 (t, J=5.0 Hz, 2H), 3.58 (t, J=5.0 Hz, 2H), 3.50-3.44 (m, 4H).

Step 1: Methyl 2-[4-[2-tetrahydropyran-2-yl-5-[(1-tetrahydropyran-2-ylindazol-5-yl)amino]-1,2,4-triazol-3-yl]phenoxy]acetate

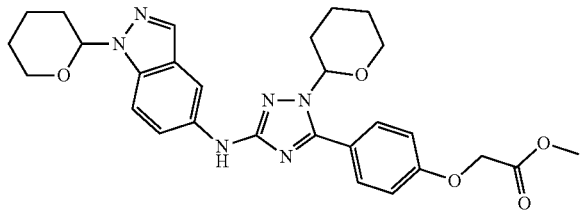 [SMILES: COC(=O)COc1ccc(-c2nc(Nc3ccc4c(cnn4C4CCCCO4)c3)nn2C2CCCCO2)cc1]

A vial was charged with N-(5-bromo-1-tetrahydropyran-2-yl-1,2,4-triazol-3-yl)-1-tetrahydropyran-2-yl-indazol-5-amine (134 mg, 0.30 mmol), [4(2-methoxy-2-oxoethoxy)phenyl]boronic acid (95 mg, 0.45 mmol) and potassium carbonate (124 mg, 0.90 mmol). 1,4-Dioxane (2.0 mL) and water (0.40 mL) were added and the solution degassed with $N_2$ for 10 min. Pd(dppf)Cl$_2$·DCM complex (25 mg, 0.03 mmol) was added, the vial sealed and the reaction heated at 80° C. for 18 h. The mixture was diluted with EtOAc (15 mL) and water (15 mL) and the layers separated. The aqueous layer was extracted with EtOAc (2×15 mL) and the combined organics dried (phase separator) and concentrated. The crude product was purified by flash column chromatography (SiO$_2$, eluting with 30-60% EtOAc in Pet. Ether) giving methyl 2-[4-[2-tetrahydropyran-2-yl-5-[(1-tetrahydropyran-2-ylindazol-5-yl)amino]-1,2,4-triazol-3-yl]phenoxy]acetate (80 mg, 0.15 mmol, 50% yield) as a yellow foamy solid. LC-MS (ES$^+$, Method C): 3.37 min, m/z 533.2 [M+H]$^+$ Step 2: 2-[4-[2-Tetrahydropyran-2-yl-5-[(1-tetrahydropyran-2-ylindazol-5-yl)amino]-1,2,4-triazol-3-yl]phenoxy]acetic acid

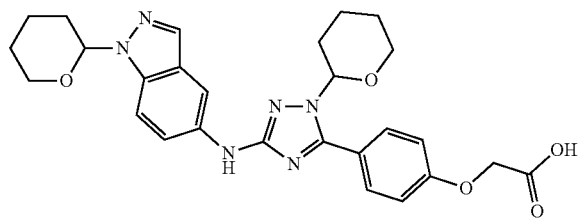 [SMILES: O=C(O)COc1ccc(-c2nc(Nc3ccc4c(cnn4C4CCCCO4)c3)nn2C2CCCCO2)cc1]

A solution of methyl 2-[4-[2-tetrahydropyran-2-yl-5-[(1-tetrahydropyran-2-ylindazol-5-yl)amino]-1,2,4-triazol-3-yl]phenoxy]acetate (80 mg, 0.15 mmol) and potassium hydroxide (25 mg, 0.45 mmol) in methanol (2.4 mL) and water (0.6 mL) was stirred at r.t. under $N_2$ overnight. The methanol was removed under reduced pressure and the residual aqueous mixture acidified to pH=4 by the addition of 5% aq. KHSO$_4$ solution. The mixture was extracted with EtOAc (3×15 mL) and the combined organics washed with brine (15 mL), dried (phase separator) and concentrated. The crude material was purified by flash column chromatography (SiO$_2$, eluting with 5-20% MeOH in DCM) giving 2-[4-[2-tetrahydropyran-2-yl-5-[(1-tetrahydropyran-2-ylindazol-5-yl)amino]-1,2,4-triazol-3-yl]phenoxy]acetic acid (71 mg, 0.14 mmol, 91% yield) as a white solid. LC-MS (ES$^+$, Method C): 2.85 min, m/z 519.3 [M+H]$^+$.

Step 3: 1-Morpholino-2-[4-[2-tetrahydropyran-2-yl-5-[(1-tetrahydropyran-2-ylindazol-5-yl)amino]-1,2,4-triazol-3-yl]phenoxy]ethanone

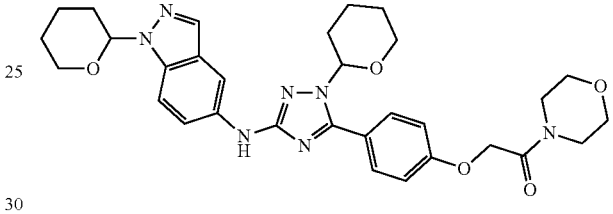

To a stirred solution of 2-[4-[2-tetrahydropyran-2-yl-5-[(1-tetrahydropyran-2-ylindazol-5-yl)amino]-1,2,4-triazol-3-yl]phenoxy]acetic acid (71 mg, 0.14 mmol) and HATU (68 mg, 0.18 mmol) in anhydrous DMF (2 mL) at r.t. under $N_2$ was added DIPEA (48 μL, 0.27 mmol) and morpholine (18 μL, 0.21 mmol) and the reaction stirred at r.t. overnight. The solvents were removed under reduced pressure and the residue taken with EtOAc (20 mL) and washed with 5% aq. KHSO$_4$ soln. (2×10 mL) and brine (10 mL). The organics were dried (phase separator) and concentrated. The crude product was purified by flash column chromatography (SiO$_2$, eluting with 0-10% MeOH in DCM) giving 1-morpholino-2-[4-[2-tetrahydropyran-2-yl-5-[(1-tetrahydropyran-2-ylindazol-5-yl)amino]-1,2,4-triazol-3-yl]phenoxy]ethanone (44 mg, 0.07 mmol, 55% yield) as a yellow oily solid. LC-MS (ES$^+$, Method C): 2.88 min, m/z 588.3 [M+H]$^+$ Compounds prepared in a similar manner to that set out above are given below in Table 12. "EX" in Table 12 signifies "Example"

TABLE 12

| Ex | Structure | LC/MS | ¹H NMR |
|---|---|---|---|
| 155 | 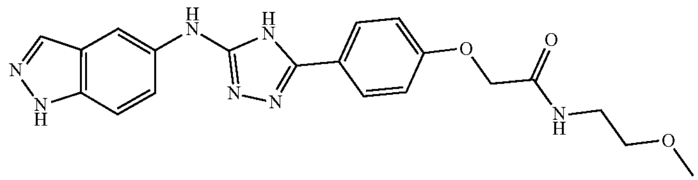 | Method E, 5.20 min, m/z 408.1 [M + H]⁺ | ¹H NMR (500 MHz, DMSO-d₆): δ 13.45 (s, 1H), 12.80 (s, 1H), 9.15 (s, 1H), 8.17 (t, J = 5.5 Hz, 1H), 8.10 (s, 1H), 8.00-7.86 (m, 3H), 7.42 (s, 2H), 7.09 (d, J = 8.5 Hz, 2H), 4.56 (s, 2H), 3.41-3.36 (m, 2H), 3.35-3.27 (m, 2H), 3.25 (s, 3H). |
| 156 | 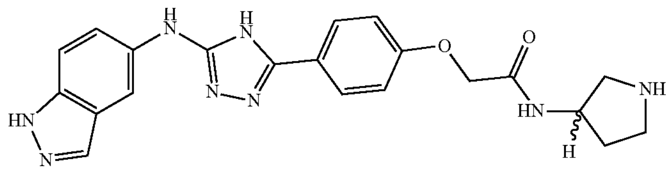 [SMILES: O=C(COc1ccc(-c2nnc(Nc3ccc4[nH]ncc4c3)[nH]2)cc1)NC1CCNC1] | Method E, 4.38 min, m/z 419.2 [M + H]⁺ | ¹H NMR (500 MHz, DMSO-d₆): 12.82 (s, 1H), 9.24 (s, 1H), 8.15-8.06 (m, 2H), 7.95 (s, 1H), 7.92 (d, J = 8.5 Hz, 2H), 7.43 (s, 2H), 7.09 (d, J = 8.5 Hz, 2H), 4.54 (s, 2H), 4.23-4.13 (m, 1H), 2.94-2.80 (m, 2H), 2.76-2.67 (m, 1H), 1.92 (td, J = 14.0, 8.0 Hz, 1H), 1.61-1.49 (m, 1H). Three protons not observed due to overlap with residual DMSO signal. |
| 157 | 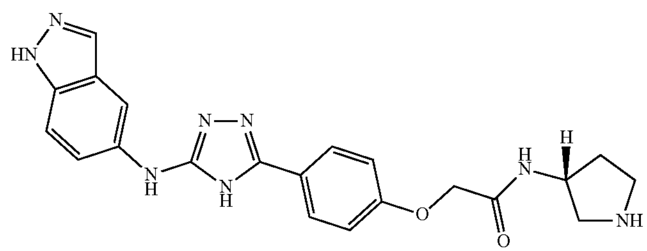 [SMILES: O=C(COc1ccc(-c2nnc(Nc3ccc4[nH]ncc4c3)[nH]2)cc1)N[C@@H]1CCNC1] | Method E, 4.45 min, m/z 419.1 [M + H]⁺ | ¹H NMR (400 MHz, DMSO-d₆): δ 12.81 (s, 1H), 9.18 (s, 1H), 8.15-8.01 (m, 2H), 7.97-7.85 (m, 3H), 7.42 (d, J = 1.5 Hz, 2H), 7.08 (d, J = 9.0 Hz, 2H), 4.53 (s, 2H), 4.17 (qd, J = 7.5, 3.5 Hz, 1H), 2.94-2.79 (m, 2H), 2.75-2.66 (m, 1H), 1.92 (dtd, J = 12.5, 8.0, 6.0 Hz, 1H), 1.54 (ddt, J = 12.5, 8.0, 5.5 Hz, 1H). Three protons not observed due to overlap with residual DMSO signal. |
| 158 | 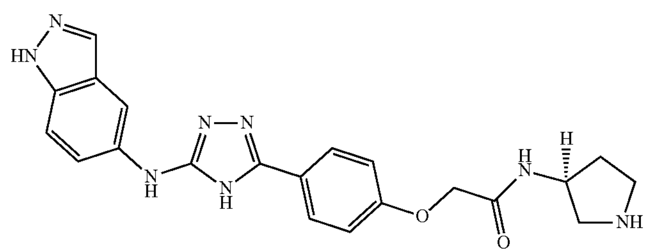 [SMILES: O=C(COc1ccc(-c2nnc(Nc3ccc4[nH]ncc4c3)[nH]2)cc1)N[C@H]1CCNC1] | Method E, 4.41 min, m/z 417.1 [M − H]⁻ | ¹H NMR (400 MHz, DMSO-d₆): δ 12.82 (s, 1H), 9.19 (s, 1H), 8.15-8.03 (m, 2H), 7.98-7.88 (m, 3H), 7.43 (d, J = 1.4 Hz, 2H), 7.09 (d, J = 8.9 Hz, 2H), 4.54 (s, 2H), 4.23-4.12 (m, 1H), 2.93-2.81 (m, 2H), 2.71 (ddd, J = 10.6, 8.1, 5.9 Hz, 1H), 1.93 (dtd, J = 12.7, 8.2, 6.1 Hz, 1H), 1.55 (ddt, J = 12.8, 8.2, 5.4 Hz, 1H). Three protons not observed due to overlap with residual DMSO signal. |

TABLE 12-continued

| Ex | Structure | LC/MS | ¹H NMR |
|---|---|---|---|
| 159 | 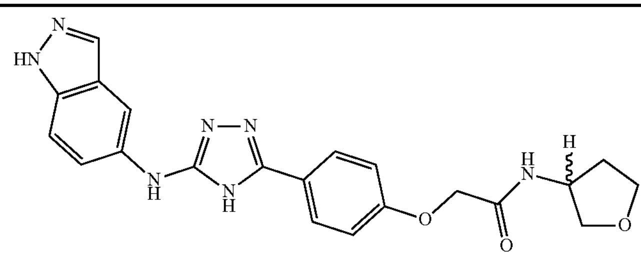 | Method E, 5.15 min, m/z 420.1 [M + H]⁺ | ¹H NMR (500 MHz, DMSO-d₆): δ 13.45 (s, 1H), 12.79 (s, 1H), 9.13 (s, 1H), 8.33 (d, J = 7.0 Hz, 1H), 8.11 (s, 1H), 8.01-7.83 (m, 3H), 7.41 (s, 2H), 7.09 (s, 2H), 4.56 (s, 2H), 4.38-4.28 (m, 1H), 3.84-3.74 (m, 2H), 3.68 (td, J = 8.0, 5.5 Hz, 1H), 3.51 (dd, J = 9.0, 4.0 Hz, 1H), 2.10 (dtd, J = 12.5, 8.0, 6.5 Hz, 1H), 1.86-1.76 (m, 1H). |
| 160 | 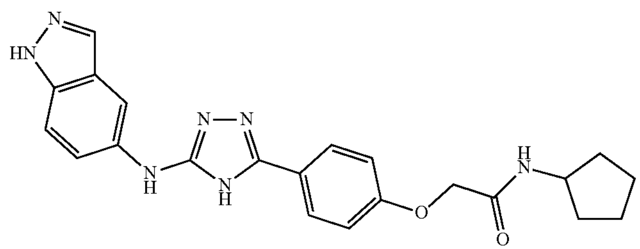 [SMILES: O=C(COc1ccc(-c2nnc(Nc3ccc4[nH]ncc4c3)[nH]2)cc1)NC1CCCC1] | Method E, 6.14 min, m/z 418.1 [M + H]⁺ | ¹H NMR (500 MHz, DMSO-d₆): δ 13.38 (s, 1H), 12.81 (s, 1H), 9.17 (s, 1H), 8.10 (s, 1H), 8.03 (d, J = 7.5 Hz, 1H), 7.95 (s, 1H), 7.93-7.88 (m, 2H), 7.42 (s, 2H), 7.08 (d, J = 8.5 Hz, 2H), 4.52 (s, 2H), 4.14-4.03 (m, 1H), 1.86-1.76 (m, 2H), 1.68-1.59 (m, 2H), 1.55-1.39 (m, 4H). |
| 161 | 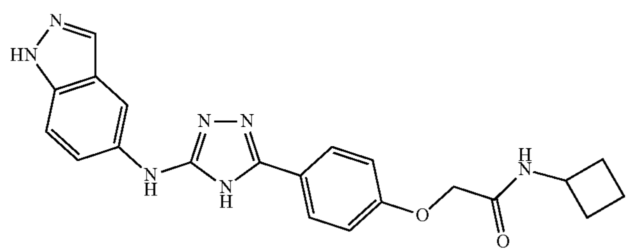 [SMILES: O=C(COc1ccc(-c2nnc(Nc3ccc4[nH]ncc4c3)[nH]2)cc1)NC1CCC1] | Method E, 5.88 min, m/z 404.1 [M + H]⁺ | ¹H NMR (500 MHz, DMSO-d₆): δ 513.37 (s, 1H), 12.80 (s, 1H), 9.17 (s, 1H), 8.33 (d, J = 8.0 Hz, 1H), 8.10 (s, 1H), 7.98-7.87 (m, 3H), 7.42 (s, 2H), 7.09 (d, J = 8.5 Hz, 2H), 4.51 (s, 2H), 4.34-4.22 (m, 1H), 2.20-2.11 (m, 2H), 2.06-1.95 (m, 2H), 1.69-1.58 (m, 2H). |
| 162 | 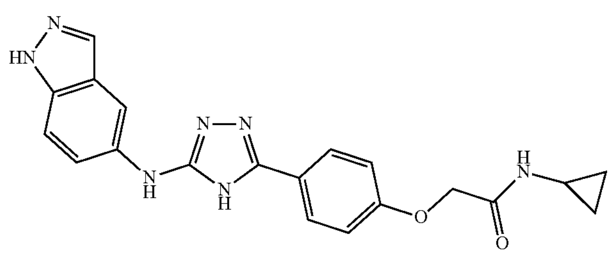 [SMILES: O=C(COc1ccc(-c2nnc(Nc3ccc4[nH]ncc4c3)[nH]2)cc1)NC1CC1] | Method E, 5.38 min, m/z 389.9 [M + H]⁺ | ¹H NMR (400 MHz, DMSO-d₆): δ 13.37 (s, 1H), 12.80 (s, 1H), 9.16 (s, 1H), 8.17 (d, J = 4.5 Hz, 1H), 8.10 (s, 1H), 7.94 (s, 1H), 7.91 (d, J = 9.0 Hz, 2H), 7.42 (d, J = 1.5 Hz, 2H), 7.07 (d, J = 8.5 Hz, 2H), 4.51 (s, 2H), 2.74-2.68 (m, 1H), 0.64 (td, J = 7.0, 4.5 Hz, 2H), 0.53-0.46 (m, 2H). |

TABLE 12-continued

| Ex | Structure | LC/MS | ¹H NMR |
|---|---|---|---|
| 163 | 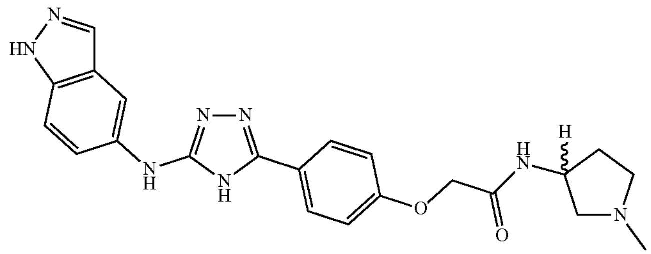 [SMILES: CN1CCC(NC(=O)COc2ccc(-c3nnc(Nc4ccc5[nH]ncc5c4)[nH]3)cc2)C1] | Method E, 4.37 min, m/z 433.1 [M + H]⁺ | ¹H NMR (400 MHz, DMSO-d₆): δ 13.33 (s, 1H), 12.80 (s, 1H), 9.15 (s, 1H), 8.21 (d, J = 7.5 Hz, 1H), 8.10 (s, 1H), 7.98-7.87 (m, 3H), 7.42 (s, 2H), 7.08 (d, J = 8.5 Hz, 2H), 4.54 (s, 2H), 4.25 (dtt, J = 9.5, 7.5, 4.5 Hz, 1H), 2.65-2.58 (m, 2H), 2.41-2.30 (m, 2H), 2.25 (s, 3H), 2.16-2.08 (m, 1H), 1.64 (dddd, J = 13.0, 8.0, 6.5, 4.5 Hz, 1H). |
| 164 | 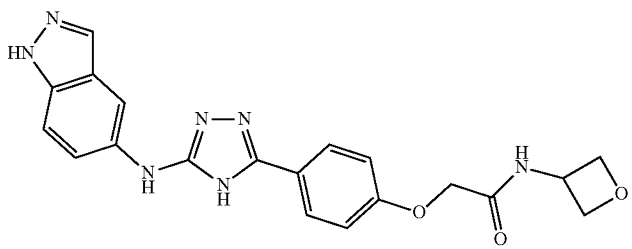 [SMILES: O=C(COc1ccc(-c2nnc(Nc3ccc4[nH]ncc4c3)[nH]2)cc1)NC1COC1] | Method E, 5.34 min, m/z 405.8 [M + H]⁺ | ¹H NMR (500 MHz, DMSO-d₆): δ 13.46 (s, 1H), 12.80 (s, 1H), 9.13 (s, 1H), 8.18-8.03 (m, 2H), 8.00-7.88 (m, 3H), 7.43 (s, 2H), 7.11 (d, J = 8.4 Hz, 2H), 4.62 (s, 2H), 4.12-4.02 (m, 1H), 3.77 (dd, J = 11.0, 5.1 Hz, 1H), 3.70 (dd, J = 11.0, 6.8 Hz, 1H), 3.54 (dd, J = 10.9, 5.1 Hz, 1H), 3.46 (dd, J = 11.0, 6.4 Hz, 1H). |
| 165 | 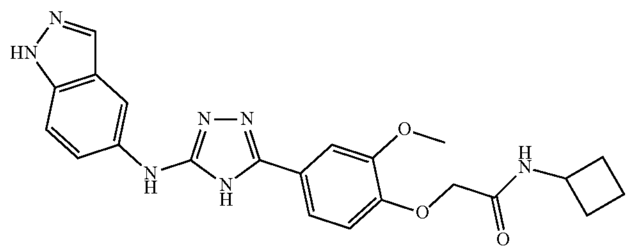 [SMILES: COc1cc(-c2nnc(Nc3ccc4[nH]ncc4c3)[nH]2)ccc1OCC(=O)NC1CCC1] | Method E, 5.94 min, m/z 433.9 [M + H]⁺ | ¹H NMR (400 MHz, DMSO-d₆): δ 13.31 (s, 1H), 12.80 (s, 1H), 9.17 (s, 1H), 8.21 (d, J = 8.0 Hz, 1H), 8.09 (s, 1H), 7.94 (d, J = 2.0 Hz, 1H), 7.58 (d, J = 2.0 Hz, 1H), 7.51 (dd, J = 8.5, 2.0 Hz, 1H), 7.41 (d, J = 1.5 Hz, 2H), 7.02 (d, J = 8.5 Hz, 1H), 4.49 (s, 2H), 4.34-4.18 (m, 1H), 3.88 (s, 3H), 2.22-2.10 (m, 2H), 2.03-1.89 (m, 2H), 1.69-1.59 (m, 2H). |
| 464 | 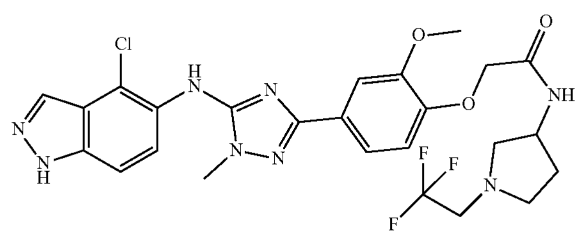 [SMILES: COc1cc(-c2nc(Nc3ccc4[nH]ncc4c3Cl)n(C)n2)ccc1OCC(=O)NC1CCN(CC(F)(F)F)C1] | Method B, 3.12 min, m/z 579.1 [M + H]⁺ | ¹H (400 MHz, CD₃OD) δ 8.09 (s, 1H), 7.61-7.49 (m, 4H), 7.01 (d, J = 8.0 Hz, 1H), 4.54 (s, 2H), 4.49-4.41 (m, 1H), 3.91 (s, 3H), 3.83 (s, 3H), 3.21 (d, J = 10 Hz, 1H), 3.16 (d, J = 9.6 Hz, 1H), 3.05-2.97 (m, 1H), 2.92 (dd, J = 6.8, 9.2, 1H), 2.74 (dd, J = 4.0, 10.0, 1H), 2.68-2.61 (m, 1H), 2.33-2.23 (m, 1H), 1.79-1.69 (m, 1H). 3NH's not observed |

General Method E:

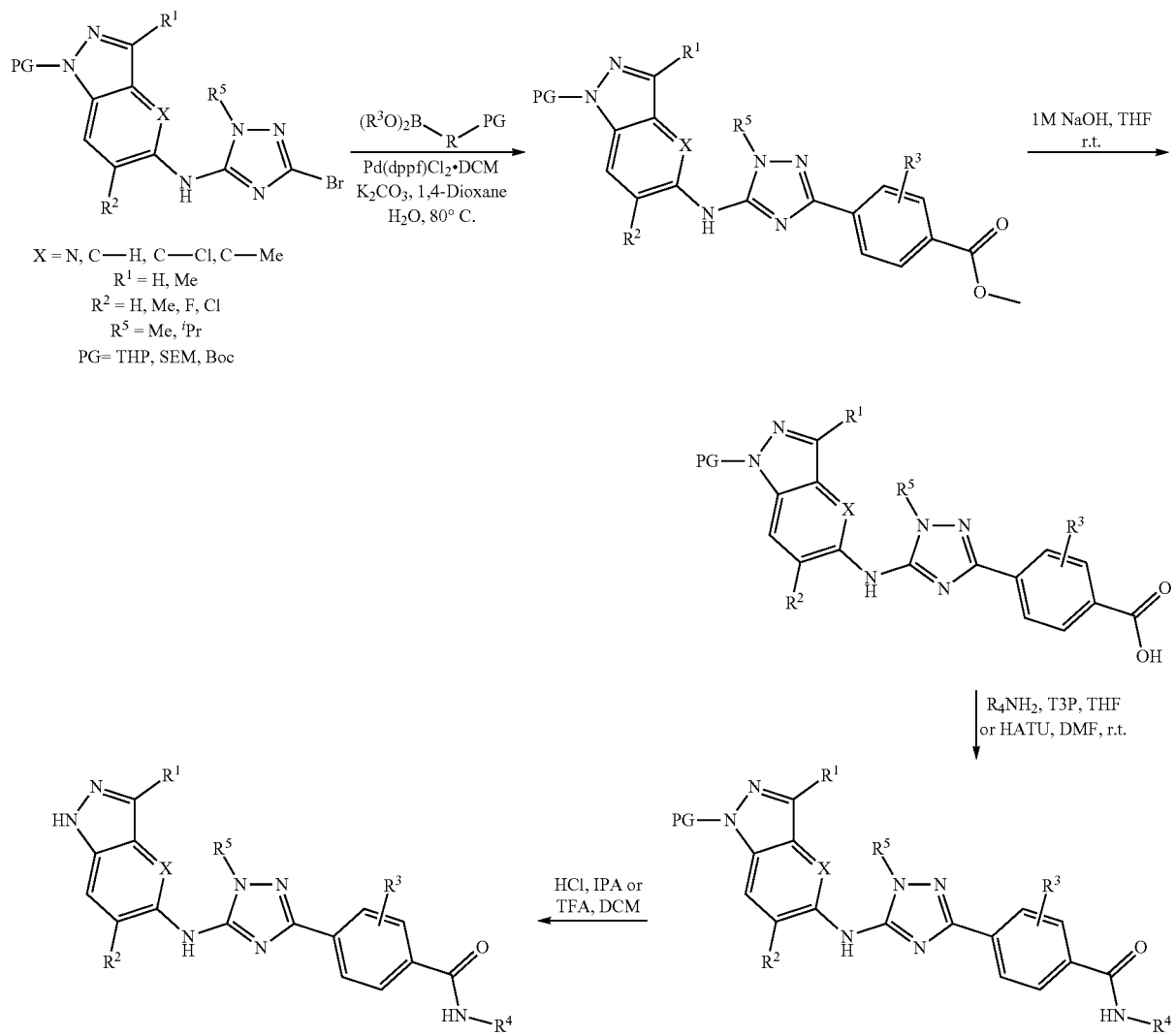

X = N, C—H, C—Cl, C—Me
R¹ = H, Me
R² = H, Me, F, Cl
R⁵ = Me, ⁱPr
PG = THP, SEM, Boc

A method for preparing a compound of the invention is given below. Further compounds that can be prepared in a similar manner from intermediates 4, 12, 13, 15 and 16 using commercially available boronic acids, boronate esters using general method E are given in Table 13.

Example 166: 4-[5[(4-chloro-1H-indazol-5-yl)amino]-1-methyl-1,2,4-triazol-3-yl]-N-isopropyl-benzamide

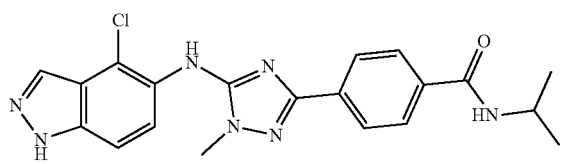 [SMILES: CC(C)NC(=O)c1ccc(-c2nc(Nc3ccc4[nH]ncc4c3Cl)n(C)n2)cc1]

Hydrogen chloride (4.0M in 1,4-dioxane) (2.49 mL, 9.94 mmol) was added slowly to a stirred solution of 4-[5-[(4-chloro-1-tetrahydropyran-2-yl-indazol-5-yl)amino]-1-methyl-1,2,4-triazol-3-yl]-N-isopropyl-benzamide (80 mg, 0.16 mmol) in MeOH (2 mL) at 25° C. The reaction was stirred at ambient temperature for 18 h. The pale yellow solution was concentrated under reduced pressure and the crude residue was purified directly by ion exchange chromatography (SCX, eluting with 1 M NH₃ in MeOH). The solution was reduced in vacuo onto silica and the product was purified by silica column chromatography on a 4 g column eluting with 30-100% EtOAc/Pet. Ether. The clean product fractions were reduced in vacuo, triturated with diethylether/Pet. Ether, filtered and dried to give 4-[5-[(4-chloro-1H-indazol-5-yl)amino]-1-methyl-1,2,4-triazol-3-yl]-N-isopropyl-benzamide (47 mg, 0.11 mmol, 70% yield) as an off-white solid. UPLC-MS (ES⁺, Method B): 3.18 min, m/z 410.3 [M+H]⁺. ¹H NMR (400 MHz, DMSO-d₆) δ 13.42 (s, 1H), 8.59 (s, 1H), 8.27 (d, J=7.8 Hz, 1H), 8.11 (s, 1H), 7.92-7.82 (m, 4H), 7.63-7.53 (m, 2H), 4.16-4.03 (m, 1H), 3.81 (s, 3H), 1.16 (d, J=6.6 Hz, 6H).

Step 1: ethyl 4-[5-[(4-chloro-1-tetrahydropyran-2-yl-indazol-5-yl)amino]-1-methyl-1,2,4-triazol-3-yl]benzoate

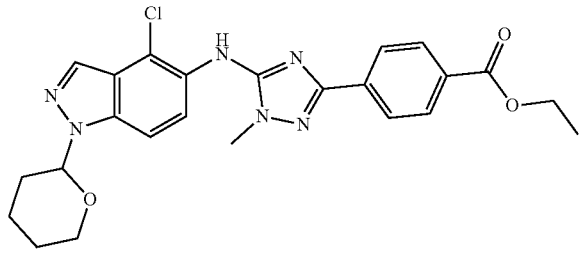 [SMILES: CCOC(=O)c1ccc(-c2nc(Nc3ccc4c(cnn4C4CCCCO4)c3Cl)n(C)n2)cc1]

Potassium carbonate (705 mg, 5.10 mmol), ethyl 4-(4,4,5,5-tetramethyl-1,3,2-dioxaborolan-2-yl)benzoate (805 mg, 2.91 mmol) and N-(5-bromo-2-methyl-1,2,4-triazol-3-yl)-4-chloro-1-tetrahydropyran-2-yl-indazol-5-amine (described in Example 43, Step 1) (1.00 g, 2.43 mmol) were dissolved/suspended in 1,4-dioxane (15 mL) and water (4 mL). The reaction mixture was fully degassed with bubbling nitrogen. [1,1'-Bis(diphenylphosphino)ferrocene]palladium(II) chloride dichloromethane complex (198 mg, 0.24 mmol) was then added followed by further degassing and then the reaction was heated to 100° C. for 3 h. Layers were separated and the organics were reduced in vacuo onto silica and purified on 80 g silica column eluting with 20-60% EtOAc in Pet. Ether to give ethyl 4-[5-[(4-chloro-1-tetrahydropyran-2-yl-indazol-5-yl)amino]-1-methyl-1,2,4-triazol-3-yl]benzoate (1.06 g, 2.19 mmol, 90%) as a white solid. UPLC-MS (ES+, Method A): 1.98 min, m/z 481.4 [M+H]+. 1H NMR (400 MHz, CDCl3) δ 8.23 (d, J=9.1 Hz, 1H), 8.19-8.02 (m, 5H), 7.60 (dd, J=9.0, 1.0 Hz, 1H), 6.51 (s, 1H), 5.72 (dd, J=9.2, 2.7 Hz, 1H), 4.40 (q, J=7.1 Hz, 2H), 4.08-3.99 (m, 1H), 3.85 (s, 3H), 3.82-3.70 (m, 1H), 2.61-2.48 (m, 1H), 2.21-2.06 (m, 2H), 1.88-1.63 (m, 3H), 1.42 (t, J=7.1 Hz, 3H).

Step 2: 4-[5-[4-chloro-1-tetrahydropyran-2-yl-indazol-5-yl)amino]-1 methyl-1,2,4-triazol-3-yl]benzoic acid

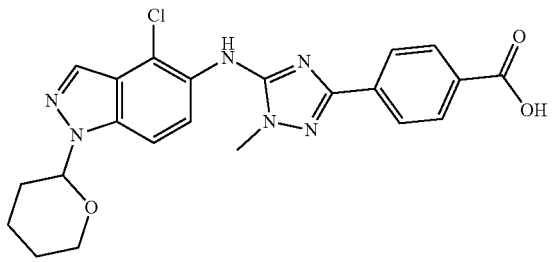 [SMILES: Cn1nc(-c2ccc(C(=O)O)cc2)nc1Nc1ccc2c(cnn2C2CCCCO2)c1Cl]

Sodium hydroxide (6.57 mL, 13.14 mmol) was added to a stirred suspension of ethyl 4-[5-[(4-chloro-1-tetrahydropyran-2-yl-indazol-5-yl)amino]-1-methyl-1,2,4-triazol-3-yl]benzoate (790 mg, 1.64 mmol) in THF (10 mL) and MeOH (10 mL) at 25° C. The reaction turned yellow and the solids dissolved. The reaction was stirred at 25° C. for 18 h. The reaction was reduced in vacuo and then slurried in water. The pH was then adjusted to pH2 by the addition of 2.0 M HCl and a solid precipitated from the solution. The solid was extracted twice with EtOAc. The combined organic layers were then washed with saturated brine, dried over MgSO4 and solvent was removed in vacuo to give 4-[5-[(4-chloro-1-tetrahydropyran-2-yl-indazol-5-yl)amino]-1-methyl-1,2,4-triazol-3-yl]benzoic add (470 mg, 1.02 mmol, 62% yield) as a yellow solid. UPLC-MS (ES+, Method A): 1.65 min, m/z 453.4 [M+H]+. 1H NMR (400 MHz, DMSO-d6) δ 12.99 (s, 1H), 8.68 (s, 1H), 8.16 (d, J=0.8 Hz, 1H), 8.00-7.90 (m, 4H), 7.76 (dd, J=8.9, 0.9 Hz, 1H), 7.67 (d, J=8.9 Hz, 1H), 5.89 (dd, J=9.6, 2.3 Hz, 1H), 3.90 (s, 1H), 3.83 (s, 3H), 3.77 (ddd, J=11.4, 8.1, 6.0 Hz, 1H), 2.49-2.34 (m, 1H), 2.02 (d, J=15.8 Hz, 2H), 1.76 (s, 1H), 1.60 (dq, J=8.1, 4.3, 3.7 Hz, 2H).

Step 3: 4-[5-[(4-chloro-1-tetrahydropyran-2-yl-indazol-5-yl)amino]-1-methyl-1,2,4-triazol-3-yl]-N-isopropyl-benzamide

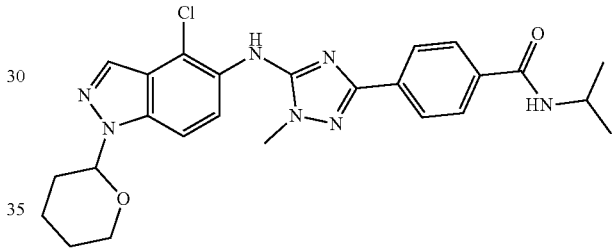

To a stirred solution of 4-[5-[(4-chloro-1-tetrahydropyran-2-yl-indazol-5-yl)amino]-1-methyl-1,2,4-triazol-3-yl]benzoic acid (80 mg, 0.18 mmol), N,N-disopropylethylamine (0.09 mL, 0.53 mmol) and 2-aminopropane (0.03 mL, 0.35 mmol) in THF (5 mL) was added propylphosphonic anhydride 50 wt % in ethyl acetate (0.16 mL, 0.27 mmol) and the solution stirred for 18 h. The yellow solution was reduced in vacuo and purified by silica column chromatography eluting with 30-100% EtOAc in Pet. Ether to give 4-[5-[(4-chloro-1-tetrahydropyran-2-yl-indazol-5-yl)amino]-1-methyl-1,2,4-triazol-3-yl]-N-isopropyl-benzamide (80 mg, 0.15 mmol, 87% yield) as an off white solid. UPLC-MS (ES+, Method A): 1.71 min, m/z 494.5 [M+H]+. 1H NMR (400 MHz, CDCl3) δ 8.21 (d, J=9.0 Hz, 1H), 8.17-8.09 (m, 2H), 8.05 (d, J=0.9 Hz, 1H), 7.85-7.77 (m, 2H), 7.60 (dd, J=9.2, 0.9 Hz, 1H), 6.51 (s, 1H), 5.97 (d, J=7.8 Hz, 1H), 5.72 (dd, J=9.2, 2.7 Hz, 1H), 4.38-4.23 (m, 1H), 4.08-3.99 (m, 1H), 3.85 (s, 3H), 3.83-3.70 (m, 1H), 2.54 (tdd, J=13.2, 9.9, 3.9 Hz, 1H), 2.23-2.02 (m, 2H), 1.89-1.66 (m, 3H), 1.29 (d, J=6.5 Hz, 6H).

Compounds prepared in a shier manner to that set out above are given below in Table 13

TABLE 13

| Example | Structure | LC/MS | ¹H NMR |
|---------|-----------|-------|--------|
| 167 | 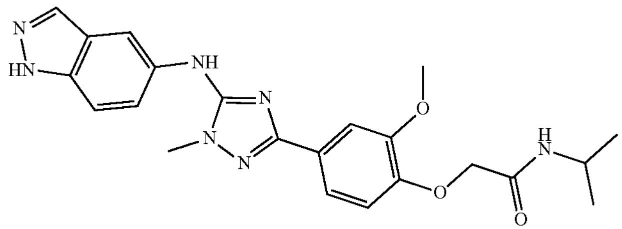 [SMILES: COc1cc(-c2nc(Nc3ccc4[nH]ncc4c3)n(C)n2)ccc1OCC(=O)NC(C)C] | Method E, 6.07 min, m/z 436.1 [M + H]⁺ | ¹H NMR (400 MHz, DMSO-d₆) δ 12.90 (s, 1H), 8.85 (s, 1H), 8.16 (d, J = 2.0 Hz, 1H), 8.01 (s, 1H), 7.77 (d, J = 8.0 Hz, 1H), 7.58-7.48 (m, 4H), 6.99 (d, J = 9.0 Hz, 1H), 4.47 (s, 2H), 3.93 (m, 1H), 3.87 (s, 3H), 3.78 (s, 3H), 1.10 (d, J = 6.5 Hz, 6H). |
| 168 | 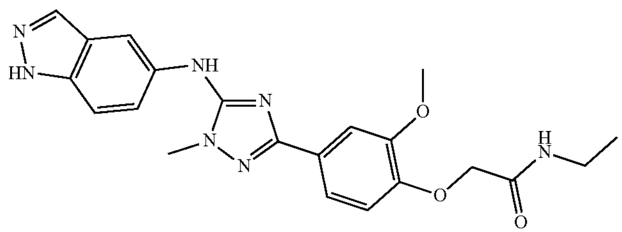 | Method B, 2.99 min, m/z 392.4 [M + H]⁺ | ¹H NMR (400 MHz, DMSO-d₆) δ 12.95 (s, 1H), 8.96 (s, 1H), 8.27-8.16 (m, 2H), 8.04 (t, J = 1.2 Hz, 1H), 7.83 (d, J = 7.9 Hz, 1H), 7.69-7.61 (m, 2H), 7.62-7.48 (m, 2H), 3.97 (s, 3H), 3.83 (s, 3H), 3.31 (qd, J = 7.2, 5.7 Hz, 2H), 1.13 (t, J = 7.2 Hz, 3H). |
| 169 | 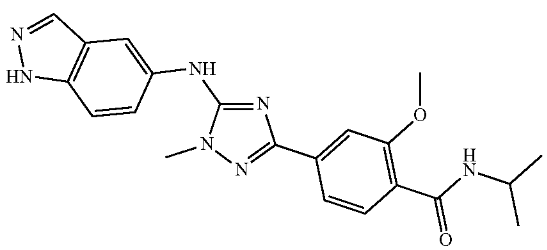 [SMILES: COc1cc(-c2nc(Nc3ccc4[nH]ncc4c3)n(C)n2)ccc1C(=O)NC(C)C] | Method B, 3.24 min, m/z 406.4 [M + H]⁺ | ¹H NMR (400 MHz, DMSO-d₆) δ 12.95 (s, 1H), 8.95 (s, 1H), 8.19 (dd, J = 2.0, 0.8 Hz, 1H), 8.04 (s, 1H), 7.97 (d, J = 7.7 Hz, 1H), 7.78 (d, J = 7.9 Hz, 1H), 7.69-7.48 (m, 4H), 4.16-3.97 (m, 1H), 3.97 (s, 3H), 3.83 (s, 3H), 1.18 (d, J = 6.5 Hz, 6H). |
| 170 | 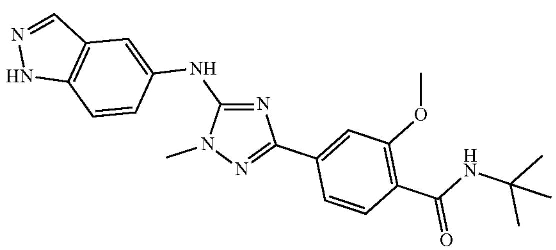 [SMILES: COc1cc(-c2nc(Nc3ccc4[nH]ncc4c3)n(C)n2)ccc1C(=O)NC(C)(C)C] | Method B, 3.57 min, m/z 420.4 [M + H]⁺ | ¹H NMR (400 MHz, DMSO-d₆) δ 12.95 (s, 1H), 8.19 (d, J = 1.9 Hz, 1H), 8.04 (t, J = 1.2 Hz, 1H), 7.92-7.81 (m, 2H), 7.70-7.61 (m, 2H), 7.58 (dd, J = 9.0, 2.0 Hz, 1H), 7.52 (d, J = 8.8 Hz, 1H), 3.99 (s, 3H), 3.83 (s, 3H), 1.39 (s, 9H). |

TABLE 13-continued

| Example | Structure | LC/MS | ¹H NMR |
|---|---|---|---|
| 171 | 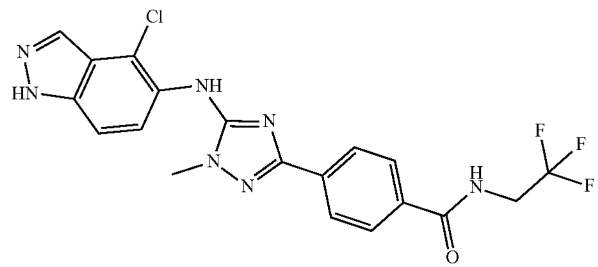 [SMILES: Cn1nc(-c2ccc(C(=O)NCC(F)(F)F)cc2)nc1Nc1ccc2[nH]ncc2c1Cl] | Method B, 3.35 min, m/z 450.3 [M + H]⁺ | ¹H NMR (400 MHz, DMSO-d₆) δ 13.42 (s, 1H), 9.14 (t, J = 6.3 Hz, 1H), 8.61 (s, 1H), 8.12 (s, 1H), 7.98-7.88 (m, 4H), 7.64-7.53 (m, 2H), 4.09 (qd, J = 9.8, 6.5 Hz, 2H), 3.82 (s, 3H). |
| 172 | 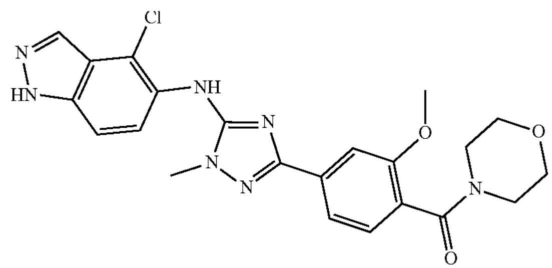 [SMILES: COc1cc(-c2nc(Nc3ccc4[nH]ncc4c3Cl)n(C)n2)ccc1C(=O)N1CCOCC1] | Method B, 2.98 min, m/z 468.4 [M + H]⁺ | ¹H NMR (400 MHz, DMSO-d₆) δ 13.40 (s, 1H), 8.56 (s, 1H), 8.10 (s, 1H), 7.62-7.44 (m, 4H), 7.21 (d, J = 7.7 Hz, 1H), 3.83 (s, 3H), 3.81 (s, 3H), 3.62 (m, 4H), 3.51 (m, 2H), 3.18-3.10 (m, 2H). |
| 173 | 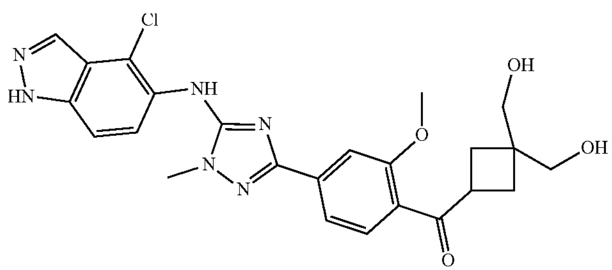 [SMILES: COc1cc(-c2nc(Nc3ccc4[nH]ncc4c3Cl)n(C)n2)ccc1C(=O)C1CC(CO)(CO)C1] | Method B, 2.62 min, m/z 498.4 [M + H]⁺ | ¹H NMR (400 MHz, DMSO-d₆) δ 13.40 (s, 1H), 8.56 (s, 1H), 8.10 (s, 1H), 7.62-7.51 (m, 2H), 7.45 (d, J = 6.7 Hz, 2H), 7.31-7.23 (m 1H), 4.83 (t, J = 5.4 Hz, 2H), 3.84 (s, 3H), 3.81 (s, 3H), 3.68 (m, 2H), 3.56 (m, 2H), 3.47 (m, J = 5.5 Hz, 4H). |

TABLE 13-continued

| Example | Structure | LC/MS | ¹H NMR |
|---|---|---|---|
| 174 | 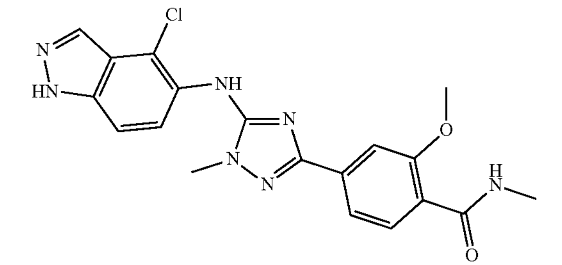 [SMILES: CNC(=O)c1ccc(-c2nc(Nc3ccc4[nH]ncc4c3Cl)n(C)n2)cc1OC] | Method B, 2.97 min, m/z 412.3 [M + H]⁺ | ¹H NMR (400 MHz, DMSO-d₆) δ 13.41 (s, 1H), 8.59 (s, 1H), 8.21-8.08 (m, 2H), 7.78 (d, J = 7.9 Hz, 1H), 7.61-7.53 (m, 2H), 7.52-7.45 (m, 2H), 3.90 (s, 3H), 3.81 (s, 3H), 2.79 (d, J = 4.6 Hz, 3H). |
| 175 | 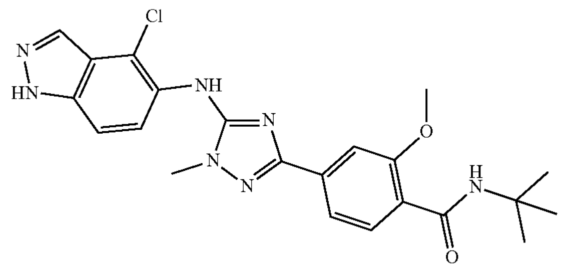 [SMILES: COc1cc(-c2nc(Nc3ccc4[nH]ncc4c3Cl)n(C)n2)ccc1C(=O)NC(C)(C)C] | Method B, 3.73 min, m/z 454.4 [M + H]⁺ | ¹H NMR (400 MHz, DMSO-d₆) δ 13.41 (s, 1H), 8.58 (s, 1H), 8.11 (s, 1H), 7.85 (s, 1H), 7.77 (d, J = 8.0 Hz, 1H), 7.67-7.45 (m 4H), 3.92 (s, 3H), 3.81 (s, J = 0.9 Hz, 3H), 1.37 (s, 9H). |
| 176 | 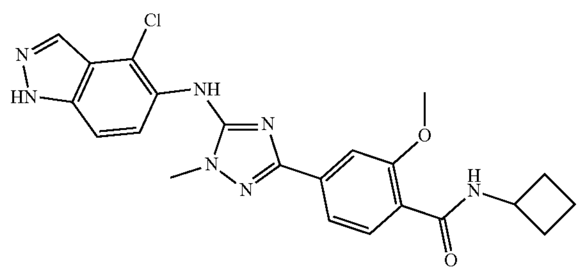 | Method B, 3.30 min, m/z 422.3 [M + H]⁺ | ¹H NMR (400 MHz, DMSO-d₆) δ 13.42 (s, 1H), 8.66 (d, J = 7.7 Hz, 1H), 8.60 (s, 1H), 8.11 (s, 1H), 7.93-7.82 (m, 4H), 7.63-7.53 (m, 2H), 4.42 (h, J = 8.2 Hz, 1H), 3.81 (s, 3H), 2.19 (ddt, J = 10.9, 6.9, 3.1 Hz, 2H), 2.14-1.97 (m, 2H), 1.66 (tt, J = 10.9, 6.9 Hz, 2H). |

TABLE 13-continued

| Example | Structure | LC/MS | ¹H NMR |
|---|---|---|---|
| 177 | 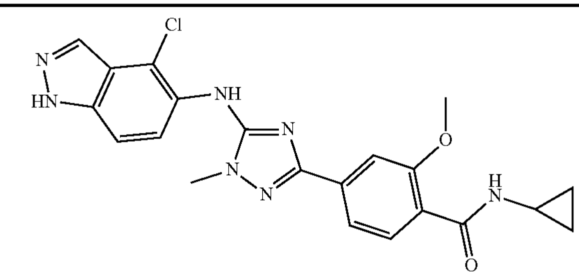 | Method B, 3.02 min, m/z 408.3 [M + H]⁺ | ¹H NMR (400 MHz, DMSO-d₆) δ 13.42 (s, 1H), 8.59 (s, 1H), 8.48 (d, J = 4.2 Hz, 1H), 8.11 (s, 1H), 7.92-7.79 (m, 4H), 7.63-7.52 (m, 2H), 3.81 (s, 3H), 2.84 (m, 1H), 0.74-0.62 (m, 2H), 0.65-0.52 (m, 2H). |
| 178 | 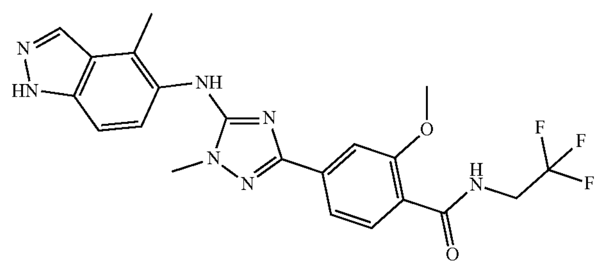 [SMILES: COc1cc(-c2nc(Nc3ccc4[nH]ncc4c3C)n(C)n2)ccc1C(=O)NCC(F)(F)F] | Method B, 3.36 min, m/z 460.4 [M + H]⁺ | ¹H NMR (400 MHz, DMSO-d₆) δ 13.03 (s, 1H), 8.68 (t, J = 6.5 Hz, 1H), 8.36 (s, 1H), 8.14 (s, 1H), 7.76 (d, J = 8.1 Hz, 1H), 7.53-7.44 (m, 2H), 7.41-7.29 (m, 2H), 4.10 (qd, J = 9.7, 6.5 Hz, 2H), 3.91 (s, 3H), 3.77 (s, 3H), 2.46 (s, 3H). |
| 179 | 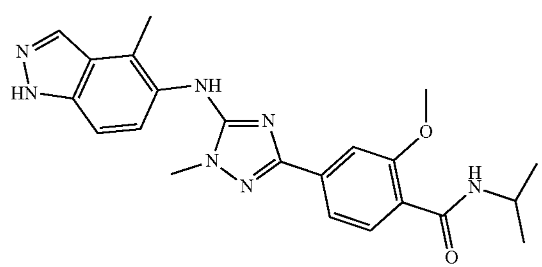 [SMILES: COc1cc(-c2nc(Nc3ccc4[nH]ncc4c3C)n(C)n2)ccc1C(=O)NC(C)C] | Method B, 3.20 min, m/z 420.4 [M + H]⁺ | ¹H NMR (400 MHz, DMSO-d₆) δ 13.03 (s, 1H), 8.34 (s, 1H), 8.14 (s, 1H), 7.92 (d, J = 7.7 Hz, 1H), 7.72-7.65 (m, 1H), 7.50-7.41 (m, 2H), 7.35 (m, J = 8.8 Hz, 2H), 4.12-3.98 (m, 1H), 3.89 (s, 3H), 3.77 (s, 3H), 2.46 (s, 3H), 1.16 (d, J = 6.5 Hz, 6H). |
| 180 | 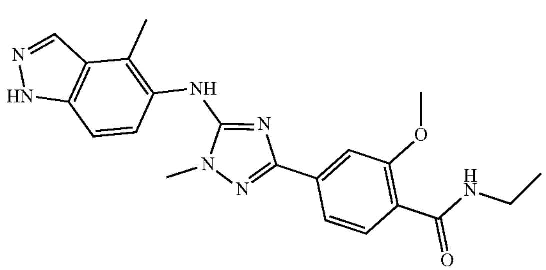 [SMILES: CCNC(=O)c1ccc(-c2nc(Nc3ccc4[nH]ncc4c3C)n(C)n2)cc1OC] | Method B, 2.97 min, m/z 406.4 [M + H]⁺ | ¹H NMR (400 MHz, DMSO-d₆) δ 13.06-13.01 (m, 1H), 8.35 (s, 1H), 8.23-8.11 (m, 2H), 7.74 (d, J = 7.9 Hz, 1H), 7.50-7.41 (m, 2H), 7.35 (q, J = 8.8 Hz, 2H), 3.89 (s, 3H), 3.77 (s, 3H), 3.28 (qd, J = 7.2, 5.6 Hz, 2H), 2.46 (s, 3H), 1.10 (t, J = 7.2 Hz, 3H). |

TABLE 13-continued

| Example | Structure | LC/MS | ¹H NMR |
|---|---|---|---|
| 181 | (structure) | Method B, 3.54 min, m/z 434.5 [M + H]⁺ | ¹H NMR (400 MHz, DMSO-d₆) δ 13.04-12.98 (m, 1H), 8.32 (s, 1H), 8.13 (t, J = 1.2 Hz, 1H), 7.83 (s, 1H), 7.75 (d, J = 8.0 Hz, 1H), 7.51-7.42 (m, 2H), 7.35 (m, J = 8.8 Hz, 2H), 3.91 (s, 3H), 3.77 (s, 3H), 2.46 (s, 3H), 1.37 (s, 9H). |
| 182 | (structure) | Method B, 3.03 min, m/z 418.3 [M + H]⁺ | ¹H NMR (400 MHz, DMSO-d₆) δ 13.01 (s, 1H), 8.32 (s, 1H), 8.20-8.05 (m, 2H), 7.65 (d, J = 7.9 Hz, 1H), 7.49-7.40 (m, 2H), 7.35 (m, 2H), 3.86 (s, 3H), 3.76 (s, 3H), 2.88-2.77 (m, 1H), 2.46 (s, 3H), 0.74-0.62 (m, 2H), 0.54 (dt, J = 7.2, 4.5 Hz, 2H). |
| 183 | (structure) | Method B, 3.25 min, m/z 424.4 [M + H]⁺ | ¹H NMR (400 MHz, DMSO-d₆) δ 13.38 (s, 1H), 8.67 (s, 1H), 8.19 (s, 1H), 7.93 (d, J = 7.7 Hz, 1H), 7.71 (d, J = 7.9 Hz, 1H), 7.59 (dd, J = 8.8, 7.4 Hz, 1H), 7.53-7.44 (m, 2H), 7.40 (d, J = 8.8 Hz, 1H), 4.06 (dq, J = 13.4, 6.7 Hz, 1H), 3.90 (s, 3H), 3.81 (s, 3H), 1.16 (d, J = 6.5 Hz, 6H). |

TABLE 13-continued

| Example | Structure | LC/MS | ¹H NMR |
|---|---|---|---|
| 184 | 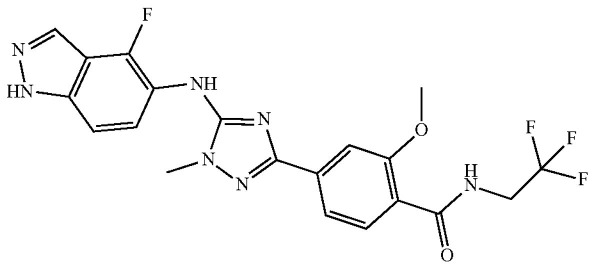 [SMILES: COc1cc(-c2nc(Nc3ccc4[nH]ncc4c3F)n(C)n2)ccc1C(=O)NCC(F)(F)F] | Method B, 3.40 min, m/z 464.4 [M + H]⁺ | ¹H NMR (400 MHz, DMSO-d₆) δ 13.38 (s, 1H), 8.19 (s, 1H), 7.78 (d, J = 8.0 Hz, 1H), 7.59 (dd, J = 8.8, 7.4 Hz, 1H), 7.40 (dd, J = 8.8, 1.1 Hz, 1H), 4.11 (qd, J = 9.7, 6.5 Hz, 2H), 3.92 (s, 3H), 8.73-8.65 (m, 2H), 7.56-7.47 (m, 2H), 3.82 (s, 3H). |
| 185 | 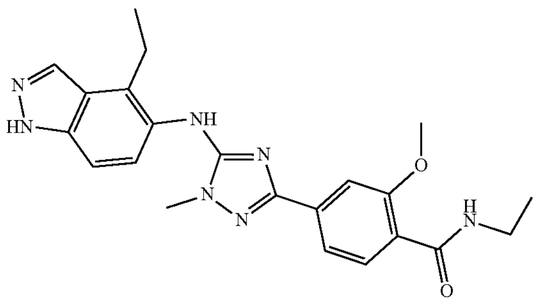 [SMILES: CCNC(=O)c1ccc(-c2nc(Nc3ccc4[nH]ncc4c3CC)n(C)n2)cc1OC] | Method B, 3.14 min, m/z 420.4 [M + H]⁺ | ¹H NMR (400 MHz, DMSO-d₆) δ 13.03 (d, J = 1.5 Hz, 1H), 8.27 (s, 1H), 8.21-8.12 (m, 2H), 7.73 (d, J = 8.0 Hz, 1H), 7.48 (d, J = 1.4 Hz, 1H), 7.44 (dd, J = 8.0, 1.4 Hz, 1H), 7.38 (dd, J = 8.7, 1.0 Hz, 1H), 7.27 (d, J = 8.7 Hz, 1H), 3.89 (s, 3H), 3.75 (s, 3H), 3.33-3.25 (m, 2H), 2.94 (q, J = 7.5 Hz, 2H), 1.23 (t, J = 7.5 Hz, 3H), 1.11 (t, J = 7.2 Hz, 3H). |
| 186 | 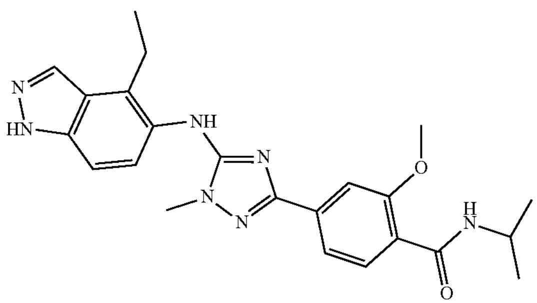 [SMILES: CCc1c(Nc2nc(-c3ccc(C(=O)NC(C)C)c(OC)c3)nn2C)ccc2[nH]ncc12] | Method B, 3.37 min, m/z 434.6 [M + H]⁺ | ¹H NMR (400 MHz, DMSO-d₆) δ 13.03 (s, 1H), 8.27 (s, 1H), 8.15 (d, J = 1.2 Hz, 1H), 7.91 (d, J = 7.7 Hz, 1H), 7.69 (d, J = 8.0 Hz, 1H), 7.47 (d, J = 1.4 Hz, 1H), 7.44 (dd, J = 8.0, 1.4 Hz, 1H), 7.38 (dd, J = 8.7, 1.0 Hz, 1H), 7.27 (d, J = 8.8 Hz, 1H), 4.12-3.98 (m, 1H), 3.88 (s, 3H), 3.75 (s, 3H), 2.94 (q, J = 7.5 Hz, 2H), 1.23 (t, J = 7.5 Hz, 3H), 1.16 (d, J = 6.6 Hz, 6H). |

TABLE 13-continued

| Example | Structure | LC/MS | ¹H NMR |
|---|---|---|---|
| 187 | 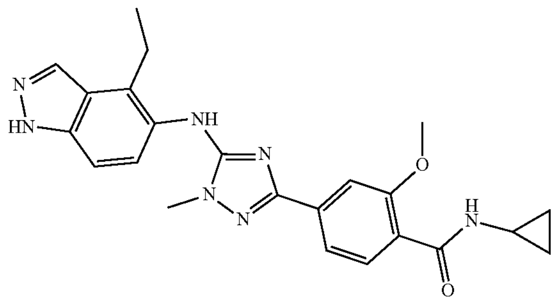 [SMILES: CCc1c(Nc2nc(-c3ccc(C(=O)NC4CC4)c(OC)c3)nn2C)ccc2[nH]ncc12] | Method B, 3.19 min, m/z 432.9 [M + H]⁺ | ¹H NMR (400 MHz, DMSO-d₆) δ 13.03 (s, 1H), 8.27 (s, 1H), 8.15 (s, 1H), 8.08 (d, J = 4.3 Hz, 1H), 7.64 (d, J = 8.0 Hz, 1H), 7.45 (d, J = 1.4 Hz, 1H), 7.43 (dd, J = 7.9, 1.4 Hz, 1H), 7.37 (dd, J = 8.7, 1.0 Hz, 1H), 7.27 (d, J = 8.7 Hz, 1H), 3.85 (s, 3H), 3.75 (s, 3H), 2.93 (q, J = 7.5 Hz, 2H), 2.88-2.76 (m, 1H), 1.23 (t, J = 7.5 Hz, 3H), 0.74-0.64 (m, 2H), 0.58-0.49 (m 2H). |
| 188 | 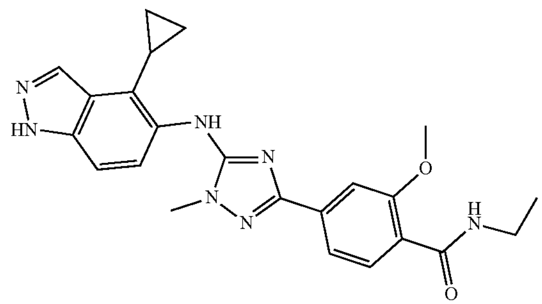 [SMILES: CCNC(=O)c1ccc(-c2nc(Nc3ccc4[nH]ncc4c3C3CC3)n(C)n2)cc1OC] | Method B, 3.23 min, m/z 432.3 [M + H]⁺ | ¹H NMR (400 MHz, DMSO-d₆) δ 13.02 (s, 1H), 8.32 (s, 1H), 8.17 (t, J = 5.7 Hz, 1H), 8.06 (t, J = 1.2 Hz, 1H), 7.75 (d, J = 8.0 Hz, 1H), 7.52-7.46 (m, 2H), 7.43-7.36 (m, 2H), 3.90 (s, 3H), 3.79 (s, 3H), 3.32-3.25 (m, 2H), 2.20-2.08 (m, 1H), 1.11 (t, J = 7.2 Hz, 3H), 1.02-0.92 (m, 2H), 0.90-0.79 (m, 2H). |
| 189 | 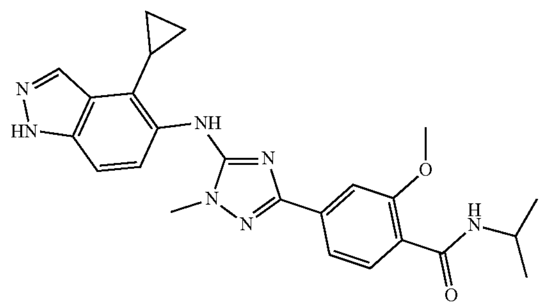 [SMILES: COc1cc(-c2nc(Nc3ccc4[nH]ncc4c3C3CC3)n(C)n2)ccc1C(=O)NC(C)C] | Method B, 3.46 min, m/z 446.5 [M + H]⁺ | ¹H NMR (400 MHz, DMSO-d₆) δ 13.02 (s, 1H), 8.32 (s, 1H), 8.06 (s, 1H), 7.91 (d, J = 7.7 Hz, 1H), 7.71 (d, J = 7.9 Hz, 1H), 7.53-7.44 (m, 2H), 7.45-7.34 (m, 2H), 4.14-3.97 (m, 1H), 3.90 (s, 3H), 3.79 (s, 3H), 2.20-2.08 (m, 1H), 1.16 (d, J = 6.6 Hz, 6H), 1.02-0.91 (m, 2H), 0.90-0.79 (m, 2H). |

TABLE 13-continued

| Example | Structure | LC/MS | ¹H NMR |
|---|---|---|---|
| 190 | 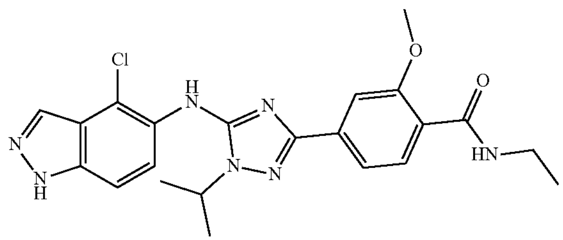 [SMILES: CCNC(=O)c1ccc(-c2nc(Nc3ccc4[nH]ncc4c3Cl)n(C(C)C)n2)cc1OC] | Method B, 3.64 min, m/z 454.4 [M + H]⁺ | ¹H NMR (400 MHz, DMSO-$d_6$) δ 13.41 (brs, 1H), 8.52 (br s, 1H), 8.20 (t, J = 5.7 Hz, 1H), 8.10 (s, 1H), 7.78 (d, J = 7.9 Hz, 1H), 7.59-7.46 (m, 4H), 4.76 (hept, J = 6.5 Hz, 1H), 3.90 (s, 3H), 3.29 (qd, J = 7.1, 5.6 Hz, 2H), 1.47 (d, J = 6.5 Hz, 6H), 1.22-1.07 (t, 3H). |
| 191 | 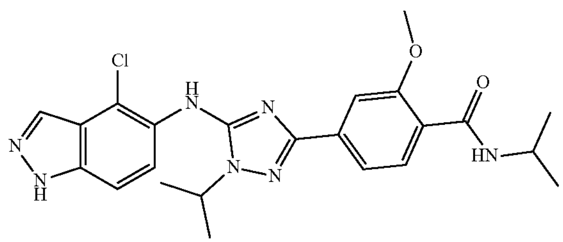 [SMILES: COc1cc(-c2nc(Nc3ccc4[nH]ncc4c3Cl)n(C(C)C)n2)ccc1C(=O)NC(C)C] | Method B, 3.87 min, m/z 468.4 [M + H]⁺ | ¹H NMR (400 MHz, DMSO-$d_6$) δ 13.41 (s, 1H), 8.52 (s, 1H), 8.10 (s, 1H), 7.93 (d, J = 7.6 Hz, 1H), 7.73 (d, J = 8.0 Hz, 1H), 7.59-7.46 (m, 4H), 4.76 (hept, J = 6.4 Hz, 1H), 4.06 (ddt, J = 13.1, 7.7, 6.6 Hz, 1H), 3.90 (s, 3H), 1.47 (d, J = 6.5 Hz, 6H), 1.16 (d, J = 6.5 Hz, 6H). |
| 192 | 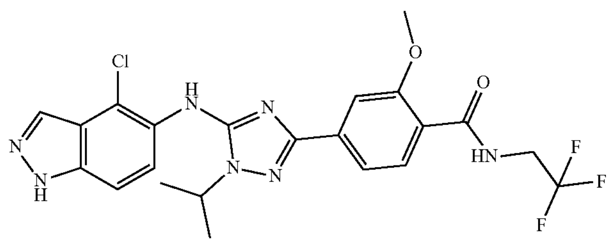 [SMILES: COc1cc(-c2nc(Nc3ccc4[nH]ncc4c3Cl)n(C(C)C)n2)ccc1C(=O)NCC(F)(F)F] | Method B, 4.02 min, m/z 508.4 [M + H]⁺ | ¹H NMR (400 MHz, DMSO-$d_6$) δ 13.41 (s, 1H), 8.68 (t, J = 6.5 Hz, 1H), 8.54 (s, 1H), 8.10 (s, 1H), 7.83-7.74 (m, 1H), 7.59-7.48 (m, 4H), 4.77 (hept, J = 6.5 Hz, 1H), 4.11 (qd, J = 9.7, 6.5 Hz, 2H), 3.92 (s, 3H), 1.48 (d, J = 6.5 Hz, 6H). |

General Method F:

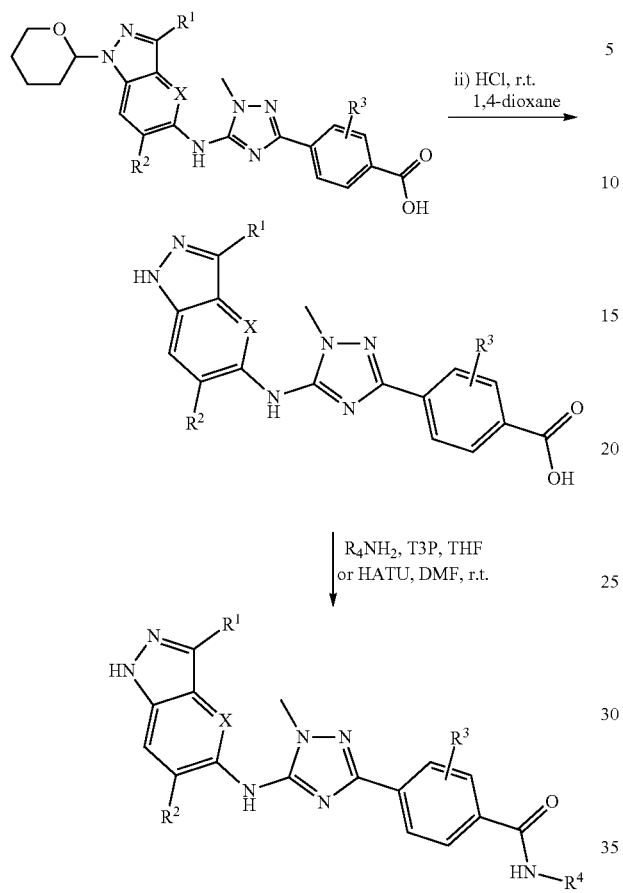

A method for preparing a compound of the invention is given below. Further compounds that can be prepared in a similar manner from intermediates 3 and 14 using commercially available boronic acids, boronate esters using general method B are given in Table 14.

Example 193: 4-[5-[(4-chloro-1H-indazol-5-yl)amino]-1-methyl-1,2,4-triazol-3-yl]-N-isopropyl-2-methoxy-benzamide

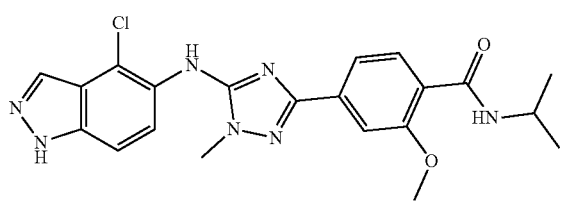 [SMILES: COc1cc(-c2nc(Nc3ccc4[nH]ncc4c3Cl)n(C)n2)ccc1C(=O)NC(C)C]

To a stirred solution of N,N-diisopropylethylamine (0.08 mL, 0.45 mmol), 2-aminopropane (0.01 mL, 0.17 mmol) and 4-[5-[(4-chloro-1H-indazol-5-yl)amino]-1-methyl-1,2,4-triazol-3-yl]-2-methoxy-benzoic add (60 mg, 0.15 mmol) in DMF (1 mL) was added 2-(7-aza-1H-benzotriazole-1-yl)-1,1,3,3-tetramethyluronium hexafluorophosphate (HATU) (63 mg, 0.17 mmol) and the solution stirred for 16 h at 25° C. The resultant brown solution was loaded onto a SCX ion-exchange cartridge and washed with methanol. the product was then eluted with 1.0 M MeOH/NH$_3$. The solution was reduced in vacuo and the resultant gum was then purified by flash column chromatography eluting 1-10% MeOH in DCM. The desired fractions were concentrated to dryness in vacuo to yield 4-[5-[(4-chloro-1H-indazol-5-yl)amino]-1-methyl-1,2,4-triazol-3-yl]-N-isopropyl-2-methoxy-benzamide (36 mg, 0.08 mmol, 53% yield) as a white solid. UPLC-MS (ES$^+$, Method B): 3.40 min, m/z 440.4 [M+H]$^+$ $^1$H NMR (400 MHz, DMSO-d$_6$) δ 13.40 (s, 1H), 8.57 (s, 1H), 8.10 (s, 1H), 7.93 (d, J=7.7 Hz, 1H), 7.71 (d, J=7.9 Hz, 1H), 7.61-7.53 (m, 2H), 7.52-7.46 (m, 2H), 4.10-4.01 (m, 1H), 3.90 (s, 3H), 3.81 (s, 3H), 1.16 (d, J=6.5 Hz, 6H).

Step 1: 4-[5-[(4-chloro-1H-indazol-5-yl)amino]-1-methyl-1,2,4-triazol-3-yl]-2-methoxy-benzoic acid

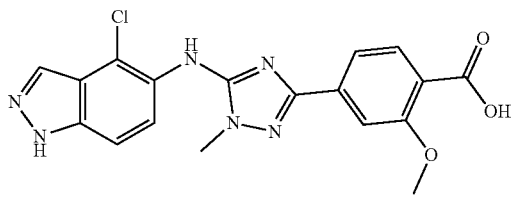 [SMILES: COc1cc(-c2nc(Nc3ccc4[nH]ncc4c3Cl)n(C)n2)ccc1C(=O)O]

4-[5-[(4-Chloro-1-tetrahydropyren-2-yl-indazol-5-yl)amino]-1-methyl-1,2,4-triazol-3-yl]-2-methoxy-benzoic acid (1.16 g, 2.4 mmol) was suspended in 1,4-dioxane (10 mL) and HCl (4.0M in dioxane) (6.01 mL, 24.02 mmol) was added. The reaction was stirred at 25° C. for 21 h forming a pink precipitates. The reaction was partially reduced in vacuo and diluted with diethyl ether and filtered and the solid was washed with further diethyl ether. The solid was then dried to give 4-[5-[(4-chloro-1H-indazol-5-yl)amino]-1-methyl-1,2,4-triazol-3-yl]-2-methoxy-benzoic acid (940 mg, 2.29 mmol, 95% yield) as a pale pink solid. UPLC-MS (ES$^+$, Method A): 1.33 min, m/z 399.3 [M+H]$^+$ $^1$H NMR (400 MHz, DMSO-d$_6$+3 drops CD$_3$CO$_2$D) δ 8.15 (d, J=0.8 Hz, 1H), 7.70 (d, J=8.0 Hz, 1H), 7.65-7.49 (m, 3H), 7.47 (dd, J=8.1, 1.5 Hz, 1H), 3.87 (s, 3H), 3.84 (s, 3H)

Step 2: 4-[5-[4-chloro-1-tetrahydropyran-2-yl-indazol-5-yl)amino]-1-methyl-1,2,4-triazol-3-yl]-2-methoxy-benzoic acid

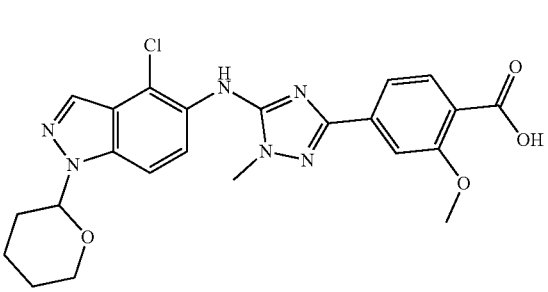 [SMILES: COc1cc(-c2nc(Nc3ccc4c(cnn4C4CCCCO4)c3Cl)n(C)n2)ccc1C(=O)O]

Sodium hydroxide (4.83 mL, 9.66 mmol) was added to a stirred suspension of methyl 4-[5-[(4-chloro-1-tetrahydropyran-2-yl-indazol-5-yl)amino]-1-methyl-1,2,4-triazol-3-yl]-2-methoxy-benzoate (1.2 g, 2.41 mmol) in THF (6 mL) and methanol (6 mL) at 25° C. The reaction was stirred for 3 h, reduced in vacuo and dissolved in 10 ml water. The pH was then adjusted to pH 4 by the addition of HCl 2.0 M and a solid precipitated form the solution. The solid was extracted with EtOAc (×2). The organics were then washed with saturated brine and dried over MgSO4. The solvent was removed in vacuo to give 4-[5-[(4-chloro-1-tetrahydropyran-2-yl-indazol-5-yl)amino]-1-methyl-1,2,4-triazol-3-yl]-2-methoxy-benzoic acid (1.16 g, 2.38 mmol, 98% yield) as a pale pink solid. UPLC-MS (ES+, Method A): 1.63 min, m/z 483.4 [M+H]+

Step 3: methyl 4-[5-[(4-chloro-1-tetrahydropyran-2-yl-indazol-5-yl)amino]-1-methyl-1,2,4-triazol-3-yl]-2-methoxy-benzoate

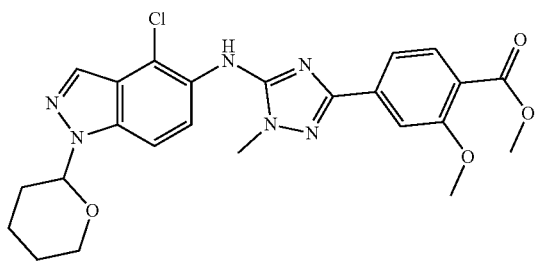 [SMILES: COC(=O)c1ccc(-c2nc(Nc3ccc4c(cnn4C4CCCCO4)c3Cl)n(C)n2)cc1OC]

Methyl 2-methoxy-4-(4,4,5,5-tetramethyl-1,3,2-dioxaborolan-2-yl)benzoate (780.6 mg, 2.67 mmol), N-(5-bromo-2-methyl-1,2,4-triazol-3-yl)-4-chloro-1-tetrahydropyran-2-yl-indazol-5-amine (1.0 g, 2.43 mmol) and potassium carbonate (705.02 mg, 5.1 mmol) were suspended in 1,4-dioxane (15 mL) and water (4 mL). The reaction mixture was fully degassed by bubbling nitrogen through. [1,1'-bis(diphenylphosphino)ferrocene]palladium(II) chloride dichloromethane complex (198 mg, 024 mmol) was then added followed by further degassing and then the reaction was heated to 90° C. for 18 h. The reaction was reduced in vacuo. Further purification by flash chromatography on silica gel eluting with 30-100% EtOAc in Pet. Ether gave methyl 4-[5-[(4-chloro-1-tetrahydropyran-2-yl-indazol-5-yl)amino]-1-methyl-1,2,4-triazol-3-yl]-2-methoxy-benzoate (800 mg, 1.59 mmol, 66% yield) as an off-white solid. UPLC-MS (ES+, Method A): 1.80 min, m/z 497.4 [M+H]+

Compounds prepared in a similar manner to that set out above are given below in Table 14.

TABLE 14

| Example | Structure | LC/MS | 1H NMR |
|---|---|---|---|
| 194 | 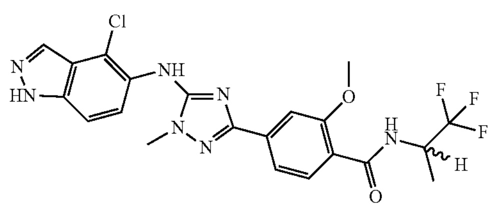 [SMILES: COc1cc(-c2nc(Nc3ccc4[nH]ncc4c3Cl)n(C)n2)ccc1C(=O)NC(C)C(F)(F)F] | Method B, 3.76 min, m/z 494.4 [M + H]+ | 1H NMR (400 MHz, DMSO-d6) δ 13.40 (s, 1H), 8.58 (s, 1H), 8.47 (d, J = 9.0 Hz, 1H), 8.10 (s, 1H), 7.67-7.47 (m, 5H), 4.85-4.81 (m, 1H), 3.89 (s, 3H), 3.82 (s, 3H), 1.34 (d, J = 7.0 Hz, 3H). |
| 195 | 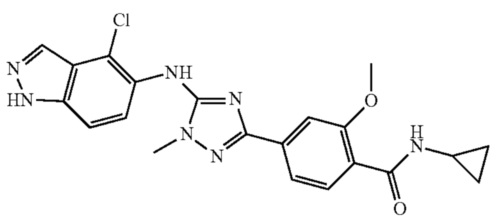 [SMILES: COc1cc(-c2nc(Nc3ccc4[nH]ncc4c3Cl)n(C)n2)ccc1C(=O)NC1CC1] | Method B, 3.22 min, m/z 438.4 [M + H]+ | 1H NMR (400 MHz, DMSO-d6) δ 13.40 (s, 1H), 8.57 (s, 1H), 8.10 (m, J = 4.5 Hz, 2H), 7.66 (d, J = 7.9 Hz, 1H), 7.61-7.53 (m, 2H), 7.51-7.44 (m, 2H), 3.87 (s, 3H), 3.81 (s, 3H), 2.87-2.79 (m, 1H), 0.69 (m, J = 7.0, 4.7 Hz, 2H), 0.57-0.51 (m, 2H). |
| 196 | 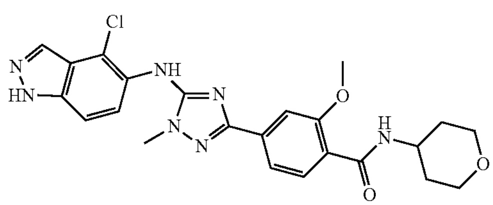 [SMILES: COc1cc(-c2nc(Nc3ccc4[nH]ncc4c3Cl)n(C)n2)ccc1C(=O)NC1CCOCC1] | Method B, 3.13 min, m/z 482.4 [M + H]+ | 1H NMR (400 MHz, DMSO-d6) δ 13.40 (s, 1H), 8.57 (s, 1H), 8.10 (s, 1H), 8.06 (d, J = 7.7 Hz, 1H), 7.70 (d, J = 7.9 Hz, 1H), 7.61-7.54 (m, 2H), 7.53-7.46 (m, 2H), 4.05-3.94 (m, 1H), 3.90 (s, 3H), 3.89-3.82 (m, 2H), 3.81 (s, 3H), 3.45-3.37 (m, 2H), 1.85-1.74 (m, 2H), 1.62-1.48 (m, 2H). |
| 197 | 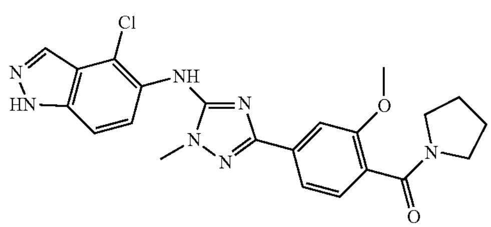 [SMILES: COc1cc(-c2nc(Nc3ccc4[nH]ncc4c3Cl)n(C)n2)ccc1C(=O)N1CCCC1] | Method B, 3.19 min, m/z 452.4 [M + H]+ | 1H NMR (400 MHz, DMSO-d6) δ 13.39 (s, 1H), 8.55 (s, 1H), 8.10 (d, J = 1.4 Hz, 1H), 7.61-7.53 (m, 2H), 7.47 (s, 1H), 7.45 (d, J = 1.4 Hz, 1H), 7.21-7.17 (m, 1H), 3.82 (s, 3H), 3.80 (s, 3H), 3.42 (t, J = 6.8 Hz, 2H), 3.11 (t, J = 6.5 Hz, 2H), 1.91-1.72 (m, 4H). |

TABLE 14-continued

| Example | Structure | LC/MS | ¹H NMR |
|---|---|---|---|
| 198 | 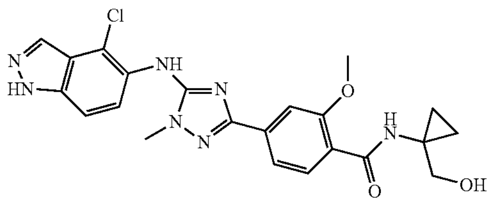 [SMILES: COc1cc(-c2nc(Nc3ccc4[nH]ncc4c3Cl)n(C)n2)ccc1C(=O)NC1(CO)CC1] | Method B, 2.96 min, m/z 468.4 [M + H]⁺ | ¹H NMR (400 MHz, DMSO-d₆) δ 13.41 (s, 1H), 8.57 (s, 1H), 8.30 (s, 1H), 8.11 (s, 1H), 7.77 (d, J = 7.9 Hz, 1H), 7.61-7.53 (m, 2H), 7.52-7.46 (m, 2H), 4.76 (t, J = 5.7 Hz, 1H), 3.90 (s, 3H), 3.81 (s, 3H), 3.52 (d, J = 5.7 Hz, 2H), 0.82-0.66 (m, 4H). |
| 199 | 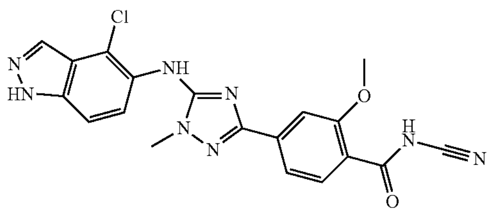 [SMILES: COc1cc(-c2nc(Nc3ccc4[nH]ncc4c3Cl)n(C)n2)ccc1C(=O)NC#N] | Method B, 3.28 min, m/z 423.4 [M + H]⁺ | ¹H NMR (400 MHz, DMSO-d₆) δ 13.41 (s, 1H), 11.22 (s, 1H), 8.64 (s, 1H), 8.11 (s, 1H), 7.80 (d, J = 8.1 Hz, 1H), 7.61-7.51 (m, 4H), 3.94 (s, 3H), 3.83 (s, 3H). |
| 200 | 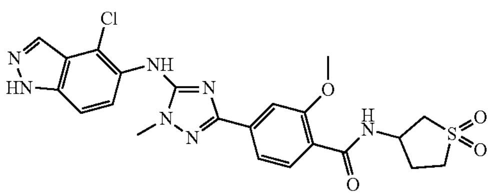 [SMILES: COc1cc(-c2nc(Nc3ccc4[nH]ncc4c3Cl)n(C)n2)ccc1C(=O)NC1CCS(=O)(=O)C1] | Method B, 3.04 min, m/z 516.4 [M + H]⁺ | ¹H NMR (400 MHz, DMSO-d₆) δ 13.40 (s, 1H), 8.61-8.54 (m, 2H), 8.10 (s, 1H), 7.75 (d, J = 7.9 Hz, 1H), 7.60-7.54 (m, 2H), 7.53-7.49 (m, 2H), 4.73 (m, J = 7.4 Hz, 1H), 3.91 (s, 3H), 3.81 (s, 3H), 3.48-3.45 (m, 1H), 3.31-3.29 (m, 1H), 3.26-3.12 (m, 2H), 2.48-2.39 (m, 1H), 2.24-2.21 (m, 1H). |
| 201 | 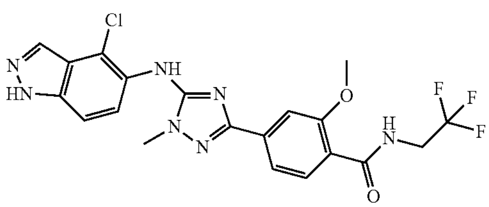 [SMILES: COc1cc(-c2nc(Nc3ccc4[nH]ncc4c3Cl)n(C)n2)ccc1C(=O)NCC(F)(F)F] | Method B, 3.56 min, m/z 480.3 [M + H]⁺ | ¹H NMR (400 MHz, DMSO-d₆) δ 13.41 (s, 1H), 8.69 (t, J = 6.4 Hz, 1H), 8.61 (s, 1H), 8.11 (s, 1H), 7.78 (d, J = 8.0 Hz, 1H), 7.62-7.47 (m, 4H), 4.13-4.10 (m, 2H), 3.92 (s, 3H), 3.82 (s, 3H). |
| 202 | 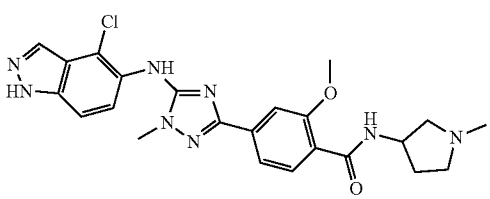 [SMILES: COc1cc(-c2nc(Nc3ccc4[nH]ncc4c3Cl)n(C)n2)ccc1C(=O)NC1CCN(C)C1] | Method B, 2.49 min, m/z 481.4 [M + H]⁺ | ¹H NMR (400 MHz, DMSO-d₆) δ 13.41 (s, 1H), 8.58 (s, 1H), 8.19 (d, J = 7.2 Hz, 1H), 8.11 (s, 1H), 7.72 (d, J = 7.9 Hz, 1H), 7.60-7.54 (m, 2H), 7.52-7.47 (m, 2H), 4.37 (m, 1H), 3.90 (s, 3H), 3.81 (s, 3H), 2.69-2.59 (m, 2H), 2.42 (dd, J = 9.4, 4.5 Hz, 1H), 2.35 (m, 1H), 2.26 (s, 3H), 2.19 (m, 1H), 1.72-1.60 (m, 1H). |
| 203 | 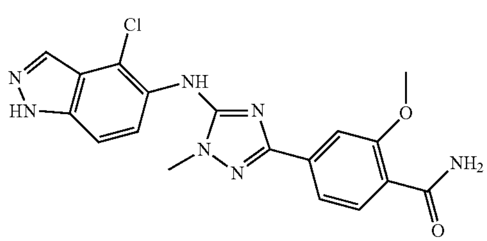 [SMILES: COc1cc(-c2nc(Nc3ccc4[nH]ncc4c3Cl)n(C)n2)ccc1C(N)=O] | Method B, 2.84 min, m/z 398.3 [M + H]⁺ | ¹H NMR (400 MHz, DMSO-d₆) δ 13.40 (s, 1H), 8.58 (s, 1H), 8.10 (s, 1H), 7.83 (d, J = 8.0 Hz, 1H), 7.65 (d, J = 2.5 Hz, 1H), 7.61-7.47 (m, 5H), 3.92 (s, 3H), 3.81 (s, 3H). |
| 465 | 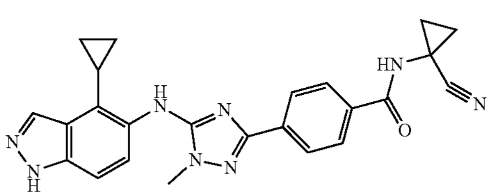 [SMILES: Cn1nc(-c2ccc(C(=O)NC3(C#N)CC3)cc2)nc1Nc1ccc2[nH]ncc2c1C1CC1] | Method B, 2.99 min, m/z 439.4 [M + H]⁺ | ¹H NMR (400 MHz, DMSO-d₆) δ 13.02 (s, 1H), 9.34 (s, 1H), 8.34 (s, 1H), 8.07 (s, 1H), 7.88 (m, 4H), 7.40 (m, 2H), 3.80 (s, 3H), 2.14 (m, 1H), 1.55 (m, 2H), 1.28 (m, 2H), 0.97 (m, 2H), 0.83 (m, 2H). |

General Method G:

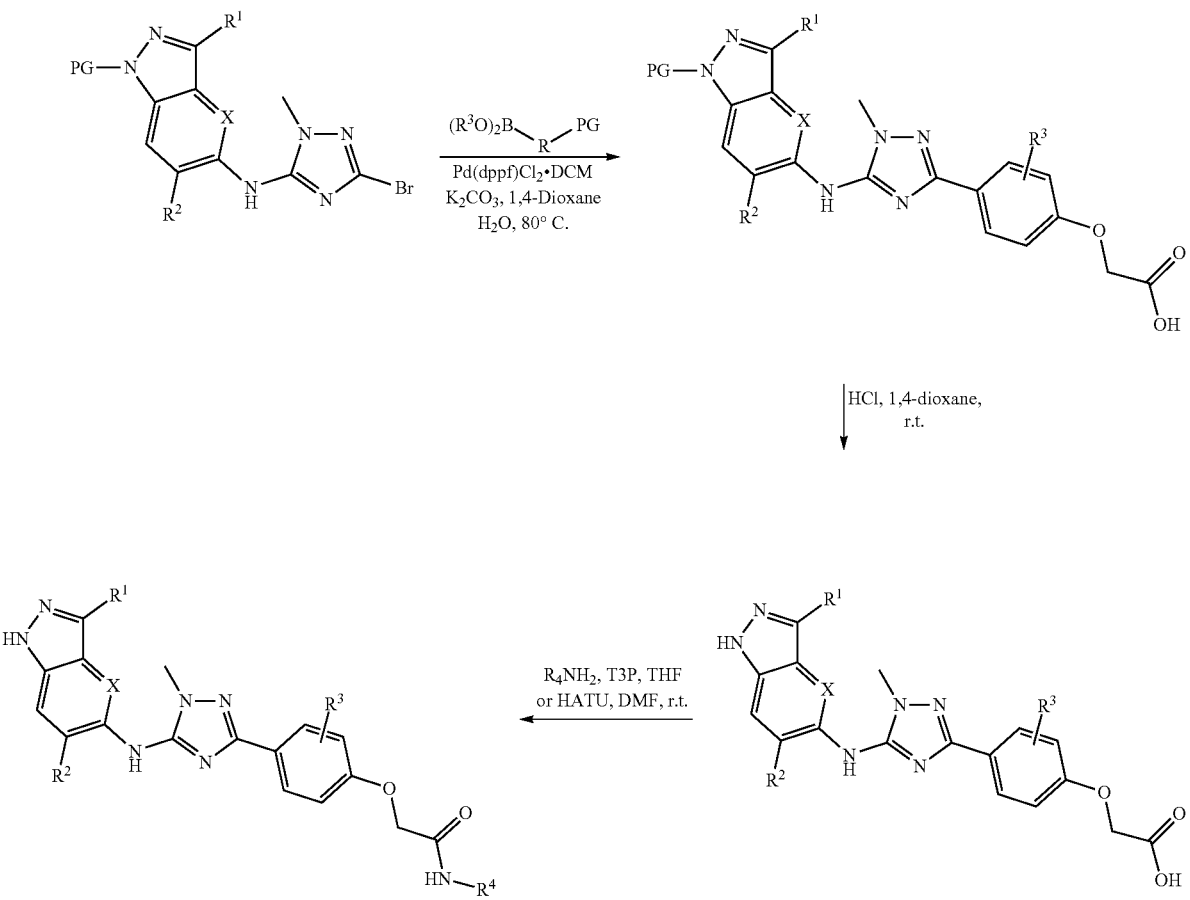

A method for preparing a compound of the invention is given below. Further compounds that can be prepared in a similar manner from commercially available boronic acids, boronate esters or intermediate 15 using general method B are given in Table 15.

Example 204: N-tert-butyl-2-[4-[5-[(4-chloro-1H-indazol-5-yl)amino]-1-methyl-1,2,4-triazol-3-yl]-2-methoxy-phenoxy]acetamide

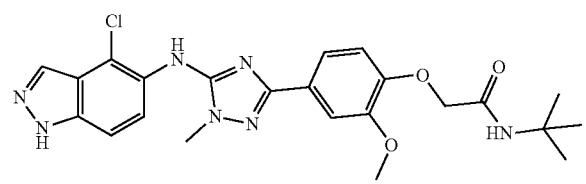 [SMILES: COc1cc(-c2nc(Nc3ccc4[nH]ncc4c3Cl)n(C)n2)ccc1OCC(=O)NC(C)(C)C]

To a stirred solution of 2-[4-[5-[(4-chloro-1H-indazol-5-yl)amino]-1-methyl-1,2,4-triazol-3-yl]-2-methoxy-phenoxy]acetic acid dihydrochloride (100 mg, 0.21 mmol), ᵗbutylamine (0.02 mL, 0.24 mmol) and N,N-diisopropylethylamine (0.11 mL, 0.64 mmol) in DMF (1 mL) was added 2-(7-aza-1H-benzotriazole-1-yl)-1,1,3,3-tetramethyluronium hexafluorophosphate (HATU) (90 mg, 0.24 mmol) and the solution stirred for 16 h. The resultant brown solution was loaded onto an SCX ion exchange cartridge and washed with methanol. The product was then eluted with 1.0M MeOH/NH$_3$. The solution was reduced in vacuo and the residue was triturated with DCM/diethyl ether to give a pale pink solid which was filtered and washed with further diethyl ether and dried to yield N-tert-butyl-2-[4-[5-[(4-chloro-1H-indazol-5-yl)amino]-1-methyl-1,2,4-triazol-3-yl]-2-methoxy-phenoxy]acetamide (52 mg, 0.11 mmol, 49% yield) as a pale pink solid. UPLC-MS (ES$^+$, Method B): 3.53 min, m/z 484.4 [M+H]$^+$ $^1$H NMR (400 MHz, DMSO-d$_6$) δ 13.37 (s, 1H), 8.46 (s, 1H), 8.16-8.06 (m, 1H), 7.66-7.50 (m, 2H), 7.45-7.33 (m, 3H), 6.94 (d, J=8.4 Hz, 1H), 4.41 (s, 2H), 3.82 (s, 3H), 3.77 (s, 3H), 1.29 (s, 9H).

Step 1: 2-[4-[5-[(4-chloro-1-tetrahydropyran-2-yl-indazol-5-yl)amino]-1-methyl-1,2,4-triazol-3-yl]-2-methoxy-phenoxy]acetic acid

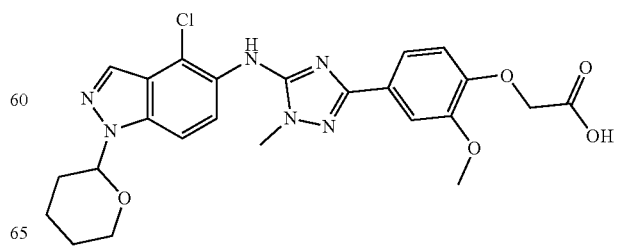

Methyl 2-[2-methoxy-4-(4,4,5,5-tetramethyl-1,3,2-dioxaborolan-2-yl)phenoxy]acetate (6.57 g, 20.40 mmol), N-(5-bromo-2-methyl-1,2,4-triazol-3-yl)-4-chloro-1-tetrahydropyran-2-yl-indazol-5-amine (described in Example 43 Step 1) (6.00 g, 14.57 mmol) and potassium carbonate (4.23 g, 30.61 mmol) were suspended in 1,4-dioxane (80 mL) and water (20 mL). The reaction mixture was fully degassed with bubbling nitrogen. [1,1'-bis(diphenylphosphino)ferrocene]palladium(II) chloride dichloromethane complex (1.19 g, 1.46 mmol) was then added followed by further degassing and then the reaction was heated to 80° C. for 18 h. The reaction was concentrated in vacuo. The residue was purified by NH₂ ion exchange column, eluting with MeOH then 2.0 M Formic acid in MeOH to give a residue which was then triturated with diethyl ether to give 2-[4-[5-[(4-chloro-1-tetrahydropyran-2-yl-indazol-5-yl)amino]-1-methyl-1,2,4-triazol-3-yl]-2-methoxy-phenoxy]acetic acid; formic acid (3.72 g, 6.65 mmol, 46% yield) as a pale brown solid. UPLC-MS (ES⁺, Method A): 1.58 min, m/z 513.4 [M+H]⁺ ¹H NMR (400 MHz, DMSO-d₆) δ 12.92 (s, 2H), 8.50 (s, 1H), 8.17-8.11 (m, 2H), 7.74 (dd, J=9.0, 0.9 Hz, 1H), 7.65 (d, J=9.0 Hz, 1H), 7.44-7.32 (m, 2H), 6.86 (d, J=8.5 Hz, 1H), 5.87 (dd, J=9.6, 2.4 Hz, 1H), 4.67 (s, 2H), 3.90 (d, J=11.5 Hz, 1H), 3.80 (s, 3H), 3.78 (s, 3H), 3.76-3.72 (m, 1H), 2.48-2.33 (m, 1H), 2.09-1.96 (m, 2H), 1.83-1.55 (m, 3H).

Step 2: 2-[4-[5-[(4-chloro-1H-indazol-5-yl)amino]-1-methyl-1,2,4-triazol-3-yl]-2-methoxy-phenoxy] acetic acid dihydrochloride

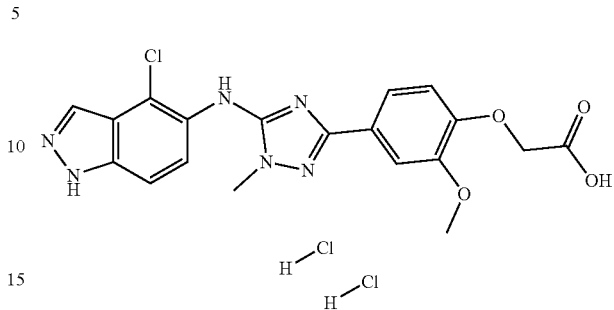

Hydrogen chloride (4.0 M in dioxane) (32.36 mL, 129.45 mmol) was added slowly to a stirred suspension of 2-[4-[5-[(4-chloro-1-tetrahydropyran-2-yl-indazol-5-yl)amino]-1-methyl-1,2,4-triazol-3-yl]-2-methoxy-phenoxy]acetic acid (3.32 g, 6.47 mmol) in 1,4-dioxane (30 mL) at 25° C. The reaction was stirred at r.t. for 6 h. The reaction was diluted with diethyl ether and filtered. The resultant solid was washed with diethyl ether and dried under high vacuum to give 2-[4-[5-[(4-chloro-1H-indazol-5-yl)amino]-1-methyl-1,2,4-triazol-3-yl]-2-methoxy-phenoxy]acetic acid dihydrochloride (3.20 g, 6.38 mmol, 98% yield) as a pale brown solid. UPLC-MS (ES⁺, Method A): 1.28 min, m/z 429.3 [M+H]⁺. ¹H NMR (400 MHz, DMSO-d₆) δ 9.89 (s, 1H), 8.17 (d, J=0.9 Hz, 1H), 7.65-7.55 (m, 2H), 7.43 (d, J=2.0 Hz, 1H), 7.38 (dd, J=8.4, 2.0 Hz, 1H), 6.93 (d, J=8.5 Hz, 1H), 4.72 (s, 2H), 3.87 (s, 3H), 3.80 (s, 3H). 2H exchanged Compounds prepared in a similar manner to that set out above are given below in Table 15 intermediates.

TABLE 15

| Example | Structure | LC/MS | ¹H NMR |
|---|---|---|---|
| 205 | 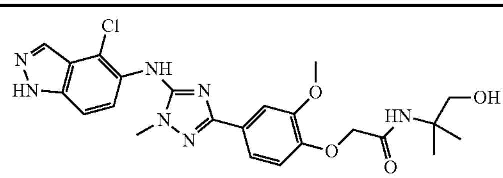 | Method B, 3.05 min, m/z 500.4 [M + H]⁺ | ¹H NMR (400 MHz, DMSO-d₆) δ 13.37 (s, 1H), 8.46 (s, 1H), 8.12-8.07 (m, 1H), 7.61-7.51 (m, 2H), 7.42 (d, J = 1.9 Hz, 1H), 7.37 (dd, J = 8.3, 1.9 Hz, 1H), 7.30 (s, 1H), 6.96 (d, J = 8.4 Hz, 1H), 4.94 (t, J = 5.6 Hz, 1H), 4.42 (s, 2H), 3.79 (d, J = 17.0 Hz, 6H), 3.38 (dd, J = 6.3, 3.9 Hz, 2H), 1.23 (s, 6H). |
| 206 | 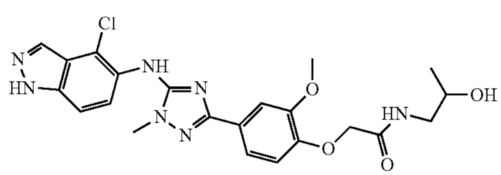 [SMILES: COc1cc(-c2nc(Nc3ccc4[nH]ncc4c3Cl)n(C)n2)ccc1OCC(=O)NCC(C)O] | Method B, 2.82 min, m/z 486.4 [M + H]⁺ | ¹H NMR (400 MHz, DMSO-d₆) δ 13.37 (s, 1H), 8.46 (s, 1H), 8.09 (s, 1H), 7.81 (t, J = 5.8 Hz, 1H), 7.56 (q, J = 8.9 Hz, 2H), 7.42 (d, J = 1.9 Hz, 1H), 7.36 (dd, J = 8.3, 1.9 Hz, 1H), 6.95 (d, J = 8.4 Hz, 1H), 4.75 (d, J = 4.7 Hz, 1H), 4.51 (s, 2H), 3.82 (s, 3H), 3.77 (s, 3H), 3.68 (ddd, J = 11.4, 6.6, 5.0 Hz, 1H), 3.19-2.99 (m, 2H), 1.01 (d, J = 6.2 Hz, 3H). |
| 207 | 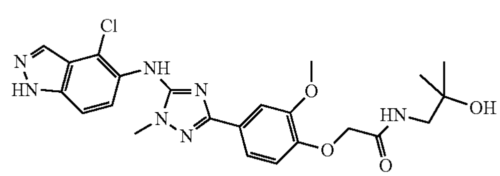 [SMILES: COc1cc(-c2nc(Nc3ccc4[nH]ncc4c3Cl)n(C)n2)ccc1OCC(=O)NCC(C)(C)O] | Method B, 2.91 min, m/z 500.5 [M + H]⁺ | ¹H NMR (400 MHz, DMSO-d₆) δ 13.37 (s, 1H), 8.46 (s, 1H), 8.09 (t, J = 1.2 Hz, 1H), 7.66 (t, J = 6.0 Hz, 1H), 7.61-7.52 (m, 2H), 7.42 (d, J = 1.9 Hz, 1H), 7.36 (dd, J = 8.3, 1.9 Hz, 1H), 6.96 (d, J = 8.5 Hz, 1H), 4.55 (d, J = 1.5 Hz, 3H), 3.82 (s, 3H), 3.77 (s, 3H), 3.10 (d, J = 6.0 Hz, 2H), 1.04 (s, 6H). |
| 208 | 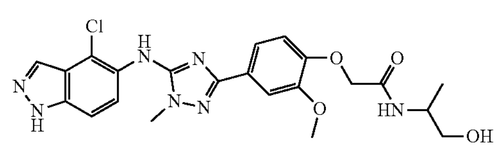 [SMILES: COc1cc(-c2nc(Nc3ccc4[nH]ncc4c3Cl)n(C)n2)ccc1OCC(=O)NC(C)CO] | Method B, 2.85 min, m/z 486.4 [M + H]⁺ | ¹H NMR (400 MHz, DMSO-d6) δ 13.38 (s, 1H), 8.46 (d, J = 2.0 Hz, 1H), 8.10 (d, J = 2.1 Hz, 1H), 7.67 (d, J = 8.1 Hz, 1H), 7.61-7.51 (m, 2H), 7.42 (d, J = 2.0 Hz, 1H), 7.36 (dt, J = 8.6, 2.1 Hz, 1H), 6.95 (dd, J = 8.5, 2.0 Hz, 1H), 4.81-4.73 (m, 1H), 4.55-4.41 (m, 2H), 3.92-3.72 (m, 7H), 3.34 (d, J = 2.0 Hz, 2H), 1.05 (dd, J = 6.7, 2.0 Hz, 3H). |

TABLE 15-continued

| Example | Structure | LC/MS | ¹H NMR |
|---|---|---|---|
| 209 | 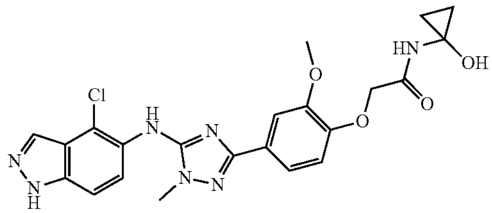 | Method B, 2.91 min, m/z 498.4 [M + H]⁺ | ¹H NMR (400 MHz, DMSO-d₆) δ 13.38 (s, 1H), 8.46 (s, 1H), 8.09 (d, J = 0.9 Hz, 1H), 7.89 (t, J = 5.7 Hz, 1H), 7.62-7.51 (m, 2H), 7.43 (d, J = 1.9 Hz, 1H), 7.37 (dd, J = 8.4, 1.9 Hz, 1H), 6.96 (d, J = 8.4 Hz, 1H), 5.41 (s, 1H), 4.52 (s, 2H), 3.82 (s, 3H), 3.77 (s, 3H), 3.28 (d, J = 5.7 Hz, 2H), 0.59-0.43 (m, 4H). |
| 210 | 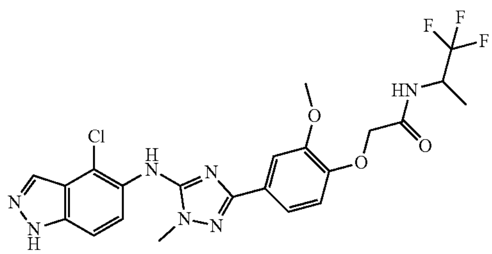 [SMILES: COc1cc(-c2nc(Nc3ccc4[nH]ncc4c3Cl)n(C)n2)ccc1OCC(=O)NC(C)C(F)(F)F] | Method B, 3.50 min, m/z 524.4 [M + H]⁺ | ¹H NMR (400 MHz, DMSO-d₆) δ 13.37 (s, 1H), 8.58 (d, J = 9.0 Hz, 1H), 8.46 (s, 1H), 8.09 (s, 1H), 7.56 (q, J = 8.9 Hz, 2H), 7.45-7.31 (m, 2H), 6.89 (d, J = 8.4 Hz, 1H), 4.67 (dt, J = 15.6, 7.6 Hz, 1H), 4.58 (s, 2H), 3.79 (d, J = 15.7 Hz, 5H), 1.28 (d, J = 7.0 Hz, 3H). |
| 211 | 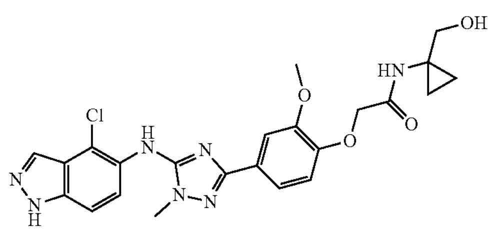 [SMILES: COc1cc(-c2nc(Nc3ccc4[nH]ncc4c3Cl)n(C)n2)ccc1OCC(=O)NC1(CO)CC1] | Method B, 2.85 min, m/z 498.4 [M + H]⁺ | ¹H NMR (400 MHz, DMSO-d₆) δ 13.37 (s, 1H), 8.45 (s, 1H), 8.11 (d, J = 17.0 Hz, 2H), 7.56 (q, J = 8.9 Hz, 2H), 7.44-7.31 (m, 2H), 6.90 (d, J = 8.4 Hz, 1H), 4.71 (t, J = 5.8 Hz, 1H), 4.42 (s, 2H), 3.79 (d, J = 15.2 Hz, 6H), 3.42 (d, J = 5.8 Hz, 2H), 0.77-0.66 (m, 2H), 0.67-0.56 (m, 2H). |
| 212 | 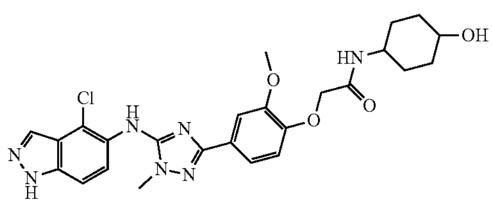 [SMILES: COc1cc(-c2nc(Nc3ccc4[nH]ncc4c3Cl)n(C)n2)ccc1OCC(=O)NC1CCC(O)CC1] | Method B, 2.92 min, m/z 526.4 [M + H]⁺ | ¹H NMR (400 MHz, DMSO-d₆) δ 13.38 (s, 1H), 8.45 (s, 1H), 8.09 (s, 1H), 7.72 (d, J = 7.9 Hz, 1H), 7.62-7.50 (m, 2H), 7.46-7.31 (m, 2H), 6.91 (d, J = 8.4 Hz, 1H), 4.54 (d, J = 4.4 Hz, 1H), 4.45 (s, 2H), 3.79 (d, J = 16.3 Hz, 6H), 3.39 (q, J = 7.0 Hz, 1H), 3.35 (s, 1H), 1.87-1.67 (m, 4H), 1.22 (q, J = 11.9, 11.4 Hz, 4H). |
| 213 | 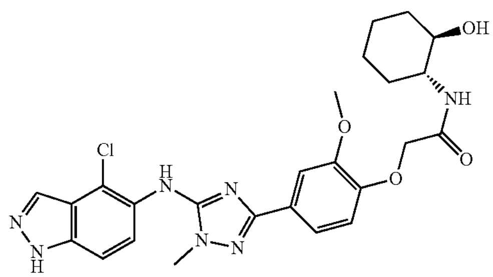 [SMILES: COc1cc(-c2nc(Nc3ccc4[nH]ncc4c3Cl)n(C)n2)ccc1OCC(=O)N[C@@H]1CCCC[C@H]1O] | Method B, 3.13 min, m/z 526.4 [M + H]⁺ | ¹H NMR (400 MHz, DMSO-d₆) δ 13.37 (s, 1H), 8.46 (s, 1H), 8.09 (s, 1H), 7.66 (d, J = 8.0 Hz, 1H), 7.56 (q, J = 8.9 Hz, 2H), 7.42 (d, J = 1.9 Hz, 1H), 7.36 (dd, J = 8.4, 1.9 Hz, 1H), 6.96 (d, J = 8.4 Hz, 1H), 4.62 (s, 1H), 4.48 (d, J = 2.7 Hz, 2H), 3.82 (s, 3H), 3.77 (s, 3H), 3.50-3.40 (m, 1H), 3.27 (t, J = 9.4 Hz, 1H), 1.88-1.76 (m, 2H), 1.59 (d, J = 21.6 Hz, 2H), 1.29-1.12 (m, 4H). |
| 214 | 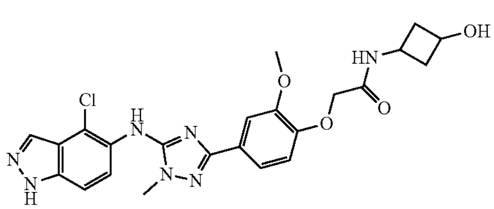 [SMILES: COc1cc(-c2nc(Nc3ccc4[nH]ncc4c3Cl)n(C)n2)ccc1OCC(=O)NC1CC(O)C1] | Method B, 2.81 min, m/z 498.4 [M + H]⁺ | ¹H NMR (400 MHz, CD₃OD) δ 8.10 (d, J = 0.9 Hz, 1H), 7.64-7.54 (m, 2H), 7.56-7.48 (m, 2H), 7.02 (dd, J = 8.5, 0.9 Hz, 1H), 4.53 (d, J = 4.0 Hz, 2H), 4.50-4.35 (m, 1H), 4.06-3.80 (m, 7H), 2.77-2.65 (m, 1H), 2.39-2.26 (m, 2H), 1.91 (dddd, J = 10.8, 9.0, 6.8, 2.9 Hz, 1H), 4 exchangeable NH's not seen.. |

TABLE 15-continued

| Example | Structure | LC/MS | ¹H NMR |
|---|---|---|---|
| 215 | 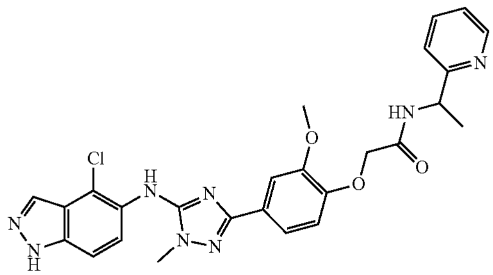 [SMILES: COc1cc(-c2nc(Nc3ccc4[nH]ncc4c3Cl)n(C)n2)ccc1OCC(=O)NC(C)c1ccccn1] | Method B, 2.86 min, m/z 533.4 [M + H]⁺ | ¹H NMR (400 MHz, DMSO-d₆) δ 13.37 (s, 1H), 8.57-8.51 (m, 1H), 8.45 (d, J = 10.8 Hz, 2H), 8.09 (s, 1H), 7.76 (td, J = 7.6, 1.8 Hz, 1H), 7.56 (q, J = 8.8 Hz, 2H), 7.45-7.33 (m, 3H), 7.27 (ddd, J = 7.5, 4.8, 1.1 Hz, 1H), 6.97 (d, J = 8.4 Hz, 1H), 5.04 (p, J = 7.0 Hz, 1H), 4.57 (s, 2H), 3.80 (d, J = 19.0 Hz, 6H), 1.40 (d, J = 6.9 Hz, 3H). |
| 216 | 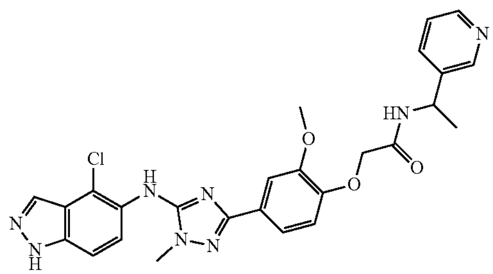 [SMILES: COc1cc(-c2nc(Nc3ccc4[nH]ncc4c3Cl)n(C)n2)ccc1OCC(=O)NC(C)c1cccnc1] | Method B, 2.62 min, m/z 533.4 [M + H]⁺ | ¹H NMR (400 MHz, DMSO-d₆) δ 13.38 (s, 1H), 8.58-8.48 (m 2H), 8.49-8.41 (m, 2H), 8.09 (s, 1H), 7.72 (dt, J = 7.9, 2.0 Hz, 1H), 7.56 (q, J = 8.9 Hz, 2H), 7.42 (d, J = 1.9 Hz, 1H), 7.38-7.30 (m, 2H), 6.91 (d, J = 8.4 Hz, 1H), 5.02 (p, J = 7.1 Hz, 1H), 4.54 (s, 2H), 3.78 (d, J = 8.6 Hz, 6H), 1.43 (d, J = 7.1 Hz, 3H). |
| 217 | 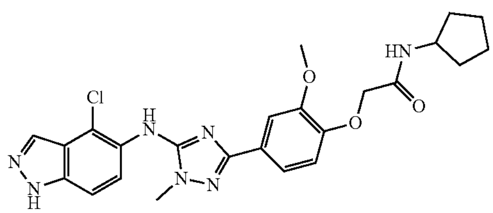 [SMILES: COc1cc(-c2nc(Nc3ccc4[nH]ncc4c3Cl)n(C)n2)ccc1OCC(=O)NC1CCCC1] | Method B, 3.48 min, m/z 496.4 [M + H]⁺ | ¹H NMR (400 MHz, DMSO-d₆) δ 13.37 (s, 1H), 8.45 (s, 1H), 8.09 (s, 1H), 7.84 (d, J = 7.5 Hz, 1H), 7.56 (q, J = 8.8 Hz, 2H), 7.44-7.32 (m, 2H), 6.92 (d, J = 8.4 Hz, 1H), 4.46 (s, 2H), 4.05 (dq, J = 14.0, 7.0 Hz, 1H), 3.79 (d, J = 17.0 Hz, 5H), 1.80 (dt, J = 12.2, 6.1 Hz, 2H), 1.63 (s, 2H), 1.58-1.46 (m, 2H), 1.49-1.33 (m, 2H), 1 exchangeable NH not seen. |
| 218 | 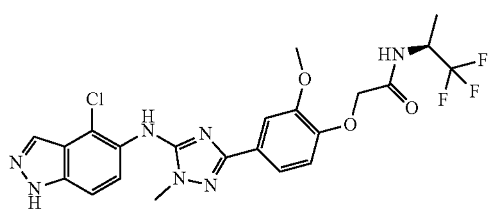 [SMILES: COc1cc(-c2nc(Nc3ccc4[nH]ncc4c3Cl)n(C)n2)ccc1OCC(=O)N[C@@H](C)C(F)(F)F] | Method B, 3.51 min, m/z 524.4 [M + H]⁺ | ¹H NMR (400 MHz, DMSO-d₆) δ 13.38 (s, 1H), 8.59 (d, J = 9.0 Hz, 1H), 8.46 (s, 1H), 8.09 (s, 1H), 7.61-7.50 (m, 2H), 7.42 (d, J = 1.9 Hz, 1H), 7.35 (dd, J = 8.4, 1.9 Hz, 1H), 6.89 (d, J = 8.4 Hz, 1H), 4.66 (dq, J = 15.7, 7.8 Hz, 1H), 4.58 (s, 2H), 3.79 (d, J = 15.4 Hz, 6H), 1.27 (d, J = 7.1 Hz, 3H). |
| 219 | 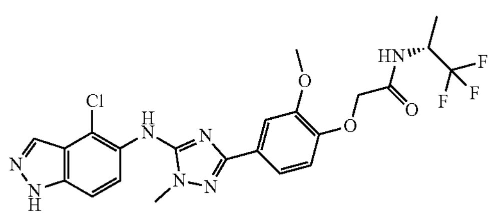 [SMILES: COc1cc(-c2nc(Nc3ccc4[nH]ncc4c3Cl)n(C)n2)ccc1OCC(=O)N[C@H](C)C(F)(F)F] | Method B, 3.05 min, m/z 524.4 [M + H]⁺ | ¹H NMR (400 MHz, DMSO-d₆) 13.38 (s, 1H), 8.59 (d, J = 9.0 Hz, 1H), 8.46 (s, 1H), 8.09 (s, 1H), 7.61-7.50 (m, 2H), 7.42 (d, J = 1.9 Hz, 1H), 7.35 (dd, J = 8.4, 1.9 Hz, 1H), 6.89 (d, J = 8.4 Hz, 1H), 4.66 (dq, J = 15.7, 7.8 Hz, 1H), 4.58 (s, 2H), 3.79 (d, J = 15.4 Hz, 6H), 1.27 (d, J = 7.1 Hz, 3H). |

General Method H:

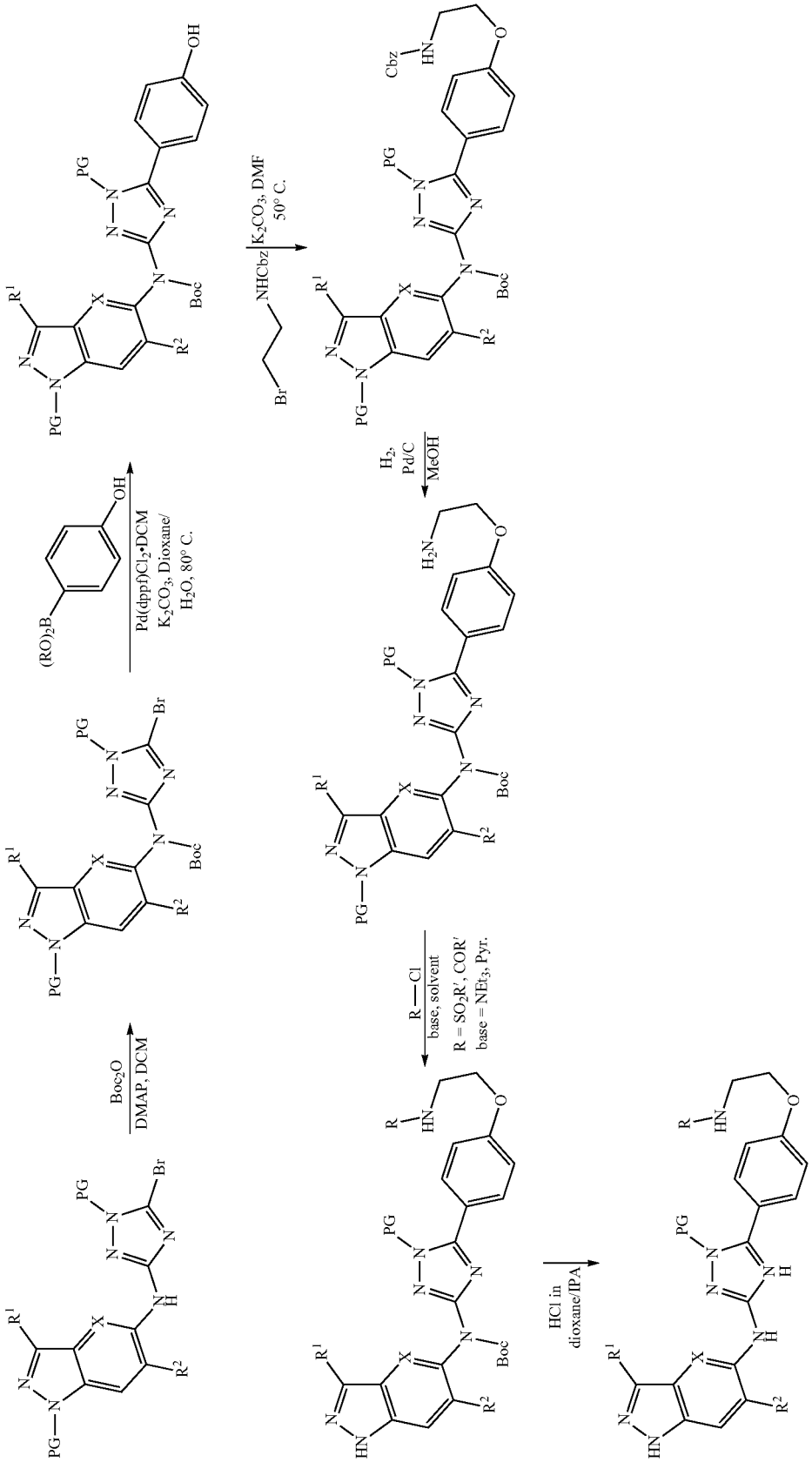

A method for preparing a compound of the invention is given below. Further compounds that can be prepared in a similar manner using commercially available sulfonyl or acid chlorides using general Method H are given in Table 16.

Example 220: N-[2-[4-[5-(1H-indazol-5-ylamino)-4H-1,2,4-triazol-3-yl]phenoxy]ethyl]methanesulfonamide

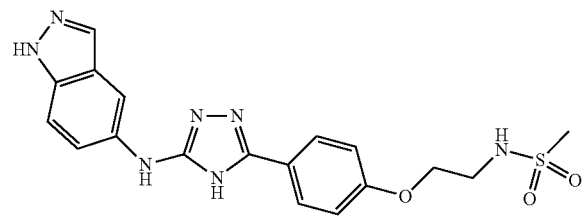 [SMILES: CS(=O)(=O)NCCOc1ccc(-c2nnc(Nc3ccc4[nH]ncc4c3)[nH]2)cc1]

A solution of tert-butyl N-[5-[4-[2-(methanesulfonamido)ethoxy]phenyl]-1-tetrahydropyran-2-yl-1,2,4-triazol-3-yl]-N-(1-tetrahydropyran-2-ylindazol-5-yl)carbamate (65 mg, 0.10 mmol) in hydrochloric acid (4 M in dioxane, 4.0 mL, 16.0 mmol) and IPA (2 mL) was stirred at r.t. overnight. The solvents were removed under reduced pressure and the residue purified by preparative HPLC to give N-[2-[4-[5-(1H-indazol-5-ylamino)-4H-1,2,4-triazol-3-yl]phenoxy]ethyl]methanesulfonamide (14 mg, 0.03 mmol, 36% yield) as a white solid. LC-MS (ES$^+$, Method E): 5.43 min, m/z 414.0 [M+H]$^+$. $^1$H NMR (400 MHz, DMSO-d$_6$): δ 13.39 (br s, 1H), 12.80 (s, 1H), 9.15 (s, 1H), 8.10 (s, 1H), 7.94 (s, 1H), 7.92 (d, 2H), 7.42 (s, 2H), 7.32 (s, 1H), 7.10 (d, J=8.5 Hz, 2H), 4.11 (t, J=5.5 Hz, 2H), 3.37 (t, J=5.5 Hz, 2H), 2.97 (s, 3H).

Step 1: tert-butyl N-(5-bromo-1-tetrahydropyran-2-yl-1,2,4-triazol-3-yl)-N-(1-tetrahydropyran-2-ylindazol-5-yl)carbamate

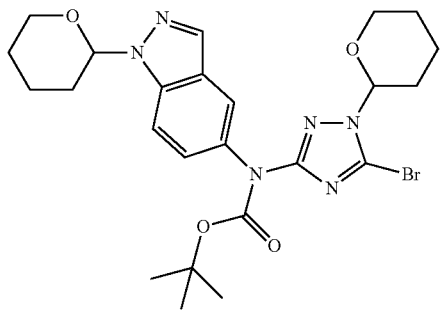 [SMILES: CC(C)(C)OC(=O)N(c1ccc2c(cnn2C2CCCCO2)c1)c1nc(Br)n(C2CCCCO2)n1]

To a stirred solution of N-(5-bromo-1-tetrahydropyran-2-yl-1,2,4-triazol-3-yl)-1-tetrahydropyran-2-yl-indazol-5-amine (500 mg, 1.12 mmol) in DCM (12.5 mL) was added di-tert-butyl dicarbonate (732 mg, 3.35 mmol) and DMAP (14 mg, 0.11 mmol) and the reaction stirred at r.t. overnight. The reaction mixture was diluted with water (10 mL), the layers separated and the aqueous portion extracted with DCM (2×10 mL). The combined organics were dried (phase separator) and concentrated in vacuo. The crude product was purified by flash column chromatography (SiO$_2$, eluting with 10-60% EtOAc in Pet. Ether) giving tert-butyl N-(5-bromo-1-tetrahydropyran-2-yl-1,2,4-triazol-3-yl)-N-(1-tetrahydropyran-2-ylindazol-5-yl)carbamate (607 mg, 1.11 mmol, 99% yield) as a yellow foam. LC-MS (ES$^+$, Method C): 3.78 min, m/z 549.0 [M+H]$^+$. $^1$H NMR (400 MHz, CDCl$_3$): δ 7.99 (d, J=1.0 Hz, 1H), 7.72 (t, J=1.5 Hz, 1H), 7.58 (dq, J=9.0, 1.0 Hz, 1H), 7.42 (dt, J=9.0, 2.0 Hz, 1H), 5.70 (dd, J=9.0, 3.0 Hz, 1H), 5.42 (ddd, J=9.0, 3.0, 1.5 Hz, 1H), 4.08-3.95 (m, 2H), 3.77-3.60 (m, 2H), 2.52 (m, 1H), 2.31 (m, 1H), 2.13 (m, 2H), 2.07 (m, 1H), 1.94 (m 1H), 1.77-1.61 (m, 6H), 1.45 (s, 9H).

Step 2: tert-butyl N-[5-(4-hydroxyphenyl)-1-tetrahydropyran-2-yl-1,2,4-triazol-3-yl]-N-(1-tetrahydropyran-2-ylindazol-5-yl)carbamate

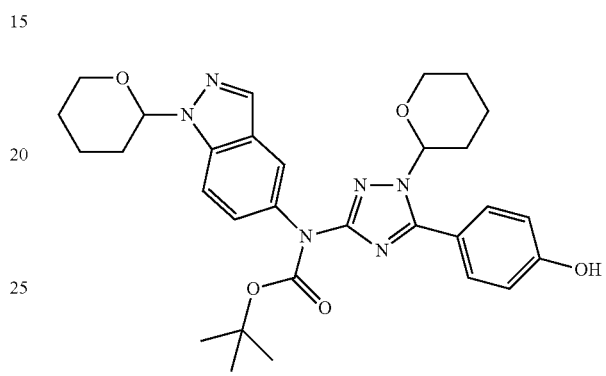

A vial was charged with tert-butyl N-(5-bromo-1-tetrahydropyran-2-yl-1,2,4-triazol-3-yl)-N-(1-tetrahydropyran-2-ylindazol-5-yl)carbamate (565 mg, 1.03 mmol), potassium carbonate (285 mg, 2.06 mmol) and 4-hydroxybenzene boronic acid (231 mg, 1.24 mmol). 1,4-dioxane (8 mL) and water (1.6 mL) were added and the mixture degassed with N$_2$ for 10 min. Pd(dppf)Cl$_2$·DCM complex (84 mg, 0.10 mmol) was added in a single portion, the vial sealed and the reaction heated at 80° C. overnight. The mixture was allowed to cool to r.t., diluted with EtOAc (15 mL) and water (10 mL) and filtered through Celite. The layers were separated, the aqueous portion extracted with EtOAc (2×10 mL) and the combined organics washed with brine (10 mL), dried (phase separator) and concentrated in vacuo. The crude material was purified by flash column chromatography (5102, eluting with 0-60% EtOAc in Pet. Ether) to give test-butyl N-[5-(4-hydroxyphenyl)-1-tetrahydropyran-2-yl-1,2,4-triazol-3-yl]-N-(1-tetrahydropyran-2-ylindazol-5-yl)carbamate (426 mg, 0.76 mmol, 74% yield) as a white foam. LC-MS (ES$^+$, Method C): 3.41 min, m/z 561.1 [M+H]$^+$ Step 3: tert-butyl N-[5-[4-[2-(benzyloxycarbonylamino)ethoxy]phenyl]-1-tetrahydropyran-2-yl-1,2,4-triazol-3-yl]-N-(1-tetrahydropyran-2-ylindazol-5-yl)carbamate

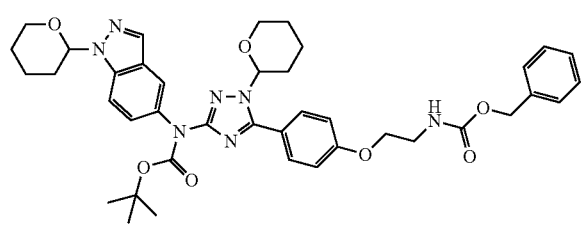 [SMILES: CC(C)(C)OC(=O)N(c1ccc2c(cnn2C2CCCCO2)c1)c1nc(-c2ccc(OCCNC(=O)OCc3ccccc3)cc2)n(C2CCCCO2)n1]

To a stirred solution of tert-butyl N-[5-(4-hydroxyphenyl)-1-tetrahydropyran-2-yl-1,2,4-triazol-3-yl]-N-(1-tetrahydropyran-2-ylindazol-5-yl)carbamate (426 mg, 0.76 mmol and potassium carbonate (210 mg, 1.52 mmol) in DMF (5 mL) was added benzyl (2-bromoethyl)carbamate (392 mg, 1.52 mmol) and the reaction stirred at r.t. overnight. Further equivalents of benzyl (2-bromoethyl)carbamate (190 mg, 0.75 mmol) were added and the reaction heated at 50° C. for a further 4 h. The mixture was allowed to cool to r.t. and the solvents removed under reduced pressure. The residue was partitioned between EtOAc (20 mL) and water (20 mL), the layers separated and the aqueous portion back-extracted with EtOAc (3×10 mL). The combined organics were dried (phase separator) and concentrated in vacuo. The chide product was purified by flash column chromatography (SiO₂, eluting with 10-60% EtOAc in Pet. Ether) to give tert-butyl N-[5-[4-[2-(benzyloxycarbonylamino)ethoxy]phenyl]-1-tetrahydropyran-2-yl-1,2,4-triazol-3-yl]-N-(1-tetrahydropyran-2-ylindazol-5-yl)carbamate (423 mg, 0.57 mmol, 75% yield) as a white foam. LC-MS (ES⁺, Method C): 4.05 min, m/z 738.3 [M+H]⁺

Step 4: tert-butyl N-[5-[4-(2-aminoethoxy)phenyl]-1-tetrahydropyran-2-yl-1,2,4-triazol-3-yl]-N-(1-tetrahydropyran-2-ylindazol-5-yl)carbamate

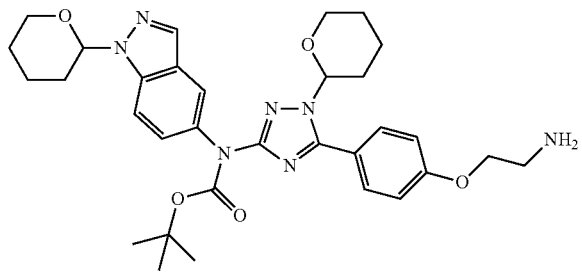 [SMILES: CC(C)(C)OC(=O)N(c1ccc2c(cnn2C2CCCCO2)c1)c1nc(-c2ccc(OCCN)cc2)n(C2CCCCO2)n1]

A slurry of paladium on carbon (10 wt %, 40 mg, 0.21 mmol) in DCM (0.2 mL) and methanol (2 mL) was added to a stirred solution of tert-butyl N-[5-[4-[2-(benzyloxycarbonylamino)ethoxy]phenyl]-1-tetrahydropyran-2-yl-1,2,4-triazol-3-yl]-N-(1-tetrahydropyran-2-ylindazol-5-yl)carbamate (399 mg, 0.54 mmol) in methanol (10 mL). The reaction was stirred under an atmosphere of H2 at r.t. overnight. The mixture was filtered through Celite (eluting with EtOAc) and the filtrate concentrated under reduced pressure to give tert-butyl N-[5-[4-(2-aminoethoxy)phenyl]-1-tetrahydropyran-2-yl-1,2,4-triazol-3-yl]-N-(1-tetrahydropyran-2-ylindazol-5-yl)carbamate (273 mg, 0.41 mmol, 75% yield) as a yellow glassy solid. LC-MS (ES⁺, Method C): 2.42 min, m/z 604.1 [M+H]⁺

Step 5: tert-butyl N-[5-[4-[2-(methanesulfonamido)ethoxy]phenyl]-1-tetrahydropyran-2-yl-1,2,4-triazol-3-yl]-N-(1-tetrahydropyran-2-ylindazol-5-yl)carbamate

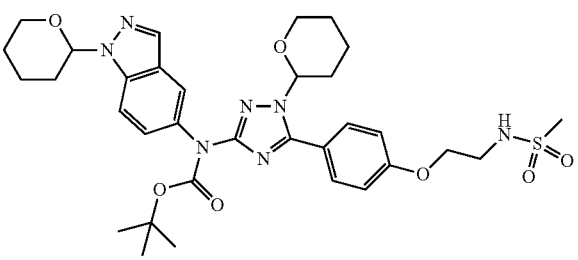 [SMILES: CC(C)(C)OC(=O)N(c1ccc2c(cnn2C2CCCCO2)c1)c1nc(-c2ccc(OCCNS(C)(=O)=O)cc2)n(C2CCCCO2)n1]

To a stirred solution of tert-butyl N-[5-[4-(2-aminoethoxy)phenyl]-1-tetrahydropyran-2-yl-1,2,4-triazol-3-yl]-N-(1-tetrahydropyran-2-ylindazol-5-yl)carbamate (80 mg, 0.13 mmol) and triethylamine (55 μL, 0.40 mmol) in DCM (2 mL) was added methanesulfonyl chloride (20 μL, 0.20 mmol) and the reaction stirred at r.t. for 1 h. The reaction was quenched with water (10 mL), the layers separated and the aqueous portion extracted with DCM (2×10 mL). The combined organics were dried (phase separator) and concentrated. The crude product was purified by flash column chromatography (SiO₂, eluting with 40-90% EtOAc in Pet. Ether) to give tert-butyl N-[5-[4-[2-(methanesulfonamido)ethoxy]phenyl]-1-tetrahydropyran-2-yl-1,2,4-triazol-3-yl]-N-(1-tetrahydropyran-2-ylindazol-5-yl)carbamate (65 mg, 0.09 mmol, 72% yield) as a white glassy solid. LC-MS (ES⁺, Method C): 3.44 min, m/z 682.0 [M+H]⁺

Compounds prepared in a similar manner to that set out above are given below in Table 16 intermediates.

TABLE 16

| Example | Structure | LC/MS | ¹H NMR |
| --- | --- | --- | --- |
| 221 | 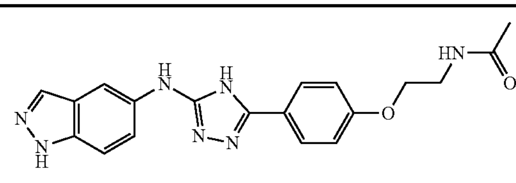 | Method E, 5.08 min, m/z 378.0 [M + H]⁺ | ¹H NMR (400 MHz, DMSO-d₆) δ 13.41 (s, 1H), 12.79 (s, 1H), 9.13 (s, 1H), 8.12 (d, J = 11.4, 5.9 Hz, 2H), 7.94 (s, 1H), 7.92-7.88 (m, 2H), 7.42 (s, 2H), 7.09 (d, J = 8.3 Hz, 2H), 4.05 (t, J = 5.7 Hz, 2H), 3.43 (q, J = 5.6 Hz, 2H), 1.84 (s, 3H). |
| 222 | 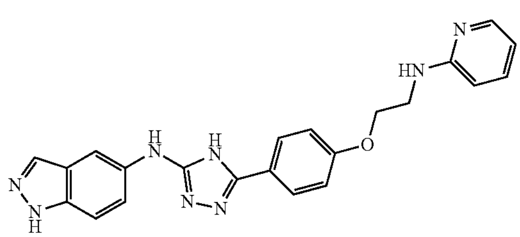 [SMILES: c1ccc(NCCOc2ccc(-c3nnc(Nc4ccc5[nH]ncc5c4)[nH]3)cc2)nc1] | Method E, 4.84 min, m/z 413.04 [M + H]⁺ | ¹H NMR (400 MHz, CD₃OD) δ 8.16 (d, J = 1.0 Hz, 1H), 7.99-7.91 (m, 2H), 7.91-7.86 (m, 3H), 7.70 (dt, J = 9.0, 0.9 Hz, 1H), 7.46 (dd, J = 8.9, 2.0 Hz, 1H), 7.20-7.10 (m, 3H), 6.95 (ddd, J = 7.6, 6.5, 1.1 Hz, 1H), 4.36 (t, J = 5.0 Hz, 2H), 3.87 (t, J = 5.0 Hz, 2H). 4 NH's not observed. |

TABLE 16-continued

| Example | Structure | LC/MS | $^1$H NMR |
|---|---|---|---|
| 223 | 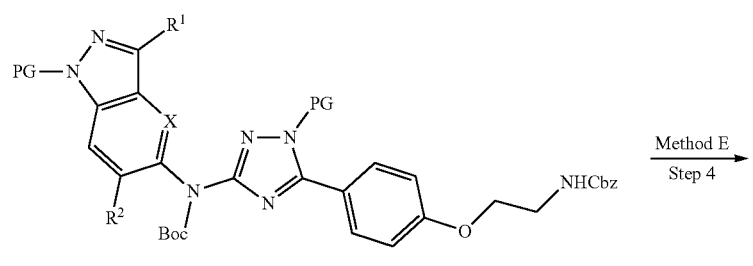 | Method E, 6.03 min, m/z 420.1 [M + H]$^+$ | $^1$H NMR (400 MHz, CD$_3$OD) δ 8.32 (s, 1H), 8.00 (s, 1H), 7.88 (d, J = 8.0 Hz, 2H), 7.74 (d, J = 8.4 Hz, 1H), 7.55 (d, J = 8.5 Hz, 1H), 7.14 (d, J = 8.0 Hz, 2H), 4.15 (d, J = 5.1 Hz, 2H), 3.61 (t, J = 5.0 Hz, 2H), 2.13-2.02 (m, 3H), 0.94 (d, J = 6.0 Hz, 6H). 4 NH's not observed. |

General Method I:

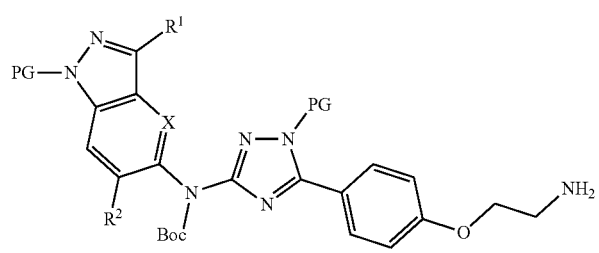

X = N, C—H, C—Cl
R$^1$ = H, Me
R$^2$ = H, Me
PG = THP, SEM, Boc

Method E
Step 4

(i) CDI, THF
(ii) R—NH$_2$, THF

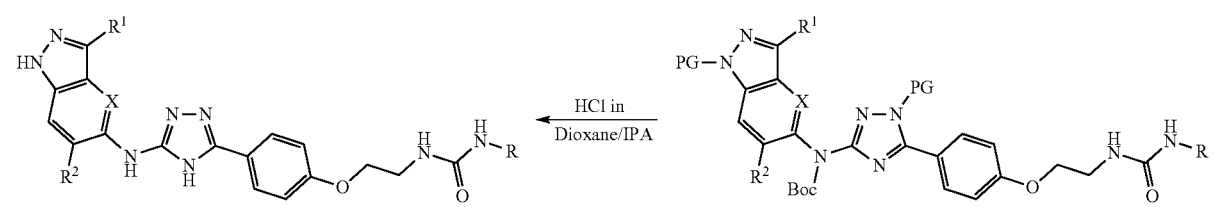

HCl in Dioxane/IPA

A method for preparing a compound of the invention is given below. Further compounds that can be prepared in a similar manner using general method I are given in Table 17.

Example 224: 1-[2-[4-[5-(1H-indazol-5-ylamino)-4H-1,2,4-triazol-3-yl]phenoxy]ethyl]-3-isopropyl-urea dihydrochloride

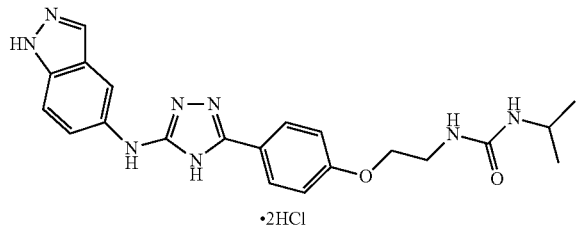 [SMILES: CC(C)NC(=O)NCCOc1ccc(-c2nnc(Nc3ccc4[nH]ncc4c3)[nH]2)cc1]

A solution of tert-butyl N-[5-[4-[2-(isopropylcarbamoylamino)ethoxy]phenyl]-1-tetrahydropyran-2-yl-1,2,4-triazol-3-yl]-N-(1-tetrahydropyran-2-ylindazol-5-yl)carbamate (55 mg, 0.08 mmol) in 4M hydrochloric acid in dioxane (4 mL, 16 mmol) and IPA (2 mL) was stirred at r.t. overnight. The solvents were removed under reduced pressure and the residue triturated with diethyl ether giving 1-[2-[4-[5-(1H-indazol-5-ylamino)-4H-1,2,4-triazol-3-yl]phenoxy]ethyl]-3-isopropyl-urea dihydrochloride (38 mg, 0.08 mmol, 96% yield) as a white solid. LC-MS (ES+, Method E): 5.64 min, m/z 421.1 [M+H]+. $^1$H NMR (400 MHz, DMSO-$d_6$): δ 9.70 (s, 1H), 8.04 (d, J=1.0 Hz, 1H), 8.01 (d, J=2.0 Hz, 1H), 7.97-7.92 (m, 2H), 7.51 (d, J=9.0 Hz, 1H), 7.42 (dd, J=9.0, 2.0 Hz, 1H), 7.14-7.09 (m, 2H), 4.02 (t, J=5.5 Hz, 2H), 3.67 (p, J=6.5 Hz, 1H), 3.38 (t, J=5.5 Hz, 2H), 1.02 (d, J=6.5 Hz, 6H).

Step 1: tert-butyl N-[5-[4-[2-(isopropylcarbamoylamino)ethoxy]phenyl]-1-tetrahydropyran-2-yl-1,2,4-triazol-3-yl]-N-(1-tetrahydropyran-2-ylindazol-5-yl)carbamate

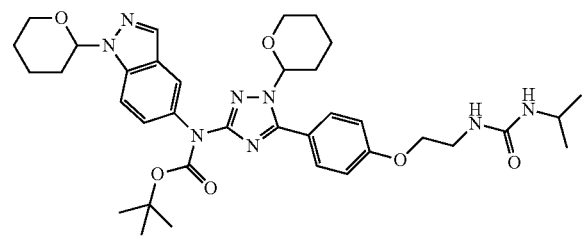 [SMILES: CC(C)NC(=O)NCCOc1ccc(-c2nc(N(C(=O)OC(C)(C)C)c3ccc4c(cnn4C4CCCCO4)c3)nn2C2CCCCO2)cc1]

To a stirred solution of tert-butyl N-[5-[4-(2-aminoethoxy)phenyl]-1-tetrahydropyran-2-yl-1,2,4-triazol-3-yl]-N-(1-tetrahydropyran-2-ylindazol-5-yl)carbamate (80 mg, 0.13 mmol) in THF (2 mL) was added 1,1'-carbonyldiimidazole (43 mg, 0.27 mmol) and the reaction stirred at r.t. for 2 h. 2-Aminopropane (46 µL, 0.54 mmol) was added and the reaction mixture was stirred at r.t. overnight. The solvents were removed under reduced pressure and the residue was partitioned between in EtOAc (10 mL) and water (10 mL). The layers were separated and the aqueous portion extracted with EtOAc (2×10 mL). The combined organics were washed with brine (10 mL), dried (phase separator) and concentrated. The crude product was purified by flash column chromatography (SiO$_2$, eluting with 50-90% EtOAc in Pet. Ether) to give tert-butyl N-[5-[4-[2-(isopropylcarbamoylamino)ethoxy]phenyl]-1-tetrahydropyran-2-yl-1,2,4-triazol-3-yl]-N-(1-tetrahydropyran-2-ylindazol-5-yl)carbamate (50 mg, 0.07 mmol, 55% yield) as a gummy solid. UPLC-MS (ES+, Method A): 1.97 min, m/z 689.6 [M+H]+.

Compounds prepared in a similar manner to that set out above are given below in Table 17.

TABLE 17

| Example | Structure | LC/MS | $^1$H NMR |
|---|---|---|---|
| 225 | 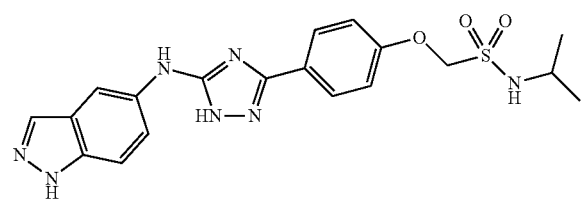 | Method B, 5.61 min, m/z 433.1 [M + H]+ | $^1$H NMR (400 MHz, DMSO-$d_6$, @ 353K) δ 13.17 (s, 1H), 12.55 (s, 1H), 8.66 (s, 1H), 8.01 (s, 1H), 7.96-7.86 (m, 3H), 7.53-7.36 (m, 2H), 7.07 (d, J = 8.3 Hz, 2H), 5.95 (s, 1H), 4.10 (t, J = 6.2 Hz, 2H), 3.44 (q, J = 6.1 Hz, 2H), 3.27-3.22 (m, 4H), 1.85-1.76 (m, 4H). |

Example 226: 1-[4-[5-(1H-indazol-5-ylamino)-4H-1,2,4-triazol-3-yl]phenoxy]-N-isopropyl-methanesulfonamide tert-Butyl N-[5-[4-(isopropylsulfamoylmethoxy)phenyl]-1-tetrahydropyran-2-yl-1,2,4-triazol-3-yl]-N-(1-tetrahydropyran-2-ylindazol-5-yl)carbamate (85 mg, 0.12 mmol) was dissolved in hydrogen chloride—1,4-dioxane solution, 4 M (3 mL, 12 mmol) and IPA (2 mL) and the reaction mixture was stirred at r.t. overnight. The solvents were removed under vacuum. The crude residue was purified by preparative HPLC (30-80% MeCN in H$_2$O) to give 1-[4-[5 (1H-indazol-5-ylamino)-4H-1,2,4-triazol-3-yl]phenoxy]-N-isopropyl-methanesulfonamide (12 mg, 0.03 mmol, 23% yield) as a white solid. LC-MS (ES+, Method E): 6.11 min, m/z 428.00 [M+H]+. 1H NMR (400 MHz, DMSO-d6) δ 13.50 (br s, 1H), 12.81 (s, 1H), 9.17 (s, 1H), 8.09 (d, J=1.5 Hz, 1H), 7.96-7.91 (m, 3H), 7.52 (s, 1H), 7.42 (d, J=1.7 Hz, 2H), 7.28-7.21 (m, 2H), 5.22 (s, 2H), 3.53 (m, J=6.6 Hz, 1H), 1.11 (d, J=6.6 Hz, 6H).

Step 1: 1-chloro-N-isopropyl-methanesulfonamide

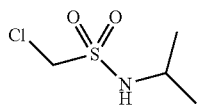

A solution of chloromesyl chloride (0.12 mL, 1.3 mmol) in ether (4 mL) was added to a stirred solution of 2-aminopropane (0.12 mL, 1.37 mmol) and 4-methylmorpholine (0.16 mL, 1.44 mmol) in ether (2 mL) at 0° C. and the reaction mixture was stirred at 0° C. for 5 h. The solution was diluted with EtOAc (10 mL) and 1 M HCl (5 mL). The layers were separated and the aqueous phase was extracted with EtOAc (2×5 mL). The combined organics were washed with brine (10 mL), dried (phase separator) and concentrated to give 1-chloro-N-isopropyl-methanesulfonamide (136 mg, 0.79 mmol, 58% yield) as a yellow oil. $^1$H NMR (400 MHz, CDCl$_3$) δ 4.48 (s, 2H), 4.45 (s, 1H), 3.75-3.63 (m, 1H), 1.28 (d, J=6.5 Hz, 6H).

Step 2: tert-butyl N-[5-[4-(isopropylsulfamoyl-methoxy)phenyl]-1-tetrahydropyran-2-yl-1,2,4-triazol-3-yl]-N-(1-tetrahydropyran-2-ylindazol-5-yl)carbamate

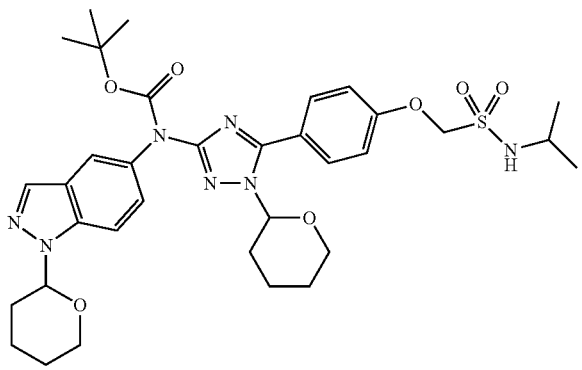 [SMILES: CC(C)NS(=O)(=O)COc1ccc(-c2nc(N(C(=O)OC(C)(C)C)c3ccc4c(cnn4C4CCCCO4)c3)nn2C2CCCCO2)cc1]

A mixture of tert-butyl N-[5-(4-hydroxyphenyl)-1-tetrahydropyran-2-yl-1,2,4-triazol-3-yl]-N-(1-tetrahydropyran-2-ylindazol-5-yl)carbamate (119 mg, 0.21 mmol), 1-chloro-N-isopropyl-methanesulfonamide (0.02 mL, 0.21 mmol) and potassium carbonate (29 mg, 0.21 mmol) in DMF (2 mL) was heated at 60° C. over the weekend. Potassium iodide (71 mg, 0.42 mmol) and further potassium carbonate (29 mg, 0.21 mmol) and 1-chloro-N-isopropyl-methanesulfonamide (0.02 mL, 0.21 mmol) were added and the reaction mixture was stirred at 60° C. for 7 days. Solvents were removed under vacuum and the residue was partitioned between EtOAc (10 mL) and water (10 mL). The layers were separated and the aqueous portion extracted with EtOAc (2×10 mL). The combined organics were washed with brine (10 mL), dried (phase sep.) and concentrated under vacuum. The crude product was purified by column chromatography (SiO$_2$, eluting with 45-55% EtOAc in Pet. Ether) giving tert-butyl N-[5-[4-(isopropylsulfamoylmethoxy)phenyl]-1-tetrahydropyran-2-yl-1,2,4-triazol-3-yl]-N-(1-tetrahydropyran-2-ylindazol-5-yl)carbamate (85 mg, 0.07 mmol, 32% yield) as a clear glassy solid. LC-MS (ES$^+$, Method C): 3.76 min, m/z 696.32 [M+H]$^+$

Example 227: N-(1-acetylazetidin-3-yl)-2-[4-[5-(1H-indazol-5-ylamino)-4H-1,2,4-triazol-3-yl]-2-methoxy-phenoxy]acetamide

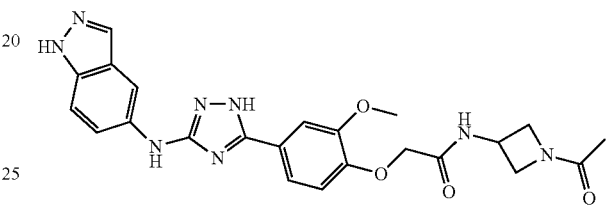

To a stirred solution of N-(1-acetylazetidin-3-yl)-2-[2-methoxy-4-[2-tetrahydropyran-2-yl-5-[(1-tetrahydropyran-2-ylindazol-5-yl)amino]-1,2,4-triazol-3-yl]phenoxy]acetamide (28 mg, 0.04 mmol) in DCM (3 mL) at room temp under nitrogen was added trifluoroacetic acid (66 μL, 0.87 mmol) and the reaction stirred at 25° C. overnight. The solvents were removed under reduced pressure and the residue purified by preparative HPLC (30-80% MeCN in H$_2$O) giving N-(1-acetylazetidin-3-yl)-2-[2-methoxy-4-[2-tetrahydropyran-2-yl-5-[(1-tetrahydropyran-2-ylindazol-5-yl)amino]-1,2,4-triazol-3-yl]phenoxy]acetamide (28 mg, 0.04 mmol) as an off-white solid. LC-MS (ES$^+$, Method E): 5.02 min, m/z 477.0 [M+H]$^+$. $^1$H NMR (400 MHz, DMSO-d$_6$, 353K): δ 13.25 (s, 1H), 12.55 (s, 1H), 8.70 (s, 1H), 8.37 (d, J=6.6 Hz, 1H), 8.06-7.95 (m, 1H), 7.91 (s, 1H), 7.62 (d, J=2.0 Hz, 1H), 7.54 (dd, J=8.3, 2.0 Hz, 1H), 7.45 (d, J=8.0 Hz, 2H), 7.09 (d, J=8.4 Hz, 1H), 4.59-4.49 (m, 3H), 4.41-3.94 (m, 3H), 3.91 (s, 3H), 3.84 (s, 1H), 1.76 (s, 3H).

Step 1: benzyl 3-[[2-[2-methoxy-4-[2-tetrahydropyran-2-yl-5-[(1-tetrahydropyran-2-ylindazol-5-yl)amino]-1,2,4-triazol-3-yl]phenoxy]acetyl]amino]azetidine-1-carboxylate

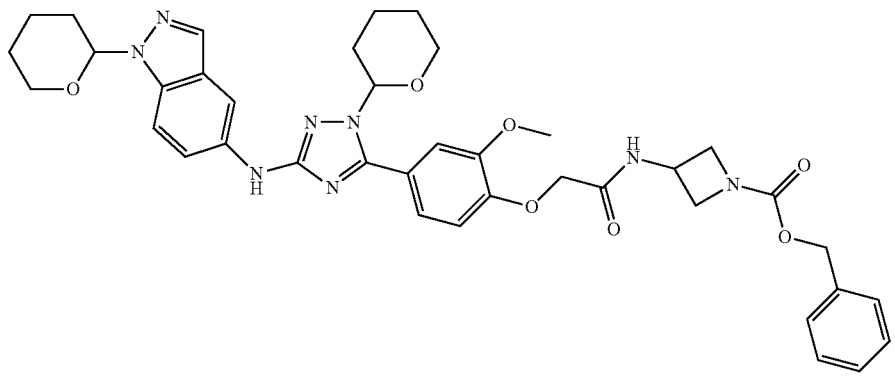 [SMILES: COc1cc(-c2nc(Nc3ccc4c(cnn4C4CCCCO4)c3)nn2C2CCCCO2)ccc1OCC(=O)NC1CN(C(=O)OCc2ccccc2)C1]

To a stirred solution of 2-[2-methoxy-4-[2-tetrahydropyran-2-yl-5-[(1-tetrahydropyran-2-ylindazol-5-yl)amino]-1,2,4-triazol-3-yl]phenoxy]acetic acid (302 mg, 0.55 mmol), 2-(7-aza-1H-benzotriazole-1-yl)-1,1,3,3-tetramethyluronium hexafluorophosphate (HATU) (272 mg, 0.72 mmol) in dry DMF (3 mL) at r.t. under nitrogen was added a solution of benzyl 3-amino-1-azetidinecarboxylate (206 µL, 0.83 mmol) in DMF (2 mL) and N,N-Diisopropylethylamine (287 µL, 1.65 mmol) and the reaction stirred at 25° C. overnight. The solvents were removed under reduced pressure and the residue taken up with EtOAc (15 mL) and washed with 5% KHSO$_4$ (2×10 mL) and brine (10 mL). The organics were dried (phase sep.) and concentrated. The crude material was purified by column chromatography (SiO$_2$, eluting with 50-100% EtOAc in Pet. Ether) to give benzyl 3-[[2-[2-methoxy-4-[2-tetrahydropyran-2-yl-5-[(1-tetrahydropyran-2-ylindazol-5-yl)amino]-1,2,4-triazol-3-yl]phenoxy]acetyl]amino]azetidine-1-carboxylate (214 mg, 0.29 mmol, 53% yield) as an oily solid. LC-MS (ES$^+$, Method C): 3.38 min, m/z 737.3 [M+H]$^+$ Step 2: N-azetidin-3-yl)-2-[2-methoxy-4-[2-tetrahydropyran-2-yl-5-[(1-tetrahydropyran-2-ylindazol-5-yl)amino]-1,2,4-triazol-3-yl]phenoxy]acetamide

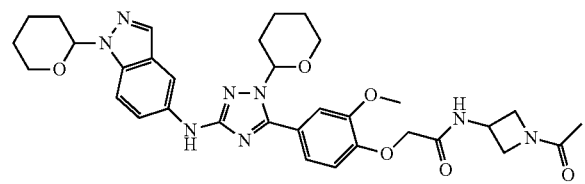 [SMILES: COc1cc(-c2nc(Nc3ccc4c(cnn4C4CCCCO4)c3)nn2C2CCCCO2)ccc1OCC(=O)NC1CN(C(C)=O)C1]

A suspension of benzyl 3-[[2-[2-methoxy-4-[2-tetrahydropyran-2-yl-5-[(1-tetrahydropyran-2-ylindazol-5-yl)amino]-1,2,4-triazol-3-yl]phenoxy]acetyl]amino]azetidine-1-carboxylate (214 mg, 0.29 mmol) and palladium, 10 wt. % on carbon powder, dry (21 mg, 0.20 mmol) in methanol (3 mL) was stirred under an atmosphere of hydrogen overnight. Further palladium, 10 wt. % on carbon powder (21 mg, 0.20 mmol) was added and the reaction stirred under hydrogen for a further 48 h. Further palladium, 10 wt. % on carbon powder (21 mg, 0.20 mmol) was added and reaction stirred under hydrogen for a further 24 h. The reaction mixture was filtered through celite (eluting with MeOH) and filtrate concentrated to give N-(azetidin-3-yl)-2-[2-methoxy-4-[2-tetrahydropyran-2-yl-5-[(1-tetrahydropyran-2-ylindazol-5-yl)amino]-1,2,4-triazol-3-yl]phenoxy]acetamide (52 mg, 0.09 mmol, 30% yield). LC-MS (ES+, Method D): 3.68 min, m/z 603.0 [M+H]$^+$.

Step 3: N-(1-acetylazetidin-3-yl)-2-[2-methoxy-4-[2-tetrahydropyran-2-yl-5-[(1-tetrahydropyran-2-ylindazol-5-yl)amino]-1,2,4-triazol-3-yl]phenoxy] acetamide To a stirred solution of N-(azetidin-3-yl)-2-[2-methoxy-4-[2-tetrahydropyran-2-yl-5-[(1-tetrahydropyran-2-ylindazol-5-yl)amino]-1,2,4-triazol-3-yl]phenoxy]acetamide (52 mg, 0.09 mmol) and triethylamine (36.09 µL, 0.26 mmol) in anhydrous DCM (2 mL) at 0° C. was added acetyl chloride (9.2 µL, 0.13 mmol) dropwise. The cooling bath was removed and the reaction stirred at room temp for 3 h. The mixture was diluted with DCM (15 mL) and washed with water (10 mL). The organics were dried (phase sep.) and concentrated and the crude product purified by column chromatography (SiO$_2$, eluting with 50-100% EtOAc in Pet. Ether) to give N-(1-acetylazetidin-3-yl)-2-[2-methoxy-4-[2-tetrahydropyran-2-yl-5-[(1-tetrahydropyran-2-ylindazol-5-yl)amino]-1,2,4-triazol-3-yl]phenoxy]acetamide (28 mg, 0.04 mmol, 50% yield) as an off-white oily solid. LC-MS (ES+, Method C): 2.47 min, m/z 645.7 [M+H]$^+$ Example 228: N-[5-[4-[(3-aminooxetan-3-yl)methoxy]phenyl]-4H-1,2,4-triazol-3-yl]-1H-indazol-5-amine Example 229: N-[5-[4-[[3-(ethylamino)oxetan-3-yl]methoxy]phenyl]-4H-1,2,4-triazol-3-yl]-1H-indazol-5-amine

Example 228

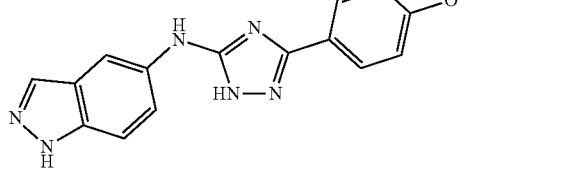

Example 229

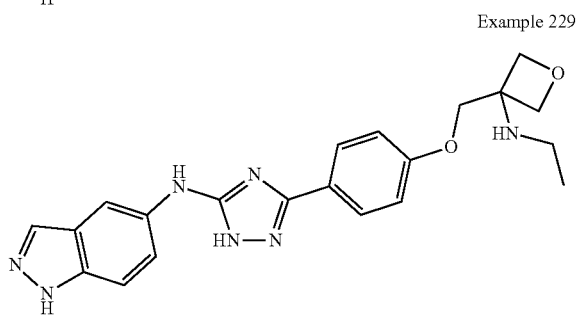

To a stirred solution of N-[5-[4-[(3-aminooxetan-3-yl)methoxy]phenyl]-1-tetrahydropyran-2-yl-1,2,4-triazol-3-yl]-1-tetrahydropyran-2-yl-indazol-5-amine (60 mg, 0.11 mmol) and N-[5-[4-[[3-(ethylamino)oxetan-3-yl]methoxy]phenyl]-1-tetrahydropyran-2-yl-1,2,4-triazol-3-yl]-1-tetrahydropyran-2-yl-indazol-5-amine (59 mg, 0.10 mmol) in dry DCM (3 mL) at r.t. under nitrogen was added trifluoroacetic acid (157.5 µL, 2.06 mmol) and the reaction stirred at 25° C. overnight. The mixture was purified by ion-exchange chromatography (SCX, eluting with 1 M NH$_3$ in MeOH) and preparative HPLC (20-50% MeCN in H$_2$O) giving N-[5-[4-[[3-(ethylamino)oxetan-3-yl]methoxy]phenyl]-4H-1,2,4-triazol-3-yl]-1H-indazol-5-amine (10.9 mg, 0.02 mmol, 20% yield) as a white solid and N-[5-[4-[(3-aminooxetan-3-yl]methoxy]phenyl]-4H-1,2,4-triazol-3-yl]-

1H-indazol-5-amine (19 mg, 0.04 mmol, 44% yield) as an off-white solid. Example 228: LC-MS (ES+, Method E): 4.25 min, m/z 378.1 [M+H]+. 1H NMR (400 MHz, DMSO-d6): δ 13.22 (s, 1H), 12.81 (s, 1H), 9.16 (s, 1H), 8.10 (s, 1H), 7.94 (d, J=2.5 Hz, 2H), 7.92 (s, 1H), 7.42 (d, J=1.5 Hz, 2H), 7.13 (d, J=9.0 Hz, 2H), 4.48 (d, J=6.0 Hz, 2H), 4.39 (d, J=6.0 Hz, 2H), 4.13 (s, 2H), 2.27 (s, 2H). Example 229: LC-MS (ES+, Method E): 4.44 min, m/z 405.9 [M+H]+. 1H NMR (400 MHz, DMSO-d6): δ 12.80 (s, 2H), 9.17 (s, 1H), 8.11 (t, J=1.5 Hz, 1H), 7.94 (s, 2H), 7.91 (d, J=2.5 Hz, 2H), 7.43-7.41 (m, 2H), 7.13 (d, J=9.0 Hz, 2H), 4.52 (d, J=6.0 Hz, 2H), 4.43 (d, J=6.0 Hz, 2H), 4.21 (s, 2H), 2.66-2.59 (m, 2H), 1.04 (t, J=7.0 Hz, 3H).

Step 1: benzyl N-[3-(hydroxymethyl)oxetan-3-yl]carbamate

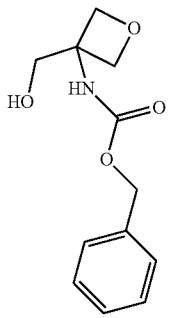

To a stirred solution of (3-amino-3-oxetanyl)methanol (103 mg, 1 mmol) in DCM (4.5 mL) was added a solution of sodium bicarbonate (252 mg, 3 mmol) in water (4.5 mL). Benzyl chloroformate (0.17 mL, 1.2 mmol) was added and the biphasic mixture stirred vigorously at 25° C. overnight. The mixture was diluted with water (5 mL) and extracted with DCM (3×15 mL). The combined organics were dried (phase separator) and concentrated and the crude product purified by column chromatography (SiO2, eluting with 50-100% EtOAc in Pet. Ether) to give benzyl N-[3-(hydroxymethyl)oxetan-3-yl]carbamate (182 mg, 0.77 mmol, 77% yield) as a colourless oily solid. LC-MS (ES+, Method C): 1.74 min, m/z 280.0 [M+Na]+. 1H NMR (400 MHz, CDCl3): δ 7.41-7.30 (m, 5H), 5.34 (s, 1H), 5.10 (s, 2H), 4.71 (d, J=6.5 Hz, 2H), 4.53 (d, J=6.5 Hz, 2H), 4.04 (s, 2H), 2.48 (s, 1H).

Step 2: [3-(benzyloxycarbonylamino)oxetan-3-yl]methyl methanesulfonate

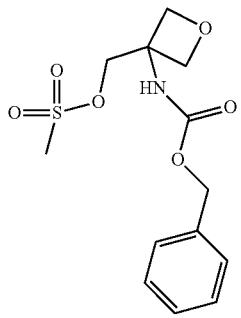 [SMILES: CS(=O)(=O)OCC1(NC(=O)OCc2ccccc2)COC1]

To a stirred solution of benzyl N-[3-(hydroxymethyl)oxetan-3-yl]carbamate (171 mg, 0.72 mmol) and triethylamine (301 μL, 2.16 mmol) in DCM (2 mL) at 0° C. under nitrogen was added methanesulfonyl chloride (84 μL, 1.08 mmol). The cooling bath was removed and the reaction stirred at 25° C. for 1.5 h. The reaction was quenched with H2O (10 mL) and extracted with DCM (3×15 mL). The combined organics were washed with brine (15 mL), dried (phase separator) and concentrated to give [3-(benzyloxycarbonylamino)oxetan-3-yl]methyl methanesulfonate (227 mg, 0.72 mmol, 100% yield). LC-MS (ES+, Method C): 2.32 min, m/z 316.1 [M+H]+

Step 3: benzyl N-[3-[(4-bromophenoxy)methyl]oxetan-3-yl]carbamate

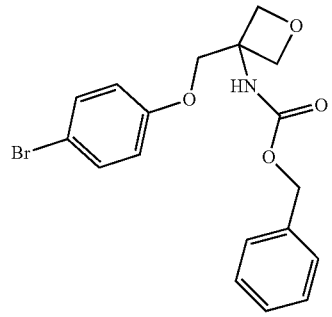 [SMILES: O=C(NC1(COc2ccc(Br)cc2)COC1)OCc1ccccc1]

A suspension of 4-bromophenol (96 mg, 0.55 mmol), [3-(benzyloxycarbonylamino)oxetan-3-yl]methyl methanesulfonate (227 mg, 0.72 mmol) and Potassium carbonate (230 mg, 1.66 mmol) in MeCN (5.5 mL) was heated at 80° C. under nitrogen overnight. The solvents were removed under reduced pressure and residue partitioned between water (15 mL) and EtOAc (20 mL). The layers were separated and the aqueous portion was extracted with EtOAc (2×20 mL). The combined organics were washed with water (20 mL) and brine (20 mL), dried (phase sep.) and concentrated. The crude product was purified by column chromatography (SiO2, eluting with 30-50% EtOAc in Pet. Ether) to give benzyl N-[3-[(4-bromophenoxy)methyl]oxetan-3-yl]carbamate (193 mg, 0.49 mmol, 89% yield) as a white solid. LC-MS (ES+, Method D): 6.02 min, m/z 392.9 [M+H]+. 1H NMR (400 MHz, CDCl3): δ 7.41-7.29 (m, 7H), 6.79 (d, J=8.5 Hz, 2H), 5.33 (s, 1H), 5.09 (s, 2H), 4.83 (d, J=6.5 Hz, 2H), 4.61 (d, J=6.5 Hz, 2H), 4.34 (s, 2H).

Step 4: benzyl N-[3-[[4-(4,4,5,5-tetramethyl-1,3,2-dioxaborolan-2-yl)phenoxy]methyl]oxetan-3-yl]carbamate

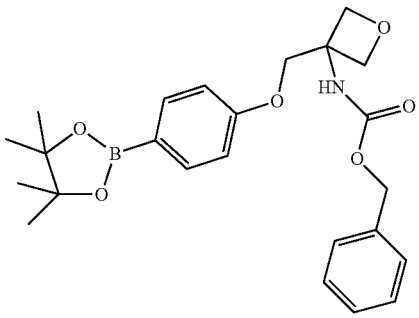 [SMILES: CC1(C)OB(c2ccc(OCC3(NC(=O)OCc4ccccc4)COC3)cc2)OC1(C)C]

A vial was charged with benzyl N-[3-[(4-bromophenoxy)methyl]oxetan-3-yl]carbamate (193 mg, 0.49 mmol), potassium acetate (251.53 mg, 2.56 mmol) and bis(pinacolato)diboron (282 mg, 1.11 mmol). 1,4-Dioxane (5 mL) was added and the solution degassed with nitrogen for 10 min. [1,1'-Bis(diphenylphosphino)ferrocene]palladium(II) chloride dichloromethane complex (70 mg, 0.09 mmol) was added, the sealed vial was heated at 100° C. overnight. The reaction mixture was cooled to r.t., filtered through a phase separator and the filtrate concentrated under reduced pressure to give benzyl N-[3-[[4-(4,4,5,5-tetramethyl-1,3,2-dioxaborolan-2-yl)phenoxy]methyl]oxetan-3-yl]carbamate (215 mg, 99% yield). LC-MS (ES+, Method C): 3.58 min, m/z 439.9 [M+H]+

Step 5: benzyl N-[3-[[4-[2-tetrahydropyran-2-yl-5-[(1-tetrahydropyran-2-ylindazol-5-yl)amino]-1,2,4-triazol-3-yl]phenoxy]methyl]oxetan-3-yl]carbamate

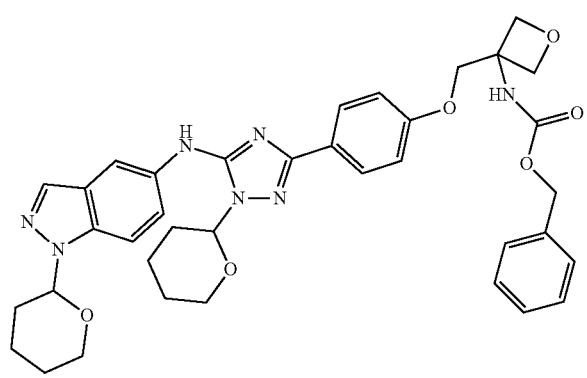 [SMILES: O=C(NC1(COc2ccc(-c3nc(Nc4ccc5c(cnn5C5CCCCO5)c4)n(C4CCCCO4)n3)cc2)COC1)OCc1ccccc1]

A vial was charged with N-(5-bromo-1-tetrahydropyran-2-yl-1,2,4-triazol-3-yl)-1-tetrahydropyran-2-yl-indazol-5-amine (169 mg, 0.38 mmol) and potassium carbonate (157 mg, 1.13 mmol). A solution of benzyl N-[3-[[4-(4,4,5,5-tetramethyl-1,3,2-dioxaborolan-2-yl)phenoxy]methyl]oxetan-3-yl]carbamate (216 mg, 0.49 mmol) in 1,4-dioxane (3 mL) and water (0.60 mL) was added and the solution degassed with nitrogen for 10 min. [1,1'-Bis(diphenylphosphino)ferrocene]palladium(II) chloride dichloromethane complex (31 mg, 0.04 mmol) was added, the sealed vial was heated at 80° C. overnight. The mixture was allowed to cool to r.t., degassed with nitrogen for 10 min and further [1,1'-bis(diphenylphosphino)ferrocene]palladium(II) chloride dichloromethane complex (31 mg, 0.04 mmol) added. The vial was resealed and the mixture heated at 80° C. overnight. The reaction mixture was filtered through celite (eluting with EtOAc) and the filtrate washed with water (15 mL). The aqueous portion was extracted with further EtOAc (2×15 mL) and the combined organics dried (phase sep) and concentrated. The crude product was purified by flash column chromatography (SiO2, eluting with 40-80% EtOAc in Pet. Ether) to give benzyl N-[3-[[4-[2-tetrahydropyran-2-yl-5-[(1-tetrahydropyran-2-ylindazol-5-yl)amino]-1,2,4-triazol-3-yl]phenoxy]methyl]oxetan-3-yl]carbamate (154 mg, 0.23 mmol, 60% yield) as a light brown oily solid. LC-MS (ES+, Method C): 3.60 min, m/z 680.3 [M+H]+

Step 6

N-[5-[4-[3-aminooxetan-3-yl)methoxy]phenyl]-1-tetrahydropyran-2-yl-1,2,4-triazol-3-yl]-1-tetrahydropyran-2-yl-indazol-5-amine N-[5-[4-[[3-(ethylamino)oxetan-3-yl]methoxy]phenyl]-1-tetrahydropyran-2-yl-1,2,4-triazol-3-yl]-1-tetrahydropyran-2-yl-indazol-5-amine

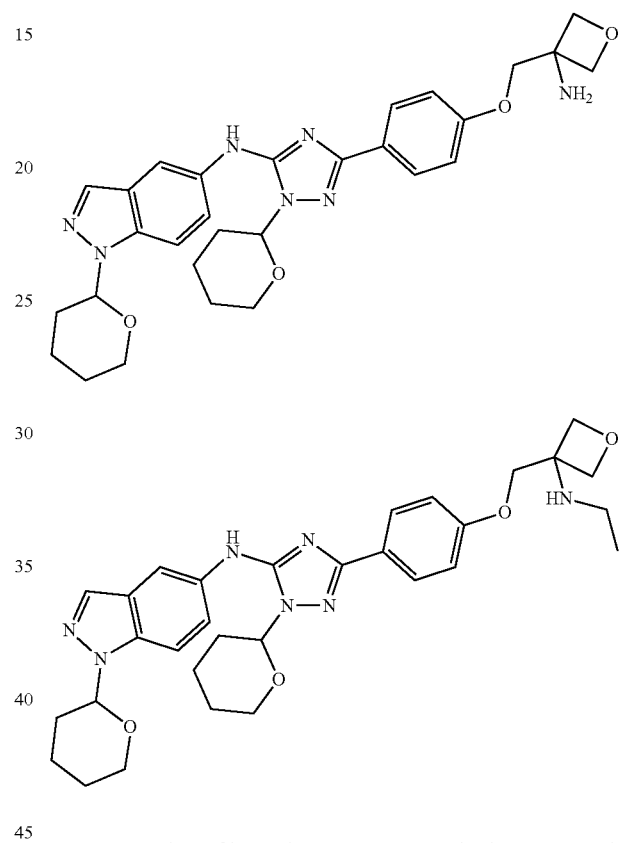

A suspension of benzyl N-[3-[[4-[2-tetrahydropyran-2-yl-5-[(1-tetrahydropyran-2-ylindazol-5-yl)amino]-1,2,4-triazol-3-yl]phenoxy]methyl]oxetan-3-yl]carbamate (154 mg, 0.23 mmol) and paladium, 10 wt. % on carbon powder, dry (15 mg, 0.14 mmol) in ethanol (3 mL) was stirred under an atmosphere of hydrogen overnight. Further paladium, 10 wt. % on carbon powder, dry (15 mg, 0.14 mmol) was added and reaction stirred under hydrogen for a further 4 h. The reaction mixture was filtered through celite (eluting with EtOH) and filtrate concentrated giving an inseparable mixture of N-[5-[4-[(3-aminooxetan-3-yl)methoxy]phenyl]-1-tetrahydropyran-2-yl-1,2,4-triazol-3-yl]-1-tetrahydropyran-2-yl-indazol-5-amine (60 mg, 0.11 mmol, 48% yield) and N-[5-[4-[[3-(ethylamino)oxetan-3-yl]methoxy]phenyl]-1-tetrahydropyran-2-yl-1,2,4-triazol-3-yl]-1-tetrahydropyran-2-yl-indazol-5-amine (59 mg, 0.10 mmol, 45% yield). LC-MS (ES+, Method C): 2.34 min, m/z 546.0 [M+H]+ (49%); 2.47 min, m/z 574.3 [M+H]+ (51%);

Example 230: N-[5-[4-[2-(isopropylamino)ethoxy]phenyl]-4H-1,2,4-triazol-3-yl]-1H-indazol-5-amine

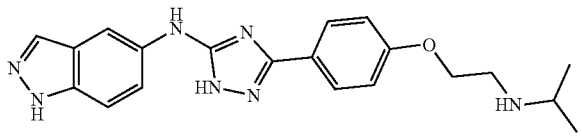 [SMILES: CC(C)NCCOc1ccc(-c2n[nH]c(Nc3ccc4[nH]ncc4c3)n2)cc1]

tert-Butyl N-[5-[4-[2-(isopropylamino)ethoxy]phenyl]-1-tetrahydropyran-2-yl-1,2,4-triazol-3-yl]-N-(1-tetrahydropyran-2-ylindazol-5-yl)carbamate (94 mg, 0.15 mmol) was dissolved in IPA (3 mL) and hydrogen chloride (4 M in 1,4-dioxane) (3.00 mL, 12 mmol) was added and the reaction mixture was stirred overnight at r.t. The solvents were removed under vacuum and the residue was triturated with diethyl ether (2×3 mL) and purified by SCX-2 column chromatography, eluting with 1M $NH_3$ in MeOH. The crude product was purified by preparative HPLC (30-80% MeCN in $H_2O$) to give N-[5-[4-[2-(isopropylamino)ethoxy]phenyl]-4H-1,2,4-triazol-3-yl]-1H-indazol-5-amine (5 mg, 0.01 mmol, 8% yield) as a white solid. LC-MS (ES$^+$, Method E): 4.72 min, m/z 378.1 [M+H]$^+$. $^1$H NMR (400 MHz, DMSO-$d_6$) δ 13.21 (s, 1H), 12.80 (s, 1H), 9.14 (s, 1H), 8.10 (d, J=1.4 Hz, 1H), 7.94 (s, 1H), 7.93-7.86 (m, 2H), 7.42 (d, J=1.4 Hz, 2H), 7.12-7.02 (m, 2H), 4.07 (t, J=5.8 Hz, 2H), 2.89 (t, J=5.7 Hz, 2H), 2.77 (hept, J=6.2 Hz, 1H), 1.00 (d, J=6.2 Hz, 6H) 1H exchangeable.

Step 1: tert-butyl N-[5-[4-[2-(isopropylamino)ethoxy]phenyl]-1-tetrahydropyran-2-yl-1,2,4-triazol-3-yl]-N-(1-tetrahydropyran-2-ylindazol-5-yl)carbamate

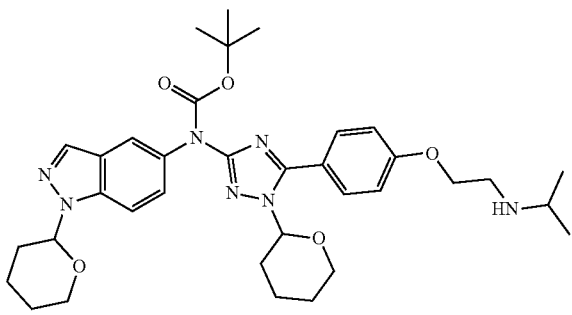 [SMILES: CC(C)NCCOc1ccc(-c2nc(N(C(=O)OC(C)(C)C)c3ccc4c(cnn4C4CCCCO4)c3)nn2C2CCCCO2)cc1]

Acetone (0.05 mL, 0.62 mmol) was added to a stirred solution of tert-butyl N-[5-[4-(2-aminoethoxy)phenyl]-1-tetrahydropyran-2-yl-1,2,4-triazol-3-yl]-N-(1-tetrahydropyran-2-ylindazol-5-yl)carbamate (75 mg, 0.12 mmol) and N,N-diisopropylethylamine (0.04 mL, 0.25 mmol) in methanol (8 mL). Sodium cyanoborohydride (31 mg, 0.50 mmol) and acetic acid (glacial) (0.01 mL, 0.25 mmol) were added and the reaction mixture was stirred at 25° C. overnight. Solvents were removed under vacuum and the residue was taken up in EtOAc (10 mL) and sat. $NaHCO_3$ solution (10 mL). The layers were separated and the aqueous portion back extracted with EtOAc (2×10 mL). The combined organic layers were washed with brine (10 mL), dried (phase sep.) and concentrated under vacuum to give tert-butyl N-[5-[4-[2-(isopropylamino)ethoxy]phenyl]-1-tetrahydropyran-2-yl-1,2,4-triazol-3-yl]-N-(1-tetrahydropyran-2-ylindazol-5-yl)carbamate (80 mg, 0.12 mmol, 100% yield) as a grey solid. LC-MS (ES$^+$, Method C): 3.21 min, m/z 646.13 [M+H]$^+$. $^1$H NMR (400 MHz, CDCl$_3$) δ 8.05-7.96 (m, 3H), 7.82-7.78 (m, 1H), 7.60-7.55 (m, 1H), 7.51 (ddd, J=8.9, 2.0, 1.1 Hz, 1H), 6.95-6.88 (m, 2H), 5.69 (dd, J=9.1, 2.8 Hz, 1H), 5.42 (dd, J=9.4, 2.7 Hz, 1H), 4.11 (dd, J=6.0, 4.6 Hz, 2H), 3.99 (d, J=11.4 Hz, 1H), 3.69 (dt, J=28.9, 10.4 Hz, 3H), 3.01 (t, J=5.2 Hz, 2H), 2.89 (p, J=6.2 Hz, 1H), 2.59-2.42 (m, 2H), 2.17 (d, J=3.5 Hz, 2H), 2.06 (s, 1H), 1.95 (d, J=13.3 Hz, 1H), 1.75-1.64 (m, 6H), 1.46 (s, 9H), 1.11 (d, J=6.2 Hz, 6H).

Example 231: [4-[5-(1H-indazol-5-ylamino)-1-methyl-1,2,4-triazol-3-yl]-2-methoxy-phenyl]methyl N-pyrrolidin-3-ylcarbamate

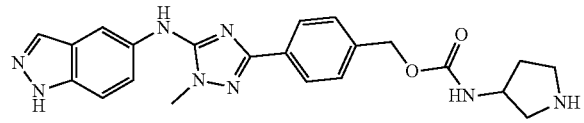 [SMILES: Cn1nc(-c2ccc(COC(=O)NC3CCNC3)cc2)nc1Nc1ccc2[nH]ncc2c1]

A solution of tert-butyl 3-[[2-methoxy-4-[1-methyl-5-[(1-tetrahydropyran-2-ylindazol-5-yl)amino]-1,2,4-triazol-3-yl]phenyl]methoxycarbonylamino]pyrrolidine-1-carboxylate (119 mg, 0.18 mmol) in DCM (1.2 mL) was treated with TFA (0.21 mL, 2.76 mmol) at 25° C. The reaction mixture was stirred for 48 h before k was diluted with sat. aq. $NaHCO_3$ and extracted with EtOAc (5×). The combined organic layers were dried ($Na_2SO_4$), filtered and concentrated. The crude product was purified by flash silica chromatography (12 g $SiO_2$, eluting with 10-100% MeOH in DCM) to give [4-[5-(1H-indazol-5-ylamino)-1-methyl-1,2,4-triazol-3-yl]-2-methoxy-phenyl]methyl N-pyrrolidin-3-ylcarbamate (36 mg, 0.08 mmol, 42% yield) as purple amorphous solid. UPLC-MS (ES$^+$, Method B): 2.54 min, m/z 463.4 [M+H]$^+$. $^1$H NMR (400 MHz, DMSO-$d_6$) δ 12.95 (br s, 1H), 8.99 (m, 1H), 8.19-8.15 (m, 1H), 8.03-8.01 (m, 1H), 7.60-7.49 (m, 3H), 7.42-7.32 (m, 1H), 5.26-4.92 (m, 2H), 3.94-3.85 (m, 4H), 3.81 (s, 3H), 3.44-3.22 (m, 1H), 3.22-3.09 (m, 1H), 2.99-2.91 (m, 1H), 1.96-1.88 (m, 1H), 1.66-1.59 (m, 1H). 3×NH not observed

Step 1: [2-methoxy-4-[1-methyl-5-[(1-tetrahydropyran-2-ylindazol-5-yl)amino]-1,2,4-triazol-3-yl]phenyl]methanol

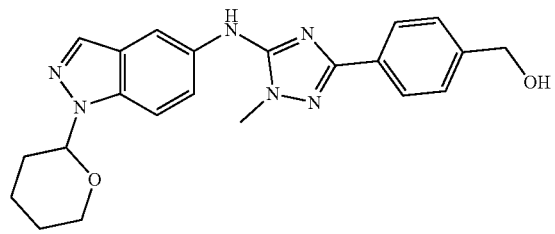 [SMILES: Cn1nc(-c2ccc(CO)cc2)nc1Nc1ccc2c(cnn2C2CCCCO2)c1]

A mixture of (4-bromo-2-methoxyphenyl)methanol (57 mg, 0.26 mmol), tetrahydroxydiborane (71 mg, 0.79 mmol) and 2-dicyclohexylphosphino-2',4',6'-triisopropylbiphenyl (12 mg, 0.03 mmol) was purged with nitrogen. Degassed ethanol (1.5 mL) was added and the solution was purged with nitrogen. XPhos Pd G2 (10 mg, 0.01 mmol) was added and the reaction mixture was purged with nitrogen again. The reaction was heated to 80° C. and stirred for 2 h. The reaction was cooled to r.t. A degassed 1.8 M potassium carbonate solution in water (0.44 mL, 0.79 mmol) was added, followed by a solution of N-(5-bromo-2-methyl-1,2,4-triazol-3-yl)-1-tetrahydropyran-2-yl-indazol-5-amine (100 mg, 0.26 mmol) in degassed ethanol (1 mL) and the mixture was purged with nitrogen. The reaction mixture was heated to 80° C. and left to stir for 16 h. The reaction mixture was diluted with methanol, filtered through a pad of Celite (washed with MeOH) and concentrated to provide crude product. The crude product was purified by flash silica chromatography (12 g SiO$_2$, eluting with 1.5-15% MeOH in DCM/DCM) to give [2-methoxy-4-[1-methyl-5-[(1-tetrahydropyran-2-ylindazol-5-yl)amino]-1,2,4-triazol-3-yl]phenyl]methanol (18 mg, 0.04 mmol, 16% yield) as brown amorphous solid. UPLC-MS (ES$^+$, Method A): 1.50 min, m/z 435.3 [M+H]$^+$.

Step 2: tert-butyl 3-[[2-methoxy-4-[1-methyl-5-[(1-tetrahydropyran-2-ylindazol-5-yl)amino]-1,2,4-triazol-3-yl]phenyl]methoxycarbonylamino]pyrrolidine-1-carboxylate

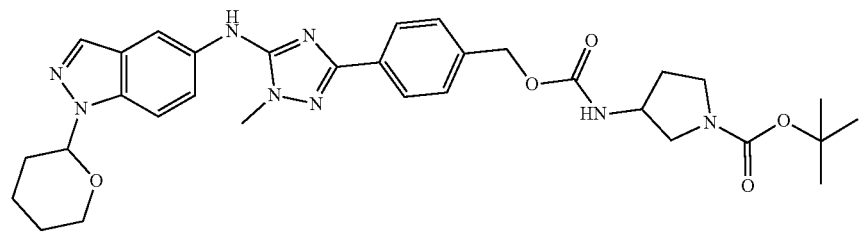 [SMILES: Cn1nc(-c2ccc(COC(=O)NC3CCN(C(=O)OC(C)(C)C)C3)cc2)nc1Nc1ccc2c(cnn2C2CCCCO2)c1]

A solution of (3R)-1-[(2-methyl-2-propanyl)oxy]carbonyl)-3-pyrrolidinecarboxylic add (51 mg, 024 mmol), diphenyl phosphoryl azide (0.06 mL, 0.27 mmol), triethylamine (0.04 mL, 0.29 mmol) in anhydrous toluene (0.50 mL) was stirred at 110° C. After 1 h, the reaction mixture was cooled to r.t. and added to a solution of [2-methoxy-4-[1-methyl-5-[(1-tetrahydropyran-2-ylindazol-5-yl)amino]-1,2,4-triazol-3-yl]phenyl]methanol (80 mg, 0.18 mmol) in anhydrous toluene (1 mL). The reaction mixture was heated to 110° C. and stirred for 72 h. The solution was diluted with sat. aq. NaHCO$_3$ and extracted with EtOAc (3×). The combined organic layers were dried (Na$_2$SO$_4$), filtered and concentrated in vacuo. The crude product was purified by flash silica chromatography (25 g SiO$_2$, eluting with 10-100% EtOAc in Heptane) to give tert-butyl 3-[[2-methoxy-4-[1-methyl-5-[(1-tetrahydropyran-2-ylindazol-5-yl)amino]-1,2,4-triazol-3-yl]phenyl]methoxycarbonylamino]pyrrolidine-1-carboxylate (116 mg, 0.18 mmol, 100% yield) as purple oil. UPLC-MS (ES$^+$, Method A): 1.85 min, m/z 647.5 [M+H]$^+$ Example 232: 2-[4-[5-(1H-indazol-5-ylamino)-2-methyl-1,2,4-triazol-3-yl]-2-methoxy-phenoxy]-N-isopropyl-acetamide

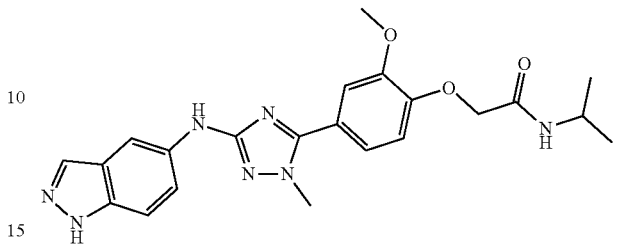

A solution of N-isopropyl-2-[2-methoxy-4-[2-methyl-5-[(1-tetrahydropyran-2-ylindazol-5-yl)amino]-1,2,4-triazol-3-yl]phenoxy]acetamide (185 mg, 0.36 mmol) and trifluoroacetic acid (0.41 mL, 5.34 mmol) in DCM (5 mL) was stirred for 16 h. The reaction mixture was concentrated and purified by flash chromatography on C-18 silica, eluting with 5-50% MeOH in water to give formic acid; 2-[4-[5-(1H-indazol-5-ylamino)-2-methyl-1,2,4-triazol-3-yl]-2-methoxy-phenoxy]-N-isopropyl-acetamide (60 mg, 0.12 mmol, 35% yield) as white amorphous solid. UPLC-MS (ES$^+$, Method B): 3.04 min, m/z 436.4 [M+H]$^+$. $^1$H NMR (400 MHz, DMSO-d$_6$) δ 12.78 (s, 1H), 9.14 (s, 1H), 8.08 (s, 1H), 7.94 (s, 1H), 7.83 (d, J=7.8 Hz, 1H), 7.40-7.35 (m, 3H), 7.31 (dd, J=8.3, 1.9 Hz, 1H), 7.05 (d, J=8.4 Hz, 1H), 4.54 (s, 2H), 3.97-3.89 (m, 1H), 3.90 (s, 3H), 3.87 (s, 3H), 1.10 (d, J=6.6 Hz, 6H).

Step 1: 2-[4-(5-amino-2-methyl-1,2,4-triazol-3-yl)-2-methoxy-phenoxy]-N-isopropyl-acetamide

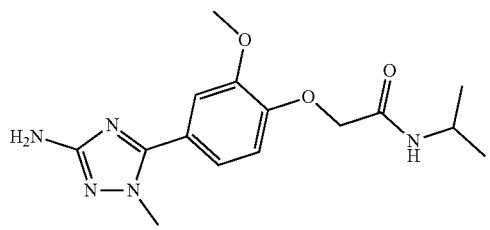 [SMILES: COc1cc(-c2nc(N)nn2C)ccc1OCC(=O)NC(C)C]

A mixture of N-isopropyl-2-[2-methoxy-4-(4,4,5,5-tetramethyl-1,3,2-dioxaborolan-2-yl)phenoxy]acetamide (646 mg, 1.85 mmol), potassium carbonate (383 mg, 2.77 mmol) and 5-bromo-1-methyl-1,2,4-triazol-3-amine (204 mg, 1.16 mmol) in 1,4-dioxane (3 mL) and water (0.75 mL) was purged with nitrogen. [1,1'-Bis(diphenylphosphino)ferrocene]palladium(II) chloride dichloromethane complex (94 mg, 0.12 mmol) was added and the reaction mixture was additionally purged with nitrogen and warmed to 80° C. The reaction mixture was left to stir for 22 h. The reaction mixture was diluted with EtOAc, passed through a pad of Celite (washed with EtOAc), filtered and concentrated to provide crude product. This was purified by flash silica chromatography (25 g SiO$_2$, eluting with 5-25% EtOAc in heptane) to give 2-[4-(5-amino-2-methyl-1,2,4-triazol-3-yl)-2-methoxy-phenoxy]-N-isopropyl-acetamide (316 mg, 0.99 mmol, 86% yield) as dark grey crystalline solid. UPLC-MS (ES$^+$, Method A): 1.13 min, m/z 320.3 [M+H]$^+$ Step Z: N-isopropyl-2-[2-methoxy-4-[2-methyl-5-[1-tetrahydropyran-2-ylindazol-5-yl)amino]-1,2,4-triazol-3-yl]phenoxy]acetamide

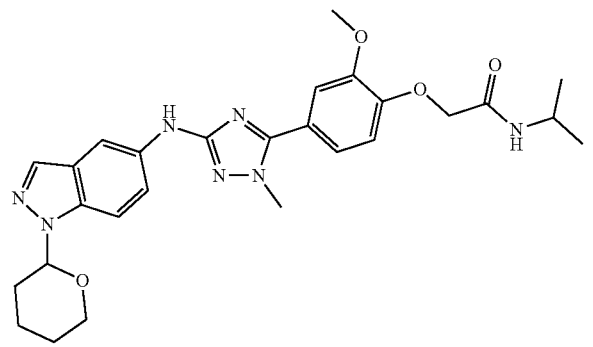 [SMILES: COc1cc(-c2nc(Nc3ccc4c(cnn4C4CCCCO4)c3)nn2C)ccc1OCC(=O)NC(C)C]

A mixture of 5-bromo-1-tetrahydropyran-2-yl-indazole (100 mg, 0.36 mmol), 2-[4-(5-amino-2-methyl-1,2,4-triazol-3-yl)-2-methoxy-phenoxy]-N-isopropyl-acetamide (125 mg, 0.39 mmol), palladium(II) chloride (2-aminoethyl)benzamide-bis(2-methyl-2-propanyl)(2',4',6'-triisopropyl-2-biphenylyl)phosphine (1:1:1:1) (24 mg, 0.04 mmol) and di-t-Bu-XPhos (15 mg, 0.04 mmol) was purged with nitrogen. Anhydrous THF (1.5 mL) was added and the reaction mixture was purged with nitrogen, followed by 2 M solution of sodium test-butoxide in THF (0.27 mL, 0.53 mmol) and additional nitrogen purge. The reaction mixture was stirred at 25° C. The reaction mixture was diluted with EtOAc, passed through a pad of Celite (washed with EtOAc), filtered and concentrated to yield N-isopropyl-2-[2-methoxy-4-[2-methyl-5-[(1-tetrahydropyran-2-ylindazol-5-yl)amino]-1,2,4-triazol-3-yl]phenoxy]acetamide (185 mg, 0.39 mmol, 100%). UPLC-MS (ES$^+$, Method A): 1.63 min, m/z 520.5 [M+H]$^+$ Example 233: N-isopropyl-2-[2-methoxy-4-[1-methyl-5-[(3-methyl-1H-indazol-5-yl)amino]-1,2,4-triazol-3-yl]phenoxy]acetamide

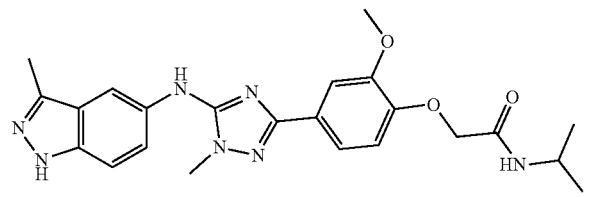 [SMILES: COc1cc(-c2nc(Nc3ccc4[nH]nc(C)c4c3)n(C)n2)ccc1OCC(=O)NC(C)C]

A 4 N solution of hydrogen chloride in dioxane (1.00 mL, 4.00 mmol) was added to a solution of N-isopropyl-2-[2-methoxy-4-[1-methyl-5-[(3-methyl-1-tetrahydropyran-2-yl-indazol-5-yl)amino]-1,2,4-triazol-3-yl]phenoxy]acetamide (143 mg, 0.27 mmol) in methanol (1 mL). The reaction was allowed to stir at r.t. for 16 h. The solvents were removed under reduced pressure and the residue was purified by SCX (methanol wash (×2) followed by 1 M NH$_3$ in MeOH (×2)). The compound was dried in vacuo to yield N-isopropyl-2-[2-methoxy-4-[1-methyl-5-[(3-methyl-1H-indazol-5-yl)amino]-1,2,4-triazol-3-yl]phenoxy]acetamide (21 mg, 0.05 mmol, 18% yield). LC-MS (ES$^+$, Method B): 3.10 min, m/z 450.4 [M+H]$^+$. $^1$H NMR (400 MHz DMSO-d$_6$): 12.48 (s 1H), 8.88 (s 1H), 8.15 (d, J 1.6 Hz 1H), 7.91 (d, 7.3 Hz 1H), 7.53-7.58 (m, 2H), 7.50 (dd, J 8.3 1.8 Hz, 1H), 7.41 (d, J 8.8 Hz 1H), 7.00 (d, J 8.3 Hz, 1H) 4.48 (s, 2H), 3.97-3.89 (m, 1H), 3.88 (s, 3H), 3.79 (s, 3H), 2.48 (s, 3H), 1.10 (d, J 6.6 Hz, 6H).

Step 1: 3-methyl-5-nitro-1H-indazole

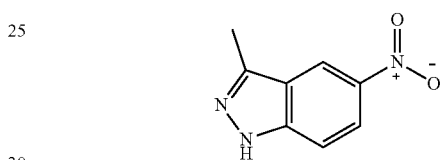

To a solution of 1-(2-fluoro-5-nitrophenyl)ethanone (300 mg, 1.63 mmol) in DMF (6.50 mL) was added hydrazine monohydrate (0.10 mL, 3.26 mmol). The reaction was heated to 110° C. and left to stir for 16 h. The reaction mixed was cooled to r.t. and quenched with 1M HCl (10 mL) and extracted with DCM (3×5 mL). The organics were combined and washed with ice cold brine (3×25 mL). The organics were dried using a phase separator and concentrated in vacuo to give 3-methyl-5-nitro-1H-indazole (228 mg, 1.29 mmol, 79%). UPLC-MS (ES$^+$, Method A): 1.38 min, m/z 178 [M+H]$^+$ Step 2: 3-methyl-5-nitro-1-tetrahydropyran-2-yl-indazole

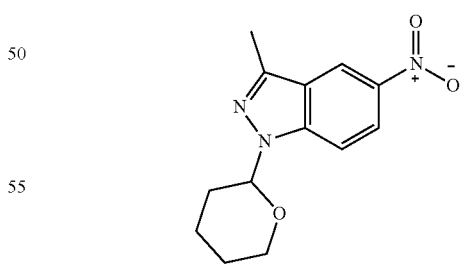

To a solution of 3-methyl-5-nitro-1H-indazole (228 mg, 1.29 mmol) and p-tosyic acid (66 mg, 0.39 mmol) in DCM (6 mL) was added 3,4-dihydro-2H-pyran (0.14 mL, 1.54 mmol) and the reaction mixture was left stir at 25° C. for 16 h. The reaction was quenched with NaHCO$_3$ (1M, 15 mL), extracted with DCM and washed through activated charcoal and concentrated in vacuo to give 3-methyl-5-nitro-1-tetrahydropyran-2-yl-indazole. (292 mg, 1.18 mmol, 87%).

UPLC-MS (ES+, Method A): 1.80 min, m/z no mass ion observed [M+H]+

Step 3:
3-methyl-1-tetrahydropyran-2-yl-indazol-5-amine

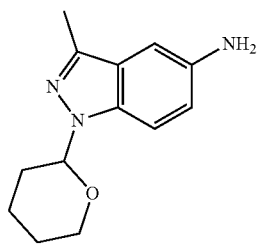 [SMILES: Cc1nn(C2CCCCO2)c2ccc(N)cc12]

Zinc powder (224 mg, 3.42 mmol) and ammonium chloride (183 mg, 3.42 mmol) were added to a stirred solution of 3-methyl-5-nitro-1-tetrahydropyran-2-yl-indazole (298 mg, 1.14 mmol) in ethyl acetate (6 mL) at r.t. The reaction was stirred at 25° C. for 18 h. The reaction mixture was diluted and filtered to remove the zinc and the cake washed with EtOAc (50 mL). The filtrate was reduced in vacuo to give 3-methyl-1-tetrahydropyran-2-yl-indazol-5-amine (249 mg, 1.08 mmol, 94% yield) as a yellow/orange solid. UPLC-MS (ES+, Method A): 1.04 min, m/z 232 [M+H]+

Step 4: N-(5-bromo-2-methyl-1,2,4-triazol-3-yl)-1-tetrahydropyran-2-yl-indazol-5-amine

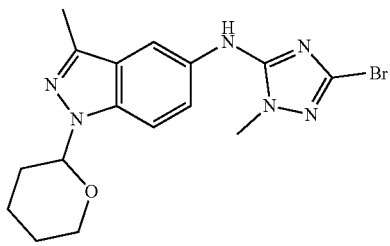 [SMILES: Cc1nn(C2CCCCO2)c2ccc(Nc3nc(Br)nn3C)cc12]

A solution of lithium diisopropylamide (1.43 mL, 2.86 mmol) in THF (10.60 mL) under a nitrogen atmosphere was cooled to −10° C. 3-Methyl-1-tetrahydropyran-2-yl-indazol-5-amine (265 mg, 1.15 mmol) in THF (5.34 mL) was added and the reaction was stirred for 15 min and 3,5-dibromo-1-methyl-1H-1,2,4-triazole (331 mg, 1.37 mmol) in THF (5.34 mL) was added. The reaction was warmed to r.t. and stirred for 16 h. The reaction was quenched with sat. aq. NH₄Cl and extracted with EtOAc (3×20 mL). The combined organics were dried with a phase separator and concentrated in vacuo. The crude product was purified by flash chromatography eluting with 20-75% EtOAc in Heptane to give N-(5-bromo-2-methyl-1,2,4-triazol-3-yl)-1-tetrahydropyran-2-yl-indazol-5-amine (98 mg, 0.26 mmol, 23% yield). UPLC-MS (ES+, Method A): 1.63 min, m/z no mass ion observed [M+H]+

Step 4: N-isopropyl-2-[2-methoxy-4-[1-methyl-5-[(3-methyl-1-tetrahydropyran-2-yl-indazol-5-yl)amino]-1,2,4-triazol-3-yl]phenoxy]acetamide

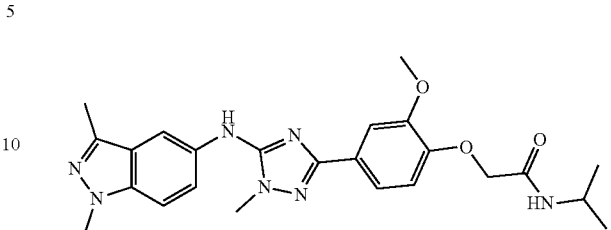

[1,1'-Bis(diphenylphosphino)ferrocene]palladium(II) chloride dichloromethane complex (22 mg, 0.03 mmol) was added to a fully degassed solution of N-isopropyl-2-[2-methoxy-4-(4,4,5,5-tetramethyl-1,3,2-dioxaborolan-2-yl)phenoxy]acetamide (100 mg, 0.29 mmol), potassium carbonate (92 mg, 0.67 mmol) and N-(5-bromo-2-methyl-1,2,4-triazol-3-yl)-3-methyl-1-tetrahydropyran-2-yl-indazol-5-amine (104 mg, 0.27 mmol) in a mixture of water (6.4 mL) and THF (6.4 mL). The reaction was heated to 100° C. and left to stir for 16 h. The reaction mixture was cooled to r.t. and quenched with NaHCO₃. The reaction mixture was extracted with EtOAc (3×20 mL), the organics were combined, dried with a phase separator and concentrated in vacuo to give N-isopropyl-2-[2-methoxy-4-[1-methyl-5-[(3-methyl-1-tetrahydropyran-2-yl-indazol-5-yl)amino]-1,2,4-triazol-3-yl]phenoxy]acetamide (142 mg, 0.29 mmol, 100%). UPLC-MS (ES+, Method A): 1.64 min, m/z 534.5 [M+H]+

Example 234: 7-[5-[(4-chloro-1H-indazol-5-yl)amino]-1-methyl-1,2,4-triazol-3-yl]chroman-4-ol

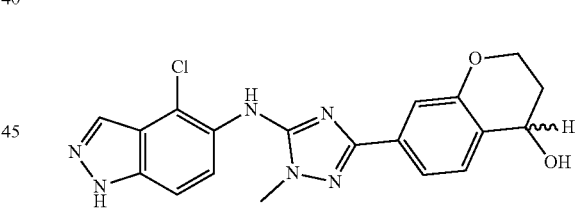

7-[5-[(4-Chloro-1H-indazol-5-yl)amino]-1-methyl-1,2,4-triazol-3-yl]chroman-4-one (55 mg, 0.14 mmol) was dissolved in MeOH (5 mL) and NaBH₄ (13 mg, 0.35 mmol) was added. The mixture was left to stir for 1 h. Further NaBH₄ (6 mg, 0.17 mmol) was added and the reaction was stirred for 30 min. The reaction was quenched by addition of sat NH₄Cl and diluted with EtOAc. The layers were separated and the aqueous was extracted with ethyl acetate twice. The organic layers were combined and concentrated under reduced pressure. The residue was purified on a 25 g C-18 column eluting with 5-60% MeCN in water (0.1% formic acid), followed by an ion exchange SCX-2 column eluting with a 1N NH₃ in MeOH solution to give 7-[5-[(4-chloro-1H-indazol-5-yl)amino]-1-methyl-1,2,4-triazol-3-yl]chroman-4-ol (32 mg, 0.08 mmol, 58% yield) as a white powder solid. UPLC-MS (ES+, Method B): 2.92 min, m/z 397.1 [M+H]+. ¹H NMR (400 MHz, DMSO-d₆): 13.38 (s, 1H), 8.47 (s, 1H), 8.08 (s, 1H), 7.62-7.53 (m, 2H), 7.37-7.28 (m, 2H), 7.17 (d, J 1.7 Hz, 1H), 5.38 (d, J 5.5 Hz, 1H), 4.60 (q, J 5.0 Hz, 1H), 4.20-4.16 (m, 2H), 3.77 (s, 3H), 2.04-1.94 (m, 1H), 1.89-1.81 (m, 1H).

Example 235: 2-[4-[5-(1H-indazol-5-ylamino)-1-methyl-1,2,4-triazol-3-yl]-2-methoxy-phenoxy]-N-(2,2,2-trifluoro-1-methyl-ethyl)acetamide

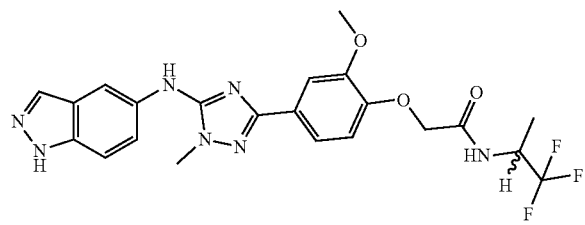 [SMILES: COc1cc(-c2nc(Nc3ccc4[nH]ncc4c3)n(C)n2)ccc1OCC(=O)NC(C)C(F)(F)F]

Palladium hydroxide (20% on carbon) (6 mg) was added to a stirring solution of 2-[4-[5-[(4 chloro-1H-indazol-5-yl)amino]-1-methyl-1,2,4 triazol-3-yl]-2-methoxy-phenoxy]-N-(2,2,2-trifluoro-1-methyl-ethyl)acetamide (113 mg, 0.21 mmol) in methanol (7 mL) under an atmosphere of nitrogen. The flask was evacuated and filled with hydrogen (×3). The reaction was then stirred vigorously for 6 h at 40° C., then filtered through a PTFE filter under vacuo to remove the palladium. The filtrate was concentrated under vacuo and the residue was purified via flash silica chromatography eluting with 0-10% MeOH in DCM. With further purification required the crude product was purified via reverse phase mass directed purification, followed by an ion exchange SCX-2 column washed with methanol and eluted with 1M NH$_3$/MeOH to yield 2-[4-[5-(1H-indazol-5-ylamino)-1-methyl-1,2,4-triazol-3-yl]-2-methoxy-phenoxy]-N-(2,2,2-trifluoro-1-methyl-ethyl)acetamide (10 mg, 0.02 mmol, 8% yield). UPLC-MS (ES$^+$, Method B): 3.33 min, m/z 490.4 [M+H]$^+$. $^1$H NMR (400 MHz, DMSO-d$_6$) δ 12.92 (s, 1H), 8.87 (s, 1H), 8.63 (d, J=9.0 Hz, 1H), 8.17 (d, J=1.9 Hz, 1H), 8.02 (t, J=1.3 Hz, 1H), 7.58-7.49 (m, 4H), 6.95 (d, J=8.2 Hz, 1H), 4.69 (dt, J=15.7, 7.6 Hz, 1H), 4.62 (s, 2H), 3.87 (s, 3H), 3.79 (s, 3H), 1.29 (d, J=7.0 Hz, 3H).

Step 1: 2-[4-[5-[(4-chloro-1H-indazol-5-yl)amino]-1-methyl-1,2,4-triazol-3-yl]-2-methoxy-phenoxy]-N-(2,2,2-trifluoro-1-methyl-ethyl)acetamide

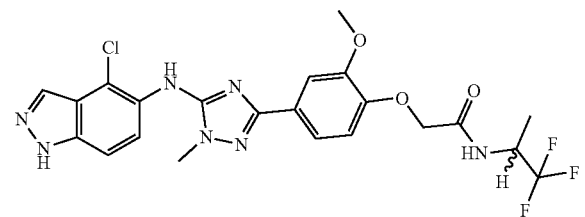 [SMILES: COc1cc(-c2nc(Nc3ccc4[nH]ncc4c3Cl)n(C)n2)ccc1OCC(=O)NC(C)C(F)(F)F]

To a stirring solution of 2-[4-[5-[(4-chloro-1H-indazol-5-yl)amino]-1-methyl-1,2,4-triazol-3-yl]-2-methoxy-phenoxy]acetic acid dihydrochloride (100 mg, 0.21 mmol) in a vial in DMF (1 mL) was added 2-(7-aza-1H-benzotriazole-1-yl)-1,1,3,3-tetramethyluronium hexafluorophosphate (HATU) (90 mg, 0.24 mmol), N,N-diisopropylethylamine (0.11 mL, 0.64 mmol) and 1,1,1-trifluoropropan-2-amine (27 mg, 0.24 mmol). The reaction mixture was stirred at 25° C. overnight. Further 1,1,1-trifluoropropan-2-amine (27 mg, 0.24 mmol) was added and the reaction mixture was stirred for a further 2 h. The crude reaction mixture was loaded onto an SCX-2 column and eluted with 1 M NH$_3$ in MeOH. The solvents were removed in vacuo to give 2-[4-[5-[(4-chloro-1H-indazol-5-yl)amino]-1-methyl-1,2,4-triazol-3-yl]-2-methoxy-phenoxy]-N-(2,2,2-trifluoro-1-methyl-ethyl)acetamide (112 mg, 021 mmol, 100%). UPLC-MS (ES$^+$, Method A): 1.54 min, m/z 524.4 [M+H]$^+$ Example 236: 1-[6-[5-[(4 chloro-1H-indazol-5-yl)amino]-1-methyl-1,2,4-triazol-3-yl]-3,4-dihydro-1H-isoquinolin-2-yl]-2-methyl-propan-1-one

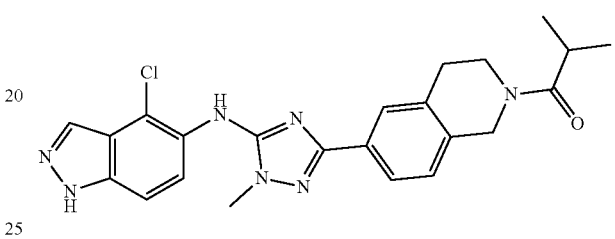

4-Chloro-N-[2-methyl-5-(1,2,3,4-tetrahydroisoquinolin-5-yl)-1,2,4-triazol-3-yl]-1H-indazol-5-amine (0.82 mL, 0.13 mmol) was dissolved in DMF (2 mL). N,N-Diisopropylethylamine (0.05 mL, 0.26 mmol) was added followed by isobutyryl chloride (0.01 mL, 0.11 mmol). The reaction was left to stir for 15 min and diluted with saturated NH$_4$Cl, a precipitate formed. DCM was added and the phases were separated. The aqueous layer was further extracted with DCM. The organic layers were combined, dried over Na$_2$SO$_4$, filtered and concentrated under reduced pressure. Further purification by flash chromatography on silica gel eluting with 5-100% (1/10 methanol/Ethyl acetate in Pet. Ether gave 1-[6-[5-[(4-chloro-1H-indazol-5-yl)amino]-1-methyl-1,2,4 triazol-3-yl]-3,4-dihydro-1H-isoquinolin-2-yl]-2-methyl-propan-1-one (45 mg, 0.1 mmol, 76% yield). UPLC-MS (ES$^+$, Method B): 3.42 min, m/z 450.3 [M+H]$^+$. $^1$H NMR (400 MHz, DMSO-d$_6$, mixture of rotamers): 13.40 (s 1H), 8.50 (s, 1H), 8.10 (s, 1H), 7.69-7.52 (m, 4H), 7.20 (d, J 8.0 Hz, 1H), 4.71 (s, 0.8H), 4.60 (s, 1.2H), 3.78 (s, 3H), 3.75-3.62 (m, 2H), 3.01-2.91 (m, 1H), 2.87 (t, J 5.3 Hz, 1.2H), 2.76 (t, J 5.3 Hz, 0.8H), 1.04-0.97 (m, 6H).

Example 237: 4-Chloro-N-[2-methyl-5-(1,2,3,4-tetrahydroisoquinolin-6-yl)-1,2,4-triazol-3-yl]-1H-indazol-5-amine

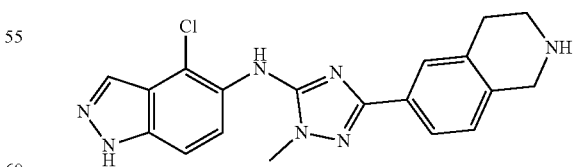

tert-Butyl 6-[5-[(4-chloro-1-tetrahydropyren-2-yl-indazol-5-yl)amino]-1-methyl-1,2,4-triazol-3-yl]-3,4-dihydro-1H-isoquinoline-2-carboxylate (430. mg, 0.7600 mmol) was dissolved in hydrogen chloride (4.0 M in dioxane) (3.81 mL, 15.25 mmol). The reaction was stirred at r.t. for 1 h and then concentrated under reduced pressure. The residue was run through a SCX-2 column eluting with 1N NH$_3$ in MeOH 4-chloro-N-[2-methyl-5-(1,2,3,4-tetrahydroisoquinolin-6-yl)-1,2,4-triazol-3-yl]-1H-indazol-5-amine hydrochloride (315 mg, 0.76 mmol, 99% yield). UPLC-MS (ES$^+$, Method B): 2.37 min, m/z 380.3 [M+H]$^+$. 1H NMR (400 MHz, DMSO-d$_6$): 13.45 (s 1H), 9.37 (s, 2H), 8.59 (s, 1H), 8.10 (s, 1H), 7.71 (d, J 8.3 Hz, 1H), 7.66 (s, 1H), 7.59-7.53 (m, 2H), 7.22 (d, J 8.0 Hz, 1H), 4.26 (s, 2H), 3.80 (s, 3H), 3.36 (s, 2H), 3.02 (t, J 6.1 Hz, 2H).

Step 1: tert-butyl 6-[5-[(4-chloro-1-tetrahydropyran-2-yl-indazol-5-yl)amino]-1-methyl-1,2,4-triazol-3-yl]-3,4-dihydro-1H-isoquinoline-2-carboxylate

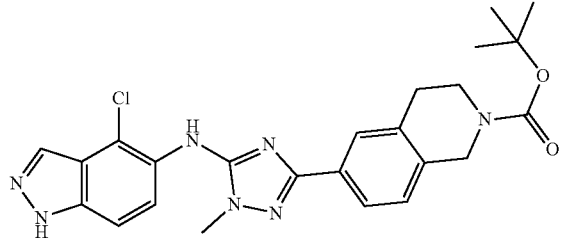 [SMILES: Cn1nc(-c2ccc3c(c2)CCN(C(=O)OC(C)(C)C)C3)nc1Nc1ccc2[nH]ncc2c1Cl]

Potassium carbonate (692 mg, 5.01 mmol), [1,1'-bis(diphenylphosphino)ferrocene]Paladium(II) chloride dichloromethane complex (205 mg, 0.25 mmol), N-(5-bromo-2-methyl-1,2,4-triazol-3-yl)-4-chloro-1-tetrahydropyran-2-yl-indazol-5-amine (1031 mg, 2.51 mmol) and tert-butyl 6-(4,4,5,5-tetramethyl-1,3,2-dioxaborolan-2-yl)-3,4-dihydro-1H-isoquinoline-2-carboxylate (900 mg, 2.51 mmol) were degassed with nitrogen. A degassed solution of 1,4-dioxane (16 mL) and water (4 mL) was added to the solid mix and the resulting suspension degassed with nitrogen for 5 min. The mixture was heated to 90° C. for 40 h, cooled to r.t., and then filtered through celite. All volatiles were removed under reduced pressure and the residue was purified by flash column chromatography eluting with 40-100% EtOAc in Pet.Ether to afford tert-butyl 6-[5-[(4-chloro-1-tetrahydropyran-2-yl-indazol-5-yl amino]-1-methyl-1,2,4-triazol-3-yl]-3,4-dihydro-1H-isoquinoline-2-carboxylate (450 mg, 0.80 mmol, 32% yield) as a yellow solid. UPLC-MS (ES$^+$, Method A): 2.08 min, m/z 564.5 [M+H]$^+$.

The compounds in the table below were made in an analogous way to the compound above.

TABLE 18

| # | Structure | LC-MS | $^1$H NMR |
|---|---|---|---|
| 238 | ![structure] | Method B, 3.33 min, m/z 448.4 [M + H]+ | $^1$H NMR (400 MHz, DMSO-d$_6$): 13.39 (s 1H), 8.50 (s, 1H), 8.10 (s, 1H), 7.69-7.52 (m, 4H), 7.20 (d, J 8.0 Hz, 1H), 4.90 (s, 0.85H), 4.61 (s, 1.15H), 3.89 (t, J 5.4 Hz, 1.15H), 3.78 (s, 3H), 3.66 (t J 5.4 Hz, 0.8H), 2.91 (t, J 5.3 Hz, 1.2H), 2.76 (t, J 5.3 Hz, 0.8H), 2.10-2.01 (m, 1H), 0.78-0.68 (m, 4H). |
| 239 | ![structure] | Method B, 3.13 min, m/z 519.5 [M + H]+ | $^1$H NMR (400 MHz, DMSO-d$_6$): 13.38 (s, 1H), 8.48 (s, 1H), 8.10 (s, 1H), 7.71-7.53 (m, 4H), 7.24-7.17 (m, 1H), 4.65-4.56 (m, 2H), 3.79 (s, 3H), 3.71-3.65 (m, 1H), 3.61-3.54 (m, 3H), 3.33-3.22 (m, 2H), 2.88 (t, J 5.6 Hz, 1H), 2.79 (t, J 5.6 Hz, 1H). 1 NH exchangeable not observed. |

Example 240: 4-[5-(1H-indazol-5-ylamino)-1-methyl-1,2,4-triazol-3-yl]-2-methoxy-N-(2,2,2-trifluoroethyl)benzamide

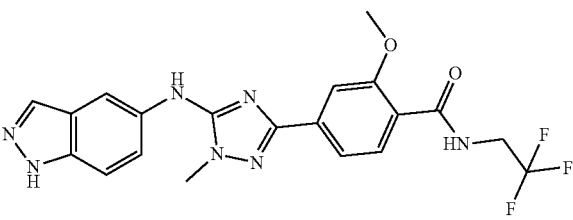 [SMILES: COc1cc(-c2nc(Nc3ccc4[nH]ncc4c3)n(C)n2)ccc1C(=O)NCC(F)(F)F]

2-Methoxy-4-[1-methyl-5-[(1-tetrahydropyran-2-ylindazol-5-yl)amino]-1,2,4-triazol-3-yl]-N-(2,2,2-trifluoroethyl)benzamide (24 mg, 0.05 mmol) was suspended in MeOH (3 mL) and hydrogen chloride (4.0 M in dioxane, 0.32 mL, 1.28 mmol) was added. The reaction was stirred at 25° C. for 18 h. The reaction was then reduced in vacuo, taken up with MeOH and passed through an ion exchange SCX column eluting with MeOH then 1.0M MeOH/NH$_3$. The solvent was removed in vacuo and the residue was triturated with DCM/diethyl ether to give a white solid which was dried overnight at 50° C. to give 4-[5-(1H-indazol-5-ylamino)-1-methyl-1,2,4-triazol-3-yl]-2-methoxy-N-(2,2,2-trifluoroethyl)benzamine (8 mg, 0.02 mmol, 39% yield) as a white solid. UPLC-MS (ES$^+$, Method B): 3.37 min, m/z 446.3 [M+H]$^+$. $^1$H NMR (400 MHz, DMSO-d$_6$) δ 12.95 (s, 1H), 8.97 (s, 1H), 8.72 (t, J=6.4 Hz, 1H), 8.20 (d, J=1.9 Hz, 1H), 8.04 (s, 1H), 7.85 (d, J=7.9 Hz, 1H), 7.72-7.64 (m, 2H), 7.58 (dd, J=8.9, 2.0 Hz, 1H), 7.52 (d, J=8.9 Hz, 1H), 4.13 (qd, J=9.7, 6.5 Hz, 2H), 3.99 (s, 3H), 3.84 (s, 3H).

Step 1: 4-[5-[(4-chloro-1-tetrahydropyran-2-yl-indazol-5-yl)amino]-1-methyl-1,2,4-triazol-3-yl]-2-methoxy-N-(2,2,2-trifluoroethyl)benzamide

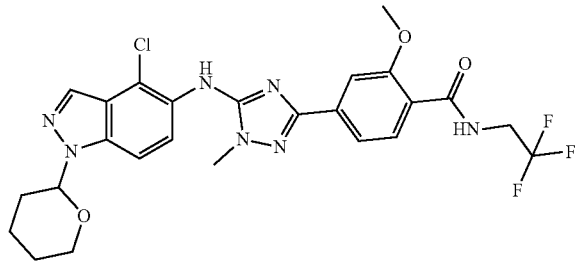 [SMILES: COc1cc(-c2nc(Nc3ccc4c(cnn4C4CCCCO4)c3Cl)n(C)n2)ccc1C(=O)NCC(F)(F)F]

To a stirred solution of N,N-diisopropylethylamine (0.65 mL, 3.73 mmol), 4-[5-[(4-chloro-1-tetrahydropyran-2-yl-indazol-5-yl)amino]-1-methyl-1,2,4-triazol-3-yl]-2-methoxybenzoic acid (600 mg, 1.24 mmol) and trifluoroethylamine (0.11 mL, 1.37 mmol) in DMF (5 mL) was added 2-(7-aza-1H-benzotriazole-1-yl)-1,1,3,3-tetramethyluronium hexafluorophosphate (HATU) (520 mg, 1.37 mmol) and the solution stirred for 16 h at 25° C. The resultant brown solution was reduced in vacuo, the crude product was dissolved in EtOAc and washed with water (×2), saturated brine, dried over MgSO₄ and concentrated in vacuo. The residue was purified by flash column chromatography eluting with 25-100% EtOAc in Pet. Ether to give 4-[5-[(4-chloro-1-tetrahydropyran-2-yl-indazol-5-yl)amino]-1-methyl-1,2,4-triazol-3-yl]-2-methoxy-N-(2,2,2-trifluoroethyl)benzamide (574 mg, 1.02 mmol, 82% yield). UPLC-MS (ES⁺, Method A): 1.84 min, m/z 564.5 [M+H]⁺

Step 2: 2-methoxy-4-[1-methyl-5-[(1-tetrahydropyran-2-ylindazol-5-yl)amino]-1,2,4-triazol-3-yl]-N-(2,2,2-trifluoroethyl)benzamide

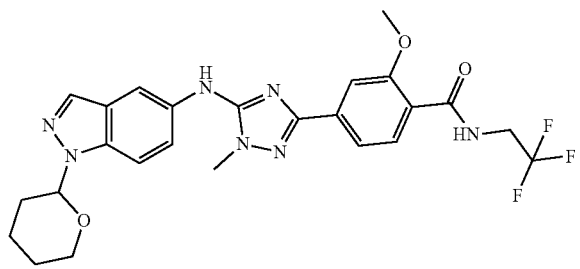 [SMILES: COc1cc(-c2nc(Nc3ccc4c(cnn4C4CCCCO4)c3)n(C)n2)ccc1C(=O)NCC(F)(F)F]

A stirring solution of 4-[5-[(4-chloro-1-tetrahydropyran-2-yl-indazol-5-yl)amino]-1-methyl-1,2,4-triazol-3-yl]-2-methoxy-N-(2,2,2-trifluoroethyl)benzamide (77 mg, 0.14 mmol) in MeOH (7 mL) was flushed with nitrogen before the addition of palladium hydroxide, (20% on carbon) (10 mg). The reaction was then evacuated and refilled with hydrogen (via balloon). The reaction was then left stirring to stir overnight at 40° C., filtered and reduced in vacuo. The residue was purified by flash column chromatography eluting with 30-100% EtOAc in Pet. Ether to give 2-methoxy-4-[1-methyl-5-[(1-tetrahydropyran-2-ylindazol-5-yl)amino]-1,2,4-triazol-3-yl]-N-(2,2,2-trifluoroethyl)benzamide (24 mg, 0.04 mmol, 33% yield). UPLC-MS (ES⁺, Method A): 1.74 min, m/z 530.5 [M+H]⁺

Example 241: 2-[4-[5-[(4-chloro-1H-indazol-5-yl)amino]-1-(2-hydroxyethyl)-1,2,4-triazol-3-yl]-2-methoxy-phenoxy]-N-isopropyl-acetamide

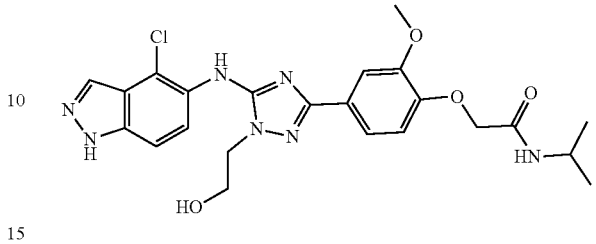

HCL in dioxane (1.03 mL, 4.12 mmol) was added slowly to a stirred solution of 2-[4-[5-[(4-chloro-1-tetrahydropyran-2-yl-indazol-5-yl)amino]-1-(2-tetrahydropyran-2-yloxy-ethyl)-1,2,4-triazol-3-yl]-2-methoxy-phenoxy]-N-isopropyl-acetamide (138 mg, 0.21 mmol) in 1,4-dioxane (3 mL) at 25° C. The reaction was stirred at r.t. for 18 h. The reaction was reduced in vacuo, taken up with MeOH and passed through an SCX ion exchange column eluting with MeOH, then eluted 1.0 M NH₃ MeOH. Further purification by flash column chromatography eluting with 50-100% EtOAc/Pet. Ether gave 2-[4-[5-[(4-chloro-1H-indazol-5-yl)amino]-1-(2-hydroxyethyl)-1,2,4-triazol-3-yl]-2-methoxy-phenoxy]-N-isopropyl-acetamide (14 mg, 0.03 mmol, 13% yield). UPLC-MS (ES⁺, Method B): 3.14 min, m/z 500.4 [M+H]⁺. ¹H NMR (400 MHz, DMSO-d₆) δ 13.36 (s, 1H), 8.70 (s, 1H), 8.07 (s, 1H), 7.94 (d, J=9.0 Hz, 1H), 7.80 (d, J=7.9 Hz, 1H), 7.56 (dd, J=8.9, 1.0 Hz, 1H), 7.49-7.40 (m, 2H), 6.96 (d, J=8.4 Hz, 1H), 5.73 (s, 1H), 4.47 (s, 2H), 4.26 (t, J=5.0 Hz, 2H), 3.91 (dq, J=7.7, 6.5 Hz, 1H), 3.84 (s, 5H), 3.17 (d, J=5.3 Hz, 0H), 1.09 (d, J=6.6 Hz, 6H).

Step 1: 2-(3,5-dibromo-1,2,4-triazol-1-yl)ethanol

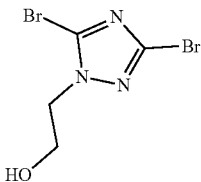

A solution of 3,5-dibromo-4H-1,2,4-triazole (500 mg, 2.2 mmol), 2-bromoethanol (0.31 mL, 4.41 mmol) and triethylamine (0.92 mL, 6.61 mmol) in DMA (8 mL) was stirred at 55° C. for 24 h, and then was filtered off. The solvent removed under reduced pressure to afford a waxy, yellow solid, which then purified by flash column chromatography (0-30% EtOAc in Pet. Ether) to yield 2-(3,5-dibromo-1,2,4-triazol-1-yl)ethanol (356 mg, 1.31 mmol, 60% yield) as a white solid. ¹H NMR (400 MHz, DMSO-d₆) δ 5.02 (s, 1H), 4.19 (t, J=5.3 Hz, 2H), 3.74 (t, J=5.3 Hz, 2H).

Step 2: 3,5-dibromo-1-(2-tetrahydropyran-2-yloxy-ethyl)-1,2,4-triazole

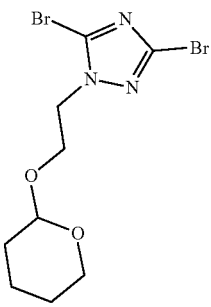 [SMILES: Brc1nc(Br)n(CCOC2CCCCO2)n1]

To a stirred solution of 2-(3,5-dibromo-1,2,4-triazol-1-yl) ethanol (350 mg, 1.29 mmol) and 3,4-dihydro-2H-pyran (0.35 mL, 3.88 mmol) in DMA (5 mL) was added TsOH (22 mg, 0.13 mmol) and the resultant mixture stirred at r.t. for 16 hr. The solvent was removed under reduced pressure and the resultant crude solid purified by flash column chromatography eluting with 30-60% EtOAc in Pet. Ether to afford 3,5-dibromo-1-(2-tetrahydropyran-2-yloxyethyl)-1,2,4-triazole (295 mg, 0.83 mmol, 64% yield) as a white solid. $^1$H NMR (400 MHz, DMSO-d$_6$) δ 4.53 (t, J=3.3 Hz, 1H), 4.42-425 (m, 2H), 3.91 (ddd, J=11.0, 7.1, 4.0 Hz, 1H), 3.72 (ddd, J=11.0, 5.6, 4.0 Hz, 1H), 3.49-3.27 (m, 2H), 1.77-1.19 (m, 6H).

Step 3: N-[5-bromo-2-(2-tetrahydropyran-2-yloxy-ethyl)-1,2,4-triazol-3-yl]-4-chloro-1-tetrahydropyran-2-yl-indazol-5-amine

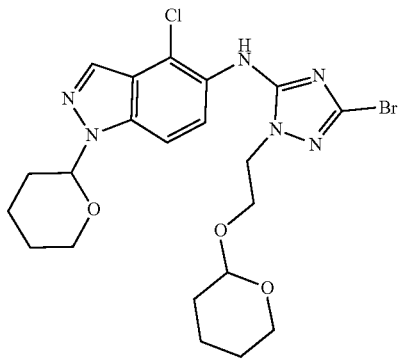

To a stirred solution of 3,5-dibromo-1-(2-tetrahydropyran-2-yloxyethyl)-1,2,4-triazole (157 mg, 0.40 mmol) and 4-chloro-1-tetrahydropyran-2-yl-indazol-5-amine (100 mg, 0.40 mmol) in dry THF (2 mL) at −20° C. under nitrogen was added sodium bis(trimethylsilyl)amide solution (2.0 M in THF) (0.40 mL, 0.79 mmol) and the mixture stirred and allowed to warm to 0° C. for 20 min. The mixture was quenched with sat. aq. NH$_4$Cl (5 mL) and extracted with EtOAc (10 mL). The layers were separated and the aqueous layer extracted with further EtOAc (1×10 mL). The combined organics were dried (MgSO$_4$.) and concentrated. The orange gum residue was purified by flash column chromatography eluting with 20-50% EtOAc in Pet. Ether to give N-[5-bromo-2-(2-tetrahydropyran-2-yloxyethyl)-1,2,4-triazol-3-yl]-4-chloro-1-tetrahydropyran-2-yl-indazol-5-amine (130 mg, 0.23 mmol, 59% yield) as a yellow/orange gum. UPLC-MS (ES$^+$, Method A): 1.98 min, m/z 527.3 [M+H]$^+$

Step 4: 2-[4-[5-[(4-chloro-1-tetrahydropyran-2-yl-indazol-5-yl)amino]-1-(2-tetrahydropyran-2-yloxy-ethyl)-1,2,4-triazol-3-yl]-2-methoxy-phenoxy]-N-isopropyl-acetamide

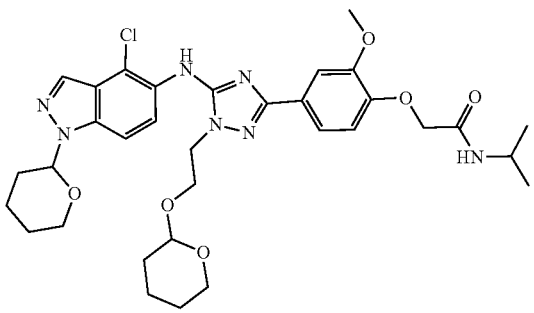

N-Isopropyl-2-[2-methyoxy-4-(4,4,5,5-tetramethyl-1,3,2-dioxaborolan-2-yl phenoxy]acetamide (104 mg, 0.30 mmol) L, N-[5-bromo-2-(2-tetrahydropyran-2-yloxyethyl)-1,2,4-triazol-3-yl]-4-chloro-1-tetrahydropyran-2-yl-indazol-5-amine (130 mg, 025 mmol) and potassium carbonate (72 mg, 0.52 mmol) were suspended in 1,4-dioxane (2 mL) and water (0.5 mL). The reaction mixture was degassed by bubbling nitrogen through. [1,1'-bis(di-tert-butylphosphino) ferrocene]dichloropalladium(II) (16 mg, 0.02 mmol) was then added followed by further degassing and then the reaction was heated to 80° C. for 18 h. The reaction was reduced in vacuo onto silica and purified by silica chromatography eluting with 30-100% EtOAC/Pet. Ether to give 2-[4-[5-[(4-chloro-1-tetrahydropyran-2-yl-indazol-5-yl) amino]-1-(2-tetrahydropyran-2-yloxyethyl)-1,2,4-triazol-3-yl]-2-methoxy-phenoxy]-N-isopropyl-acetamide (52 mg, 0.07 mmol, 30% yield) as a pale brown gum. UPLC-MS (ES$^+$, Method A): 1.98 min, m/z 668.6 [M+H]$^+$

Example 242: 2-[4-[5-[(4-chloro-1H-indazol-5-yl)amino]-1-methyl-1,2,4-triazol-3-yl]-2-methoxy-phenoxy]-N-(2-methoxyethyl)acetamide

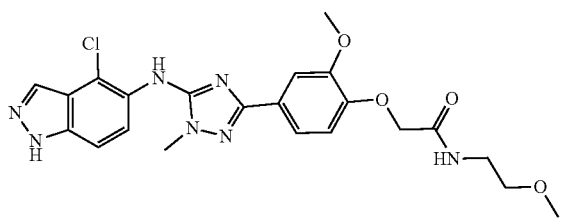 [SMILES: COCCNC(=O)COc1ccc(-c2nc(Nc3ccc4[nH]ncc4c3Cl)n(C)n2)cc1OC]

2-Methoxyethylamine (0.16 mL, 1.81 mmol) was added to a solution/suspension of methyl 2-[4-[5-[(4-chloro-1H-indazol-5-yl)amino]-1-methyl-1,2,4-triazol-3-yl]-2-methoxy-phenoxy]acetate (80 mg, 0.18 mmol) in THF (1 mL) and stirred at 25° C. for 16 h. The reaction was diluted with water (20 mL) and the resulting solid was filtered. The solid was washed with further water and dried under high vacuum for 16 h to give 2-[4-[5-[(4-chloro-1H-indazol-5-yl)amino]-1-methyl-1,2,4-triazol-3-yl]-2-methoxy-phenoxy]-N-(2-methoxyethyl)acetamide (59 mg, 0.12 mmol, 66% yield) as a beige solid. UPLC-MS (ES+, Method B): 2.98 min, m/z 486.4 [M+H]+. 1H NMR (400 MHz, DMSO-d6) δ 13.38 (s, 1H), 8.46 (s, 1H), 8.09 (s, 1H), 7.93 (t, J=5.7 Hz, 1H), 7.61-7.52 (m, 2H), 7.42 (d, J=2.0 Hz, 1H), 7.37 (dd, J=8.3, 1.9 Hz, 1H), 6.94 (d, J=8.4 Hz, 1H), 4.49 (s, 2H), 3.82 (s, 3H), 3.77 (s, 3H), 3.37 (dd, J=6.7, 5.2 Hz, 2H), 3.33-3.28 (m, 2H), 3.25 (s, 3H).

Step 1: methyl 2-[4-[5-[(4-chloro-1H-indazol-5-yl)amino]-1 methyl-1,2,4-triazol-3-yl]-2-methoxy-phenoxy]acetate

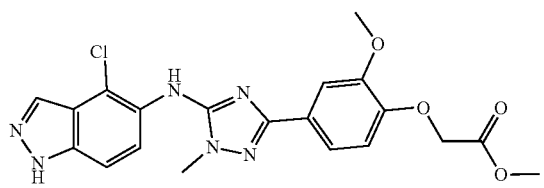

Hydrogen chloride (1.25 M in MeOH, 2.05 mL, 46.79 mmol) was added to a solution of 2-[4-[5-[(4-chloro-1-tetrahydropyran-2-yl-indazol-5-yl)amino]-1-methyl-1,2,4-triazol-3-yl]-2-methoxy-phenoxy]acetic acid (400 mg, 0.78 mmol) in MeOH (1 mL) at 25° C. and stirred at room temp overnight. Further 4.0 M HCl in dioxane (1.0 mL) was added to the reaction and stirred at r.t. for 2 h. The reaction was diluted with diethyl ether and filtered, washed through with diethyl ether and dried to give a pale brown solid. methyl 2-[4-[5-[(4-chloro-1H-indazol-5-yl)amino]-1-methyl-1,2,4-triazol-3-yl]-2-methoxy-phenoxy]acetate (240 mg, 0.54 mmol, 69% yield). UPLC-MS (ES+, Method B): 1.42 min, m/z 443.3 [M+H]+. 1H NMR (400 MHz, DMSO-d6) δ 9.26 (s, 1H), 8.14 (d, J=0.7 Hz, 1H), 7.61-7.55 (m, 2H), 7.42 (d, J=2.0 Hz, 1H), 7.36 (dd, J=8.4, 2.0 Hz, 1H), 6.93 (d, J=8.5 Hz, 1H), 4.82 (s, 2H), 3.82 (s, 3H), 3.81 (s, 3H), 3.69 (s, 3H). 1H exchanged.

The compounds in the table below were made in an analogous way to that described above.

Example 244: 2-[4-[5-[4-chloro-1H-indazol-5-yl)amino]-1-methyl-1,2,4-triazol-3-yl]-2-methoxy-phenoxy]-N-(2-methoxyethyl)acetamide

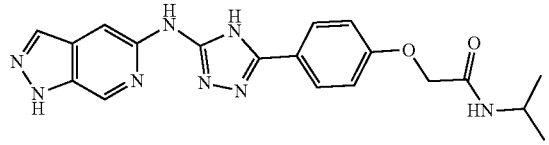

N-Isopropyl-2-[4-[5-[(1-tetrahydropyran-2-ylpyrazolo[3,4-c]pyridin-5-yl)amino]-4H-1,2,4-triazol-3-yl]phenoxy]acetamide (9 mg, 0.02 mmol) was stirred in hydrogen chloride-methanol solution, 1.25 M (2 mL, 2.5 mmol) overnight. Solvents removed under reduced pressure to afford N-isopropyl-2-[4-[5-(1H-pyrazolo[3,4-c]pyridin-5-ylamino)-4H-1,2,4-triazol-3-yl]phenoxy]acetamide hydrochloride (8 mg, 0.02 mmol, 99% yield) as a brown solid. UPLC-MS (ES+, Method B): 2.72 min, m/z 393.3 [M+H]+. H NMR (400 MHz, DMSO-d6) δ 11.00 (s, 1H), 9.05 (s, 1H), 8.32 (s, 1H), 8.13-7.92 (m, 3H), 7.86 (s, 1H), 7.15-7.01 (m, 2H), 4.53 (s, 2H), 3.94 (s, 1H), 1.09 (d, J=5.3 Hz, 6H)

Step 1: methyl 4-[2-(isopropylamino)-2-oxo-ethoxy]benzoate

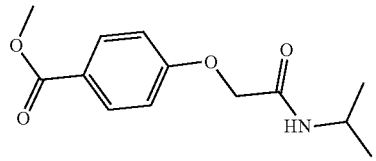 [SMILES: COC(=O)c1ccc(OCC(=O)NC(C)C)cc1]

To a stirred solution of 2-chloro-N-isopropylacetamide (602 mg, 4.44 mmol) and methyl 4-hydroxybenzoate (500 mg, 3.29 mmol) in DMF (18 mL) at r.t. under N2 was added potassium carbonate (1817 mg, 13.15 mmol) in a single portion. The mixture was heated at 80° C. overnight, cooled and partitioned between EtOAc and H2O. The layers were separated and the aqueous layer was extracted with EtOAc (2×). The combined organics were washed with H2O and brine, dried (phase sep.) and concentrated to give crude methyl 4-[2-(isopropylamino)-2-oxo-ethoxy]benzoate (870 mg, 3.18 mmol, 97% yield). LC-MS (ES+, Method C): 2.32 min, m/z 252.0 [M+H]+

TABLE 19

| Example | Structure | LC/MS | 1H NMR |
| --- | --- | --- | --- |
| 243 | 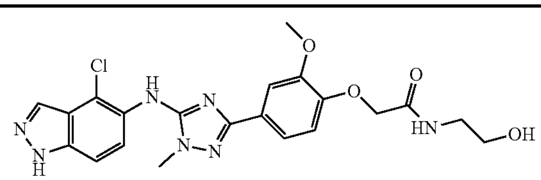 | Method B, 2.74 min, m/z 472.4 [M + H]+ | 1H NMR (400 MHz, DMSO-d6) δ 13.37 (s, 1H), 8.46 (s, 1H), 8.09 (s, 1H), 7.88 (t, J = 5.7 Hz, 1H), 7.56 (q, J = 8.9 Hz, 2H), 7.42 (d, J = 1.9 Hz, 1H), 7.37 (dd, J = 8.3, 1.8 Hz, 1H), 6.95 (d, J = 8.4 Hz, 1H), 4.49 (s, 2H), 3.82 (s, 3H), 3.77 (s, 3H), 3.43 (t, J = 6.0 Hz, 2H), 3.21 (q, J = 5.9 Hz, 2H). OH not observed |

Step 2: 2-[4-(5-amino-4H-1,2,4-triazol-3-yl)phenoxy]-N-isopropyl-acetamide

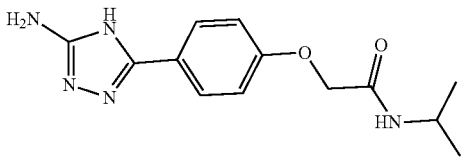 [SMILES: CC(C)NC(=O)COc1ccc(-c2nnc(N)[nH]2)cc1]

To a stirred solution of aminoguanidine hydrochloride (1148 mg, 10.38 mmol) in anhydrous methanol (12 mL), cooled at 0° C., was added sodium methoxide (5.2 mL, 10.38 mmol). The cooling bath was then removed and the mixture stirred at r.t. for 10 min. A solution of methyl 4-[2-(isopropylamino)-2-oxo-ethoxy]benzoate (870 mg, 3.46 mmol) in anhydrous MeOH (8 mL) was added and the reaction heated at 65° C. overnight. The mixture was cooled and concentrated under reduced pressure. The residue was partitioned with EtOAc and sat. NaHCO$_3$. The layers were separated and the aqueous layer was extracted with EtOAc (2×). The combined organics extracts were dried (phase sep.) and concentrated under reduced pressure to give 2-[4-(5-amino-4H-1,2,4-triazol-3-yl)phenoxy]-N-isopropyl-acetamide (398.5 mg, 1.45 mmol, 42% yield) as a yellow solid. UPLC-MS (ES$^+$, Method A): 1.33 min, m/z 276.0 [M+H]$^+$

Step 3: N-isopropyl-2-[4-[5-[(1-tetrahydropyran-2-ylpyrazolo[3,4-c]pyridin-5-yl)amino]4H-1,2,4-triazol-3-yl]phenoxy]acetamide

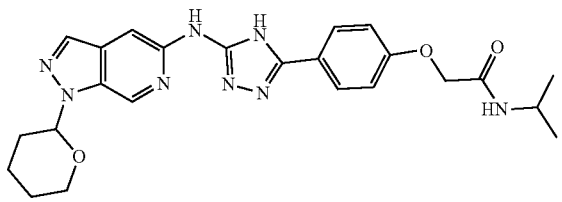 [SMILES: CC(C)NC(=O)COc1ccc(-c2nnc(Nc3cc4cnn(C5CCCCO5)c4cn3)[nH]2)cc1]

A vial charged with 2-[4-(5-amino-4H-1,2,4 triazol-3-yl)phenoxy]-N-isopropyl-acetamide (100 mg, 0.36 mmol), sodium tert-butoxide (73 mg, 0.76 mmol), 5-bromo-1-tetrahydropyran-2-yl-pyrazolo[3,4-c]pyridine (133 mg, 0.47 mmol) and test-butanol (4 mL) was degassed under nitrogen before Palladium(II) chloride (2-aminoethyl)benzenide-bis(2-methyl-2-propanyl)(2',4',6'-triisopropyl-2-biphenylyl)phosphine (1:1:1:1) (5 mg, 0.01 mmol) and phosphine, bis(1,1-dimethylethyl[2',4',6'-tris(1-methylethyl)[1,1'-biphenyl]-2-yl]- (4 mg, 0.01 mmol) were added. The vial was sealed and the reaction heated at 90° C. overnight, cooled, filtered through a phase separator and concentrated under reduced pressure. The crude material was purified by flash column chromatography (SiO$_2$), eluting with 0-6% MeOH in DCM to give N-isopropyl-2-[4-[5-[(1-tetrahydropyran-2-ylpyrazolo[3,4-c]pyridin-5-yl)amino]-4H-1,2,4-triazol-3-yl]phenoxy]acetamide (9 mg, 0.02 mmol, 5% yield). UPLC-MS (ES$^+$, Method A): 1.54 min, m/z 477.4 [M+H]$^+$

Example 245: 1-[6-[5-[(4-Chloro-1H-indazol-5-yl)amino]-1-methyl-1,2,4-triazol-3-yl]-3,4-dihydro-1H-isoquinolin-2-yl]-2-methyl-propan-1-one

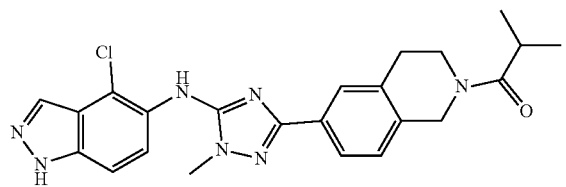 [SMILES: CC(C)C(=O)N1CCc2cc(-c3nc(Nc4ccc5[nH]ncc5c4Cl)n(C)n3)ccc2C1]

4-Chloro-N-[2-methyl-5-(1,2,3,4-tetrahydroisoquinolin-6-yl)-1,2,4-triazol-3-yl]-1H-indazol-5-amine (0.82 mL, 0.13 mmol) was dissolved in DMF (2 mL). N,N-Diisopropylethylamine (0.05 mL, 0.26 mmol) was added followed by isobutyryl chloride (0.01 mL, 0.11 mmol). The reaction was left to stir for 15 min and diluted with saturated NH$_4$Cl. DCM was added and the layers partitioned. The aqueous layer was extracted with DCM. The combined organic layers were dried over Na$_2$SO$_4$, filtered and concentrated under reduced pressure. The residue was purified by flash column chromatography eluting with a 5-100% (1/10 methanol/Ethyl acetate in Pet. Ether) to give 1-[6-[5-[(4-chloro-1H-indazol-5-yl)amino]-1-methyl-1,2,4-triazol-3-yl]-3,4-dihydro-1H-isoquinolin-2-yl]-2-methyl-propan-1-one (45 mg, 0.1 mmol, 76% yield). UPLC-MS (ES$^+$, Method E): 3.42 min, m/z 450.3 [M+H]$^+$. $^1$H NMR (400 MHz, DMSO-d$_6$): 13.40 (s 1H), 8.50 (s, 1H), 8.10 (s, 1H), 7.69-7.52 (m, 4H), 7.20 (d, J 8.0 Hz, 1H), 4.71 (s, 0.8H), 4.60 (s, 1.2H), 3.78 (s, 3H), 3.75-3.62 (m, 2H), 3.01-2.91 (m, 1H), 2.87 (t, J 5.3 Hz, 1.2H), 2.76 (t, J 5.3 Hz, 0.8H), 1.04-0.97 (m, 6H). NMR suggests the presence of 0.8/1.2 rotamers.

The compounds in Table 20 below were made in an analogous way to that described above.

TABLE 20

| Example | Structure | LC/MS | $^1$H NMR |
|---|---|---|---|
| 246 | 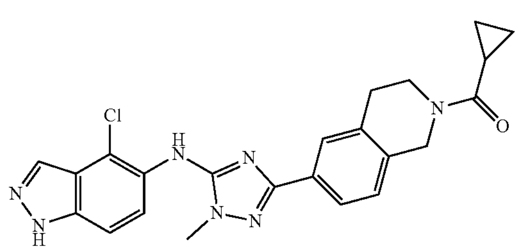 [SMILES: Cn1nc(-c2ccc3c(c2)CCN(C(=O)C2CC2)C3)nc1Nc1ccc2[nH]ncc2c1Cl] | Method B, 3.33 min, m/z 448.4 [M + H]$^+$ | $^1$H NMR (400 MHz, DMSO-d$_6$): 13.39 (s 1H), 8.50 (s, 1H), 8.10 (s, 1H), 7.69-7.52 (m, 4H), 7.20 (d, J 8.0 Hz, 1H), 4.90 (s, 0.85H), 4.61 (s, 1.15H), 3.89 (t, J 5.4 Hz, 1.15H), 3.78 (s, 3H), 3.66 (t J 5.4 Hz, 0.8H), 2.91 (t, J 5.3 Hz, 1.2H), 2.76 (t, J 5.3 Hz, 0.8H), 2.10-2.01 (m, 1H), 0.78-0.68 (m, 4H). |

TABLE 20-continued

| Example | Structure | LC/MS | ¹H NMR |
|---|---|---|---|
| 247 | 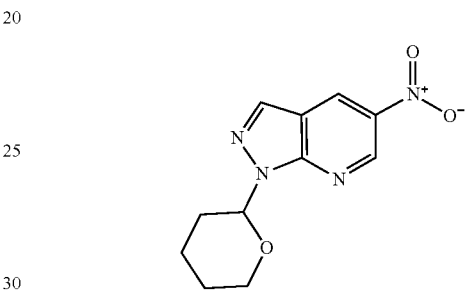 | Method B, 3.13 min, m/z 519.5 [M + H]⁺ | ¹H NMR (400 MHz, DMSO-d₆): 13.38 (s, 1H), 8.48 (s, 1H), 8.10 (s, 1H), 7.71-7.53 (m, 4H), 7.24-7.17 (m, 1H), 4.65-4.56 (m, 2H), 3.79 (s, 3H), 3.71-3.65 (m, 1H), 3.61-3.54 (m, 3H), 3.33-3.22 (m, 2H), 2.88 (t, J 5.6 Hz, 1H), 2.79 (t, J 5.6 Hz, 1H). 1 NH exchangeable not observed. |

Intermediate 66: 1-Tetrahydropyran-2-ylindazol-5-ol

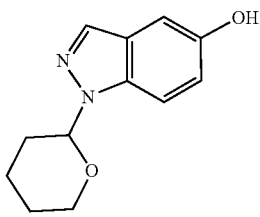

Methanesulfonic acid (0.02 mL, 0.37 mmol) was added to a stirred solution of 1H-indazol-5-ol (0.5 g, 3.7 mmol), 3,4-dihydro-2H-pyran (0.34 mL, 3.73 mmol), DCM (20 mL) and THF (20 mL) at RT under a nitrogen atmosphere. The reaction was stirred at RT for 72 h. The solvent was removed in vacuo and the residue was partitioned between water (100 mL) and DCM (100 mL). The organic layer was separated, dried over sodium sulfate and solvent removed in vacuo. The residue was purified by flash column chromatography on silica gel eluting with 0-100% EtOAc in Pet. Ether to give 1-tetrahydropyran-2-ylindazol-5-ol (442 mg, 2.03 mmol, 54% yield) as a white solid. UPLC-MS (ES+, Method A), 1.34 min, m/z 219.1 [M+H]⁺

Intermediate 67: 1-Tetrahydropyran-2-ylpyrazolo[3,4-b]pyridin-5-amine

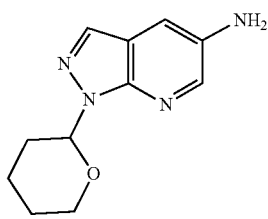

A suspension of 5-nitro-1-tetrahydropyran-2-yl-pyrazolo[3,4-b]pyridine (1.2 g, 4.83 mmol) in EtOAc (12 mL) and 10% palladium on carbon (dry, 0.03 g, 0.3 mmol) was vigorously stirred for 6 h at RT under 1 atm of H2. The mixture was filtered over Celite™ and the filtrate was evaporated to give 1-tetrahydropyran-2-ylpyrazolo[3,4-b]pyridin-5-amine (1.05 g, 4.8 mmol, 99% yield) as a colourless foam. UPLC-MS (ES+, Method A): 1.04 min, m/z 219.3 [M+H]+

Step 1: 5-nitro-1-tetrahydropyran-2-yl-pyrazolo[3,4-b]pyridine

To a suspension of 5-nitro-1H-pyrazolo[3,4-b]pyridine (1 g, 6.1 mmol) in DCM (12 mL) was added p-toluenesulfonic acid monohydrate (0.12 g, 0.61 mmol) and the solution stirred at RT. 3,4-Dihydro-2H-pyran (1.7 mL, 18.3 mmol) was then added slowly and the reaction stirred at RT for 1 h. The mixture was partially evaporated and purified by silica column chromatography eluting with 10-50% EtOAc in Pet. Ether to yield 5-nitro-1-tetrahydropyran-2-yl-pyrazolo[3,4-b]pyridine (1.2 g, 4.8 mmol, 79% yield) as an off-white solid. UPLC-MS (ES⁺, Method A): 1.60 min, m/z 249.1 [M+H]⁺

Intermediate 68: 6-Methyl-1-tetrahydropyran-2-yl-indazol-5-amine

A suspension of 6-methyl-5-nitro-1-tetrahydropyran-2-yl-indazole (1250 mg, 4.78 mmol) in EtOAc (12 mL) and 10% palladium on carbon (dry, 0.03 g, 0.3 mmol) was vigorously stirred for 18 h at RT under 1 atm of H2. The mixture was filtered over Celite™. The filtrate was concentrated under reduced pressure and purified by silica column chromatography eluting with 10-70% EtOAc in Pet. Ether to give a brown oil which was triturated with diethyl ether to give 6-methyl-1-tetrahydropyran-2-yl-indazol-5-amine (833 mg, 3.6 mmol, 75% yield) as a beige solid. UPLC-MS (ES+, Method A): 1.07 min, m/z 232.2 [M+H]+

Step 1:
6-methyl-5-nitro-1-tetrahydropyran-2-yl-indazole

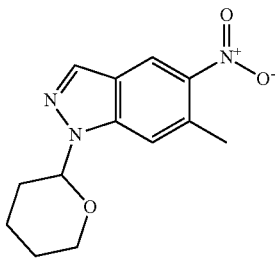 [SMILES: Cc1cc2c(cnn2C2CCCCO2)cc1[N+](=O)[O-]]

To a cream suspension of 5-nitro-1H-pyrazolo[3,4-b]pyridine (1.00 g, 6.1 mmol) in DCM (12 mL) was added p-toluenesulfonic acid monohydrate (0.12 g, 0.61 mmol) and the solution stirred at RT. 3,4-dihydro-2H-pyran (1.7 mL, 18.3 mmol) was then added slowly and the reaction stirred at RT for an h. The mixture was partially evaporated and purified by silica column chromatography eluting with 10-50% EtOAc in Pet. Ether to yield 5-nitro-1-tetrahydropyran-2-yl-pyrazolo[3,4-b]pyridine (1.2 g, 4.8 mmol, 79% yield) as an off-white solid. UPLC-MS (ES+, Method A): 1.79 min, m/z 262.1 [M+H]+

Intermediate 69:
3-Methyl-1-tetrahydropyran-2-yl-indazol-5-amine

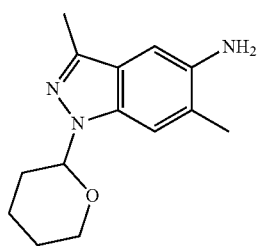 [SMILES: Cc1cc2c(cc1N)c(C)nn2C1CCCCO1]

A suspension of 3-methyl-5-nitro-1-tetrahydropyran-2-yl-indazole (620 mg, 2.4 mmol) in EtOAc (40 mL) and 10% palladium on carbon (65% wet, 400 mg) was vigorously stirred for 18 h at RT under 1 atm of H2. The mixture was filtered over Celite™. The filtrate was concentrated under reduced pressure to give 3-methyl-1-tetrahydropyran-2-yl-indazol-5-amine (540 mg, 2.3 mmol, 98% yield) as a pink solid. LC-MS (ES+, Method F), 1.50 min, m/z 232.1 [M+H]+

Step 1:
3-methyl-5-nitro-1-tetrahydropyran-2-yl-indazole

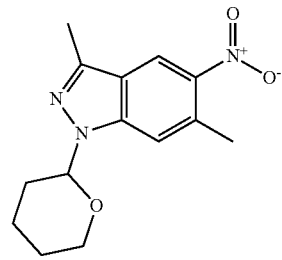 [SMILES: Cc1cc2c(cc1[N+](=O)[O-])c(C)nn2C1CCCCO1]

A solution of 3-methyl-5-nitro-1H-indazole (500 mg, 2.82 mmol) was treated with p-toluenesulfonamide (48 mg, 0.28 mmol) and 3,4-Dihydro-2H-pyran (0.39 mL, 4.23 mmol) at RT and was left stirring overnight. The reaction mixture was neutralized with saturated aqueous NaHCO3 (100 mL) and then extracted with DCM (50 mL×3), the combined organic layers were dried over Na2SO4 and reduced in vacuo. The crude product was purified by silica column chromatography eliding with 10% EtOAc in Pet. Ether to afford 3-methyl-5-nitro-1-tetrahydropyran-2-yl-indazole (640 mg, 2.45 mmol, 87% yield) as a white solid. LC-MS (ES+, Method F), 3.74 min, m/z 262.1 [M+H]+

Intermediate 16:
4-Ethyl-1-tetrahydropyran-2-yl-indazol-5-amine

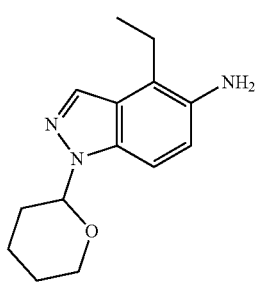 [SMILES: CCc1c(N)ccc2c1cnn2C1CCCCO1]

A suspension of 1-tetrahydropyran-2-yl-4-vinyl-indazol-5-amine (17 g, 70 mmol) was dissolved in MeOH (150 mL) and 10% palladium on carbon (dry, 0.7 g, 7 mmol) was vigorously stirred for 2 h at RT under 1 atm of H2. The mixture was filtered over Celite™. The filtrate was concentrated under reduced pressure and purified by silica column chromatography eluting with 10-60% EtOAc in Pet. Ether to give 4-ethyl-1-tetrahydropyran-2-yl-indazol-5-amine (7.9 g, 32.2 mmol, 46% yield) as an oil. UPLC-MS (ES+, Method A): 1.06 min, m/z 246.5 [M+H]+

Step 1:
1-tetrahydropyran-2-yl-4-vinyl-indazol-5-amine

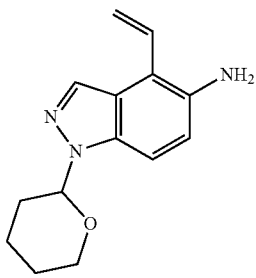 [SMILES: C=Cc1c(N)ccc2c1cnn2C1CCCCO1]

4-Bromo-1-tetrahydropyran-2-yl-indazol-5-amine (30 g, 101 mmol), potassium trifluoro(vinyl)borate(1-) (20.35 g, 151.96 mmol) and cesium carbonate (99 g, 304 mmol) were suspended in 1,4-dioxane (750 mL) and water (250 mL) and fully degassed with bubbling nitrogen. [1,1'-bis(diphenylphosphino)ferrocene]palladium(II) chloride dichloromethane complex (2.1 g, 2.5 mmol) was added followed by further degassing and the reaction was heated to 100° C. for 5 h. The reaction was cooled then diluted with 500 mL of EtOAc and 250 mL of saturated brine. The reaction was filtered, separated and the organics were dried over magnesium sulfate, filtered and reduced in-vacuo to give a brown oil. This was chromatographed via silica column chromatography eluting with 0-60% EtOAc in Pet. Ether to give 1-tetrahydropyran-2-yl-4-vinyl-indazol-5-amine (19.3 g, 75.4 mmol, 74% yield) as an oil. UPLC-MS (ES+, Method A): 1.21 min, m/z 244.4 [M+H]+

Step 1:
3-chloro-5-nitro-1-tetrahydropyran-2-yl-indazole

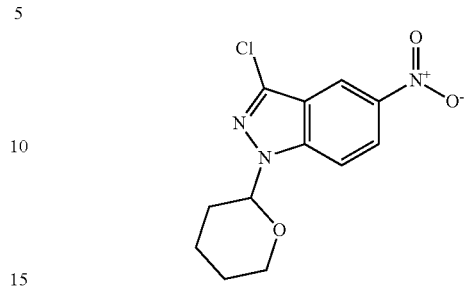

A solution of 3-chloro-5-nitro-1H-indazole (5 g, 25.3 mmol) was treated with p-toluenesulfonic acid (435 mg, 2.5 mmol) and 3,4-dihydro-2H-pyran (3.5 mL, 38 mmol) at RT and was left stirring for 18 h. The reaction mixture was neutralized with saturated aqueous NaHCO$_3$ (100 mL) and then extracted with DCM (3×100 mL). The combined organic layers were dried over sodium sulfate and reduced in vacuo. The crude product was purified by silica column chromatography eluting with 10-20% EtOAc in Pet. Ether to afford 3-chloro-5-nitro-1-tetrahydropyran-2-yl-indazole (5 g, 17.8 mmol, 70% yield). $^1$H NMR (400 MHz, DMSO-d$_6$) δ 8.62 (d, J=2.1 Hz, 1H), 8.36 (dd, J=9.3, 2.2 Hz, 1H), 8.05 (d, J=9.3 Hz, 1H), 6.00 (dd, J=9.5, 2.2 Hz, 1H), 3.94-3.84 (m, 1H), 3.85-3.68 (m, 1H), 2.38-2.24 (m, 1H), 2.08-1.97 (m, 2H), 1.82-1.66 (m, 1H), 1.65-1.51 (m, 2H).

Intermediate 70:
3-Chloro-1-tetrahydropyran-2-yl-indazol-5-amine

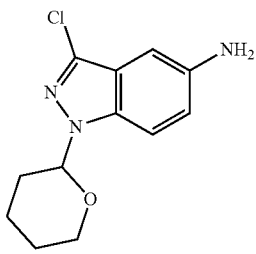 [SMILES: Nc1ccc2c(c1)c(F)nn2C1CCCCO1]

A suspension of 3-chloro-5-nitro-1-tetrahydropyran-2-yl-indazole (2.5 g, 8.9 mmol) in EtOAc (50 mL) and 10% palladium on carbon (65% wet, 1 g) was vigorously stirred for 18 h at RT under 1 atm of H2. The mixture was filtered over Celite™. The filtrate was concentrated under reduced pressure and purified by silica column chromatography eluting with 15-25% EtOAc in Pet. Ether to afford 3-chloro-1-tetrahydropyran-2-yl-indazol-5-amine (1.4 g, 63% yield) as a yellow solid. $^1$H NMR (400 MHz, DMSO-d$_6$) δ 7.47 (d, J=8.9 Hz, 1H), 6.91 (dd, J=9.0, 2.1 Hz, 1H), 6.61 (d, J=2.0 Hz, 1H), 5.67 (dd, J=9.7, 2.5 Hz, 1H), 5.12 (s, 2H), 3.90-3.81 (m, 1H), 3.76-3.58 (m, 1H), 2.35-2.20 (m, 1H), 2.05-1.86 (m, 2H), 1.77-1.63 (m, 1H), 1.54 (m, 2H).

Intermediate 71:
3-Fluoro-1-tetrahydropyran-2-yl-indazol-5-amine

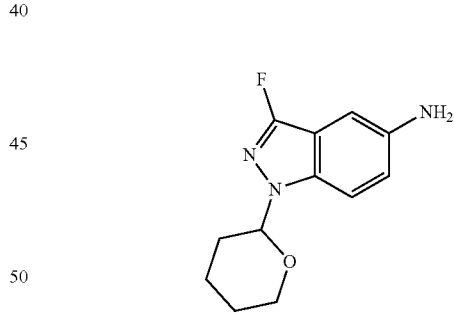

To a suspension of 3-fluoro-5-nitro-1-tetrahydropyran-2-yl-indazole (800 mg, 3.02 mmol) in EtOH (30 mL) and water (5 mL) were added iron (842 mg, 15.1 mmol) and ammonium chloride (484 mg, 9.0 mmol) and the mixture was heated at 70° C. for 3 h. The reaction was cooled to RT, EtOAc (50 mL) was added and the mixture was stirred for 10 min then filtered through a pad of Celite™. The combined filtrate was washed with brine, dried over sodium sulfate and concentrated to afford 3-fluoro-1-tetrahydropyran-2-yl-indazol-5-amine (560 mg, 2.4 mmol, 79% yield) as a yellow solid. LC-MS (ES+, Method F), 2.21 min, m/z 236.1 [M+H]+

Step 1: 3-fluoro-5-nitro-1H-indazole

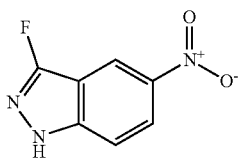 [SMILES: O=[N+]([O-])c1ccc2[nH]nc(F)c2c1]

To a solution of 5-nitroindazole (6 g, 5.63 mmol) in acetonitrile (8 mL) was added Selectfluor (13.03 g, 36.8 mmol) and acetic acid (8 mL). The reaction mixture was heated in the microwave at 150° C. for 1 h. The reaction was quenched with water and extracted with EtOAc. The combined organic layers were dried by sodium sulfate, reduced in vacuo and purified by silica column chromatography eluting with 10-20% EtOAc in Pet. Ether to afford 3-fluoro-5-nitro-1H-indazole (1020 mg, 5.6 mmol, 15% yield) as a brown solid. $^1$H NMR (400 MHz, DMSO-$d_6$) δ 13.29 (s, 1H), 8.74 (d, J=1.6 Hz, 1H), 8.24 (dd, J=9.2, 2.0 Hz, 1H), 7.69 (dd, J=9.2, 2.0 Hz, 1H)

Step 2: 3-fluoro-5-nitro-1-tetrahydropyran-2-yl-indazole

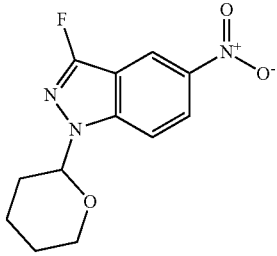 [SMILES: O=[N+]([O-])c1ccc2c(c1)c(F)nn2C1CCCCO1]

A solution of 3-fluoro-5-nitro-1H-indazole (500 mg, 2.8 mmol) was treated with p-toluenesulfonamide (47 mg, 0.28 mmol) and 3,4-Dihydro-2H-pyran (0.4 mL, 4.2 mmol) at 15° C. and was left stirring overnight. The reaction mixture was neutralized with saturated aqueous NaHCO$_3$ (100 mL) and then extracted with DCM (3×100 mL), the combined organic layers were dried over Na$_2$SO$_4$ and reduced in vacuo. The crude product was purified by silica column chromatography eluting with 10-20% EtOAc in Pet. Ether to afford 3-fluoro-5-nitro-1-tetrahydropyran-2-yl-indazole (370 mg, 0.91 mmol, 33% yield) as a yellow oil. $^1$H NMR (400 MHz, DMSO-$d_6$) δ 8.77 (d, J=2.1 Hz, 1H), 8.34 (dd, J=9.4, 2.2 Hz, 1H), 7.99 (dd, J=9.4, 2.0 Hz, 1H), 5.93 (m, 1H), 3.94-3.84 (m, 1H), 3.85-3.67 (m, 1H), 2.31-2.16 (m, 1H), 2.08-1.92 (m, 2H), 1.74 (m, 1H), 1.57 (m, 2H).

Intermediate 72: 4-isopropyl-1-tetrahydropyran-2-yl-indazol-5-amine

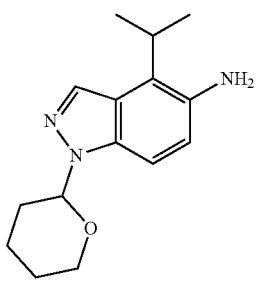 [SMILES: CC(C)c1c(N)ccc2c1cnn2C1CCCCO1]

4-isopropenyl-1-tetrahydropyran-2-yl-indazol-5-amine (190 mg, 0.74 mmol) was dissolved in MeOH (10 mL) and purged with nitrogen. 10% Palladium on carbon (dry, 8 mg, 0.07 mmol) was then added and the reaction placed under an atmosphere of hydrogen and vigorously stirred for 30 minutes. The reaction was filtered and reduced in-vacuo to give 4-isopropyl-1-tetrahydropyran-2-yl-indazol-5-amine (180 mg, 0.7 mmol, 94% yield) as an oil. UPLC-MS (ES$^+$, Method A): 1.14 min, m/z 260.4 [M+H]$^+$

Step 1: 4-isopropenyl-1-tetrahydropyran-2-yl-indazol-5-amine

4-Bromo-1-tetrahydropyran-2-yl-indazol-5-amine (250 mg, 0.84 mmol), potassium isopropenyltrifluoroborate (137 mg, 0.93 mmol) and cesium carbonate (1100 mg, 3.4 mmol) were suspended in 1,4-dioxane (5 mL) and water (2 mL) and fully degassed with bubbling nitrogen. [1,1'-Bis(diphenylphosphino)ferrocene]palladium(II) chloride dichloromethane complex (69 mg, 0.08 mmol) was added followed by further degassing and the reaction was heated to 100° C. for 3 h. The reaction was cooled then diluted with 100 mL of EtOAc and 25 mL of saturated brine, separated and the organics were dried over magnesium sulfate, filtered and reduced in-vacuo to give a brown oil. Further purification by silica column chromatography eluting with 0-75% EtOAc in Pet. Ether gave 4-isopropenyl-1-tetrahydropyran-2-yl-indazol-5-amine (200 mg, 0.78 mmol, 92% yield) as an oil. UPLC-MS (ES$^+$, Method A): 1.22 min, m/z 258.4 [M+H]$^+$

Intermediate 73:
7-Chloro-1-tetrahydropyran-2-yl-indazol-5-amine

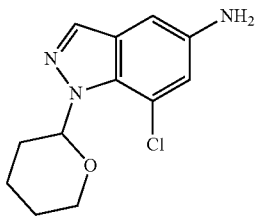 [SMILES: Nc1cc(Cl)c2c(cnn2C2CCCCO2)c1]

To a suspension of 7-chloro-5-nitro-1-tetrahydropyran-2-yl-indazole (450 mg, 1.6 mmol) in EtOH (10 ml) and water (2 mL) was added iron powder (446 mg, 8.0 mmol) and ammonium chloride (256 mg, 4.8 mmol) and the mixture was heated at 70° C. for 5 h. After cooling to RT, EtOAc (30 mL) was added and the mixture was stirred for 10 min then filtered through a pad of Celite™. The combined filtrate was washed with brine, dried over $Na_2SO_4$ and concentrated to afford 7-chloro-1-tetrahydropyran-2-yl-indazol-5-amine (400 mg, 1.59 mmol, 99% yield) as a yellow solid. LC-MS ($ES^+$, Method F): 2.67 min, m/z 252.1 $[M+H]^+$

Step 1:
7-chloro-5-nitro-1-tetrahydropyran-2-yl-indazole

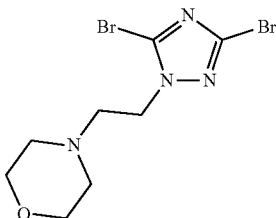

A solution of 7-chloro-5-nitro-1H-indazole (1200 mg, 6.07 mmol) was treated with p-toluenesulfonic acid (117 mg, 0.61 mmol) and 3,4-dihydro-2H-pyran (0.8 mL, 9.1 mmol) at 15° C. and was left stirring for 18 h. The reaction mixture was neutralized with saturated aqueous $NaHCO_3$ (50 mL) and then extracted with DCM (3×50 mL). The combined organic layers were dried over $Na_2SO_4$ and reduced in vacuo to give the crude product, which was purified by silica column chromatography eluting with 5-20% EtOAc in Pet. Ether to afford 7-chloro-5-nitro-1-tetrahydropyran-2-yl-indazole (450 mg, 1.6 mmol, 26% yield) as a yellow solid. LC-MS ($ES^+$, Method F): 3.98 min, m/z mass ion not observed $[M+H]^+$

Intermediate 74: 1-[2-(3,5-Dibromo-1,2,4-triazol-1-yl)ethyl]piperidine

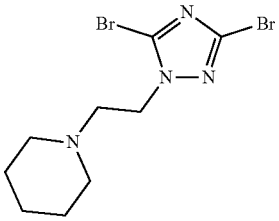 [SMILES: Brc1nc(Br)n(CCN2CCCCC2)n1]

1-(2-Chloroethyl)piperidine hydrochloride (243 mg, 1.32 mmol), 3,5-dibromo-1H-1,2,4-triazole (250 mg, 1.1 mmol) and potassium carbonate (640 mg, 4.6 mmol) were added to DMF (5 mL) in a 25 mL round bottom flask. The reaction was then stirred for 18 h at 50° C. under nitrogen. The solvent was removed in vacuo, water was added, and the product extracted with DCM (3 times). The organic phase was dried over a phase separator and the solvent removed in vacuo. The product was purified by silica column chromatography eluting with 0-10% MeOH in DCM to give [1-[2-(3,5-dibromo-1,2,4-triazol-1-yl)ethyl]piperidine (224 mg, 0.66 mmol, 60% yield)] as a yellow oil. UPLC-MS (ES+, Method A), 0.87 min, m/z 339.0 $[M+H]^+$

Intermediate 75: 4-[2-(3,5-Dibromo-1,2,4-triazol-1-yl)ethyl]morpholine

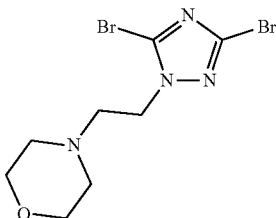

N-Chloroethylmorpholine hydrochloride (197 mg, 1.32 mmol), 3,5-dibromo-1H-1,2,4-triazole (250 mg, 1.1 mmol) and potassium carbonate (456 mg, 3.3 mmol) were added to DMF (5 mL) in a 25 mL round bottom flask. The reaction was then stirred at 50° C. under nitrogen. The solvent was removed in vacuo, water was added, and the product extracted with DCM (3×). The organic phase was dried over a phase separator and the solvent removed in vacuo. The product was purified by silica column chromatography eluting with 0-10% MeOH in DCM to yield [4-[2-(3,5-dibromo-1,2,4-triazol-1-yl)ethyl]morpholine (374 mg, 1.1 mmol, 99% yield)]. UPLC-MS (ES+, Method A), 0.65 min, m/z 341.0 $[M+H]^+$

Intermediate 76:
3,5-Dibromo-1-(2-methoxyethyl)-1,2,4-triazole

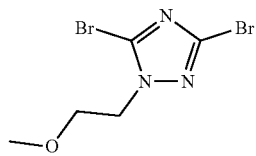

A solution of 3,5-dibromo-1H-1,2,4-triazole (250 mg, 1.1 mmol), 2-bromoethyl methyl ether (0.17 mL, 2.2 mmol) and triethylamine (0.46 mL, 3.3 mmol) in DMA (5 mL) was stirred at 55° C. for 18 h. The reaction mixture was filtered and the solvent removed in vacuo. The product was purified via silica column chromatography eluting with 0-100% EtOAc in Pet. Ether to yield 3,5-dibromo-1-(2-methoxyethyl)-1,2,4-triazole (260 mg, 0.91 mmol, 83% yield) as a colourless oil. UPLC-MS (ES+, Method A), 1.34 min, m/z 285.9 [M+H]⁺.

Intermediate 77:
3,5-Dibromo-1-isobutyl-1,2,4-triazole

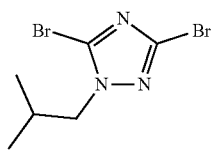

Sodium tert-butoxide (372 mg, 3.9 mmol) was added to a solution of 3,5-dibromo-1H-1,2,4-triazole (800 mg, 3.53 mmol) in DMF (5 mL), and stirred at RT for 15 min. 1-bromo-2-methylpropane (531 mg, 3.9 mmol) was added dropwise and the reaction heated to 50° C. for 2 h and then RT for 18 h. The reaction was quenched with water (50 mL) and extracted with diethyl ether (3×10 mL). The combined organics were washed with brine and dried over sodium sulfate. The solvent was removed in vacuo to yield 3,5-dibromo-1-isobutyl-1,2,4-triazole (276 mg, 0.97 mmol, 27% yield) as a colourless oil. ¹H NMR (400 MHz, CDCl₃) δ 3.94 (dd, J=7.3, 1.0 Hz, 2H), 2.34-2.22 (m, 1H), 0.96 (dd, J=6.8, 0.9 Hz, 6H).

Intermediate 78:
3,5-Dibromo-1-cyclopropyl-1,2,4-triazole

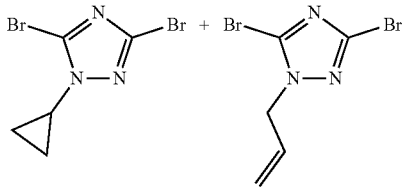

A mixture of 3,5-dibromo-1H-1,2,4-triazole (700 mg, 3.1 mmol), 2,2'-bipyridyl (60 mg, 0.39 mmol), copper(II) acetate (140 mg, 0.77 mmol), potassium carbonate (852 mg, 6.2 mmol) and cyclopropylboronic acid (795 mg, 9.3 mmol) was dissolved in toluene (5 mL) and water (1.5 mL) and stirred at 70° C. for 18 h. The reaction mixture was cooled to RT, quenched with NH₄Cl (sat. aq.) and the products extracted in DCM. The combined organic fractions were dried with a phase separator and reduced in vacuo. The crude mixture was dissolved in DCM and dry-loaded onto silica. Purification via silica column chromatography eluting with 10-60% EtOAc in Pet. Ether afforded 5-dibromo-1-cyclopropyl-1,2,4-triazole and 1-allyl-3,5-dibromo-1,2,4-triazole (123 mg, 0.46 mmol, 15% yield) as an inseparable mixture. UPLC-MS (ES+, Method A): 1.52 min, m/z 267.9 [M+H]⁺

Intermediate 79: 3,5-Dibromo-1-ethyl-1,2,4-triazole

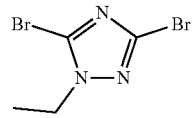

Sodium test-butoxide (372 mg, 3.9 mmol) was added to a solution of 3,5-dibromo-1H-1,2,4-triazole (800 mg, 3.53 mmol) in DMF (5 mL), and stirred at RT for 15 minutes. Bromoethane (422 mg, 3.9 mmol) was added dropwise and the reaction heated to 50° C. for 2 h. The reaction was quenched with water (50 mL) and extracted with diethyl ether (3×10 mL). The organics were washed with brine and dried over sodium sulfate and reduced in vacuo to give 3,5-dibromo-1-ethyl-1,2,4-triazole (663 mg, 2.6 mmol, 74% yield) as a colourless oil. ¹H NMR (400 MHz, CDCl₃) δ 4.19 (q, J=7.3 Hz, 2H), 1.47 (t, J=7.2 Hz, 3H).

Intermediate 80: tert-Butyl 4-(3,5-dibromo-1,2,4-triazol-1-yl)piperidine-1-carboxylate

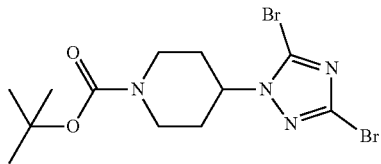 [SMILES: CC(C)(C)OC(=O)N1CCC(n2nc(Br)nc2Br)CC1]

Sodium hydride (34 mg, 0.86 mmol) was slowly added to a solution of 3,5-dibromo-1H-1,2,4-triazole (150 mg, 0.66 mmol) and DMF (3.9 mL) at RT and the solution was stirred at 45° C. for 30 min. tert-Butyl 4-methylsulfonyloxypiperidine-1-carboxylate (0.15 mL, 0.79 mmol) was then added portion-wise. The reaction mixture was stirred at 85° C. for 2 days. The reaction was quenched with NH₄Cl (aq. sat.) and extracted with DCM. The combined organic fractions were dried via a phase separator and reduced in vacuo. The crude residue was dissolved in DCM, reduced in vacuo onto silica and purified by silica flash chromatography eluting with 10-90% EtOAc in Pet. Ether to yield tert-butyl 4-(3,5-dibromo-1,2,4-triazol-1-yl)piperidine-1-carboxylate (140 mg, 0.34 mmol, 52% yield) as a pale yellow oil. UPLC-MS (ES+, Method A): 1.82 min, m/z 411.0 [M+H]⁺.

Step 1: tert-butyl 4-methylsulfonyloxypiperidine-1-carboxylate

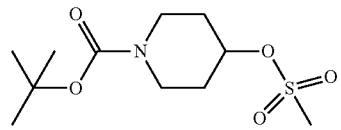 [SMILES: CC(C)(C)OC(=O)N1CCC(OS(C)(=O)=O)CC1]

Methanesulfonyl chloride (0.23 mL, 3.0 mmol) was slowly added to a solution of N-boc-4-hydroxypiperidine (0.49 mL, 2.5 mmol), triethylamine (0.69 mL, 4.9 mmol) and DCM (4 mL) under nitrogen in a dried flask. The reaction mixture was stirred at RT for 2 days. The reaction mixture was quenched with NH₄Cl (sat. aq.) and extracted with DCM. The combined organic fractions were washed with Na₂CO₃ (sat. aq.) and dried with a phase separator and reduced in vacuo to give tert-butyl 4-methylsulfonyloxypiperidine-1-carboxylate (625 mg, 22 mmol, 90% yield) as an off-white solid. ¹H NMR (400 MHz, CDCl₃) δ 4.88 (m, 1H), 3.71 (m, 2H), 3.31 (m, 2H), 3.01 (s, 3H), 1.97 (m, 2H), 1.82 (m, 2H), 1.46 (s, 9H).

Intermediate 81: tert-Butyl N-[2-(3,5-dibromo-1,2,4-triazol-1-yl)ethyl]-N-methyl-carbamate A 100 mL RBF was charged with 2-(3,5-dibromo-1,2,4-triazol-1-ye-N-methyl-ethanamine (644 mg, 2.27 mmol) and DCM (35 mL). DI-tert-butyl dicarbonate (505 mg, 2.3 mmol) and triethylamine (0.47 mL, 3.4 mmol) were added and the reaction mixture was stirred at RT for 18 h. The reaction mixture was quenched with brine and extracted with DCM. The combined organic fractions were dried with a phase separator and reduced in vacuo to afford tert-butyl N-[2-(3,5-dibromo-1,2,4-triazol-1-yl)ethyl]-N-methyl-carbamate (81 mg, 0.21 mmol, 9% yield) as a colourless oil. UPLC-MS (ES+, Method A): 1.64 min, m/z 385.1 [M+H]⁺

Step 1: 2-[tert-butoxycarbonyl(methyl)amino]ethyl methanesulfonate

Methanesulfonyl chloride (0.6 mL, 7.7 mmol) was slowly added to a solution of tert-butyl (2-hydroxyethyl)methylcarbamate (1120 mg, 6.4 mmol), triethylamine (1.8 mL, 12.8 mmol) and DCM (11 mL) under nitrogen. The reaction mixture was stirred at RT for 2 h. The reaction mixture was quenched with NH₄Cl (sat. aq.) and extracted in DCM. The combined organic fractions were washed with Na₂CO₃ (sat. aq), dried with a phase separator and reduced in vacuo to afford 2-[tert-butoxycarbonyl(methyl)amino]ethyl methanesulfonate (1.33 g, 5.24 mmol, 82% yield) as a yellow oil. ¹H NMR (400 MHz, CDCl₃) δ 4.32 (m, 2H), 3.55 (m, 2H), 3.01 (s, 3H), 2.92 (s, 3H), 1.45 (s, 9H).

Step 2: 2-(3,5-dibromo-1,2,4-triazol-1-yl)-N-methyl-ethanamine

Triethylamine (2.0 mL, 14.5 mmol) was slowly added to a solution of 3,5-dibromo-1H-1,2,4-triazole (1.1 g, 4.83 mmol), 2-[tert-butoxycarbonyl(methyl)amino]ethyl methanesulfonate (1467 mg, 5.8 mmol) in DMF (22 mL). The reaction mixture was them stirred at 65° C. for 18 h. The reaction mixture was quenched with NH₄Cl (sat. aq.) and extracted with DCM. The combined organic fractions were dried with a phase separator and reduced in vacuo. The residue was dissolved in DCM and reduced onto silica. Purification by silica column chromatography eluting with 0-5% MeOH in DCM afforded 2-(3,5-dibromo-1,2,4-triazol-1-yl)-N-methyl-ethanamine (644 mg, 2.27 mmol, 47% yield) as an orange liquid. UPLC-MS (ES+, Method A): 1.70 min, m/z 283.9 [M+H]⁺.

Intermediate 82: 3,5-Dibromo-1-[2-(methoxymethoxy)propyl]-1,2,4-triazole

Chloromethyl methyl ether (0.12 mL, 1.35 mmol) was added to a solution of 1-(3,5-dibromo-1,2,4-triazol-1-yl)propan-2-ol (257 mg, 0.9 mmol), N,N-Diisopropylethylamine (0.3 mL, 1.8 mmol) and DCM (4.5 mL). The reaction mixture was then stirred at RT for 18 h. The reaction mixture was quenched with brine and extracted with DCM. The combined organic fractions were dried with a phase separator and reduced in vacuo. The residue was dissolved in DCM and reduced onto silica and purified by silica column chromatography eluting with 10-90% EtOAc in Pet. Ether to afford 3,5-dibromo-1-[2-(methoxymethoxy)propyl]-1,2,4-triazole (173 mg, 0.53 mmol, 59% yield) as a colourless oil which solidified into a white solid upon standing. UPLC-MS (ES+, Method A): 1.50 min, m/z 330.0 [M+H]⁺

Step 1: 1-(3,5-dibromo-1,2,4-triazol-1-yl)propan-2-one

Chloroacetone (0.7 mL, 8.8 mmol) was slowly added to a solution of 3,5-dibromo-1H-1,2,4-triazole (1000 mg, 4.4 mmol), triethylamine (1.84 mL, 13 mmol) and DMF (20 mL) at RT and the reaction mixture was stirred at 65° C. for 3 h and RT for 2 days. The reaction mixture was quenched with NH$_4$Cl (sat. aq.) and extracted with DCM. The combined organic fractions were dried with a phase separator and reduced in vacuo. The residue was dissolved in DCM and reduced onto silica and purified by silica column chromatography eluting with 10-90% EtOAc in Pet. Ether to afford 1-(3,5-dibromo-1,2,4-triazol-1-yl)propan-2-one (1102 mg, 3.9 mmol, 88% yield) as a white solid. UPLC-MS (ES+, Method A): 1.19 min, m/z 283.9 [M+H]$^+$ Step 2: 1-(3,5-dibromo-1,2,4-triazol-1-yl)propan-2-ol

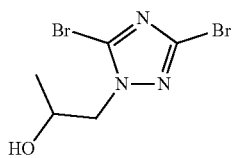

Sodium borohydride (67 mg, 1.8 mmol) was slowly added to a solution of 1-(3,5-dibromo-1,2,4-triazol-1-yl)propan-2-one (250 mg, 0.88 mmol) and MeOH (5 mL). The reaction mixture was stirred at RT for 1 h. The reaction was quenched with NH$_4$Cl (sat. aq.) and extracted in DCM. The combined organic fractions were dried with a phase separator and reduced in vacuo to afford 1-(3,5-dibromo-1,2,4-triazol-1-yl)propan-2-ol (257 mg, 0.9 mmol, 100% yield) as a colourless oil. UPLC-MS (ES+, Method A): 1.16 min, m/z 286.0 [M+H]$^+$ Intermediate 83: 2-[3-Chloro-4-(4,4,5,5-tetramethyl-1,3,2-dioxaborolan-2-yl)phenoxy]-N-isopropyl-acetamide

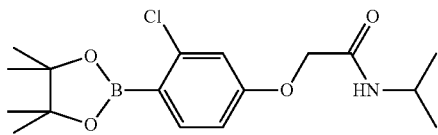 [SMILES: CC(C)NC(=O)COc1ccc(B2OC(C)(C)C(C)(C)O2)c(Cl)c1]

To a solution of 2-(4-bromo-3-chloro-phenoxy)-N-isopropyl-acetamide (1 g, 3.26 mmol), potassium acetate (960 mg, 9.8 mmol) and bis(pinacolato)diboron (1240 mg, 4.9 mmol) in 1,4-dioxane (50 mL) was added 1,1'-bis(diphenylphosphino)ferrocene]dichloropalladium(II) (238 mg, 0.33 mmol) and the reaction heated at 85° C. under N$_2$ for 18 h. The reaction mixture was cooled to RT, filtered through a phase separator and the filtrate concentrated under reduced pressure. The residue was taken up with DCM, washed with water, saturated brine, dried over Na$_2$SO$_4$, filtered and reduced in vacuo to afford 2-[3-chloro-4-(4,4,5,5-tetramethyl-1,3,2-dioxaborolan-2-yl)phenoxy]-N-isopropyl-acetamide (1.5 g, 3.18 mmol, 98% yield). LC-MS (ES+, Method F): 3.79 min, m/z 354.1 [M+H]$^+$ Step 1:
2-(4-bromo-3-chloro-phenoxy)-N-isopropyl-acetamide

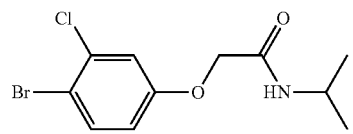

A mixture of 4-bromo-3-chloro-phenol (5 g, 24.1 mmol), 2-chloro-N-isopropylacetamide (4.25 g, 31.3 mmol), potassium carbonate (33.3 g, 241 mmol) in acetone (100 mL) was stirred at reflux overnight. The reaction mixture was filtered and the filtrate was concentrated under reduced pressure. The residue was purified by silica column chromatography eluting with 15-50% EtOAc in Pet. Ether to afford 2-(4-bromo-3-chloro-phenoxy)-N-isopropyl-acetamide (6.9 g, 21.4 mmol, 89% yield) as a white solid. LC-MS (ES+, Method F): 2.31 min, m/z 306.0 [M+H]$^+$ The following boronate intermediates in Table 21 were made by using the same procedure shown for intermediate 83.

TABLE 21

| Intermediate No | Structure | Analysis |
| --- | --- | --- |
| Intermediate 84 | ![structure] | $^1$H NMR (400 MHz, DMSO-d$_6$) δ 7.95 (s, 1H), 7.76 (d, J = 7.8 Hz, 1H), 7.46 (s, 1H), 6.80 (d, J = 8.6 Hz, 1H), 4.48 (s, 2H), 3.92 (h, J = 6.7 Hz, 1H), 2.21 (s, 3H), 1.27 (s, 12H), 1.08 (d, J = 6.7 Hz, 6H). |
| Intermediate 85 | ![structure] | Method F, 4.26 min, m/z 388.2 [M + H]$^+$ |

TABLE 21-continued

| Intermediate No | Structure | Analysis |
| --- | --- | --- |
| Intermediate 86 | 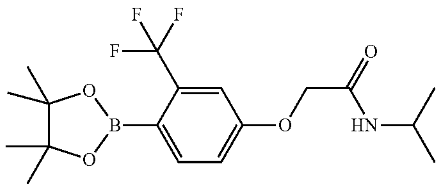 [SMILES: CC(C)NC(=O)COc1ccc(B2OC(C)(C)C(C)(C)O2)c(C(F)(F)F)c1] | Method F, 3.91 min, m/z 388.1 [M + H]+ |
| Intermediate 87 | 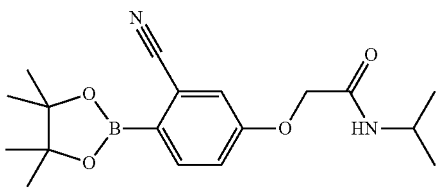 [SMILES: CC(C)NC(=O)COc1ccc(B2OC(C)(C)C(C)(C)O2)c(C#N)c1] | $^1$H NMR (400 MHz, DMSO-d$_6$) δ 7.97 (d, J = 8.0 Hz, 1H), 7.75 (d, J = 8.5 Hz, 1H), 7.41 (d, J = 2.5 Hz, 1H), 7.27 (dd, J = 8.4, 2.5 Hz, 1H), 4.57 (s, 2H), 3.94 (h, J = 6.8 Hz, 1H), 1.30 (s, 12H), 1.09 (d, J = 6.7 Hz, 6H). |
| Intermediate 88 | 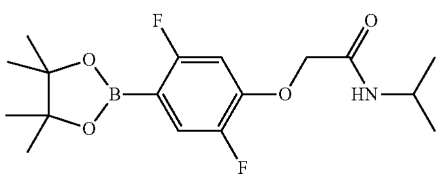 [SMILES: CC(C)NC(=O)COc1cc(F)c(B2OC(C)(C)C(C)(C)O2)cc1F] | $^1$H NMR (400 MHz, DMSO-d$_6$) δ 7.97 (d, J = 7.8 Hz, 1H), 7.30 (dd, J = 11.2, 5.4 Hz, 1H), 6.92 (dd, J = 10.4, 6.6 Hz, 1H), 4.62 (s, 2H), 3.91 (dq, J = 13.6, 6.8 Hz, 1H), 1.28 (s, 12H), 1.08 (d, J = 5.9 Hz, 6H). |

Intermediate 89: 2,2-dimethyl-1-[6-(4,4,5,5-tetramethyl-1,3,2-dioxaborolan-2-yl)-3,4-dihydro-1H-isoquinolin-2-yl]propan-1-one

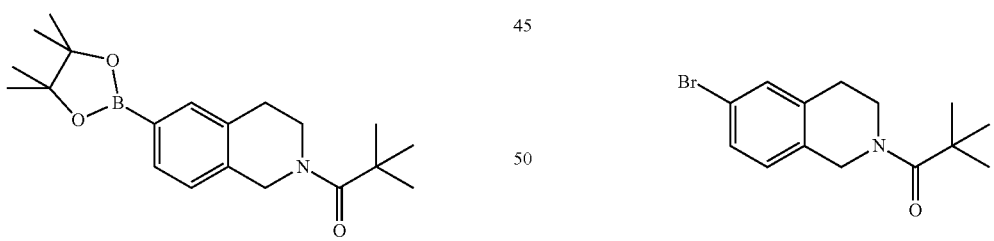

To a solution of 1-(6-bromo-3,4-dihydro-1H-isoquinolin-2-yl)-2,2-dimethyl-propan-1-one (500 mg, 1.69 mmol), potassium acetate (497 mg, 5 mmol) and bis(pinacolato)diboron (514 mg, 2.0 mmol) in 1,4-dioxane (10 mL) was added Pd(dppf)Cl$_2$ (247 mg, 0.34 mmol) and the reaction heated at 85° C. under N$_2$ for 18 h. The reaction mixture was cooled to RT, filtered through a phase separator and the filtrate concentrated under reduced pressure. The crudes were dissolved in DCM and washed with water, saturated brine and dried over Na$_2$SO$_4$, filtered and reduced in vacuo to afford crude 2,2-dimethyl-1-[6-(4,4,5,5-tetramethyl-1,3,2-dioxaborolan-2-yl)-3,4-dihydro-1H-isoquinolin-2-yl]propan-1-one (assumed quantitative yield). UPLC-MS (ES+, Method F), 3.22 min, m/z 344.2 [M+H]+

Step 1: 1-(6-bromo-3,4-dihydro-1H-isoquinolin-2-yl)-2,2-dimethyl-propan-1-one

To a stirred solution of 6-bromo-1,2,3,4-tetrahydroisoquinoline (1000 mg, 4.7 mmol) and triethylamine (1.0 mL, 7.0 mmol) in DCM (20 mL) was added trimethyl acetyl chloride (0.64 mL, 5.2 mmol) at 0° C. and the solution stirred at 25° C. for 2 h. Water (60 mL) was added and extracted with DCM (30 mL×3), the combined organics were washed with brine and dried over Na$_2$SO$_4$. The solution was filtered and reduced in vacuo to afford 1-(6-bromo-3,4-dihydro-1H-isoquinolin-2-yl)-2,2-dimethyl-propan-1-one (1390 mg, 4.7 mmol, 99% yield) as a light-yellow solid. UPLC-MS (ES+, Method F), 4.02 mkt, m/z 298.0 [M+H]+

The following compound was made in an analogous way

Intermediate 90: 1-[6-(4,4,5,5-tetramethyl-1,3,2-dioxaborolan-2-yl)-3,4-dihydro-1H-isoquinolin-2-yl]propan-1-one

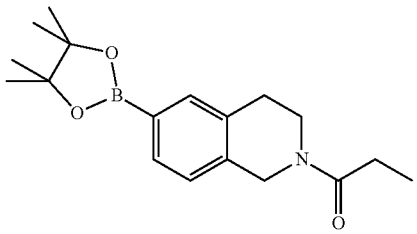 [SMILES: CCC(=O)N1CCc2cc(B3OC(C)(C)C(C)(C)O3)ccc2C1]

UPLC-MS (ES+, Method A), 1.79 min, m/z 316.3 [M+H]$^+$

Intermediate 91: 6-(4,4,5,5-tetramethyl-1,3,2-dioxaborolan-2-yl)-2-(2,2,2-trifluoroethyl)-3,4-dihydro-1H-isoquinoline

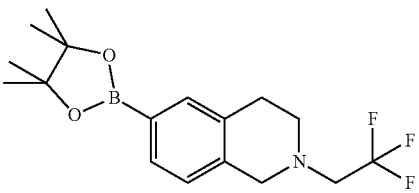 [SMILES: CC1(C)OB(c2ccc3c(c2)CCN(CC(F)(F)F)C3)OC1(C)C]

To a solution of 6-bromo-2-(2,2,2-trifluoroethyl)-3,4-dihydro-1H-isoquinoline (200 mg, 0.68 mmol), potassium acetate (200 mg, 2.0 mmol) and bis(pinacolato)diboron (259 mg, 1.0 mmol) in 1,4-dioxane (10 mL) was added [1,1'-bis(diphenylphosphino)ferrocene]dichloropalladium(II) (50 mg, 0.07 mmol) and the reaction was heated at 85° C. under N$_2$ for 18 h. The reaction mixture was cooled to RT, filtered through a phase separator and the filtrate reduced in vacuo. The crudes were dissolved in DCM and washed with water, saturated brine and dried over Na$_2$SO$_4$, filtered and reduced in vacuo to afford 6-(4,4,5,5-tetramethyl-1,3,2-dioxaborolan-2-yl)-2-(2,2,2-trifluoroethyl)-3,4-dihydro-1H-isoquinoline (assumed quantitative yield). $^1$H NMR (400 MHz, DMSO-d$_6$) δ 7.25 (d, J=52.8 Hz, 2H), 6.54 (s, 1H), 3.67-3.45 (m, 1H), 3.43-3.23 (m, 2H), 3.21-2.93 (m, 2H), 2.75-2.48 (m, 2H), 2.35-2.18 (m, 1H), 0.92 (s, 12H).

Step 1: 6-bromo-2-(2,2,2-trifluoroethyl)-3,4-dihydro-1H-isoquinoline

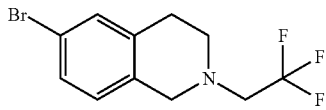 [SMILES: FC(F)(F)CN1CCc2cc(Br)ccc2C1]

A mixture of 6-bromo-1,2,3,4-tetrahydroisoquinoline (800 mg, 3.8 mmol), 2,2,2-trifluoroethyl trifluoromethanesulfonate (1051 mg, 4.5 mmol) and potassium carbonate (1043 mg, 7.5 mmol) in NMP (10 mL) was stirred at 40° C. for 18 h. The reaction mixture was filtered and the filtrate was reduced in vacuo. The residue was purified by silica column chromatography eluting with 2% EtOAc in Pet. Ether to afford 6-bromo-2-(2,2,2-trifluoroethyl)-3,4-dihydro-1H-isoquinoline (800 mg, 2.72 mmol, 72% yield) as a white solid. $^1$H NMR (400 MHz, DMSO-d$_6$) δ 7.36-7.26 (m, 2H), 7.03 (d, J=8.1 Hz, 1H), 3.79-3.74 (m, 2H), 3.38-3.28 (m, 2H), 2.90 (m, 2H), 2.82 (m, 2H).

Example 248: 1-[6-[5-[(4-cyclopropyl-1H-indazol-5-yl)amino]-1-methyl-1,2,4-triazol-3-yl]-1-methyl-3,4-dihydro-1H-isoquinolin-2-yl]ethanone

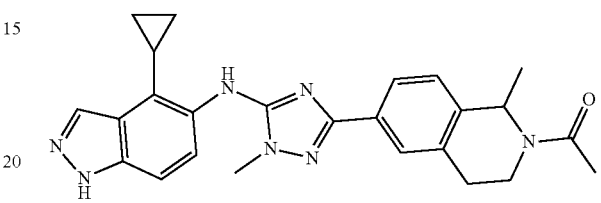

Hydrogen Chloride (0.38 mL, 1.52 mmol) was added to a solution of 1-[6-[5-[(4-cyclopropyl-1-tetrahydropyran-2-yl-indazol-5-yl)amino]-1-methyl-1,2,4-triazol-3-yl]-1-methyl-3,4-dihydro-1H-isoquinolin-2-yl]ethanone (32 mg, 0.06 mmol) in MeOH (5 mL). The mixture was stirred at 45° C. for 2 h and concentrated under reduced pressure. The residue was taken up with MeOH (1 mL) and purified via anion-exchange chromatography (SCX-2 cartridge) eluting with 3 M NH$_3$ in MeOH to give 1-[6-[5-[(4-cyclopropyl-1H-indazol-5-yl)amino]-1-methyl-1,2,4-triazol-3-yl]-1-methyl-3,4-dihydro-1H-isoquinolin-2-yl]ethanone (19 mg, 0.04 mmol, 72% yield) as yellow solid. UPLC-MS (ES+, Method B): 3.04 min, m/z 442.6 [M+H]$^+$. 1H NMR (400 MHz, DMSO-d6): 13.00 (s, 1H), 8.23 (s, 1H), 8.05 (s, 1H), 7.66 (m, 1H), 7.60 (m, 1H), 7.41 (d, J=8.8 Hz, 1H), 7.37 (d, J=8.8 Hz, 1H), 7.21 (m, 1H), 5.45 (q, J=6.8 Hz, 0.6H), 5.05 (q, J=6.8 Hz, 0.4H), 4.43 (m, 0.3H), 3.82 (m, 0.7H), 3.76 (s, 3H), 3.43 (m, 0.5H), 2.94 (m, 0.5H), 2.87 (m, 0.5H), 2.80 (m, 0.5H), 2.71 (m, 1.0H), 2.21 (m, 2H), 2.10 (s, 1.2H), 2.07 (s, 1.8H), 1.45 (d, J=6.8 Hz, 1.1H), 1.33 (d, J=6.8 Hz, 1.9H), 0.99-0.93 (m, 2H), 0.84-0.77 (m, 2H).

Step 1: N-[2-(3-bromophenyl)ethyl]acetamide

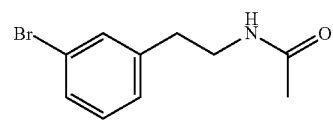

A mixture of 2-(3-bromophenyl)ethanamine (0.7 mL, 4.9 mmol), acetic anhydride (1 mL, 10.6 mmol), triethylamine (1.4 mL, 10.0 mmol) and DCM (25 mL) was stirred at RT or 18 h, diluted with DCM (50 mL) and washed with NaHCO$_3$ (aq. sat.) (50 mL). The organic phase was separated and dried over Na$_2$SO$_4$, filtered reduced in vacuo. The residue was purified by silica column chromatography eluting with 20-100% EtOAc in Pet. Ether to afford N-[2-(3-bromophenyl)ethyl]acetamide (1.19 g, 4.92 mmol, 99% yield). UPLC-MS (ES+, Method A): 1.41 min, m/z 243.9 [M+H]+.

Step 2: 6-bromo-1-methyl-3,4-dihydroisoquinoline

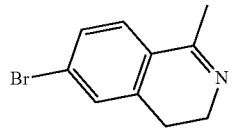

N-[2-(3-Bromophenyl)ethyl]acetamide (1 g, 4.1 mmol) was mixed with polyphosphoric acid 83% (3.4 g, 41 mmol) and heated to 200° C. for 4 h. The mixture was poured into stirred ice-cold water (80 mL) and the pH was adjusted to 10 with 28% aq. NH₄OH. The aqueous layer was extracted with DCM (3×80 mL). The combined organic phases were dried over Na₂SO₄, filtered and reduced in vacuo to give 6-bromo-1-methyl-3,4-dihydroisoquinoline (840 mg, 3.75 mmol, 91% yield as brown oil. UPLC-MS (ES+, Method A): 0.97 min, m/z 223.7 [M+H]+

Step 3: 6-bromo-1-methyl-1,2,3,4-tetrahydroisoquinoline

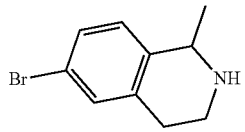

6-Bromo-1-methyl-3,4-dihydroisoquinoline (520 mg, 2.3 mmol) was dissolved in MeOH (15 mL) and cooled to 0° C. Sodium borohydride (175 mg, 4.6 mmol) was added and the reaction was left to warm to RT. After 1 h, further sodium borohydride (175. mg, 4.63 mmol) was added and the reaction stirred at RT for 1 h. The mixture was quenched with water (0.1 mL) and dropwise addition of 4 N HCl in 1,4-dioxane (3 mL) until mixture reached pH 3-4. The reaction was reduced in vacuo and the resultant solid was dissolved in water (30 mL). The mixture was basified to pH 11-12 with 5 M NaOH. The aqueous phase was extracted with EtOAc (3×40 mL) and the combined organic fractions were dried over Na₂SO₄ and reduced in vacuo to give 6-bromo-1-methyl-1,2,3,4-tetrahydroisoquinoline (522 mg, 2.3 mmol, 99% yield) as an amber oil. UPLC-MS (ES+, Method A): 1.04 min, m/z 228.0 [M+H]+.

Step 4: 1-(6-bromo-1-methyl-3,4-dihydro-1H-isoquinolin-2-yl)ethanone

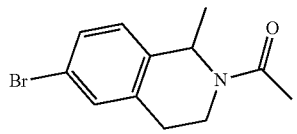

A mixture of 6-bromo-1-methyl-1,2,3,4-tetrahydroisoquinoline (519 mg, 2.3 mmol) in DCM (15 mL), triethylamine (0.65 mL, 4.66 mmol) and acetic anhydride (0.33 mL, 3.5 mmol) was stirred at 20° C. for 18 h, diluted with DCM (30 mL) and washed with saturated aq. NaHCO₃ (20 mL). The organic phase was separated, dried over Na₂SO₄, filtered and concentrated in vacuo. The residue was purified by silica column chromatography eluting with 20-100% EtOAc in Pet. Ether to afford 1-(6-bromo-1-methyl-3,4-dihydro-1H-isoquinolin-2-yl)ethanone (380 mg, 1.42 mmol, 62% yield) as yellow oil. UPLC-MS (ES+, Method A): 1.60 min, m/z 269.9 [M+H]+.

Step 5: 1-[1-methyl-6-(4,4,5,5-tetramethyl-1,3,2-dioxaborolan-2-yl)-3,4-dihydro-1H-isoquinolin-2-yl]ethanone

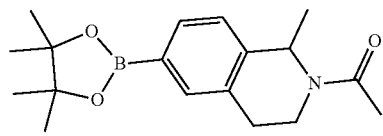 [SMILES: CC(=O)N1CCc2cc(B3OC(C)(C)C(C)(C)O3)ccc2C1C]

Bis(pinacolato)diboron (306 mg, 1.2 mmol), 1-(6-bromo-1-methyl-3,4-dihydro-1H-isoquinolin-2-yl)ethanone (162 mg, 0.6 mmol), potassium acetate (178 mg, 1.8 mmol) and 1,4-dioxane (6 mL) were mixed and degassed for 5 min via N2 bubbling. [1,1'-Bis(diphenylphosphino)ferrocene]palladium(II) chloride dichloromethane complex (49 mg, 0.06 mmol) was added and the mixture was degassed for 5 min via N2 bubbling. The reaction was stirred overnight at 90° C. The reaction was reduced in vacuo and the crude product purified by silica column chromatography, eluting with 60-100% EtOAc in Pet. Ether to afford 1-[1-methyl-6-(4,4,5,5-tetramethyl-1,3,2-dioxaborolan-2-yl)-3,4-dihydro-1H-isoquinolin-2-yl]ethanone (126 mg, 0.4 mmol, 66% yield), obtained as colourless oil. UPLC-MS (ES+, Method A): 1.74 min, m/z 316.1 [M+H]+.

Step 6: 1-[6-[5-[(4-cyclopropyl-1-tetrahydropyran-2-yl-indazol-5-yl)amino]-1-methyl-1,2,4-triazol-3-yl]-1-methyl-3,4-dihydro-1H-isoquinolin-2-yl]ethanone

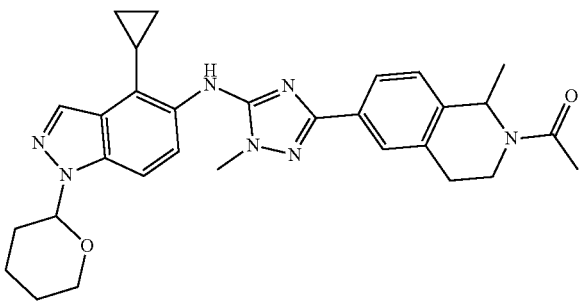 [SMILES: CC(=O)N1CCc2cc(-c3nc(Nc4ccc5c(cnn5C5CCCCO5)c4C4CC4)n(C)n3)ccc2C1C]

N-(5-bromo-2-methyl-1,2,4-triazol-3-yl)-4-cyclopropyl-1-tetrahydropyran-2-yl-indazol-5-amine (182 mg, 0.44 mmol), 1-[1-methyl-6-(4,4,5,5-tetramethyl-1,3,2-dioxaborolan-2-yl)-3,4-dihydro-1H-isoquinolin-2-yl]ethanone (125 mg, 0.40 mmol), potassium carbonate (137 mg, 0.99 mmol) in 1,4-dioxane (4 mL) and water (0.4000 mL) were mixed and degassed for 5 min via N2 bubbling. [1,1'-Bis(diphenylphosphino)ferrocene]Palladium(II) chloride dichloromethane complex (32 mg, 0.04 mmol) was added and the mixture was degassed for 5 min via N2 bubbling. The reaction was irradiated for 3 h at 100° C. in the microwave reactor. Volatiles were evaporated, the chide dissolved in DCM and adsorbed onto silica. Purification by silica chromatography eluting with 20-100% EtOAc in Pet. Ether afforded 1-[6-[5-[(4-cyclopropyl-1-tetrahydropyran-2-yl-indazol-5-yl)amino]-1-methyl-1,2,4-triazol-3-yl]-1-methyl-3,4-dihydro-1H-isoquinolin-2-yl]ethenone (32 mg, 0.06 mmol, 15% yield). UPLC-MS (ES+, Method A): 1.64 min, m/z 526.7 [M+H]+

Example 249: 4-cyclopropyl-N-[5-(2-ethyl-1-methyl-3,4-dihydro-1H-isoquinolin-6-yl)-2-methyl-1,2,4-triazol-3-yl]-1H-indazol-5-amine

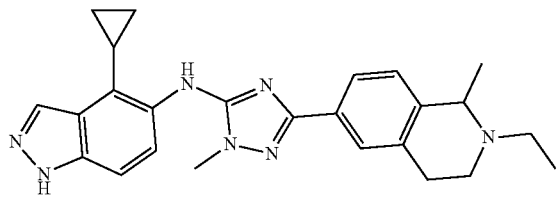 [SMILES: CCN1CCc2cc(-c3nc(Nc4ccc5[nH]ncc5c4C4CC4)n(C)n3)ccc2C1C]

4-Cyclopropyl-N-[5-(2-ethyl-1-methyl-3,4-dihydro-1H-isoquinolin-6-yl)-2-methyl-1,2,4-triazol-3-yl]-1H-indazol-5-amine (21 mg, 0.05 mmol, 88% yield) was synthesised following Example XX procedure. From 4-cyclopropyl-N-[5-(2-ethyl-1-methyl-3,4-dihydro-1H-isoquinolin-6-yl)-2-methyl-1,2,4-triazol-3-yl]-1-tetrahydropyran-2-yl-indazol-5-amine (29 mg, 0.06 mmol). UPLC-MS (ES+, Method B): 2.43 min, m/z 428.4 [M+H]$^+$. 1H NMR (400 MHz, DMSO-d6): 13.00 (s, 1H), 8.21 (s, 1H), 8.06 (s, 1H), 7.58 (br. d, J=8.0 Hz, 1H), 7.51 (s, 1H), 7.42-7.34 (m, 2H), 7.10 (d, J=8.0 Hz, 1H), 3.89-3.78 (m, 1H), 3.75 (s, 3H), 2.89 (m, 1H), 2.79 (m, 1H), 2.71-2.61 (m, 2H), 2.60-2.53 (m, 2H), 2.11 (m, 1H), 1.21 (d, J=6.6 Hz, 3H), 1.05 (t, J=7.0 Hz, 3H), 0.98-0.92 (m, 2H), 0.83-0.77 (m, 2H).

Step 1: 6-bromo-2-ethyl-1-methyl-3,4-dihydro-1H-isoquinoline

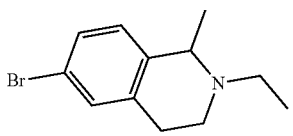

Di-methylsulfide borane (2.07 mL, 4.13 mmol) was added slowly to a solution of 1-(6-bromo-1-methyl-3,4-dihydro-1H-isoquinolin-2-yl)ethanone (213 mg, 0.79 mmol) in anhydrous THF (8 mL), cooled to 0° C. The mixture was then heated to 70° C. Upon completion, the mixture was slowly quenched with MeOH (2 mL) at RT and heated to 70° C. for 1 h, cooled, diluted with EtOAc (30 mL) and washed with NaHCO$_3$ (aq. sat.) (20 mL). The layers were partitioned, and the organic phase was dried over Na$_2$SO$_4$, filtered and concentrated under reduced pressure. The crude material dissolved in MeOH (2 mL) and purified via anion-exchange chromatography (SCX-2 cartridge) eluting with 3.5 M NH$_3$ in MeOH to give 6-bromo-2-ethyl-1-methyl-3,4-dihydro-1H-isoquinoline (173 mg, 0.68 mmol, 85% yield) as yellow oil. UPLC-MS (ES+, Method A): 1.07 min, m/z 255.9 [M+H]+

Step 2: 2-Ethyl-1-methyl-6-(4,4,5,5-tetramethyl-1,3,2-dioxaborolan-2-yl)-3,4-dihydro-1H-isoquinoline

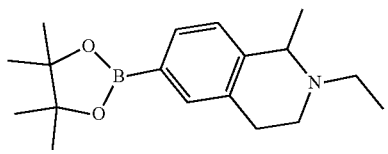 [SMILES: CCN1CCc2cc(B3OC(C)(C)C(C)(C)O3)ccc2C1C]

The intermediate from example 248 Step 5, 6-bromo-2-ethyl-1-methyl-3,4-dihydro-1H-isoquinoline (75 mg, 0.3 mmol), bis(pinacolato)diboron (150 mg, 0.59 mmol), potassium acetate (87 mg, 0.89 mmol) and 1,4-dioxane (3 mL) gave after purification by silica column chromatography, eluting with 20-100% EtOAc in Pet. Ether to afford 2-ethyl-1-methyl-6-(4,4,5,5-tetramethyl-1,3,2-dioxaborolan-2-yl)-3,4-dihydro-1H-isoquinoline (36 mg, 0.12 mmol, 40% yield) as yellow oil. UPLC-MS (ES+, Method A): 1.26 min, m/z 302.1 [M+H]+

Intermediate 92: N-ethyl-2,2,2-trifluoro-1-[4-(4,4,5,5-tetramethyl-1,3,2-dioxaborolan-2-yl)phenyl]ethanamine

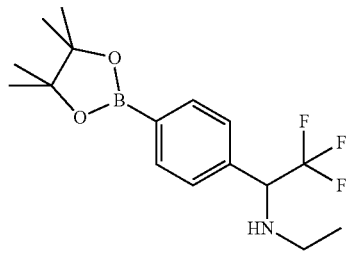 [SMILES: CCNC(c1ccc(B2OC(C)(C)C(C)(C)O2)cc1)C(F)(F)F]

A 50 mL flask was charged with 2,2,2-trifluoro-1-[4-(4,4,5,5-tetramethyl-1,3,2-dioxaborolan-2-yl)phenyl]ethanamine (150 mg, 0.5 mmol), MeOH (5 mL) and acetaldehyde (0.03 mL, 0.5 mmol). The reaction mixture was stirred at RT for 1 h and sodium borohydride (28 mg, 0.75 mmol) was slowly added. The reaction mixture was stirred at RT for a further 1 h. The reaction was quenched with Na$_2$CO$_3$ (aq. sat.) and extracted with DCM and EtOAc. The organic fractions were reduced in vacuo and the residue was dissolved in DCM. Insolubles were filtered off and the filtrate was reduced in vacuo to afford N-ethyl-2,2,2-trifluoro-1-[4-(4,4,5,5-tetramethyl-1,3,2-dioxaborolan-2-yl)phenyl]ethanamine (108 mg, 0.33 mmol, 66% yield) as a clear oil. UPLC-MS (ES+, Method A): 1.68 min, m/z 330.1 [M+H]$^+$ Step 1: 1-(4-bromophenyl)-2,2,2-trifluoro-ethanamine

A 250 mL RBF was charged with 4-bromo-2,2,2-trifluoroacetophenone (1.5 g, 5.9 mmol) and toluene (30 mL). The solution was cooled to 0° C. and lithium bis(trimethylsilyl)amide (6.5 mL, 6.5 mmol) was added dropwise. The reaction mixture was stirred at RT for 30 min and di-methylsulfide borane (5.9 mL, 11.8 mmol) was slowly added at 0° C. The mixture was stirred at RT for an additional 1 h, cooled to 0° C. and 2 N NaOH (9 mL) was added. The mixture was stirred at RT for 1.5 h before being partitioned between EtOAc and water. The organic layer was washed with water and brine, dried with a phase separator and reduced in vacuo. The crude product was purified by silica column chromatography eluting with 0% to 70% EtOAc in Pet. Ether to afford 1-(4-bromophenyl)-2,2,2-trifluoro-ethanamine (1339 mg, 5.27 mmol, 88.9% yield) as a colourless liquid. UPLC-MS (ES+, Method A): 1.27 min, m/z 256.0 [M+H]$^+$ Intermediate 93: 1-2,2,2-trifluoro-1-[4-(4,4,5,5-tetramethyl-1,3,2-dioxaborolan-2-yl)phenyl]ethanamine

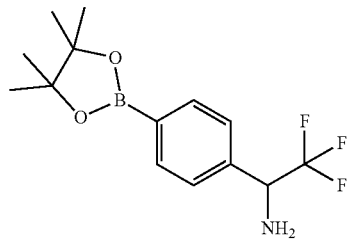 [SMILES: CC1(C)OB(c2ccc(C(N)C(F)(F)F)cc2)OC1(C)C]

A 100 mL RBF was charged with 1-(4-bromophenyl)-2,2,2-trifluoro-ethanamine (1.34 g, 5.27 mmol), bis(pinacolato)diboron (1605 mg, 6.32 mmol), [1,1'-bis(diphenylphosphino)ferrocene]palladium(II) chloride dichloromethane complex (430 mg, 0.53 mmol) and potassium acetate (1550 mg, 15.8 mmol) and flushed with nitrogen. 1,4-dioxane (24 mL) was degassed with bubbling N$_2$ and then added to the mixture and the suspension was stirred at 90° C. for 1.5 h. The reaction mixture was cooled to RT and partitioned between EtOAc and water. The organic layer was washed with water, saturated brine, and reduced in vacuo. The residue was dissolved in DCM and adsorbed onto silica and purified by silica column chromatography eluting with 0% to 60% EtOAc in Pet. Ether to afford 2,2,2-trifluoro-1-[4-(4,4,5,5-tetramethyl-1,3,2-dioxaborolan-2-yl)phenyl]ethanamine (917 mg, 3.05 mmol, 58% yield) as a clear oil. UPLC-MS (ES+, Method A): 1.48 min, m/z 302.1 [M+H]$^+$ Intermediate 94: N-ethyl-2,2-difluoro-1-[4-(4,4,5,5-tetramethyl-1,3,2-dioxaborolan-2-yl)phenyl]ethanamine

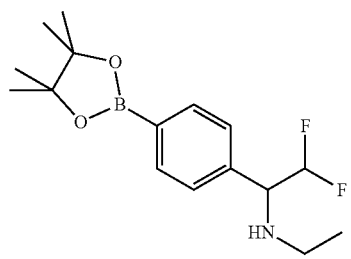 [SMILES: CCNC(c1ccc(B2OC(C)(C)C(C)(C)O2)cc1)C(F)F]

A 100 mL flask was charged with 1-(4-bromophenyl)-N-ethyl-2,2-difluoro-ethanamine (185 mg, 0.7 mmol), bis(pinacolato)diboron (214 mg, 0.84 mmol), [1,1'-bis(diphenylphosphino)ferrocene]palladium(II) chloride dichloromethane complex (57 mg, 0.07 mmol) and potassium acetate (207 mg, 2.1 mmol) and flushed with N$_2$. Degassed 1,4-dioxane (3 mL) was added to the mixture and the suspension was stirred at 90° C. for 1.5 h. The reaction mixture was cooled to RT and partitioned between DCM and water. The organic layer was washed with water, saturated brine and reduced in vacuo. The residue was dissolved in DCM and reduced in vacuo onto silica. The product was purified by silica column chromatography eluting with 10% to 100% EtOAc in Pet. Ether, then 0% to 5% MeOH in DCM to afford N-ethyl-2,2-difluoro-1-[4-(4,4,5,5-tetramethyl-1,3,2-dioxaborolan-2-yl)phenyl]ethanamine (115 mg, 0.37 mmol, 53% yield) as a clear oil. UPLC-MS (ES+, Method A): 1.30 min, m/z 312.3 [M+H]$^+$ Step 1: 1-(4-bromophenyl)-2,2-difluoro-ethanone

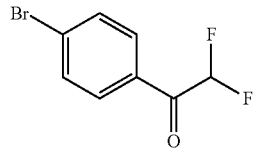 [SMILES: O=C(c1ccc(Br)cc1)C(F)F]

A dry 100 mL flask was charged with 4-iodobromobenzene (2 g, 7.0 mmol) and THF (20 mL). The solution was cooled to −78° C. and n-butyllithium solution (3.1 mL, 7.8 mmol) was slowly added to the solution. The reaction mixture was stirred at −78° C. for 30 min. Ethyl difluoroacetate (0.8 mL, 7.8 mmol) was then added dropwise and the reaction mixture was stirred at −78° C. for 1 h. The reaction mixture was stirred at −78° C. for an additional 1 h, then at 0° C. for 1 h. The reaction was then quenched with 1N HCl (3 mL) and extracted with DCM. The combined organic fractions were washed with brine, dried with a phase separator and reduced in vacuo. The crude residue was dissolved in DCM and reduced in vacuo onto silica and purified by silica column chromatography eluting with 0% to 50% EtOAc in Pet. Ether to afford 1-(4-bromophenyl)-2,2-difluoro-ethanone (1123 mg, 4.78 mmol, 68% yield) as a yellow liquid. UPLC-MS (ES+, Method A): 2.05 min, m/z 233.1 [M−H]$^−$ Step 2: 1-(4-bromophenyl)-N-ethyl-2,2-difluoro-ethanamine

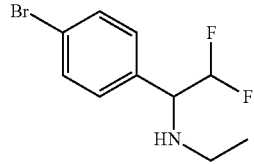

A dry 100 mL flask was charged with 1-(4-bromophenyl)-2,2-difluoro-ethanone (287 mg, 1.2 mmol), MeOH (5 mL), ethylamine (1.8 mL, 3.66 mmol) and titanium(IV) isopropoxide (0.7 mL, 2.44 mmol). The reaction mixture was stirred at 55° C. for 18 h. The resulting suspension was cooled down to 0° C. and sodium borohydride (92 mg, 2.44 mmol) was added portion-wise. The reaction mixture was stirred at RT for 2.5 h. The reaction mixture was quenched with ammonium hydroxide (33% in water) and the solvents were removed in vacuo. The residue was suspended in EtOAc and the insolubles (TiO$_2$) were filtered off through a Celite™ plug. The filtrate was reduced in vacuo and the crude product was purified by silica column chromatography eluting with 10% to 100% EtOAc in Pet. Ether to afford 1-(4-bromophenyl)-N-ethyl-2,2-difluoro-ethanamine (185 mg, 0.70 mmol, 58% yield) as a colourless oil. UPLC-MS (ES+, Method A): 1.11 min, m/z 264.0 [M+H]$^+$. The following boronate intermediates in Table 22 were made by using the same procedure shown in Step 1 and Step 2 for Example 343.

TABLE 22

| Method C | Structure | Analysis |
|---|---|---|
| Intermediate 95 | 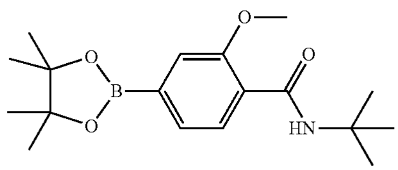 [SMILES: COc1cc(B2OC(C)(C)C(C)(C)O2)ccc1C(=O)NC(C)(C)C] | Method A, 1.99 min, m/z 334.3 [M + H]$^+$ |
| Intermediate 96 | 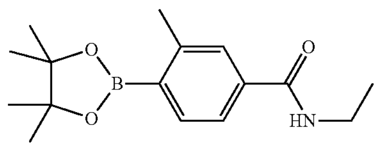 [SMILES: CCNC(=O)c1ccc(B2OC(C)(C)C(C)(C)O2)c(C)c1] | $^1$H NMR (400 MHz, DMSO-d$_6$) δ 8.45 (t, J = 5.7 Hz, 1H), 7.72-7.41 (m, 3H), 3.57 (s, 3H), 3.34-3.18 (m, 2H), 1.18-1.15 (m, 12H), 1.14-1.09 (m, 3H). |
| Intermediate 97 | 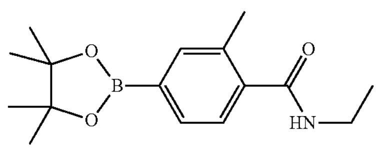 [SMILES: CCNC(=O)c1ccc(B2OC(C)(C)C(C)(C)O2)cc1C] | Method F, 3.28 min, m/z 290.2 [M + H]$^+$ |
| Intermediate 98 | 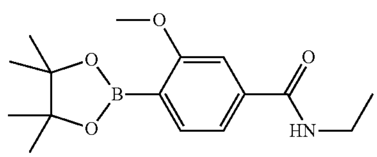 [SMILES: CCNC(=O)c1ccc(B2OC(C)(C)C(C)(C)O2)c(OC)c1] | Method F, 3.02 min, m/z 306.2 [M + H]$^+$ |
| Intermediate 99 | 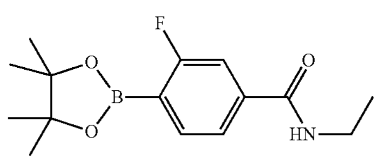 [SMILES: CCNC(=O)c1ccc(B2OC(C)(C)C(C)(C)O2)c(F)c1] | Method F, 2.07 min, m/z 294.2 [M + H]$^+$ |
| Intermediate 100 | 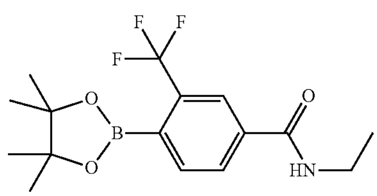 [SMILES: CCNC(=O)c1ccc(B2OC(C)(C)C(C)(C)O2)c(C(F)(F)F)c1] | Method F, 3.79 min, m/z 344.1 [M + H]$^+$ |
| Intermediate 101 | 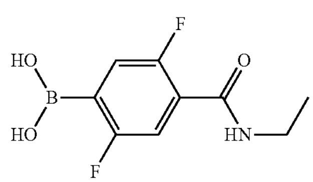 [SMILES: CCNC(=O)c1cc(F)c(B(O)O)cc1F] | Method F, 1.80 min, m/z 230.1 [M + H]$^+$ |
| Intermediate 102 | 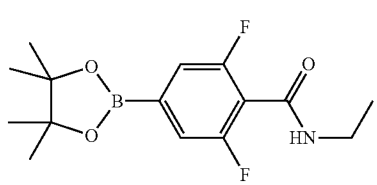 [SMILES: CCNC(=O)c1c(F)cc(B2OC(C)(C)C(C)(C)O2)cc1F] | Method F, 3.53 min, m/z 312.2 [M + H]$^+$ |

TABLE 22-continued

| Method C | Structure | Analysis |
|---|---|---|
| Intermediate 103 | 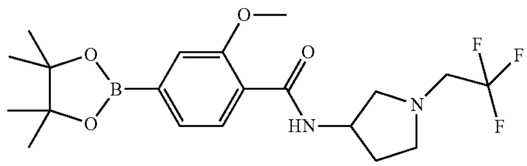 [SMILES: COc1cc(B2OC(C)(C)C(C)(C)O2)ccc1C(=O)NC1CCN(CC(F)(F)F)C1] | Method A, 1.81 min, m/z 429.1 [M + H]+ |
| Intermediate 104 | 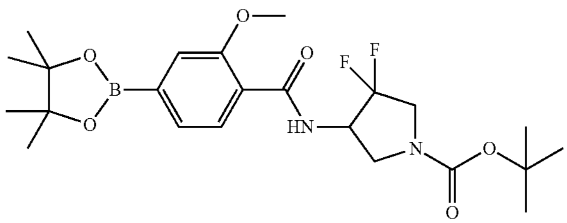 [SMILES: COc1cc(B2OC(C)(C)C(C)(C)O2)ccc1C(=O)NC1CN(C(=O)OC(C)(C)C)CC1(F)F] | Method A, 2.10 min, m/z 483.2 [M + H]+ |
| Intermediate 105 | 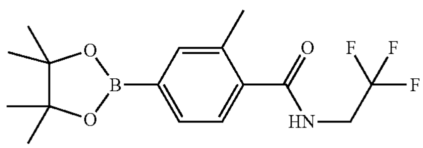 [SMILES: Cc1cc(B2OC(C)(C)C(C)(C)O2)ccc1C(=O)NCC(F)(F)F] | Method A, 1.86 min, m/z 344.1 [M + H]+ |
| Intermediate 106 | 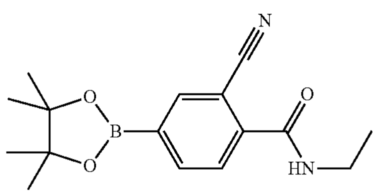 | Method F, 1.50 min, m/z 219.1 [M-Pinacol + H]+ |
| Intermediate 107 | 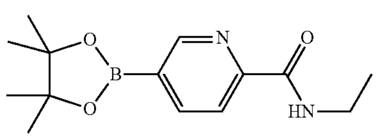 | Method F, 1.70 min, m/z 195.1 [M-Pinacol + H]+ |
| Intermediate 108 | 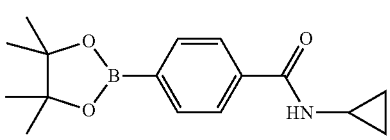 [SMILES: CC1(C)OB(c2ccc(C(=O)NC3CC3)cc2)OC1(C)C] | Method A, 1.67 min, m/z 288.1 [M + H]+ |
| Intermediate 109 | 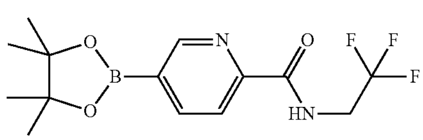 | Method A, 1.22 min, m/z 249.0 [M-Pinacol + H]+ |
| Intermediate 110 | 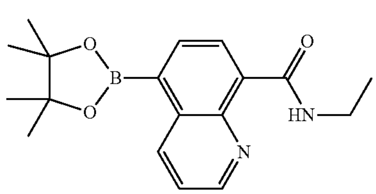 [SMILES: CCNC(=O)c1ccc(B2OC(C)(C)C(C)(C)O2)c2cccnc12] | Method F, 4.10 min, m/z 327.10 [M + H]+ |
| Intermediate 111 | 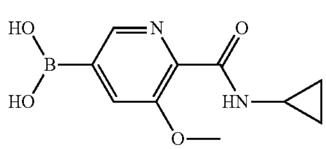 [SMILES: COc1cc(B(O)O)cnc1C(=O)NC1CC1] | Method A, 0.90 min, m/z 236.9 [M + H]+ |

TABLE 22-continued

| Method C | Structure | Analysis |
| --- | --- | --- |
| Intermediate 112 | 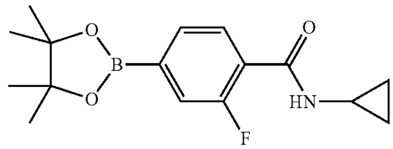 [SMILES: CC1(C)OB(c2ccc(C(=O)NC3CC3)c(F)c2)OC1(C)C] | Method A, 1.78 min, m/z 306.2 [M + H]+ |
| Intermediate 113 | 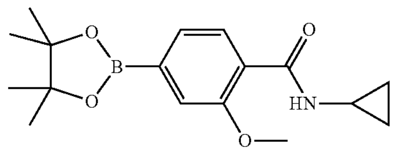 [SMILES: COc1cc(B2OC(C)(C)C(C)(C)O2)ccc1C(=O)NC1CC1] | Method A, 1.72 min, m/z 318.2 [M + H]+ |
| Intermediate 114 | 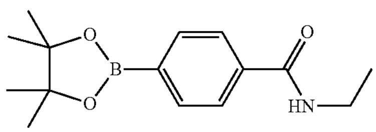 [SMILES: CCNC(=O)c1ccc(B2OC(C)(C)C(C)(C)O2)cc1] | Method A, 1.62 min, m/z 276.2 [M + H]+ |
| Intermediate 115 | 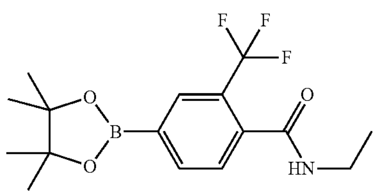 [SMILES: CCNC(=O)c1ccc(B2OC(C)(C)C(C)(C)O2)cc1C(F)(F)F] | $^1$H NMR (400 MHz, DMSO-d$_6$) δ 8.49 (t, J = 5.6 Hz, 1H), 7.95 (d, J = 7.5 Hz, 1H), 7.92 (d, J = 7.0 Hz, 1H), 7.52 (d, J = 7.5 Hz, 1H), 3.28-3.20 (m, 2H), 1.32 (s, 12H), 1.10 (t, J = 7.4 Hz, 3H). |
| Intermediate 116 | 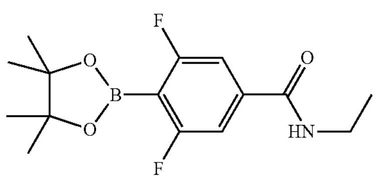 [SMILES: CCNC(=O)c1cc(F)c(B2OC(C)(C)C(C)(C)O2)c(F)c1] | $^1$H NMR (400 MHz, DMSO-d$_6$) δ 8.69 (t, J = 7.3 Hz, 1H), 7.77-7.45 (m, 2H), 3.29 (t, J = 6.8 Hz, 2H), 1.22-1.07 (m, 15H). |
| Intermediate 117 | 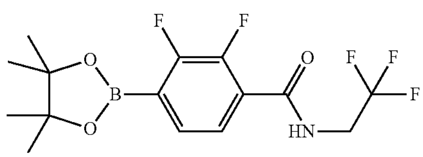 [SMILES: CC1(C)OB(c2ccc(C(=O)NCC(F)(F)F)c(F)c2F)OC1(C)C] | Method F, 4.07 min, m/z 366.10 [M + H]+ |

General method J: A method for preparing a compound of the invention is given below. Further compounds that can be prepared in a similar manner using general method J are given in Table 23.

Example 259: 2-[2-chloro-4-[5-(1H-indazol-5-ylamino)-1-methyl-1,2,4-triazol-3-yl]phenoxy]-N-isopropyl-acetamide

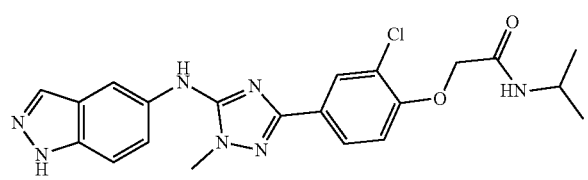

To a stirred solution of HCl-MeOH (1.6 M, 3 mL, 4.8 mmol) was added 2-[2-chloro-4-[1-methyl-5-[(1-tetrahydropyran-2-ylindazol-5-yl)amino]-1,2,4-triazol-3-yl]phenoxy]-N-isopropyl-acetamide (100 mg, 0.19 mmol), the resulting mixture was stirred at RT for 18 h. The reaction mixture was concentrated under reduced pressure. The residue was purified by reverse phase column (40 g, C 18, 50% MeCN in water) to afford desired product 2-[2-chloro-4-[5-(1H-indazol-5-ylamino)-1-methyl-1,2,4-triazol-3-yl]phenoxy]-N-isopropyl-acetamide (50 mg, 0.11 mmol, 60% yield) as a white solid. LC-MS (ES+, Method F): 2.82 min, m/z 440.1 [M+H]+. $^1$H NMR (400 MHz, DMSO-d$_6$) δ 12.91 (s, 1H), 8.89 (s, 1H), 8.15 (s, 1H), 8.03 (s, 1H), 7.94 (s, 1H), 7.88 (m, 2H), 7.5 (dd, J=8.8 Hz, 2H), 7.09 (d, J=8.8 Hz, 1H), 4.61 (s, 2H), 3.97-3.88 (m, 1H), 3.79 (s, 3H), 1.11 (d, J=2.4 Hz, 6H).

Step 1: 2-chloro-4-[1-methyl-5-[(1-tetrahydropyran-2-ylindazol-5-yl)amino]-1,2,4-triazol-3-yl]phenol Step 2: 2-[2-chloro-4-[1-methyl-5-[1-tetrahydropyran-2-ylindazol-5-yl)amino]-1,2,4-triazol-3-yl]phenoxy]-N-isopropylacetamide

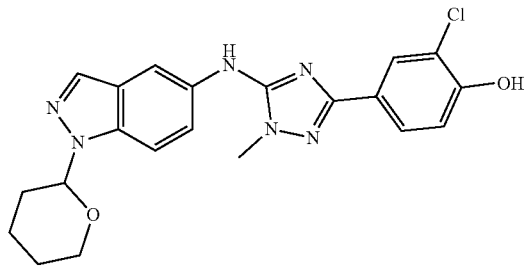

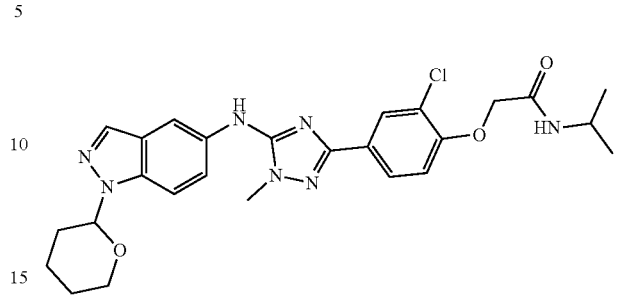

The mixture of N-(5-bromo-2-methyl-1,2,4-triazol-3-yl)-1-tetrahydropyran-2-yl-indazol-5-amine (250 mg, 0.66 mmol), 2-chloro-4-(4,4,5,5-tetramethyl-1,3,2-dioxaborolan-2-yl)phenol (337 mg, 1.33 mmol), potassium carbonate (275 mg, 2.0 mmol) and [1,1'-bis(diphenylphosphino)ferrocene]dichloropalladium(II) (49 mg, 0.07 mmol) was stirred at 110° C. in water (4 mL) and 1,4-dioxane (20 mL). The reaction mixture was filtered and concentrated and then purified by silica column chromatography eluding with 50% EtOAc in Pet. Ether to give 2-chloro-4-[1-methyl-5-[(1-tetrahydropyran-2-ylindazol-5-yl)amino]-1,2,4-triazol-3-yl]phenol (200 mg, 0.47 mmol, 71% yield). LC-MS (ES+, Method F): 3.10 min, m/z 425.1 [M+H]+

The mixture of 2-chloro-4-[1-methyl-5-[(1-tetrahydropyran-2-ylindazol-5-yl)amino]-1,2,4-triazol-3-yl]phenol (200 mg, 0.47 mmol), 2-chloro-N-isopropylacetamide (96 mg, 0.71 mmol) and potassium carbonate (520 mg, 3.8 mmol) in acetone (15 mL) was stirred at 65° C. for 36 h. Then filtered and purified by silica column chromatography eluting with 0-100% EtOAc in Pet. Ether to give 2-[2-chloro-4-[1-methyl-5-[(1-tetrahydropyran-2-ylindazol-5-yl)amino]-1,2,4-triazol-3-yl]phenoxy]-N-isopropyl-acetamide (108 mg, 0.20 mmol, 44% yield). LC-MS (ES+, Method F): 3.76 min, m/z 524.1 [M+H]+

TABLE 23

| Example | Structure | LC/MS | 1H NMR |
|---|---|---|---|
| 470 | 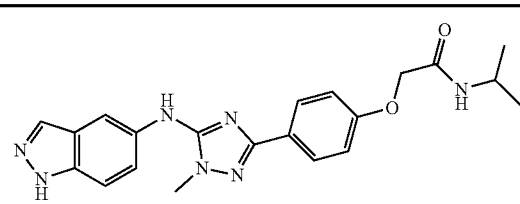 | Method F, 2.35 min, m/z 406.2 [M + H]+ | 1H NMR (400 MHz, DMSO-$d_6$) δ 12.90 (s, 1H), 8.84 (s, 1H), 8.22 (s, 1H), 8.02 (s, 1H), 7.89 (d, J = 8.8 Hz, 3H), 7.56 (d, J = 8 Hz, 1H), 7.48 (d, J = 8.8 Hz, 1H), 7.01 (d, J = 8.8 Hz, 2H), 4.48 (s, 2H), 4.00-3.91 (m, 1H), 3.78 (s, 3H), 1.09 (d, J = 7.2 Hz, 6H) |
| 471 | 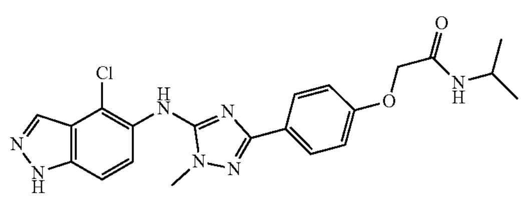 [SMILES: CC(C)NC(=O)COc1ccc(-c2nc(Nc3ccc4[nH]ncc4c3Cl)n(C)n2)cc1] | Method F, 2.65 min, m/z 440.1 [M + H]+ | 1H NMR (400 MHz, DMSO-$d_6$) δ 13.36 (s 1H), 8.43 (s, 1H), 8.08 (s, 1H), 7.87 (d, J = 8.0 Hz, 1H), 7.75 (d, J = 8.7 Hz, 2H), 7.61-7.52 (dd, J = 8.8 Hz, 2H), 6.97 (d, J = 8.8 Hz, 2H), 4.44 (s, 2H), 3.98-3.89 (m, 1H), 3.76 (s, 3H), 1.09 (d, J = 6.8 Hz, 6H). |
| 472 | 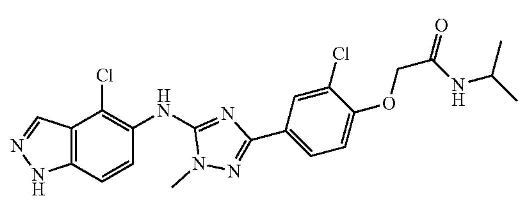 [SMILES: CC(C)NC(=O)COc1ccc(-c2nc(Nc3ccc4[nH]ncc4c3Cl)n(C)n2)cc1Cl] | Method F, 3.0 min, m/z 474.1 [M + H]+ | 1H NMR (400 MHz, DMSO-$d_6$) δ 13.38 (s, 1H), 8.52 (s, 1H), 8.09 (s, 1H), 7.80 (d, J = 7.8 Hz, 2H), 7.72 (dd, J = 8.6, 1.8 Hz, 1H), 7.63-7.51 (m, 2H), 7.03 (d, J = 8.7 Hz, 1H), 4.58 (s, 2H), 3.97-3.85 (m, 1H), 3.77 (s, 3H), 1.08 (d, J = 6.6 Hz, 6H). |
| 473 | 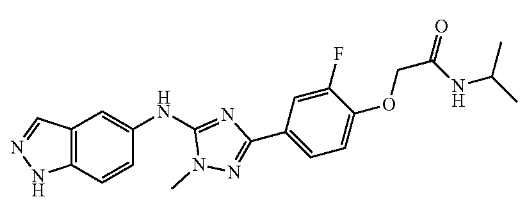 [SMILES: CC(C)NC(=O)COc1ccc(-c2nc(Nc3ccc4[nH]ncc4c3)n(C)n2)cc1F] | Method F, 2.62 min, m/z 424.2 [M + H]+ | 1H NMR (400 MHz, DMSO-$d_6$) δ 12.89 (s, 1H), 8.87 (s, 1H), 8.17 (s, 1H), 8.03 (s, 1H), 7.93 (d, J = 7.9 Hz, 1H), 7.72 (s, 1H), 7.70 (d, J = 6.8 Hz, 1H), 7.57-7.49 (dd, J = 8.8 Hz, 2H), 7.12 (t, J = 8.8 Hz, 1H), 4.58 (s, 2H), 3.99-3.89 (m, 1H), 3.79 (s, 3H) 1.10 (d, J = 6.8 Hz, 6H). |

TABLE 23-continued

| Example | Structure | LC/MS | $^1$H NMR |
|---|---|---|---|
| 474 | 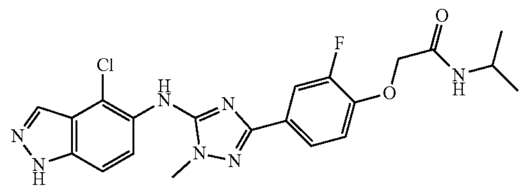 [SMILES: CC(C)NC(=O)COc1ccc(-c2nc(Nc3ccc4[nH]ncc4c3Cl)n(C)n2)cc1F] | Method F, 2.82 min, m/z 458.1 [M + H]+ | 1H NMR (400 MHz, DMSO-d$_6$) δ 13.38 (s, 1H), 8.51 (s, 1H), 8.08 (s, 1H), 7.91 (d, J = 7.8 Hz, 1H), 7.56 (d, J = 8.9 Hz, 4H), 7.05 (t, J = 8.7 Hz, 1H), 4.54 (s, 2H), 3.91 (m, J = 6.8 Hz, 1H), 3.76 (s, 3H), 1.06 (d, J = 6.5 Hz, 6H). |
| 475 | 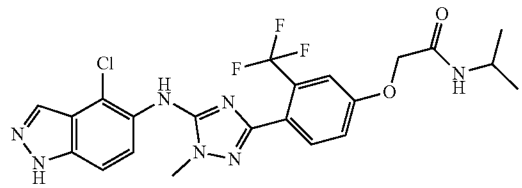 [SMILES: CC(C)NC(=O)COc1ccc(-c2nc(Nc3ccc4[nH]ncc4c3Cl)n(C)n2)c(C(F)(F)F)c1] | Method F, 2.91 min, m/z 508.1 [M + H]+ | 1H NMR (400 MHz, DMSO-d$_6$) δ 13.33 (s, 1H), 8.47 (s, 1H), 8.07 (s, 1H), 7.99 (d, J = 8.0 Hz, 1H), 7.67 (d, J = 8.4 Hz, 1H), 7.61 (d, J = 9.2 Hz, 1H), 7.50 (d, J = 8.8 Hz, 1H), 7.33 (d, J = 2.4 Hz, 1H), 7.26-7.23 (m, 1H), 4.56 (s, 2H), 3.99-3.90 (m, 1H), 3.78 (s, 3H), 1.09-1.08 (d, J = 6.8 Hz, 6H) |

Example 251: 4-[5-[(4-cyclopropyl-1H-indazol-5-yl)amino]-1 methyl-1,2,4-triazol-3-yl]-N-ethyl-benzamide

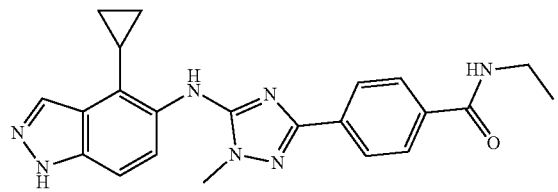

Hydrogen chloride (1.65 mL, 6.6 mmol) was added to a solution of 4-[5-[(4-cyclopropyl-1-tetrahydropyran-2-yl-indazol-5-yl)amino]-1-methyl-1,2,4-triazol-3-yl]-N-ethyl-benzamide (64 mg, 0.13 mmol) in MeOH (2 mL). The reaction was then stirred at RT for 18 h. The solvent was removed in vacuo, and the crude product purified by SCX SPE cartridge. The resulting product was purified by silica column chromatography, eluting with 60-100% EtOAc in Pet. Ether to afford 4-[5-[(4-cyclopropyl-1H-indazol-5-yl)amino]-1-methyl-1,2,4-triazol-3-yl]-N-ethyl-benzamide (14 mg, 0.035 mmol, 28% yield). UPLC-MS (ES+, Method B): 2.91 min, m/z 402.4 [M+H]+. $^1$H NMR (400 MHz, DMSO-d$_6$) δ 13.02 (s, 1H), 8.48 (t, J=5.5 Hz, 1H), 8.32 (s, 1H), 8.07 (s, 1H), 7.86 (q, J=8.5 Hz, 4H), 7.49-7.27 (m, 2H), 3.79 (s, 3H), 3.26 (q, 2H), 2.13 (m, 1H), 1.12 (t, J=7.2 Hz, 3H), 1.02-0.92 (m, 2H), 0.83 (m, 2H).

Step 1: N-(5-bromo-2-methyl-1,2,4-triazol-3-yl)-4-cyclopropyl-1-tetrahydropyran-2-yl-indazol-5-amine

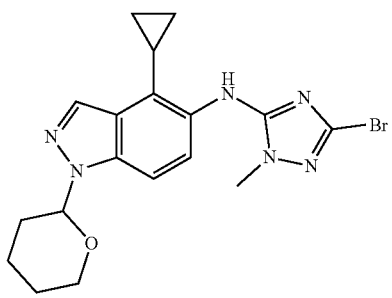

To a stirred solution of 3,5-dibromo-1-methyl-1H-1,2,4-triazole (7.96 g, 33 mmol) and 4-cyclopropyl-1-tetrahydropyran-2-yl-indazol-5-amine (8.5 g, 33 mmol) in dry THF (300 mL) at −20° C. under nitrogen was added sodium bis(trimethylsilyl)amide solution (1.0 M in THF) (72.7 mL, 72.7 mmol). The reaction was then stirred and allowed to warm to 0° C. over 30 min. The mixture was quenched with sat. aq. NH$_4$Cl (150 mL) and extracted with EtOAc (250 mL). The layers were separated, and the aqueous layer extracted with further EtOAc 250 mL. The combined organics were dried over magnesium sulfate, filtered and reduced in-vacuo. The resultant solid was triturated with diethyl ether and filtered to give N-(5-bromo-2-methyl-1,2,4-triazol-3-yl)-4-cyclopropyl-1-tetrahydropyran-2-yl-indazol-5-amine (11.05 g, 26.5 mmol, 80% yield) as a cream solid. UPLC-MS (ES+, Method A): 1.65 min, m/z 417.3/419.3 [M+H]+

Step 2: methyl 4-[5-[(4-cyclopropyl-1-tetrahydropyran-2-yl-indazol-5-yl)amino]-1-methyl-1,2,4-triazol-3-yl]benzoate

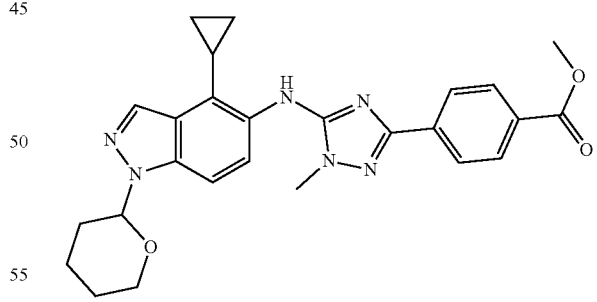

To a stirring solution of N-(5-bromo-2-methyl-1,2,4-triazol-3-yl)-4-cyclopropyl-1-tetrahydropyran-2-yl-indazol-5-amine (9 g, 21.6 mmol) and 4-(methoxycarbonyl)benzeneboronic acid (4.7 g, 25.9 mmol) in 1,4-dioxane (200 mL) and water (40 mL) was added potassium carbonate (9 g, 65 mmol). This was thoroughly degassed with nitrogen then [1,1'-bis(diphenylphosphino)ferrocene]Palladium(II) chloride dichloromethane complex (0.88 g, 1.08 mmol) was added. The suspension was degassed for 5 min and then stirred at 100° C. for 5 h. The reaction mixture was cooled to RT and was diluted with 100 mL of water and 250 mL of EtOAc. The organics were washed once with 100 mL of saturated brine then the organics were dried over magnesium sulfate, filtered and reduced in-vacuo to give a brown semi-solid. This was triturated with diethyl ether to give methyl 4-[5-[(4-cyclopropyl-1-tetrahydropyran-2-yl-indazol-5-yl)amino]-1-methyl-1,2,4-triazol-3-yl]benzoate (9.65 g, 20.4 mmol, 95% yield) as a cream solid. UPLC-MS (ES⁺, Method A): 1.85 min, m/z 473.6 [M+H]⁺

Step 3: 4-[5-[(4-cyclopropyl-1-tetrahydropyran-2-yl-indazol-5-yl)amino]-1-methyl-1,2,4-triazol-3-yl]benzoic acid

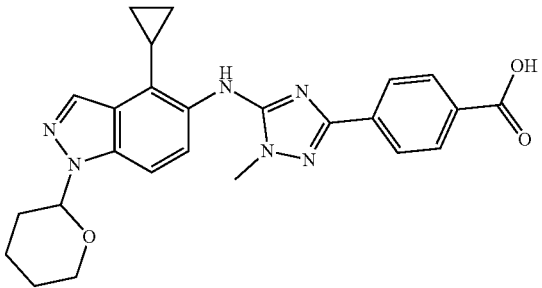

Sodium hydroxide 2M aqueous solution (51 mL, 102 OH mmol) was added to a stirred suspension of methyl 4-[5-[(4-cyclopropyl-1-tetrahydropyran-2-yl-indazol-5-yl)amino]-1-methyl-1,2,4-triazol-3-yl]benzoate (9.65 g, 20.4 mmol) in THF (150 mL) and MeOH (150 mL) at 25° C. The reaction was stirred at RT for 3 h. The organic solvent was removed in-vacuo and the aqueous diluted with 350 mL of water, adjusted to pH4 by the addition of 4M HCl and extracted with 500 mL of DCM. The organics were dried over magnesium sulfate, filtered and reduced in-vacuo to give a cream solid. The solid was slurried with diethyl ether and filtered to give 4-[5-[(4-cyclopropyl-1-tetrahydropyran-2-yl-indazol-5-yl)amino]-1-methyl-1,2,4-triazol-3-yl]benzoic acid (8.7 g, 19 mmol, 93% yield) as a pale cream solid. UPLC-MS (ES⁺, Method A): 1.60 min, m/z 459.5 [M+H]⁺

Step 4: 4-[5-[(4-cyclopropyl-1-tetrahydropyran-2-yl-indazol-5-yl)amino]-1-methyl-1,2,4-triazol-3-yl]-N-ethyl-benzamide

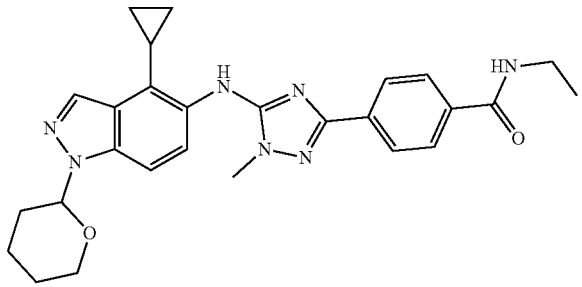 [SMILES: CCNC(=O)c1ccc(-c2nc(Nc3ccc4c(cnn4C4CCCCO4)c3C3CC3)n(C)n2)cc1]

Propylphosphonic anhydride (0.1 mL, 0.33 mmol) was added to a stirred solution of N,N-diisopropylethylamine (0.11 mL, 0.65 mmol) ethylamine in THF (2M) (0.07 mL, 1.09 mmol) and 4-[5-[(4-cyclopropyl-1-tetrahydropyran-2-yl-indazol-5-yl)amino]-1-methyl-1,2,4-triazol-3-yl]benzoic acid (100 mg, 0.22 mmol) in DCM (5 mL) and the reaction mixture was stirred for 16 h at RT. The reaction was washed with aq. saturated sodium bicarbonate and brine, and dried through a phase separator. The resulting solution was reduced onto silica and purified by silica column chromatography, eluting with 50-100% EtOAc in Pet. Ether to afford 4-[5-[(4-cyclopropyl-1-tetrahydropyran-2-yl-indazol-5-yl)amino]-1-methyl-1,2,4-triazol-3-yl]-N-ethyl-benzamide (64 mg, 0.13 mmol, 60% yield) as a pale yellow solid. UPLC-MS (ES⁺, Method A): 1.59 min, m/z 486.6 [M+H]⁺

Example 252: N-cyclopropyl-4-[5-[(4-ethyl-1H-indazol-5-yl)amino]-1-methyl-1,2,4-triazol-3-yl]-2-methoxy-benzamide

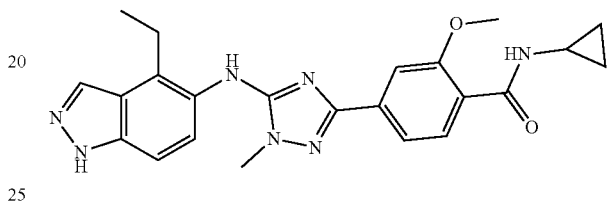

Hydrogen chloride (4.0M in dioxane) (2.24 mL, 9.0 mmol) was added slowly to a stirred solution of N-cyclopropyl-4-[5-[(4-ethyl-1-tetrahydropyran-2-yl-indazol-5-yl)amino]-1-methyl-1,2,4-triazol-3-yl]-2-methoxy-benzamide (85 mg, 0.16 mmol) in MeOH (2 mL) at RT. The reaction was stirred at RT for 18 h. The pale-yellow solution was reduced in vacuo and purified by SCX SPE cartridge. The resulting product was purified by silica column chromatography eluting with 30-100% EtOAc in Pet. Ether and reduced in vacuo to yield N-cyclopropyl-4-[5-[(4-ethyl-1H-indazol-5-yl)amino]-1-methyl-1,2,4-triazol-3-yl]-2-methoxy-benzamide (10 mg, 0.023 mmol, 14% yield) as a white solid. UPLC-MS (ES⁺, Method B): 3.19 min, m/z 432.3 [M+H]⁺. ¹H NMR (400 MHz, DMSO-$d_6$) δ 13.03 (s, 1H), 8.27 (s, 1H), 8.15 (s, 1H), 8.08 (d, J=4.3 Hz, 1H), 7.64 (d, J=8.0 Hz, 1H), 7.45 (d, J=1.4 Hz, 1H), 7.43 (dd, J=7.9, 1.4 Hz, 1H), 7.37 (dd, J=8.7, 1.0 Hz, 1H), 7.27 (d, J=8.7 Hz, 1H), 3.85 (s, 3H), 3.75 (s, 3H), 2.93 (q, J=7.5 Hz, 2H), 2.88-2.76 (m, 1H), 1.23 (t, J=7.5 Hz, 3H), 0.74-0.64 (m, 2H), 0.58-0.49 (m, 2H).

Step 1: methyl 4-[5-[(4-ethyl-1-tetrahydropyran-2-yl-indazol-5-yl)amino]-1-methyl-1,2,4-triazol-3-yl]-2-methoxy-benzoate

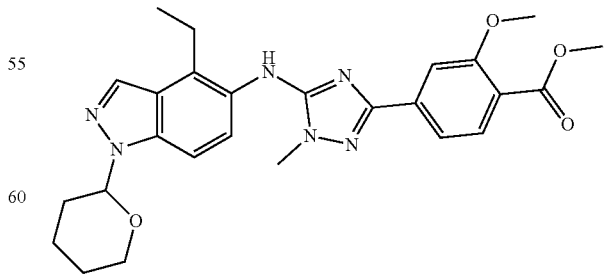

[3-Methoxy-4-(methoxycarbonyl)phenyl]boronic acid (435 mg, 2.07 mmol), N-(5-bromo-2-methyl-1,2,4-triazol-3-yl)-4-ethyl-1-tetra hydropyran-2-yl-indazol-5-amine (800 mg, 1.97 mmol) and potassium carbonate (573 mg, 4.15 mmol) were dissolved/suspended in 1,4-dioxane (15 mL) and water (4 mL). The reaction mixture was fully degassed by bubbling nitrogen through. [1,1'-Bis(diphenylphosphino)ferrocene]palladium(II) chloride dichloromethane complex (161 mg, 0.2 mmol) was then added followed by further degassing and then the reaction was heated to 90° C. for 18 h. The reaction was reduced in vacuo onto silica and purified using silica column chromatography eluting with 25-100% EtOAc in Pet. Ether to give methyl 4-[5-[(4-ethyl-1-tetrahydropyran-2-yl-indazol-5-yl)amino]-1-methyl-1,2,4-triazol-3-yl]-2-methoxy-benzoate (755 mg, 1.54 mmol, 78% yield) as a pale-yellow gum. UPLC-MS (ES+, Method A): 1.73 min, m/z 491.5 [M+H]+

Step 2: 4-[5-[(4-ethyl-1-tetrahydropyran-2-yl-indazol-5-yl)amino]-1-methyl-1,2,4-triazol-3-yl]-2-methoxy-benzoic acid hydrochloride

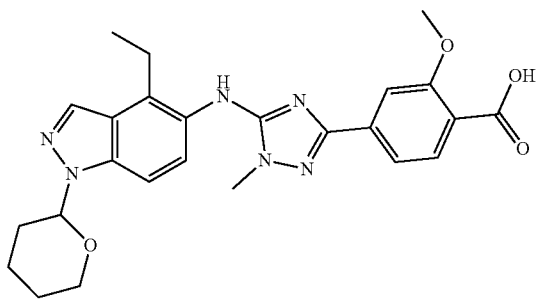 [SMILES: CCc1c(Nc2nc(-c3ccc(C(=O)O)c(OC)c3)nn2C)ccc2c1cnn2C1CCCCO1]

Sodium hydroxide 2.0M (6.0 mL, 12 mmol) was added to a stirred suspension of ethyl 4-[5-[(4-ethyl-1-tetrahydropyran-2-yl-indazol-5-yl)amino]-1-methyl-1,2,4-triazol-3-yl]-2-methoxy-benzoate (755 mg, 1.5 mmol) in THF (10 mL) and MeOH (10 mL) at RT. The reaction was stirred at RT for 18 h. The reaction was reduced in vacuo and then dissolved in water. The pH was then adjusted to pH2 by the addition of HCl 2.0M and the resultant solid was extracted with EtOAc×2. The organics were washed with saturated brine and dried over MgSO4. The solvent was removed in vacuo and the resultant solid triturated in diethyl ether, filtered and washed with further diethyl ether to give 4-[5-[(4-ethyl-1-tetrahydropyran-2-yl-indazol-5-yl)amino]-1-methyl-1,2,4-triazol-3-yl]-2-methoxy-benzoic acid hydrochloride (505 mg, 0.98 mmol, 66% yield) as a beige solid. UPLC-MS (ES+, Method A): 1.56 min, m/z 477.5 [M+H]+

Step 3: N-cyclopropyl-4-[(5-[(4-ethyl-1-tetrahydropyran-2-yl-indazol-5-yl)amino]-1-methyl-1,2,4-triazol-3-yl]-2-methoxy-benzamide

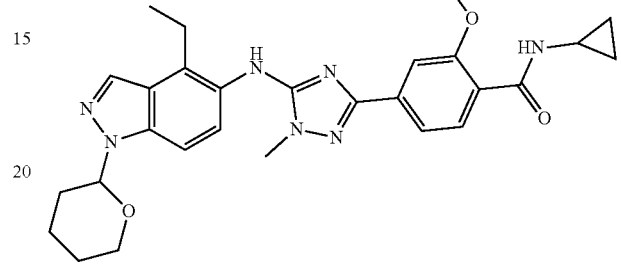

To a stirred solution of 4-[5-[(4-ethyl-1-tetrahydropyran-2-yl-indazol-5-yl)amino]-1-methyl-1,2,4-triazol-3-yl]-2-methoxy-benzoic acid (80 mg, 0.17 mmol), N,N-diisopropylethylamine (0.09 mL, 0.5 mmol) and cyclopropylamine (0.02 mL, 0.34 mmol) in THF (5 mL) was added propylphosphonic anhydride (0.08 mL, 0.25 mmol) and the solution stirred for 16 hr. The pale yellow solution was reduced in vacuo onto silica and the crude material was purified by silica column chromatography, eluting with 30-100% EtOAc in Pet. Ether to give N-cyclopropyl-4-[5-[(4-ethyl-1-tetrahydropyran-2-yl-indazol-5-yl)amino]-1-methyl-1,2,4-triazol-3-yl]-2-methoxy-benzamide (85 mg, 0.16 mmol, 97% yield) as a colourless gum. UPLC-MS (ES+, Method A): 1.65 min, m/z 516.5 [M+H]+.

The following examples (250) described in Table 24 were made by using the same procedure shown in examples 251, 252. Various coupling reagents could be used other than the one described in step 1 example 251 such as BOP, PyBOP, EDC/HoBT, HATU or via the acyl chloride.

TABLE 24

| Example | Structure | LC/MS | 1H NMR |
|---|---|---|---|
| 253 | 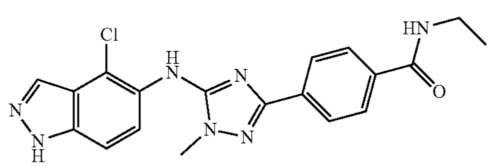 [SMILES: CCNC(=O)c1ccc(-c2nc(Nc3ccc4[nH]ncc4c3Cl)n(C)n2)cc1] | Method F, 2.39 min, m/z 396.1 [M + H]+ | 1H NMR (400 MHz, DMSO-d6) δ 13.38 (s, 1H), 8.55 (s, 1H), 8.48 (t, J = 5.2 Hz, 1H), 8.1 (s, 1H), 7.87 (m, 4H), 7.57 (m, 2H), 3.81 (s, 3H), 3.29-3.24 (m, 2H), 1.12 (t, J = 6.8 Hz, 3H) |
| 254 | 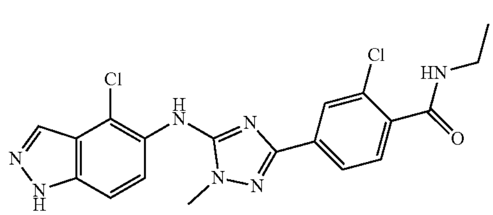 [SMILES: CCNC(=O)c1ccc(-c2nc(Nc3ccc4[nH]ncc4c3Cl)n(C)n2)cc1Cl] | Method F, 2.57 min, m/z 430.0 [M + H]+ | 1H NMR (400 MHz, DMSO-d6) δ 13.4 (s, 1H), 8.61 (s, 1H), 8.43 (1, J = 5.2 Hz, 1H), 8.1 (s, 1H), 7.81-7.79 (m, 2H), 7.58 (m, 2H), 7.43 (d, J = 7.6 Hz, 1H), 3.81 (s, 3H), 3.27-3.2 (m, 2H), 1.1 (t, J = 7.2 Hz, 3H) |

TABLE 24-continued

| Example | Structure | LC/MS | ¹H NMR |
|---|---|---|---|
| 255 | 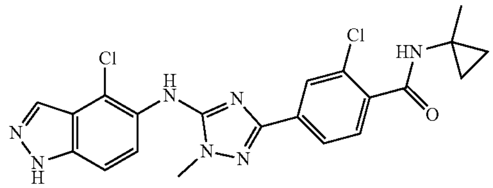 [SMILES: Cn1nc(-c2ccc(C(=O)NC3(C)CC3)c(Cl)c2)nc1Nc1ccc2[nH]ncc2c1Cl] | Method F, 2.81 min, m/z 456.1 [M + H]⁺ | ¹H NMR (400 MHz, DMSO-d$_6$) δ 13.4 (s, 1H), 8.62 (d, J = 7.2 Hz, 2H), 8.1 (s, 1H), 7.79-7.77 (m, 2H), 7.58 (m, 2H), 7.37 (d, J = 7.6 Hz, 1H), 3.81 (s, 3H), 1.37 (s, 3H), 0.73-0.7 (m, 2H), 0.6-0.57 (m, 2H) |
| 256 | 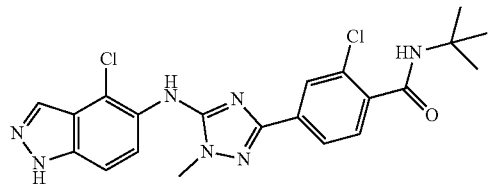 [SMILES: Cn1nc(-c2ccc(C(=O)NC(C)(C)C)c(Cl)c2)nc1Nc1ccc2[nH]ncc2c1Cl] | Method F, 3.07 min, m/z 458.1 [M + H]⁺ | ¹H NMR (400 MHz, DMSO-d$_6$) δ 13.4 (s, 1H), 8.59 (s, 1H), 8.1 (s, 1H), 8.04 (s, 1H), 7.79-7.77 (m, 2H), 7.58 (m, 2H), 7.37 (d, J = 7.6 Hz, 1H), 3.8 (s, 3H), 1.35 (s, 9H) |
| 257 | 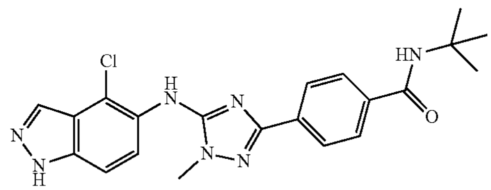 [SMILES: Cn1nc(-c2ccc(C(=O)NC(C)(C)C)cc2)nc1Nc1ccc2[nH]ncc2c1Cl] | Method F, 2.90 min, m/z 424.1 [M + H]⁺ | ¹H NMR (400 MHz, DMSO-d$_6$) δ 13.4 (s, 1H), 8.54 (s, 1H), 8.1 (s, 1H), 7.87-7.85 (m, 2H), 7.81-7.76 (m, 3H), 7.57 (m, 2H), 3.8 (s, 3H), 1.37 (s, 9H) |
| 258 | 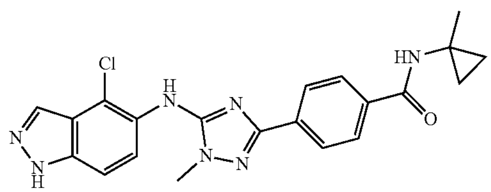 [SMILES: Cn1nc(-c2ccc(C(=O)NC3(C)CC3)cc2)nc1Nc1ccc2[nH]ncc2c1Cl] | Method F, 2.60 min, m/z 422.1 [M + H]⁺ | ¹H NMR (400 MHz, DMSO-d$_6$) δ 13.4 (s, 1H), 8.66 (s, 1H), 8.56 (s, 1H), 8.1 (s, 1H), 7.84 (m, 4H), 7.57 (m, 2H), 3.8 (s, 3H), 1.36 (s, 3H), 0.74-0.71 (m, 2H), 0.61-0.58 (m, 2H) |
| 259 | 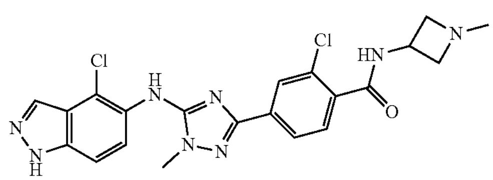 [SMILES: CN1CC(NC(=O)c2ccc(-c3nc(Nc4ccc5[nH]ncc5c4Cl)n(C)n3)cc2Cl)C1] | Method F, 1.95 min, m/z 471.1 [M + H]⁺ | ¹H NMR (400 MHz, DMSO-d$_6$) δ 13.41 (s, 1H), 8.89 (d, J = 6.8 Hz, 1H), 8.61 (s, 1H), 8.1 (s, 1H), 7.82-7.8 (m, 2H), 7.61-7.55 (m, 2H), 7.44 (d, J = 7.6 Hz, 1H), 4.4-4.35 (m, 1H), 3.81 (s, 3H), 3.58 (t, J = 6 Hz, 2H), 2.95 (t, J = 6 Hz, 2H), 2.24 (s, 3H) |
| 260 | 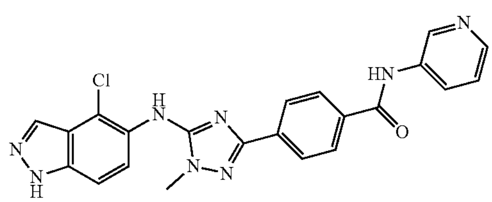 [SMILES: Cn1nc(-c2ccc(C(=O)Nc3cccnc3)cc2)nc1Nc1ccc2[nH]ncc2c1Cl] | Method F, 2.12 min, m/z 445.1 [M + H]⁺ | ¹H NMR (400 MHz, DMSO-d$_6$) δ 13.4 (s, 1H), 10.58 (s, 1H), 9.0 (s, 1H), 8.6 (s, 1H), 8.36 (d, J = 4.8 Hz, 1H), 8.27 (d, J = 8.4 Hz, 1H), 8.11 (s, 1H), 8.0 (q, J1 = 8 Hz, J2 = 14 Hz, 4H), 7.58 (q, J1 = 8.4 Hz, J2 = 16.4 Hz, 2H), 7.51-7.48 (m, 1H), 3.83 (s, 3H) |
| 261 | 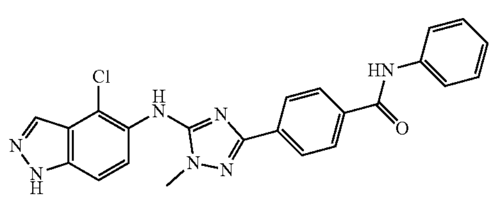 [SMILES: Cn1nc(-c2ccc(C(=O)Nc3ccccc3)cc2)nc1Nc1ccc2[nH]ncc2c1Cl] | Method F, 3.06 min, m/z 444.1 [M + H]⁺ | ¹H NMR (400 MHz, DMSO-d$_6$) δ 13.39 (s, 1H), 10.26 (s, 1H), 8.57 (s, 1H), 8.190 (s, 1H), 7.98 (t, 8.8 Hz, 4H), 7.77 (d, J = 8 Hz, 2H), 7.62-7.55 (m, 2H), 7.35 (t, J = 8.4 Hz, 2H), 7.1 (t, J = 7.2 Hz, 1H), 3.82 (s, 3H) |
| 262 | 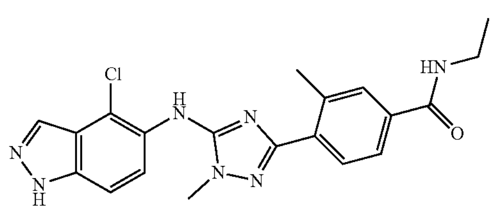 [SMILES: CCNC(=O)c1ccc(-c2nc(Nc3ccc4[nH]ncc4c3Cl)n(C)n2)c(C)c1] | Method F, 2.56 min, m/z 410.1 [M + H]⁺ | ¹H NMR (400 MHz, DMSO-d$_6$) δ 13.36 (s, 1H), 8.51 (s, 1H), 8.43 (t, J = 5.6 Hz, 1H), 8.09 (s, 1H), 7.81 (d, J = 8 Hz, 1H), 7.71 (s, 1H), 7.65-7.6 (m, 2H), 7.54 (d, J = 8.8 Hz, 1H), 3.82 (s, 3H), 3.29-3.24 (m, 2H), 2.59 (s, 3H), 1.11 (t, J = 7.2 Hz, 3H) |

TABLE 24-continued

| Example | Structure | LC/MS | ¹H NMR |
|---|---|---|---|
| 263 | 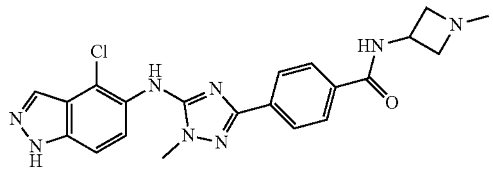 [SMILES: CN1CC(NC(=O)c2ccc(-c3nc(Nc4ccc5[nH]ncc5c4Cl)n(C)n3)cc2)C1] | Method F, 1.85 min, m/z 437.1 [M + H]⁺ | ¹H NMR (400 MHz, DMSO-d₆) δ 13.42 (s, 1H), 9.07-9.05 (d, J = 6.4 Hz, 1H), 8.56 (s, 1H), 8.10 (s, 1H), 7.93-7.88 (m, 4H), 7.59-7.54 (m, 2H), 4.69-4.64 (m, 1H), 4.09 (t, J = 8.4 Hz, 2H) 3.81 (m, 5H), 2.68 (s, 3H) |
| 264 | 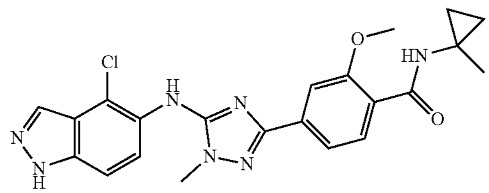 [SMILES: COc1cc(-c2nc(Nc3ccc4[nH]ncc4c3Cl)n(C)n2)ccc1C(=O)NC1(C)CC1] | Method F, 2.87 min, m/z 452.1 [M + H]⁺ | ¹H NMR (400 MHz, DMSO-d₆) δ 13.39 (s, 1H), 8.56 (s, 1H), 8.24 (s, 1H), 8.10 (s, 1H), 7.68-7.70 (m, 1H), 7.53-7.59 (m, 2H), 7.46-7.48 (m, 2H), 3.88 (s, 3H), 3.80 (s, 3H), 1.37 (s, 3H), 0.71-0.72 (m, 2H), 0.59-0.60 (m, 2H). |
| 265 | 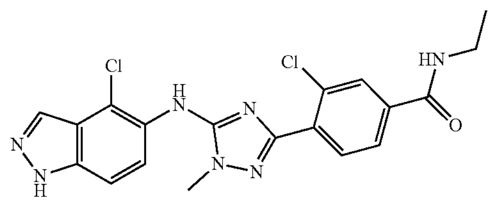 [SMILES: CCNC(=O)c1ccc(-c2nc(Nc3ccc4[nH]ncc4c3Cl)n(C)n2)c(Cl)c1] | Method F, 2.59 min, m/z 430.1 [M + H]⁺ | ¹H NMR (400 MHz, DMSO-d₆) δ 13.36 (s, 1H), 8.62 (t, J = 5.2 Hz, 1H), 8.57 (s, 1H), 8.09 (s, 1H), 7.59 (s, 1H), 7.84-7.78 (m, 2H), 7.60 (d, J = 8.8 Hz, 1H), 7.53 (d, J = 8.8 Hz, 1H), 3.8 (s, 3H), 3.32-3.27 (m, 2H), 1.12 (t, J = 7.2 Hz, 3H) |
| 266 | 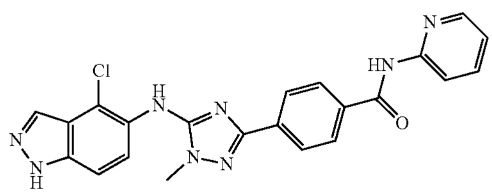 [SMILES: Cn1nc(-c2ccc(C(=O)Nc3ccccn3)cc2)nc1Nc1ccc2[nH]ncc2c1Cl] | Method F, 2.53 min, m/z 445.2 [M + H]⁺ | ¹H NMR (400 MHz, DMSO-d₆) δ 13.39 (s, 1H), 10.78 (s, 1H), 8.58 (s, 1H), 8.39 (d, J = 4.8 Hz, 1H), 8.18 (d, J = 8.4 Hz, 1H), 8.1 (s, 1H), 8.05 (d, J = 8.4 Hz, 2H), 7.94 (d, J = 8.4 Hz, 2H), 7.86-7.82 (m, 1H), 7.59 (q, J1 = 8.8 Hz, J2 = 21.2 Hz, 2H), 7.18-7.15 (m, 1H), 3.82 (s, 3H) |
| 267 | 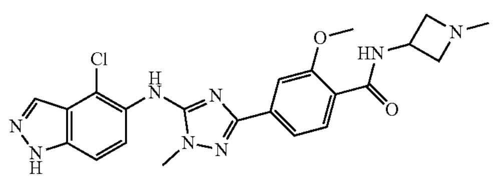 [SMILES: COc1cc(-c2nc(Nc3ccc4[nH]ncc4c3Cl)n(C)n2)ccc1C(=O)NC1CN(C)C1] | Method F, 1.93 min, m/z 467.2 [M + H]⁺ | ¹H NMR (400 MHz, DMSO-d₆) δ 13.44 (s, 1H), 8.59 (s, 1H), 8.41 (d, J = 6.9 Hz, 1H), 8.09 (s, 1H), 7.67 (d, J = 8 Hz, 1H), 7.59-7.54 (m, 2H), 7.51 (s, 1H), 7.48 (d, J = 8.0 Hz, 1H), 4.45-4.36 (m, 1H), 3.90 (s, 3H), 3.81 (s, 3H), 3.55 (t, J = 6.8 Hz, 2H), 2.93 (t, J = 6.7 Hz, 2H), 2.24 (s, 3H). |
| 268 | 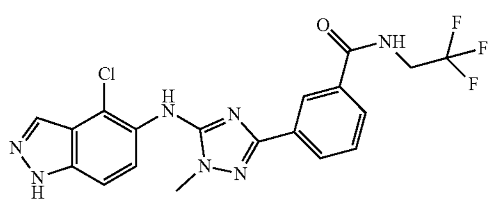 [SMILES: Cn1nc(-c2cccc(C(=O)NCC(F)(F)F)c2)nc1Nc1ccc2[nH]ncc2c1Cl] | Method B, 3.35 min, m/z 450.3 [M + H]⁺ | ¹H NMR (400 MHz, DMSO-d₆) δ 13.39 (s, 1H), 9.20 (t, J = 6.3 Hz, 1H), 8.59-8.54 (m, 1H), 8.35 (s, 1H), 8.10 (s, 1H), 8.02 (m, 1H), 7.86 (m, 1H), 7.63-7.47 (m, 3H), 4.08 (m, 2H), 3.82 (s, 3H). |
| 269 | 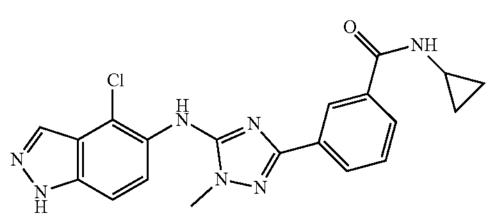 [SMILES: Cn1nc(-c2cccc(C(=O)NC3CC3)c2)nc1Nc1ccc2[nH]ncc2c1Cl] | Method B, 3.03 min, m/z 408.1 [M + H]⁺ | ¹H NMR (400 MHz, DMSO-d₆) δ 13.39 (s, 1H), 8.53 (d, J = 4.1 Hz, 2H), 8.27 (s, 1H), 8.10 (s, 1H), 7.95 (m, 1H), 7.77 (m, 1H), 7.58 (q, J = 8.8 Hz, 2H), 7.45 (m, 1H), 3.81 (s, 3H), 2.85 (m, 1H), 0.68 (m, 2H), 0.61-0.54 (m, 2H). |
| 270 | 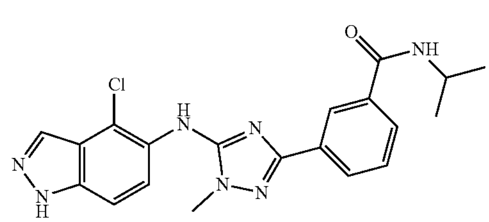 [SMILES: CC(C)NC(=O)c1cccc(-c2nc(Nc3ccc4[nH]ncc4c3Cl)n(C)n2)c1] | Method B, 3.18 min, m/z 410.2 [M + H]⁺ | ¹H NMR (400 MHz, DMSO-d₆) δ 13.39 (s, 1H), 8.54 (s, 1H), 8.33 (d, J = 7.8 Hz, 1H), 8.29 (t, J = 1.7 Hz, 1H), 8.10 (s, 1H), 7.95 (m, 1H), 7.80 (m, 1H), 7.64-7.52 (m, 2H), 7.46 (t, J = 7.8 Hz, 1H), 4.16-4.01 (m, 1H), 3.82 (s, 3H), 1.16 (d, J = 6.6 Hz, 6H). |

TABLE 24-continued

| Example | Structure | LC/MS | $^1$H NMR |
|---|---|---|---|
| 271 | 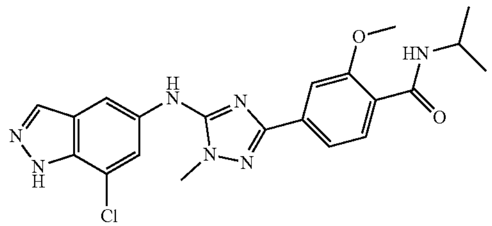 [SMILES: COc1cc(-c2nc(Nc3cc(Cl)c4[nH]ncc4c3)n(C)n2)ccc1C(=O)NC(C)C] | Method F, 2.95 min, m/z 440.1 [M + H]$^+$ | $^1$H NMR (400 MHz, DMSO-d$_6$) δ 13.43 (s, 1H), 9.07 (s, 1H), 8.18-8.16 (m, 2H), 7.94 (d, J = 8 Hz, 1H), 7.79-7.77 (m, 2H), 7.66-7.64 (m, 2H), 4.12-4.03 (m, 1H), 3.97 (s, 3H), 3.83 (s, 3H), 1.18 (d, J = 6.4 Hz, 6H) |
| 272 | 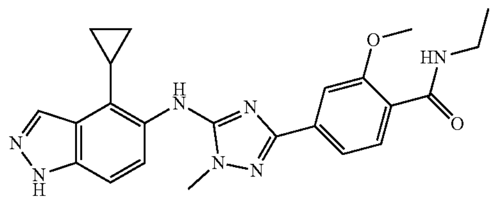 [SMILES: CCNC(=O)c1ccc(-c2nc(Nc3ccc4[nH]ncc4c3C3CC3)n(C)n2)cc1OC] | Method B, 3.23 min, m/z 432.3 [M + H]$^+$ | $^1$H NMR (400 MHz, DMSO-d$_6$) δ 13.02 (s, 1H), 8.32 (s, 1H), 8.17 (t, J = 5.7 Hz, 1H), 8.06 (t, J = 1.2 Hz, 1H), 7.75 (d, J = 8.0 Hz, 1H), 7.52-7.46 (m, 2H), 7.43-7.36 (m, 2H), 3.90 (s, 3H), 3.79 (s, 3H), 3.32-3.25 (m, 2H), 2.20-2.08 (m, 1H), 1.11 (t, J = 7.2 Hz, 3H), 1.02-0.92 (m, 2H), 0.90-0.79 (m, 2H). |
| 273 | 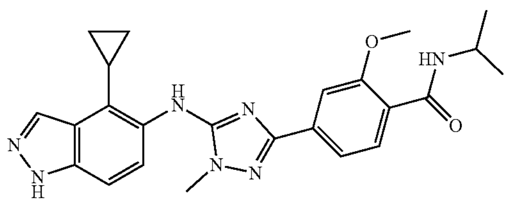 [SMILES: COc1cc(-c2nc(Nc3ccc4[nH]ncc4c3C3CC3)n(C)n2)ccc1C(=O)NC(C)C] | Method B, 3.46 min, m/z 446.5 [M + H]$^+$ | $^1$H NMR (400 MHz, DMSO-d$_6$) δ 13.02 (s, 1H), 8.32 (s, 1H), 8.06 (s, 1H), 7.91 (d, J = 7.7 Hz, 1H), 7.71 (d, J = 7.9 Hz, 1H), 7.53-7.44 (m, 2H), 7.45-7.34 (m, 2H), 4.14-3.97 (m, 1H), 3.90 (s, 3H), 3.79 (s, 3H), 2.20-2.08 (m, 1H), 1.16 (d, J = 6.6 Hz, 6H), 1.02-0.91 (m, 2H), 0.90-0.79 (m, 2H). |
| 274 | 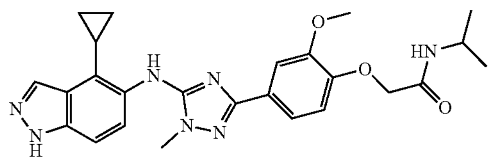 [SMILES: COc1cc(-c2nc(Nc3ccc4[nH]ncc4c3C3CC3)n(C)n2)ccc1OCC(=O)NC(C)C] | Method B, 3.17 min, m/z 476.4 [M + H]$^+$ | $^1$H NMR (400 MHz, DMSO-d$_6$) δ 13.00 (s, 1H), 8.22 (s, 1H), 8.06 (d, J = 1.2 Hz, 1H), 7.74 (d, J = 7.9 Hz, 1H), 7.45-7.31 (m, 4H), 6.92 (d, J = 8.4 Hz, 1H), 4.44 (s, 2H), 3.91 (m, 1H), 3.81 (s, 3H), 3.33 (s, 3H), 2.13 (m, 1H), 1.08 (d, J = 6.6 Hz, 6H), 1.02-0.90 (m, 2H), 0.89-0.77 (m, 2H) |
| 275 | 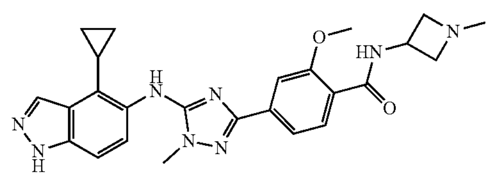 [SMILES: COc1cc(-c2nc(Nc3ccc4[nH]ncc4c3C3CC3)n(C)n2)ccc1C(=O)NC1CN(C)C1] | Method B, 2.51 min, m/z 473.3 [M + H]$^+$ | $^1$H NMR (400 MHz, MeOH-d$_4$) δ 8.17 (s, 1H), 7.87 (d, J = 8.2 Hz, 1H), 7.70 (d, J = 1.4 Hz, 1H), 7.63 (dd, J = 8.2, 1.4 Hz, 1H), 7.44 (m, 2H), 4.61 (p, J = 6.9 Hz, 1H), 4.01 (s, 3H), 3.86 (s, 3H), 3.84-3.79 (m, 2H), 3.28 (m, 2H), 2.45 (s, 3H), 2.14 (m, 1H), 1.11-0.98 (m, 2H), 0.96-0.81 (m, 2H) 3 NH not observed |
| 276 | 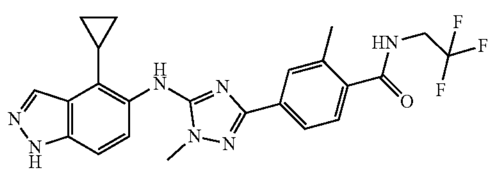 [SMILES: Cc1cc(-c2nc(Nc3ccc4[nH]ncc4c3C3CC3)n(C)n2)ccc1C(=O)NCC(F)(F)F] | Method B, 3.38 min, m/z 470.5 [M + H]$^+$ | $^1$H NMR (400 MHz, DMSO-d$_6$) δ 13.02 (s, 1H), 8.95 (t, J = 6.4 Hz, 1H), 8.30 (s, 1H), 8.07 (s, 1H), 7.75-7.67 (m, 2H), 7.44-7.37 (m, 2H), 7.37-7.33 (m, 1H), 4.05 (m, 2H), 3.79 (s, 3H), 2.34 (s, 3H), 2.21-2.08 (m, 1H), 1.03-0.90 (m, 2H), 0.89-0.76 (m, 2H) |
| 277 | 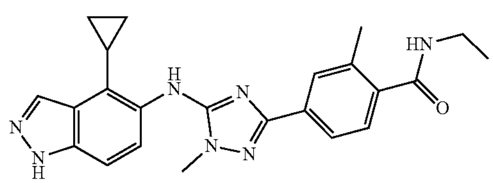 [SMILES: CCNC(=O)c1ccc(-c2nc(Nc3ccc4[nH]ncc4c3C3CC3)n(C)n2)cc1C] | Method B, 3.00 min, m/z 416.3 [M + H]$^+$ | $^1$H NMR (400 MHz, DMSO-d$_6$) δ 13.02 (s, 1H), 8.28 (s, 1H), 8.23 (t, J = 5.6 Hz, 1H), 8.10-8.04 (m, 1H), 7.71-7.63 (m, 2H), 7.50-7.35 (m, 2H), 7.30 (d, J = 7.7 Hz, 1H), 3.78 (s, 3H), 3.24 (m, 2H), 2.34 (s, 3H), 2.20-2.08 (m, 1H), 1.11 (t, J = 7.2 Hz, 3H), 1.02-0.90 (m, 2H), 0.89-0.78 (m, 2H). |
| 278 | 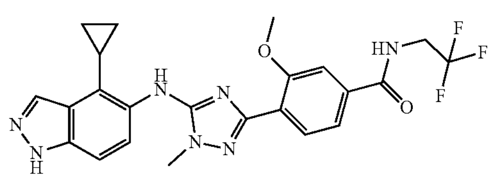 [SMILES: COc1cc(C(=O)NCC(F)(F)F)ccc1-c1nc(Nc2ccc3[nH]ncc3c2C2CC2)n(C)n1] | Method B, 3.04 min, m/z 486.4 [M + H]$^+$ | $^1$H NMR (400 MHz, DMSO-d$_6$) δ 13.01-12.96 (m, 1H), 9.13 (t, J = 6.3 Hz, 1H), 8.23 (s, 1H), 8.06 (d, J = 1.3 Hz, 1H), 7.73 (d, J = 7.9 Hz, 1H), 7.55 (d, J = 1.6 Hz, 1H), 7.48 (dd, J = 8.0, 1.6 Hz, 1H), 7.41 (d, J = 8.8 Hz, 1H), 7.36 (d, J = 8.8 Hz, 1H), 4.18-4.04 (m, 2H), 3.86 (s, 3H), 3.78 (s, 3H), 2.21-2.09 (m, 1H), 1.03-0.93 (m, 2H), 0.87-0.78 (m, 2H). |

TABLE 24-continued

| Example | Structure | LC/MS | ¹H NMR |
|---|---|---|---|
| 279 | 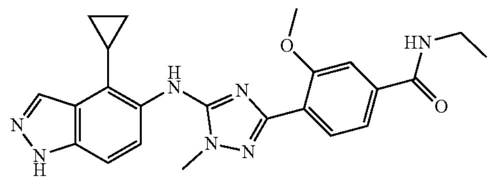 [SMILES: CCNC(=O)c1ccc(-c2nc(Nc3ccc4[nH]ncc4c3C3CC3)n(C)n2)c(OC)c1] | Method B, 2.72 min, m/z 432.5 [M + H]⁺ | ¹H NMR (400 MHz, DMSO-d₆) δ 13.01-12.96 (m, 1H), 8.51 (t, J = 5.6 Hz, 1H), 8.21 (s, 1H), 8.06 (t, J = 1.2 Hz, 1H), 7.67 (d, J = 8.0 Hz, 1H), 7.49 (d, J = 1.6 Hz, 1H), 7.42 (dd, J = 8.2, 1.7 Hz, 2H), 7.36 (d, J = 8.8 Hz, 1H), 3.84 (s, 3H), 3.77 (s, 3H), 3.34-3.24 (m, 2H), 2.15 (m, 1H), 1.13 (t, J = 7.2 Hz, 3H), 1.03-0.93 (m, 2H), 0.86-0.77 (m, 2H). |
| 280 | 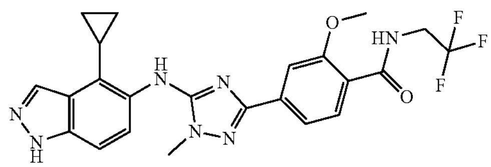 [SMILES: COc1cc(-c2nc(Nc3ccc4[nH]ncc4c3C3CC3)n(C)n2)ccc1C(=O)NCC(F)(F)F] | Method B, 3.54 min, m/z 486.4 [M + H]⁺ | ¹H NMR (400 MHz, DMSO-d₆) δ 13.02 (s, 1H), 8.66 (t, J = 6.4 Hz, 1H), 8.35 (s, 1H), 8.07 (s, 1H), 7.77 (d, J = 8.0 Hz, 1H), 7.56-7.49 (m, 2H), 7.45-7.35 (m, 2H), 4.11 (m, 2H), 3.80 (s, 3H), 3.33 (s, 3H), 2.20-2.08 (m, 1H), 1.02-0.91 (m, 2H), 0.90-0.79 (m, 2H). |
| 281 | 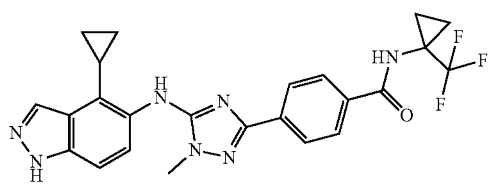 [SMILES: Cn1nc(-c2ccc(C(=O)NC3(C(F)(F)F)CC3)cc2)nc1Nc1ccc2[nH]ncc2c1C1CC1] | Method B, 3.38 min, m/z 482.4 [M + H]⁺ | ¹H NMR (400 MHz, DMSO-d₆) δ 13.01 (s, 1H), 9.17 (s, 1H), 8.32 (s, 1H), 8.06 (d, J = 1.2 Hz, 1H), 7.91-7.83 (m, 4H), 7.45-7.35 (m, 2H), 3.79 (s, 3H), 2.18-2.09 (m, 1H), 1.34-1.28 (m, 2H), 1.14 (s, 2H), 1.00-0.93 (m, 2H), 0.86-0.79 (m, 2H). |
| 282 | 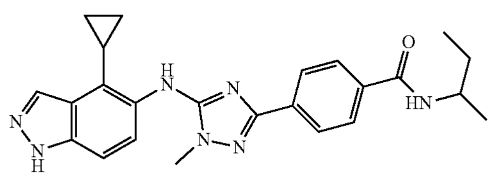 [SMILES: CCC(C)NC(=O)c1ccc(-c2nc(Nc3ccc4[nH]ncc4c3C3CC3)n(C)n2)cc1] | Method B, 3.28 min, m/z 430.5 [M + H]⁺ | ¹H NMR (400 MHz, DMSO-d₆) δ 13.01 (s, 1H), 8.31 (s, 1H), 8.15 (d, J = 8.2 Hz, 1H), 8.06 (s, 1H), 7.91-7.81 (m, 4H), 7.43-7.34 (m, 2H), 3.91 (p, J = 7.0 Hz, 1H), 3.78 (s, 3H), 2.13 (m, 1H), 1.60-1.41 (m, 2H), 1.12 (d, J = 6.6 Hz, 3H), 0.96 (m, 2H), 0.90-0.79 (m, 5H). |
| 283 | 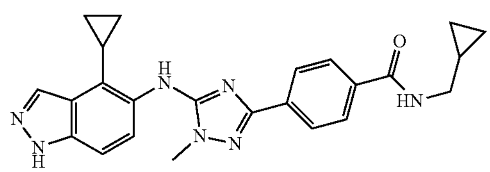 [SMILES: Cn1nc(-c2ccc(C(=O)NCC3CC3)cc2)nc1Nc1ccc2[nH]ncc2c1C1CC1] | Method B, 3.18 min, m/z 428.5 [M + H]⁺ | ¹H NMR (400 MHz, DMSO-d₆) δ 13.01 (s, 1H), 8.57 (t, J = 5.7 Hz, 1H), 8.31 (s, 1H), 8.06 (t, J = 1.2 Hz, 1H), 7.93-7.80 (m, 4H), 7.46-7.32 (m, 2H), 3.79 (s, 3H), 3.13 (t, J = 6.2 Hz, 2H), 2.14 (m, 1H), 1.08-0.99 (m, 1H), 0.99-0.92 (m, 2H), 0.82 (m, 2H), 0.46-0.39 (m, 2H), 0.25-0.19 (m, 2H). |
| 284 | 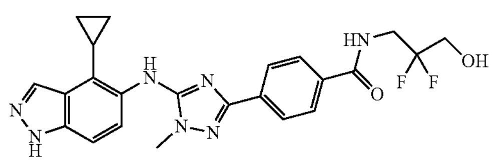 [SMILES: Cn1nc(-c2ccc(C(=O)NCC(F)(F)CO)cc2)nc1Nc1ccc2[nH]ncc2c1C1CC1] | Method B, 2.88 min, m/z 468.3 [M + H]⁺ | ¹H NMR (400 MHz, DMSO-d₆) δ 13.02 (s, 1H), 8.78 (t, J = 6.3 Hz, 1H), 8.33 (s, 1H), 8.07 (t, J = 1.1 Hz, 1H), 7.95-7.85 (m, 4H), 7.46-7.35 (m, 2H), 5.49 (t, J = 6.4 Hz, 1H), 3.80 (s, 3H), 3.85-3.71 (m, 2H), 3.71-3.58 (m, 2H), 2.20-2.08 (m, 1H), 1.02-0.91 (m, 2H), 0.90-0.78 (m, 2H). |
| 285 | 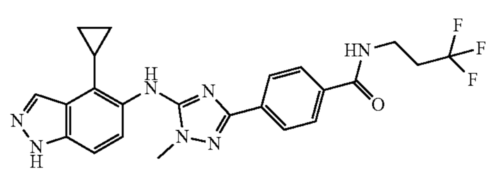 [SMILES: Cn1nc(-c2ccc(C(=O)NCCC(F)(F)F)cc2)nc1Nc1ccc2[nH]ncc2c1C1CC1] | Method B, 3.31 min, m/z 470.4 [M + H]⁺ | ¹H NMR (400 MHz, DMSO-d₆) δ 13.05-13.00 (m, 1H), 8.70 (t, J = 5.6 Hz, 1H), 8.33 (s, 1H), 8.07 (t, J = 1.2 Hz, 1H), 7.95-7.81 (m, 4H), 7.46-7.35 (m, 2H), 3.80 (s, 3H), 3.50 (m, 2H), 2.64-2.51 (m, 2H), 2.20-2.06 (m, 1H), 1.02-0.92 (m, 2H), 0.83 (m, 2H) |
| 286 | 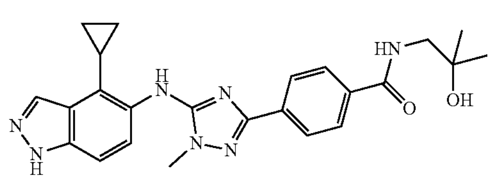 [SMILES: Cn1nc(-c2ccc(C(=O)NCC(C)(C)O)cc2)nc1Nc1ccc2[nH]ncc2c1C1CC1] | Method B, 2.80 min, m/z 446.4 [M + H]⁺ | ¹H NMR (400 MHz, DMSO-d₆) δ 13.05-12.99 (m 1H), 8.32 (s, 1H), 8.26 (t, J = 6.1 Hz, 1H), 8.07 (d, J = 1.2 Hz, 1H), 7.94-7.81 (m, 4H), 7.46-7.35 (m, 2H), 4.56 (s, 1H), 3.80 (s, 3H), 3.25 (d, J = 6.1 Hz, 2H), 2.20-2.06 (m, 1H), 1.10 (s, 6H), 1.02-0.92 (m, 2H), 0.87-0.78 (m, 2H). |

TABLE 24-continued

| Example | Structure | LC/MS | ¹H NMR |
| --- | --- | --- | --- |
| 287 | 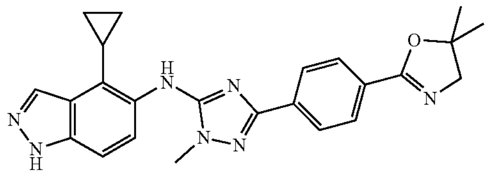 [SMILES: Cn1nc(-c2ccc(C3=NCC(C)(C)O3)cc2)nc1Nc1ccc2[nH]ncc2c1C1CC1] | Method B, 2.88 min, m/z 428.4 [M + H]⁺ | ¹H NMR (400 MHz, DMSO-d₆) δ 13.02 (s, 1H), 8.33 (s, 1H), 8.07 (s, 1H), 7.90 (d, J = 8.1 Hz, 2H), 7.83 (d, J = 8.2 Hz, 2H), 7.41 (t, J = 6.5 Hz, 2H), 3.80 (s, 3H), 3.69 (s, 2H), 2.14 (m, 1H), 1.42 (s, 6H), 1.02-0.92 (m, 2H), 0.83 (m, 2H). |
| 288 | 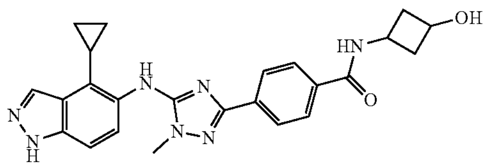 [SMILES: Cn1nc(-c2ccc(C(=O)NC3CC(O)C3)cc2)nc1Nc1ccc2[nH]ncc2c1C1CC1] | Method B, 2.70 min, m/z 444.4 [M + H]⁺ | ¹H NMR (400 MHz, DMSO-d₆) δ 13.02 (s, 1H), 8.59 (dd, J = 9.1, 7.1 Hz, 1H), 8.32 (s, 1H), 8.07 (s, 1H), 7.92-7.82 (m, 4H), 7.46-7.35 (m, 2H), 5.06 (dd, J = 30.2, 5.4 Hz, 1H), 4.37 (dq, J = 43.1, 5.8 Hz, 1H), 3.97-3.80 (m, 1H), 3.80 (s, 3H), 2.58-2.53 (m, 1H), 2.28 (m, 1H), 2.21-2.06 (m, 2H), 1.92 (m, 1H), 1.02-0.91 (m, 2H), 0.83 (m, 2H) |
| 289 | 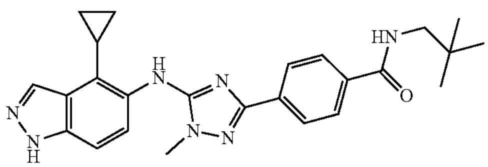 [SMILES: Cn1nc(-c2ccc(C(=O)NCC(C)(C)C)cc2)nc1Nc1ccc2[nH]ncc2c1C1CC1] | Method B, 3.52 min, m/z 444.4 [M + H]⁺ | ¹H NMR (400 MHz, DMSO-d₆) δ 13.01 (s, 1H), 8.42-8.26 (m, 2H), 8.06 (s, 1H), 7.86 (q, J = 8.5 Hz, 4H), 7.45-7.34 (m, 2H), 3.79 (s, 3H), 3.09 (d, J = 6.3 Hz, 2H), 2.13 (m, 1H), 0.96 (m, 2H), 0.89 (s, 9H), 0.82 (m, 2H). |
| 290 | 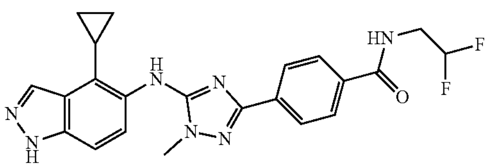 [SMILES: Cn1nc(-c2ccc(C(=O)NCC(F)F)cc2)nc1Nc1ccc2[nH]ncc2c1C1CC1] | Method B, 3.07 min, m/z 438.4 [M + H]⁺ | ¹H NMR (400 MHz, DMSO-d₆) δ 13.02 (s, 1H), 8.48 (t, J = 5.5 Hz, 1H), 8.32 (s, 1H), 8.07 (s, 1H), 7.86 (q, J = 8.5 Hz, 4H), 7.49-7.27 (m, 2H), 3.79 (s, 3H), 2.13 (m, 1H), 1.12 (t, J = 7.2 Hz, 3H), 1.02-0.92 (m, 2H), 0.83 (m, 2H). |
| 251 | 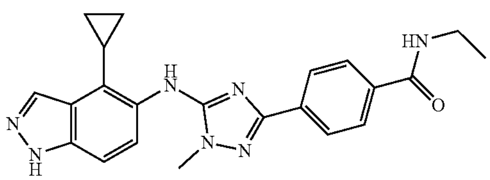 [SMILES: CCNC(=O)c1ccc(-c2nc(Nc3ccc4[nH]ncc4c3C3CC3)n(C)n2)cc1] | Method B, 2.91 min, m/z 402.4 [M + H]⁺ | ¹H NMR (400 MHz, DMSO-d₆) δ 13.02 (s, 1H), 8.48 (t, J = 5.5 Hz, 1H), 8.32 (s, 1H), 8.07 (s, 1H), 7.86 (q, J = 8.5 Hz, 4H), 7.49-7.27 (m, 2H), 3.79 (s, 3H), 3.30 (q, 2H underwater), 2.13 (m, 1H), 1.12 (t, J = 7.2 Hz, 3H), 1.02-0.92 (m, 2H), 0.83 (m, 2H). |
| 291 | 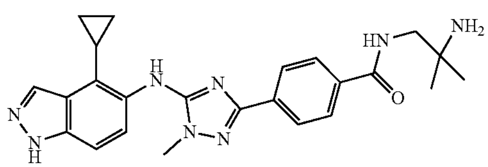 [SMILES: Cn1nc(-c2ccc(C(=O)NCC(C)(C)N)cc2)nc1Nc1ccc2[nH]ncc2c1C1CC1] | Method B, 2.41 min, m/z 445.3 [M + H]⁺ | ¹H NMR (400 MHz, CDCl₃) δ 13.03 (brs, 1H), 8.33 (m, 2H), 8.07 (s, 1H), 7.88 (m, 4H), 7.40 (m, 2H), 3.79 (s, 3H), 3.21 (d, J = 6.12 Hz, 2H), 2.87 (br s, 2H), 2.14 (m, 1H), 1.04 (s, 6H), 0.97 (m, 2H), 0.83 (m, 2H). |
| 292 | 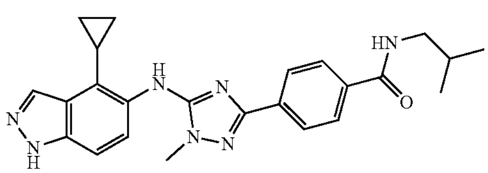 [SMILES: CC(C)CNC(=O)c1ccc(-c2nc(Nc3ccc4[nH]ncc4c3C3CC3)n(C)n2)cc1] | Method B, 3.32 min, m/z 430.4 [M + H]⁺ | ¹H NMR (400 MHz, CDCl₃) δ 13.02 (s, 1H), 8.47 (t, J = 5.80 Hz, 1H), 8.31 (s, 1H), 8.07 (s, 1H), 7.87 (q, J = 8.45 Hz, 4H), 7.40 (m, 2H), 3.80 (s, 3H), 3.08 (t, J = 6.42 Hz, 2H), 2.16 (m, 1H), 1.84 (m, 1H), 0.97 (m, 2H), 0.89 (d, J = 6.85 Hz, 6H), 0.83 (m, 2H). |
| 293 | 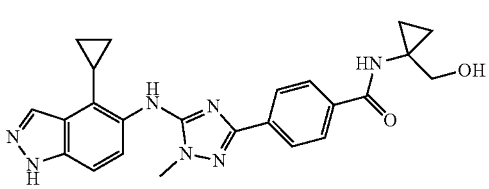 [SMILES: Cn1nc(-c2ccc(C(=O)NC3(CO)CC3)cc2)nc1Nc1ccc2[nH]ncc2c1C1CC1] | Method B, 2.75 min, m/z 444.3 [M + H]⁺ | ¹H NMR (400 MHz, CDCl₃) δ 13.02 (s, 1H), 8.68 (s, 1H), 8.31 (s, 1H), 8.06 (s, 1H), 7.85 (s, 4H), 7.40 (m, 2H), 4.75 (t, J = 5.78 Hz, 1H), 3.79 (s, 3H), 3.52 (d, J = 5.87 Hz, 2H), 2.14 (m, 1H), 0.97 (m, 2H), 0.83 (m, 2H), 0.76 (m, 2H), 0.70 (m, 2H). |

TABLE 24-continued

| Example | Structure | LC/MS | ¹H NMR |
|---------|-----------|-------|--------|
| 294 | 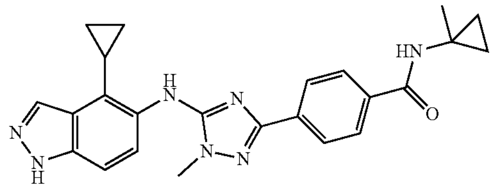 [SMILES: Cn1nc(-c2ccc(C(=O)NC3(C)CC3)cc2)nc1Nc1ccc2[nH]ncc2c1C1CC1] | Method B, 3.10 min, m/z 428.4 [M + H]⁺ | ¹H NMR (400 MHz, DMSO-d₆) δ 13.01 (s, 1H), 8.64 (s, 1H), 8.30 (s, 1H), 8.06 (s, 1H), 7.90-7.76 (m, 4H), 7.47-7.30 (m, 2H), 3.78 (s, 3H), 2.13 (m, 1H), 1.35 (s, 3H), 1.03-0.90 (m, 2H), 0.83-0.79 (m, 2H), 0.77-0.69 (m, 2H), 0.64-0.55 (m, 2H). |
| 295 | 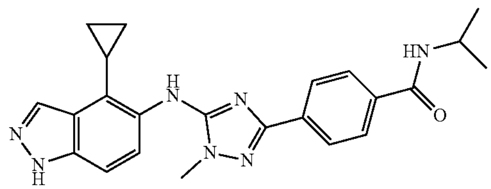 [SMILES: CC(C)NC(=O)c1ccc(-c2nc(Nc3ccc4[nH]ncc4c3C3CC3)n(C)n2)cc1] | Method B, 3.10 min, m/z 416.4 [M + H]⁺ | ¹H NMR (400 MHz, DMSO-d₆) δ 13.01 (s, 1H), 8.31 (s, 1H), 8.22 (d, J = 7.8 Hz, 1H), 8.06 (s, 1H), 7.92-7.79 (m, 4H), 7.47-7.28 (m, 2H), 4.17-4.02 (m, 1H), 3.79 (s, 3H), 2.13 (m, 1H), 1.15 (d, J = 6.6 Hz, 6H), 1.00-0.92 (m, 2H), 0.86-0.78 (m, 2H). |
| 296 | 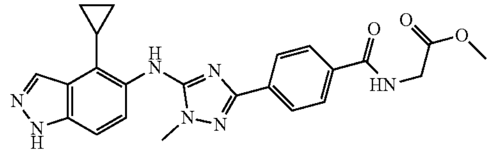 [SMILES: COC(=O)CNC(=O)c1ccc(-c2nc(Nc3ccc4[nH]ncc4c3C3CC3)n(C)n2)cc1] | Method B, 2.88 min, m/z 446.3 [M + H]⁺ | ¹H NMR (400 MHz, DMSO-d₆) δ 13.02 (s, 1H), 8.97 (t, J = 5.8 Hz, 1H), 8.33 (s, 1H), 8.07 (s, 1H), 7.90 (q, J = 8.6 Hz, 4H), 7.42 (t, J = 7.6 Hz, 2H), 4.01 (d, J = 5.8 Hz, 2H), 3.80 (s, 3H), 3.66 (s, 3H), 2.20-2.10 (m, 1H), 0.97 (m, 2H), 0.83 (m, 2H). |
| 297 | 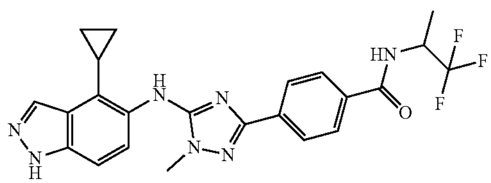 [SMILES: CC(NC(=O)c1ccc(-c2nc(Nc3ccc4[nH]ncc4c3C3CC3)n(C)n2)cc1)C(F)(F)F] | Method B, 3.43 min, m/z 470.4 [M + H]⁺ | ¹H NMR (400 MHz, DMSO-d₆) δ 13.02 (s, 1H), 8.87 (d, J = 8.72 Hz, 1H), 8.34 (s, 1H), 8.07 (s, 1H), 7.91 (m, 4H), 7.40 (m, 2H), 4.86 (m, 1H), 3.80 (s, 3H), 2.14 (m, 1H), 1.37 (d, J = 7.01 Hz, 3H), 0.97 (m, 2H), 0.83 (m, 2H). |
| 298 | 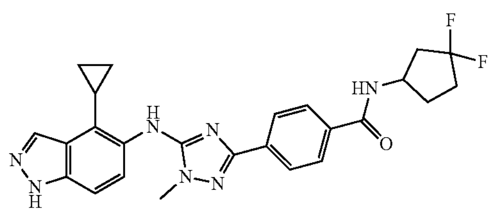 [SMILES: Cn1nc(-c2ccc(C(=O)NC3CCC(F)(F)C3)cc2)nc1Nc1ccc2[nH]ncc2c1C1CC1] | Method B, 3.37 min, m/z 478.5 [M + H]⁺ | ¹H NMR (400 MHz, DMSO-d₆) δ 13.02 (s, 1H), 8.59 (d, J = 7.20 Hz, 1H), 8.33 (s, 1H), 8.07 (s, 1H), 7.88 (q, J = 8.42 Hz, 4H), 7.40 (m, 2H), 4.43 (m, 1H), 3.80 (s, 3H), 2.17 (m, 6H), 1.84 (m, 1H), 0.97 (m, 2H), 0.83 (m, 2H). |
| 299 | 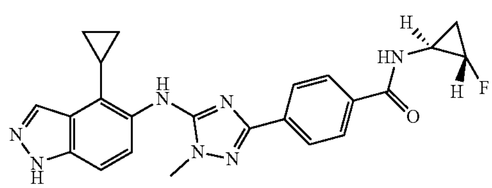 [SMILES: Cn1nc(-c2ccc(C(=O)N[C@H]3C[C@@H]3F)cc2)nc1Nc1ccc2[nH]ncc2c1C1CC1] | Method B, 2.93 min, m/z 432.3 [M + H]⁺ | ¹H NMR (400 MHz, DMSO-d₆) δ 13.02 (s, 1H), 8.57 (d, J = 3.84 Hz, 1H), 8.32 (s, 1H), 8.07 (s, 1H), 7.88 (q, J = 7.70 Hz, 4H), 7.40 (q, J = 7.51 Hz, 2H), 4.75 (m, 1H), 3.79 (s, 3H), 2.83 (m, 1H), 2.14 (m, 1H), 1.14 (m, 2H), 0.96 (m, 2H), 0.82 (m, 2H). |
| 300 | 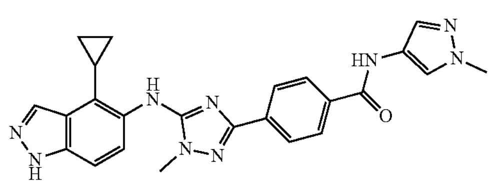 [SMILES: Cn1cc(NC(=O)c2ccc(-c3nc(Nc4ccc5[nH]ncc5c4C4CC4)n(C)n3)cc2)cn1] | Method B, 2.91 min, m/z 454.3 [M + H]⁺ | ¹H NMR (400 MHz, DMSO-d₆) δ 13.02 (s, 1H), 10.43 (s, 1H), 8.34 (s, 1H), 8.07 (s, 1H), 8.02 (s, 1H), 7.95 (m, 4H), 7.57 (s, 1H), 7.41 (q, J = 7.63 Hz, 2H), 3.82 (s, 3H), 3.81 (s, 3H), 2.15 (m, 1H), 0.96 (m, 2H), 0.84 (m, 2H). |
| 301 | 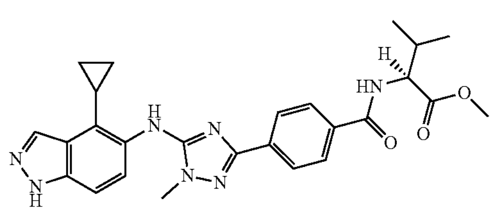 [SMILES: COC(=O)[C@@H](NC(=O)c1ccc(-c2nc(Nc3ccc4[nH]ncc4c3C3CC3)n(C)n2)cc1)C(C)C] | Method B, 3.43 min, m/z 488.5 [M + H]⁺ | ¹H NMR (400 MHz, DMSO-d₆) δ 13.02 (s, 1H), 8.63 (d, J = 7.7 Hz, 1H), 8.33 (s, 1H), 8.07 (br. s, 1H), 7.90 (s, 4H), 7.43 (d, J = 8.8 Hz, 1H), 7.39 (d, J = 8.8 Hz, 1H), 4.29 (m, 1H), 3.80 (s, 3H), 3.66 (s, 3H), 2.25-2.10 (m, 2H), 0.99-0.95 (m, 2H), 0.98 (d, J = 6.8 Hz, 3H), 0.94 (d, J = 6.8 Hz, 3H), 0.86-0.81 (m, 2H). |

TABLE 24-continued

| Example | Structure | LC/MS | $^1$H NMR |
|---|---|---|---|
| 302 | 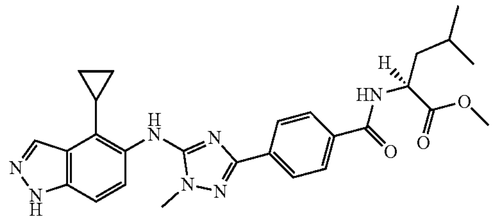 [SMILES: COC(=O)[C@H](CC(C)C)NC(=O)c1ccc(-c2nc(Nc3ccc4[nH]ncc4c3C3CC3)n(C)n2)cc1] | Method B, 3.64 min, m/z 502.5 [M + H]$^+$ | $^1$H NMR (400 MHz, DMSO-d$_6$) δ 13.02 (s, 1H), 8.75 (d, J = 7.6 Hz, 1H), 8.33 (s, 1H), 8.07 (br. s, 1H), 7.93-7.87 (m, 4H), 7.45-7.37 (m, 2H), 4.50 (m, 1H), 3.80 (s, 3H), 3.65 (s, 3H), 2.15 (m, 1H), 1.80 (m, 1H), 1.70 (m, 1H), 1.58 (m, 1H), 1.00-0.95 (m, 2H), 0.93 (d, J = 6.5 Hz, 3H), 0.88 (d, J = 6.5 Hz, 3H), 0.86-0.81 (m, 2H). |
| 303 | 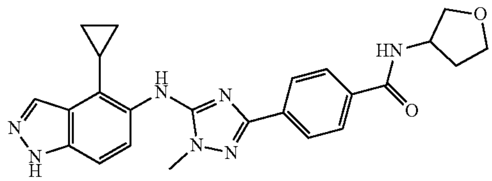 [SMILES: Cn1nc(-c2ccc(C(=O)NC3CCOC3)cc2)nc1Nc1ccc2[nH]ncc2c1C1CC1] | Method B, 2.84 min, m/z 444.4 [M + H]$^+$ | $^1$H NMR (400 MHz, DMSO-d$_6$) δ 13.02 (s, 1H), 8.55 (d, J = 6.5 Hz, 1H), 8.32 (s, 1H), 8.07 (br. s, 1H), 7.91-7.85 (m, 4H), 7.42 (d, J = 8.8 Hz, 1H), 7.38 (d, J = 8.8 Hz, 1H), 4.45 (m, 1H), 3.89-3.82 (m, 2H), 3.80 (s, 3H), 3.71 (m, 1H), 3.58 (m, 1H), 2.20-2.09 (m, 2H), 1.93 (m, 1H), 1.00-0.94 (m, 2H), 0.86-0.80 (m, 2H). |
| 304 | 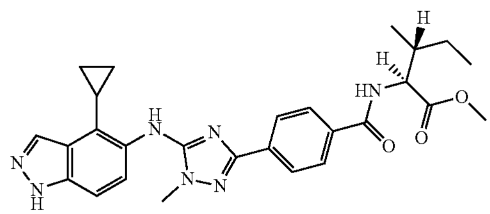 [SMILES: CC[C@@H](C)[C@H](NC(=O)c1ccc(-c2nc(Nc3ccc4[nH]ncc4c3C3CC3)n(C)n2)cc1)C(=O)OC] | Method B, 3.64 min, m/z 502.5 [M + H]$^+$ | $^1$H NMR (400 MHz, DMSO-d$_6$) δ 13.02 (s, 1H), 8.64 (d, J = 7.6 Hz, 1H), 8.33 (s, 1H), 8.07 (br. s., 1H), 7.93-7.87 (m, 4H), 7.43 (d, J = 8.8 Hz, 1H), 7.39 (d, J = 8.8 Hz, 1H), 4.35 (m, 1H), 3.80 (s, 3H), 3.65 (s, 3H), 2.15 (m, 1H), 1.97 (m, 1H), 1.52 (m, 1H), 1.27 (m, 1H), 1.00-0.94 (m, 2H), 0.90 (d, J = 6.80 Hz, 3H), 0.87 (t, J = 7.4 Hz, 3H), 0.85-0.81 (m, 2H). |
| 305 | 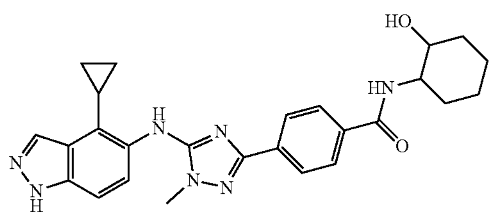 [SMILES: Cn1nc(-c2ccc(C(=O)NC3CCCCC3O)cc2)nc1Nc1ccc2[nH]ncc2c1C1CC1] | Method B, 3.02 min, m/z 472.5 [M + H]$^+$ | $^1$H NMR (400 MHz, DMSO-d$_6$) δ 13.02 (s, 1H), 8.31 (s, 1H), 8.11 (d, J = 8.0 Hz, 1H), 8.07 (br.s, 1H), 7.90-7.85 (m, 4H), 7.43 (d, J = 8.8 Hz, 1H), 7.39 (d, J = 8.8 Hz, 1H), 4.60 (d, J = 5.2 Hz, 1H), 3.80 (s, 3H), 3.64 (m, 1H), 3.42 (m, 1H), 2.14 (m, 1H), 1.91 (m, 1H), 1.83 (m, 1H), 1.70-1.57 (m, 2H), 1.32-1.14 (m,4H), 1.00-0.94 (m, 2H), 0.87-0.80 (m, 2H). |
| 306 | 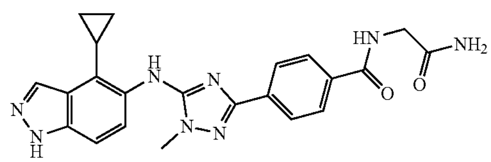 [SMILES: Cn1nc(-c2ccc(C(=O)NCC(N)=O)cc2)nc1Nc1ccc2[nH]ncc2c1C1CC1] | Method B, 2.56 min, m/z 431.3 [M + H]$^+$ | $^1$H NMR (400 MHz, DMSO-d$_6$) δ 13.02 (s, 1H), 8.68 (t, J = 5.9 Hz, 1H), 8.32 (s, 1H), 8.07 (s, 1H), 7.90 (s, 4H), 7.50-7.33 (m, 3H), 7.03 (s, 1H), 3.81 (d, J = 5.0 Hz, 5H), 2.14 (d, J = 5.5 Hz, 1H), 0.98 (t, J = 7.1 Hz, 2H), 0.83 (d, J = 4.5 Hz, 2H). |
| 307 | 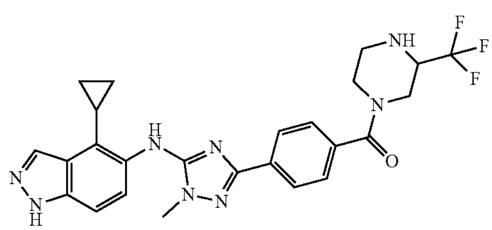 [SMILES: Cn1nc(-c2ccc(C(=O)N3CCNC(C(F)(F)F)C3)cc2)nc1Nc1ccc2[nH]ncc2c1C1CC1] | Method B, 2.87 min, m/z 511.4 [M + H]$^+$ | $^1$H NMR (400 MHz, DMSO-d$_6$) δ 13.01 (s, 1H), 8.32 (s, 1H), 8.07 (d, J = 1.5 Hz, 1H), 7.94-7.82 (m, 2H), 7.40 (q, J = 10.1, 9.4 Hz, 4H), 7.32 (d, J = 5.1 Hz, 1H), 5.17 (t, J = 5.7 Hz, 1H), 4.50 (t, J = 5.7 Hz, 2H), 4.10 (q, J = 5.2 Hz, 2H), 3.79 (s, 3H), 3.08 (d, J = 4.7 Hz, 1H), 2.13 (m, 1H), 0.96 (m, 2H), 0.86-0.78 (m, 2H). |
| 308 | 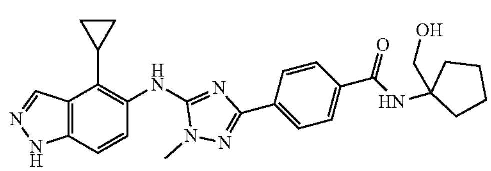 [SMILES: Cn1nc(-c2ccc(C(=O)NC3(CO)CCCC3)cc2)nc1Nc1ccc2[nH]ncc2c1C1CC1] | Method B, 3.14 min, m/z 472.4 [M + H]$^+$ | $^1$H NMR (400 MHz, DMSO-d$_6$ + D$_2$O) δ 8.06 (s, 1H), 7.86-7.81 (m, 2H), 7.79-7.74 (m, 2H), 7.73 (s, 1H), 7.42-7.35 (m, 2H), 3.75 (s, 3H), 3.55 (s, 2H), 2.07 (m, 1H), 2.00-1.89 (m, 2H), 1.77-1.58 (m, 4H), 1.58-1.46 (m, 2H), 0.99-0.90 (m, 2H), 0.78-0.72 (m, 2H). 3 NH not observed. |

TABLE 24-continued

| Example | Structure | LC/MS | ¹H NMR |
|---|---|---|---|
| 309 | 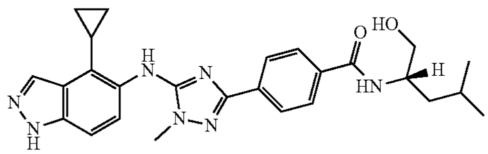 [SMILES: CC(C)C[C@@H](CO)NC(=O)c1ccc(-c2nc(Nc3ccc4[nH]ncc4c3C3CC3)n(C)n2)cc1] | Method B, 3.23 min, m/z 474.4 [M + H]⁺ | ¹H NMR (400 MHz, DMSO-d₆ + D₂O) δ 8.07-8.02 (m, 2H), 7.88-7.84 (m, 2H), 7.84-7.80 (m 2H), 7.42-7.35 (m, 2H), 4.04 (m, 1H), 3.76 (s, 3H), 3.39 (dd, J = 10.7, 6.0 Hz, 1H), 3.32 (dd, J = 10.7, 6.0 Hz, 1H), 2.09 (m, 1H), 1.58 (m, 1H), 1.49-1.29 (m, 2H), 0.99-0.91 (m, 2H), 0.86 (d, J = 6.6 Hz, 3H), 0.84 (d, J = 6.6 Hz, 3H), 0.80-0.74 (m, 2H). 3 NH not observed. |
| 310 | 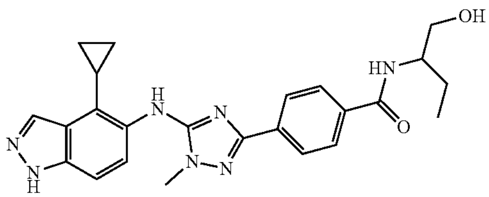 [SMILES: CCC(CO)NC(=O)c1ccc(-c2nc(Nc3ccc4[nH]ncc4c3C3CC3)n(C)n2)cc1] | Method B, 2.86 min, m/z 446.4 [M + H]⁺ | ¹H NMR (400 MHz, DMSO-d₆ + D₂O) δ 8.08 (s, 1H), 8.05 (d, J = 8.6 Hz, 1H), 7.90-7.83 (m, 4H), 7.44-7.37 (m, 2H), 3.86 (m, 1H), 3.78 (s, 3H), 3.45 (dd, J = 10.8, 6.0 Hz, 1H), 3.38 (dd, J = 10.8, 6.0 Hz, 1H), 2.11 (m, 1H), 1.64 (m, 1H), 1.44 (m, 1H), 0.99-0.91 (m, 2H), 0.86 (t, J = 7.4 Hz, 3H), 0.82-0.77 (m, 2H) 3 NH not observed |
| 311 | 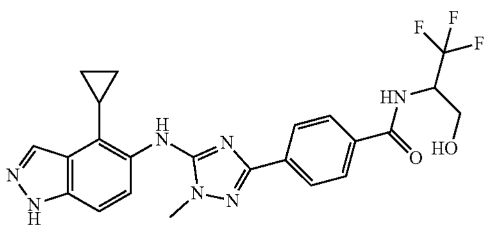 [SMILES: Cn1nc(-c2ccc(C(=O)NC(CO)C(F)(F)F)cc2)nc1Nc1ccc2[nH]ncc2c1C1CC1] | Method B, 3.07 min, m/z 486.4 [M + H]⁺ | ¹H NMR (400 MHz, DMSO-d₆) δ 13.02 (s, 1H), 8.79 (d, J = 8.92 Hz, 1H), 8.34 (s, 1H), 8.07 (s, 1H), 7.93 (s, 4H), 7.41 (m, 2H), 5.17 (t, J = 6.02 Hz, 1H), 4.80 (m, 1H), 3.80 (m, 4H), 3.73 (m, 1H), 2.14 (m, 1H), 0.97 (m, 2H), 0.84 (m, 2H). |
| 312 | 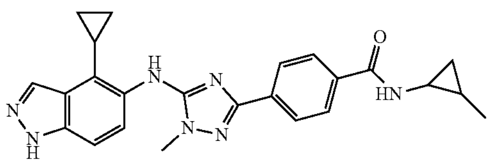 [SMILES: CC1CC1NC(=O)c1ccc(-c2nc(Nc3ccc4[nH]ncc4c3C3CC3)n(C)n2)cc1] | Method B, 3.17 min, m/z 428.4 [M + H]⁺ | ¹H NMR (400 MHz, DMSO-d₆) δ 13.02 (s, 1H), 8.42 (d, J = 4.28 Hz, 1H), 8.31 (s, 1H), 8.06 (s, 1H), 7.84 (m, 4H), 7.40 (m, 2H), 3.79 (s, 3H), 2.54 (m, 1H), 2.14 (m, 1H), 1.06 (d, J = 6.04 Hz, 3H), 0.95 (m, 3H), 0.82 (m, 2H), 0.74 (m, 1H), 0.48 (m, 1H) |
| 313 | 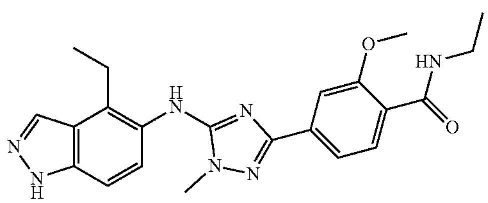 [SMILES: CCNC(=O)c1ccc(-c2nc(Nc3ccc4[nH]ncc4c3CC)n(C)n2)cc1OC] | Method B, 3.14 min, m/z 420.4 [M + H]⁺ | ¹H NMR (400 MHz, DMSO-d₆) δ 13.03 (d, J = 1.5 Hz, 1H), 8.27 (s, 1H), 8.21-8.12 (m, 2H), 7.73 (d, J = 8.0 Hz, 1H), 7.48 (d, J = 1.4 Hz, 1H), 7.44 (dd, J = 8.0, 1.4 Hz, 1H), 7.38 (dd, J = 8.7, 1.0 Hz, 1H), 7.27 (d, J = 8.7 Hz, 1H), 3.89 (s, 3H), 3.75 (s, 3H), 3.33-3.25 (m, 2H), 2.94 (q, J = 7.5 Hz, 2H), 1.23 (t, J = 7.5 Hz, 3H), 1.11 (t, J = 7.2 Hz, 3H). |
| 314 | 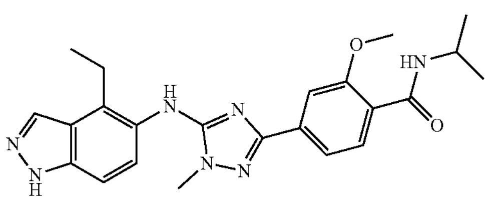 [SMILES: CCc1c(Nc2nc(-c3ccc(C(=O)NC(C)C)c(OC)c3)nn2C)ccc2[nH]ncc12] | Method B, 3.37 min, m/z 434.6 [M + H]⁺ | ¹H NMR (400 MHz, DMSO-d₆) δ 13.03 (s, 1H), 8.27 (s, 1H), 8.15 (d, J = 1.2 Hz, 1H), 7.91 (d, J = 7.7 Hz, 1H), 7.69 (d, J = 8.0 Hz, 1H), 7.47 (d, J = 1.4 Hz, 1H), 7.44 (dd, J = 8.0, 1.4 Hz, 1H), 7.38 (dd, J = 8.7, 1.0 Hz, 1H), 7.27 (d, J = 8.8 Hz, 1H), 4.12-3.98 (m, 1H), 3.88 (s, 3H), 3.75 (s, 3H), 2.94 (q, J = 7.5 Hz, 2H), 1.23 (t, J = 7.5 Hz, 3H), 1.16 (d, J = 6.6 Hz, 6H). |
| 252 | 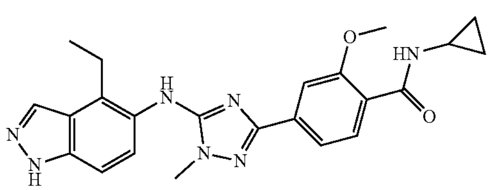 [SMILES: CCc1c(Nc2nc(-c3ccc(C(=O)NC4CC4)c(OC)c3)nn2C)ccc2[nH]ncc12] | Method B, 3.19 min, m/z 432.3 [M + H]⁺ | ¹H NMR (400 MHz, DMSO-d₆) δ 13.03 (s, 1H), 8.27 (s, 1H), 8.15 (s, 1H), 8.08 (d, J = 4.3 Hz, 1H), 7.64 (d, J = 8.0 Hz, 1H), 7.45 (d, J = 1.4 Hz, 1H), 7.43 (dd, J = 7.9, 1.4 Hz, 1H), 7.37 (dd, J = 8.7, 1.0 Hz, 1H), 7.27 (d, J = 8.7 Hz, 1H), 3.85 (s, 3H), 3.75 (s, 3H), 2.93 (q, J = 7.5 Hz, 2H), 2.88-2.76 (m, 1H), 1.23 (t, J = 7.5 Hz, 3H), 0.74-0.64 (m, 2H), 0.58-0.49 (m, 2H). |

TABLE 24-continued

| Example | Structure | LC/MS | ¹H NMR |
|---|---|---|---|
| 315 | 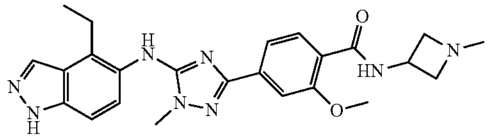 [SMILES: CCc1c(Nc2nc(-c3ccc(C(=O)NC4CN(C)C4)c(OC)c3)nn2C)ccc2[nH]ncc12] | Method B, 2.46 min, m/z 461.3 [M + H]⁺ | ¹H NMR (400 MHz, CD₃OD) δ 8.16 (d, J = 1.0 Hz, 1H), 7.86 (d, J = 8.2 Hz, 1H), 7.68 (d, J = 1.4 Hz, 1H), 7.60 (dd, J = 8.2, 1.5 Hz, 1H), 7.43 (dd, J = 8.8, 1.0 Hz, 1H), 7.34 (d, J = 8.8 Hz, 1H), 4.61 (m, 1H), 3.98 (s, 3H), 3.88-3.78 (m, 5H), 3.32-3.29 (m, 2H), 3.05 (q, J = 7.5 Hz, 2H), 2.46 (s, 3H), 1.34 (t, J = 7.6 Hz, 3H). 3 NH not observed |
| 316 | 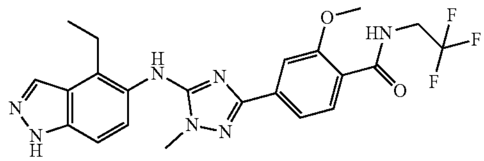 [SMILES: CCc1c(Nc2nc(-c3ccc(C(=O)NCC(F)(F)F)c(OC)c3)nn2C)ccc2[nH]ncc12] | Method B, 3.45 min, m/z 474.4 [M + H]⁺ | ¹H NMR (400 MHz, DMSO-d₆) δ 13.03 (s, 1H), 8.66 (t, J = 6.5 Hz, 1H), 8.29 (s, 1H), 8.15 (s, 1H), 7.75 (d, J = 8.1 Hz, 1H), 7.51 (d, J = 1.4 Hz, 1H), 7.47 (dd, J = 8.1, 1.4 Hz, 1H), 7.38 (dd, J = 8.7, 1.0 Hz, 1H), 7.27 (d, J = 8.7 Hz, 1H), 4.10 (m, 2H), 3.90 (s, 3H), 3.76 (s, 3H), 2.94 (q, J = 7.5 Hz, 2H), 1.23 (t, J = 7.5 Hz, 3H). |
| 317 | 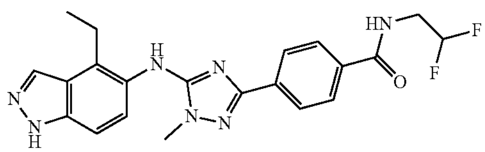 [SMILES: CCc1c(Nc2nc(-c3ccc(C(=O)NCC(F)F)cc3)nn2C)ccc2[nH]ncc12] | Method B, 2.96 min, m/z 426.3 [M + H]⁺ | ¹H NMR (400 MHz, DMSO-d₆) δ 13.03 (s, 1H), 8.85 (t, J = 5.9 Hz, 1H), 8.26 (s, 1H), 8.15 (s, 1H), 7.86 (s, 4H), 7.37 (d, J = 8.8 Hz, 1H), 7.28 (t, J = 9.3 Hz, 1H), 6.12 tt, 1H), 3.76 (s, 3H), 3.65 (m, 2H), 2.93 (q, J = 7.5 Hz, 2H), 1.21 (t, J = 7.5 Hz, 3H). |
| 318 | 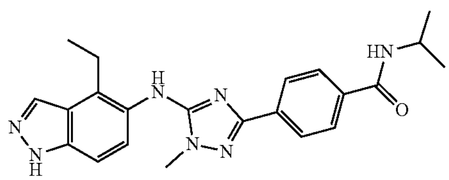 [SMILES: CCc1c(Nc2nc(-c3ccc(C(=O)NC(C)C)cc3)nn2C)ccc2[nH]ncc12] | Method B, 3.00 min, m/z 404.4 [M + H]⁺ | ¹H NMR (400 MHz, DMSO-d₆) δ 13.03 (s, 1H), 8.20 (d, J = 40.7 Hz, 2H), 7.84 (s, 4H), 7.38 (d, J = 8.7 Hz, 1H), 7.32 (s, 1H), 7.28 (d, J = 8.8 Hz, 1H), 4.17-4.00 (m, 1H), 3.75 (s, 3H), 2.94 (q, J = 7.5 Hz, 2H), 1.22 (t, J = 7.5 Hz, 3H), 1.16 (d, J = 6.6 Hz, 6H). |
| 319 | 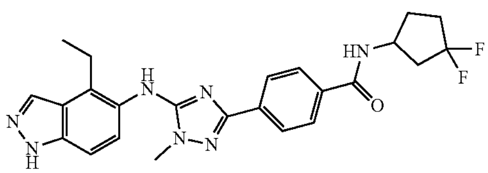 [SMILES: CCc1c(Nc2nc(-c3ccc(C(=O)NC4CCC(F)(F)C4)cc3)nn2C)ccc2[nH]ncc12] | Method B, 3.29 min, m/z 466.4 [M + H]⁺ | ¹H NMR (400 MHz, DMSO-d₆) δ 13.03 (s, 1H), 8.56 (d, J = 7.2 Hz, 1H), 8.34-8.07 (m, 2H), 7.95-7.76 (m, 4H), 7.47-7.18 (m, 2H), 4.48-4.35 (m, 1H), 3.75 (s, 3H), 2.98-2.89 (m, 2H), 2.32-2.20 (m, 1H), 2.20-2.03 (m, 2H), 1.88-1.77 (m, 1H), 1.21 (t, J = 7.5 Hz, 3H). 2H not observed |
| 320 | 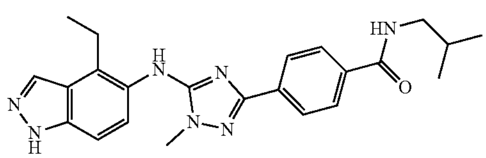 [SMILES: CCc1c(Nc2nc(-c3ccc(C(=O)NCC(C)C)cc3)nn2C)ccc2[nH]ncc12] | Method B, 3.23 min, m/z 418.4 [M + H]⁺ | ¹H NMR (400 MHz, DMSO-d₆) δ 13.02 (s, 1H), 8.45 (t, J = 6.0 Hz, 1H), 8.25 (s, 1H), 8.14 (d, J = 1.3 Hz, 1H), 7.83 (d, J = 2.0 Hz, 4H), 7.37 (d, J = 8.7 Hz, 1H), 7.27 (d, J = 8.8 Hz, 1H), 3.75 (s, 3H), 3.06 (t, J = 6.4 Hz, 2H), 2.93 (q, J = 7.4 Hz, 2H), 1.83 (m, 1H), 1.21 (t, J = 7.5 Hz, 3H), 0.87 (d, J = 6.7 Hz, 6H). |
| 321 | 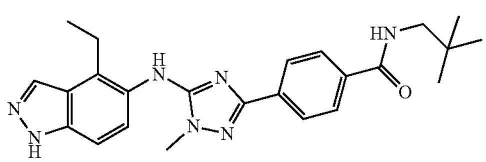 [SMILES: CCc1c(Nc2nc(-c3ccc(C(=O)NCC(C)(C)C)cc3)nn2C)ccc2[nH]ncc12] | Method B, 3.43 min, m/z 432.4 [M + H]⁺ | ¹H NMR (400 MHz, DMSO-d₆) δ 13.08-12.97 (m, 1H), 8.34 (t, J = 6.4 Hz, 1H), 8.25 (s, 1H), 8.14 (t, J = 1.3 Hz, 1H), 7.90-7.79 (m, 4H), 7.37 (dd, J = 8.7, 1.1 Hz, 1H), 7.27 (d, J = 8.7 Hz, 1H), 3.75 (s, 3H), 3.09 (d, J = 6.4 Hz, 2H), 2.93 (q, J = 7.5 Hz, 2H), 1.21 (t, J = 7.5 Hz, 3H), 0.89 (s, 9H). |
| 322 | 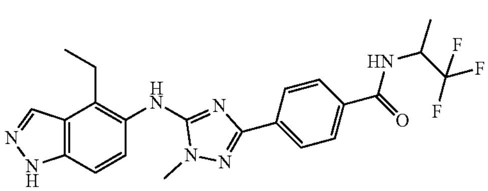 [SMILES: CCc1c(Nc2nc(-c3ccc(C(=O)NC(C)C(F)(F)F)cc3)nn2C)ccc2[nH]ncc12] | Method B, 3.35 min, m/z 458.4 [M + H]⁺ | ¹H NMR (400 MHz, DMSO-d₆) δ 13.04 (s, 1H), 8.86 (d, J = 8.8 Hz, 1H), 8.28 (s, 1H), 8.16 (d, J = 1.3 Hz, 1H), 7.89 (s, 4H), 7.41-7.36 (m, 1H), 7.28 (d, J = 8.7 Hz, 1H), 4.93-4.78 (m, 1H), 3.77 (s, 3H), 2.94 (q, J = 7.5 Hz, 2H), 1.36 (d, J = 7.1 Hz, 3H), 1.22 (t, J = 7.5 Hz, 3H). |

TABLE 24-continued

| Example | Structure | LC/MS | ¹H NMR |
|---|---|---|---|
| 323 | 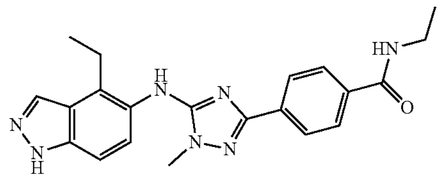 [SMILES: CCNC(=O)c1ccc(-c2nc(Nc3ccc4[nH]ncc4c3CC)n(C)n2)cc1] | Method B, 2.81 min, m/z 390.4 [M + H]⁺ | ¹H NMR (400 MHz, DMSO-d₆) δ 13.02 (s, 1H), 8.45 (t, J = 5.5 Hz, 1H), 8.24 (s, 1H), 8.13 (br. s, 1H), 7.85-7.78 (m, 4H), 7.36 (d, J = 8.7 Hz, 1H), 7.26 (d, J = 8.7 Hz, 1H), 3.74 (s, 3H), 3.29-3.21 (m, 2H), 2.92 (q, J = 7.5 Hz, 2H), 1.20 (t, J = 7.5 Hz, 3H), 1.09 (t, J = 7.2 Hz, 3H). |
| 324 | 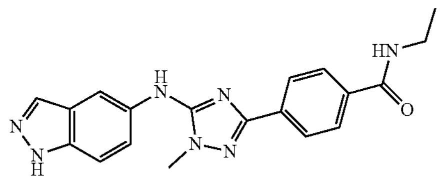 [SMILES: CCNC(=O)c1ccc(-c2nc(Nc3ccc4[nH]ncc4c3)n(C)n2)cc1] | Method F, 2.22 min, m/z 362.2 [M + H]⁺ | ¹H NMR (400 MHz, DMSO-d₆) δ 12.92 (s, 1H), 8.93 (s, 1H), 8.52 (t, J = 5.2 Hz, 1H), 8.19 (s, 1H), 8.04-8.02 (m, 3H), 7.91 (d, J = 8 Hz, 2H), 7.58 (d, J = 8.8 Hz, 1H), 7.51 (d, J = 8.8 Hz, 1H), 3.82 (s, 3H), 3.33-3.27 (m, 2H), 1.14 (t, J = 7.2 Hz, 3H) |
| 325 | 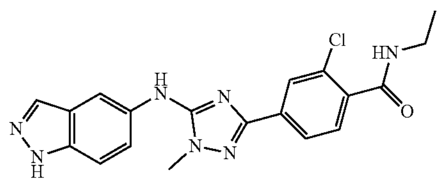 [SMILES: CCNC(=O)c1ccc(-c2nc(Nc3ccc4[nH]ncc4c3)n(C)n2)cc1Cl] | Method F, 2.39 min, m/z 396.1 [M + H]⁺ | ¹H NMR (400 MHz, DMSO-d₆) δ 12.94 (s, 1H), 9.01 (s, 1H), 8.48 (t, J = 5.2 Hz, 1H), 8.16 (s, 1H), 8.04 (s, 1H), 7.96-7.93 (m, 2H), 7.61-7.59 (m, 1H), 7.53-7.48 (m, 2H), 3.83 (s, 3H), 3.33-3.23 (m, 2H), 1.14 (t, J = 7.2 Hz, 3H) |
| 326 | 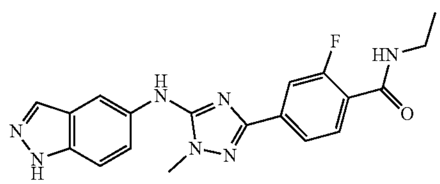 [SMILES: CCNC(=O)c1ccc(-c2nc(Nc3ccc4[nH]ncc4c3)n(C)n2)cc1F] | Method F, 2.41 min, m/z 380.1 [M + H]⁺ | ¹H NMR (400 MHz, DMSO-d₆) δ 12.92 (s, 1H), 8.96 (s, 1H), 8.33 (s, 1H), 8.18 (s, 1H), 8.04 (s, 1H), 7.86-7.84 (d, J = 8 Hz, 1H), 7.74-7.67 (m, 2H), 7.60-7.51 (m, 2H), 3.83 (s, 3H), 3.30-3.25 (m, 2H), 1.12 (t, J = 7.2 Hz, 3H) |
| 327 | 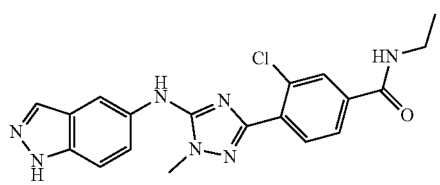 [SMILES: CCNC(=O)c1ccc(-c2nc(Nc3ccc4[nH]ncc4c3)n(C)n2)c(Cl)c1] | Method F, 2.44 min, m/z 396.1 [M + H]⁺ | ¹H NMR (400 MHz, DMSO-d₆) δ 2.90 (s, 1H), 8.96 (s, 1H), 8.65 (t, J = 5.6 Hz, 1H), 8.15 (s, 1H), 7.99 (m, 3H), 7.87 (d, J = 8.4 Hz, 1H), 7.56 (d, J = 9.2 Hz, 1H), 7.49 (d, J = 8.4 Hz, 1H), 3.84 (s, 3H), 3.29-3.27 (m, 2H), 1.14 (t, J = 7.2 Hz, 3H) |
| 328 | 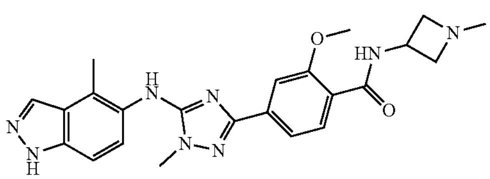 [SMILES: COc1cc(-c2nc(Nc3ccc4[nH]ncc4c3C)n(C)n2)ccc1C(=O)NC1CN(C)C1] | Method B, 2.32 min, m/z 447.3 [M + H]⁺ | ¹H NMR (400 MHz, DMSO-d₆) δ 13.01 (s, 1H), 8.41 (d, J = 7.1 Hz, 1H), 8.33 (s, 1H), 8.13 (s, 1H), 7.65 (d, J = 7.9 Hz, 1H), 7.48 (d, J = 1.4 Hz, 1H), 7.45 (dd, J = 8.0, 1.4 Hz, 1H), 7.41-7.29 (m, 2H), 4.48-4.34 (m, 1H), 3.89 (s, 3H), 3.77 (s, 3H), 3.62-3.53 (m, 2H), 3.01-2.92 (m, 2H), 2.46 (s, 3H), 2.26 (s, 3H). |
| 329 | 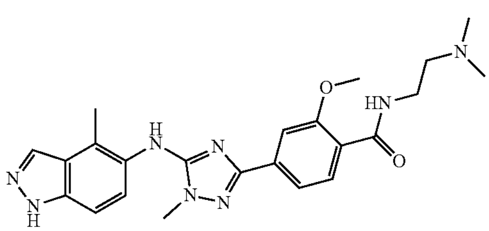 [SMILES: COc1cc(-c2nc(Nc3ccc4[nH]ncc4c3C)n(C)n2)ccc1C(=O)NCCN(C)C] | Method B, 2.34 min, m/z 449.3 [M + H]⁺ | ¹H NMR (400 MHz, DMSO-d₆) δ 13.04-12.99 (m, 1H), 8.36-8.27 (m, 2H), 8.13 (t, J = 1.2 Hz, 1H), 7.82 (d, J = 8.0 Hz, 1H), 7.50 (d, J = 1.4 Hz, 1H), 7.47 (dd, J = 8.0, 1.4 Hz, 1H), 7.41-7.29 (m, 2H), 3.91 (s, 3H), 3.77 (s, 3H), 3.38 (m, 2H), 2.48-2.43 (m, 5H), 2.24 (s, 6H) |
| 330 | 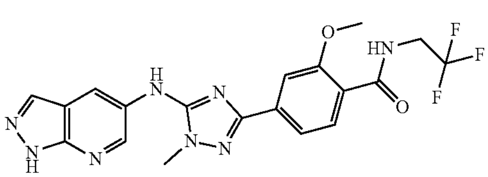 [SMILES: COc1cc(-c2nc(Nc3cnc4[nH]ncc4c3)n(C)n2)ccc1C(=O)NCC(F)(F)F] | Method B, 3.19 min, m/z 447.2 [M + H]⁺ | ¹H NMR (400 MHz, DMSO-d₆) δ 13.51 (s, 1H), 9.24 (s, 1H), 8.74 (d, J = 2.5 Hz, 1H), 8.71 (t, J = 6.4 Hz, 1H), 8.66 (d, J = 2.5 Hz, 1H), 8.13 (s, 1H), 7.85 (d, J = 8.0 Hz, 1H), 7.69 (dd, J = 8.0, 1.4 Hz, 1H), 7.67 (d, J = 1.3 Hz, 1H), 4.13 (m, 6.4 Hz, 2H), 3.99 (s, 3H), 3.87 (s, 3H). |

TABLE 24-continued

| Example | Structure | LC/MS | ¹H NMR |
|---|---|---|---|
| 331 | 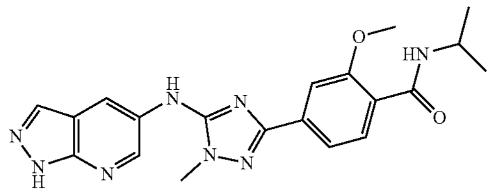 [SMILES: COc1cc(-c2nc(Nc3cnc4[nH]ncc4c3)n(C)n2)ccc1C(=O)NC(C)C] | Method B, 3.05 min, m/z 407.3 [M + H]⁺ | ¹H NMR (400 MHz, DMSO-d₆) δ 13.51 (s, 1H), 9.22 (s, 1H), 8.74 (d, J = 2.5 Hz, 1H), 8.66 (d, J = 2.4 Hz, 1H), 8.13 (s, 1H), 7.95 (d, J = 7.7 Hz, 1H), 7.78 (d, J = 7.9 Hz, 1H), 7.66 (dd, J = 7.9, 1.4 Hz, 1H), 7.63 (d, J = 1.3 Hz, 1H), 4.15-4.01 (m, 1H), 3.97 (s, 3H), 3.86 (s, 3H), 1.18 (d, J = 6.6 Hz, 6H). |
| 332 | 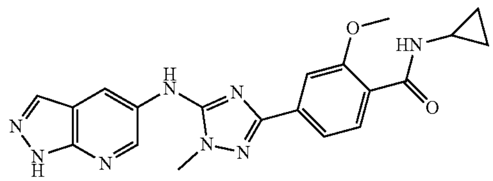 [SMILES: COc1cc(-c2nc(Nc3cnc4[nH]ncc4c3)n(C)n2)ccc1C(=O)NC1CC1] | Method B, 2.87 min, m/z 405.3 [M + H]⁺ | ¹H NMR (400 MHz, DMSO-d₆) δ 13.51 (s, 1H), 9.22 (s, 1H), 8.73 (d, J = 2.5 Hz, 1H), 8.65 (d, J = 2.4 Hz, 1H), 8.12 (d, J = 4.1 Hz, 2H), 7.73 (d, J = 7.9 Hz, 1H), 7.64 (dd, J = 7.9, 1.4 Hz, 1H), 7.61 (d, J = 1.5 Hz, 1H), 3.94 (s, 3H), 3.86 (s, 3H), 2.91-2.79 (m, 1H), 0.76-0.64 (m, 2H), 0.61-0.52 (m, 2H). |
| 333 | 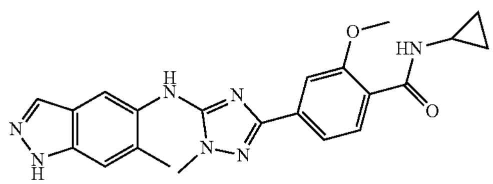 [SMILES: COc1cc(-c2nc(Nc3cc4cn[nH]c4cc3C)n(C)n2)ccc1C(=O)NC1CC1] | Method B, 3.01 min, m/z 418.2 [M + H]⁺ | ¹H NMR (400 MHz, DMSO-d₆) δ 12.89 (s, 1H), 8.20 (s, 1H), 8.09 (d, J = 4.3 Hz, 1H), 7.98 (t, J = 1.3 Hz, 1H), 7.70 (s, 1H), 7.67 (d, J = 7.9 Hz, 1H), 7.51-7.46 (m, 2H), 7.42 (m, 1H), 3.87 (s, 3H), 3.75 (s, 3H), 2.83 (m, 1H), 2.37 (s, 3H), 0.74-0.64 (m, 2H), 0.59-0.50 (m, 2H) |
| 334 | 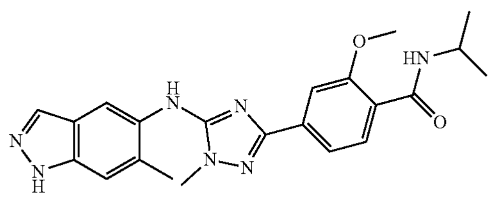 [SMILES: COc1cc(-c2nc(Nc3cc4cn[nH]c4cc3C)n(C)n2)ccc1C(=O)NC(C)C] | Method B, 3.18 min, m/z 420.3 [M + H]⁺ | ¹H NMR (400 MHz, DMSO-d₆) δ 12.89 (s, 1H), 8.20 (s, 1H), 7.98 (d, J = 1.2 Hz, 1H), 7.92 (d, J = 7.7 Hz, 1H), 7.71 (d, J = 8.0 Hz, 2H), 7.54-7.45 (m, 2H), 7.42 (s, 1H), 4.13-3.99 (m, 1H), 3.90 (s, 3H), 3.76 (s, 3H), 2.38 (s, 3H), 1.16 (d, J = 6.5 Hz, 6H) |
| 335 | 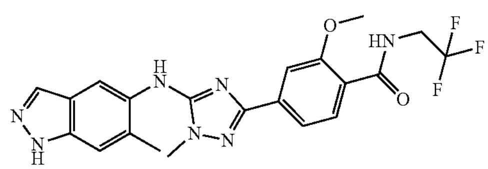 [SMILES: COc1cc(-c2nc(Nc3cc4cn[nH]c4cc3C)n(C)n2)ccc1C(=O)NCC(F)(F)F] | Method B, 3.33 min, m/z 460.2 [M + H]⁺ | ¹H NMR (400 MHz, DMSO-d₆) δ 12.90 (s, 1H), 8.67 (t, J = 6.4 Hz, 1H), 8.22 (s, 1H), 7.98 (s, 1H), 7.78 (d, J = 8.0 Hz, 1H), 7.71 (s, 1H), 7.57-7.49 (m, 2H), 7.42 (s, 1H), 4.12 (m, 2H), 3.93 (s, 3H), 3.76 (s, 3H), 2.38 (s, 3H) |
| 336 | 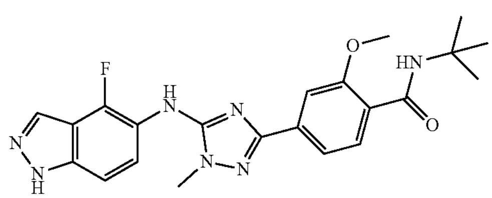 [SMILES: COc1cc(-c2nc(Nc3ccc4[nH]ncc4c3F)n(C)n2)ccc1C(=O)NC(C)(C)C] | Method B, 3.53 min, m/z 438.4 [M + H]⁺ | ¹H NMR (400 MHz, DMSO-d₆) δ 13.36 (s, 1H), 8.65 (s, 1H), 8.19 (s, 1H), 7.84 (s, 1H), 7.77 (d, J = 8.0 Hz, 1H), 7.66-7.55 (m, 1H), 7.55-7.45 (m, 2H), 7.40 (dd, J = 8.8, 1.1 Hz, 1H), 3.92 (s, 3H), 3.81 (s, 3H), 1.37 (s, 9H). |
| 337 | 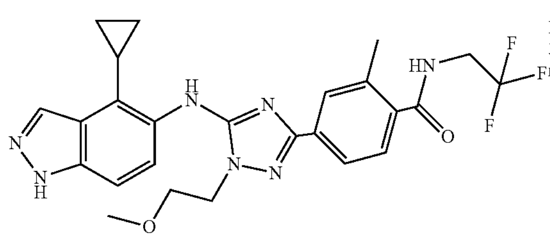 [SMILES: COCCn1nc(-c2ccc(C(=O)NCC(F)(F)F)c(C)c2)nc1Nc1ccc2[nH]ncc2c1C1CC1] | Method B, 3.66 min, Fm/z 514.5 [M + H]⁺ | ¹H NMR (400 MHz, DMSO-d₆) δ 13.03-12.98 (m, 1H), 8.97 (t, J = 6.3 Hz, 1H), 8.19 (s, 1H), 8.08 (t, J = 1.3 Hz, 1H), 7.78-7.70 (m, 2H), 7.60 (d, J = 8.8 Hz, 1H), 7.47-7.34 (m, 2H), 4.35 (t, J = 5.2 Hz, 2H), 4.06 (m, 2H), 3.78 (t, J = 5.2 Hz, 2H), 3.33 (s, 3H), 2.36 (s, 3H), 2.11 (m, 1H), 1.12-0.97 (m, 2H), 0.90-0.79 (m, 2H). |
| 338 | 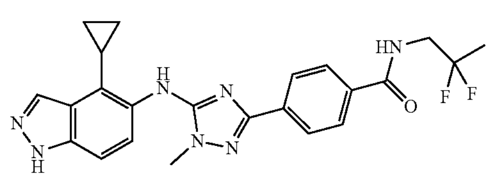 [SMILES: Cn1nc(-c2ccc(C(=O)NCC(C)(F)F)cc2)nc1Nc1ccc2[nH]ncc2c1C1CC1] | Method B, 3.19 min, m/z 452.4 [M + H]⁺ | ¹H NMR (400 MHz, DMSO-d₆) δ 13.02 (s, 1H), 8.84 (t, J = 6.32 Hz, 1H), 8.33 (s, 1H), 8.07 (s, 1H), 7.91 (m, 4H), 7.41 (q, J = 7.58 Hz, 2H), 3.80 (s, 3H), 3.72 (m, 2H), 2.14 (m, 1H), 1.62 (m, 3H), 0.97 (m, 2H), 0.83 (m, 2H). |

TABLE 24-continued

| Example | Structure | LC/MS | ¹H NMR |
|---|---|---|---|
| 339 | 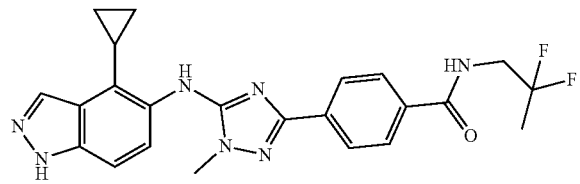 [SMILES: Cn1nc(-c2ccc(C(=O)NCC(C)(F)F)cc2)nc1Nc1ccc2[nH]ncc2c1C1CC1] | Method B, 2.98 min, m/z 454.4 [M + H]⁺ | ¹H NMR (400 MHz, DMSO-d₆) δ 13.02 (s, 1H), 10.81 (s, 1H), 8.33 (s, 1H), 8.07 (s, 1H), 8.00 (d, J = 8.60 Hz, 2H), 7.91 (d, J = 8.60 Hz, 2H), 7.60 (d, J = 2.20 Hz, 1H), 7.42 (q, J = 9.39 Hz, 2H), 6.59 (d, J = 2.20 Hz, 1H), 3.80 (s, 3H), 3.78 (s, 3H), 2.14 (m, 1H), 0.97 (m, 2H), 0.82 (m, 2H). |

Example 338: 4-[5-[4-cyclopropyl-1H-indazol-5-yl)amino]-1-methyl-1,2,4-triazol-3-yl]-N-(2,2-difluoropropyl)benzamide

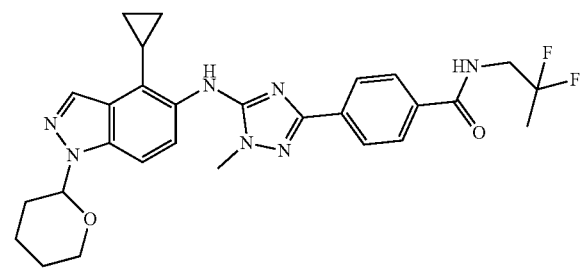 [SMILES: Cn1nc(-c2ccc(C(=O)NCC(C)(F)F)cc2)nc1Nc1ccc2c(cnn2C2CCCCO2)c1C1CC1]

A 100 mL RBF was charged with 4-[5-[(4-cyclopropyl-1-tetrahydropyran-2-yl-indazol-5-yl)amino]-1-methyl-1,2,4-triazol-3-yl]-N-(2,2-difluoropropyl)benzamide (37 mg, 0.07 mmol) and MeOH (2 mL). Hydrogen chloride 4N in dioxane (0.87 mL, 3.5 mmol) was added dropwise to the solution and the reaction mixture was stirred at RT for 18 h. The solvent was removed in vacuo, and then purified by SCX SPE cartridge. The resulting product was reduced in vacuo, dissolved in DCM and MeOH, washed with brine and reduced in vacuo. The residue was dissolved in water and acetonitrile (9:1) and freeze-dried overnight to afford 4-[5-[(4-cyclopropyl-1H-indazol-5-yl)amino]-1-methyl-1,2,4-triazol-3-yl]-N-(2,2-difluoropropyl)benzamide (23.9 mg, 0.05 mmol, 76% yield) as a white powder. UPLC-MS (ES+, Method B): 3.19 min, m/z 452.4 [M+H]⁺. ¹H NMR (400 MHz, DMSO-d₆) δ 13.02 (s, 1H), 8.84 (t, J=6.32 Hz, 1H), 8.33 (s, 1H), 8.07 (s, 1H), 7.91 (m, 4H), 7.41 (q, J=7.58 Hz, 2H), 3.80 (s, 3H), 3.72 (m, 2H), 2.14 (m, 1H), 1.62 (t, J=19.01 Hz, 3H), 0.97 (m, 2H), 0.83 (m, 2H).

Step 1: 4-[5-[(4-cyclopropyl-1-tetrahydropyran-2-yl-indazol-5-yl)amino]-1-methyl-1,2,4-triazol-3-yl]-N-(2,2-difluoropropyl)benzamide

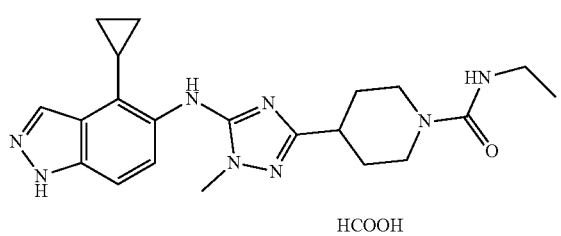 [SMILES: CCNC(=O)N1CCC(c2nc(Nc3ccc4[nH]ncc4c3C3CC3)n(C)n2)CC1 ; "HCOOH"]

A 50 mL RBF was charged with 4-[5-[(4-cyclopropyl-1-tetrahydropyran-2-yl-indazol-5-yl)amino]-1-methyl-1,2,4-triazol-3-yl]benzoic acid (300 mg, 0.65 mmol), DCM (6 mL) and DMF (0.03 mL). Oxalyl chloride (0.08 mL, 0.98 mmol) was slowly added and the reaction mixture was stirred at RT for 40 min. The solvents were removed in vacuo and the residue was dissolved in DCM. The solution was then added to a Carousel tube charged with 2,2-Difluoro-1-propanamine hydrochloride (30 mg, 0.23 mmol), DCM (2 mL) and triethylamine (0.15 mL, 1.09 mmol) and the reaction mixture was stirred at RT for 1 h. The solvents were removed in vacuo and the residue was dissolved in DCM and evaporated onto silica. The compound was then purified by silica column chromatography eluting with 10-100% EtOAc in Pet. Ether to afford 4-[5-[(4-cyclopropyl-1-tetrahydropyran-2-yl-indazol-5-yl)amino]-1-methyl-1,2,4-triazol-3-yl]-N-(2,2-difluoropropyl)benzamide (37 mg, 0.07 mmol, 31% yield) as an off-white solid. UPLC-MS (ES+, Method A): 1.69 min, m/z 536.5 [M+H]⁺

Example 340: 4-[5-[4-cyclopropyl-1H-indazol-5-yl)amino]-1-methyl-1,2,4-triazol-3-yl]-N-ethyl-piperidine-1-carboxamido Palladium, 10 wt. % on carbon powder, dry (2.4 mg, 0.02 mmol) added to 4-[5-[(4-cyclopropyl-1H-indazol-5-yl)amino]-1-methyl-1,2,4-triazol-3-yl]-N-ethyl-3,6-dihydro-2H-pyridine-1-carboxamide (90 mg, 0.22 mmol) in EtOH (5 mL) and stirred for 18 h at RT under an atmosphere of hydrogen. Further palladium, 10 wt. % on carbon powder, dry (2.4 mg, 0.02 mmol) was added, with 6 drops of 1M HCl in MeOH and the reaction was stirred for 48 h at RT under an atmosphere of hydrogen. Further palladium, 10 wt. % on carbon powder, dry (2.4 mg, 0.02 mmol) was added, with 6 drops of 4N HCl in 1,4-dioxane and the reaction was stirred for 18 h at RT under an atmosphere of hydrogen. The reaction mixture was filtered through a pad of Celite™ and washed with MeOH. The solvents were reduced in vacuo and purified by silica column chromatography eluting with 10% MeOH in EtOAc gradient to afford 4-[5-[(4-cyclopropyl-1H-indazol-5-yl)amino]-1-methyl-1,2,4-triazol-3-yl]-N-ethyl-piperidine-1-carboxamide (53 mg, 0.12 mmol, 53% yield) as a cream solid. UPLC-MS (ES⁺, Method B): 2.32 min, m/z 409.3 [M+H]⁺. ¹H NMR (400 MHz, DMSO-d₆) δ

12.95 (s, 1H), 8.16 (s, 1H), 8.03 (s, 1H), 8.01 (s, 1H), 7.35 (m, 2H), 6.39 (m, 1H), 3.88 (m, 2H), 3.63 (s, 3H), 2.13 (s, 1H), 3.02 (m, 2H), 2.73 (m, 2H), 2.05 (m, 1H), 1.76 (m, 2H), 1.44 (m, 2H), 0.99 (m, 5H), 0.77 (m, 2H).

Example 341 4-[5-[(4-cyclopropyl-1H-indazol-5-yl)amino]-1 methyl-1,2,4-triazol-3-yl]-N-ethyl-3,6-dihydro-2H-pyridine-1-carboxamide

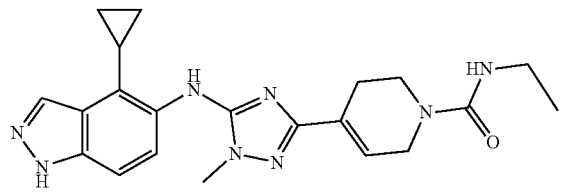 [SMILES: CCNC(=O)N1CC=C(c2nc(Nc3ccc4[nH]ncc4c3C3CC3)n(C)n2)CC1]

A 4 M solution of hydrogen chloride in 1,4-dioxane (1.25 mL, 4.99 mmol) was added to a solution of 4-[5-[(4-cyclopropyl-1-tetrahydropyran-2-yl-indazol-5-yl)amino]-1-methyl-1,2,4-triazol-3-yl]-N-ethyl-3,6-dihydro-2H-pyridine-1-carboxamide (245. mg, 0.5000 mmol) in MeOH (5 mL). The reaction mixture was stirred for 18 h at RT, concentrated under reduced pressure vacuum. Further purification by flash column chromatography on silica gel eluting with 10% MeOH in EtOAc afforded 4-[5-[(4-cyclopropyl-1H-indazol-5-yl)amino]-1-methyl-1,2,4-triazol-3-yl]-N-ethyl-3,6-dihydro-2H-pyridine-1-carboxamide (129 mg, 0.31 mmol, 61% yield) as a cream solid. UPLC-MS (ES+, Method B): 2.59 min, m/z 407.3 [M+H]$^+$. 1H NMR (400 MHz, DMSO-d6) δ 12.99 (s, 1H), 8.14 (s, 1), 8.05 (s, 1H), 7.35 (s, 1H), 7.73 (t, J=5.3 Hz, 1H), 6.31 (m, 1H), 3.87 (d, J=3.1 Hz, 2H), 3.69 (s, 3H), 3.43 (t, J=5.6 Hz, 2H), 3.05 (m, 2H), 2.38 (m, 2H), 2.09 (m, 1H), 1.01 (t, J=7.1 Hz, 3H), 0.95 (m, 2H), 0.78 (m, 2H).

Step 1: 4-(4,4,5,5-tetramethyl-1,3,2-dioxaborolan-2-yl)-1,2,3,6-tetrahydropyridine

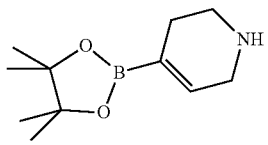

To N-Boc-1,2,3,6-tetrahydropyridine-4-boronic acid pinacol ester (0.5 g, 1.6 mmol) in DCM (30 mL) at RT was added trifluoroacetic acid (1.2 mL, 16.2 mmol) and the reaction was stirred for 1 h. The solvent was removed in vacuo. Further DCM was added and the reaction was again reduced in vacuo to afford 4-(4,4,5,5-tetramethyl-1,3,2-dioxaborolan-2-yl)-1,2,3,6-tetrahydropyridine 2,2,2-trifluoroacetic acid salt (637 mg, 1.46 mmol, 90% yield). UPLC-MS (ES$^+$, Method A): 1.03 min, m/z 210.2 [M+H]$^+$

Step 2: N-ethyl-4-(4,4,5,5-tetramethyl-1,3,2-dioxaborolan-2-yl)-3,6-dihydro-2H-pyridine-1-carboxamide

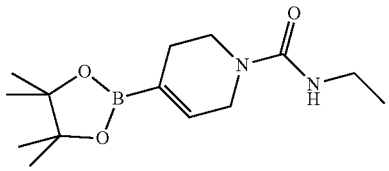 [SMILES: CCNC(=O)N1CC=C(B2OC(C)(C)C(C)(C)O2)CC1]

A solution of ethyl isocyanate (0.11 mL, 1.43 mmol) in DCM (10 mL) was added, dropwise over 15 min, to a vigorously stirred solution of 4-(4,4,5,5-tetramethyl-1,3,2-dioxaborolan-2-yl)-1,2,3,6-tetrahydropyridine-di-trifluoroacetic acid salt (627 mg, 1.43 mmol) and N,N-diisopropylethylamine (1.25 mL, 7.2 mmol) in water (15 mL) at 0° C. The reaction mixture was stirred at RT for 20 h. Sodium chloride (7.0 g) was added to the reaction mixture and the organic phase was separated. The aqueous phase was extracted with further DCM (3×75 mL). The crude was then purified by silica column chromatography, eluting with 0-6% MeOH in EtOAc to give N-ethyl-4-(4,4,5,5-tetramethyl-1,3,2-dioxaborolan-2-yl)-3,6-dihydro-2H-pyridine-1-carboxamide (251 mg, 0.78 mmol, 54% yield). UPLC-MS (ES$^+$, Method A): 1.48 min, m/z 281 [M+H]$^+$

Step 3: 4-[5-[(4-cyclopropyl-1-tetrahydropyran-2-yl-indazol-5-yl)amino]-1-methyl-1,2,4-triazol-3-yl]-N-ethyl-3,6-dihydro-2H-pyridine-1-carboxamide

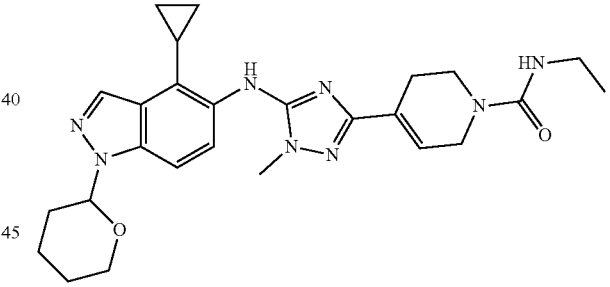

A mixture of N-ethyl-4-(4,4,5,5-tetramethyl-1,3,2-dioxaborolan-2-yl)-3,6-dihydro-2H-pyridine-1-carboxamide (219 mg, 0.7800 mmol), N-(5-bromo-2-methyl-1,2,4-triazol-3-yl)-4-cyclopropyl-1-tetrahydropyran-2-yl-indazol-5-amine (Step 1 in Example 251) (217 mg, 0.52 mol) and potassium carbonate (144 mg, 1.04 mmol) in 1,4-dioxane and water (3:1, 8 mL) was degassed by bubbling nitrogen through k for 15 min. 1,1'-bis(diphenylphosphino)ferrocene-palladium(II) dichloride dichloromethane complex (42 mg, 0.05 mmol) was added and the mixture was degassed again by bubbling nitrogen through it for 15 min. The mixture was then heated under microwave irradiation at 130° C. for 90 min. The mixture was filtered through a pad of Celite®. The cake was rinsed with EtOAc. Water was added to the filtrate and the layers were partitioned. The aqueous layer was extracted with EtOAc (×2). The combined organic extracts were washed with water, brine, dried over MgSO$_4$, filtered and then concentrated under reduced pressure. Further purification by flash column chromatography gave 4-[5-[(4-cyclopropyl-1-tetrahydropyran-2-yl-indazol-5-yl)amino]-1-methyl-1,2,4-triazol-3-yl]-N-ethyl-3,6-dihydro-2H-pyridine-1-carboxamide (256 mg, 0.50 mmol, 96% yield). UPLC-MS (ES+, Method A): 1.45 min, m/z 491 [M+H]+ (96%)

Example 342: 1-[4-[5-[(4-cyclopropyl-1H-indazol-5-yl)amino]-1-methyl-1,2,4-triazol-3-yl]-1-piperidyl]propan-1-one

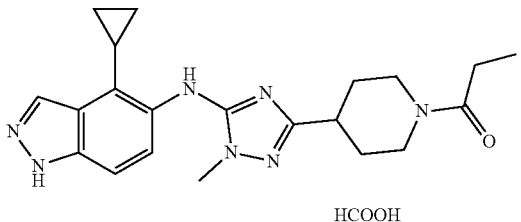 [SMILES: CCC(=O)N1CCC(c2nc(Nc3ccc4[nH]ncc4c3C3CC3)n(C)n2)CC1 ; "HCOOH"]

HCOOH

Following the experimental procedure described for Example 340, Example 342 was synthesised in an analogous method. UPLC-MS (ES+, Method B): 2.42 min, m/z 394.3 [M+H]+. $^1$H NMR (400 MHz, DMSO-$d_6$) δ 12.96 (s, 1H), 8.20 (s, 1H), 8.03 (s, 2H), 7.34 (m, 2H), 4.29 (d, J=13.4 Hz, 1H), 3.80 (d, J=13.4 Hz, 1H), 3.63 (s, 3H), 3.06 (m, 1H), 2.29 (q, J=7.4 Hz, 2H), 2.05 (m, 2H), 1.82 (m, 2H), 1.51 (m, 2H), 1.39 (m, 2H), 0.97 (t, J=7.4 Hz, 3H), 0.93 (m, 2H), 0.77 (m, 2H).

Intermediate 88: 1-[4-(4,4,5,5-tetramethyl-1,3,2-dioxaborolan-2-yl)-3,6-dihydro-2H-pyridin-1-yl]propan-1-one

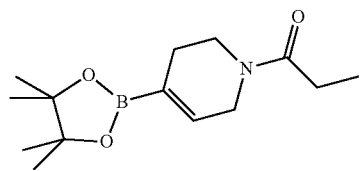 [SMILES: CCC(=O)N1CC=C(B2OC(C)(C)C(C)(C)O2)CC1]

Propylphosphonic anhydride (0.21 mL, 0.72 mmol) was added to 4-(4,4,5,5-tetramethyl-1,3,2-dioxaborolan-2-yl)-1,2,3,6-tetrahydropyridine; 2,2,2-trifluoroacetic acid (209 mg, 0.48 mmol), N,N-diisopropylethylamine (0.42 mL, 2.4 mmol) and propionic acid (propanoic acid) (0.04 mL, 0.48 mmol) in THF (1.6 mL) and the reaction stirred at RT for 3 h. The reaction was reduced in vacuo and the residue was taken up in EtOAc (20 mL) and the organics washed with 20 mL water and 10 mL saturated brine solution. The organics were then separated and dried (MgSO$_4$) and reduced in vacuo. The crude was then purified by silica column chromatography eluting with 20-100% EtOAc in Pet. Ether to give 1-[4-(4,4,5,5-tetramethyl-1,3,2-dioxaborolan-2-yl)-3,6-dihydro-2H-pyridin-1-yl]propan-1-one (152 mg, 0.41 mmol, 86% yield). UPLC-MS (ES+, Method A): 1.57 min, m/z 266 [M+H]+

Example 343: 4-[5-[(4-cyclopropyl-1H-indazol-5-yl)amino]-1 methyl-1,2,4-triazol-3-yl]-N-(2,2,2-trifluoroethyl)benzamide

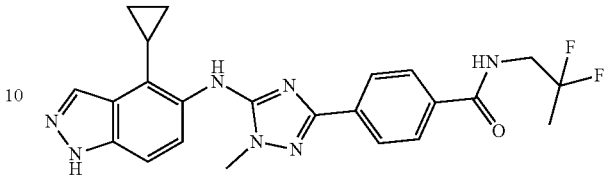

Hydrogen chloride (4.0M in dioxane) (2.6 mL, 10.4 mmol) was added slowly to a stirred solution of 4-[5-[(4-cyclopropyl-1-tetrahydropyran-2-yl-indazol-5-yl)amino]-1-methyl-1,2,4-triazol-3-yl]-N-(2,2,2-trifluoroethyl)benzamide (104 mg, 0.19 mmol) in MeOH (2 mL) at RT. The reaction was stirred at RT for 18 h. The pale-yellow solution was concentrated under reduced pressure and the crude residue purified by SCX SPE cartridge. The resulting product was purified by silica column chromatography eluting with 30-100% EtOAc in Pet. Ether. The product was then freeze dried overnight from acetonitrile/water to give 4-[5-[(4-cyclopropyl-1H-indazol-5-yl)amino]-1-methyl-1,2,4-triazol-3-yl]-N-(2,2,2-trifluoroethyl)benzamide (57 mg, 0.124 mmol, 66% yield) as a white solid. UPLC-MS (ES+, Method B): 3.31 min, m/z 456.4 [M+H]+. $^1$H NMR (DMSO-$d_6$) δ 13.02 (s, 1H), 9.10 (t, J=6.3 Hz, 1H), 8.34 (s, 1H), 8.07 (s, 1H), 8.00-7.86 (m, 4H), 7.46-7.35 (m, 2H), 4.09 (m, 2H), 3.80 (s, 3H), 2.14 (m, 1H), 1.04-0.91 (m, 2H), 0.91-0.76 (m, 2H).

Step 1: 4-[5-[(4-cyclopropyl-1-tetrahydropyran-2-yl-indazol-5-yl)amino]-1-methyl-1,2,4-triazol-3-yl]-N-(2,2,2-trifluoroethyl)benzamide

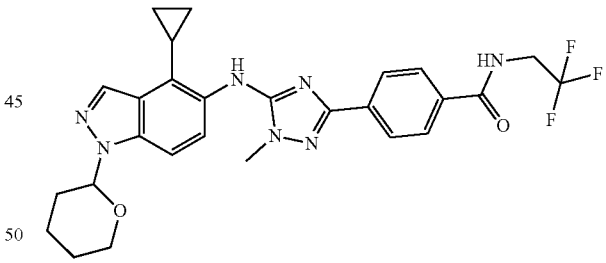

Potassium carbonate (56 mg, 0.4 mmol), N-(5-bromo-2-methyl-1,2,4-triazol-3-yl)-4-cyclopropyl-1-tetrahydropyran-2-yl-indazol-5-amine (80 mg, 0.19 mmol) and 4-(4,4,5,5-tetramethyl-1,3,2-dioxaborolan-2-yl)-N-(2,2,2-trifluoroethyl)benzamide (69 mg, 021 mmol) were dissolved/suspended in 1,4-dioxane (3 mL) and water (2 mL). The reaction mixture was fully degassed by bubbling nitrogen through. [1,1'-Bis(diphenylphosphino)ferrocene] Paladium(II) chloride dichloromethane complex (16 mg, 0.02 mmol) was then added followed by further degassing and then the reaction was heated to 90° C. for 18 h. The reaction was reduced onto silica and purified by silica column chromatography eluting with 20-100% EtOAc in Pet. Ether to give 4-[5-[(4-cyclopropyl-1-tetrahydropyran-2-yl-indazol-5-yl amino]-1-methyl-1,2,4-triazol-3-yl]-N-(2, 2,2-trifluoroethyl)benzamide (104 mg, 0.19 mmol, 99% yield) as a pale yellow gum. UPLC-MS (ES+, Method A): 1.76 min, m/z 540.5 [M+H]+

Step 1: 4-bromo-N-(2,2,2-trifluoroethyl)benzamide

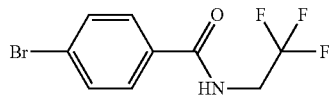

To a stirred solution of trifluoroethylamine (1.5 mL, 18.7 mmol), N,N-diisopropylethylamine (4.9 mL, 28 mmol) and 4-bromobenzoic acid (1.88 g, 9.35 mmol) in THF (50 mL) was added propylphosphonic anhydride (8.35 mL, 14 mmol) and the solution stirred for 3 h at RT. The pale-yellow solution was reduced in vacuo and dissolved in EtOAc. The organics were washed with water (×2), saturated brine, dried over MgSO4, filtered and reduced in vacuo to give 4-bromo-N-(2,2,2-trifluoroethyl)benzamide (2.62 g, 9.3 mmol, 99% yield) as a cream coloured solid. UPLC-MS (ES+, Method A): 1.65 min, m/z 283.9 [M+H]+

Step 2: 4-(4,4,5,5-tetramethyl-1,3,2-dioxaborolan-2-yl)-N-(2,2,2-trifluoroethyl)benzamide

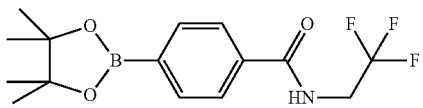 [SMILES: CC1(C)OB(c2ccc(C(=O)NCC(F)(F)F)cc2)OC1(C)C]

4-Bromo-N-(2,2,2-trifluoroethyl)benzamide (2610 mg, 9.25 mmol) was added to a stirred mixture of bis(pinacolato)diboron (2.82 g, 11.1 mmol), potassium acetate (2.72 g, 27.8 mmol) in 1,4-dioxane (40 mL) at RT. The reaction was degassed, flushed with nitrogen and [1,1'-bis(diphenylphosphino)ferrocene]palladium(II) chloride dichloromethane complex (755 mg, 0.93 mmol) was added followed by further degassing. The reaction was capped and stirred at 85° C. for 3 h. The reaction was cooled to RT and solvent removed in vacuo. EtOAc (50 mL) was added and the resulting suspension was dry loaded onto silica and the residue purified by column chromatography using an eluent of 10-50% EtOAc in Pet. Ether to give 4-(4,4,5,5-tetramethyl-1,3,2-dioxaborolan-2-yl)-N-(2,2,2-trifluoroethyl)benzamide (2.68 g, 8.14 mmol, 88% yield) as a pale yellow/cream solid. UPLC-MS (ES+, Method A), 1.82 min, m/z 330 [M+H]+

Example 344: N-Cyclopropyl-4-[5-[(4-cyclopropyl-1H-indazol-5-yl)amino]-1-methyl-1,2,4-triazol-3-yl]benzamide

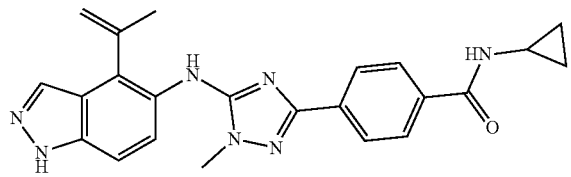

Hydrogen chloride (4.0M in dioxane) (2.1 mL, 8.5 mmol) was added slowly to a stirred solution of N-cyclopropyl-4-[5-[(4-cyclopropyl-1-tetrahydropyran-2-yl-indazol-5-yl)amino]-1-methyl-1,2,4-triazol-3-yl]benzamide (78 mg, 0.16 mmol) in MeOH (2 mL) at RT. The reaction was stirred at RT for 18 h. The pale-yellow solution was concentrated under reduced pressure and the crude residue purified by SCX SPE cartridge. The resulting solution was reduced in vacuo onto silica and the product was purified by silica column chromatography eluting with 30-100% EtOAc in Pet. Ether. The product was freeze dried from acetonitrile/water overnight to give N-cyclopropyl-4-[5-[(4-cyclopropyl-1H-indazol-5-yl)amino]-1-methyl-1,2,4-triazol-3-yl]benzamide (40 mg, 0.096 mmol, 61% yield) as a white solid. UPLC-MS (ES+, Method A): 2.95 min, m/z 414.3 [M+H]+. 1H NMR (400 MHz, DMSO-d6) δ 13.02 (s, 1H), 8.45 (d, J=4.2 Hz, 1H), 8.32 (s, 1H), 8.07 (s, 1H), 7.91-7.79 (m, 4H), 7.413-7.35 (m, 2H), 3.79 (s, 3H), 2.85 (m, 1H), 2.13 (m, 1H), 0.96 (m, 2H), 0.83 (m, 2H), 0.68 (m, 2H), 0.57 (m, 2H).

Step 1: N-cyclopropyl-4-[5-[(4-cyclopropyl-1-tetrahydropyran-2-yl-indazol-5-yl)amino]-1-methyl-1,2,4-triazol-3-yl]benzam Ide

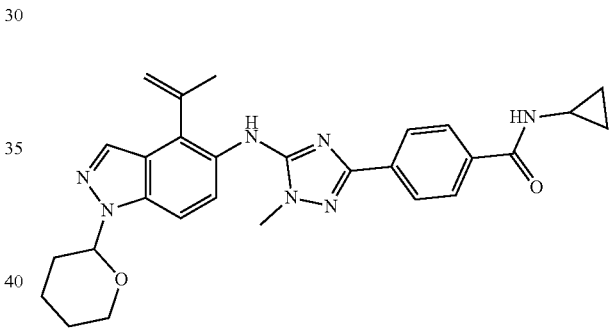

Potassium carbonate (83 mg, 0.6 mmol), N-cyclopropyl-4-(4,4,5,5-tetramethyl-1,3,2-dioxaborolan-2-yl)benzamide (56 mg, 0.19 mmol) and N-(5-bromo-2-methyl-1,2,4-triazol-3-yl)-4-cyclopropyl-1-tetrahydropyran-2-yl-indazol-5-amine (82 mg, 0.19 mmol) were dissolved/suspended in 1,4-dioxane (3 mL) and water (1 mL). The reaction mixture was fully degassed by bubbling nitrogen through. [1,1'-Bis(diphenylphosphino)ferrocene]palladium(II) chloride dichloromethane complex (23 mg, 0.03 mmol) was then added followed by further degassing and then the reaction was heated to 90° C. for 18 h. The reaction was reduced onto silica and purified by flash column chromatography eluting with 30-100% EtOAc in Pet. Ether to give N-cyclopropyl-4-[5-[(4-cyclopropyl-1-tetrahydropyran-2-yl-indazol-5-yl)amino]-1-methyl-1,2,4-triazol-3-yl]benzamide (78 mg, 0.16 mmol, 80% yield) as a pale yellow dry film. LC-MS (ES+, Method A): 1.60 min, m/z 498.6 [M+H]+

Compounds prepared in a similar manner to that set out above are given below in Table 25.

TABLE 25

| Example | Structure | LC/MS | ¹H NMR |
|---|---|---|---|
| 345 | 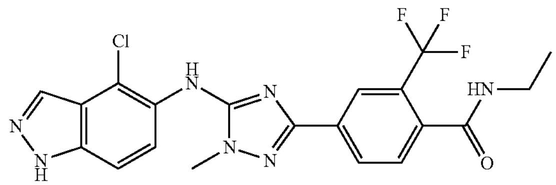 [SMILES: CCNC(=O)c1ccc(-c2nc(Nc3ccc4[nH]ncc4c3Cl)n(C)n2)cc1C(F)(F)F] | Method F, 2.76 min, m/z 464.1 [M + H]⁺ | ¹H NMR (400 MHz, DMSO-d₆) δ 13.4 (s, 1H), 8.65 (s, 1H), 8.5 (t, J = 5.6 Hz, 1H), 8.1-8.08 (m, 3H), 7.6-7.5 (m, 3H), 3.82 (s, 3H), 3.27-3.2 (m, 2H), 1.09 (t, J = 7.2 Hz, 3H) |
| 346 | 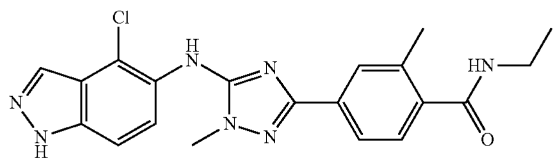 [SMILES: CCNC(=O)c1ccc(-c2nc(Nc3ccc4[nH]ncc4c3Cl)n(C)n2)cc1C] | Method F, 2.44 min, m/z 410.1 [M + H]⁺ | ¹H NMR (400 MHz, DMSO-d⁶) δ 13.38 (s, 1H), 8.51 (s, 1H), 8.24 (t, J = 6.4 Hz, 1H), 8.09 (s, 1H), 7.68-7.66 (m, 2H), 7.60-7.54 (q, J = 8.8 Hz, 2H), 7.31-7.29 (d, J = 7.6 Hz, 1H), 3.79 (s, 3H), 3.26-3.20 (m, 2H), 2.33 (s, 3H), 1.10 (t, J = 7.2 Hz, 3H) |
| 347 | 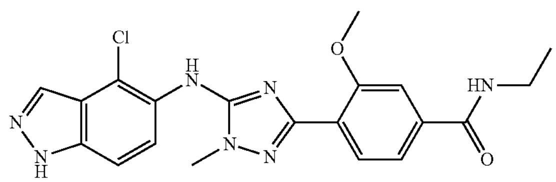 [SMILES: CCNC(=O)c1ccc(-c2nc(Nc3ccc4[nH]ncc4c3Cl)n(C)n2)c(OC)c1] | Method F, 2.21 min, m/z 426.1 [M + H]⁺ | ¹H NMR (400 MHz, DMSO-d₆) δ 13.36 (s, 1H), 8.51 (t, J = 5.6, 1H), 8.43 (s, 1H), 8.08 (s, 1H), 7.68-7.66 (d, J = 8 Hz, 1H), 7.60-7.50 (m, 3H), 7.43-7.41 (d, J = 8 Hz, 1H), 3.84 (s, 3H), 3.78 (s, 3H), 3.31-3.26 (m, 2H), 1.13 (t, J = 7.2 Hz, 3H) |
| 348 | 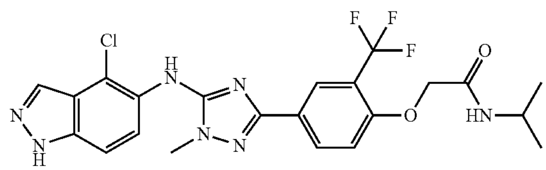 [SMILES: CC(C)NC(=O)COc1ccc(-c2nc(Nc3ccc4[nH]ncc4c3Cl)n(C)n2)cc1C(F)(F)F] | Method F, 3.24 min, m/z 508.1 [M + H]⁺ | ¹H NMR (400 MHz, DMSO-d₆) δ 13.38 (s, 1H), 8.55 (s, 1H), 8.09 (s, 1H), 8.03-8.00 (m, 2H), 7.64-7.62 (d, J = 8.0 Hz, 1H), 7.58-7.52 (m, 2H), 7.18-7.15 (d, J = 8.8 Hz, 1H), 4.64 (s, 2H), 3.91-3.86 (m, 1H), 3.78 (s, 3H), 1.09-1.07 (d, J = 6.8 Hz, 6H) |
| 349 | 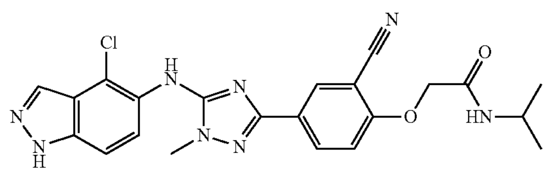 [SMILES: CC(C)NC(=O)COc1ccc(-c2nc(Nc3ccc4[nH]ncc4c3Cl)n(C)n2)cc1C#N] | Method F, 2.80 min, m/z 465.1 [M + H]⁺ | ¹H NMR (400 MHz, DMSO-d₆) δ 13.38 (s, 1H), 8.55 (s, 1H), 8.09-8.01 (m, 3H), 7.93 (d, J = 7.6 Hz, 1H), 7.6 (d, J = 8.8 Hz, 1H), 7.54 (d, J = 8.8 Hz, 1H), 7.1 (d, J = 8.8 Hz, 1H), 4.68 (s, 2H), 3.93-3.85 (m, 1H), 3.78 (s, 3H), 1.07 (d, J = 6.4 Hz, 6H) |
| 350 | 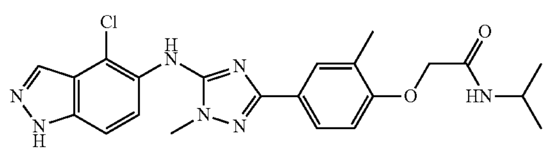 [SMILES: Cc1cc(-c2nc(Nc3ccc4[nH]ncc4c3Cl)n(C)n2)ccc1OCC(=O)NC(C)C] | Method F, 2.83 min, m/z 454.1 [M + H]⁺ | ¹H NMR (400 MHz, DMSO-d₆) δ 13.36 (s, 1H), 8.42 (s, 1H), 8.08 (s, 1H), 7.74 (d, J = 7.6 Hz, 1H), 7.63-7.57 (m, 3H), 7.55-7.51 (m, 1H), 6.81 (d, J = 8.4 Hz, 1H), 4.46 (s, 2H), 3.97-3.88 (m, 1H), 3.76 (s, 3H), 2.22 (s, 3H), 1.08 (d, J = 6.4 Hz, 6H) |
| 351 | 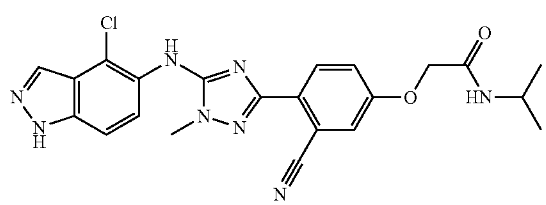 [SMILES: CC(C)NC(=O)COc1ccc(-c2nc(Nc3ccc4[nH]ncc4c3Cl)n(C)n2)c(C#N)c1] | Method F, 2.74 min, m/z 465.1 [M + H]⁺ | ¹H NMR (400 MHz, DMSO-d₆) δ 13.35 (s, 1H), 8.58 (s, 1H), 8.09 (s, 1H), 7.95 (d, J = 7.6 Hz, 1H), 7.87 (d, J = 8.8 Hz, 1H), 7.74 (d, J = 8.8 Hz, 1H), 7.5 (d, J = 8.8 Hz, 1H), 7.42 (d, J = 2.4 Hz, 1H), 7.31 (d, J = 2.4 Hz, 1H), 4.56 (s, 2H), 3.98-3.9 (m, 1H), 3.82 (s, 3H), 1.08 (d, J = 6.4 Hz, 6H) |
| 352 | 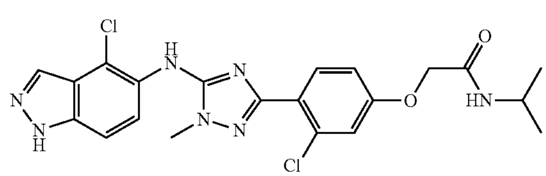 [SMILES: CC(C)NC(=O)COc1ccc(-c2nc(Nc3ccc4[nH]ncc4c3Cl)n(C)n2)c(Cl)c1] | Method F, 2.77 min, m/z 474.1 [M + H]⁺ | ¹H NMR (400 MHz, DMSO-d₆) δ 13.35 (s, 1H), 8.52 (s, 1H), 8.08 (s, 1H), 7.93 (d, J = 7.7 Hz, 1H), 7.65 (d, J = 8.7 Hz, 1H), 7.60 (d, J = 8.9 Hz, 1H), 7.52 (d, J = 8.8 Hz, 1H), 7.09 (d, J = 2.4 Hz, 1H), 6.96 (dd, J = 8.7, 2.4 Hz, 1H), 4.49 (s, 2H), 4.01-3.86 (m, 1H), 3.79 (s, 3H), 1.08 (d, J = 6.6 Hz, 6H). |

TABLE 25-continued

| Example | Structure | LC/MS | ¹H NMR |
|---|---|---|---|
| 353 | 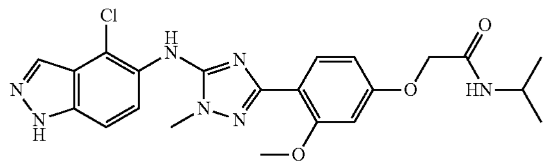 [SMILES: COc1cc(OCC(=O)NC(C)C)ccc1-c1nc(Nc2ccc3[nH]ncc3c2Cl)n(C)n1] | Method F, 2.39 min, m/z 470.1 [M + H]⁺ | ¹H NMR (400 MHz, DMSO-d₆) δ 13.34 (s, 1H), 8.40 (s, 1H), 8.07 (s, 1H), 7.90-7.88 (d, J = 7.6 Hz, 1H), 7.60-7.50 (m, 3H), 6.67 (s, 1H), 6.54-6.52 (d, J = 8.4 Hz, 1H), 4.46 (s, 2H), 3.99-3.90 (m, 1H), 3.76 (s, 3H), 3.75 (s, 3H), 1.10-1.083 (d, J = 6.8 Hz, 6H) |
| 354 | 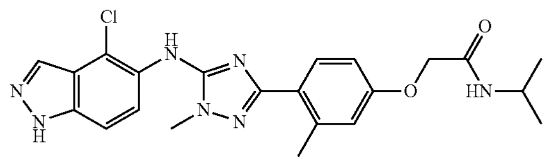 [SMILES: Cc1cc(OCC(=O)NC(C)C)ccc1-c1nc(Nc2ccc3[nH]ncc3c2Cl)n(C)n1] | Method F, 2.80 min, m/z 454.2 [M + H]⁺ | ¹H NMR (400 MHz, DMSO-d₆) δ 13.34 (s, 1H), 8.41 (s, 1H), 8.07 (s, 1H), 7.86-7.84 (d, J = 8.0, 1H), 7.67-7.65 (d, J = 8.4, 1H), 7.62-7.59 (d, J = 8.8 Hz, 1H), 7.53-7.50 (d, J = 8.8 Hz, 1H), 6.82 (s., 1H), 6.79-6.76 (d, J = 8.4 Hz, 1H), 4.42 (s, 2H), 3.94 (s, 1H), 3.77 (s, 3H), 2.50 (s, 3H), 1.07 (s, 6H) |
| 355 | 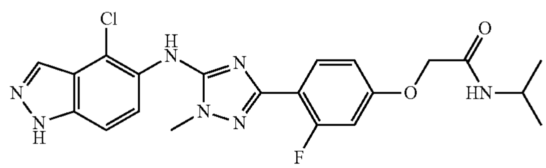 | Method F, 2.64 min, m/z 458.1 [M + H]⁺ | ¹H NMR (400 MHz, DMSO-d₆) δ 13.35 (s, 1H), 8.47 (s, 1H), 8.08 (s, 1H), 7.91 (d, J = 7.6 Hz, 1H), 7.72 (t, J = 8.8 Hz, 1H), 7.59 (d, J = 8.8 Hz, 1H), 7.53 (d, J = 8.8 Hz, 1H), 6.87 (d, J = 14.0 Hz, 1H), 6.82 (d, J = 8.8 Hz, 1H), 4.48 (s, 2H), 3.94 (s, 1H), 3.78 (s, 3H), 1.08 (d, J = 6.8 Hz, 6H) |
| 356 | 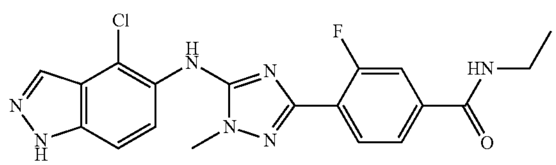 [SMILES: CCNC(=O)c1ccc(-c2nc(Nc3ccc4[nH]ncc4c3Cl)n(C)n2)c(F)c1] | Method F, 2.45 min, m/z 414.1 [M + H]⁺ | ¹H NMR (400 MHz, DMSO-d₆) δ 13.38 (s, 1H), 8.59-8.56 (m, 2H), 8.09 (s, 1H), 7.88 (t, J = 8.0 Hz, 1H), 7.70-7.68 (m, 2H), 7.60-7.53 (m, 2H), 3.82 (s, 3H), 3.30-3.25 (m, 2H), 1.12 (t, J = 7.2 Hz, 3H) |
| 357 | 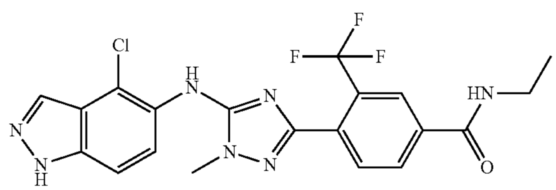 [SMILES: CCNC(=O)c1ccc(-c2nc(Nc3ccc4[nH]ncc4c3Cl)n(C)n2)c(C(F)(F)F)c1] | Method F, 2.77 min, m/z 464.1 [M + H]⁺ | ¹H NMR (400 MHz, DMSO-d₆) δ 13.36 (bs, 1H), 8.78 (t, 1H), 8.58 (s, 1H), 8.25 (s, 1H), 8.13 (d, 1H), 8.09 (s, 1H), 7.86 (d, 1H) 7.61 (d, 1H), 7.51 (d, 1H), 3.82 (s, 3H), 3.35-3.28 (m, 2H), 1.14 (t, 3H) |
| 358 | 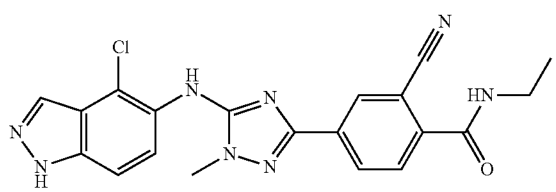 [SMILES: CCNC(=O)c1ccc(-c2nc(Nc3ccc4[nH]ncc4c3Cl)n(C)n2)cc1C#N] | Method F, 2.48 min, m/z 421.1 [M + H]⁺ | ¹H NMR (400 MHz, DMSO-d₆) δ 13.99 (s, 1H), 10.32 (s, 1H), 8.61 (d, J = 5.2 Hz, 2H), 8.15 (d, J = 8.0 Hz, 1H), 8.10 (s, 1H), 7.78 (d, J = 8 Hz, 1H), 7.58 (m, 2H), 3.85 (s, 3H), 3.75-3.70 (m, 2H), 1.16 (t, J = 7.2 Hz, 3H). |
| 359 | 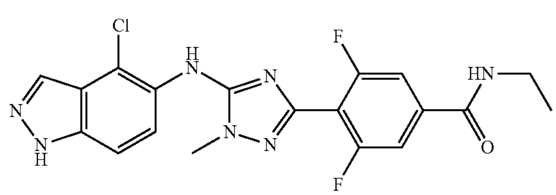 [SMILES: CCNC(=O)c1cc(F)c(-c2nc(Nc3ccc4[nH]ncc4c3Cl)n(C)n2)c(F)c1] | Method F, 2.65 min, m/z 432.1 [M + H]⁺ | ¹H NMR (400 MHz, DMSO-d₆) δ 12.92 (s, 1H), 8.93 (s, 1H), 8.52 (t, J = 5.2 Hz, 1H), 8.19 (s, 1H), 8.04-8.02 (m, 2H), 7.91 (d, J = 8 Hz, 1H), 7.58 (d, J = 8.8 Hz, 1H), 3.82 (s, 3H), 3.33-3.27 (m, 2H), 1.14 (t, J = 7.2 Hz, 3H) |
| 360 | 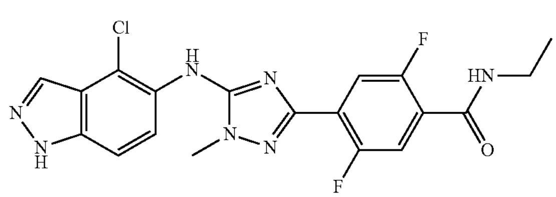 [SMILES: CCNC(=O)c1cc(F)c(-c2nc(Nc3ccc4[nH]ncc4c3Cl)n(C)n2)cc1F] | Method F, 2.85 min, m/z 432.1 [M + H]⁺ | ¹H NMR (400 MHz, DMSO-d₆) δ 13.38 (s, 1H), 8.84 (s, 1H), 8.39 (t, J = 5.2 Hz, 1H), 8.09 (s, 1H), 7.61-7.53 (m, 3H), 7.53 (dd, J = 10.4 Hz, 1H), 3.82 (s, 3H), 3.31-3.24 (m, 2H), 1.14 (t, J = 7.2 Hz, 3H) |

TABLE 25-continued

| Example | Structure | LC/MS | ¹H NMR |
|---|---|---|---|
| 361 | 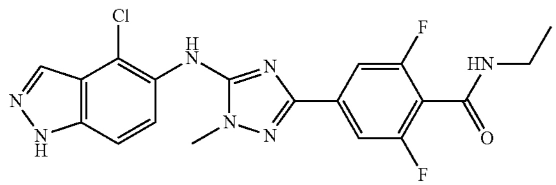 [SMILES: CCNC(=O)c1c(F)cc(-c2nc(Nc3ccc4[nH]ncc4c3Cl)n(C)n2)cc1F] | Method F, 2.81 min, m/z 432.1 [M + H]⁺ | ¹H NMR (400 MHz, DMSO-d₆) δ 13.39 (s, 1H), 8.70 (t, J = 5.6 Hz, 1H), 8.65 (s, 1H), 8.10 (s, 1H), 7.58 (q, J = 20.0 Hz, 2H), 7.46-7.44 (m, 2H), 3.81 (s, 3H), 3.29-3.22 (m, 2H), 1.10 (t, J = 7.2 Hz, 3H) |
| 362 | 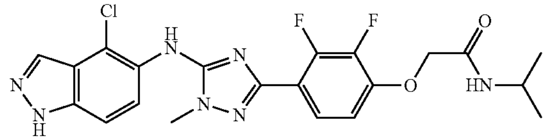 [SMILES: CC(C)NC(=O)COc1ccc(-c2nc(Nc3ccc4[nH]ncc4c3Cl)n(C)n2)c(F)c1F] | Method F, 2.97 min, m/z 476.1 [M + H]⁺ | ¹H NMR (400 MHz, DMSO-d₆) δ 13.36 (s, 1H), 8.54 (s, 1H), 8.08 (s, 1H), 7.94 (d, J = 7.6 Hz, 1H), 7.58-7.49 (m, 3H), 6.89 (t, J = 7.6 Hz, 1H), 4.59 (s, 2H), 3.94-3.86 (m, 1H), 3.79 (s, 3H), 1.06 (d, J = 6.4 Hz, 6H) |
| 363 | 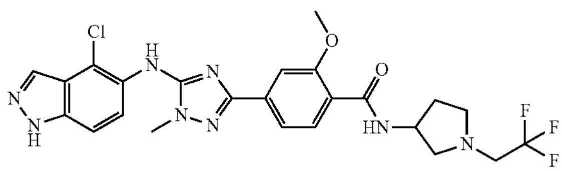 [SMILES: COc1cc(-c2nc(Nc3ccc4[nH]ncc4c3Cl)n(C)n2)ccc1C(=O)NC1CCN(CC(F)(F)F)C1] | Method B, 3.21 min, m/z 549.3 [M + H]⁺ | ¹H-NMR (400 MHz, DMSO-d₆) δ 13.43 (s, 1H), 8.60 (s, 1H), 8.28 (d, J = 7.2 Hz, 1H), 8.14 (s, 1H), 7.75 (d, J = 8 Hz, 1H), 7.62-7.51 (m, 4H), 4.47-4.35 (m, 1H), 3.93 (s, 3H), 3.85 (s, 3H), 3.36-3.29 (m, 2H), 3.02-2.88 (m, 2H), 2.75-2.64 (m, 2H), 2.25-2.12 (m, 1H), 1.83-1.70 (m,1H). |
| 364 | 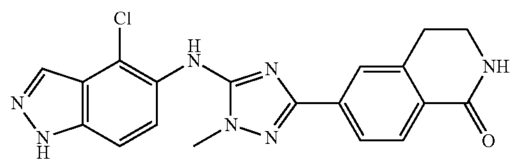 [SMILES: Cn1nc(-c2ccc3c(c2)CCNC3=O)nc1Nc1ccc2[nH]ncc2c1Cl] | Method B, 2.82 min, m/z 394.1 [M + H]⁺ | ¹H NMR (400 MHz, DMSO-d₆) δ 13.38 (s, 1H), 8.55 (s, 1H), 8.09 (s, 1H), 7.91 (brs, 1H), 7.84 (d, J = 8.16 Hz, 1H), 7.79 (d, J = 8.48 HZ, 1H), 7.73 (s, 1H), 7.57 (q, J = 8.07 Hz, 2H), 3.81 (s, 3H), 3.35 (m, 2H), 2.91 (m, 2H). |
| 365 | 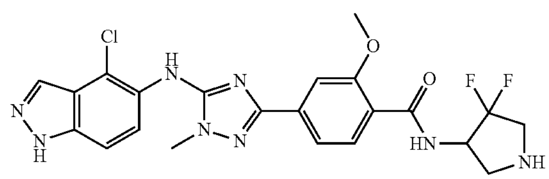 [SMILES: COc1cc(-c2nc(Nc3ccc4[nH]ncc4c3Cl)n(C)n2)ccc1C(=O)NC1CNCC1(F)F] | Method B, 2.66 min, m/z 503.2 [M + H]⁺ | ¹H NMR (400 MHz, DMSO-d₆) δ 13.43 (s, 1H), 8.61 (s, 1H), 8.31 (d, J = 8.5 Hz, 1H), 8.14 (s, 1H), 7.79 (d, J = 8.0 Hz, 1H), 7.66-7.51 (m, 4H), 4.68-4.50 (m, 1H), 3.95 (s, 3H), 3.85 (s, 3H), 3.37-3.23 (m, 2H), 3.06 (q, J = 14.3 Hz, 1H), 2.85-2.73 (m, 1H) 1 NH not observed |
| 366 | 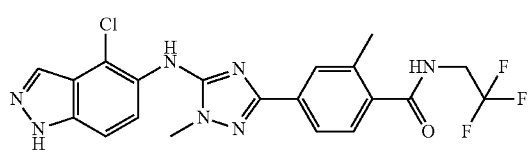 [SMILES: Cc1cc(-c2nc(Nc3ccc4[nH]ncc4c3Cl)n(C)n2)ccc1C(=O)NCC(F)(F)F] | Method B, 3.34 min, m/z 464.3 [M + H]⁺ | ¹H NMR (400 MHz, DMSO-d₆) δ 13.39 (s, 1H), 8.97 (t, J = 6.4 Hz, 1H), 8.54 (s, 1H), 8.10 (s, 1H), 7.75-7.70 (m, 2H), 7.62-7.54 (m, 2H), 7.36 (d, J = 8.4 Hz, 1H), 4.05 (m, 2H), 3.81 (s, 3H), 2.24 (s, 3H). |
| 367 | 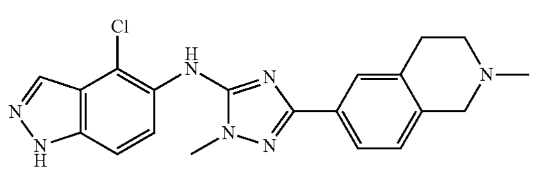 [SMILES: CN1CCc2cc(-c3nc(Nc4ccc5[nH]ncc5c4Cl)n(C)n3)ccc2C1] | Method F, 1.88 min, m/z 394.0 [M + H]⁺ | ¹H NMR (400 MHz, DMSO-d₆) δ 13.53 (s, 1H), 8.46 (s, 1H), 8.09 (s, 1H), 7.59-7.53 (m, 4H), 7.04 (d, J = 7.6 Hz, 1H), 3.77 (s, 3H), 3.46 (s, 2H), 2.81 (t, J = 5.6 Hz, 2H), 2.58 (t, J = 5.6 Hz, 2H), 2.32 (s, 3H) |
| 368 | 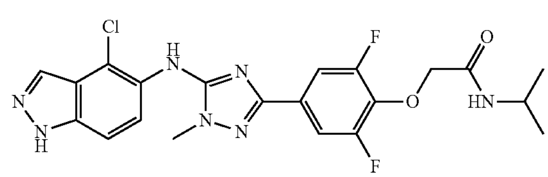 [SMILES: CC(C)NC(=O)COc1c(F)cc(-c2nc(Nc3ccc4[nH]ncc4c3Cl)n(C)n2)cc1F] | Method F, 3.09 min, m/z 476.1 [M + H]⁺ | ¹H NMR (400 MHz, DMSO-d₆) δ 13.39 (s, 1H), 8.59 (s, 1H), 8.09 (s, 1H), 7.88-7.86 (d, J = 7.6 Hz, 1H), 7.57 (q, J = 19.6 Hz, 2H), 7.47-7.41 (m, 2H), 4.54 (s, 2H), 3.97-3.87 (m, 1H), 3.79 (s, 3H), 1.07 (d, J = 6.4 Hz, 6H) |
| 369 | 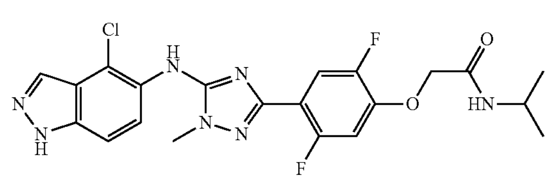 [SMILES: CC(C)NC(=O)COc1cc(F)c(-c2nc(Nc3ccc4[nH]ncc4c3Cl)n(C)n2)cc1F] | Method F, 2.85 min, m/z 476 [M + H]⁺ | ¹H NMR (400 MHz, DMSO-d₆) δ 13.38 (s, 1H), 8.55 (s, 1H), 8.08 (s, 1H), 7.95 (d, J = 7.6,1H), 7.60-7.51 (m, 3H), 7.06-7.01 (m, 1H), 4.59 (s, 2H), 3.94-3.86 (m, 1H), 3.78 (s, 3H), 1.07 (d, J = 6.4 Hz, 6H) |

TABLE 25-continued

| Example | Structure | LC/MS | ¹H NMR |
|---|---|---|---|
| 370 | 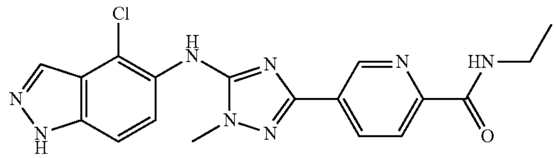 [SMILES: CCNC(=O)c1ccc(-c2nc(Nc3ccc4[nH]ncc4c3Cl)n(C)n2)cn1] | Method F, 2.70 min, m/z 397.0 [M + H]⁺ | ¹H NMR (400 MHz, DMSO-d₆) δ 13.4 (s, 1H), 9.03 (d, J = 1.2 Hz, 1H), 8.82 (t, J = 6.0 Hz, 1H), 8.68 (s, 1H), 8.3 (dd, J = 8.0 Hz, 1H), 8.1 (s, 1H), 8.06 (d, J = 8.0 Hz, 1H), 7.58 (q, J1 = 7.2 Hz, J2 = 14.0 Hz, 2H), 3.83 (s, 3H), 3.31-3.28 (m, 2H), 1.1 (t, J = 7.2 Hz, 3H) |
| 371 | 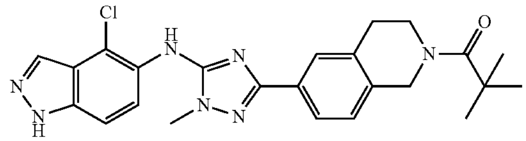 [SMILES: Cn1nc(-c2ccc3c(c2)CCN(C(=O)C(C)(C)C)C3)nc1Nc1ccc2[nH]ncc2c1Cl] | Method F, 3.25 min, m/z 464.1 [M + H]⁺ | ¹H NMR (400 MHz, DMSO-d₆) δ 13.38 (s, 1H), 8.47 (s, 1H), 8.09 (s, 1H), 7.65-7.53 (m, 4H), 7.21 (d, J = 8 Hz, 1H), 4.67 (s, 2H), 3.78-3.75 (m, 5H), 1.22 (s, 9H), 2.82 (m, 2H) |
| 372 | 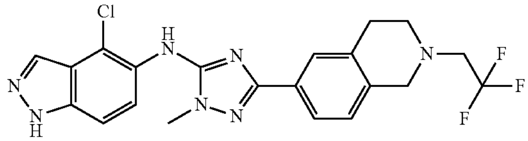 [SMILES: Cn1nc(-c2ccc3c(c2)CCN(CC(F)(F)F)C3)nc1Nc1ccc2[nH]ncc2c1Cl] | Method F, 3.50 min, m/z 462.1 [M + H]⁺ | ¹H NMR (400 MHz, DMSO-d₆) δ 13.37 (s, 1H), 8.46 (s, 1H), 8.09 (s, 1H), 7.60-7.53 (m, 4H), 7.06 (d, J = 8 Hz, 1H), 3.80 (s, 2H), 3.77 (s, 3H), 3.38-3.35 (m, 2H), 2.90 (t, J = 6.0 Hz, 2H), 2.82 (t, J = 5.6 Hz, 2H). |
| 373 | 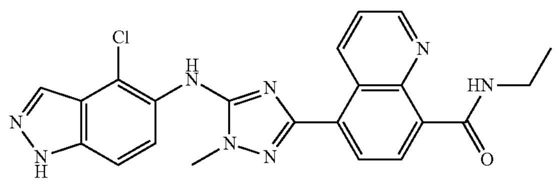 [SMILES: CCNC(=O)c1ccc(-c2nc(Nc3ccc4[nH]ncc4c3Cl)n(C)n2)c2cccnc12] | Method F, 2.94 min, m/z 447.0 [M + H]⁺ | ¹H NMR (400 MHz, DMSO-d₆) δ 13.40 (s, 1H), 10.78 (t, J = 5.6 Hz, 1H), 9.74 (m, 1H), 9.05 (m, 1H), 8.73 (s, 1H), 8.53 (d, J = 7.6 Hz, 1H), 8.19 (d, J = 8.0 Hz, 1H), 8.12 (s, 1H), 7.71 (m, 1H), 7.60 (m, 2H), 3.91 (8, 3H), 3.46 (m, 2H), 1.22 (t, J = 7.2 Hz,3H) |
| 374 | 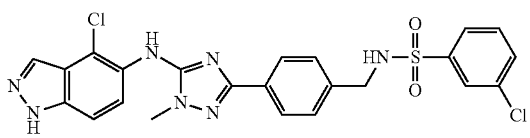 [SMILES: Cn1nc(-c2ccc(CNS(=O)(=O)c3cccc(Cl)c3)cc2)nc1Nc1ccc2[nH]ncc2c1Cl] | Method A, 1.66 min, m/z 528.1 [M + H]⁺ | ¹H NMR (400 MHz, DMSO-d₆) δ 13.38 (s, 1H), 8.50 (s, 1H), 8.39-8.29 (bs, 1H), 8.09 (s, 1H), 7.79-7.72 (m, 3H), 7.72-7.62 (m, 1H), 7.63-7.52 (m, 3H), 7.26-7.22 (m, 2H), 7.18-7.01 (bs, 1H), 4.04 (s, 2H), 3.78 (s, 3H) |
| 375 | 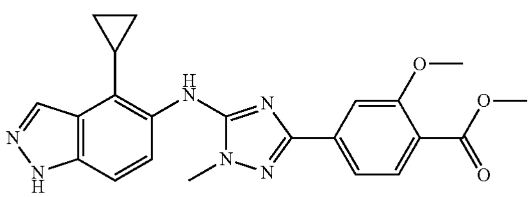 [SMILES: COC(=O)c1ccc(-c2nc(Nc3ccc4[nH]ncc4c3C3CC3)n(C)n2)cc1OC] | Method B, 3.35 min, m/z 419.4 [M + H]⁺ | ¹H NMR (400 MHz, DMSO-d₆) δ 13.02 (s, 1H), 8.35 (s, 1H), 8.07 (t, J = 1.1 Hz, 1H), 7.68 (d, J = 8.0 Hz, 1H), 7.52 (d, J = 1.4 Hz, 1H), 7.47 (dd, J = 8.1, 1.4 Hz, 1H), 7.42-7.36 (m, 2H), 3.84 (s, 3H), 3.80 (s, 3H), 3.78 (s, 3H), 2.20-2.08 (m, 1H), 1.02-0.91 (m, 2H), 0.90-0.79 (m,2H). |
| 376 | 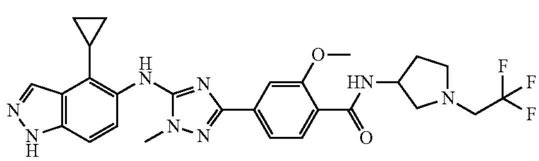 [SMILES: COc1cc(-c2nc(Nc3ccc4[nH]ncc4c3C3CC3)n(C)n2)ccc1C(=O)NC1CCN(CC(F)(F)F)C1] | Method B, 3.26 min, m/z 555.3 [M + H]⁺ | ¹H-NMR (400 MHz, DMSO-d₆) δ 13.05 (s, 1H), 8.36 (s, 1H), 8.27 (d, J = 7.2 Hz, 1H), 8.10 (s, 1H), 7.74 (d, J = 8.0 Hz, 1H), 7.56-7.50 (m, 2H), 7.43-7.22 (m, 2H), 4.47-4.35 (m, 1H), 3.93 (s, 3H), 3.82 (s, 3H), 3.36-3.27 (m, 2H), 3.02-2.88 (m, 2H), 2.75-2.65 (m, 2H), 2.25-2.12 (m, 2H), 1.82-1.71 (m, 1H), 1.06-0.96 (m, 2H), 0.90-0.83 (m, 2H). |
| 377 | 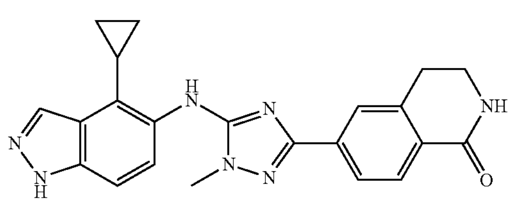 [SMILES: Cn1nc(-c2ccc3c(c2)CCNC3=O)nc1Nc1ccc2[nH]ncc2c1C1CC1] | Method B, 2.87 min, m/z 400.2 [M + H]⁺ | ¹H NMR (400 MHz, DMSO-d₆) δ 13.00 (s, 1H), 8.31 (s, 1H), 8.06 (s, 1H), 7.90 (brs, 1H), 7.83 (d, J = 8.08 Hz, 1H), 7.78 (dd, J = 8.08 Hz, 1.46 Hz, 1H), 7.72 (s,1H), 7.39 (q, J= 7.21 Hz, 2H), 3.79 (s, 3H), 3.35 (m, 2H), 2.91 (t, J= 6.72 Hz, 2H), 2.12 (m, 1H), 0.95 (m, 2H), 0.81 (m, 2H). |

TABLE 25-continued

| Example | Structure | LC/MS | ¹H NMR |
|---|---|---|---|
| 343 | 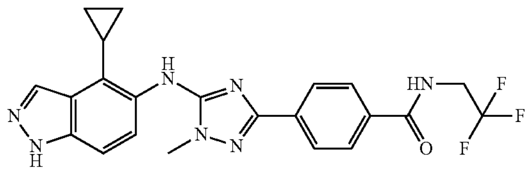 [SMILES: Cn1nc(-c2ccc(C(=O)NCC(F)(F)F)cc2)nc1Nc1ccc2[nH]ncc2c1C1CC1] | Method B, 3.31 min, m/z 456.4 [M + H]⁺ | ¹H NMR (400 MHz, DMSO-d₆) δ 13.02 (s, 1H), 9.10 (t, J = 6.3 Hz, 1H), 8.34 (s, 1H), 8.07 (s, 1H), 8.00-7.86 (m, 4H), 7.46-7.35 (m, 2H), 4.09 (m, 2H), 3.80 (s, 3H), 2.14 (m, 1H), 1.04-0.91 (m, 2H), 0.91-0.76 (m, 2H) |
| 378 | 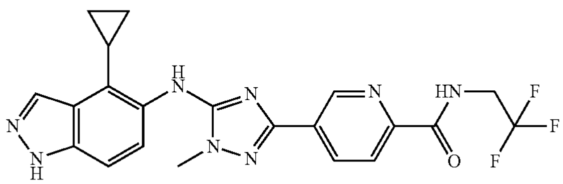 [SMILES: Cn1nc(-c2ccc(C(=O)NCC(F)(F)F)nc2)nc1Nc1ccc2[nH]ncc2c1C1CC1] | Method B, 3.50 min, m/z 457.3 [M + H]⁺ | ¹H NMR (400 MHz, DMSO-d₆) δ 13.03 (s, 1H), 9.34 (t, J = 6.7 Hz, 1H), 9.07 (dd, J = 0.9, 2.1 Hz, 1H), 8.46 (s, 1H), 8.33 (dd, J = 2.1, 8.0 Hz, 1H), 8.12-8.04 (m, 2H), 7.42-7.37 (m, 2H), 4.15-4.02 (m, 2H), 3.82 (s, 3H), 2.21-2.10 (m, 1H), 1.03-0.93 (m, 2H), 0.89-0.80 (m, 2H). |
| 379 | 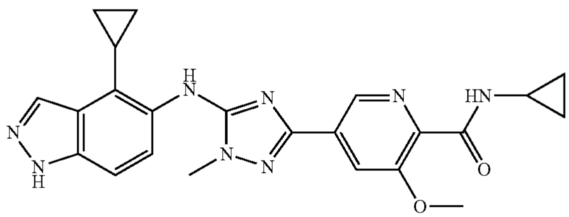 [SMILES: COc1cc(-c2nc(Nc3ccc4[nH]ncc4c3C3CC3)n(C)n2)cnc1C(=O)NC1CC1] | Method B, 2.86 min, m/z 445.4 [M + H]⁺ | ¹H NMR (400 MHz, DMSO-d₆) δ 13.02 (s, 1H), 8.52 (d, J = 1.4 Hz, 1H), 8.40 (s, 1H), 8.34 (d, J = 4.7 Hz, 1H), 8.05 (s, 1H), 7.74 (d, J = 1.4 Hz, 1H), 7.38 (s, 2H), 3.83 (s, 3H), 3.79 (s, 3H), 2.81 (m, 1H), 2.13 (m, 1H), 0.96 (m, 2H), 0.84 (m, 2H), 0.66 (m, 2H), 0.55-0.49 (m, 2H). |
| 380 | 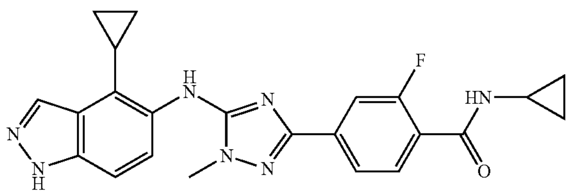 [SMILES: Cn1nc(-c2ccc(C(=O)NC3CC3)c(F)c2)nc1Nc1ccc2[nH]ncc2c1C1CC1] | Method B, 3.15 min, m/z 432.5 [M + H]⁺ | ¹H NMR (400 MHz, DMSO-d₆) δ 13.01 (s, 1H), 8.39-8.32 (m, 2H), 8.06 (s, 1H), 7.68 (dd, J = 8.1, 1.5 Hz, 1H), 7.59-7.50 (m, 2H), 7.44-7.35 (m, 2H), 3.79 (s, 3H), 2.82 (m, 1H), 2.13 (m, 1H), 1.00-0.92 (m, 2H), 0.85-0.79 (m, 2H), 0.68 (td, J = 7.1, 4.7 Hz, 2H), 0.56-0.50 (m, 2H). |
| 381 | 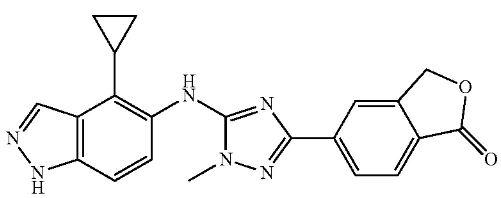 [SMILES: Cn1nc(-c2ccc3c(c2)COC3=O)nc1Nc1ccc2[nH]ncc2c1C1CC1] | Method B, 3.09 min, m/z 387.3 [M + H]⁺ | ¹H NMR (400 MHz, DMSO-d₆) δ 13.02 (s, 1H), 8.40 (s, 1H), 8.05 (d, J = 14.7 Hz, 3H), 7.83 (d, J = 8.0 Hz, 1H), 7.46-7.33 (m, 2H), 5.39 (s, 2H), 3.82 (s, 3H), 2.13 (m, 1H), 0.99-0.91 (m, 2H), 0.81 (m, 2H). |
| 344 | 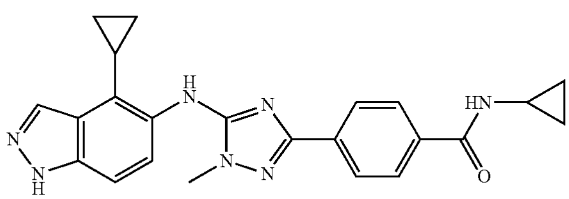 [SMILES: Cn1nc(-c2ccc(C(=O)NC3CC3)cc2)nc1Nc1ccc2[nH]ncc2c1C1CC1] | Method B, 2.95 min, m/z 414.3 [M + H]⁺ | ¹H NMR (400 MHz, DMSO-d₆) δ 13.02 (s, 1H), 8.45 (d, J = 4.2 Hz, 1H), 8.32 (s, 1H), 8.07 (s, 1H), 7.91-7.79 (m, 4H), 7.46-7.35 (m, 2H), 3.79 (s, 3H), 2.85 (m, 1H), 2.13 (m, 1H), 0.96 (m, 2H), 0.83 (m, 2H), 0.68 (m, 2H), 0.57 (m, 2H). |
| 382 | 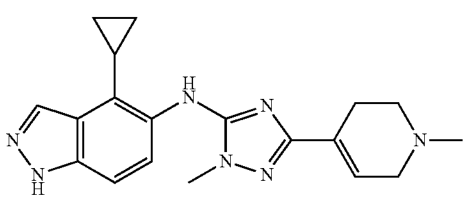 [SMILES: CN1CC=C(c2nc(Nc3ccc4[nH]ncc4c3C3CC3)n(C)n2)CC1] | Method B, 2.08 min, m/z 350.4 [M + H]⁺ | ¹H NMR (400 MHz, DMSO-d₆) δ 12.97 (s, 1H), 8.17-8.00 (m, 2H), 7.42-7.27 (m, 2H), 6.29 (s, 1H), 3.68 (s, 3H), 3.28 (t, 2H) 2.94 (s, 2H), 2.41 (s, 2H), 2.25 (s, 3H), 2.09 (m, 1H), 1.01-0.92 (m, 2H), 0.83-0.73 (m, 2H). |
| 383 | 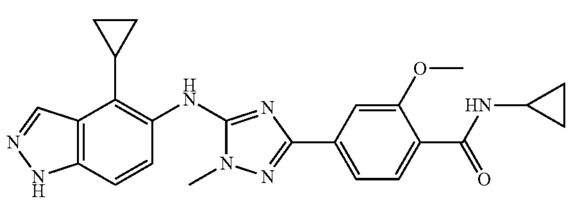 [SMILES: COc1cc(-c2nc(Nc3ccc4[nH]ncc4c3C3CC3)n(C)n2)ccc1C(=O)NC1CC1] | Method B, 3.15 min, m/z 444.4 [M + H]⁺ | ¹H NMR (DMSO-d₆) δ 13.02 (s, 1H), 8.32 (s, 1H), 8.11-8.04 (m, 2H), 7.66 (d, J = 7.9 Hz, 1H), 7.52-7.44 (m, 2H), 7.46-7.33 (m, 2H), 3.87 (s, 3H), 3.79 (s, 3H), 2.82 (m, 1H), 2.14 (m, 1H), 1.02-0.92 (m, 2H), 0.83 (m, 2H), 0.69 (m, 2H), 0.59-0.50 (m, 2H) |

TABLE 25-continued

| Example | Structure | LC/MS | ¹H NMR |
|---|---|---|---|
| 384 | 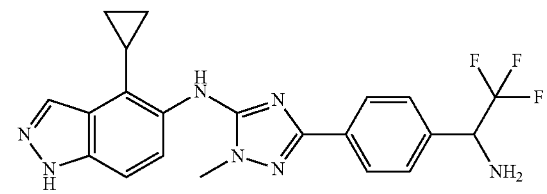 [SMILES: Cn1nc(-c2ccc(C(N)C(F)(F)F)cc2)nc1Nc1ccc2[nH]ncc2c1C1CC1] | Method B, 2.67 min, m/z 428.4 [M + H]⁺ | ¹H NMR (400 MHz, DMSO-d₆) δ 13.01 (s, 1H), 8.27 (s, 1H), 8.06 (s, 1H), 7.83 (d, J = 8.40 Hz, 2H), 7.49 (d, J = 8.20 Hz, 2H), 7.40 (q, J = 8.91 Hz, 2H), 4.48 (m, 1H), 3.77 (s, 3H), 2.13 (m, 1H), 0.96 (m, 2H), 0.82 (m, 2H). 2H not observed |
| 385 | 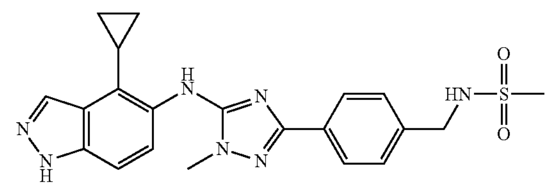 [SMILES: Cn1nc(-c2ccc(CNS(C)(=O)=O)cc2)nc1Nc1ccc2[nH]ncc2c1C1CC1] | Method B, 2.85 min, m/z 438.3 [M + H]⁺ | ¹H NMR (400 MHz, DMSO-d₆) δ 8.10 (br. d., J = 0.6 Hz, 1H), 7.84-7.79 (m, 2H), 7.60 (t, J = 6.1 Hz, 1H), 7.44-7.36 (m, 4H), 4.17 (d, J = 6.1 Hz, 2H), 3.82 (s, 3H), 2.85 (s, 3H), 2.15 (m, 1H), 1.00-0.94 (m, 2H), 0.90-0.84 (m, 2H). 2 NH not observed. |
| 386 | 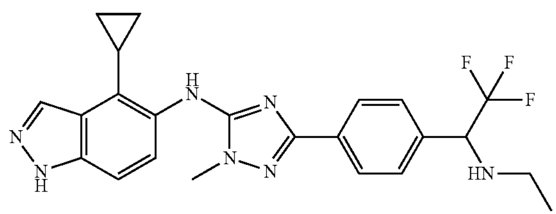 [SMILES: CCNC(c1ccc(-c2nc(Nc3ccc4[nH]ncc4c3C3CC3)n(C)n2)cc1)C(F)(F)F] | Method B, 2.85 min, m/z 456.4 [M + H]⁺ | ¹H NMR (400 MHz, DMSO-d₆) δ 13.01 (s, 1H), 8.28 (s, 1H), 8.06 (s, 1H), 7.84 (d, J = 8.32 Hz, 2H), 7.49 (d, J = 8.20 Hz, 2H), 7.39 (m, 2H), 4.38 (m, 1H), 3.78 (s, 3H), 2.72 (m, 1H), 2.46 (m, 1H), 2.12 (m, 1H), 0.99 (t, J = 7.24 Hz, 3H), 0.95 (m, 2H), 0.81 (m, 2H). 1 NH not observed |
| 387 | 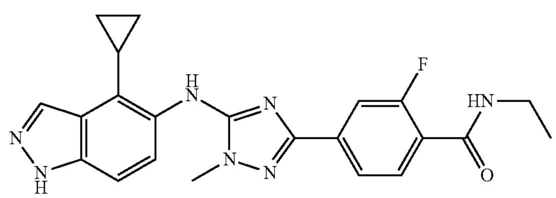 [SMILES: CCNC(=O)c1ccc(-c2nc(Nc3ccc4[nH]ncc4c3C3CC3)n(C)n2)cc1F] | Method B, 3.12 min, m/z 420.3 [M + H]⁺ | ¹H NMR (400 MHz, DMSO-d₆) δ 13.02 (s, 1H), 8.37 (s, 1H), 8.29 (m, 1H), 8.07 (s, 1H), 7.70 (dd, J = 8.06, 1.42 Hz, 1H), 7.62 (t, J = 7.72 Hz, 1H), 7.56 (dd, J = 11.58, 1.30 Hz, 1H), 7.40 (m, 2H), 3.80 (s, 3H), 3.27 (m, 2H), 2.13 (m, 1H), 1.11 (t, J = 7.18 Hz, 3H), 0.97 (m, 2H), 0.83 (m, 2H). |
| 388 | 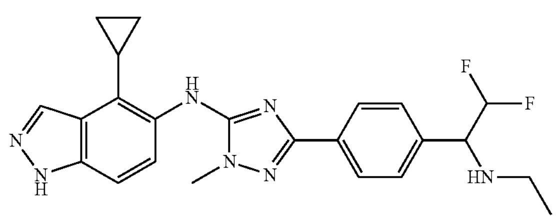 [SMILES: CCNC(c1ccc(-c2nc(Nc3ccc4[nH]ncc4c3C3CC3)n(C)n2)cc1)C(F)F] | Method B, 2.50 min, m/z 438.4 [M + H]⁺ | ¹H NMR (400 MHz, DMSO-d₆) δ 13.01 (s, 1H), 8.27 (s, 1H), 8.06 (s, 1H), 7.82 (d, J = 7.42 Hz, 2H), 7.40 (m, 4H), 6.06 (t, J = 55.75 Hz, 1H), 4.00-3.90 (m, 1H), 3.78 (s, 3H), 2.48-2.40 (m, 2H), 2.12 (m, 1H), 0.98 (m, 5H), 0.81 (m, 2H) 1 NH not observed |
| 389 | 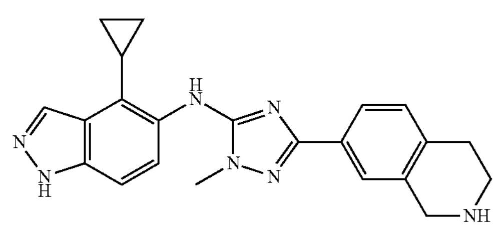 [SMILES: Cn1nc(-c2ccc3c(c2)CNCC3)nc1Nc1ccc2[nH]ncc2c1C1CC1] | Method B, 2.32 min, m/z 386.3 [M + H]⁺ | ¹H NMR (400 MHz, DMSO-d₆) δ 13.00 (s, 1H), 8.21 (s, 1H), 8.06 (s, 1H), 7.58 (dd, J = 8.0 Hz, 1H), 7.48 (br. s, 1H), 7.41 (d, J = 8.8 Hz, 1H), 7.37 (d, J = 8.8 Hz, 1H), 7.07 (d, J = 8.0 Hz, 1H), 3.88 (s, 2H), 3.75 (s, 3H), 2.97 (t, J = 5.9 Hz, 2H), 2.70 (t, J = 5.9 Hz, 2H), 2.11 (m, 1H), 0.99-0.93 (m, 2H), 0.84-0.77 (m, 2H). 1 NH not observed |
| 390 | 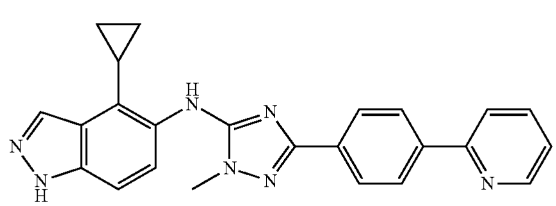 [SMILES: Cn1nc(-c2ccc(-c3ccccn3)cc2)nc1Nc1ccc2[nH]ncc2c1C1CC1] | Method B, 2.90 min, m/z 408.3 [M + H]⁺ | ¹H NMR (400 MHz, DMSO-d₆) δ 13.02 (s, 1H), 8.67 (m, 1H), 8.30 (s, 1H), 8.15-8.06 (m, 3H), 8.01-7.92 (m, 3H), 7.88 (td, J = 7.7, 1.9 Hz, 1H), 7.48-7.32 (m, 3H), 3.80 (s, 3H), 2.15 (m, 1H), 1.06-0.91 (m, 2H), 0.83 (m, 2H). |

TABLE 25-continued

| Example | Structure | LC/MS | ¹H NMR |
|---|---|---|---|
| 391 | 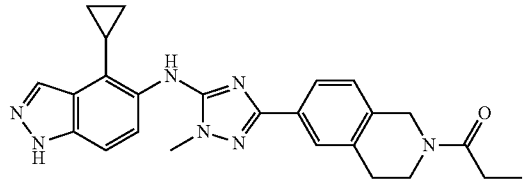 [SMILES: CCC(=O)N1CCc2cc(-c3nc(Nc4ccc5[nH]ncc5c4C4CC4)n(C)n3)ccc2C1] | Method B, 3.10 min, m/z 442.4 [M + H]⁺ | ¹H NMR (400 MHz, DMSO-d₆) δ 13.00 (s, 1H), 8.23 (s, 1H), 8.05 (s, 1H), 7.65 (m, 1H), 7.61 (s, 1H), 7.41 (d, J = 8.6 Hz, 1H), 7.37 (d, J = 8.6 Hz, 1H), 7.18 (d, J = 8.0 Hz, 1H), 4.63 (s, 0.87H), 4.59 (s, 1.13H), 3.76 (s, 3H), 3.67-3.61 (m 2H), 2.86 (t, J = 5.7 Hz, 1.16H), 2.75 (t, J = 5.7 Hz, 0.84H), 2.40 (q, J = 7.2 Hz, 2H), 2.12 (m, 1H), 1.03-0.97 (m, 3H), 0.97-0.92 (m, 2H), 0.83-0.78 (m, 2H). rotamers |
| 392 | 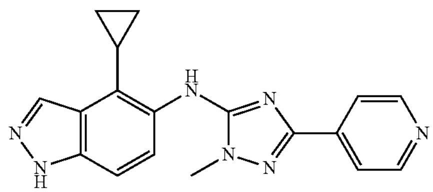 [SMILES: Cn1nc(-c2ccncc2)nc1Nc1ccc2[nH]ncc2c1C1CC1] | Method B, 2.24 min, m/z 332.3 [M + H]⁺ | ¹H NMR (400 MHz, DMSO-d₆) δ 13.04 (s, 1H), 8.57 (dd, J = 6.04, 1.50 Hz, 2H), 8.44 (s, 1H), 8.07 (m, 1H), 7.73 (dd, J = 6.04, 1.50 Hz, 2H), 7.40 (dd, J = 11.0, 8.86 Hz, 2H), 3.82 (m, 3H), 2.13 (m, 1H), 0.95 (m, 2H), 0.82 (m, 2H). |
| 341 | 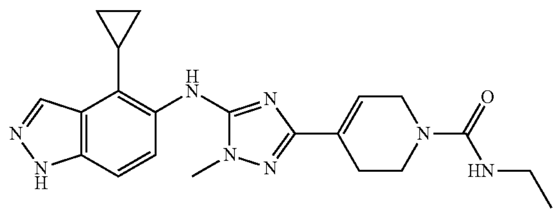 [SMILES: CCNC(=O)N1CC=C(c2nc(Nc3ccc4[nH]ncc4c3C3CC3)n(C)n2)CC1] | Method B, 2.59 min, m/z 407.3 [M + H]⁺ | ¹H NMR (400 MHz, DMSO-d₆) δ 12.99 (s, 1H), 8.14 (s, 1H), 8.05 (s, 1H), 7.73 (t, J = 5.3 Hz, 1H), 7.35 (s, 2H), 6.31 (m, 1H), 3.87 (d, J = 3.1 Hz, 2H), 3.69 (s, 3H), 3.43 (t, J = 5.6 Hz, 2H), 3.05 (m, 2H), 2.38 (m, 2H), 2.09 (m, 1H), 1.01 (t, J = 7.1 Hz, 3H), 0.95 (m, 2H), 0.78 (m, 2H). |
| 393 | 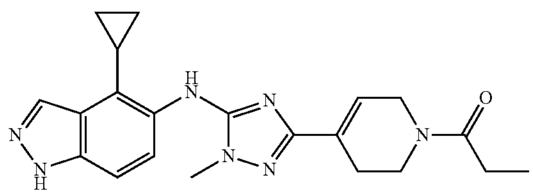 [SMILES: CCC(=O)N1CC=C(c2nc(Nc3ccc4[nH]ncc4c3C3CC3)n(C)n2)CC1] | Method B, 2.69 min, m/z 392.2 [M + H]⁺ | ¹H NMR (400 MHz, DMSO-d₆) δ 12.98 (s, 1H), 8.15 (s, 1H), 8.05 (s, 1H), 7.35 (s, 2H), 6.33 (m, 1H), 4.03 (m, 2H), 3.69 (s, 3H), 3.56 (dt, J = 19.6, 5.5 Hz, 2H), 2.33 (m, 5H), 0.97 (m, 5H), 0.77 (m, 2H). |
| 394 | 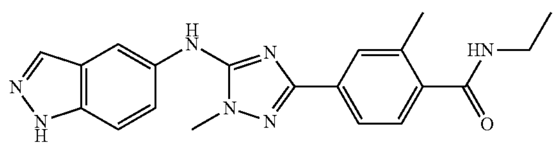 [SMILES: CCNC(=O)c1ccc(-c2nc(Nc3ccc4[nH]ncc4c3)n(C)n2)cc1C] | Method F, 2.24 min, m/z 376.2 [M + H]⁺ | ¹H NMR (400 MHz, DMSO-d₆) δ 12.93 (s, 1H), 8.96 (s, 1H), 8.28 (t, J = 5.6 Hz, 1H), 8.18 (s, 1H), 8.03 (s, 1H), 7.83-7.80 (m, 2H), 7.60 (d, J = 9.2 Hz, 1H), 7.51 (d, J = 8.8 Hz, 1H), 7.37 (d, J = 7.6 Hz, 1H), 3.82 (s, 3H), 3.29-3.22 (m, 2H), 2.40 (s, 3H), 1.12 (t, J = 7.2 Hz, 3H) |
| 395 | 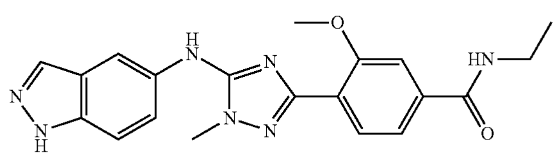 [SMILES: CCNC(=O)c1ccc(-c2nc(Nc3ccc4[nH]ncc4c3)n(C)n2)c(OC)c1] | Method F, 2.03 min, m/z 392.1 [M + H]⁺ | ¹H NMR (400 MHz, DMSO-d₆) δ 12.89 (s, 1H), 8.86 (s, 1H), 8.54 (t, J = 5.2 Hz, 1H), 8.14 (s, 1H), 7.99 (s, 1H), 7.85 (d, J = 8.0 Hz, 1H), 7.56-7.48 (m, 4H), 3.86 (s, 3H), 3.80 (s, 3H) 3.32-3.28 (m, 2H), 1.15 (t, J = 7.2 Hz, 3H) |
| 396 | 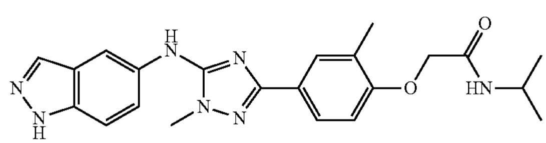 [SMILES: Cc1cc(-c2nc(Nc3ccc4[nH]ncc4c3)n(C)n2)ccc1OCC(=O)NC(C)C] | Method F, 2.63 min, m/z 420.2 [M + H]⁺ | ¹H NMR (400 MHz, DMSO-d₆) δ 12.90 (s, 1H), 8.82 (s, 1H), 8.17 (s, 1H), 8.02 (s, 1H), 7.77-7.74 (m, 3H), 7.57-7.49 (m, 2H), 6.88 (d, J = 8.4 Hz, 1H), 4.50 (s, 2H), 3.99-3.90 (m, 1H), 3.77 (s, 3H), 2.28 (s, 3H), 1.10 (d, J = 6.4 Hz, 6H) |
| 397 | 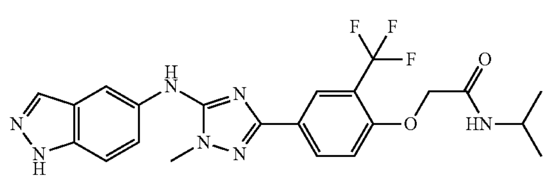 [SMILES: CC(C)NC(=O)COc1ccc(-c2nc(Nc3ccc4[nH]ncc4c3)n(C)n2)cc1C(F)(F)F] | Method F, 3.04 min, m/z 474.2 [M + H]⁺ | ¹H NMR (400 MHz, DMSO-d₆) δ 12.92 (s, 1H), 8.91 (s, 1H), 8.18-8.16 (d, J = 8.4 Hz, 1H), 8.13 (s, 2H), 7.67-7.65 (d, J = 7.2 Hz, 2H), 7.57-7.50 (m, 2H), 7.24-7.22 (d, J = 8.8 Hz, 1H), 4.67 (s, 2H), 3.95-3.87 (m, 1H), 3.80 (s, 3H), 1.11-1.09 (d, J = 6.8 Hz, 6H) |

TABLE 25-continued

| Example | Structure | LC/MS | ¹H NMR |
|---|---|---|---|
| 398 | 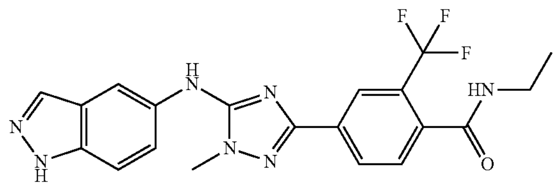 [SMILES: CCNC(=O)c1ccc(-c2nc(Nc3ccc4[nH]ncc4c3)n(C)n2)cc1C(F)(F)F] | Method F, 2.56 min, m/z 430.1 [M + H]⁺ | ¹H NMR (400 MHz, DMSO₆) δ 12.94 (s, 1H), 8.98 (s, 1H), 8.54 (t, J = 5.6 Hz, 1H), 8.26-8.23 (m, 2H), 8.14 (s, 1H), 8.03 (s, 1H), 7.59 (d, J = 8 Hz, 2H), 7.52 (d, J = 8.8 Hz, 1H), 3.84 (s, 3H), 3.32-3.22 (m, 2H), 1.11 (t, J = 7.2 Hz, 3H) |
| 399 | 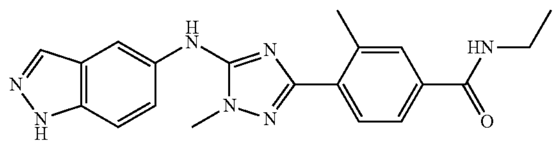 [SMILES: CCNC(=O)c1ccc(-c2nc(Nc3ccc4[nH]ncc4c3)n(C)n2)c(C)c1] | Method F, 2.33 min, m/z 376.2 [M + H]⁺ | ¹H NMR (400 MHz, DMSO-d₆) δ 12.91 (s, 1H), 8.91 (s, 1H), 8.47 (t, J = 5.2 Hz, 1H), 8.16 (s, 1H), 8.0-7.99 (m, 2H), 7.76-7.71 (m, 2H), 7.58 (d, J = 9.2 Hz, 1H), 7.5 (d, J = 8.8 Hz, 1H), 3.83 (s, 3H), 3.3-3.26 (m, 2H), 2.68 (s, 3H), 1.14 (t, J = 7.2 Hz, 3H) |
| 400 | 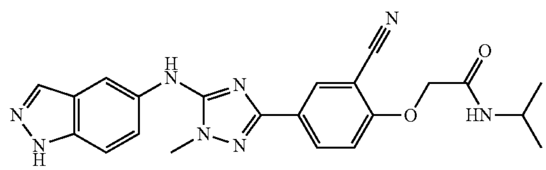 [SMILES: CC(C)NC(=O)COc1ccc(-c2nc(Nc3ccc4[nH]ncc4c3)n(C)n2)cc1C#N] | Method F, 2.70 min, m/z 431.2 [M + H]⁺ | ¹H NMR (400 MHz, DMSO-d₆) δ 12.91 (s, 1H), 8.92 (s, 1H), 8.19-8.17 (m, 3H), 8.03 (s, 1H), 7.96 (d, J = 7.2 Hz, 1H), 7.58 (d, J = 9.2 Hz, 1H), 7.51 (d, J = 8.8 Hz, 1H), 7.17 (d, J = 9.2 Hz, 1H), 4.72 (s, 2H), 3.98-3.88 (m 1H), 3.8 (s, 3H), 1.09 (d, J = 6.4 Hz, 6H) |
| 401 | 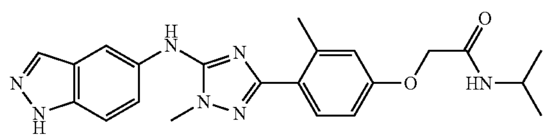 | Method F, 2.60 min, m/z 420.2 [M + H]⁺ | ¹H NMR (400 MHz, DMSO-d₆) δ 12.90 (s, 1H), 8.86 (s, 1H), 8.16 (s, 1H), 7.99 (s, 1H), 7.91-7.89 (d, J = 8.0, 1H), 7.85-7.83 (d, J = 8.4 Hz, 1H), 7.58-7.56 (d, J = 8.8 Hz, 1H), 7.50-7.48 (d, J = 9.2 Hz, 1H), 6.87-6.84 (d, J = 12.0, 2H), 4.6 (s, 2H), 3.99-3.94 (m, 1H), 3.80 (s, 3H), 2.59 (s, 3H), 1.11-1.09 (d, J = 6.8, 6H) |
| 402 | 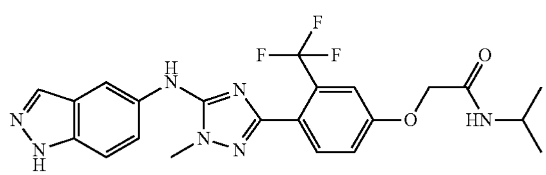 [SMILES: CC(C)NC(=O)COc1ccc(-c2nc(Nc3ccc4[nH]ncc4c3)n(C)n2)c(C(F)(F)F)c1] | Method F, 2.70 min, m/z 474.2 [M + H]⁺ | ¹H NMR (400 MHz, DMSO-d₆) δ 12.87 (s, 1H), 8.89 (s, 1H), 8.15 (s, 1H), 8.02-8.00 (d, J = 7.2 Hz, 1H), 7.94 (s, 1H), 7.80-7.78 (d, J = 8.4 Hz, 1H), 7.56-7.46 (m, 2H), 7.38 (s, 1H), 7.31-7.29 (d, J = 8.4 Hz, 1H), 4.60 (s, 2H), 4.00-3.92 (m, 1H), 3.80 (s, 3H), 1.11-1.10 (d, J = 6.4 Hz, 6H) |
| 403 | 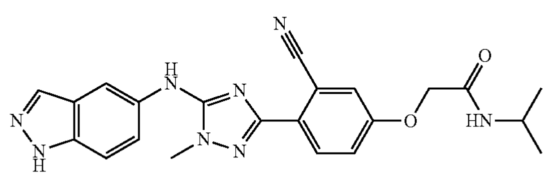 [SMILES: CC(C)NC(=O)COc1ccc(-c2nc(Nc3ccc4[nH]ncc4c3)n(C)n2)c(C#N)c1] | Method F, 2.55 min, m/z 431.2 [M + H]⁺ | ¹H NMR (400 MHz, DMSO-d₆) δ 12.88 (s, 1H), 9.0 (s, 1H), 8.39 (s, 1H), 8.05 (d, J = 8.8 Hz, 1H), 7.98 (d, J = 7.6 Hz, 1H), 7.9 (s, 1H), 7.61-7.59 (m, 1H), 7.48-7.47 (m, 2H), 7.37 (dd, J = 2.8 Hz, 1H), 4.59 (s, 2H), 4.0-3.91 (m, 1H), 3.83 (s, 3H), 1.1 (d, J = 6.4 Hz, 6H) |
| 404 | 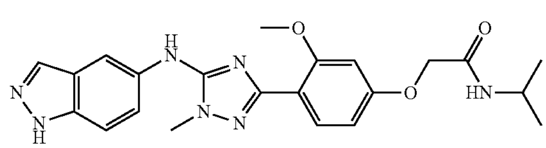 [SMILES: COc1cc(OCC(=O)NC(C)C)ccc1-c1nc(Nc2ccc3[nH]ncc3c2)n(C)n1] | Method F.2.18 min, m/z 436.2 [M + H]⁺ | ¹H NMR (400 MHz, DMSO-d₆) δ 12.87 (s, 1H), 8.81 (s, 1H), 8.12 (s, 1H), 7.99 (s, 1H), 7.92-7.90 (d, J = 7.6 Hz, 1H), 7.68-7.66 (d, J = 8.8 Hz, 1H), 7.54-7.47 (m, 2H), 6.71 (s, 1H), 6.61-6.59 (m, 1H), 4.49 (s, 2H), 4.01-3.93 (m, 1H), 3.80 (s, 3H), 3.76 (s, 3H), 1.12.1.10 (d, J = 6.4 Hz, 6H) |

TABLE 25-continued

| Example | Structure | LC/MS | ¹H NMR |
|---|---|---|---|
| 405 | 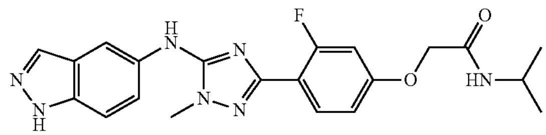 [SMILES: CC(C)NC(=O)COc1ccc(-c2nc(Nc3ccc4[nH]ncc4c3)n(C)n2)c(F)c1] | Method F, 2.52 min, m/z 424.2 [M + H]⁺ | ¹H NMR (400 MHz, DMSO-d₆) δ 12.90 (s, 1H), 8.89 (s, 1H), 8.15 (s, 1H), 7.99 (s, 1H), 7.95-7.92 (d, J = 10.4 Hz, 1H), 7.90-7.88 (d, J = 5.2 Hz, 1H), 7.57-7.54 (d, J = 8.8 Hz, 1H), 7.49-7.47 (d, J = 8.8 Hz, 1H), 6.91-6.90 (d, J = 4.4 Hz, 1H), 6.88 (s, 1H), 4.52 (s, 2H), 3.96 (s, 1H), 3.79 (s, 3H), 1.11-1.09 (d, J = 6.4 Hz, 6H) |
| 406 | 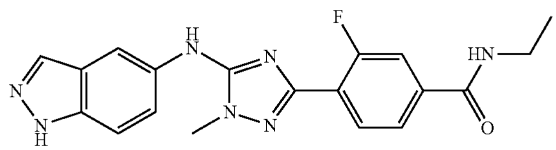 [SMILES: CCNC(=O)c1ccc(-c2nc(Nc3ccc4[nH]ncc4c3)n(C)n2)c(F)c1] | Method F, 2.27 min, m/z 380.2 [M + H]⁺ | ¹H NMR (400 MHz, DMSO-d₆) δ 12.92 (s, 1H), 8.96 (s, 1H), 8.61 (t, J = 5.6, 1H), 8.16 (s, 1H), 8.09 (t, J = 8.0, 1H), 8.02 (s, 1H), 7.78-7.72 (m, 2H), 7.58-7.50 (m, 2H), 3.83 (s, 3H), 3.31-3.27 (m, 2H), 1.12 (t, J = 7.2 Hz, 3H) |
| 407 | 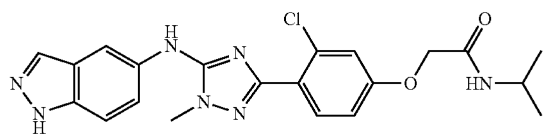 | Method F, 2.63 min, m/z 440.1 [M + H]⁺ | ¹H NMR (400 MHz, DMSO-d₆) δ 12.89 (s, 1H), 8.89 (s 1H), 8.15 (s, 1H), 8.03-7.90 (m, 2H), 7.80 (d, J = 8.7 Hz, 1H), 7.58-7.53 (m, 1H), 7.48 (d, J = 8.9 Hz, 1H), 7.13 (d, J = 2.3 Hz, 1H), 7.02 (dd, J = 8.6, 1.9 Hz, 1H), 4.53 (s, 2H), 4.00-3.91 (m, 1H), 3.80 (s, 3H), 1.10 (d, J = 6.6 Hz, 6H). |
| 408 | 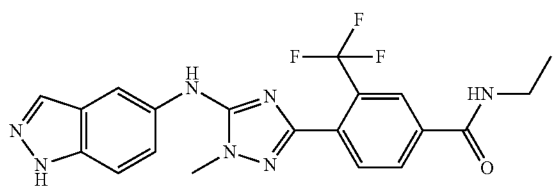 [SMILES: CCNC(=O)c1ccc(-c2nc(Nc3ccc4[nH]ncc4c3)n(C)n2)c(C(F)(F)F)c1] | Method F.2.61 min, m/z 430.2 [M + H]⁺ | ¹H NMR (400 MHz, DMSO-d₆) δ 12.92 (s, 1H), 8.97 (s, 1H), 8.80 (t, J = 5.2 Hz, 1H), 8.30 (s, 1H), 8.20-8.17 (m, 2H), 8.00 (m, 1H), 7.95 (s, 1H), 7.55 (m, 1H), 7.48 (m, 1H) 3.84 (s, 3H), 3.33-3.27 (m, 2H), 1.14 (t, J = 7.2 Hz, 3H) |
| 409 | 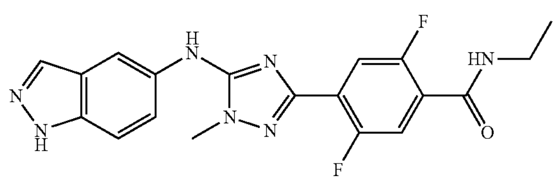 [SMILES: CCNC(=O)c1cc(F)c(-c2nc(Nc3ccc4[nH]ncc4c3)n(C)n2)cc1F] | Method F, 2.66 min, m/z 398.2 [M + H]⁺ | ¹H NMR (400 MHz, DMSO-d₆) δ 12.92 (s, 1H), 8.99 (s, 1H), 8.43 (t, J = 5.2 Hz, 1H), 8.15 (s, 1H), 8.03 (s, 1H), 7.83-7.79 (m, 1H), 7.59 (dd, J = 8 Hz, 1H), 7.53 (dd, J = 8.8 Hz, 2H), 3.83 (s, 3H), 3.33-3.25 (m, 2H), 1.14 (t, J = 7.2 Hz, 3H) |
| 410 | 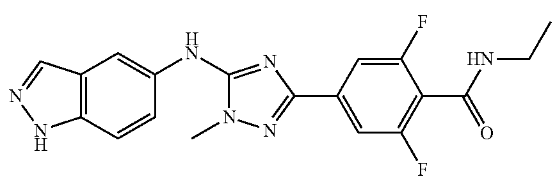 [SMILES: CCNC(=O)c1c(F)cc(-c2nc(Nc3ccc4[nH]ncc4c3)n(C)n2)cc1F] | Method F, 2.63 min, m/z 398.1 [M + H]⁺ | ¹H NMR (400 MHz, DMSO-d₆) δ 12.91 (s, 1H), 8.99 (s, 1H), 8.74 (t, J = 5.6 Hz, 1H), 8.19 (s, 1H), 8.05 (s, 1H), 7.62-7.50 (m, 4H), 3.83 (s, 3H), 3.29-3.24 (m, 2H), 1.12 (t, J = 7.2 Hz, 3H) |
| 411 | 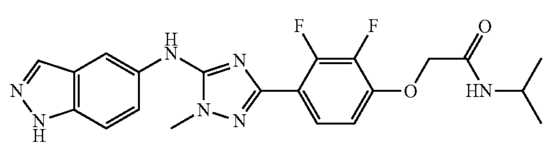 [SMILES: CC(C)NC(=O)COc1ccc(-c2nc(Nc3ccc4[nH]ncc4c3)n(C)n2)c(F)c1F] | Method F, 2.8 min, m/z 442.2 [M + H]⁺ | ¹H NMR (400 MHz, DMSO-d₆) δ 12.89 (s, 1H), 8.92 (s, 1H), 8.16 (s, 1H), 8.0-7.96 (m, 2H), 7.72 (t, J = 7.2 Hz, 1H), 7.57-7.48 (m, 2H), 6.98 (t, J = 8 Hz, 1H), 4.64 (s, 2H), 3.97-3.81 (m, 1H), 3.41 (s, 3H), 1.09 (d, J = 6.4 Hz, 6H) |
| 412 | 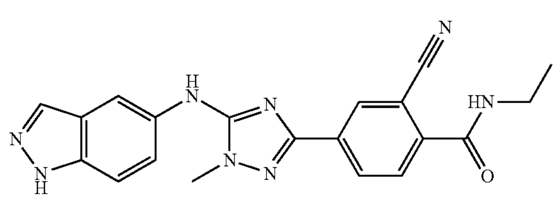 [SMILES: CCNC(=O)c1ccc(-c2nc(Nc3ccc4[nH]ncc4c3)n(C)n2)cc1C#N] | Method F, 2.33 min, m/z 387.1 [M + H]⁺ | ¹H NMR (400 MHz, DMSO-d₆) δ 12.93 (s, 1H), 10.36 (s, 1 H),8.99 (s, 1H), 8.77 (s, 1H) 8.28 (d, J = 8 Hz, 1H), 8.23 (s, 1H), 8.04 (s, 1H), 7.84 (d, J = 8 Hz, 1H), 7.58 (d, J = 8 Hz, 1H), 7.51 (s, 1H), 3.86 (s, 3H), 3.79-3.73 (m,2H), 1.19 (t, J = 6.8 Hz, 3H) |

TABLE 25-continued

| Example | Structure | LC/MS | ¹H NMR |
|---|---|---|---|
| 413 | 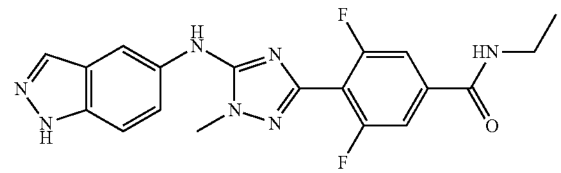 [SMILES: CCNC(=O)c1cc(F)c(-c2nc(Nc3ccc4[nH]ncc4c3)n(C)n2)c(F)c1] | Method F, 2.60 min, m/z 398.2 [M + H]⁺ | ¹H NMR (400 MHz, DMSO-d₆) δ 12.92 (s, 1H), 8.99 (s, 1H), 8.45-8.42 (m, 1H), 8.16 (d, J = 1.2 Hz, 1H), 8.03 (s, 1H), 7.83-7.79 (m, 1H), 7.61-7.57 (m, 1H), 7.54-7.50 (m, 2H), 3.84 (s, 3H), 3.30-3.27 (m, 2H), 1.13 (t, J = 7.2 Hz, 3H) |
| 414 | 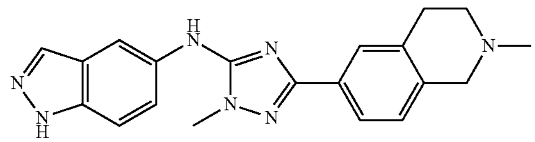 [SMILES: CN1CCc2cc(-c3nc(Nc4ccc5[nH]ncc5c4)n(C)n3)ccc2C1] | Method F, 1.70 min, m/z 360.1 [M + H]⁺ | ¹H NMR (400 MHz, DMSO-d₆) δ 12.92 (s, 1H), 8.87 (s, 1H), 8.17 (s, 1H), 8.02 (s, 1H), 7.73-7.71 (m, 2H), 7.58-7.49 (m, 2H), 7.10 (d, J = 8.4 Hz, 1H), 3.79 (s, 3H), 3.50 (s, 2H), 2.88 (t, J = 5.6 Hz, 2H), 2.61 (t, J = 5.6 Hz, 2H), 2.35 (S. 3H) |
| 415 | 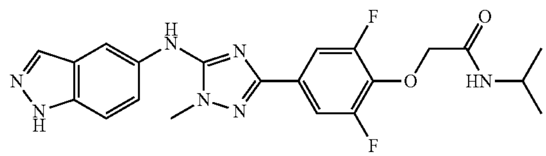 [SMILES: CC(C)NC(=O)COc1c(F)cc(-c2nc(Nc3ccc4[nH]ncc4c3)n(C)n2)cc1F] | Method F, 2.90 min, m/z 442.1 [M + H]⁺ | ¹H NMR (400 MHz, DMSO-d₆) δ 12.91 (s, 1H), 8.94 (s, 1H), 8.18 (s, 1H), 8.04 (s, 1H), 7.90 (d, J = 7.6 Hz, 1H), 7.63-7.49 (m, 4H), 4.57 (s, 2H), 3.97-3.89 (m, 1H), 3.80 (s, 3H), 1.09 (d, J = 6.4 Hz, 6H) |
| 416 | 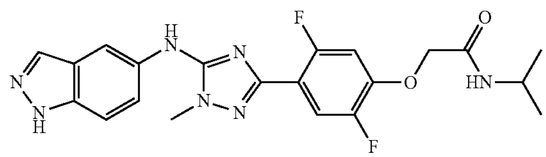 [SMILES: CC(C)NC(=O)COc1cc(F)c(-c2nc(Nc3ccc4[nH]ncc4c3)n(C)n2)cc1F] | Method F, 2.74 min, m/z 442.1 [M + H]⁺ | ¹H NMR (400 MHz, DMSO-d₆) δ 12.89 (s, 1H), 8.95 (s, 1H), 8.15 (s, 1H), 8.02-7 98 (m 2H), 7.75 (dd, J = 11.9, 6.9 Hz, 1H), 7.57-7.49 (m, 2H), 7.08 (dd, J = 11.9, 7.1 Hz, 1H), 4.63 (s, 2H), 3.96-3.88 (m, 1H), 3.80 (s, 3H), 1.09 (d, J = 6.6 Hz, 6H) |
| 417 | 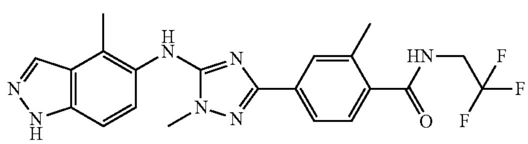 [SMILES: Cc1cc(-c2nc(Nc3ccc4[nH]ncc4c3C)n(C)n2)ccc1C(=O)NCC(F)(F)F] | Method B, 3.12 min, m/z 444.5 [M + H]⁺ | ¹H NMR (400 MHz, DMSO-d₆) δ 13.01 (s, 1H), 8.95 (t, J = 6.4 Hz, 1H), 8.30 (s, 1H), 8.13 (s, 1H), 7.70-7.67 (m, 2H), 7.39-7.31 (m, 3H), 4.05 (m, 2H), 3.75 (s, 3H), 2.45 (s, 3H), 2.33 (s, 3H). |
| 418 | 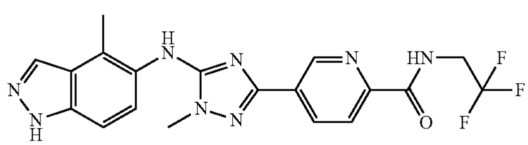 [SMILES: Cc1c(Nc2nc(-c3ccc(C(=O)NCC(F)(F)F)nc3)nn2C)ccc2[nH]ncc12] | Method F, 2.89 min, m/z 431.1 [M + H]⁺ | ¹H NMR (400 MHz, DMSO-d₆) δ 13.03 (s, 1H), 9.34 (t, J = 6.4 Hz, 1H), 9.04 (s, 1H), 8.46 (s, 1H), 8.3-8.28 (m, 1H), 8.13 (s, 1H), 8.07 (d, J = 8.4 Hz, 1H), 7.35 (q, J = 8.8 Hz, 2H), 4.11-4.03 (m, 2H), 3.8 (s, 3H), 2.45 (s, 3H) |
| 419 | 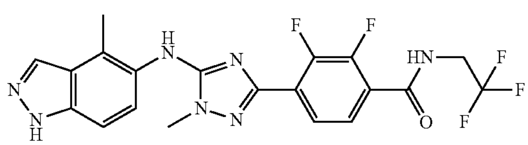 | Method F, 3.02 min, m/z 466.1 [M + H]⁺ | ¹H NMR (400 MHz, DMSO-d₆) δ 13.01 (s, 1H), 9.154 J = 6.0 Hz, 1H), 8.43 (s, 1H), 8.12 (s, 1H), 7.66 (t, J = 7.2 Hz, 1H), 7.40-7.30 (m, 3H), 4.13-4.05 (m, 2H), 3.79 (s, 3H), 2.45 (s, 3H). |
| 420 | 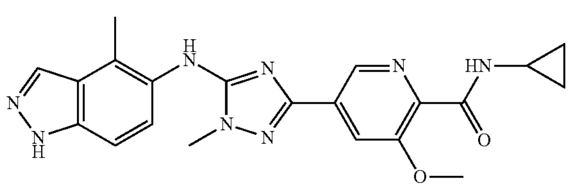 [SMILES: COc1cc(-c2nc(Nc3ccc4[nH]ncc4c3C)n(C)n2)cnc1C(=O)NC1CC1] | Method B, 2.64 min, m/z 419.3 [M + H]⁺ | ¹H NMR (400 MHz, Chloroform-d) δ 8.50 (d, J = 1.4 Hz, 1H), 8.39 (s, 1H), 8.34 (d, J = 4.7 Hz, 1H), 8.13 (s, 1H), 7.71 (d, J = 1.5 Hz, 1H), 7.34 (m, 2H), 3.82 (s, 3H), 3.77 (s, 3H), 2.80 (m, 1H), 2.45 (s, 3H), 0.66 (m, 2H), 0.52 (m, 2H). 1 NH not observed |
| 421 | 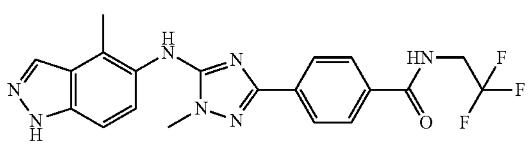 [SMILES: Cc1c(Nc2nc(-c3ccc(C(=O)NCC(F)(F)F)cc3)nn2C)ccc2[nH]ncc12] | Method B, 3.03 min, m/z 430.3 [M + H]⁺ | ¹H NMR (400 MHz, DMSO-d₆) δ 13.02 (s, 1H), 9.10 (t, J = 6.3 Hz, 1H), 8.34 (s, 1H), 8.17-8.11 (m, 1H), 7.90 (m, 4H), 7.36 (q, J = 8.8 Hz, 2H), 4.08 (m, 2H), 3.78 (s, 3H), 2.46 (s, 3H) |

TABLE 25-continued

| Example | Structure | LC/MS | ¹H NMR |
|---|---|---|---|
| 422 | 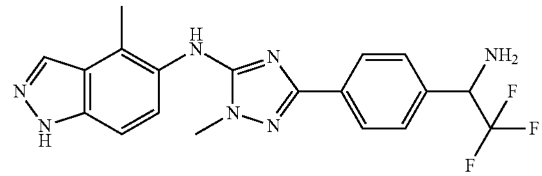 [SMILES: Cc1c(Nc2nc(-c3ccc(C(N)C(F)(F)F)cc3)nn2C)ccc2[nH]ncc12] | Method B, 2.46 min, m/z 402.3 [M + H]⁺ | ¹H NMR (400 MHz, DMSO-d₆) δ 13.00 (s, 1H), 8.27 (s, 1H), 8.13 (s, 1H), 7.80 (d, J = 8.40 Hz, 2H), 7.48 (d, J = 8.24 Hz, 2H), 7.34 (m, 2H), 4.49 (m, 1H), 3.75 (s, 3H), 2.45 (s, 3H). 2 NH not observed |
| 423 | 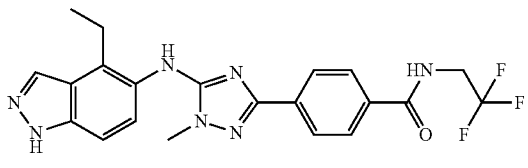 [SMILES: CCc1c(Nc2nc(-c3ccc(C(=O)NCC(F)(F)F)cc3)nn2C)ccc2[nH]ncc12] | Method B, 3.18 min, m/z 444.3 [M + H]⁺ | ¹H NMR (400 MHz, DMSO-d₆) δ 13.04 (s, 1H), 9.10 (t, J = 6.3 Hz, 1H), 8.28 (s, 1H), 8.16 (s, 1H), 7.89 (s, 4H), 7.38 (dd, J = 8.7,1.0 Hz, 1H), 7.28 (d, J = 8.8 Hz, 1H), 4.15-4.01 (m, 2H), 3.77 (s, 3H), 2.94 (q, J = 7.5 Hz, 2H), 1.22 (t, J = 7.5 Hz, 3H). |
| 424 | 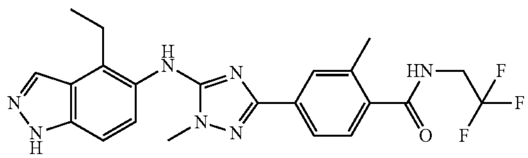 | Method B, 3.22 min, m/z 458.4 [M + H]⁺ | ¹H NMR (400 MHz, Chloroform-d) δ 10.32 (s, 1H), 8.10 (s, 1H), 7.95-7.84 (m, 2H), 7.45-7.28 (m, 3H), 6.13-6.02 (m, 2H), 4.11 (m, 2H), 3.57 (s, 3H), 3.04 (q, J = 7.6 Hz, 2H), 2.48 (s, 3H), 1.34 (t, J = 7.6 Hz, 3H). |
| 425 | 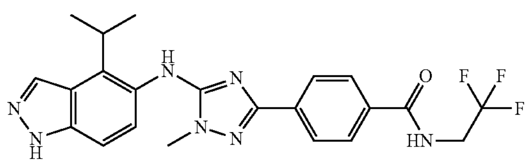 [SMILES: CC(C)c1c(Nc2nc(-c3ccc(C(=O)NCC(F)(F)F)cc3)nn2C)ccc2[nH]ncc12] | Method B, 3.33 min, m/z 458.4 [M + H]⁺ | ¹H NMR (400 MHz, DMSO-d₆) δ 13.07 (s, 1H), 9.08 (t, J = 6.29 Hz, 1H), 8.31 (d, J = 17.84 Hz, 2H), 7.87 (s, 4H), 7.37 (d, J = 8.56 Hz, 1H), 7.20 (d, J = 8.68 Hz, 1H), 4.07 (m, 2H), 3.77 (s, 3H), 3.51 (quintuplet, J = 7.03 Hz, 1H), 1.39 (d, J = 7.09 Hz, 6H). |
| 426 | 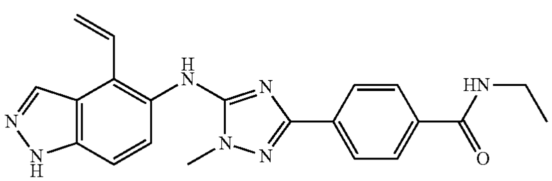 [SMILES: C=Cc1c(Nc2nc(-c3ccc(C(=O)NCC)cc3)nn2C)ccc2[nH]ncc12] | Method B, 2.78 min, m/z 388.3 [M + H]⁺ | 1H NMR (400 MHz, DMSO-d₆) δ: 13.22 (s, 1H), 8.55 (s, 1H), 8.49 (t, J = 5.6 Hz, 1H), 8.35 (d, J = 1.0 Hz, 1H), 7.92-7.78 (m, 4H), 7.52 (m, 1H), 7.39 (d, J = 8.8 Hz, 1H), 7.16 (m, 1H), 6.06 (m, 1H), 5.56 (m, 1H), 3.78 (s, 3H), 3.28 (m, 2H), 1.12 (t, J = 7.2 Hz, 3H) |
| 427 | 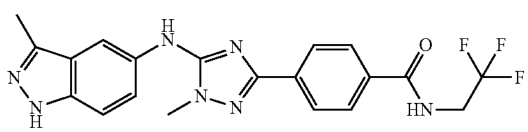 [SMILES: Cc1n[nH]c2ccc(Nc3nc(-c4ccc(C(=O)NCC(F)(F)F)cc4)nn3C)cc12] | Method B, 3.11 min, m/z 430.3 [M + H]⁺ | ¹H NMR (400 MHz, DMSO-d₆) δ 12.50 (s, 1H), 9.14 (t, J = 6.3 Hz, 1H), 8.94 (s, 1H), 8.11-8.04 (m, 3H), 7.98 (d, J = 8.5 Hz, 2H), 7.61 (dd, J = 8.9, 2.1 Hz, 1H), 7.44 (dd, J = 8.8, 0.7 Hz, 1H), 4.11 (m, 6.5 Hz, 2H), 3.83 (s, 3H), 2.49 (s, 3H). |
| 428 | 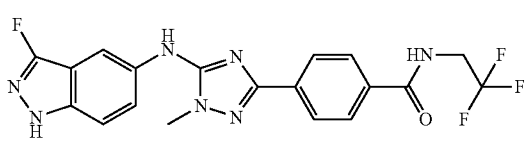 [SMILES: Cn1nc(-c2ccc(C(=O)NCC(F)(F)F)cc2)nc1Nc1ccc2[nH]nc(F)c2c1] | Method B, 3.32 min, m/z 434.3 [M + H]⁺ | ¹H NMR (400 MHz, DMSO-d₆) δ 12.42 (s, 1H), 9.19 - 9.08 (m, 2H), 8.15 (d, J = 1.9 Hz, 1H), 8.07 (d, J = 8.4 Hz, 2H), 7.99 (d, J = 8.5 Hz, 2H), 7.69 (dd, J = 9.2,2.1 Hz, 1H), 7.49 (dd, J = 9.0, 2.3 Hz, 1H), 4.12 (m, 6.2 Hz, 2H), 3.85 (s, 3H). |
| 429 | 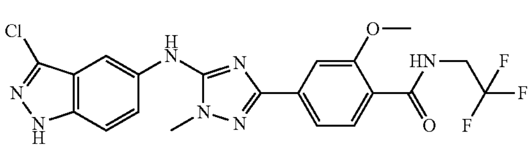 [SMILES: COc1cc(-c2nc(Nc3ccc4[nH]nc(Cl)c4c3)n(C)n2)ccc1C(=O)NCC(F)(F)F] | Method B, 3.61 min, m/z 480.2 [M + H]⁺ | ¹H NMR (400 MHz, DMSO-d₆) δ 13.16 (s, 1H), 9.17 (s, 1H), 8.71 (t, J = 6.4 Hz, 1H), 8.26 (d, J = 2.0 Hz, 1H), 7.86 (d, J = 8.0 Hz, 1H), 7.74-7.63 (m, 3H), 7.56 (d, J = 9.0 Hz, 1H), 4.14 (m, 2H), 4.00 (s, 3H), 3.86 (s, 3H). |
| 430 | 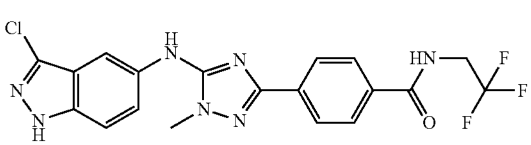 [SMILES: Cn1nc(-c2ccc(C(=O)NCC(F)(F)F)cc2)nc1Nc1ccc2[nH]nc(Cl)c2c1] | Method B, 3.39 min, m/z 450.2 [M + H]⁺ | ¹H NMR (400 MHz, DMSO-d₆) δ 13.17 (s, 1H), 9.15 (d, J = 6.9 Hz, 2H), 8.16 (dd, J = 2.1, 0.8 Hz, 1H), 8.13-8.04 (m, 2H), 8.04-7.96 (m, 2H), 7.74 (dd, J = 9.1, 2.1 Hz, 1H), 7.57 (dd, J = 9.0, 0.7 Hz, 1H), 4.11 (m, 2H), 3.85 (s, 3H). |

TABLE 25-continued

| Example | Structure | LC/MS | ¹H NMR |
|---|---|---|---|
| 431 | 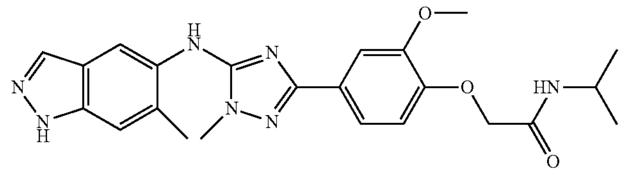 [SMILES: COc1cc(-c2nc(Nc3cc4cn[nH]c4cc3C)n(C)n2)ccc1OCC(=O)NC(C)C] | Method B, 2.98 min, m/z 450.3 [M + H]⁺ | ¹H NMR (400 MHz, DMSO-d₆) δ 12.87 (s, 1H), 8.09 (s, 1H), 7.97 (t, J = 1.2 Hz, 1H), 7.75 (d, J = 7.9 Hz, 1H), 7.68 (s, 1H), 7.41 (dd, J = 8.3, 1.5 Hz, 2H), 7.36 (dd, J = 8.3,1.9 Hz, 1H), 6.93 (d, J = 8.4 Hz, 1H), 4.44 (s, 2H), 3.98-3.84 (m, 1H), 3.82 (s, 3H), 3.72 (s, 3H), 2.37 (s, 3H), 1.08 (d, J = 6.6 Hz, 6H) |
| 432 | 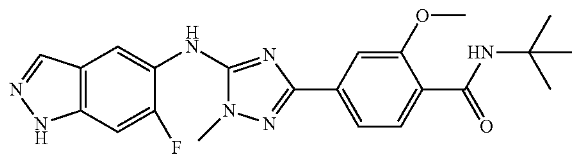 [SMILES: COc1cc(-c2nc(Nc3cc4cn[nH]c4cc3F)n(C)n2)ccc1C(=O)NC(C)(C)C] | Method B, 3.64 min, m/z 438.4 [M + H]⁺ | ¹H NMR (400MHz, DMSO-d₆) δ 13.07 (s, 1H), 8.61 (s, 1H), 8.12-8.08 (m, 2H), 7.86 (s, 1H), 7.79 (d, J = 8.8 Hz, 1H), 7.58-7.49 (m, 2H), 7.46 (d, J = 10.8 Hz, 1H), 3.95 (s, 3H), 3.82 (s, 3H), 1.38 (s, 9H). |
| 433 | 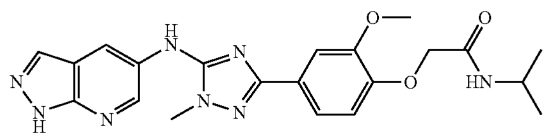 [SMILES: COc1cc(-c2nc(Nc3cnc4[nH]ncc4c3)n(C)n2)ccc1OCC(=O)NC(C)C] | Method B, 2.89 min, m/z 437.3 [M + H]⁺ | ¹H NMR (400 MHz, DMSO-d₆) δ 13.49 (s, 1H), 9.16 (s, 1H), 8.72 (d, J = 2.4 Hz, 1H), 8.66 (d, J = 2.5 Hz, 1H), 8.12 (s, 1H), 7.78 (d, J = 7.8 Hz, 1H), 7.53 (dt, J = 3.9, 1.8 Hz, 2H), 7.00 (d, J = 8.8 Hz, 1H), 4.48 (s, 2H), 3.98-3.90 (m, 1H), 3.88 (s, 3H), 3.82 (s, 3H), 1.10 (d, J = 6.6 Hz, 6H). |
| 434 | 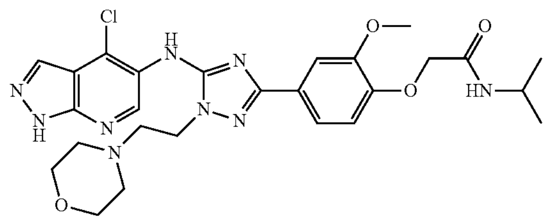 [SMILES: COc1cc(-c2nc(Nc3cnc4[nH]ncc4c3Cl)n(CCN3CCOCC3)n2)ccc1OCC(=O)NC(C)C] | Method B, 2.60 min, m/z 569.3 [M + H]⁺ | ¹H NMR (400 MHz, DMSO-d₆) δ 13.41 (s, 1H), 8.67 (s, 1H), 8.12 (s, 1H), 7.78 (d, J = 8.4 Hz, 1H), 7.63 (d, J = 9.2 Hz, 1H), 7.58 (d, J = 9.2 Hz, 1H), 7.45 (d, J = 2.0 Hz, 1H), 7.40 (dd, J = 8.4,2.0 Hz, 1H), 6.96 (d, J = 8.4 Hz, 1H), 4.47 (s, 2H), 4.32 (t, J = 6.0 Hz, 2H), 4.00-3.89 (m, 1H), 3.85 (s, 3H), 3.56 (t, J = 4.4 Hz, 4H), 2.80 (t, J = 6.0 Hz, 2H), 2.53-2.48 (m, 4H), 1.11 (d, J = 6.4 Hz, 6H). |
| 435 | 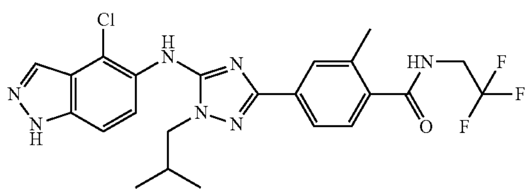 | Method B, 3.98 min, m/z 506.3 [M + H]⁺ | ¹H NMR (400 MHz, DMSO-d₆) δ 13.40 (s, 1H), 8.94 (t, J = 6.4 Hz, 1H), 8.49 (s, 1H), 8.10 (s, 1H), 7.69 (d, J = 8.1 Hz, 2H), 7.59-7.47 (m, 2H), 7.34 (d, J = 7.8 Hz, 1H), 4.06 (m, 2H), 3.99 (d, J = 7.3 Hz, 2H), 2.33 (s, 3H), 2.28-2.21 (m, 1H), 0.96 (d, J = 6.6 Hz, 6H). |
| 436 | 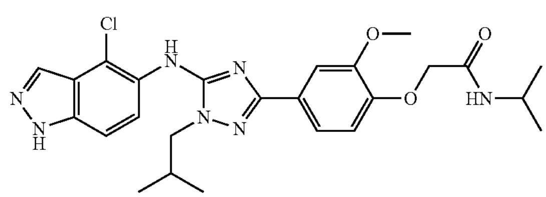 [SMILES: COc1cc(-c2nc(Nc3ccc4[nH]ncc4c3Cl)n(CC(C)C)n2)ccc1OCC(=O)NC(C)C] | Method 3,3.78 min, m/z 512.4 [M + H]⁺ | ¹H NMR (400 MHz, DMSO-d₆) δ 13.38 (s, 1H), 8.40 (s, 1H), 8.09 (s, 1H), 7.74 (d, J = 7.8 Hz, 1H), 7.53 (d, J = 1.4 Hz, 2H), 7.39 (d, J = 1.9 Hz, 1H), 7.34 (dd, J = 8.3, 1.9 Hz, 1H), 6.91 (d, J = 8.4 Hz, 1H), 4.43 (s, 2H), 3.96 (d, J = 7.3 Hz, 2H), 3.94-3.85 (m, 1H), 3.80 (s, 3H), 2.22 (m, 1H), 1.07 (d, J = 6.6 Hz, 6H), 0.94 (d, J = 6.7 Hz, 6H). |
| 437 | 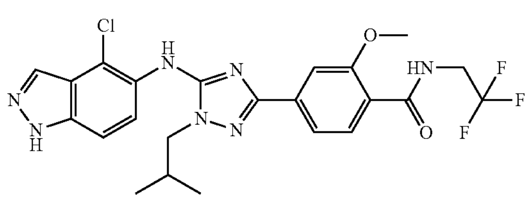 [SMILES: COc1cc(-c2nc(Nc3ccc4[nH]ncc4c3Cl)n(CC(C)C)n2)ccc1C(=O)NCC(F)(F)F] | Method B, 4.10 min, m/z 522.4 [M + H]⁺ | ¹H NMR (400 MHz, DMSO-d₆) δ 13.40 (s, 1H), 8.65 (t, J = 6.5 Hz, 1H), 8.53 (s, 1H), 8.10 (s, 1H), 7.77 (d, J = 8.1 Hz, 1H), 7.60-7.47 (m, 4H), 4.16-4.05 (m, 2H), 4.01 (d, J = 7.3 Hz, 2H), 3.91 (s, 3H), 2.30-2.20 (m, 1H), 0.96 (d, J = 6.7 Hz, 6H). |

TABLE 25-continued

| Example | Structure | LC/MS | ¹H NMR |
|---|---|---|---|
| 438 | 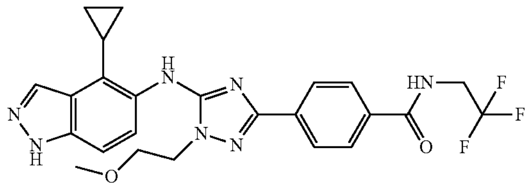 [SMILES: COCCn1nc(-c2ccc(C(=O)NCC(F)(F)F)cc2)nc1Nc1ccc2[nH]ncc2c1C1CC1] | Method B, 3.61 min, m/z 500.5 [M + H]⁺ | ¹H NMR (400 MHz, DMSO-d₆) δ 13.01 (s, 1H), 9.12 (t, J = 6.3 Hz, 1H), 8.22 (s, 1H), 8.09 (s, 1H), 7.95 (q, J = 8.4 Hz, 4H), 7.59 (d, J = 8.8 Hz, 1H), 7.41 (d, J = 8.8 Hz, 1H), 4.37 (t, J = 5.3 Hz, 2H), 4.10 (m, 2H), 3.79 (t, J = 5.3 Hz, 2H), 3.34 (s, 3H), 2.18-2.06 (m, 1H), 1.08-0.98 (m, 2H), 0.88-0.79 (m, 2H) |
| 439 | 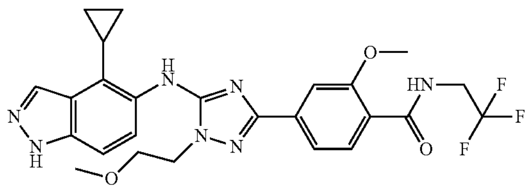 [SMILES: COCCn1nc(-c2ccc(C(=O)NCC(F)(F)F)c(OC)c2)nc1Nc1ccc2[nH]ncc2c1C1CC1] | Method B, 3.79 min, m/z 530.4 [M + H]⁺ | ¹H NMR (400 MHz, DMSO-d₆) δ 13.00 (s, 1H), 8.67 (t, J = 6.5 Hz, 1H), 8.21 (s, 1H), 8.08 (s, 1H), 7.80 (d, J = 8.2 Hz, 1H), 7.63-7.52 (m, 3H), 7.39 (d, J = 8.8 Hz, 1H), 4.37 (t, J = 5.3 Hz, 2H), 4.18-4.04 (m, 2H), 3.93 (s, 3H), 3.78 (t, J = 5.2 Hz, 2H), 3.34 (s, 3H), 2.11 (m, 1H), 1.08-0.98 (m, 2H), 0.84 (m, 2H) |
| 440 | 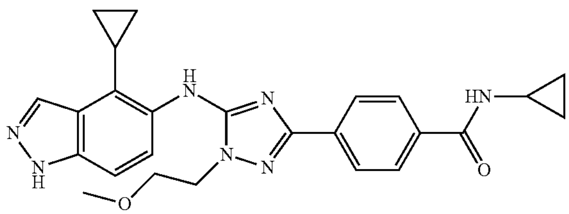 [SMILES: COCCn1nc(-c2ccc(C(=O)NC3CC3)cc2)nc1Nc1ccc2[nH]ncc2c1C1CC1] | Method B, 3.30 min, m/z 458.5 [M + H]⁺ | ¹H NMR (400 MHz, DMSO-d₆) δ 13.03-12.98 (m, 1H), 8.47 (d, J = 4.3 Hz, 1H), 8.20 (s, 1H), 8.09 (t, J = 1.3 Hz, 1H), 7.95-7.88 (m, 2H), 7.89-7.81 (m, 2H), 7.60 (d, J = 8.8 Hz, 1H), 7.40 (d, J = 8.8 Hz, 1H), 4.36 (t, J = 5.2 Hz, 2H), 3.78 (t, J = 5.3 Hz, 2H), 3.33 (s, 3H), 2.91-2.79 (m, 1H), 2.12 (m, 1H), 1.08-0.98 (m, 2H), 0.88-0.79 (m, 2H), 0.74-0.63 (m, 2H), 0.66-0.54 (m, 2H). |
| 441 | 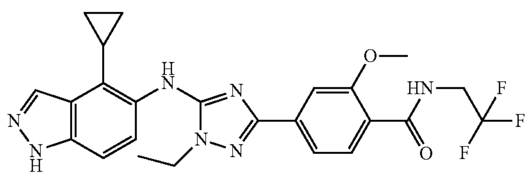 [SMILES: CCn1nc(-c2ccc(C(=O)NCC(F)(F)F)c(OC)c2)nc1Nc1ccc2[nH]ncc2c1C1CC1] | MethodB, 3.70 min, m/z 500.6 [M + H]⁺ | ¹H NMR (400 MHz, DMSO-d₆) δ 13.02 (s, 1H), 8.66 (t, J = 6.5 Hz, 1H), 8.34 (s, 1H), 8.07 (d, J = 1.4 Hz, 1H), 7.77 (d, J = 8.0 Hz, 1H), 7.55-7.48 (m, 2H), 7.38 (s, 2H), 4.28-4.02 (m, 4H), 3.92 (s, 3H), 2.15 (m, 1H), 1.41 (t, J = 7.1 Hz, 3H), 1.01-0.89 (m, 2H), 0.82 (td, J = 6.1, 4.2 Hz, 2H). |
| 442 | 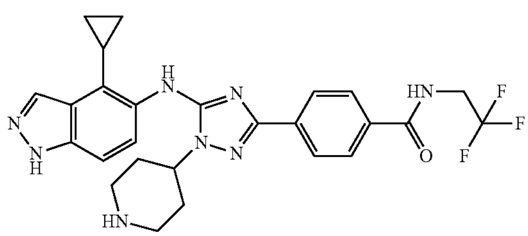 [SMILES: O=C(NCC(F)(F)F)c1ccc(-c2nc(Nc3ccc4[nH]ncc4c3C3CC3)n(C3CCNCC3)n2)cc1] | Method B, 2.61 min, m/z 525.4 [M + H]⁺ | ¹H NMR (400 MHz, DMSO-d₆) δ 13.05 (s, 1H), 9.10 (t, J = 6.24 Hz, 1H), 8.35 (s, 1H), 8.08 (s, 1H), 7.91 (s, 4H), 7.38 (s, 1H), 7.37 (s, 1H), 4.49 (m, 1H), 4.08 (m, 2H), 3.17 (m, 2H), 2.68 (m, 2H), 2.13 (m, 1H), 1.98 (m, 4H), 0.93 (m, 2H), 0.80 (m, 2H). 1 NH not observed |
| 443 | 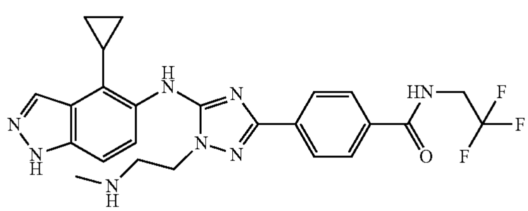 [SMILES: CNCCn1nc(-c2ccc(C(=O)NCC(F)(F)F)cc2)nc1Nc1ccc2[nH]ncc2c1C1CC1] | Method B, 2.58 min, m/z 499.3 [M + H]⁺ | ¹H NMR (400 MHz, DMSO-d₆) δ 12.99 (s, 1H), 9.10 (brs, 1H), 9.10 (t, J = 6.24 Hz, 1H), 8.07 (s, 1H), 7.94 (q, J = 8.60 Hz, 4H), 7.53 (d, J = 9.05 Hz, 1H), 7.39 (d, J = 8.80 Hz, 1H), 4.27 (m, 2H), 4.09 (m, 2H), 3.04 (m, 2H), 2.41 (s, 3H), 2.12 (m, 1H), 1.03 (m, 2H), 0.83 (m, 2H). 1 NH not observed |
| 444 | 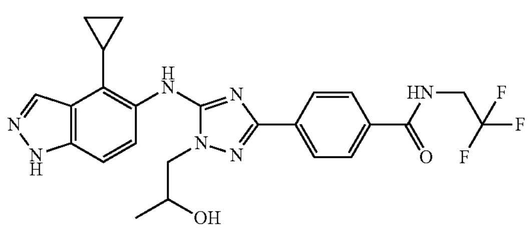 [SMILES: CC(O)Cn1nc(-c2ccc(C(=O)NCC(F)(F)F)cc2)nc1Nc1ccc2[nH]ncc2c1C1CC1] | Method B, 3.34 min, m/z 500.3 [M + H]⁺ | ¹H NMR (400 MHz, DMSO-d₆) δ 12.97 (s, 1H), 9.12 (t, J = 6.41 Hz, 1H), 8.44 (s, 1H), 8.09 (s, 1H), 7.97 (m, 4H), 7.77 (d, J = 8.92 Hz, 1H), 7.41 (d, J = 8.80 Hz, 1H), 5.62 (d, J = 3.91 Hz, 1H), 4.15 (m, 5H), 2.03 (m, 1H), 1.21 (d, J = 6.04 Hz, 3H), 1.09 (m, 2H), 0.81 (m, 2H). |

TABLE 25-continued

| Example | Structure | LC/MS | ¹H NMR |
|---|---|---|---|
| 445 | 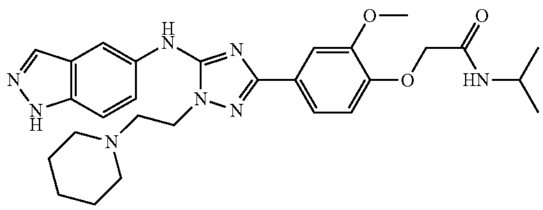 [SMILES: COc1cc(-c2nc(Nc3ccc4[nH]ncc4c3)n(CCN3CCCCC3)n2)ccc1OCC(=O)NC(C)C] | Method B, 2.63 min, m/z 533.4 [M + H]⁺ | ¹H NMR (400 MHz, DMSO-d₆) δ 12.91 (s, 1H), 9.27 (s, 1H), 8.14 (s, 1H), 8.02 (s, 1H), 7.77 (d, J = 7.6 Hz, 1H), 7.55-7.48 (m 4H), 6.99 (d, J = 8.0 Hz, 1H), 4.47 (s, 2H), 4.27 (t, J = 6.0 Hz, 2H), 3.97-3.89 (m, 1H), 3.87 (s, 3H), 2.74-2.65 (m, 2H), 2.49-2.42 (m, 4H), 1.55-1.46 (m, 4H), 1.43-1.34 (m, 2H), 1.10 (d, J = 6.4 Hz, 6H). |
| 446 | 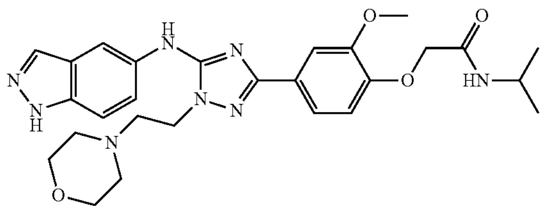 [SMILES: COc1cc(-c2nc(Nc3ccc4[nH]ncc4c3)n(CCN3CCOCC3)n2)ccc1OCC(=O)NC(C)C] | Method B, 2.54 min, m/z 535.4 [M + H]⁺ | ¹H NMR (400 MHz, DMSO-d₆) δ 12.91 (s, 1H), 8.98 (s, 1H), 8.14 (s, 1H), 8.02 (s, 1H), 7.77 (d, J = 7.6 Hz, 1H), 7.59-7.46 (m, 4H), 7.00 (d, J = 6.4 Hz, 1H), 4.47 (s, 2H), 4.29 (t, J = 6.8 Hz, 2H), 3.98-3.89 (m, 1H), 3.87 (s, 3H), 3.57-3.48 (m, 4H), 2.73 (t, J = 7.2 Hz, 2H), 2.49-2.45 (m, 4H), 1.09 (d, J = 7.6 Hz, 6H). |
| 447 | 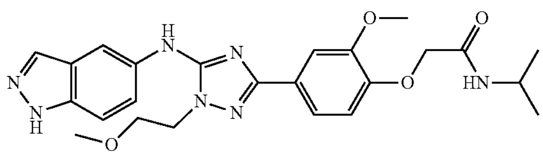 [SMILES: COCCn1nc(-c2ccc(OCC(=O)NC(C)C)c(OC)c2)nc1Nc1ccc2[nH]ncc2c1] | Method B, 3.19 min, m/z 480.4 [M + H]⁺ | ¹H NMR (400 MHz, DMSO-d₆) δ 12.94 (s, 1H), 8.81 (s, 1H), 8.25 8.21 (m, 1H), 8.06 (s, 1H), 7.81 (d, J = 7.6 Hz, 1H), 7.62-7.51 (m, 4H), 7.04 (d, J = 8.8 Hz, 1H), 4.52 (s, 2H), 4.39 (t, J = 5.6 Hz, 2H), 4.02-3.93 (m, 1H), 3.92 (s, 3H), 3.78 (t, J = 5.2 Hz, 2H), 3.32 (s, 3H), 1.13 (d, J = 6.4 Hz, 6H). |
| 448 | 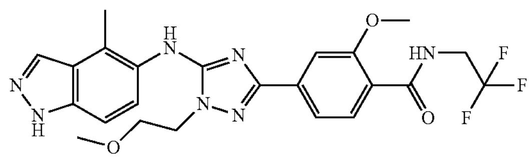 [SMILES: COCCn1nc(-c2ccc(C(=O)NCC(F)(F)F)c(OC)c2)nc1Nc1ccc2[nH]ncc2c1C] | Method B, 3.52 min, m/z 504.3 [M + H]⁺ | ¹H NMR (400 MHz, DMSO-d₆) δ 13.00 (s, 1H), 8.66 (t, J = 6.4 Hz, 1H), 8.23 (s, 1H), 8.13 (s, 1H), 7.77 (d, J = 7.9 Hz, 1H), 7.51 (s, 2H), 7.44-7.33 (m, 2H), 4.35 (t, J = 5.4 Hz, 2H), 4.11 (m, 2H), 3.92 (s, 3H), 3.77 (t, J = 5.3 Hz, 2H), 3.33 (s, 3H), 2.46 (s, 3H). |
| 449 | 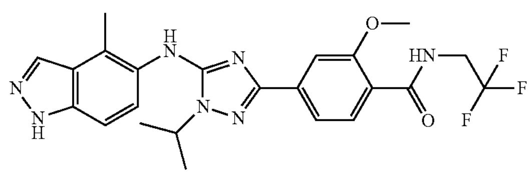 [SMILES: COc1cc(-c2nc(Nc3ccc4[nH]ncc4c3C)n(C(C)C)n2)ccc1C(=O)NCC(F)(F)F] | Method B, 3.69 min, m/z 488.4 [M + H]⁺ | ¹H NMR (400 MHz, DMSO-d₆) δ 13.01 (s, 1H), 8.65 (t, J = 6.4 Hz, 1H), 8.28 (s, 1H), 8.13 (s, 1H), 7.78 (d, J = 8.1 Hz, 1H), 7.51 (d, J = 7.2 Hz, 2H), 7.40-121 (m, 2H), 4.71 (m, 1H), 4.11 (m, 2H), 3.91 (s, 3H), 2.45 (s, 3H), 1.47 (d, J = 6.5 Hz, 6H) |
| 450 | 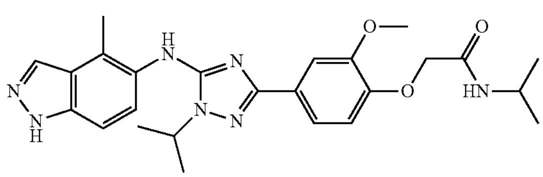 [SMILES: COc1cc(-c2nc(Nc3ccc4[nH]ncc4c3C)n(C(C)C)n2)ccc1OCC(=O)NC(C)C] | Method B, 3.29 min, m/z 478.4 [M + H]⁺ | ¹H NMR (400 MHz, DMSO-d₆) δ 13.02-12.97 (m, 1H), 8.13 (d, J = 12.9 Hz, 2H), 7.74 (d, J = 7.9 Hz, 1H), 7.41-7.25 (m, 4H), 6.91 (d, J = 8.4 Hz, 1H), 4.67 (m, 1H), 4.43 (s, 2H), 3.98-3.84 (m, 1H), 3.80 (s, 3H), 2.43 (s, 3H), 1.44 (d, J = 6.5 Hz, 6H), 1.08 (d, J = 6.6 Hz, 6H) |
| 451 | 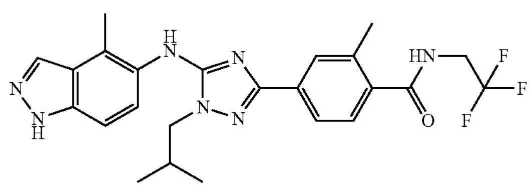 [SMILES: Cc1cc(-c2nc(Nc3ccc4[nH]ncc4c3C)n(CC(C)C)n2)ccc1C(=O)NCC(F)(F)F] | Method B, 3.73 min, m/z 486.5 [M + H]⁺ | ¹H NMR (400 MHz, DMSO-d₆) δ 13.03- 3.00 (m, 1H), 8.92 (t, J = 6.4 Hz, 1H), 8.29-8.08 (m, 2H), 7.66 (d, J = 7.9 Hz, 2H), 7.40-7.25 (m, 3H), 4.12-3.98 (m, 2H), 3.95 (d, J = 7.3 Hz, 2H), 2.44 (s, 3H), 2.32 (s, 3H), 2.24 (m, 6.9 Hz, 1H), 0.96 (d, J = 6.7 Hz, 6H). |
| 452 | 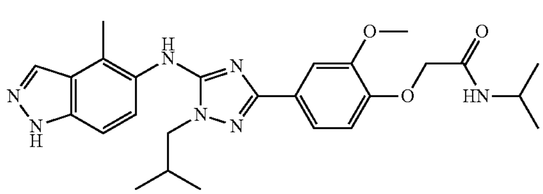 [SMILES: COc1cc(-c2nc(Nc3ccc4[nH]ncc4c3C)n(CC(C)C)n2)ccc1OCC(=O)NC(C)C] | MethodB, 3.49 min, m/z 492.4 [M + H]⁺ | ¹H NMR (400 MHz, DMSO-d₆) δ 12.99 (s, 1H), 8.20-8.10 (m,2H), 7.73 (d, J = 7.9 Hz, 1H), 7.41-7.24 (m, 4H), 6.89 (d, J = 8.4 Hz, 1H), 4.42 (s, 2H), 3.86-3.96 (m, 3H), 3.79 (s, 3H), 2.44 (s, 3H), 2.23 (m, 1H), 1.07 (d, J = 6.6 Hz, 6H), 0.95 (d, J = 6.7 Hz, 6H). |

TABLE 25-continued

| Example | Structure | LC/MS | ¹H NMR |
|---|---|---|---|
| 453 | 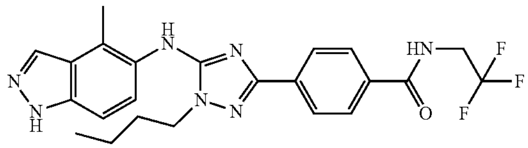 [SMILES: CCCCn1nc(-c2ccc(C(=O)NCC(F)(F)F)cc2)nc1Nc1ccc2[nH]ncc2c1C] | Method B, 3.34 min, m/z 474.4 [M + H]⁺ | ¹H NMR (400 MHz, DMSO-d₆) δ 13.01 (d, J= 1.6 Hz, 1H), 9.11 (t, J = 6.3 Hz, 1H), 8.24 (s, 1H), 8.13 (dd, J = 1.6, 0.8 Hz, 1H), 7.98-7.86 (m, 4H), 7.44-7.34 (m, 2H), 4.35 (t, J = 5.4 Hz, 2H), 4.16-4.02 (m, 2H), 3.78 (t, J = 5.4 Hz, 2H), 3.33 (s, 3H), 2.46 (s, 3H). |
| 454 | 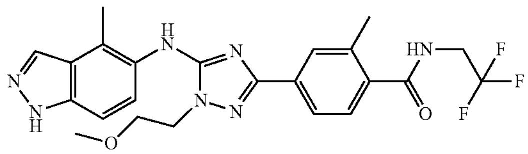 [SMILES: COCCn1nc(-c2ccc(C(=O)NCC(F)(F)F)c(C)c2)nc1Nc1ccc2[nH]ncc2c1C] | Method B, 3.38 min, m/z 488.4 [M + H]⁺ | ¹H NMR (400 MHz, DMSO-d₆) δ 13.04-12.98 (m, 1H), 8.96 (t, J = 6.3 Hz, 1H), 8.20 (s, 1H), 8.13 (dd, J = 1.6, 0.9 Hz, 1H), 7.74-7.66 (m, 2H), 7.45-7.32 (m, 3H), 4.34 (t, J = 5.4 Hz, 2H), 4.06 (m, 2H), 3.78 (t, J = 5.4 Hz, 2H), 3.35 (s, 3H), 2.46 (s, 3H), 2.35 (s, 3H). |
| 455 | 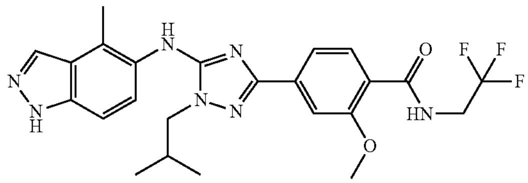 [SMILES: COc1cc(-c2nc(Nc3ccc4[nH]ncc4c3C)n(CC(C)C)n2)ccc1C(=O)NCC(F)(F)F] | Method B, 3.87 min, m/z 502.5 [M + H]⁺ | ¹H NMR (400 MHz, DMSO-d₆) δ 13.03-13.00 (m, 1H), 8.64 (t, J = 6.5 Hz, 1H), 8.29 (s, 1H), 8.13 (t, J = 1.2 Hz, 1H), 7.76 (d, J = 8.0 Hz, 1H), 7.50-7.44 (m, 2H), 7.37 (d, J = 8.7 Hz, 1H), 7.29 (d, J = 8.7 Hz, 1H), 4.16-4.03 (m, 2H), 3.97 (d, J = 7.3 Hz, 2H), 3.90 (s, 3H), 2.45 (s, 3H), 2.25 (m, 1H), 0.96 (d, J = 6.7 Hz, 6H). |
| 456 | 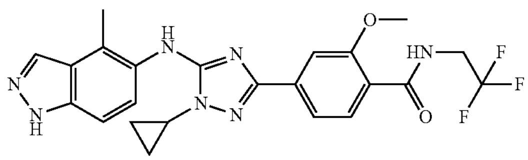 [SMILES: COc1cc(-c2nc(Nc3ccc4[nH]ncc4c3C)n(C3CC3)n2)ccc1C(=O)NCC(F)(F)F] | Method B, 3.54 min, m/z 486.3 [M + H]⁺ | ¹H NMR (400 MHz, DMSO-d₆) δ 13.01 (s, 1H), 8.65 (brt, J = 6.48 Hz, 1H), 8.33 (s, 1H), 8.13 (s, 1H), 7.75 (d, J = 7.92 Hz, 1H), 7.46 (m, 2H), 7.38 (m, 2H), 4.10 (m, 2H), 3.90 (s, 3H), 3.43 (m, 1H), 2.49 (s, 3H), 1.13 (m, 2H), 1.08 (m, 2H). |
| 457 | 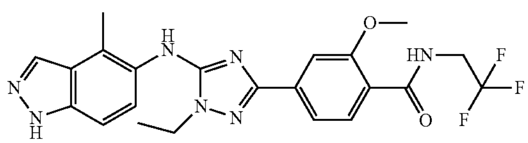 [SMILES: CCn1nc(-c2ccc(C(=O)NCC(F)(F)F)c(OC)c2)nc1Nc1ccc2[nH]ncc2c1C] | Method B, 3.47 min, m/z 474.5 [M + H]⁺ | ¹H NMR (400 MHz, DMSO-d₆) δ 13.01 (s, 1H), 8.65 (t, J = 6.5 Hz, 1H), 8.32 (s, 1H), 8.13 (d, J = 1.2 Hz, 1H), 7.75 (d, J = 8.0 Hz, 1H), 7.52-7.44 (m, 2H), 7.39-7.27 (m, 2H), 4.21-4.06 (m, 4H), 3.90 (s, 3H), 2.45 (s, 3H), 1.39 (t, J = 7.1 Hz, 3H). |

Intermediate 118: tert-butyl 4-amino-3,3-difluoro-pyrrolidine-1-carboxylate

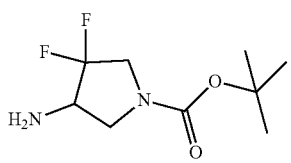

tert-butyl 3,3-difluoro-4-(trifluoromethylsulfonyloxy) pyrrolidine-1-carboxylate (1500 mg, 4.22 mmol), prepared following WO2017103611 example 160, was dissolved in DMF (20 mL) and cooled in an ice bath under N₂ atmosphere. tetrabutylammonium azide (1200 mg, 4.22 mmol) in DMF (20 mL) was added slowly over 15 min via an addition funnel. The reaction mixture was stirred in the cold bath and allowed to warm to ambient temperature gradually and stirred for 3 h. The reaction was diluted with ethyl acetate (50 mL), washed with sat. aq. NaHCO₃ (×2) and brine (×2). The organic phase was dried over a phase separator and purged with vacuum/N₂ (3 times) followed by the addition of palladium, 10 wt. % on carbon powder, dry (150 mg, 1.4 mmol). 3 cycles vacuum/H2 were then performed and the reaction was left stirring at RT overnight under an atmosphere of hydrogen. The crude was filtered through a plug of Celite™ and the solvent removed in vacuo. The product was purified by silica column chromatography using as eluting with 0-5% MeOH in DCM to afford [feint-butyl 4-amino-3,3-difluoro-pyrrolidine-1-carboxylate (934 mg, 4.2 mmol, 99% yield)] as a colourless oil. UPLC-MS (ES+, Method A), 1.04 min, m/z 167.0 [M−(tBu)+H]⁺

Example 458: 4-[5-[(4-isopropenyl-1H-indazol-5-yl)amino]-1-methyl-1,2,4-triazol-3-yl]-N-(2,2,2-trifluoroethyl)benzamide

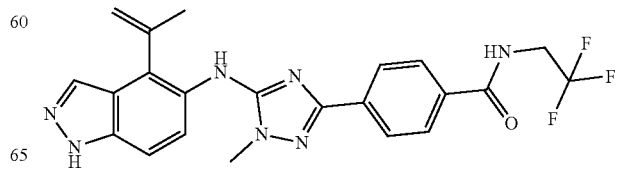

Hydrogen Chloride (4.0M in dioxane) (2.2 mL, 8.8 mmol) was added slowly to a stirred solution of 4-[5-[(4-isopropenyl-1-tetrahydropyran-2-yl-indazol-5-yl)amino]-1-methyl-1,2,4-triazol-3-yl]-N-(2,2,2-trifluoroethyl)benzamide (64 mg, 0.12 mmol) in MeOH (2 mL) at RT. The reaction was stirred at ambient temperature for 18 h. The reaction was reduced in vacuo and purified by SCX SPE cartridge. The resulting product was purified by silica column chromatography eluting with 20-70% EtOAc in Pet. Ether to give the product as a pale-yellow gum. This was dissolved in 1.5 mL of CH₃CN and diluted with ~5 mL of water. The sample was then freeze dried to give 4-[5-[(4-isopropenyl-1H-indazol-5-yl)amino]-1-methyl-1,2,4-triazol-3-yl]-N-(2,2,2-trifluoroethyl)benzamide (27 mg, 0.06 mmol, 47% yield) as a pale yellow powder solid. UPLC-MS (ES⁺, Method B): 3.32 min, m/z 456.3 [M+H]⁺. ¹H NMR (400 MHz, DMSO-d₆) δ 13.10 (s, 1H), 9.10 (t, J=6.3 Hz, 1H), 8.18 (s, 1H), 7.95 (s, 1H), 7.93-7.87 (m, 4H), 7.48 (m, 1H), 7.40 (d, J=8.8 Hz, 1H), 5.33 (q, J=1.7 Hz, 1H), 5.11 (dd, J=2.2, 1.1 Hz, 1H), 4.08 (m, 2H), 3.73 (s, 3H), 2.10 (d, J=1.2 Hz, 3H).

Step 1: ethyl 4-[5-[4-isopropenyl-1-tetrahydropyran-2-yl-indazol-5-yl)amino]-1-methyl-1,2,4-triazol-3-yl]benzoate

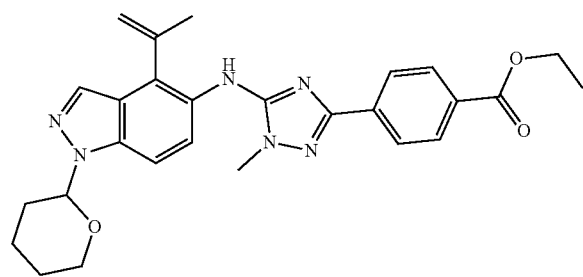

Ethyl 4-[5-[(4-chloro-1-tetrahydropyran-2-yl-indazol-5-yl)amino]-1-methyl-1,2,4-triazol-3-yl]benzoate (166 mg, 0.35 mmol), potassium isopropenyltrifluoroborate (56 mg, 0.38 mmol) and cesium carbonate (450 mg, 1.38 mmol) were dissolved/suspended in 1,4-dioxane (5 mL) and water (2 mL) and fully degassed with bubbling nitrogen. [1,1'-Bis(di-tert-butylphosphino)ferrocene]dichloropalladium(II) (23 mg, 0.03 mmol) was added followed by further degassing and the reaction was heated to 100° C. for 18 h. The reaction was cooled and the water was pipetted away. The organics were reduced directly onto silica and the compound was purified by silica column chromatography eluting with 25-80% EtOAc in Pet. Ether to give ethyl 4-[5-[(4-isopropenyl-1-tetrahydropyran-2-yl-indazol-5-yl)amino]-1-methyl-1,2,4-triazol-3-yl]benzoate (149 mg, 0.30 mmol, 89% yield) as a yellow gum. UPLC-MS (ES⁺, Method A): 1.96 min, m/z 487.6 [M+H]⁺

Step 2: 4-[5-[(4-isopropenyl-1-tetrahydropyran-2-yl-indazol-5-yl)amino]-1-methyl-1,2,4-triazol-3-yl] benzoic acid

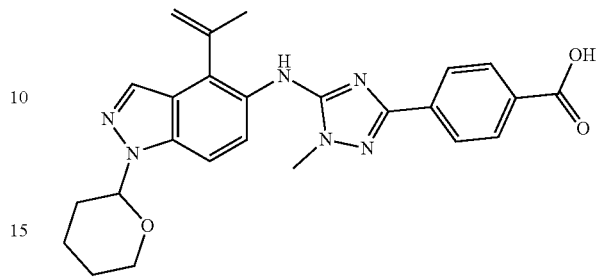

Sodium hydroxide (1.22 mL, 2.45 mmol) was added to a stirred suspension of ethyl 4-[5-[(4-isopropenyl-1-tetrahydropyran-2-yl-indazol-5-yl)amino]-1-methyl-1,2,4-triazol-3-yl]benzoate (149 mg, 0.31 mmol) in THF (10 mL) and MeOH (10 mL) at RT. The reaction turned yellow and the solids dissolved. The reaction was stirred at RT for 18 h. The reaction was reduced in vacuo and then slurried in water. The pH was adjusted to pH2 by the addition of HCl 2.0M and a solid precipitated from the solution. The solid was extracted with EtOAc×2. The organics were then washed with saturated brine and dried over MgSO₄. The solvent was removed in vacuo to give 4-[5-[(4-isopropenyl-1-tetrahydropyran-2-yl-indazol-5-yl)amino]-1-methyl-1,2,4-triazol-3-yl]benzoic add (128 mg, 0.28 mmol, 91% yield) as a yellow solid. UPLC-MS (ES⁺, Method A): 1.63 min, m/z 459.4 [M+H]⁺

Step 3: 4-[5-[(4-isopropenyl-1-tetrahydropyran-2-yl-indazol-5-yl)amino]-1-methyl-1,2,4-triazol-3-yl]-N-(2,2,2-trifluoroethyl)benzamide

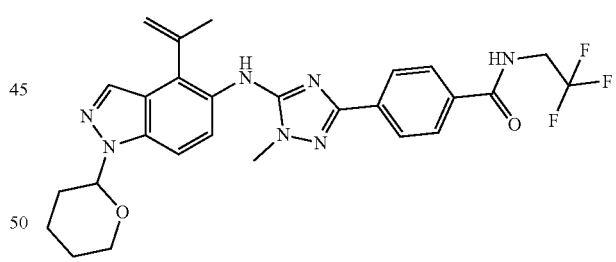

To a stirred solution of 4-[5-[(4-isopropenyl-1-tetrahydropyran-2-yl-indazol-5-yl)amino]-1-methyl-1,2,4-triazol-3-yl]benzoic acid (64 mg, 0.14 mmol), N,N-diisopropylethylamine (0.07 mL, 0.42 mmol) and trifluoroethylamine (21 mg, 0.21 mmol) in THF (5 mL) was added propylphosphonic anhydride (0.12 mL, 0.21 mmol) and the solution stirred for 16 h. The pale-yellow solution was reduced in vacuo onto silica and the crude material was purified by silica column chromatography eluting with 20-100% EtOAc in Pet. Ether to give 4-[5-[(4-isopropenyl-1-tetrahydropyran-2-yl-indazol-5-yl)amino]-1-methyl-1,2,4-triazol-3-yl]-N-(2,2,2-trifluoroethyl)benzamide (64 mg, 0.12 mmol, 85% yield) as a pale yellow gum. UPLC-MS (ES⁺, Method A): 1.75 min, m/z 540.6 [M+H]⁺

Example 459: N-ethyl-4-[5-[(4-isopropenyl-1H-indazol-5-yl)amino]-1-methyl-1,2,4-triazol-3-yl]benzamide

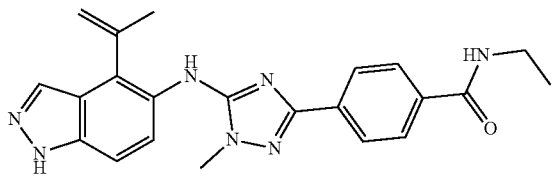 [SMILES: C=C(C)c1c(Nc2nc(-c3ccc(C(=O)NCC)cc3)nn2C)ccc2[nH]ncc12]

UPLC-MS (ES+, Method B): 2.96 min, m/z 402.5 [M+H]+. 1H NMR (400 MHz, DMSO-d6) δ 13.15 (bs, 1H), 8.49 (t, J=5.6 Hz, 2H), 7.97 (d, J=1.0 Hz, 1H), 7.93-7.81 (m, 4H), 7.50 (dd, J=8.8, 1.0 Hz, 1H), 7.41 (d, J=8.8 Hz, 1H), 5.34 (t, J=1.9 Hz, 1H), 5.12 (dd, J=2.2, 1.1 Hz, 1H), 3.74 (s, 3H), 3.28 (m, 2H), 2.10 (s, 3H), 1.12 (t, J=7.2 Hz, 3H).

1-Methyl-4-[4-(4,4,5,5-tetramethyl-1,3,2-dioxaborolan-2-yl)phenyl]pyrazole

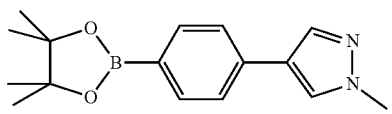

Potassium acetate (199 mg, 2.0 mmol), bis(pinacolato)diboron (257 mg, 1.0 mmol) and 4-(4-bromophenyl)-1-methyl-pyrazole (160 mg, 0.67 mmol) were mixed in DMF (1 mL) and MeCN (4 mL) and the mixture degassed with N2. [1,1'-Bis(diphenylphosphino)ferrocene]Palladium(II) chloride dichloromethane complex (55 mg, 0.07 mmol) was added and the mixture heated for 18 h at 80° C. The reaction mixture was concentrated and purified by silica column chromatography, eluting with 5-20% EtOAc in Pet. Ether to afford 1-methyl-4-[4-(4,4,5,5-tetramethyl-1,3,2-dioxaborolan-2-yl)phenyl]pyrazole (163 mg, 0.57 mmol, 85% yield) as a white solid. LC-MS (ES+, Method A): 1.79 min, m/z 285.0 [M+H]+

Step 1: 4-(4-bromophenyl)-1-methyl-pyrazole

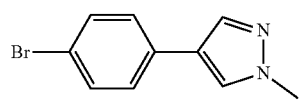

1-Methylpyrazole-4-boronic acid pinacol ester (300 mg, 1.44 mmol) 1,4-dibromobenzene (0.2 mL, 1.6 mmol) and potassium carbonate (399 mg, 2.9 mmol) were mixed in water (1 mL) and 1,4-dioxane (4 mL) and the mixture degassed with N2. Tetrakis(triphenylphosphine)paladium(0) (167 mg, 0.14 mmol) was added and the tube sealed and heated at 80° C. for 18 h. The reaction mixture was reduced in vacuo directly onto silica and purified by silica column chromatography, eluting with 5-40% EtOAc in Pet. Ether to afford 4-(4-bromophenyl)-1-methyl-pyrazole (160 mg, 0.67 mmol, 47% yield) as a white solid. LC-MS (ES+, Method A): 1.66 min, m/z 237.1 [M+H]+.

The following intermediates were made in an analogous manner.

| Name | Structure | Analysis |
|---|---|---|
| 1-methyl-3-[4-(4,4,5,5-tetramethyl-1,3,2-dioxaborolan-2-yl)phenyl]pyrazole | 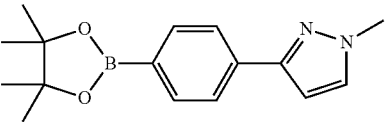 | Method A, 1.85 min, m/z 285.3 [M + H]+ |
| 1-Methyl-5-[4-(4,4,5,5-tetramethyl-1,3,2-dioxaborolan-2-yl)phenyl]pyrazole | 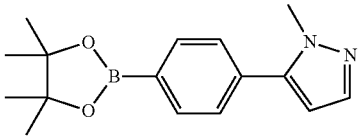 [SMILES: Cn1nccc1-c1ccc(B2OC(C)(C)C(C)(C)O2)cc1] | Method A, 1.85 min, m/z 285.3 [M + H]+ |
| 2-[4-(4,4,5,5-tetramethyl-1,3,2-dioxaborolan-2-yl)phenyl]-1H-imidazole | 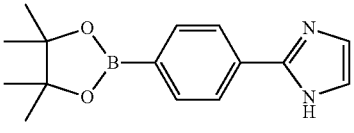 [SMILES: CC1(C)OB(c2ccc(-c3ncc[nH]3)cc2)OC1(C)C] | Method A, 1.21 min, m/z 271.0 [M + H]+ |
| Trimethyl-[2-[[5-methyl-2-[4-(4,4,5,5-tetramethyl-1,3,2-dioxaborolan-2-yl)phenyl]imidazol-1-yl]methoxy]ethyl]silane | 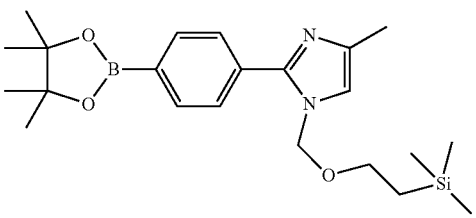 | Method A, 1.69 min, m/z 415.1 [M + H]+. |

-continued

| Name | Structure | Analysis |
|---|---|---|
| tert-Butyl 5-ethyl-3-[4-(4,4,5,5-tetramethyl-1,3,2-dioxaborolan-2-yl) phenyl] pyrazole-1-carboxylate | 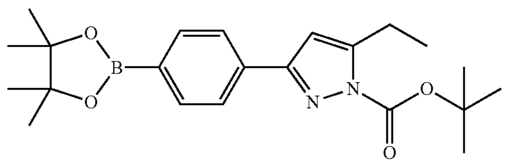 [SMILES: CCc1cc(-c2ccc(B3OC(C)(C)C(C)(C)O3)cc2)nn1C(=O)OC(C)(C)C] | Method A, 2.29 min, m/z 399.3 [M + H]+ |
| 2-[4-(4,4,5,5-Tetramethyl-1,3,2-dioxaborolan-2-yl)phenyl]-3,4,6,7-tetrahydropyrano[3,4-d]imidazole | 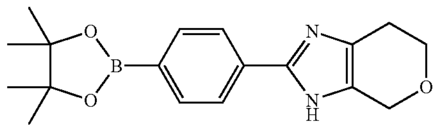 [SMILES: CC1(C)OB(c2ccc(-c3nc4c([nH]3)COCC4)cc2)OC1(C)C] | Method A, 1.24 min, m/z 327.1 [M + H]+ |
| 5-ethyl-2-[4-(4,4,5,5-tetramethyl-1,3,2-dioxaborolan-2-yl)phenyl]-1,4,6,7-tetrahydroimidazo[4,5-c]pyridine | 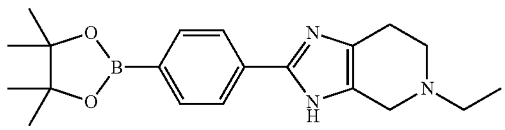 [SMILES: CCN1CCc2nc(-c3ccc(B4OC(C)(C)C(C)(C)O4)cc3)[nH]c2C1] | Method A, 1.15 min, m/z 354.2 [M + H]+ |

2-(4-Bromophenyl)-4-methyl-1H-imidazole

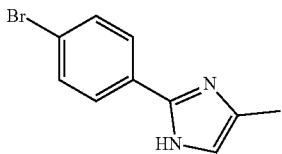

4-Bromobenzamidine HCl salt (2005 mg, 10.07 mmol) and chloroacetone (1.2 mL, 15.1 mmol) were taken up in DMF (50 mL) and then treated with potassium carbonate (5.57 g, 40.3 mmol) and heated to 100° C. for 18 h. The reaction was reduced in vacuo and then taken up in DCM (70 ml). The organics were washed with water (70 mL) and then passed through a phase separator. The product was adsorbed onto silica and then purified by silica column chromatography eluting with 0-40% EtOAc in DCM to afford 2-(4-bromophenyl)-4-methyl-1H-imidazole (1206 mg, 5.09 mmol, 50% yield) as a cream/yellow powdery solid. UPLC-MS (ES+, Method A): 1.02 min, m/z 236/238 [M+H]+

2-[[2-(4-Bromophenyl)-4-methyl-imidazol-1-yl]methoxy]ethyl-trimethyl-silane

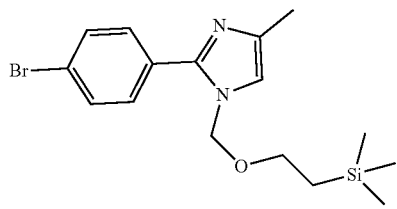 [SMILES: Cc1cn(COCC[Si](C)(C)C)c(-c2ccc(Br)cc2)n1]

2-(4-Bromophenyl)-4-methyl-1H-imidazole (474 mg, 2 mmol) was taken up in dry DMF (10 mL) and then treated with potassium carbonate (553 mg, 4 mmol) and 2-(trimethylsilyl)ethoxymethyl chloride (0.42 mL, 2.4 mmol) and then heated to 60° C. for 14 hrs. The reaction was reduced in vacuo and the residue was treated with sat.aq. NH4Cl solution. The aqueous was extracted with DCM (25 ml) and then washed with water. The organics were passed through phase separator frit and evaporated to dryness. The residue was purified by silica column chromatography eluting with 25-75% EtOAc in DCM to afford 2-[[2-(4-bromophenyl)-4-methyl-imidazol-1-yl]methoxy]ethyl-trimethyl-silane (108 mg, 0.29 mmol, 15% yield) as colourless oil. UPLC-MS (ES+, Method A): 1.57 min, m/z 367.2, 369.2 [M+H]+

1-(4-Bromophenyl)pentane-1,3-dione

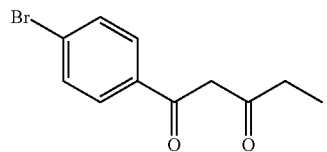

Lithium bis(trimethylsilyl)amide (10.05 mL, 10.05 mmol) was added slowly to 4'-bromoacetophenone (1 g, 5.0 mmol) in THF (30 mL) under N2 and stirred for 30 min at 0° C. Propionyl chloride (0.66 mL, 7.5 mmol) was added and the mixture warmed to room temperature and stirred for 1 h. The solvent was removed in vacuo and EtOAc (30 mL) added. The organics were washed with saturated brine, dried with a phase separator and reduced onto silica. The product was purified by silica column chromatography eluting with isocratic 10% DCM in Pet. Ether to afford 1-(4-bromophenyl)pentane-1,3-dione (461 mg, 1.8 mmol, 36% yield) as a pale yellow solid. LC-MS (ES+, Method A): 2.05 min, m/z 256.9 [M+H]+

3-(4-Bromophenyl)-5-ethyl-1H-pyrazol

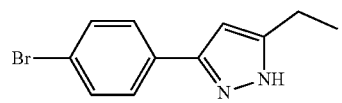

Hydrazine hydrate (0.26 mL, 5.3 mmol) was added slowly to a solution of 1-(4-bromophenyl)pentane-1,3-dione (670 mg, 2.63 mmol) in MeOH (20 mL) and the mixture heated for 1.5 h at 80° C. The reaction mixture was reduced in vacuo, dissolved in EtOAc and the organic solution washed with saturated brine. The organics were dried through a phase separator and reduced to afford the crude product 3-(4-bromophenyl)-5-ethyl-1H-pyrazole (593 mg, 2.4 mmol, 90% yield) as a pale yellow solid. LC-MS (ES+, Method A): 1.73 min, m/z 251.1 [M+H]+ tert-Butyl 3-(4-bromophenyl)-5-ethyl-pyrazole-1-carboxylate

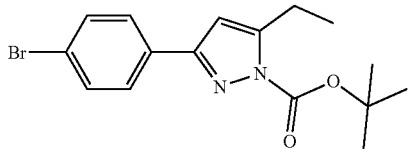 [SMILES: CCc1cc(-c2ccc(Br)cc2)nn1C(=O)OC(C)(C)C]

Sodium hydride, (60% dispersed in mineral oil) (113 mg, 4.7 mmol) was added to a solution of 3-(4-bromophenyl)-5-ethyl-1H pyrazole (593 mg, 2.4 mmol) in DMF (20 mL) and stirred for 15 min at RT. DI-tert-butyl dicarbonate (618 mg, 2.8 mmol) was added and the mixture stirred at RT for 18 h. The reaction mixture was diluted with DCM, dried with phase separator and reduced onto silica. The product was purified by silica column chromatography, eluting with 5-10% EtOAc in Pet. Ether to afford test-butyl 3-(4-bromophenyl)-5-ethyl-pyrazole-1-carboxylate (330 mg, 0.94 mmol, 40% yield) as a pale yellow oil. LC-MS (ES+, Method A): 220 min, m/z 351.2 [M+H]+

2-(4-Bromophenyl)-1,4,6,7-tetrahydropyrano[3,4-d]imidazole

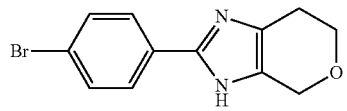

3-Bromotetrahydro-4H-pyran-4-one (0.26 mL, 2.1 mmol) and potassium carbonate (880 mg, 6.4 mmol) were added to a solution of 4-bromobenzenecarboximidamide hydrochloride (1:1) (0.26 mL, 2.1 mmol) in MeCN (3 mL) and the mixture heated to 80° C. for 18 h. The reaction was then heated in the microwave for 8 h at 140° C. The reaction was cooled and diluted with EtOAc, washed with brine×2 and dried using a phase separator. The solvents were reduced in vacuo, and the residue purified by silica column chromatography, eluting with 70-100% EtOAc in Pet. Ether to afford 2-(4-bromophenyl)-1,4,6,7-tetrahydropyrano[3,4-d]imidazole (75 mg, 0.27 mmol, 13% yield) as a pale yellow solid. LC-MS (ES+, Method A): 1.09 min, m/z 279.0 [M+H]+ tert-Butyl 2-(4-bromophenyl)-3,4,6,7-tetrahydroimidazo[4,5-c]pyridine-5-carboxylate

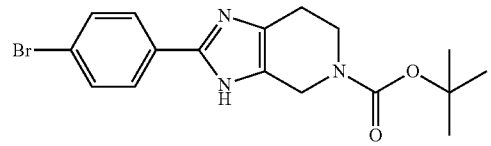 [SMILES: CC(C)(C)OC(=O)N1CCc2nc(-c3ccc(Br)cc3)[nH]c2C1]

1-tert-Butoxycarbonyl-3-bromo-4-oxopiperidine (0.26 mL, 3.6 mmol) and potassium carbonate (1490 mg, 11 mmol) were added to a solution of 4-bromobenzenecarboximidamide hydrochloride (1:1) (0.26 mL, 3.6 mmol) in acetonitrile (10 mL) and the mixture heated to 120° C. for 4 h in the microwave. The mixture was diluted with EtOAc and the organic layer washed with brine (×2) and dried through a phase sep. The solvent was removed in vacuo and the residue purified by silica column chromatography, eluting with 30-100% EtOAc in Pet. Ether to afford tert-butyl 2-(4-bromophenyl)-3,4,6,7-tetrahydroimidazo[4,5-c]pyridine-5-carboxylate (929 mg, 2.45 mmol, 68% yield) as a yellow solid. UPLC-MS (ES+, Method A): 1.31 min, m/z 378.0 [M+H]+.

2-(4-Bromophenyl)-4,5,6,7-tetrahydro-3H-Imidazo[4,5-c]pyridine

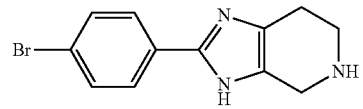

Hydrogen chloride (4.0M in dioxane) (4.16 mL, 16.63 mmol) was added to s solution of tert-butyl 2-(4-bromophenyl)-3,4,6,7-tetrahydroimidazo[4,5-c]pyridine-5-carboxylate (629 mg, 1.7 mmol) and the mixture stirred for 3 h at 25° C. The reaction mixture was reduced in vacuo and passed through an ion-exchange cartridge (SCX, eluting with 1M NH3 in MeOH). The resulting solution was reduced in vacuo to afford 2-(4-bromophenyl)-4,5,6,7-tetrahydro-3H-Imidazo[4,5-c]pyridine (460 mg, 1.65 mmol, 99% yield) as a pale yellow solid. UPLC-MS (ES+, Method A): 0.91 min, m/z 278.0 [M+H]+.

1-[2-(4-Bromophenyl)-1,4,6,7-tetrahydroimidazo[4,5-c]pyridin-5-yl]ethanone

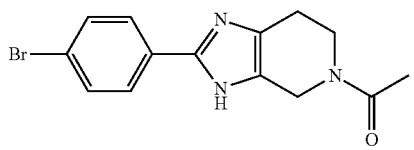 [SMILES: CC(=O)N1CCc2nc(-c3ccc(Br)cc3)[nH]c2C1]

Acetic acid (glacial) (0.14 mL, 2.48 mmol) propylphosphonic anhydride (0.74 mL, 2.48 mmol) and N,N-diisopropylethylamine (1.15 mL, 6.62 mmol) were added to a solution of 2-(4-bromophenyl)-4,5,6,7-tetrahydro-1H-imidazo[4,5-c]pyridine (460 mg, 1.65 mmol) in THF (5 mL) and the mixture stirred for 2 h at 25° C. The reaction mixture was reduced in vacuo, and the residue dissolved in EtOAc, washed with saturated sodium bicarbonate (aq) and brine, and dried over MgSO$_4$. The organics were reduced in vacuo to afford 1-[2-(4-bromophenyl)-1,4,6,7-tetrahydroimidazo[4,5-c]pyridin-5-yl]ethanone (500 mg, 1.56 mmol, 94% yield) as a yellow solid. UPLC-MS (ES+, Method A): 1.04 min, m/z 320.0 [M+H]$^+$.

2-(4-Bromophenyl)-5-ethyl-1,4,6,7-tetrahydroimidazo[4,5-c]pyridine

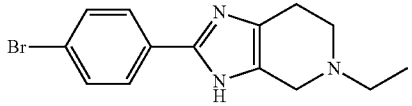

Diisobutylaluminium hydride (1.0M in THF) (4.26 mL, 4.26 mmol) was added to a solution of 1-[2-(4-bromophenyl)-1,4,6,7-tetrahydroimidazo[4,5-c]pyridin-5-yl]ethanone (682 mg, 2.13 mmol) in THF (5 mL) and stirred for 3 h at 40° C. Water was added, and the aqueous extracted with EtOAc. The combined organics were washed with saturated brine and dried over phase sep, reduced in vacuo onto celite and purified by reverse phase column (25 g, C 18, 5-95% MeCN in water) to afford 2-(4-bromophenyl)-5-ethyl-1,4,6,7-tetrahydroimidazo[4,5-c]pyridine (204 mg, 0.67 mmol, 31% yield) as a pale yellow oil. LC-MS (ES+, Method A): 0.98 min, m/z 306.0 [M+H]$^+$.

| Example | Structure | LC/MS | $^1$H NMR |
|---|---|---|---|
| 460 | 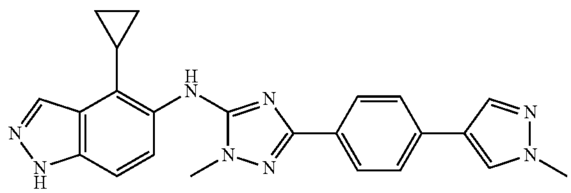 [SMILES: Cn1cc(-c2ccc(-c3nc(Nc4ccc5[nH]ncc5c4C4CC4)n(C)n3)cc2)cn1] | Method B, 3.08 min, m/z 411.4 [M + H]+ | $^1$H NMR (400 MHz, DMSO-d$_6$) δ 13.00 (s, 1H), 8.23 (s, 1H), 8.14 (s, 1H), 8.06 (d, J = 1.3 Hz, 1H), 7.86 (d, J = 0.8 Hz, 1H), 7.82-7.77 (m, 2H), 7.58-7.52 (m 2H), 7.48-7.34 (m, 2H), 3.85 (s, 3H), 3.76 (s, 3H), 2.20-2.07 (m, 1H), 1.03-0.91 (m, 2H), 0.87-0.76 (m, 2H). |
| 461 | 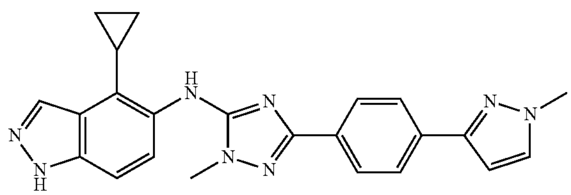 [SMILES: Cn1ccc(-c2ccc(-c3nc(Nc4ccc5[nH]ncc5c4C4CC4)n(C)n3)cc2)n1] | Method B, 3.34 min, m/z 411.3 [M + H]+ | $^1$H NMR (400 MHz, DMSO-d$_6$) δ 13.01 (s, 1H), 8.30 (s, 1H), 8.06 (s, 1H), 7.93 (d, J = 8.1 Hz, 2H), 7.54 (d, J = 8.3 Hz, 2H), 7.50-7.41 (m, 2H), 7.39 (s, 1H), 6.42 (d, J = 1.9 Hz, 1H), 3.86 (s, 3H), 3.79 (s, 3H), 2.14 (s,1H), 0.99-0.93 (m,2H), 0.81 (m, 2H). |
| 462 | 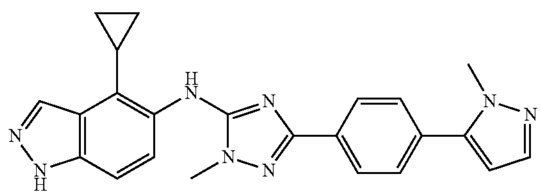 [SMILES: Cn1nccc1-c1ccc(-c2nc(Nc3ccc4[nH]ncc4c3C3CC3)n(C)n2)cc1] | Method B, 3.24 min, m/z 411.3 [M + H]+ | $^1$H NMR (400 MHz, DMSO-d$_6$) δ 13.02 (s, 1H), 8.31 (s, 1H), 8.07 (d, J = 1.3 Hz, 1H), 7.98-7.91 (m, 2H), 7.59-7.52 (m, 2H), 7.51-7.43 (m, 2H), 7.40 (s, 1H), 6.43 (d, J = 1.9 Hz, 1H), 3.87 (s, 3H), 3.80 (s, 3H), 2.20-2.09 (m, 1H), 0.97 (m, 2H), 0.82 (m, 2H). |
| 463 | 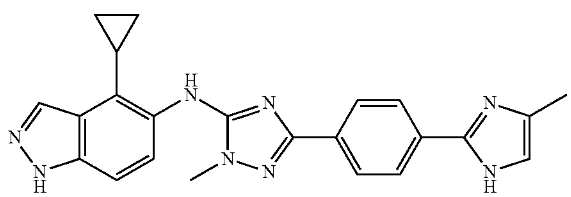 [SMILES: Cc1c[nH]c(-c2ccc(-c3nc(Nc4ccc5[nH]ncc5c4C4CC4)n(C)n3)cc2)n1] | Method B, 2.48 min, m/z 411.3 [M + H]+ | $^1$H NMR (400 MHz, DMSO-d$_6$) δ 13.01 (s, 1H), 12.23 d, J = 23.3 Hz, 1H), 8.27 (s, 1H), 8.06 (s, 1H), 7.93-7.80 (m 4H), 7.41 (t, J = 9.0 Hz, 2H), 6.80 (d, J = 92.7 Hz, 1H), 3.78 (s, 3H), 1.56 (s, 1H), 1.24 (s, 3H), 0.97-0.91 (m, 2H), 0.88-0.78 (m 2H). |
| 464 | 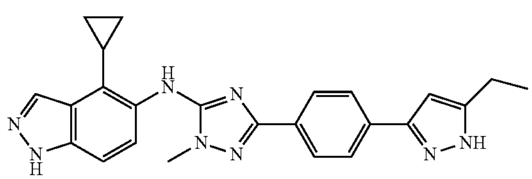 [SMILES: CCc1cc(-c2ccc(-c3nc(Nc4ccc5[nH]ncc5c4C4CC4)n(C)n3)cc2)n[nH]1] | Method B, 3.31 min, m/z 425.3 [M + H]+ | $^1$H NMR (400 MHz, DMSO-d$_6$ + D$_4$ Acetic acid) δ 8.06 (d, J = 1.0 Hz, 1H), 7.89-7.81 (m, 2H), 7.79-7.71 (m 2H), 7.50-7.35 (m, 2H), 6.47 (s, 1H), 3.78 (s, 3H), 2.62 (q, J = 7.6 Hz, 2H), 2.14 (m, 1H), 1.21 (t, J = 7.6 Hz, 3H), 1.03-0.93 (m, 2H), 0.86-0.78 (m, 2H). 3 × NH not observed |
| 465 | 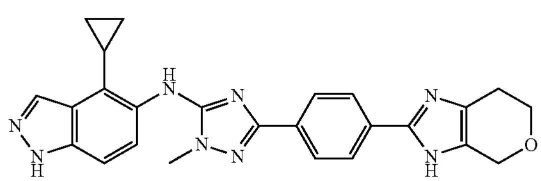 [SMILES: Cn1nc(-c2ccc(-c3nc4c([nH]3)COCC4)cc2)nc1Nc1ccc2[nH]ncc2c1C1CC1] | Method B, 2.48 min, m/z 453.2 [M + H]+ | $^1$H NMR (400 MHz, DMSO-d$_6$) δ 13.02 (s, 1H), 12.39 (s, 1H), 8.28 (s, 1H), 8.07 (s, 1H), 7.86 (s, 4H), 7.50-7.36 (m, 2H), 4.54 (s, 2H), 3.92-3.84 (m, 2H), 3.79 (d, J = 1.8 Hz, 3H), 2.14 (s, 1H), 1.24 (s, 2H), 0.97 (d, J = 8.3 Hz, 2H), 0.82 (d, J = 5.5 Hz, 2H). |

| Example | Structure | LC/MS | ¹H NMR |
|---|---|---|---|
| 466 | 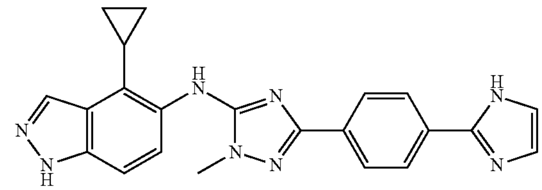 [SMILES: Cn1nc(-c2ccc(-c3ncc[nH]3)cc2)nc1Nc1ccc2[nH]ncc2c1C1CC1] | Method B, 2.38 min, m/z 397.2 [M + H]+ | ¹H NMR (400 MHz, DMSO-$d_6$) δ 13.00 (s, 1H), 12.65 (br. s, 1H), 8.27 (s, 1H), 8.06 (s, 1H), 7.93 (d, J = 8.3 Hz, 2H), 7.87 (d, J = 8.3 Hz, 2H), 7.43 (d, J = 8.8 Hz, 1H), 7.38 (d, J = 8.8 Hz, 1H), 7.15 (br. s, 2H), 3.79 (s, 3H), 2.14 (m, 1H), 1.00-0.93 (m, 2H), 0.85-0.79 (m, 2H). |
| REDX11069 467 | 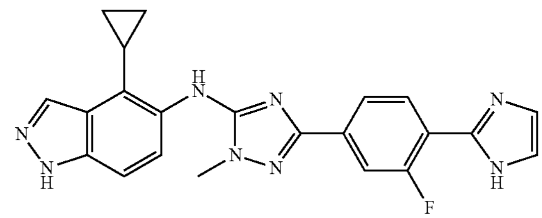 [SMILES: Cn1nc(-c2ccc(-c3ncc[nH]3)c(F)c2)nc1Nc1ccc2[nH]ncc2c1C1CC1] | Method B, 2.41 min, m/z 415.3 [M + H]+ | ¹H NMR (400 MHz, DMSO-$d_6$): 13.01 (s, 1H), 12.19 (s, 1H), 8.34 (s, 1H) 8.06 (s, 1H), 8.02 (t, J = 8.0 Hz, 1H), 7.73 (dd, J = 8.0, 1.5 Hz, 1H), 7.62 (dd, J = 12.4, 1.5 Hz, 1H), 7.42 (d, J = 8.8 Hz, 1H), 7.39 (d, J = 8.8 Hz, 1H), 7.24 (br.s, 1H), 7.08 (br. s, 1H), 3.79 (s, 3H), 2.14 (m, 1H), 0.99-0.93 (m, 2H), 0.85-0.79 (m, 2H). |
| 468 | 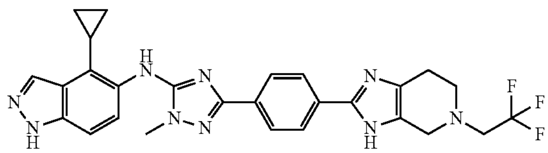 [SMILES: Cn1nc(-c2ccc(-c3nc4c([nH]3)CN(CC(F)(F)F)CC4)cc2)nc1Nc1ccc2[nH]ncc2c1C1CC1] | Method B, 2.80 min, m/z 534.3 [M + H]+ | 1H NMR (400 MHz, Methanol-$d_6$): 8.15 (d, J = 0.9 Hz, 1H), 8.01-7.93 (m, 2H), 7.86-7.79 (m, 2H), 7.44 (q, J = 8.9 Hz, 2H), 3.83 (s, 3H), 3.80 (s, 2H), 3.31 (q, 2H), 3.06 (t, J = 5.7 Hz, 2H), 2.75 (t, J = 5.7 Hz, 2H), 2.13 (tt, J = 8.5, 5.5 Hz, 1H), 1.07-0.99 (m, 2H), 0.83 (td, J = 6.0, 4.1 Hz, 2H). 3 exchangeable NH's not seen |
| 469 | 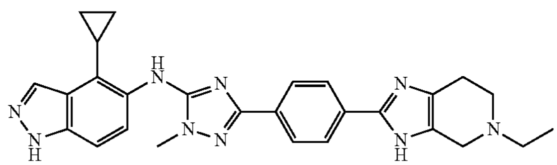 | Method B, 2.43 min, m/z 428.4 [M + H]+ | ¹H NMR (400 MHz, DMSO-$d_6$) δ: 13.03 (s, 1H), 12.24 (s, 1H), 8.28 (s, 1H), 8.07 (d, J = 1.0 Hz, 1H), 7.84 (s, 4H), 7.41 (q, J = 8.8 Hz, 2H), 3.78 (s, 3H), 2.70 (t, J = 5.5 Hz, 2H), 2.56 (q, J = 7.1 Hz, 2H), 2.14 (tt, J = 8.6, 5.5 Hz, 1H), 1.08 (t, J = 7.1 Hz, 3H), 1.01-0.93 (m, 2H), 0.81 (1d, J = 6.1, 4.2 Hz, 2H). |

ROCK2 Binding Activity:

Assay for ROCK2 inhibition was performed using the protein construct N-terminal 6His-tagged ROCK2 catalytic domain 11-552 (Dundee University, UK). Protein was purified from a baculovirus expression system. Long S6 peptide (KEAKEKRQEQIAKRRRLSSLRASTSKSGGSQK) was used as substrate. Kinase reactions were carried out in 15 μl volume in a 96-well plate (black, half area) using 1.25 nM constitutively active ROCK2 kinase, 100 μM long S6 peptide, 20 μM ATP and test compound in DMSO (or DMSO only for controls). The final concentration of DMSO was ≤1%. Assay buffer was 50 mM HEPES pH 7.5 supplemented with 0.2 mM EDTA, 10 mM magnesium acetate, 0.01% Tween-20, 1 mM DTT and 0.01% BSA. Test compounds were pre-incubated with ROCK2 kinase for 1 hour before addition of ATP and long S6 peptide. After incubation for a further 1 hour, the amount of ADP produced was measured using ADP-Glo Kinase Assay (Promega) as per manufacturer's instructions. The luminescence was measured on a PHERAstar FS (BMG Labtech). The concentration of test compound required to inhibit ADP production by 50% (the $IC_{50}$) was calculated using a four-parameter logistic function with software by Dotmatics.

Table 26 shows the ROCK2 binding activity, as determined by the assay described above, for certain compounds of the formula, categorised based on the ROCK2 IC50 value of the compound as "+", "++", "+++" and "++++". The category "+" refers to compounds with a ROCK2 $IC_{50}$ value of >10 μM. The category "++" refers to compounds with a ROCK2 $IC_{50}$ value of 10 to 3 μM. The category "+++" refers to compounds with a ROCK2 $IC_{50}$ value of 3 to 0.3 μM. The category "++++" refers to compounds with a ROCK2 $IC_{50}$ value of <0.3 μM.

TABLE 26

| Example ID | ADP-Glo kinase activity assay ROCK2 Category | Example ID | ADP-Glo kinase activity assay ROCK2 Category | Example ID | ADP-Glo kinase activity assay ROCK2 Category |
|---|---|---|---|---|---|
| 188 | ++++ | 105 | ++++ | 52 | +++ |
| 144 | ++ | 104 | ++++ | 148 | ++++ |
| 150 | ND | 103 | ++++ | 147 | ++++ |
| 182 | ++++ | 102 | ++++ | 11 | ++ |
| 181 | ++++ | 101 | ++++ | 51 | ++++ |
| 184 | +++ | 100 | ++++ | 223 | ++ |
| 177 | ++++ | 99 | ++++ | 50 | ++++ |
| 176 | ++++ | 98 | + | 231 | ++++ |
| 166 | ++++ | 219 | ++++ | 49 | ++++ |
| 190 | ND | 47 | ++++ | 48 | ++++ |
| 175 | ++++ | 97 | ++++ | 45 | ++++ |
| 170 | ++++ | 96 | +++ | 243 | +++ |
| 169 | ++++ | 95 | ++++ | 167 | ++++ |
| 168 | ++++ | 94 | ++++ | 42 | ++++ |
| 174 | ++++ | 93 | ++ | 41 | ++ |
| 180 | ++++ | 92 | +++ | 40 | +++ |
| 240 | ++++ | 91 | ++++ | 39 | +++ |
| 192 | ++++ | 90 | ++++ | 38 | ++++ |
| 191 | ++++ | 89 | ++++ | 222 | ++++ |

TABLE 26-continued

| Example ID | ADP-Glo kinase activity assay ROCK2 Category | Example ID | ADP-Glo kinase activity assay ROCK2 Category | Example ID | ADP-Glo kinase activity assay ROCK2 Category |
|---|---|---|---|---|---|
| 179 | ++++ | 88 | +++ | 37 | +++ |
| 178 | ++++ | 87 | ++++ | 225 | +++ |
| 137 | +++ | 86 | ++++ | 230 | +++ |
| 138 | ++++ | 85 | ++++ | 36 | +++ |
| 173 | ++ | 84 | + | 35 | +++ |
| 184 | ++++ | 83 | ++++ | 146 | ++++ |
| 183 | ++++ | 82 | +++ | 229 | +++ |
| 172 | +++ | 81 | ++ | 228 | +++ |
| 136 | +++ | 80 | +++ | 227 | +++ |
| 171 | ++++ | 79 | ++++ | 34 | ++++ |
| 239 | ++++ | 78 | ++ | 226 | ++++ |
| 237 | +++ | 77 | ++++ | 33 | + |
| 240 | ++++ | 218 | ++++ | 44 | ++++ |
| 238 | ++++ | 76 | +++ | 221 | +++ |
| 236 | ++++ | 75 | ++++ | 224 | ++++ |
| 43 | ++++ | 74 | +++ | 165 | ++++ |
| 235 | ++++ | 73 | +++ | 220 | +++ |
| 135 | ++++ | 72 | +++ | 30 | ++++ |
| 134 | +++ | 145 | ++++ | 164 | ++++ |
| 133 | +++ | 71 | ++++ | 163 | +++ |
| 132 | +++ | 70 | +++ | 32 | ++++ |
| 131 | ++++ | 69 | ++++ | 28 | ++ |
| 130 | ++++ | 234 | +++ | 158 | ++++ |
| 141 | ++++ | 68 | ++++ | 157 | ++++ |
| 149 | ++++ | 233 | ++++ | 22 | +++ |
| 129 | +++ | 67 | +++ | 29 | +++ |
| 128 | ++++ | 66 | ++++ | 26 | ++++ |
| 127 | +++ | 65 | ++ | 161 | ++++ |
| 193 | ++++ | 64 | ++++ | 23 | +++ |
| 203 | ++++ | 217 | ++++ | 24 | +++ |
| 202 | ++++ | 216 | ++++ | 5 | ++ |
| 201 | ++++ | 215 | ++++ | 162 | ++++ |
| 200 | ++++ | 214 | ++++ | 27 | +++ |
| 199 | +++ | 213 | ++++ | 25 | +++ |
| 198 | ++++ | 212 | ++++ | 31 | +++ |
| 197 | +++ | 204 | ++++ | 21 | +++ |
| 196 | ++++ | 211 | ++++ | 160 | ++++ |
| 195 | ++++ | 63 | ++++ | 159 | +++ |
| 194 | ++++ | 62 | ++++ | 20 | +++ |
| 126 | ++++ | 61 | +++ | 18 | +++ |
| 125 | ++++ | 60 | +++ | 156 | ++++ |
| 124 | ++++ | 210 | ++++ | 19 | +++ |
| 123 | +++ | 209 | ++++ | 155 | +++ |
| 122 | ++++ | 59 | +++ | 17 | ++++ |
| 121 | ++ | 58 | ++++ | 154 | +++ |
| 120 | ++ | 208 | ++++ | 14 | ++++ |
| 119 | ++ | 207 | ++++ | 16 | +++ |
| 118 | ++++ | 206 | ++++ | 15 | +++ |
| 117 | +++ | 205 | ++++ | 10 | ++++ |
| 116 | +++ | 242 | ++++ | 9 | +++ |
| 115 | ++++ | 243 | ++++ | 12 | ++++ |
| 114 | ++++ | 57 | +++ | 13 | +++ |
| 113 | + | 56 | ++++ | 8 | ++++ |
| 112 | +++ | 55 | ++++ | 7 | ++++ |
| 111 | +++ | 232 | +++ | 4 | + |
| 110 | +++ | 46 | + | 3 | +++ |
| 109 | ++ | 45 | ++++ | 1 | +++ |
| 108 | +++ | 44 | +++ | 6 | ++++ |
| 107 | +++ | 54 | ++++ | 2 | +++ |
| 106 | ++++ | 53 | +++ | 293 | ++++ |
| 466 | ND | 385 | ++++ | 292 | ++++ |
| 469 | ++++ | 310 | ++++ | 291 | ++ |
| 248 | ++++ | 309 | ++++ | 251 | ++++ |
| 249 | ++ | 308 | ++++ | 290 | ++++ |
| 459 | ++++ | 307 | +++ | 289 | ++++ |
| 458 | ++++ | 306 | +++ | 288 | ++++ |
| 426 | ++++ | 384 | +++ | 383 | ++++ |
| 340 | + | 339 | ++++ | 287 | ++++ |
| 88 | +++ | 425 | +++ | 286 | ++++ |
| 465 | ++++ | 305 | +++ | 285 | ++++ |
| 341 | +++ | 304 | ++++ | 444 | ++++ |
| 392 | +++ | 338 | ++++ | 424 | ++++ |
| 464 | ++++ | 303 | ++++ | 428 | ++++ |
| 463 | ++++ | 302 | ++++ | 443 | ++++ |
| 391 | ++++ | 301 | ++++ | 430 | ++++ |
| 390 | ++++ | 300 | ++++ | 344 | ++++ |
| 389 | ++ | 299 | ++++ | 429 | ++++ |
| 312 | ++++ | 298 | ++++ | 284 | ++++ |
| 388 | +++ | 297 | ++++ | 423 | ++++ |
| 387 | ++++ | 322 | ++++ | 427 | ++++ |
| 465 | ++++ | 321 | ++++ | 381 | ++++ |
| 323 | ++++ | 320 | ++++ | 283 | ++++ |
| 462 | ++++ | 319 | ++++ | 282 | ++++ |
| 461 | ++++ | 318 | ++++ | 281 | ++++ |
| 460 | ++++ | 317 | ++++ | 442 | ++++ |
| 386 | +++ | 296 | +++ | 421 | ++++ |
| 311 | ++++ | 295 | ++++ | 380 | ++++ |
| 422 | + | 294 | ++++ | 379 | +++ |
| 420 | +++ | 364 | ++++ | 353 | ++++ |
| 374 | ++++ | 280 | ++++ | 352 | ++++ |
| 373 | +++ | 316 | ++++ | 403 | ++++ |
| 419 | ++++ | 268 | ++++ | 351 | ++++ |
| 372 | ++++ | 464 | ++++ | 260 | ++++ |
| 271 | ++++ | 335 | + | 259 | ++ |
| 418 | +++ | 376 | ++++ | 275 | +++ |
| 371 | ++++ | 363 | ++++ | 315 | +++ |
| 378 | ++++ | 411 | ++++ | 336 | ++++ |
| 441 | ++++ | 362 | ++++ | 375 | ++++ |
| 457 | ++++ | 361 | +++ | 274 | ++++ |
| 456 | ++++ | 410 | +++ | 402 | ++++ |
| 337 | ++++ | 360 | ++++ | 326 | ++++ |
| 440 | ++++ | 409 | ++++ | 350 | ++++ |
| 437 | ++++ | 408 | +++ | 349 | ++++ |
| 455 | ++++ | 359 | +++ | 258 | +++ |
| 454 | ++++ | 267 | ++++ | 257 | ++++ |
| 453 | ++++ | 358 | ++++ | 256 | ++++ |
| 439 | ++++ | 266 | ++++ | 255 | +++ |
| 438 | ++++ | 332 | ++ | 254 | +++ |
| 436 | ++++ | 331 | +++ | 253 | ++++ |
| 435 | ++++ | 330 | ++++ | 401 | ++++ |
| 452 | ++++ | 279 | ++++ | 348 | ++++ |
| 451 | ++++ | 278 | ++++ | 347 | ++++ |
| 343 | ++++ | 277 | ++++ | 346 | ++++ |
| 463 | ++++ | 276 | ++++ | 400 | ++++ |
| 462 | ++++ | 433 | +++ | 399 | ++++ |
| 370 | ++++ | 447 | ++++ | 325 | +++ |
| 369 | ++++ | 434 | ++++ | 324 | ++++ |
| 416 | ++++ | 327 | ++++ | 345 | ++ |
| 368 | ++++ | 265 | ++++ | 398 | ++ |
| 415 | ++++ | 357 | ++++ | 397 | ++++ |
| 367 | ++ | 407 | ++++ | 250 | ++++ |
| 414 | ++ | 264 | ++++ | 396 | ++++ |
| 413 | ++++ | 263 | +++ | 395 | ++++ |
| 412 | ++++ | 406 | ++++ | 394 | +++ |
| 450 | ++++ | 356 | ++++ | 153 | ++++ |
| 449 | ++++ | 262 | ++++ | 152 | ++++ |
| 417 | ++++ | 446 | ++++ | 151 | + |
| 366 | ++++ | 445 | ++++ | 432 | ++ |
| 270 | ++++ | 329 | ++ | 252 | ++++ |
| 269 | ++++ | 328 | ++ | 314 | ++++ |
| 461 | ++++ | 405 | ++++ | 313 | ++++ |
| 460 | ++++ | 355 | ++++ | 273 | ++++ |
| 365 | ++++ | 354 | ++++ | 272 | ++++ |
| 448 | ++++ | 261 | ++++ | 201 | ++++ |
| 377 | ++++ | 404 | ++++ | 470 | ++++ |
| 471 | ++++ | 472 | ++++ | 473 | ++++ |
| 474 | ++++ | 475 | ++++ | | |

Throughout the description and claims of this specification, the words "comprise" and "contain" and variations of them mean "including but not limited to", and they are not intended to (and do not) exclude other moieties, additives, components, Integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are flied concurrently with or previous to this specification in connection with this application and which are open to public inspection with this specification, and the contents of all such papers and documents are incorporated herein by reference.

The invention claimed is:

1. A compound of formula (I) and pharmaceutically acceptable salts thereof:

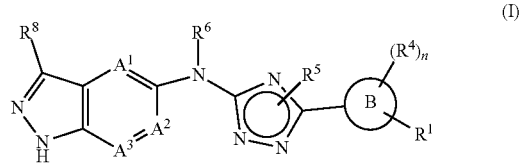

wherein

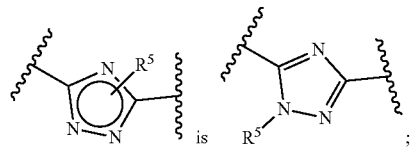

$A^1$, $A^2$ or $A^3$ are each independently selected from the group consisting of C—H, C—F, C—Cl, C-Me, C-Et, C-i-Pr, C-cyclopropyl, C-ethenyl, C-propenyl, C—CN, C—CF$_3$, and N;

B represents a 5 or 6 membered carbocyclic ring which is aromatic or unsaturated, a 5 or 6 membered heterocyclic ring which is aromatic or unsaturated, a 9 or 10 membered carbocyclic bicyclic ring system, or a 9 or 10 membered heterocyclic bicyclic ring system; wherein the bicyclic ring system is either aromatic or one of the rings within the bicyclic ring system is aromatic or unsaturated and the other ring is saturated;

$R^1$ is L-$R^2$, wherein

L is a bond or -$L^1$-$L^2$-, wherein $L^1$ is selected from the group consisting of a bond, —(CR$^A$R$^B$)$_{1-3}$—, —O(CR$^A$R$^B$)$_{1-3}$—, —(CR$^A$R$^B$)$_{0-3}$O—, and —NR$^C$(CR$^A$R$^B$)$_{1-3}$—; and $L^2$ is selected from the group consisting of a bond, —(CR$^A$R$^B$)$_{1-3}$—, —O—, —NR$^D$—, —C(O)NR$^D$—, —NR$^D$C(O)—, —C(O)O—, —OC(O)—, —C(O)—, —S(O)$_2$NR$^D$—, —NR$^D$S(O)$_2$—, —S(O)$_2$—, —S(O)(NR$^D$)—, —NR$^D$C(O)NR$^E$—, —OC(O)NR$^D$—, and —C(O)NR$^D$S(O)$_2$—; and $R^2$ is selected from the group consisting of H, CN, C$_{1-6}$ alkyl, C$_{1-6}$ haloalkyl, C$_{1-6}$ alkyl substituted with —OR$^F$, C$_{1-6}$ alkyl substituted with —NR$^F$R$^G$, C$_{1-4}$ haloalkyl substituted with —OR$^F$, C$_{3-8}$ cycloalkyl substituted with OH, C$_{1-4}$ alkyl substituted with 3 to 8 membered heterocycloalkyl, C$_{1-4}$ alkyl substituted with 6 membered heteroaryl, —(CR$^H$R$^I$)$_{1-3}$OR$^F$, —(CR$^H$R$^I$)$_{1-3}$NR$^F$R$^G$, —(CR$^N$R$^O$)$_{1-3}$C(O)OR$^F$, —(CR$^N$R$^O$)$_{1-3}$C(O)NR$^F$R$^G$, C$_{3-10}$ carbocyclic ring system, and 3 to 10 membered heterocyclic ring system; wherein the carbocyclic ring or heterocyclic ring system is unsubstituted or substituted with: =O, —NR$^F$R$^G$, —C(O)R$^F$, halo, —CN, C$_{1-4}$ alkyl, C$_{1-4}$ haloalkyl or C$_{1-4}$ alkyl substituted with —OR$^F$;

$R^4$ is independently selected at each occurrence from the group consisting of halo, C$_{1-4}$ alkyl, C$_{1-4}$ haloalkyl, —CN, C$_{1-4}$ alkyl substituted with —OR$^J$, C$_{1-4}$ alkyl substituted with —NR$^J$R$^K$, and 3 to 8 membered heterocycloalkyl;

$R^5$ is selected from the group consisting of H, C$_{1-4}$ alkyl, C$_{1-4}$ alkyl substituted with —OR$^F$, C$_{1-4}$ alkyl substituted with —NR$^L$R$^L$, C$_{3-8}$ cycloalkyl, substituted or unsubstituted phenyl, C$_{1-4}$ alkyl substituted with a 3 to 8 membered heterocycloalkyl, and substituted or unsubstituted 5 or 6 membered heteroaryl; wherein the phenyl or heteroaryl group may be substituted by 1 or 2 $R^9$;

$R^6$ is selected from the group consisting of H and methyl;

$R^8$ is selected from the group consisting of H, Cl, F, CN, and Me;

$R^9$ is selected from the group consisting of halo and C$_{1-4}$ alkyl;

n is 0, 1, or 2;

$R^A$ and $R^B$ are selected from the group consisting of H, C$_{1-4}$ alkyl, and C$_{1-4}$ haloalkyl; or $R^A$ and $R^B$ together with the atom to which they are attached form a 3 to 6 membered cycloalkyl ring or a 3 to 6 membered heterocycloalkyl ring;

$R^C$, $R^D$, $R^E$, $R^F$ and $R^G$ are each independently selected from the group consisting of H, C$_{1-4}$ alkyl, and C$_{1-4}$ haloalkyl;

$R^H$ and $R^I$ are each H except one pair of $R^H$ and $R^I$ on the same carbon atom, together with that carbon atom, form a 3 to 6 membered cycloalkyl ring or a 3 to 6 membered heterocycloalkyl ring; and $R^J$, $R^K$, $R^L$, $R^M$, $R^N$ and $R^O$ are each independently at each occurrence selected from the group consisting of H and C$_{1-4}$ alkyl.

2. The compound of claim 1, wherein $A^1$ is selected from the group consisting of C—H, C—F, C—Cl, C-Me, C-Et, C-i-Pr, C-cyclopropyl, C—CN, C—CF$_3$, and N.

3. The compound of claim 1, wherein $A^2$ is selected from the group consisting of C—H and C—F.

4. The compound of claim 1, wherein $A^3$ is C—H.

5. The compound of claim 1, wherein $R^8$ is selected from the group consisting of H and Me.

6. The compound of claim 1 wherein $R^6$ is H.

7. The compound of claim 1, wherein

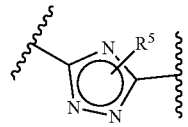

is selected from the group consisting of

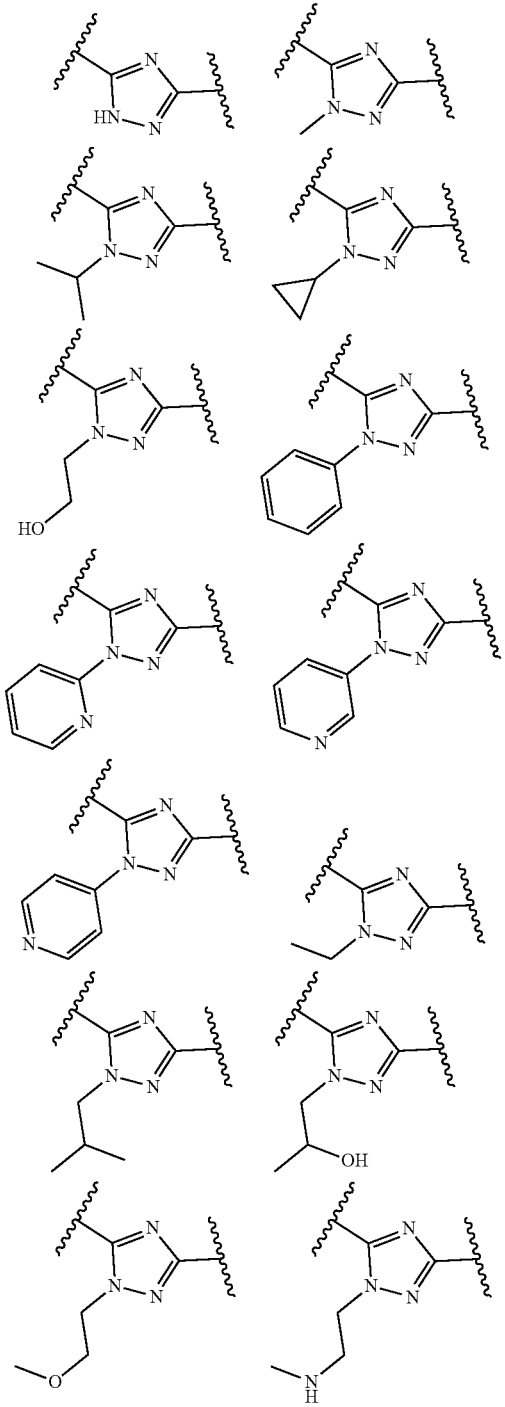

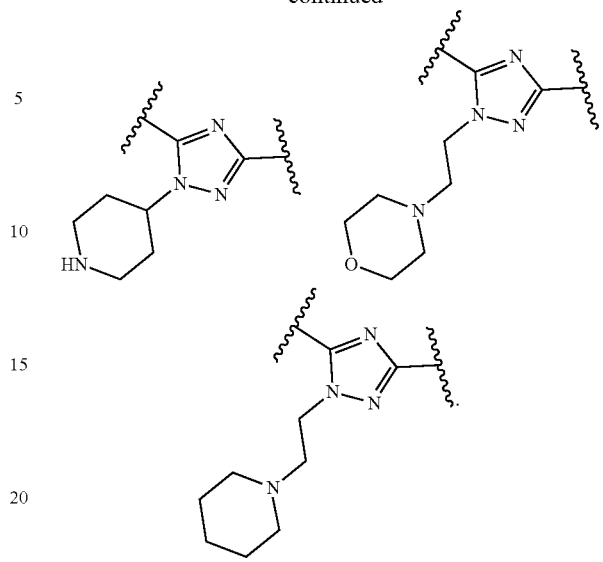

8. The compound of claim 1, wherein the compound is represented by formula (Ia):

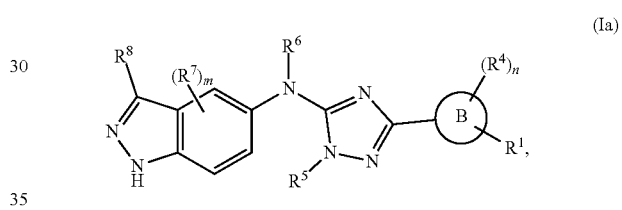

(Ia)

wherein m is 1 or 2; and
R⁷ is selected independently for each occurrence from the group consisting of H, F, Cl, Me, Et, i-Pr, cyclopropyl, ethenyl, propenyl, CN and CF₃.

9. The compound of claim 1, wherein

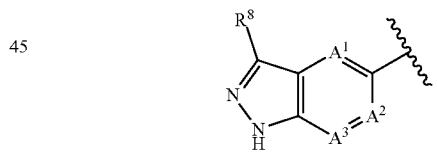

is selected from the group consisting of

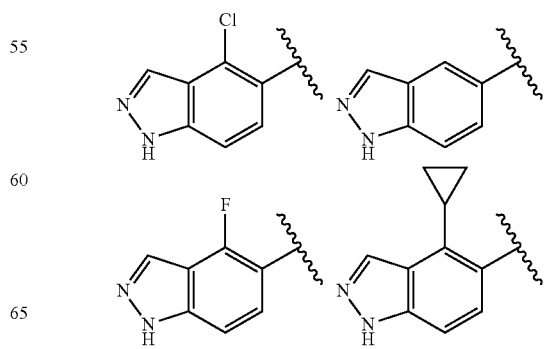

-continued

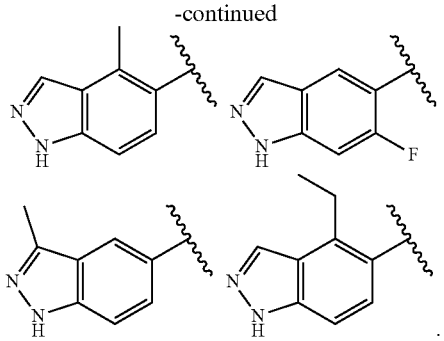

10. The compound of claim 1, wherein B is selected from the group consisting of a 6 membered carbocyclic ring, and a 10 membered heterocyclic fused bicyclic ring system.

11. The compound of claim 1, wherein B is selected from the group consisting of phenyl, pyrazole, pyridyl, piperidyl, azaindole, isoindoline, tetrahydroisoquionoline, tetrahydroisoquinolone, furan, indazole, benzpyrazole, pyrimidine, pyridone, tetrahydropyridine, dihydropyran, cyclopentene, cyclohexenyl, chromane, chromanone, benzodioxan, tetrahydronapthalene, dihydrobenzoxazine, benzomorpholine, tetrahydroquinoline, napthyridine, quinoline, isoquinoline, and dihydroisobenzofuran; or B is:

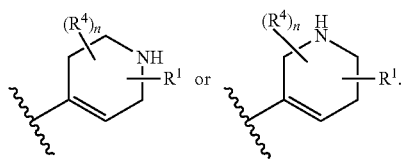

12. The compound of claim 1, wherein

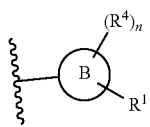

is selected from the group consisting of

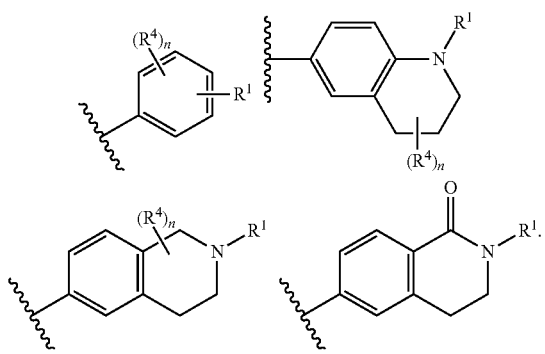

13. The compound of claim 1, wherein $L^1$ is selected from the group consisting of a bond, —$(CR^A R^B)_{1-3}$—, and —$O(CR^A R^B)_{1-3}$—.

14. The compound of claim 1, wherein $L^2$ is selected from the group consisting of a bond, —$NR^D$—, —$C(O)NR^D$—, —$NR^D C(O)$—, —$C(O)O$—, —$C(O)$—, —$NR^D C(O)NR^E$—, and —$OC(O)NR^D$—.

15. The compound of claim 1, wherein $R^A$ and $R^B$ are independently selected from the group consisting of H, $C_{1-4}$ alkyl, and $C_{1-4}$ haloalkyl; and/or $R^C$ and $R^D$ are independently selected from H and methyl.

16. The compound of claim 1, wherein $R^2$ is selected from the group consisting of H, CN, methyl, ethyl, n-propyl, i-propyl, n-butyl, i-butyl, tert-butyl, sec-butyl, tert-pentyl, allyl, propargyl, difluoroethyl, difluoropropyl, trifluoroethyl, trifluoropropyl, trifluoroisopropyl, isopropanol, n-butanol, sec-butanol, propanol, tert-butanol, cyclopropyl, cyclobutyl, cyclopentyl, cyclohexyl, cycloheptyl, cyclopropanol, cyclobutanol, cyclopentanol, cyclohexanol, cycloheptanol, aziridinyl, N-acetylaziridinyl, N-alkylaziridinyl, azetidinyl, N-acetylazetidinyl, N-alkylazetidinyl, 2-methylpropan-2-amine, phenyl, chlorophenyl, pyrrolidinyl, difluoropyrrolidinyl, trifluoroethylpyrrolidinyl, N-methylpyrrolidinyl, tetrahydrofuranyl, sulfolanyl, dihydropyran, tetrahydropyranyl, tetrahydropyranoimidazolyl, morpholinyl, imidazolyl, ethyltetrahydroimidazopyridine, methylimidazolyl, piperazinyl, N-methylpiperazinyl, trifluoromethylpiperazinyl, oxadiazolyl, dimethyldihydrooxazolyl, pyrazolyl, N-methylpyrazolyl, ethylpyrazolyl, 4-pyridone, 2-pyridone, pyridyl, methyl substituted with tetrahydrofuran, ethyl substituted with pyridine, ethyl substituted with —$NMe_2$, ethyl substituted with OMe, and ethyl substituted with OH; or $R^2$ is selected from the group consisting of

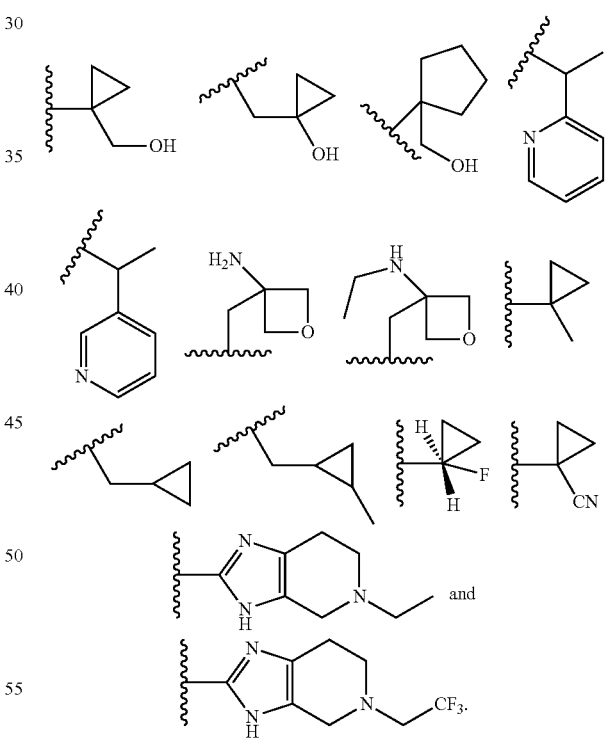

17. The compound of claim 1, wherein $R^4$ is selected from the group consisting of F, Cl, methyl, $CF_3$, Et, iPr, CN, OH, OMe, Oi-Pr, =O, $CH_2OH$, $CH_2OMe$, $NH_2$, $NMe_2$, $CH_2NH_2$, $CH_2NMe_2$, and morpholinyl.

18. The compound of claim 1, wherein $R^5$ is selected from H and methyl.

19. A pharmaceutical composition, comprising a compound of claim 1; and a pharmaceutically acceptable excipient.

20. The pharmaceutical composition of claim 19, further comprising an additional pharmaceutically active agent.

\* \* \* \* \*